(12) United States Patent
Aicher et al.

(10) Patent No.: US 11,059,796 B2
(45) Date of Patent: *Jul. 13, 2021

(54) ARYL DIHYDRO-2H BENZO[B][1,4]OXAZINE SULFONAMIDE AND RELATED COMPOUNDS FOR USE AS AGONISTS OF RORγ AND THE TREATMENT OF DISEASE

(71) Applicant: The Regents of the University of Michigan, Ann Arbor, MI (US)

(72) Inventors: Thomas Daniel Aicher, Ann Arbor, MI (US); Clarke B. Taylor, Ann Arbor, MI (US); Chad A. VanHuis, Hartland, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/812,538

(22) Filed: Mar. 9, 2020

(65) Prior Publication Data

US 2021/0061778 A1 Mar. 4, 2021

Related U.S. Application Data

(63) Continuation of application No. 15/580,414, filed as application No. PCT/US2016/036889 on Jun. 10, 2016, now Pat. No. 10,611,740.

(60) Provisional application No. 62/210,078, filed on Aug. 26, 2015, provisional application No. 62/174,094, filed on Jun. 11, 2015.

(51) Int. Cl.
| | |
|---|---|
| *C07D 265/36* | (2006.01) |
| *C07D 413/14* | (2006.01) |
| *C07D 215/58* | (2006.01) |
| *C07D 413/06* | (2006.01) |
| *C07D 413/12* | (2006.01) |
| *C07D 417/14* | (2006.01) |
| *C07D 471/04* | (2006.01) |
| *C07D 413/04* | (2006.01) |
| *C07D 417/12* | (2006.01) |
| *C07D 279/16* | (2006.01) |
| *C07D 417/04* | (2006.01) |
| *A61P 35/00* | (2006.01) |
| *C07D 413/10* | (2006.01) |
| *C07D 417/06* | (2006.01) |
| *C07D 417/10* | (2006.01) |

(52) U.S. Cl.
CPC ............ *C07D 265/36* (2013.01); *A61P 35/00* (2018.01); *C07D 215/58* (2013.01); *C07D 279/16* (2013.01); *C07D 413/04* (2013.01); *C07D 413/06* (2013.01); *C07D 413/10* (2013.01); *C07D 413/12* (2013.01); *C07D 413/14* (2013.01); *C07D 417/04* (2013.01); *C07D 417/06* (2013.01); *C07D 417/10* (2013.01); *C07D 417/12* (2013.01); *C07D 417/14* (2013.01); *C07D 471/04* (2013.01)

(58) Field of Classification Search
None
See application file for complete search history.

(56) References Cited

U.S. PATENT DOCUMENTS

| | | |
|---|---|---|
| 3,803,184 A | 4/1974 | Njimi et al. |
| 3,936,478 A | 2/1976 | Takeshita et al. |
| 4,952,235 A | 8/1990 | Andree et al. |
| 5,229,109 A | 7/1993 | Grimm et al. |
| 5,229,115 A | 7/1993 | Lynch |
| 5,583,152 A | 12/1996 | Bernstein et al. |
| 5,776,451 A | 7/1998 | Hsu et al. |
| 5,985,903 A | 11/1999 | Assmann et al. |
| 6,020,354 A | 2/2000 | Assmann et al. |
| 6,037,367 A | 3/2000 | Christensen, IV et al. |
| 6,160,001 A | 12/2000 | Assmann et al. |
| 6,172,092 B1 | 1/2001 | Assmann et al. |
| 6,180,643 B1 | 1/2001 | Zablocki et al. |
| 6,348,032 B1 | 2/2002 | Sperl et al. |
| 6,352,985 B1 | 3/2002 | Yamasaki et al. |
| 6,387,939 B1 | 5/2002 | Assmann et al. |
| 6,392,010 B1 | 5/2002 | Salvino et al. |
| 6,403,607 B1 | 6/2002 | Hidaka et al. |
| 6,440,973 B1 | 8/2002 | Zablocki et al. |
| 6,534,535 B1 | 3/2003 | Zhu et al. |
| 6,605,634 B2 | 8/2003 | Zablocki et al. |
| 6,638,960 B2 | 10/2003 | Assmann et al. |
| 6,683,091 B2 | 1/2004 | Asberom et al. |
| 6,828,344 B1 | 12/2004 | Seehra et al. |

(Continued)

FOREIGN PATENT DOCUMENTS

| | | |
|---|---|---|
| EP | 0882718 A1 | 12/1998 |
| EP | 1531848 A2 | 5/2005 |

(Continued)

OTHER PUBLICATIONS

International Search Report and Written Opinion for International Application No. PCT/US2015/017977 dated Jun. 23, 2015 (10 pages).
Zhang et al., "Increasing Human Th17 Differentiation Through Activation of Orphan Nuclear Receptor Retinoid Acid-Related Orphan Receptor γ (RORγ) by a Class of Aryl Amide Compounds," Molecular Pharmacology, vol. 82, pp. 583-590 (2012).
English Abstract JP6-250441 published 1994 (1 page).
English Abstract of JP2004307487A published 2004 (2 pages).
International Search Report and Written Opinion for PCT/US2011/059788 dated May 23, 2012 (23 pages).

(Continued)

*Primary Examiner* — Samantha L Shterengarts
(74) *Attorney, Agent, or Firm* — Dechert LLP

(57) ABSTRACT

The invention provides aryl dihydro-2H-benzo[b][1,4] oxazine sulfonamide and related compounds, pharmaceutical compositions, methods of promoting RORγ activity, methods of increasing the amount of IL-17 in a subject, and methods of treating cancer and other medical disorders using such compounds.

20 Claims, No Drawings

(56) References Cited

U.S. PATENT DOCUMENTS

| | | |
|---|---|---|
| 7,084,176 B2 | 8/2006 | Morie et al. |
| 7,115,750 B1 | 10/2006 | Kato et al. |
| 7,138,401 B2 | 11/2006 | Kasibhatla et al. |
| 7,329,675 B2 | 2/2008 | Cox et al. |
| 7,420,059 B2 | 9/2008 | O'Connor et al. |
| 7,482,342 B2 | 1/2009 | D'Orchymont et al. |
| 7,569,571 B2 | 8/2009 | Dong et al. |
| 7,652,043 B2 | 1/2010 | Beachy et al. |
| 7,696,200 B2 | 4/2010 | Ackermann et al. |
| 7,713,996 B2 | 5/2010 | Ackermann et al. |
| 7,741,495 B2 | 6/2010 | Liou et al. |
| 7,799,933 B2 | 9/2010 | Ceccarelli et al. |
| 7,973,135 B2 | 7/2011 | Liik et al. |
| 7,993,638 B2 | 8/2011 | Cai et al. |
| 7,998,736 B2 | 8/2011 | Morgan et al. |
| 8,067,608 B2 | 11/2011 | Beachy et al. |
| 8,383,099 B2 | 2/2013 | Dudley et al. |
| 8,389,738 B2 | 3/2013 | Kousaka et al. |
| 8,389,739 B1 | 3/2013 | Thacher et al. |
| 8,541,185 B2 | 9/2013 | Oved et al. |
| 8,741,812 B2 | 6/2014 | Javitt |
| 9,095,583 B2 | 8/2015 | Karstens et al. |
| 9,212,134 B2 | 12/2015 | Basu et al. |
| 9,266,827 B2 | 2/2016 | Aicher et al. |
| 9,394,315 B2 | 7/2016 | Aicher et al. |
| 9,487,490 B2 | 11/2016 | Barr et al. |
| 9,512,111 B2 | 12/2016 | Glick et al. |
| 9,556,168 B2 | 1/2017 | Barr et al. |
| 9,603,838 B2 | 3/2017 | Karstens et al. |
| 9,657,033 B2 | 5/2017 | Aicher et al. |
| 9,663,502 B2 | 5/2017 | Aicher et al. |
| 9,663,522 B2 | 5/2017 | Barr et al. |
| 9,783,511 B2 | 10/2017 | Aicher et al. |
| 9,802,958 B2 | 10/2017 | Aicher et al. |
| 9,809,561 B2 | 10/2017 | Aicher et al. |
| 9,896,441 B2 | 2/2018 | Aicher et al. |
| 10,189,777 B2 | 1/2019 | Aicher et al. |
| 10,208,061 B2 | 2/2019 | Aicher et al. |
| 10,221,146 B2 | 3/2019 | Aicher et al. |
| 10,364,237 B2 | 7/2019 | Aicher et al. |
| 10,421,751 B2 | 9/2019 | Aicher et al. |
| 10,442,798 B2 | 10/2019 | Aicher et al. |
| 10,532,088 B2 | 1/2020 | Glick et al. |
| 10,611,740 B2 | 4/2020 | Aicher et al. |
| 2005/0037925 A1 | 2/2005 | Tsukamoto et al. |
| 2006/0004000 A1 | 1/2006 | D'Orchymont et al. |
| 2006/0100230 A1 | 5/2006 | Bischoff et al. |
| 2006/0111421 A1 | 5/2006 | Chadwick et al. |
| 2007/0010537 A1 | 1/2007 | Hamamura et al. |
| 2007/0010670 A1 | 1/2007 | Hirata et al. |
| 2007/0049556 A1 | 3/2007 | Zhang et al. |
| 2007/0060567 A1 | 3/2007 | Ackermann et al. |
| 2007/0154487 A1 | 7/2007 | Littman et al. |
| 2007/0185136 A1 | 8/2007 | Courtemanche et al. |
| 2007/0191603 A1 | 8/2007 | Ackermann et al. |
| 2007/0197782 A1 | 8/2007 | Clough et al. |
| 2007/0219257 A1 | 9/2007 | Beachy et al. |
| 2007/0232661 A1 | 10/2007 | Beachy et al. |
| 2007/0281922 A1 | 12/2007 | Liu et al. |
| 2008/0027002 A1 | 1/2008 | Liik et al. |
| 2008/0027100 A1 | 1/2008 | McCormick et al. |
| 2008/0058386 A1 | 3/2008 | Liou et al. |
| 2008/0153805 A1 | 6/2008 | Ceccarelli et al. |
| 2008/0199486 A1 | 8/2008 | Argon et al. |
| 2008/0305169 A1 | 12/2008 | Miki et al. |
| 2009/0005410 A1 | 1/2009 | Charvat et al. |
| 2009/0042851 A1 | 2/2009 | Despeyroux et al. |
| 2009/0075973 A1 | 3/2009 | Newcom et al. |
| 2009/0131523 A1 | 5/2009 | Yosef |
| 2009/0247502 A1 | 10/2009 | Newcom et al. |
| 2009/0275586 A1 | 11/2009 | Govek et al. |
| 2010/0022515 A1 | 1/2010 | Alper et al. |
| 2010/0087376 A1 | 4/2010 | Kazantseva et al. |
| 2010/0130484 A1 | 5/2010 | Ackermann et al. |
| 2010/0234340 A1 | 9/2010 | Schunk et al. |
| 2010/0310533 A1 | 12/2010 | Yee |
| 2011/0053915 A1 | 3/2011 | Ivaschenko et al. |
| 2011/0112070 A1 | 5/2011 | Baldwin et al. |
| 2011/0118246 A1 | 5/2011 | Baldwin et al. |
| 2011/0130384 A1 | 6/2011 | Setoh et al. |
| 2011/0142814 A1 | 6/2011 | Zanin-Zhorov et al. |
| 2011/0151478 A1 | 6/2011 | Liik et al. |
| 2011/0178063 A1 | 7/2011 | Baldwin et al. |
| 2011/0229504 A1 | 9/2011 | Fritsche et al. |
| 2011/0236363 A1 | 9/2011 | Chang et al. |
| 2012/0135011 A1 | 5/2012 | Podack et al. |
| 2013/0039911 A1 | 2/2013 | Bedi et al. |
| 2013/0045191 A1 | 2/2013 | Weinschenk et al. |
| 2013/0102075 A1 | 4/2013 | Vera et al. |
| 2013/0102542 A1 | 4/2013 | Kazantseva et al. |
| 2014/0038942 A1 | 2/2014 | Karstens et al. |
| 2014/0088094 A1 | 3/2014 | Glick et al. |
| 2014/0186295 A1 | 7/2014 | Kupper et al. |
| 2014/0187504 A1 | 7/2014 | Chaturvedi |
| 2014/0187554 A1 | 7/2014 | Kamenecka et al. |
| 2014/0314795 A1 | 10/2014 | Riddell et al. |
| 2014/0343023 A1 | 11/2014 | Wolfrum et al. |
| 2015/0017120 A1 | 1/2015 | Wittrup et al. |
| 2015/0111877 A1 | 4/2015 | Aicher et al. |
| 2015/0126493 A1 | 5/2015 | Aicher et al. |
| 2015/0133437 A1 | 5/2015 | Aicher et al. |
| 2015/0191434 A1 | 7/2015 | Barr et al. |
| 2015/0210687 A1 | 7/2015 | Barr et al. |
| 2015/0218096 A1 | 8/2015 | Barr et al. |
| 2015/0218169 A1 | 8/2015 | Barr et al. |
| 2015/0297566 A1 | 10/2015 | Karstens et al. |
| 2016/0304476 A1 | 10/2016 | Aicher et al. |
| 2016/0304505 A1 | 10/2016 | Aicher et al. |
| 2016/0311787 A1 | 10/2016 | Aicher et al. |
| 2016/0318951 A1 | 11/2016 | Aicher et al. |
| 2017/0007686 A1 | 1/2017 | Glick et al. |
| 2017/0183331 A1 | 6/2017 | Aicher et al. |
| 2017/0190659 A1 | 7/2017 | Aicher et al. |
| 2017/0313722 A1 | 11/2017 | Aicher et al. |
| 2018/0030005 A1 | 2/2018 | Aicher et al. |
| 2018/0111922 A1 | 4/2018 | Aicher et al. |
| 2018/0179224 A1 | 6/2018 | Aicher et al. |
| 2018/0208587 A1 | 7/2018 | Aicher et al. |
| 2018/0265502 A1 | 9/2018 | Aicher et al. |
| 2020/0207726 A1 | 7/2020 | VanHuis et al. |

FOREIGN PATENT DOCUMENTS

| | | |
|---|---|---|
| EP | 1768662 A2 | 4/2007 |
| EP | 1820515 A1 | 8/2007 |
| EP | 2038301 A2 | 3/2009 |
| EP | 2158327 A2 | 3/2010 |
| EP | 2181710 A1 | 5/2010 |
| EP | 2321407 A1 | 5/2011 |
| EP | 2462165 A1 | 6/2012 |
| EP | 2542590 A2 | 1/2013 |
| EP | 2547354 A2 | 1/2013 |
| EP | 2158327 B1 | 5/2013 |
| EP | 2649086 A1 | 10/2013 |
| EP | 2688594 A2 | 1/2014 |
| EP | 2689010 A1 | 1/2014 |
| EP | 2825197 A1 | 1/2015 |
| JP | 6250441 A | 9/1994 |
| JP | 2000-511558 A | 9/2000 |
| JP | 2004307487 A | 11/2004 |
| JP | 2006-512357 A | 4/2006 |
| JP | 2013-541597 A | 11/2013 |
| JP | 2017-507950 A | 3/2017 |
| JP | 2018-515491 A | 6/2018 |
| WO | WO-92/13856 A1 | 8/1992 |
| WO | WO-97/01561 A1 | 1/1997 |
| WO | WO-97/48697 A1 | 12/1997 |
| WO | WO-98/22457 A1 | 5/1998 |
| WO | WO-00/17202 A1 | 3/2000 |
| WO | WO-01/012600 A1 | 2/2001 |
| WO | WO-2001/012186 A1 | 2/2001 |
| WO | WO-02/14361 A2 | 2/2002 |
| WO | WO-2002/058622 A2 | 8/2002 |
| WO | WO-02/100819 A1 | 12/2002 |

(56) References Cited

FOREIGN PATENT DOCUMENTS

| | | |
|---|---|---|
| WO | WO-03/014075 A2 | 2/2003 |
| WO | WO-03/104428 A2 | 12/2003 |
| WO | WO-2004/050631 A1 | 6/2004 |
| WO | WO-2004/056820 A1 | 7/2004 |
| WO | WO-2004/056830 A1 | 7/2004 |
| WO | WO-05/028434 A2 | 3/2005 |
| WO | WO-2005/030225 A2 | 4/2005 |
| WO | WO-2005/033048 A2 | 4/2005 |
| WO | WO-2005/033288 A2 | 4/2005 |
| WO | WO-2005/037834 A1 | 4/2005 |
| WO | WO-2005/058847 A1 | 6/2005 |
| WO | WO-2005/084208 A2 | 9/2005 |
| WO | WO-2005/120558 A2 | 12/2005 |
| WO | WO-2006/007486 A2 | 1/2006 |
| WO | WO-2006/057460 A1 | 6/2006 |
| WO | WO-2006/065495 A2 | 6/2006 |
| WO | WO-2006/115509 A2 | 11/2006 |
| WO | WO-2007/010259 A1 | 1/2007 |
| WO | WO-2007/024944 A1 | 3/2007 |
| WO | WO-2007/031429 A1 | 3/2007 |
| WO | WO-2007/093507 A1 | 8/2007 |
| WO | WO-2007/113337 A1 | 10/2007 |
| WO | WO-2007/125405 A2 | 11/2007 |
| WO | WO-2007/138998 A1 | 12/2007 |
| WO | WO-2008/003703 A1 | 1/2008 |
| WO | WO-2008/008923 A2 | 1/2008 |
| WO | WO-2008/045664 A2 | 4/2008 |
| WO | WO-2008/062740 A1 | 5/2008 |
| WO | WO-2008/074692 A1 | 6/2008 |
| WO | WO-2008/097428 A2 | 8/2008 |
| WO | WO-2008/150827 A1 | 12/2008 |
| WO | WO-2008/151200 A2 | 12/2008 |
| WO | WO-2009/032667 A1 | 3/2009 |
| WO | WO-2009/035997 A2 | 3/2009 |
| WO | WO-2009/077956 A2 | 6/2009 |
| WO | WO-2009/147187 A1 | 12/2009 |
| WO | WO-2009/149819 A1 | 12/2009 |
| WO | WO-2009/149820 A1 | 12/2009 |
| WO | WO-2009/157196 A1 | 12/2009 |
| WO | WO-2010/017827 A1 | 2/2010 |
| WO | WO-2010/030947 A1 | 3/2010 |
| WO | WO-2010/038901 A1 | 4/2010 |
| WO | WO-2010/057101 A2 | 5/2010 |
| WO | WO-2010/058023 A1 | 5/2010 |
| WO | WO-2010/059602 A2 | 5/2010 |
| WO | WO-2010/071853 A1 | 6/2010 |
| WO | WO-2010/102958 A1 | 9/2010 |
| WO | WO-2010/117425 A1 | 10/2010 |
| WO | WO-2010/123139 A1 | 10/2010 |
| WO | WO-2010/125082 A1 | 11/2010 |
| WO | WO-2011/017303 A1 | 2/2011 |
| WO | WO-2011/019634 A2 | 2/2011 |
| WO | WO-2011/059839 A1 | 5/2011 |
| WO | WO-2011057892 A1 | 5/2011 |
| WO | WO-2011/067364 A1 | 6/2011 |
| WO | WO-2011/067365 A1 | 6/2011 |
| WO | WO-2011/067366 A1 | 6/2011 |
| WO | WO-2011/109059 A1 | 9/2011 |
| WO | WO-2011/109789 A1 | 9/2011 |
| WO | WO-2011/113819 A2 | 9/2011 |
| WO | WO-2011/115892 A1 | 9/2011 |
| WO | WO-2012/020100 A2 | 2/2012 |
| WO | WO-2012/032065 A1 | 3/2012 |
| WO | WO-2012/032067 A1 | 3/2012 |
| WO | WO-2012/037108 A1 | 3/2012 |
| WO | WO-2012/064744 A2 | 5/2012 |
| WO | WO-2012/079000 A1 | 6/2012 |
| WO | WO-2012/127464 A2 | 9/2012 |
| WO | WO-2012/129394 A2 | 9/2012 |
| WO | WO-2012/129514 A1 | 9/2012 |
| WO | WO-2012/139775 A1 | 10/2012 |
| WO | WO-2012130306 A1 | 10/2012 |
| WO | WO-2012/129394 A9 | 11/2012 |
| WO | WO-2012/178108 A1 | 12/2012 |
| WO | WO-2013/045431 A1 | 4/2013 |
| WO | WO-2013/074916 A1 | 5/2013 |
| WO | WO-2013/135588 A1 | 9/2013 |
| WO | WO-2013/167136 A1 | 11/2013 |
| WO | WO-2013/169588 A1 | 11/2013 |
| WO | WO-2013/169704 A2 | 11/2013 |
| WO | WO-2013/169864 A2 | 11/2013 |
| WO | WO-2013/176740 A1 | 11/2013 |
| WO | WO-2014/028669 A1 | 2/2014 |
| WO | WO-2014/031174 A1 | 2/2014 |
| WO | WO-2014/095757 A1 | 6/2014 |
| WO | WO-2014/201378 A1 | 12/2014 |
| WO | WO-2014/201378 A9 | 1/2015 |
| WO | WO-2015/131035 A1 | 9/2015 |
| WO | WO-2015/171610 A2 | 11/2015 |
| WO | WO-2016/179343 A1 | 11/2016 |

OTHER PUBLICATIONS

International Search Report and Written Opinion for PCT/US2013/040085 dated Oct. 23, 2013 (9 pages).
Annunziato et al., "Type 17 T helper cells-origins, features and possible roles in rheumatic disease," 5 Nat. Rev. Rheumatol. 325-31 (2009).
Boaventura et al., "Human mucosal leishmaniasis: Neutrophils infiltrate areas of tissue damage that express high levels of Th17-related cytokines," 40 Eur. J. Immunol. 2830-36 (2010).
Buonocore et al., "Innate lymphoid cells drive interleukin-23-dependent innate intestinal pathology," 464 Nature 1371-75 (2010).
Eberl et al., "An essential function for the nuclear receptor RORγt in the generation of fetal lymphoid tissue inducer cells," 5(1) Nat. Immunol. 64-73 (2004).
Figueroa-Vega et al., "Increased Circulating Pro-Inflammatory Cytokines and Th17 Lymphocytes in Hashimoto's Thyroiditis," 95(2) J. Clin. Endocrinol. Metab. 953-62 (2010).
Gennaro (ed.), Remington: The Science and Practice of Pharmacy, 20th edition (2000).
He et al., "RORγt, a Novel Isoform of an Orphan Receptor, Negatively Regulates Fas Ligand Expression and IL-2 Production in T Cells," 9 Immunity 797-806 (1998).
Hirose et al., "RORγ: the third member of ROR/RZR orphan receptor subfamily that is highly expressed in skeletal muscle," 205 Biochem. Biophys. Res. Comm. 1976-83 (1994).
Hueber et al., "Cutting Edge: Mast Cells Express IL-17A in Rheumatoid Arthritis Synovium," 184 J. Immunol. 3336-40 (2010).
Ivanov et al., "The Orphan Nuclear Receptor RORγt Directs the Differentiation Program of Proinflammatory IL-17+ T Helper Cells," 126 *Cell* 1121-33 (2006).
Jia et al., "The T helper type 17/regulatory T cell imbalance in patients with acute Kawasaki disease," 162 Clin. Exp. Immunol. 131-37 (2010).
Jin et al., "Structural Basis for Hydroxycholesterols as Natural Ligands of Orphan Nuclear Receptor RORγ," *Mol. Endocrinol.* (2010) vol. 24, No. 5, pp. 923-929.
Kastelein et al., "Discovery and Biology of IL-23 and IL-27: Related but Functionally Distinct Regulators of Inflammation," 25 Annu. Rev. Immunol. 221-42 (2007).
Kurebayashi et al., "Selective LXXLL peptides antagonize transcriptional activation by the retinoid-related orphan receptor RORγ," 315 Biochem. Biophys. Res. Comm. 919-27 (2004).
Louten et al., "Development and function of TH17 cells in health and disease," 123(5) J. Allergy Clin. Immunol. 1004-11 (2009).
Miossec et al., "Interleukin-17 and Type 17 Helper T Cells," 361(9) New Eng. J. Med. 888-98 (2009).
Sun et al., "Requirement for RORγ in Thymocyte Survival and Lymphoid Organ Development," 288 Science 2369-72 (2000).
Sutton et al., "Interleukin-1 and IL-23 Induce Innate IL-17 Production from γδ T Cells, Amplifying Th17 Responses and Autoimmunity," 31 Immunity 331-41 (2009).
Wang et al., "Identification of SR1078, a Synthetic Agonist for the Orphan Nuclear Receptors RORα and RORγ," 5(11) ACS Chem. Biol. 1029-34 (2010).
Xie et al., "RORγt Recruits Steroid Receptor Coactivators to Ensure Thymocyte Survival," 175(6) J. Immunol. 3800-09 (2005).

(56) References Cited

OTHER PUBLICATIONS

Yang et al., "T Helper 17 Lineage Differentiation is programmed by Orphan Nuclear Receptors RORα and RORγ," 28 Immunity 29-39 (2008).
André et al., "Disruption of retinoid-related orphan receptor ß changes circadian behaviour, causes retinal degeneration and leads to vacillans phenotype in mice," 17(14) The EMBO J. 3867-77 (1998).
Becker-André et al., "Identification of nuclear receptor mRNAs by RT-PCR amplification of conserved zinc-finger motif sequences," 194(3) Biochem. Biophys. Res. Comm. 1371-79 (1993).
Burris et al., "Targeting Orphan Nuclear Receptors for Treatment of Metabolic Diseases and Autoimmunity," 19(1) Chem. Biol. 51-59 (2012).
Cai, et al., "Pivotal Role of Dermal IL-17-Producing γδ T Cells in Skin Inflammation", Immunity (2011) vol. 35, pp. 596-610.
Carlberg et al., "RZRs, a new family of retinoid-related orphan receptors that function as both monomers and homodimers," 8 Mol. Endocrinol. 757-70 (1994).
D. van der Heijde, et al., "Secukinumab Provides Significant and Sustained Inhibition of Joint Structural Damage in a Phase III Study of Active Psoriatic Arthritis" Arthritis & Rheumatology Brief Report, Accepted Article DOI: 10.1002/art.39685, American College of Rheumatology, (2016) pp. 1-27.
Baeten, et al., "Secukinumab, an Interleukin-17A Inhibitor, in Ankylosing Spondylitis", The New England Journal of Medicine, (2015) vol. 373, pp. 2534-2548.
Dussault et al., "Orphan nuclear receptor RORα-deficient mice display the cerebellar defects of staggerer," 70 Mech. Develop. 147-53 (1998).
Giguère et al., "Isoform-specific amino-terminal domains dictate DNA-binding properties of RORα, a novel family of orphan hormone nuclear receptors," 8 Genes & Develop. 538-53 (1994).
Huh et al., "Small molecule inhibitors of RORγt: Targeting Th17 cells and other applications," 42 Eur. J. Immunol. 2232-2237 (2012).
Krueger, "A welcome surprise in psoriasis", Nature Medicine, (2012) vol. 18, No. 12, pp. 1750-1751.
Leonardi, et al., "Anti-Interleukin-17 Monoclonal Antibody Ixekizumab in Chronic Plaque Psoriasis", The New England Journal of Medicine, (2012) vol. 366, Iss. 13, pp. 1-10.
Martinez, "Th17-biased RORγt transgenic mice become susceptible to a viral model for multiple sclerosis", Brain, Behavior, and Immunity, (2014) vol. 43, pp. 86-97.
Medvedev et al., "Cloning of a cDNA encoding the murine orphan receptor RZR/RORγ and characterization of its response element," 181 Gene 199-206 (1996).
Nakajima, et al., "IL-17A as an Inducer for Th2 Immune Responses in Murine Atopic Dermatitis Models", Journal of Investigative Dermatology, (2014) vol. 134, pp. 2122-2130.
Ortiz et al., "TOR: a new orphan receptor expressed in the thymus that can modulate retinoid and thyroid hormone signals," 9 Mol. Endocrinol. 1679-91 (1995).
Papp, et al. "Brodalumab, an Anti-Interleukin-17-Receptor Antibody for Psoriasis", The New England Journal of Medicine, (2012) vol. 366, Iss. 13, 9 pgs.
Skepner, J. et al. "Pharmacologic Inhibition of RORγt Regulates Th17 Signature Gene Expression and Suppresses Cutaneous Inflammation In Vivo," downloaded from the Internet at http://www.jimmunol.org/cgi/doi/10.4049/jimmuno1.1302190 on Feb. 17, 2014, published in final edited form in J. Immunol. (2014) vol. 192, No. 6, pp. 2564-2575.
Smith, "The Bench-to-Bedside Story of IL-17 and the Therapeutic Efficacy of its Targeting in Spondyloarthritis", Curr Rheumatol Rep. (2016) vol. 18, pp. 1-10.
Solt et al., "Action of RORs and their ligands in (patho)physiology," 23(12) Trends in Endocrinology and Metabolism. 619-627 (2012).
Tlustochowicz, et al. "Efficacy and Safety of Subcutaneous and Intravenous Loading Dose Regimens of Secukinumab in Patients with Active Rheumatoid Arthritis: Results from a Randomized Phase II Study," The Journal of Rheumatology, (2016) vol. 43, No. 3, pp. 495-503.
Villey et al., "RORγT, a thymus-specific isoform of the orphan nuclear receptor RORγ/TOR, is up-regulated by signaling through the pre-T cell receptor and binds to the TEA promoter," 29 Eur. J. Immunol. 4072-80 (1999).
Wiesenberg et al., "Transcriptional activation of the nuclear receptor RZRα by the pineal gland hormone melatonin and identification of CGP 52608 as a synthetic ligand," 23(3) Nucl. Acids Res. 327-33 (1995).
Xiao, et al., "Small-Molecule RORγt Antagonists Inhibit T Helper 17 Cell Transcriptional Network by Divergent Mechanisms", Immunity (2014) vol. 40, pp. 477-489.
Arisawa et al., "Development of Isomerization and Cycloisomerization with Use of a Ruthenium Hydride with N-Heterocyclic Carbene and Its Application to the Synthesis of Heterocycles," 71 J. Org. Chem. 4255-61 (2006).
Berge et al., "Pharmaceutical salts," 66(1) J. Pharm. Sci. 1-19 (1977).
Bhagawanth et al., "Room-Temperature Pd-Catalyzed Amidation of Aryl Bromides Using tert-Butyl Carbamate," 74 J. Org. Chem. 4634-37 (2009).
Boger et al., "Regiocontrolled Nucleophilic Addition to Selectively Activated p-Quinone Diimines: Alternative Preparation of a Key Intermediate Employed in the Preparation of the CC-1065 Left-Hand Subunit," 55 J. Org. Chem. 1379-90 (1990).
Carroll et al., "Synthesis, Nicotinic Acetylcholine Receptor Binding, and Antinociceptive Properties of 2-exo-2-(2',3'-Disubstituted 5'-pyridinyl)-y-azabicyclo[2.2.1]heptanes: Epibatidine Analogues," 45 J. Med. Chem. 4755-61 (2002).
Chang et al., "7-Aroyl-aminoindoline-1-sulfonamides as a Novel Class of Potent Antitubulin Agents," 49 J. Med. Chem. 6656-59 (2006).
Colbon et al., "Double Arylation of Allyl Alcohol via a One-Pot Heck Arylation—Isomerization—Acylation Cascade," 13 Org. Lett. 5456-59 (2011).
De et al., Methods in Molecular Biology 1184, second edition, Human Press (2014).
Gould, "Salt selection for basic drugs," 33 Int'l J. Pharmaceutics 201-217 (1986).
Grasa et al., "Amination Reactions of Aryl Halides with Nitrogen-Containing Reagents Mediated by Palladium/Imidazolium Salt Systems," 66 J. Org. Chem. 7729-37 (2001).
Greene & Wuts, Protective Groups in Organic Synthesis, 2d Edition (1991).
Guimond et al., "Rhodium(III)-Catalyzed Isoquinolone Synthesis: The N—O Bond as a Handle for C—N Bond Formation and Catalyst Turnover," 132(20) J. Am. Chem. Soc. 6908-09 (2010).
Hanessian et al., "A versatile protocol for the stereocontrolled elaboration of vicinal secondary and tertiary centers of relevance to natural product synthesis," 52(6) J. Org. Chem. 1170-72 (1987).
Hauser et al., "Relative Ease of Cyclization of 2-, 3-, and 4-Aminopyridine Derivatives. Synthesis of Naphthyridines," 15 J. Org. Chem. 1224-32 (1950).
International Search Report and Written Opinion for PCT/US2013/039422 dated Oct. 11, 2013 (9 pages).
International Search Report and Written Opinion for PCT/US2013/039839 dated Oct. 18, 2013 (8 pages).
Ishikura et al., "An Efficient Synthesis of 3-Heteroarylpyridines via Diethyl-(3-pyridyl)-borane," Synthesis 936-38 (1984).
Jayashree et al., "Design and synthesis of 2-quinolones as antioxidants and antimicrobials: a rational approach," 19 Med. Chem. Res. 193-209 (2010).
Jiang et al., "Synthesis and Cytotoxicity Evaluation of Novel Indolylpyrimidines and Indolylpyrazines as Potential Antitumor Agents," 9 Bioorg. Med. Chem. 1149-54 (2001).
Li et al., "Chemical Libraries via Sequential C—H Functionalization of Phenols," 10 J. Comb. Chem. 170-74 (2008).
Li et al., "Synthesis and Resolution of a Novel Chiral Diamine Ligand and Application to Asymmetric Lithiation-Substitution," 2 Org. Lett. 875-78 (2000).

(56) References Cited

OTHER PUBLICATIONS

Liu et al., "1-Sulfonylindazoles as potent and selective 5-HT6 ligands," 19 Bioorg. Med. Chem. Lett. 2413-15 (2009).
Murase et al., "A New Concise Synthesis of Arcyriacyanin A and Its Unique Inhibitory Activity against a Panel of Human Cancer Cell Line," 48(1) Chem. Pharm. Bull. 81-84 (2000).
Ninomiya et al., "Phosphorous in Organic Synthesis—VII: Diphenyl Phosphorazidate (DPPA). A New Convenient Reagent for a Modified Curtius Reaction," 30 Tetrahedron 2151-57 (1975).
Nyrkova et al., "Synthesis of a New Heterocyclic System—3,4-Diazaphenoxazine," 1(9) J. Org. Chem. USSR, 1711-14, translating 1(9) Zh. Org. Khimii, 1688-91 (1965).
Santilli et al., "Synthesis of 5,6,7,8-Tetrahydro-5-oxopyrido[2,3-d] pyrimidine-6-carbonitriles and -6-carboxylic Acid Esters," 12 J. Het. Chem. 311-16 (1975).
Skraup, "Eine Synthese des Chinolins," 13 Berichte 2086-87 (1880).
Stefko et al., "General and Modular Synthesis of Isomeric 5-Substituted Pyridin-2-yl and 6-Substituted Pyridin-3-yl C-Ribonucleosides Bearing Diverse Alkyl, Aryl, Hetaryl, Amino, Carbamoyl, and Hydroxy Groups," 76 J. Org. Chem. 6619-35 (2011).
STN Columbus, pp. 1-40 (2011).
Takano et al., "A new synthesis of a steroid side chain via stereocontrolled protonation: synthesis of (-)-desmosterol," 14 J. Chem. Soc., Chem. Commun. 760-61 (1983).
Van Heerden et al., "Dibutylboron triflate promoted conjugate addition of benzylic and allylic organocopper reagents to chiral α,β-unsaturated N-acyl imidazolidinones" 38(10) Tet. Lett. 182-124 (1997).
Wang et al., "Synthesis of new carbon-11-labeled 7-aroyl-aminoindoline-1-sulfonamides as potential PET agents for imaging of tubulin polymerization in cancers," 51(1) J. Label. Compd. Radiopharm. 6-11 (2008).
Yeh et al., "Practical Cu-catalyzed amination of functionalized heteroaryl halides," 47(34) Tetrahedron Lett. 6011-16 (2006).
Zhu et al., "The Direct Formulation of Functionalized Alkyl(aryl)zinc halides by Oxidative Addition of Highly Reactive Zinc with Organic Halides and Their Reactions with Acid Chlorides, α,β-Unsaturated Ketones, and Allylic, Aryl, and Vinyl Halides," 56 J. Org. Chem. 1445-53 (1991).
International Search Report and Written Opinion for PCT/US2014/071663 dated Apr. 17, 2015 (6 pages).
International Search Report and Written Opinion for PCT/US2014/071671 dated Apr. 28, 2015 (10 pages).
International Search Report and Written Opinion for PCT/US2014/071656 dated Mar. 12, 2015 (8 pages).
Yang, T. et al. "Discovery of Tertiary Amine and Indole Derivatives as Potent RORγt Inverse Agonists," ACS Med. Chem. Lett. (2014) vol. 5, pp. 65-68.
Jun., C. H. "Adoptive T cell therapy for cancer in the clinic," J. Clin. Invest. (2007) vol. 117, No. 6, pp. 1466-1476.
Zhu, J. et al. "Differentiation of Effector CD4 T Cell Populations," Author manuscript available in PMC on Nov. 20, 2012, published in final edited form in Annu. Rev. Immunol. (2010) vol. 28, pp. 445-489.
Martin-Orozco, N. et al. "Th17 cells promote cytotoxic T cell activation in tumor immunity," Author manuscript available in PMC on Nov. 20, 2010, published in final edited form in Immunity (2009) vol. 31, pp. 787-798.
Pardoll, D. M. "The blockade of immune checkpoints in cancer immunotherapy," Nature Rev. Cancer (2012) vol. 12, pp. 252-264.
Restifo, N. P. et al. "Adoptive immunotherapy for cancer: harnessing the T cell response," Nature Rev. Immunol. (2012) vol. 12, pp. 269-281.
Drug Discovery & Development "Lycera's Oral Immunotherapy May Have Anti-Cancer Activity," Dated Nov. 7, 2014. (2 pages).
Lycera "Lycera Announces Research Showing Promising Anti-Cancer Activity of Novel, Oral Immunotherapy Candidates," Press release dated Feb. 9, 2015. (2 pages).

X. Hu et al. In Poster Presentation Entitled "Novel, Synthetic RORgamma Agonist Compounds as a Potential Anti-Cancer Approach" at Society for Immunotherapy of Cancer (SITC) Meeting 2014, Nov. 6-9, 2014.
Huang, Z. et al. "Retinoid-related orphan receptor γt is a potential therapeutic target for controlling inflammatory autoimmunity," Expert Opin. Ther. Targets (2007) vol. 11, No. 6, pp. 737-743.
Wang et al., "Modulation of Retinoic Acid Receptor-related Orphan Receptor α and γ Activity by 7-Oxygenated Sterol Ligands," J. Biol. Chem. (2010) vol. 285, No. 7, pp. 5013-5025.
Bai et al., "Sulfation of 25-hydroxycholesterol by SULT2B1b decreases cellular lipids via the LXR/SREBP-1c signaling pathway in human aortic endothelial cells," Atherosclerosis, vol. 214, pp. 350-356 (author's manuscript pp. 1-14) (2011).
Bensinger et al., "LXR signaling couples sterol metabolism to proliferation in the acquired immune response," Cell, vol. 134, pp. 97-111 (2008).
Brown et al., "Oxysterols and atherosclerosis," Atherosclerosis, vol. 142, pp. 1-28 (1999).
Chen et al., "Enzymatic reduction of oxysterols impairs LXR signaling in cultured cells and the livers of mice," Cell Metab., vol. 5, pp. 73-79 (2007).
Cheng et al., "Increased cholesterol content in Gammadelta (γδ) T lymphocytes differentially regulates their activation," PLoS ONE 8, pp. 1-9 (2013).
Cook et al., "24-hydroxycholesterol sulfation by human cytosolic sulfotransferases: formation of monosulfates and disulfates, molecular modeling, sulfatase sensitivity, and inhibition of liver X receptor activation," Drug Metab. Dispos., vol. 37, pp. 2069-2078 (2009).
Hanyu et al., "Cholesterol sulfate induces expression of the skin barrier protein filaggrin in normal human epidermal keratinocytes through induction of RORα," Biochem. Biophys. Res. Commun., vol. 428, pp. 99-104 (2012).
Hu et al., "Sterol metabolism controls $T_H17$ differentiation by generating endogenous RORγ agonists," Nature Chemical Biology, vol. 11, pp. 141-147 (2015).
Iida et al., "Tumor-Infiltrating CD4+Th17 Cells Produce IL-17 in Tumor Microenvironment and Promote Tumor Progression in Human Gastric Cancer," Oncology Reports, vol. 25, pp. 1271-1277 (2011).
Ikonen, "Cellular cholesterol trafficking and compartmentalization," Nat. Rev. Mol. Cell Biol., vol. 9, pp. 125-138 (2008).
Kallen et al., "Crystal structure of the human RORα ligand binding domain in complex with cholesterol sulfate at 2.2 Å," J. Biol. Chem., vol. 279, pp. 14033-14038 (2004).
Kidani et al., "The sterol regulatory element binding proteins are essential for the metabolic programming of effector T cells and adaptive immunity," Nat. Immunol., vol. 14, pp. 489-499 (2013).
Liao et al., "Association Between Th17-Related Cytokines and Risk of Non-Small Cell Lung Cancer Among Patients With or Without Chronic Obstructive Pulmonary Disease," Cancer, pp. 3122-3129 (2015).
Ma et al., "25-Hydroxycholesterol-3-sulfate regulates macrophage lipid metabolism via the LXR/SREBP-1 signaling pathway," Am. J. Physiol. Endocrinol. Metab., vol. 295, pp. E1369-E1379 (2008).
Solt et al., "Identification of a selective RORγ ligand that suppresses $T_H17$ cells and stimulates T regulatory cells," ACS Chem. Biol., vol. 7, pp. 1515-1519 (2012).
Song et al., "Auto-oxidized cholesterol sulfates are antagonistic ligands of liver X receptors: implications for the development and treatment of atherosclerosis," Steroids, vol. 66, pp. 473-479 (2001).
Spann et al., "Regulated accumulation of desmosterol integrates macrophage lipid metabolism and inflammatory responses," Cell, vol. 151, pp. 138-152 (2012).
Spann et al., "Sterols and oxysterols in immune cell function," Nat. Immunol., vol. 14, pp. 893-900 (2013).
Wang et al., "A second class of nuclear receptors for oxysterols: Regulation of RORα and RORγ activity by 24S-hydroxycholesterol (cerebrosterol)," Biochim. Biophys. Acta, vol. 1801, pp. 917-923 (2010).
Yang et al., "Sterol intermediates from cholesterol biosynthetic pathway as liver X receptor ligands," J. Biol. Chem., vol. 281, pp. 27816-27826 (2006).

(56) References Cited

OTHER PUBLICATIONS

Arellano et al., "Clinical uses of GM-CSF, a critical appraisal and update," *Biologics: Targets & Therapy*, vol. 2, pp. 13-27 (2008).
Chang et al., "Synthetic RORγt Agonists Enhance Protective Immunity," ACS Chem. Biol., Just Accepted Manuscript—DOI: 10.1021/acschembio.5b00899—Publication Date (Web): Jan. 19, 2016, (30 pages).
Chen et al., "Th1-, Th2-, and Th17-associated cytokine expression in hypopharyngeal carcinoma and clinical significance," *Eur Arch Otorhinolaryngol*, DOI: 10.1007/s00405-015-3779-2, 8 pages, (2015).
Codarri et al., "RORγt drives production of the cytokine GM-CSF in helper T cells, which is essential for the effector phase of autoimmune neuroinflammation," *Nature Immunology*, vol. 12, pp. 560-568, (2011).
Gnerlich et al., "Induction of Th17 Cells in the Tumor Microenvironment Improves Survival in a Murine Model of Pancreatic Cancer," *The Journal of Immunology*, vol. 185, pp. 4063-4071, (2010).
Hinrichs et al., "Type 17 CD8+ T cells display enhanced antitumor immunity," *Blood*, vol. 114, pp. 596-599, (2009).
Hu et al. in "RORγ Agonists as a Novel Immunotherapy Approach for Cancer" in American Association for Cancer Research Annual Meeting in Philadelphia, Pennsylvania, Apr. 21, 2015, Poster Session: Novel Immunomodulators, Abstract No. 4273.
Kryczek et al., "Phenotype, distribution, generation, and functional and clinical relevance of Th17 cells in the human tumor environments," *The American Society of Hematology*, vol. 114, pp. 1141-1149, (2009).
Ma et al., "Contribution of IL-17-producing γ8 T cells to the efficacy of anticancer chemotherapy," *J. Exp. Med.*, vol. 208, pp. 491-503, (2011).
Munegowda et al., "Th17 and Th17-stimulated CD8 + T cells play a distinct role in Th17-induced preventive and therapeutic antitumor immunity," *Cancer Immunol Immunother*, vol. 60, (2011), one page, Abstract only.
Muranski et al., "Tumor-specific Th17-polarized cells eradicate large established melanoma," *Blood*, vol. 112, pp. 362-373, (2008).
Nelson et al., "The Inducible Costimulator Augments Tc17 Cell Responses to Self and Tumor Tissue," *The Journal of Immunology*, vol. 194, pp. 1737-1747, (2015).
Nunez et al., "T helper type 17 cells contribute to anti-tumour immunity and promote the recruitment of T helper type 1 cells to the tumour," *Immunology*, vol. 139, pp. 61-71, (2012).
Soroosh et al.,"Oxysterols are agonist ligands of RORγt and drive Th17 cell differentiation," PNAS, vol. 111, pp. 12163-12168, (2014).
International Search Report and Written Opinion for International Application No. PCT/US2015/029167 dated Jun. 13, 2017 (25 pages).
International Search Report and Written Opinion for International Application No. PCT/US2015/029240 dated Jan. 29, 2016 (14 pages).
International Search Report and Written Opinion for International Application No. PCT/US2016/030882 dated Jun. 6, 2016 (17 pages).
International Search Report and Written Opinion for International Application No. PCT/US2016/036889 dated Sep. 9, 2016 (17 pages).
Yang, S. M. and Murray, W. V. "Microwave assisted ring-opening of epoxides with N-biaryl sulfonamides in the synthesis of matrix metalloproteinase-9 inhibitors," *Tetrahedron Lett.* (2008) vol. 49, No. 5, pp. 835-839.
CAS Registry No. 1012413-39-6; STN Entry Date: Apr. 6, 2008; Chemical name: Benzenesulfonamide, N-[4-[(2-fluorophenyl)methoxy]phenyl]-N-methyl.
CAS Registry No. 632292-33-2; STN Entry Date: Dec. 30, 2003; Chemical name: 2-[[1,2,3,4-tetrahydro-1-[(4-methylphenyl)sulfonyl]-6-quinolinyl]methyl]-1H-isoindole-1,3(2H)-dione.
Zhu, W. et al. "Potent 11β-Hydroxylase Inhibitors with Inverse Metabolic Stability in Human Plasma and Hepatic S9 Fractions to Promote Wound Healing," *J. Med. Chem.* (2014) vol. 57, No. 18, pp. 7811-7817.
Zhao, S.-H. et al. "3,4-Dihydro-2H-benzo[1,4]oxazine Derivatives as 5-$HT_6$ Receptor Antagonists," *Bloorg. Med. Chem. Lett.* (2007) vol. 17, pp. 3504-3507.
Tavares, F. X. et al. "Potent, Selective, and Orally Efficacious Antagonists of Melanin-Concentrating Hormone Receptor 1," *J. Med. Chem.* (2006) vol. 49, No. 24, pp. 7095-7107.
STN Chemical Structure Search Results (dated Jun. 5, 2015; 13 pages).
STN Chemical Structure Search Results (dated May 2, 2014; 10 pages).
STN Chemical Structure Search Results (dated May 2, 2014; 28 pages).
International Preliminary Report on Patentability for International Application No. PCT/US2015/029167 dated Jul. 4, 2017 (13 pages).
Starck et al (1993): STN International, NCAPLUS database, (Columbus, Ohio), Accession No. 2014:1493781.
Garcia-Hernandez, M. et al. "Adoptive Transfer of Tumor-Specific Tc17 Effector T Cells Controls the Growth of B16 Melanoma in Mice," J. Immunology. (2010), vol. 184, No. 8, pp. 4215-4227.
U.S. Appl. No. 16/797,104, Treatment of Cancer Using Aryl Dihydro-2H-Benzo[B][1,4]Oxazine Sulfonamide Compounds, filed Feb. 21, 2020.

ARYL DIHYDRO-2H BENZO[B][1,4]OXAZINE SULFONAMIDE AND RELATED COMPOUNDS FOR USE AS AGONISTS OF RORγ AND THE TREATMENT OF DISEASE

CROSS-REFERENCE TO RELATED APPLICATIONS

This application is a continuation of U.S. patent application Ser. No. 15/580,414, filed Dec. 7, 2017, which is the national stage of International (PCT) Patent Application Serial No. PCT/US2016/036889, filed Jun. 10, 2016, which claims the benefit of and priority to U.S. Provisional Patent Application Ser. No. 62/174,094, filed Jun. 11, 2015, and U.S. Provisional Patent Application Ser. No. 62/210,078, filed Aug. 26, 2015; the contents of each of which are hereby incorporated by reference in their entirety.

FIELD OF THE INVENTION

The invention provides aryl dihydro-2H-benzo[b][1,4]oxazine sulfonamide and related compounds, methods of promoting RORγ activity and/or increasing the amount of IL-17 in a subject, and therapeutic uses of the aryl dihydro-2H-benzo[b][1,4]oxazine sulfonamide and related compounds, such as treating medical conditions in which activation of immune response is beneficial.

BACKGROUND

Retinoid-related orphan receptors (ROR) are reported to have an important role in numerous biological processes. See, for example, Dussault et al. in *Mech. Dev.* (1998) vol. 70, 147-153; and Andre et al. in *EMBO J.* (1998) vol. 17, 3867-3877. Scientific investigations relating to each of retinoid-related orphan receptors RORα, RORβ, and RORγ have been described in the literature. See, for example, Hirose et al. in *Biochem. Biophys. Res. Commun.* (1994) vol. 205, 1976-1983; Giguere et al. in *Genes. Dev.* (1994) vol. 8, 538-553; Medvedev et al. in *Gene* (1996) vol. 181, 199-206; Ortiz et al. in *Mol. Endocrinol.* (1995) vol. 9, 1679-1691; and A. M. Jetten in *Curr Drug Targets Inflamm Allergy* (2004) vol. 3, 395-412). Continuing research in this field is spurred by the promise of developing new therapeutic agents to treat medical disorders associated with retinoid-related orphan receptor activity.

RORγ has been reported to be expressed in high concentration in various tissues, such as thymus, kidney, liver, muscle, and certain fat tissue. See, for example, Hirose et al. in *Biochem. Biophys. Res. Commun.* (1994) vol. 205, 1976-1983; Medvedev et al. in *Gene* (1996) vol. 181, 199-206; Ortiz et al. in *Mol. Endocrinol.* (1995) vol. 9, 1679-1691; and He et al. in *Immunity* (1998) vol. 9, 797-806. Two isoforms of RORγ have been identified and are referred to as γ1 and γ2 (also referred to as RORγt). See, for example, He et al. in *Immunity* (1998) vol. 9, 797-806. Expression of the γ2 isoform has been reported to appear in, for example, double-positive thymocytes. See, for example, He et al. in *Immunity* (1998) vol. 9, 797-806; and Villey et al. in *Eur. J. Immunol.* (1999) vol. 29, 4072-4080. RORγt plays a critical role in regulating differentiation of Th17 cells, a subset of T helper lymphocytes. See, for example, Ivanov et al. in *Cell*(2006) vol. 126, 1121-1133. Th17 cells are important for recruiting tumor-killing cytotoxic CD8+ T cells and natural killer cells into the tumor microenvironment. The level of Th17 cells correlated positively with patient survival or slower disease progression in certain cancers. See, for example, Kryczek et al. in *Blood* (2009) vol 114, 1141-1149; and Sfanos et al. in *Clinical Cancer Research* (2008) vol 14, 3254-3261. Compounds capable of enhancing RORγt activity are thus contemplated to provide a therapeutic benefit in the treatment of cancer.

Cancer continues to be a significant health problem despite the substantial research efforts and scientific advances reported in the literature for treating this disease. Some of the most frequently diagnosed cancers include prostate cancer, breast cancer, and lung cancer. Prostate cancer is the most common form of cancer in men. Breast cancer remains a leading cause of death in women. Current treatment options for these cancers are not effective for all patients and/or can have substantial adverse side effects.

Accordingly, a need exists for improved treatments for cancer. The present invention addresses this need and provides other related advantages.

SUMMARY

The invention provides dihydro-2H-benzo[b][1,4]oxazine and related compounds, pharmaceutical compositions, methods of promoting RORγ activity and/or increasing the amount of IL-17 in a subject, and methods of treating various medical disorders using such compounds. In particular, one aspect of the invention provides a collection of aryl dihydro-2H-benzo[b][1,4]oxazine sulfonamide and related compounds, such as a compound represented by Formula I:

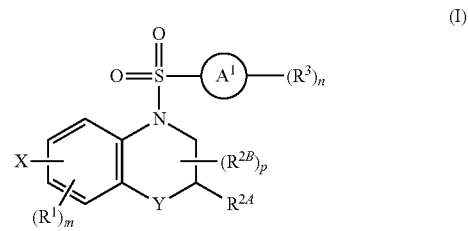

or a pharmaceutically acceptable salt thereof; wherein the variables are as defined in the detailed description. Further description of additional collections of aryl dihydro-2H-benzo[b][1,4]oxazine sulfonamide and related compounds are described in the detailed description. The compounds may be part of a pharmaceutical composition comprising a pharmaceutically acceptable carrier.

Another aspect of the invention provides a method of treating a subject suffering from a medical disorder. The method comprises administering to the subject a therapeutically effective amount of one or more aryl dihydro-2H-benzo[b][1,4]oxazine sulfonamide or related compounds described herein, e.g., a compound of Formula I, I-A, or II, to treat the disorder. A large number of disorders can be treated using the aryl dihydro-2H-benzo[b][1,4]oxazine sulfonamide and related compounds described herein. For example, the compounds described herein can be used to treat cancer, a bacterial infection, a fungal infection, or an immune deficiency disorder.

Another aspect of the invention provides a method of promoting the activity of RORγ. The method comprises exposing a RORγ to an effective amount of one or more aryl dihydro-2H-benzo[b][1,4]oxazine sulfonamide or related compounds described herein, e.g., a compound of Formula I, I-A, or II, or a pharmaceutical composition described herein.

Another aspect of the invention provides a method of increasing the amount of IL-17 in a subject. The method comprises administering to a subject an effective amount of one or more aryl dihydro-2H-benzo[b][1,4]oxazine sulfonamide or related compounds described herein, e.g., a compound of Formula I, I-A, or II, or a pharmaceutical composition described herein, to increase the amount of IL-17 in the subject.

DETAILED DESCRIPTION

The invention provides aryl dihydro-2H-benzo[b][1,4] oxazine sulfonamide and related compounds, pharmaceutical compositions, methods of promoting RORγ activity and/or increasing the amount of IL-17 in a subject, and therapeutic uses of the aryl dihydro-2H-benzo[b][1,4] oxazine sulfonamide and related compounds. The practice of the present invention employs, unless otherwise indicated, conventional techniques of organic chemistry, pharmacology, molecular biology (including recombinant techniques), cell biology, biochemistry, and immunology. Such techniques are explained in the literature, such as in "Comprehensive Organic Synthesis" (B. M. Trost & I. Fleming, eds., 1991-1992); "Handbook of experimental immunology" (D. M. Weir & C. C. Blackwell, eds.); "Current protocols in molecular biology" (F. M. Ausubel et al., eds., 1987, and periodic updates); and "Current protocols in immunology" (J. E. Coligan et al., eds., 1991), each of which is herein incorporated by reference in its entirety.

Various aspects of the invention are set forth below in sections; however, aspects of the invention described in one particular section are not to be limited to any particular section. Further, when a variable is not accompanied by a definition, the previous definition of the variable controls.

Definitions

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. If a chemical compound is referred to using both a chemical structure and a chemical name, and an ambiguity exists between the structure and the name, the structure predominates. These definitions apply regardless of whether a term is used by itself or in combination with other terms, unless otherwise indicated. Hence, the definition of "alkyl" applies to "alkyl" as well as the "alkyl" portions of "—O-alkyl" etc.

The term "alkyl" refers to a saturated straight or branched hydrocarbon, such as a straight or branched group of 1-12, 1-10, or 1-6 carbon atoms, referred to herein as $C_1$-$C_{12}$ alkyl, $C_1$-$C_{10}$ alkyl, and $C_1$-$C_6$ alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, etc.

The term "alkylene" refers to a diradical of an alkyl group. Exemplary alkylene groups include —$CH_2$—, —$CH_2CH_2$—, and —$CH_2C(H)(CH_3)CH_2$—. The term "—($C_0$ alkylene)-" refers to a bond. Accordingly, the term "—($C_{0-3}$ alkylene)-" encompasses a bond (i.e., $C_0$) and a —($C_{1-3}$ alkylene) group.

The term "heteroalkylene" refers to an alkylene group in which one or more carbon atoms has been replaced by a heteroatom (e.g., N, O, or S). Exemplary heteroalkylene groups include —$CH_2O$—, —$CH_2OCH_2$—, and —$CH_2CH_2O$—. The heteroalkylene group may contain, for example, from 2-4, 2-6, or 2-8 atoms selected from the group consisting of carbon and a heteroatom (e.g., N, O, or S).

The term "cycloalkyl" refers to a monovalent saturated cyclic, bicyclic, or bridged cyclic (e.g., adamantyl) hydrocarbon group of 3-12, 3-8, 4-8, or 4-6 carbons, referred to herein, e.g., as "$C_3$-$C_6$ cycloalkyl," derived from a cycloalkane. Exemplary cycloalkyl groups include cyclohexyl, cyclopentyl, cyclobutyl, and cyclopropyl.

The term "cycloalkylene" refers to a diradical of a cycloalkyl group. Exemplary cycloalkylene groups include

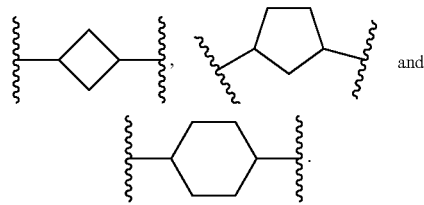

The term "haloalkyl" refers to an alkyl group that is substituted with at least one halogen. Exemplary haloalkyl groups include —$CH_2F$, —$CHF_2$, —$CF_3$, —$CH_2CF_3$, —$CF_2CF_3$, and the like.

The term "hydroxyalkyl" refers to an alkyl group that is substituted with at least one hydroxyl. Exemplary hydroxyalkyl groups include —$CH_2CH_2OH$, —$C(H)(OH)CH_3$, —$CH_2C(H)(OH)CH_2CH_2OH$, and the like.

The term "hydroxyhaloalkyl" refers to an alkyl group that is substituted with (i) at least one hydroxyl, and (ii) at least one halogen. Exemplary hydroxyalkyl groups include —$C(H)(F)CH_2OH$ and —$C(H)(OH)C(F)H_2$, and the like.

The term "aralkyl" refers to an alkyl group substituted with an aryl group. Exemplary aralkyl groups include

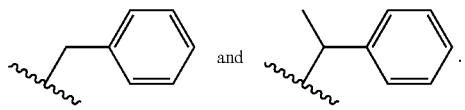

The term "heteroaralkyl" refers to an alkyl group substituted with a heteroaryl group.

The terms "alkenyl" and "alkynyl" are art-recognized and refer to unsaturated aliphatic groups analogous in length and possible substitution to the alkyls described above, but that contain at least one double or triple bond respectively.

The term "cycloalkenyl" refers to a monovalent unsaturated cyclic, bicyclic, or bridged (e.g., adamantyl) carbocyclic hydrocarbon containing at least one C=C double bond. In certain embodiments, the cycloalkenyl contains 5-10, 5-8, or 5-6 carbons, referred to herein, e.g., as "$C_5$-$C_6$ cycloalkenyl". Exemplary cycloalkenyl groups include cyclohexenyl and cyclopentenyl. The term "cycloalkenylene" refers to a diradical of a cycloalkenyl group.

The term "carbocyclylene" refers to a diradical of a carbocyclyl group, wherein a carbocyclyl group is a saturated or unsaturated cyclic, bicyclic, or bridged (e.g., adamantyl) carbocyclic hydrocarbon. In certain embodiments, the carbocyclylene contains 4-10, 5-8, or 5-6 carbons, referred to herein, e.g., as "$C_5$-$C_6$ carbocyclylene".

The term "aryl" is art-recognized and refers to a carbocyclic aromatic group. Representative aryl groups include phenyl, naphthyl, anthracenyl, and the like. Unless specified otherwise, the aromatic ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, aryl or heteroaryl moieties, —CF$_3$, —CN, or the like. The term "aryl" also includes polycyclic aromatic ring systems having two or more carbocyclic rings in which two or more carbons are common to two adjoining rings (the rings are "fused rings") wherein all of the fused rings are aromatic rings, e.g., in a naphthyl group.

The term "phenylene" refers to a multivalent radical (e.g., a divalent or trivalent radical) of benzene. To illustrate, a divalent valent radical of benzene is illustrated by the formula

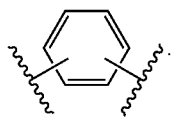

The term "heteroaryl" is art-recognized and refers to aromatic groups that include at least one ring heteroatom. In certain instances, a heteroaryl group contains 1, 2, 3, or 4 ring heteroatoms (e.g., O, N, and S). Representative examples of heteroaryl groups include pyrrolyl, furanyl, thiophenyl, imidazolyl, oxazolyl, thiazolyl, triazolyl, pyrazolyl, pyridinyl, pyrazinyl, pyridazinyl and pyrimidinyl, and the like. Unless specified otherwise, the heteroaryl ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, aryl or heteroaryl moieties, —CF$_3$, —CN, or the like. The term "heteroaryl" also includes polycyclic aromatic ring systems having two or more rings in which two or more ring atoms are common to two adjoining rings (the rings are "fused rings") wherein all of the fused rings are heteroaromatic, e.g., in a naphthyridinyl group. In certain embodiments, the heteroaryl is a 5-6 membered monocyclic ring or a 9-10 membered bicyclic ring.

The term "heteroarylene" refers to a multi-valent (e.g., di-valent or trivalent) aromatic group that comprises at least one ring heteroatom. An exemplary "heteroarylene" is pyridinylene, which is a multi-valent radical of pyridine. For example, a divalent radical of pyridine is illustrated by the formula

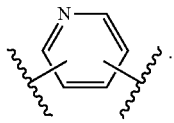

In certain embodiments, the "heteroarylene" is a divalent, 5-6 membered heteroaromatic group containing 1, 2, or 3 ring heteroatoms (e.g., O, N, or S).

The terms ortho, meta, and para are art-recognized and refer to 1,2-, 1,3- and 1,4-disubstituted benzenes, respectively. For example, the names 1,2-dimethylbenzene and ortho-dimethylbenzene are synonymous.

As used herein, the terms "heterocyclic" and "heterocyclyl" represent, for example, an aromatic or nonaromatic ring (e.g., a monocyclic or bicyclic ring) containing one or more heteroatoms. The heteroatoms can be the same or different from each other. Examples of heteroatoms include, but are not limited to nitrogen, oxygen and sulfur. Aromatic and nonaromatic heterocyclic rings are well-known in the art. Some nonlimiting examples of aromatic heterocyclic rings include, but are not limited to, pyridine, pyrimidine, indole, purine, quinoline and isoquinoline. Nonlimiting examples of nonaromatic heterocyclic compounds include, but are not limited to, piperidine, piperazine, morpholine, pyrrolidine and pyrazolidine. Examples of oxygen containing heterocyclic rings include, but are not limited to, furan, oxirane, 2H-pyran, 4H-pyran, 2H-chromene, benzofuran, and 2,3-dihydrobenzo[b][1,4]dioxine. Examples of sulfur-containing heterocyclic rings include, but are not limited to, thiophene, benzothiophene, and parathiazine. Examples of nitrogen containing rings include, but are not limited to, pyrrole, pyrrolidine, pyrazole, pyrazolidine, imidazole, imidazoline, imidazolidine, pyridine, piperidine, pyrazine, piperazine, pyrimidine, indole, purine, benzimidazole, quinoline, isoquinoline, triazole, and triazine. Examples of heterocyclic rings containing two different heteroatoms include, but are not limited to, phenothiazine, morpholine, parathiazine, oxazine, oxazole, thiazine, and thiazole. The heterocyclic ring is optionally further substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, aryl or heteroaryl moieties, —CF$_3$, —CN, or the like. In certain embodiments, the heterocyclyl group is a 3-7 membered ring that, unless specified otherwise, is substituted or unsubstituted.

The term "heterocycloalkyl" refers to a saturated heterocyclyl group having, for example, 3-7 ring atoms selected from carbon and heteroatoms (e.g., O, N, or S).

The term "heterocycloalkylene" refers to a multi-valent (e.g., di-valent or trivalent) saturated heterocyclyl group having, for example, 3-7 ring atoms. An exemplary "heterocycloalkylene" is piperidinylene, which is a multi-valent radical of piperidine. In certain embodiments, the "heterocycloalkylene" is a divalent, 5-6 membered saturated heterocyclyl containing 1 or 2 ring heteroatoms (e.g., O, N, or S).

The phrase "5-6 membered heterocyclic group containing at least one unsaturated carbon atom in the ring" refers to a 5-6 membered heterocyclic group containing at least one ring carbon atom where said carbon atom has a double bond to another atom, such as another atom in the heterocyclic ring or to an exocyclic oxygen atom such that the ring carbon atom is part of a C=O group. Exemplary 5-6 membered heterocyclic groups containing at least one unsaturated carbon atom in the ring include, for example:

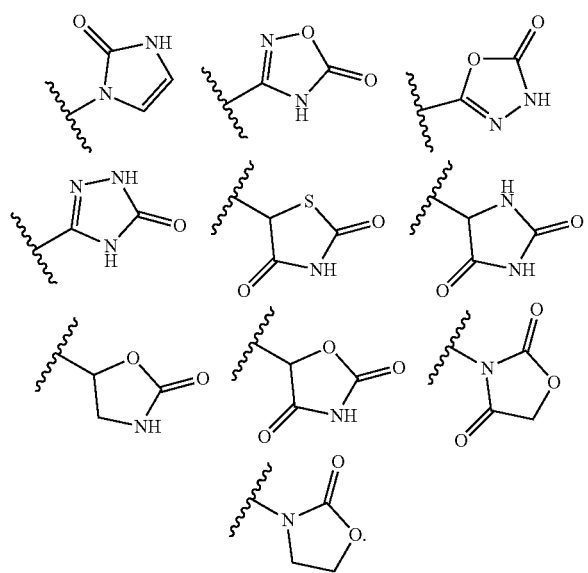

The terms "amine" and "amino" are art-recognized and refer to both unsubstituted and substituted amines, e.g., a moiety that may be represented by the general formulas:

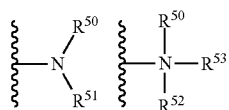

wherein $R^{50}$, $R^{51}$, $R^{52}$ and $R^{53}$ each independently represent a hydrogen, an alkyl, an alkenyl, —$(CH_2)_m$—$R^{61}$, or $R^{50}$ and $R^{51}$, taken together with the N atom to which they are attached complete a heterocycle having from 4 to 8 atoms in the ring structure; $R^{61}$ represents an aryl, a cycloalkyl, a cycloalkenyl, a heterocycle or a polycycle; and m is zero or an integer in the range of 1 to 8. In certain embodiments, only one of $R^{50}$ or $R^{51}$ may be a carbonyl, e.g., $R^{50}$, $R^{51}$ and the nitrogen together do not form an imide. In other embodiments, $R^{50}$ and $R^{51}$ (and optionally $R^{52}$) each independently represent a hydrogen, an alkyl, an alkenyl, or —$(CH_2)_m$—$R^{61}$.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O— alkenyl, —O-alkynyl, and —O—$(CH_2)_m$—$R^{61}$, where m and $R^{61}$ are described above.

The term "oxo" is art-recognized and refers to a "═O" substituent. For example, a cyclopentane substituted with an oxo group is cyclopentanone.

The symbol ⌇ indicates a point of attachment.

The term "substituted" means that one or more hydrogens on the atoms of the designated group are replaced with a selection from the indicated group, provided that the atoms' normal valencies under the existing circumstances are not exceeded, and that the substitution results in a stable compound. Combinations of substituents and/or variables are permissible only if such combinations result in stable compounds. The terms "stable compound" or "stable structure" refer to a compound that is sufficiently robust to survive isolation to a useful degree of purity from a reaction mixture, and formulation into an efficacious therapeutic agent.

When any substituent or variable occurs more than one time in any constituent or the compound of the invention, its definition on each occurrence is independent of its definition at every other occurrence, unless otherwise indicated.

It should also be noted that any carbon as well as heteroatom with unsatisfied valences in the text, schemes, examples and tables herein is assumed to have the sufficient number of hydrogen atom(s) to satisfy the valences.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

Certain compounds contained in compositions of the present invention may exist in particular geometric or stereoisomeric forms. Further, certain compounds described herein may be optically active. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. The compounds may contain one or more stereogenic centers. For example, asymmetric carbon atoms may be present in a substituent such as an alkyl group. All such isomers, as well as mixtures thereof, are intended to be included in this invention, such as, for example, racemic mixtures, single enantiomers, diastereomeric mixtures and individual diastereomers. Additional asymmetric centers may be present depending upon the nature of the various substituents on the molecule. Each such asymmetric center will independently produce two optical isomers, and it is intended that all of the possible optical isomers, diastereomers in mixtures, and pure or partially purified compounds are included within the ambit of this invention.

Diastereomeric mixtures can be separated into their individual diastereomers on the basis of their physical chemical differences by methods known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Alternatively, a particular enantiomer of a compound of the present invention may be prepared by asymmetric synthesis. Still further, where the molecule contains a basic functional group (such as amino) or an acidic functional group (such as carboxylic acid) diastereomeric salts are formed with an appropriate optically-active acid or base, followed by resolution of the diastereomers thus formed by fractional crystallization or chromatographic means known in the art, and subsequent recovery of the pure enantiomers.

Individual stereoisomers of the compounds of the invention may, for example, be substantially free of other isomers, or may be admixed, for example, as racemates or with all other, or other selected, stereoisomers. Chiral center(s) in a compound of the present invention can have the S or R configuration as defined by the IUPAC 1974 Recommendations. Further, to the extent a compound described herein may exist as a atropisomer (e.g., substituted biaryls), all forms of such atropisomer are considered part of this invention.

As used herein, the terms "subject" and "patient" are used interchangeable and refer to organisms to be treated by the methods of the present invention. Such organisms preferably include, but are not limited to, mammals (e.g., murines, simians, equines, bovines, porcines, canines, felines, and the like), and most preferably includes humans.

The term "$EC_{50}$" is art-recognized and refers to the concentration of a compound that is required to achieve 50% of the maximum possible activation of the target.

As used herein, the term "effective amount" refers to the amount of a compound sufficient to effect beneficial or desired results (e.g., a therapeutic, ameliorative, inhibitory or preventative result). An effective amount can be administered in one or more administrations, applications or dosages and is not intended to be limited to a particular formulation or administration route. As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants, see e.g., Martin, Remington's Pharmaceutical Sciences, 15th Ed., Mack Publ. Co., Easton, Pa. [1975].

As used herein, the term "pharmaceutically acceptable salt" refers to any pharmaceutically acceptable salt (e.g., acid or base) of a compound of the present invention which, upon administration to a subject, is capable of providing a compound of this invention or an active metabolite or residue thereof. As is known to those of skill in the art, "salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate (also known as toluenesulfonate), undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like. Further examples of salts include, but are not limited to: ascorbate, borate, nitrate, phosphate, salicylate, and sulfate. Further, acids which are generally considered suitable for the formation of pharmaceutically useful salts from basic pharmaceutical compounds are discussed, for example, by P. Stahl et al., Camille G. (eds.) Handbook of Pharmaceutical Salts. Properties, Selection and Use. (2002) Zurich: Wiley-VCH; S. Berge et al., Journal of Pharmaceutical Sciences (1977) 6) 1-19; P. Gould, International J. of Pharmaceutics (1986) 33 201-217; Anderson et al., The Practice of Medicinal Chemistry (1996), Academic Press, New York; and in The Orange Book (Food & Drug Administration, Washington, D.C. on their website). These disclosures are incorporated herein by reference.

Additional exemplary basic salts include, but are not limited to: ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

In addition, when a compound of the invention contains both a basic moiety (such as, but not limited to, a pyridine or imidazole) and an acidic moiety (such as, but not limited to, a carboxylic acid) zwitterions ("inner salts") may be formed. Such acidic and basic salts used within the scope of the invention are pharmaceutically acceptable (i.e., non-toxic, physiologically acceptable) salts. Such salts of the compounds of the invention may be formed, for example, by reacting a compound of the invention with an amount of acid or base, such as an equivalent amount, in a medium such as one in which the salt precipitates or in an aqueous medium followed by lyophilization.

The present invention includes the compounds of the invention in all their isolated forms (such as any solvates, hydrates, stereoisomers, and tautomers thereof). Further, the invention includes compounds in which one or more of the atoms may be artificially enriched in a particular isotope having the same atomic number, but an atomic mass or mass number different from the atomic mass or mass number predominantly found in nature. The present invention is meant to include all suitable isotopic variations of the compounds of the invention. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds can be prepared without undue experimentation by conventional techniques known to those skilled in the art or by processes analogous to those described in the Schemes and Examples herein using appropriate isotopically-enriched reagents and/or intermediates.

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

The terms "a" and "an" as used herein mean "one or more" and include the plural unless the context is inappropriate.

The abbreviation "THF" is art-recognized and refers to tetrahydrofuran. The abbreviation "DCM" is art-recognized and refers to dichloromethane. The abbreviation "DMF" is art-recognized and refers to dimethylformamide. The abbreviation "DMA" is art-recognized and refers to dimethylacetamide. The abbreviation "EDTA" is art-recognized and refers to ethylenediaminetetraacetic acid. The abbreviation "TFA" is art-recognized and refers to trifluoroacetic acid. The abbreviation "Ts" is art-recognized and refers to tosylate. The abbreviation "TBS" is art-recognized and refers to tert-butyldimethylsilyl. The abbreviation "DMSO" is art-recognized and refers to dimethylsulfoxide. The abbreviation "Tf" is art-recognized and refers to triflate, or trifluoromethylsulfonate. The abbreviation "Pin" is art-recognized and refers to pinacolato.

As a general matter, compositions specifying a percentage are by weight unless otherwise specified.

I. Aryl Dihydro-2H-Benzo[b][1,4]Oxazine Sulfonamide and Related Compounds

The invention provides aryl dihydro-2H-benzo[b][1,4] oxazine sulfonamide and related compounds. Exemplary compounds are described in the following sections, along with exemplary procedures for making the compounds. Additional exemplary compounds and synthetic procedures are described in the Examples.

One aspect of the invention provides a compound represented by Formula I:

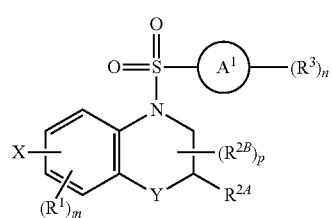

(I)

or a pharmaceutically acceptable salt thereof; wherein:

$A^1$ is phenylene, 5-6 membered heteroarylene, or 3-6 membered heterocycloalkylene;

X is phenyl or 5-10 membered heteroaryl, each of which is optionally substituted by 1, 2, 3, or 4 substituents independently selected from the group consisting of $C_{1-6}$ alkyl, $C_{3-6}$ cycloalkyl, halogen, $C_{1-6}$ haloalkyl, hydroxyl, $C_{1-6}$ alkoxy, $C_{1-6}$ haloalkoxy, —O—$C_{3-6}$ cycloalkyl, —O—($C_{1-6}$ alkylene)-OH, cyano, —N($R^4$)($R^5$), —S(O)$_2$—$R^6$, and $C_{6-10}$ aryl;

$R^1$ represents independently for each occurrence halogen, $C_{1-6}$ alkyl, $C_{1-6}$ haloalkyl, or $C_{3-6}$ cycloalkyl;

$R^{2A}$ is one of the following:
(i) —($C_{1-6}$ alkylene)-$A^2$, —($C_{3-6}$ cycloalkylene)-$A^2$, -(2-6 membered heteroalkylene)-$A^2$, —($C_{1-3}$ alkylene)-($C_{3-6}$ cycloalkylene)-($C_{0-3}$ alkylene)-$A^2$, —($C_{1-3}$ alkylene)-(3-6 membered heterocycloalkylene)-($C_{0-3}$ alkylene)-$A^2$, $C_{2-6}$ hydroxyalkyl, or —CO$_2R^4$; where
$A^2$ is —CO$_2R^4$, —C(O)-$A^3$, —C(O)$R^6$, —C(O)N($R^4$)($R^5$), —C(O)N($R^4$)—($C_{1-4}$ alkylene)-CO$_2R^4$, —C(O)N($R^4$)SO$_2R^4$, —C(O)N($R^4$)SO$_2A^3$, —C(O)N($R^4$)—($C_{1-6}$ alkylene)-N($R^7$)C(O)$R^6$, —C(O)N($R^4$)—($C_{1-6}$ alkylene)-SO$_2$N($R^7$)$_2$, —C(O)N($R^4$)—($C_{1-6}$ alkylene)-CN, —C(O)N($R^4$)—($C_{1-6}$ alkylene)-OC(O)$R^6$, —N($R^4$)C(O)$R^7$, —N($R^4$)C(O)$A^3$, —N($R^4$)C(O)—($C_{1-6}$ alkylene)-CO$_2R^4$, —N($R^4$)C(O)—($C_{1-6}$ alkylene)-N($R^7$)C(O)$R^6$, —N($R^4$)C(O)—($C_{1-6}$ alkylene)-SO$_2$N($R^7$)$_2$, —N($R^4$)C(O)—($C_{1-6}$ alkylene)-CN, —N($R^4$)C(O)—($C_{1-6}$ alkylene)-OC(O)$R^6$, —N($R^4$)C(O)N($R^4$)—($C_{1-6}$ alkylene)-CO$_2R^4$, —N($R^4$)C(O)N($R^7$)$_2$, —N($R^4$)CO$_2R^6$, —N($R^4$)S(O)$_2R^7$, —N($R^4$)S(O)$_2$N($R^4$)($R^5$), —N($R^4$)$R^5$), hydroxyl, or -$A^3$;

$A^3$ is aryl, $C_{3-6}$ cycloalkyl, or a 5-8 membered heterocyclic group, each of which is optionally substituted with 1, 2, or 3 substituents independently selected from the group consisting of $C_{1-6}$ alkyl, $C_{1-6}$ haloalkyl, $C_{3-6}$ cycloalkyl, halogen, $C_{1-6}$ alkoxy, $C_{1-6}$ haloalkoxy, oxo, —C(O)$R^6$, —CO$_2R^7$, —C(O)(N$^4$)($R^5$), —N($R^4$)C(O)($R^6$), and —N($R^4$)($R^3$); and any alkylene, cycloalkylene, or heteroalkylene within the definition of $R^{2A}$ is optionally substituted by 1, 2, or 3 substitutents independently selected from the group consisting of hydroxyl and $C_{1-6}$ alkoxy; or (ii) —OH, —N($R^4$)C(O)$R^6$, —N($R^4$)CO$_2R^6$, or —N($R^4$)C(O)N($R^7$)$_2$;

$R^{2B}$ represents independently for each occurrence $C_{1-6}$ alkyl or $C_{1-3}$ haloalkyl;

$R^3$ represents independently for each occurrence hydrogen, $C_{1-6}$ haloalkyl, halogen, hydroxyl, $C_{1-6}$ alkyl, $C_{3-6}$ cycloalkyl, $C_{1-6}$ alkoxy, $C_{1-6}$ haloalkoxy, —O—($C_{1-6}$ alkylene)-OH, or —O—($C_{1-6}$ alkylene)-CO$_2R^4$; or two vicinal occurrences of $R^3$ are taken together with intervening atoms to form a 4-6 membered ring optionally substituted with 1, 2, or 3 substituents independently selected from the group consisting of $C_{1-6}$ alkyl, $C_{1-6}$ haloalkyl, $C_{3-6}$ cycloalkyl, halogen, $C_{1-6}$ alkoxy, $C_{1-6}$ haloalkoxy, —C(O)$R^6$, and —CO$_2R^7$;

$R^4$ and $R^5$ each represent independently for each occurrence hydrogen, $C_{1-6}$ alkyl, $C_{1-6}$ haloalkyl, $C_{1-6}$ hydroxylalkyl, or $C_{3-6}$ cycloalkyl; or an occurrence of $R^4$ and $R^5$ attached to the same nitrogen atom are taken together with the nitrogen atom to which they are attached to form a 3-7 membered heterocyclic ring;

$R^6$ represents independently for each occurrence $C_{1-6}$ alkyl, $C_{3-6}$ cycloalkyl, or aralkyl;

R$^7$ represents independently for each occurrence hydrogen, $C_{1-6}$ alkyl, $C_{1-6}$ hydroxyalkyl, $C_{1-6}$ haloalkyl, $C_{1-6}$ hydroxyhaloalkyl, $C_{3-6}$ cycloalkyl, $C_{3-6}$ hydroxycycloalkyl, —($C_{1-6}$ alkylene)-($C_{3-6}$ cycloalkyl), —($C_{1-6}$ alkylene)-($C_{2-4}$ alkenyl), or aralkyl;

R$^8$ and R$^9$ each represent independently for each occurrence hydrogen, halogen, or $C_{1-6}$ alkyl, or R$^8$ and R$^9$ are taken together with the carbon atom to which they are attached to form a 3-6 membered carbocyclic ring; or R$^8$ and R$^{2B}$ may taken together to form a bond when R$^{2B}$ is attached to the same carbon atom as R$^{2A}$;

Y is —O—, —C(O)—, —S(O)$_p$—, or —C(R$^8$)(R$^9$)—.

m and p each represent independently for each occurrence 0, 1, or 2; and n is 1, 2, or 3.

In certain embodiments, the compound is a compound of Formula I.

In certain embodiments, A$^1$ is phenylene or 5-6 membered heteroarylene. In certain embodiments, A$^1$ is phenylene. In certain embodiments, A$^1$ is phenylene, and one occurrence of R$^3$ is attached at the meta-position on the phenyl group. In certain embodiments, A$^1$ is a 5-6 membered heteroarylene. In certain embodiments, A$^1$ is

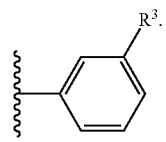

In certain embodiments, Y is —O—. In certain embodiments, Y is —O—, and X is attached at the 6-position of the 3,4-dihydro-2H-benzo[b][1,4]oxazinyl ring. In certain embodiments, Y is —C(R$^8$)(R$^9$)—. In certain embodiments, R$^8$ and R$^9$ are independently hydrogen or methyl. In certain embodiments, Y is —C(R$^8$)(R$^9$)—, R$^8$ and R$^9$ are independently hydrogen or methyl, and X is attached at the 7-position of the 1,2,3,4-tetrahydroquinolinyl ring.

In certain embodiments, X is phenyl substituted by 1, 2, 3, or 4 substituents independently selected from the group consisting of $C_{1-6}$ alkyl, $C_{3-6}$ cycloalkyl, halogen, $C_{1-6}$ haloalkyl, hydroxyl, $C_{1-6}$ alkoxy, $C_{1-6}$ haloalkoxy, —O—$C_{3-6}$ cycloalkyl, and —O—($C_{1-6}$ alkylene)-OH. In certain embodiments, X is phenyl substituted by 1, 2, or 3 substituents independently selected from the group consisting of $C_{1-6}$ alkyl, $C_{3-6}$ cycloalkyl, halogen, $C_{1-6}$ haloalkyl, hydroxyl, $C_{1-6}$ alkoxy, $C_{1-6}$ haloalkoxy, —O—$C_{3-6}$ cycloalkyl, and —O—($C_{1-6}$ alkylene)-OH. In certain embodiments, X is phenyl substituted by 1, 2, or 3 substituents independently selected from the group consisting of $C_{1-6}$ alkyl, $C_{3-6}$ cycloalkyl, halogen, $C_{1-6}$ haloalkyl, hydroxyl, $C_{1-6}$ alkoxy, and $C_{1-6}$ haloalkoxy. In certain embodiments, X is phenyl substituted by 1, 2, or 3 substituents independently selected from the group consisting of $C_{1-6}$ alkyl, cyclopropyl, halogen, $C_{1-3}$ haloalkyl, hydroxyl, $C_{1-3}$ alkoxy, and $C_{1-3}$ haloalkoxy. In certain embodiments, X is phenyl substituted by 1 or 2 substituents independently selected from the group consisting of $C_{1-6}$ alkyl, cyclopropyl, chloro, fluoro, $C_{1-3}$ haloalkyl, hydroxyl, $C_{1-3}$ alkoxy, and $C_{1-3}$ haloalkoxy.

In certain embodiments, X is phenyl or 5-10 membered heteroaryl, each of which is optionally substituted by 1, 2, or 3 substituents independently selected from the group consisting of $C_{1-6}$ alkyl, $C_{3-6}$ cycloalkyl, halogen, $C_{1-6}$ haloalkyl, hydroxyl, $C_{1-6}$ alkoxy, $C_{1-6}$ haloalkoxy, —O—$C_{3-6}$ cycloalkyl, —O—($C_{1-6}$ alkylene)-OH, cyano, —N(R$^4$)(R$^5$), and $C_{6-10}$ aryl. In certain embodiments, X is a 5-6 membered heteroaryl optionally substituted by 1, 2, or 3 substituents independently selected from the group consisting of $C_{1-6}$ alkyl, $C_{3-6}$ cycloalkyl, halogen, $C_{1-6}$ haloalkyl, hydroxyl, $C_{1-6}$ alkoxy, $C_{1-6}$ haloalkoxy, —O—$C_{3-6}$ cycloalkyl, —O—($C_{1-6}$ alkylene)-OH, cyano, —N(R$^4$)(R$^5$), and $C_{6-10}$ aryl. In certain embodiments, X is a 6-membered heteroaryl substituted by 1, 2, or 3 substituents independently selected from the group consisting of $C_{1-6}$ alkyl, $C_{3-6}$cycloalkyl, halogen, $C_{1-6}$ haloalkyl, hydroxyl, $C_{1-6}$ alkoxy, and $C_{1-6}$ haloalkoxy. In certain embodiments, X is pyridinyl, pyrimidinyl, pyrazolyl, imidazolyl, triazolyl, thiazolyl, oxazolyl, or thiadiazolyl, each of which is optionally substituted by 1, 2, or 3 substituents independently selected from the group consisting of $C_{1-6}$ alkyl, $C_{3-6}$ cycloalkyl, halogen, $C_{1-6}$ haloalkyl, hydroxyl, $C_{1-6}$alkoxy, and $C_{1-6}$ haloalkoxy.

In certain embodiments, X is pyridinyl optionally substituted by 1, 2, or 3 substituents independently selected from the group consisting of $C_{1-6}$ alkyl, $C_{3-6}$ cycloalkyl, halogen, $C_{1-6}$ haloalkyl, hydroxyl, $C_{1-6}$ alkoxy, and $C_{1-6}$ haloalkoxy. In certain embodiments, X is pyridinyl optionally substituted by 1 or 2 substituents independently selected from the group consisting of $C_{1-6}$alkyl, cyclopropyl, chloro, fluoro, $C_{1-6}$ haloalkyl, $C_{1-6}$ alkoxy, and $C_{1-6}$ haloalkoxy.

In certain embodiments, R$^1$ is halogen. In certain embodiments, R$^1$ is chloro or fluoro. In certain embodiments, R$^1$ represents independently for each occurrence halogen, $C_{1-6}$ alkyl, or $C_{1-6}$ haloalkyl. In certain embodiments, R$^1$ is halogen, and m is 1.

In certain embodiments, m is 1. In certain embodiments, m is 0.

In certain embodiments, R$^{2A}$ is —($C_{1-6}$alkylene)-A$^2$. In certain embodiments, R$^{2A}$ is —($C_{2-3}$ alkylene)-A$^2$. In certain embodiments, R$^{2A}$ is -(2-6 membered heteroalkylene)-A$^2$. In certain embodiments, R$^{2A}$ is —CO$_2$R$^4$. In certain embodiments, R$^{2A}$ is —($C_{2-3}$ alkylene)-O-A$^2$. In certain embodiments, R$^{2A}$ is $C_{2-6}$ hydroxyalkyl.

In certain embodiments, A$^2$ is —CO$_2$R$^4$. In certain embodiments, A$^2$ is —CO$_2$H. In certain embodiments, A$^2$ is —C(O)-A$^3$. In certain embodiments, R$^{2A}$ is —($C_{1-6}$alkylene)-A$^2$, and A$^2$ is —CO$_2$R$^4$. In certain embodiments, R$^{2A}$ is —($C_{1-6}$ alkylene)-A$^2$, and A$^2$ is —C(O)-A$^3$.

In certain embodiments, R$^{2A}$ is —($C_{1-6}$alkylene)-A$^2$, and A$^2$ is —C(O)N(R$^4$)—($C_{1-4}$ alkylene)-CO$_2$R$^4$, —C(O)N(R$^4$)SO$_2$R$^4$, or —C(O)N(R$^4$)SO$_2$A$^3$. In certain embodiments, R$^{2A}$ is —($C_{1-6}$ alkylene)-A$^2$, and A$^2$ is —C(O)N(R$^4$)—($C_{1-6}$ alkylene)-N(R$^7$)C(O)R$^6$, —C(O)N(R$^4$)—($C_{1-6}$ alkylene)-SO$_2$N(R$^7$)$_2$, —C(O)N(R$^4$)—($C_{1-6}$ alkylene)-CN, or —C(O)N(R$^4$)—($C_{1-6}$ alkylene)-OC(O)R$^6$. In certain embodiments, R$^{2A}$ is —($C_{1-6}$alkylene)-A$^2$, and A$^2$ is —N(R$^4$)C(O)R$^7$, —N(R$^4$)C(O)A$^3$, —N(R$^4$)C(O)—($C_{1-6}$alkylene)-CO$_2$R$^4$, —N(R$^4$)C(O)—($C_{1-6}$ alkylene)-N(R$^7$)C(O)R$^6$, —N(R$^4$)C(O)—($C_{1-6}$ alkylene)-SO$_2$N(R$^7$)$_2$, —N(R$^4$)C(O)—($C_{1-6}$ alkylene)-CN, —N(R$^4$)C(O)—($C_{1-6}$ alkylene)-OC(O)R$^6$, or —N(R$^4$)C(O)N(R$^4$)—($C_{1-6}$ alkylene)-CO$_2$R$^4$. In certain embodiments, R$^{2A}$ is —($C_{1-6}$ alkylene)-A$^2$, and A$^2$ is —N(R$^4$)C(O)N(R$^7$)$_2$, —N(R$^4$)CO$_2$R$^6$, —N(R$^4$)S(O)$_2$R$^7$, or —N(R$^4$)S(O)$_2$N(R$^4$)(R$^5$). In certain embodiments, R$^{2A}$ is —($C_{1-6}$ alkylene)-A$^2$, and A$^2$ is —N(R$^4$R$^5$) or hydroxyl. In certain embodiments, R$^{2A}$ is —($C_{1-6}$alkylene)-A$^2$, and A$^2$ is A$^3$.

In certain embodiments, A$^3$ comprises at least two ring nitrogen atoms. In certain embodiments, A$^3$ comprises at least two ring nitrogen atoms, and at least one ring oxygen atom.

In certain embodiments, A$^3$ is a 5-6 membered heterocyclic group optionally substituted with 1, 2, or 3 substituents independently selected from the group consisting of $C_{1-6}$ alkyl, $C_{1-6}$haloalkyl, halogen, $C_{1-6}$ alkoxy, oxo, —C(O)R$^6$, and —CO$_2$R$^7$. In certain embodiments, A$^3$ is a 5-6 membered saturated heterocyclic group optionally substituted by 1 or 2 substituents independently selected from the group consisting of $C_{1-6}$ alkyl, $C_{1-6}$ haloalkyl, $C_{3-6}$ cycloalkyl, halogen, $C_{1-6}$ alkoxy, $C_{1-6}$ haloalkoxy, oxo, —C(O)R$^6$, —CO$_2$R$^7$, —C(O)(N$^4$)(R$^5$), —N(R$^4$)C(O)(R$^6$), and —N(R$^4$)(R$^5$). In certain embodiments, A$^3$ is a 5-6 membered heterocyclic group containing at least one ring carbon atom substituted by oxo and the heterocyclic group being optionally substituted by 1 or 2 substituents independently selected from the group consisting of $C_{1-6}$ alkyl, $C_{1-6}$ haloalkyl, $C_{3-6}$ cycloalkyl, halogen, $C_{1-6}$ alkoxy, $C_{1-6}$ haloalkoxy, oxo, —C(O)R$^6$, —CO$_2$R$^7$, —C(O)(N$^4$)(R$^5$), —N(R$^4$)C(O)(R$^6$), and —N(R$^4$)(R$^5$). In certain embodiments, A$^3$ is a 5-6 membered heterocyclic group containing (i) at least one ring carbon atom substituted by oxo and (ii) at least one double bond between two ring atoms, and the heterocyclic group being optionally substituted by 1 or 2 substituents independently selected from the group consisting of $C_{1-6}$ alkyl, $C_{1-6}$ haloalkyl, $C_{3-6}$ cycloalkyl, halogen, $C_{1-6}$ alkoxy, $C_{1-6}$ haloalkoxy, oxo, —C(O)R$^6$, —CO$_2$R$^7$, —C(O)(N$^4$)(R$^5$), —N(R$^4$)C(O)(R$^6$), and —N(R$^4$)(R$^5$). In certain embodiments, A$^3$ is a 5-6 membered saturated heterocyclic group optionally substituted by 1 or 2 substituents independently selected from the group consisting of methyl, ethyl, isopropyl, trifluoromethyl, cyclopropyl, $C_{1-6}$ alkoxy, oxo, and —CO$_2$R$^7$.

In certain embodiments, A$^3$ is a 5-membered heterocyclic group. In certain embodiments, A$^3$ is a 5-6 membered heteroaromatic group comprising at least two ring nitrogen atoms, at least one unsaturated carbon atom in the ring, and the heteroaromatic group being optionally substituted by 1 or 2 substituents independently selected from the group consisting of $C_{1-6}$ alkyl, $C_{1-6}$ haloalkyl, $C_{3-6}$ cycloalkyl, halogen, $C_{1-6}$ alkoxy, $C_{1-6}$ haloalkoxy, —C(O)R$^6$, —CO$_2$R$^7$, —C(O)(N$^4$)(R$^5$), —N(R$^4$)C(O)(R$^6$), and —N(R$^4$)(R$^5$).

In certain embodiments, A$^3$ is imidazolyl; pyrazolyl; 1,2,3-triazolyl; tetrazolyl; 1,2,4-oxadiazol-5(4H)-onyl; 1,3,4-oxadiazol-2(3H)-onyl; 1,3-dihydro-2H-imidazol-2-onyl; or 2,4-dihydro-3H-1,2,4-triazol-3-onyl; each of which is optionally substituted by 1, 2, or 3 substituents independently selected from the group consisting of $C_{1-6}$ alkyl, $C_{1-6}$ haloalkyl, $C_{3-6}$ cycloalkyl, halogen, $C_{1-6}$ alkoxy, $C_{1-6}$ haloalkoxy, oxo, —C(O)R$^6$, —CO$_2$R$^7$, —C(O)(N$^4$)(R$^5$), —N(R$^4$)C(O)(R$^6$), and —N(R$^4$)(R$^5$).

In certain embodiments, A$^3$ is one of the following:

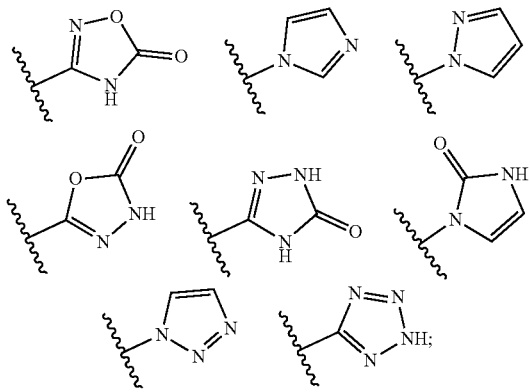

each of which is optionally substituted by 1, 2, or 3 substituents independently selected from the group consisting $C_{1-6}$ alkyl, $C_{1-6}$ haloalkyl, $C_{3-6}$ cycloalkyl, halogen, $C_{1-6}$ alkoxy, $C_{1-6}$ haloalkoxy, oxo, —C(O)R$^6$, —CO$_2$R$^7$, —C(O)(N$^4$)(R$^5$), —N(R$^4$)C(O)(R$^6$), and —N(R$^4$)(R$^5$).

In certain embodiments, A$^3$ is one of the following:

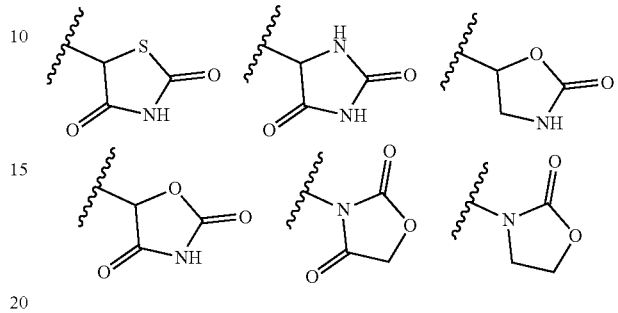

each of which is optionally substituted by 1, 2, or 3 substituents independently selected from the group consisting of $C_{1-6}$ alkyl, $C_{1-6}$ haloalkyl, $C_{3-6}$ cycloalkyl, halogen, $C_{1-6}$ alkoxy, $C_{1-6}$ haloalkoxy, oxo, —C(O)R$^6$, —CO$_2$R$^7$, —C(O)(N$^4$)(R$^3$), —N(R$^4$)C(O)(R$^6$), and —N(R$^4$)(R$^5$).

In certain embodiments, R$^2$ is methyl.

In certain embodiments, R$^3$ represents independently for each occurrence $C_{1-6}$ haloalkyl, halogen, $C_{1-6}$alkyl, $C_{1-6}$ alkoxy, or —O—($C_{1-6}$alkylene)-OH. In certain embodiments, R$^3$ is trifluoromethyl, fluoro, chloro, or methoxy. In certain embodiments, R$^3$ is trifluoromethyl.

In certain embodiments, R$^4$ and R$^5$ each represent independently for each occurrence hydrogen or $C_{1-6}$ alkyl. In certain embodiments, R$^4$ is hydrogen. In certain embodiments, R$^5$ is hydrogen.

In certain embodiments, R$^6$ represents independently for each occurrence $C_{1-6}$ alkyl or $C_{3-6}$ cycloalkyl. In certain embodiments, R$^6$ is $C_{1-6}$ alkyl.

In certain embodiments, R$^7$ represents independently for each occurrence hydrogen, $C_{1-6}$ alkyl, or $C_{1-6}$ hydroxyalkyl. In certain embodiments, R$^7$ is hydrogen. In certain embodiments, R$^7$ is $C_{1-6}$ alkyl.

In certain embodiments, p is 0. In certain embodiments, p is 1.

In certain embodiments, -A$^1$-(R$^3$)$_n$ is

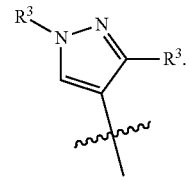

In certain embodiments, -A$^1$-(R$^3$)$_n$ is one of the following:

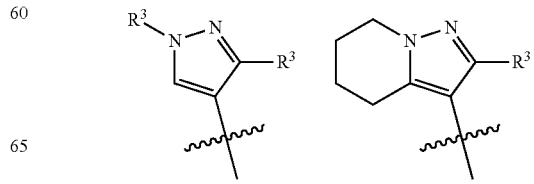

-continued

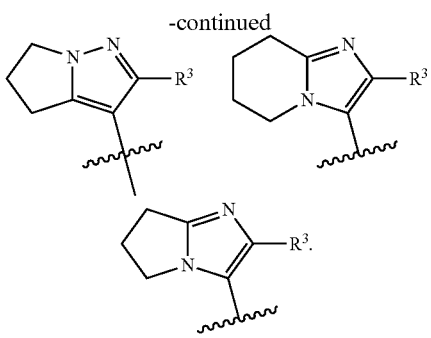

The definitions of variables in Formula I above encompass multiple chemical groups. The application contemplates embodiments where, for example, i) the definition of a variable is a single chemical group selected from those chemical groups set forth above, ii) the definition of a variable is a collection of two or more of the chemical groups selected from those set forth above, and iii) the compound is defined by a combination of variables in which the variables are defined by (i) or (ii), e.g., such as where A is phenylene and $R^3$ is selected from the group consisting of $C_{1-6}$ haloalkyl, halogen, hydroxyl, and $C_{1-6}$ alkyl.

Another aspect of the invention provides a compound represented by Formula I-1:

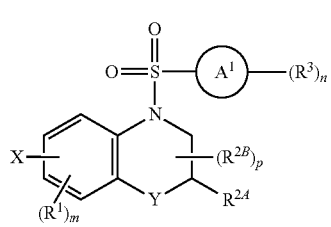

(I-1)

or a pharmaceutically acceptable salt thereof; wherein:
$A^1$ is phenylene, 5-6 membered heteroarylene, or 3-6 membered heterocycloalkylene; X is phenyl or 5-10 membered heteroaryl, each of which is optionally substituted by 1, 2, or 3 substituents independently selected from the group consisting of $C_{1-6}$ alkyl, $C_{3-6}$ cycloalkyl, halogen, $C_{1-6}$ haloalkyl, hydroxyl, $C_{1-6}$ alkoxy, $C_{1-6}$ haloalkoxy, —O—$C_{3-6}$ cycloalkyl, —O—($C_{1-6}$ alkylene)-OH, cyano, —N($R^4$)($R^5$), and $C_{6-10}$ aryl;

$R^1$ represents independently for each occurrence halogen, $C_{1-6}$ alkyl, $C_{1-6}$ haloalkyl, or $C_{3-6}$ cycloalkyl;

$R^{2A}$ is one of the following:
(i) —($C_{1-6}$ alkylene)-$A^2$, —($C_{3-6}$ cycloalkylene)-$A^2$, -(2-6 membered heteroalkylene)-$A^2$, —($C_{1-3}$ alkylene)-($C_{3-6}$ cycloalkylene)-($C_{0-3}$ alkylene)-$A^2$, or —$CO_2R^4$;
where $A^2$ is —$CO_2R^4$, —C(O)-$A^3$, —C(O)$R^6$, —C(O)N($R^4$)($R^3$), —C(O)N($R^4$)—($C_{1-4}$ alkylene)-$CO_2R^4$, —C(O)N($R^4$)$SO_2R^4$, —C(O)N($R^4$)$SO_2A^3$, —N($R^4$)C(O)$R^7$, —N($R^4$)C(O)$A^3$, —N($R^4$)C(O)—($C_{1-6}$ alkylene)-$CO_2R^4$, —N($R^4$)C(O)N($R^4$)—($C_{1-6}$ alkylene)-$CO_2R^4$, —N($R^4$)C(O)N($R^7$)$_2$, —N($R^4$)$CO_2R^6$, —N($R^4$)S(O)$_2R^7$, —N($R^4$)S(O)$_2$N($R^4R^5$), hydroxyl, or -$A^3$; and $A^3$ is aryl or a 5-8 membered heterocyclic group, each of which is optionally substituted with 1, 2 or 3 substituents independently selected from the group consisting of $C_{1-6}$ alkyl, $C_{1-6}$ haloalkyl, $C_{3-6}$ cycloalkyl, halogen, $C_{1-6}$ alkoxy, $C_{1-6}$ haloalkoxy, oxo, —C(O)$R^6$, —$CO_2R^7$, —C(O)(N$^4$)($R^5$), —N($R^4$)C(O)($R^6$), and —N($R^4$)($R^3$); or
(ii) —OH, —N($R^4$)C(O)$R^6$, —N($R^4$)$CO_2R^6$, or —N($R^4$)C(O)N($R^7$)$_2$;

$R^{2B}$ represents independently for each occurrence $C_{1-6}$ alkyl or $C_{1-3}$ haloalkyl;

$R^3$ represents independently for each occurrence hydrogen, $C_{1-6}$ haloalkyl, halogen, hydroxyl, $C_{1-6}$ alkyl, $C_{3-6}$ cycloalkyl, $C_{1-6}$ alkoxy, $C_{1-6}$ haloalkoxy, —O—($C_{1-6}$ alkylene)-OH, or —O—($C_{1-6}$ alkylene)-$CO_2R^4$; or two vicinal occurrences of $R^3$ are taken together with intervening atoms to form a 4-6 membered ring optionally substituted with 1, 2, or 3 substituents independently selected from the group consisting of $C_{1-6}$ alkyl, $C_{1-6}$ haloalkyl, $C_{3-6}$ cycloalkyl, halogen, $C_{1-6}$ alkoxy, $C_{1-6}$ haloalkoxy, —C(O)$R^6$, and —$CO_2R^7$;

$R^4$ and $R^5$ each represent independently for each occurrence hydrogen, $C_{1-6}$ alkyl, $C_{1-6}$ haloalkyl, or $C_{3-6}$ cycloalkyl; or an occurrence of $R^4$ and $R^5$ attached to the same nitrogen atom are taken together with the nitrogen atom to which they are attached to form a 3-7 membered heterocyclic ring;

$R^6$ represents independently for each occurrence $C_{1-6}$ alkyl, $C_{3-6}$ cycloalkyl, or aralkyl;

$R^7$ represents independently for each occurrence hydrogen, $C_{1-6}$ alkyl, $C_{1-6}$ hydroxyalkyl, $C_{1-6}$ haloalkyl, $C_{1-6}$ hydroxyhaloalkyl, $C_{3-6}$ cycloalkyl, $C_{3-6}$ hydroxycycloalkyl, or aralkyl;

$R^8$ and $R^9$ each represent independently for each occurrence hydrogen, halogen, or $C_{1-6}$ alkyl, or $R^8$ and $R^9$ are taken together with the carbon atom to which they are attached to form a 3-6 membered carbocyclic ring; or $R^8$ and $R^{2B}$ may taken together to form a bond when $R^{2B}$ is attached to the same carbon atom as $R^{2A}$;

Y is —O—, —C(O)—, —S(O)$_p$—, or —C($R^8$)($R^9$)—.

m and p each represent independently for each occurrence 0, 1, or 2; and n is 1, 2, or 3.

In certain embodiments, the compound is a compound of Formula I-1.

In certain embodiments, $A^1$ is phenylene or 5-6 membered heteroarylene. In certain embodiments, $A^1$ is phenylene. In certain embodiments, A is phenylene, and one occurrence of $R^3$ is attached at the meta-position on the phenyl group. In certain embodiments, $A^1$ is a 5-6 membered heteroarylene. In certain embodiments, $A^1$ is

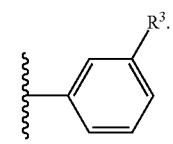

In certain embodiments, Y is —O—. In certain embodiments, Y is —O—, and X is attached at the 6-position of the 3,4-dihydro-2H-benzo[b][1,4]oxazinyl ring. In certain embodiments, Y is —C($R^8$)($R^9$)—. In certain embodiments, $R^8$ and $R^9$ are independently hydrogen or methyl. In certain embodiments, Y is —C($R^8$)($R^9$)—, $R^8$ and $R^9$ are independently hydrogen or methyl, and X is attached at the 7-position of the 1,2,3,4-tetrahydroquinolinyl ring.

In certain embodiments, X is phenyl substituted by 1, 2, or 3 substituents independently selected from the group consisting of $C_{1-6}$ alkyl, $C_{3-6}$ cycloalkyl, halogen, $C_{1-6}$ haloalkyl, hydroxyl, $C_{1-6}$ alkoxy, $C_{1-6}$ haloalkoxy, —O—C$_{3-6}$ cycloalkyl, and —O—(C$_{1-6}$ alkylene)-OH. In certain embodiments, X is phenyl substituted by 1, 2, or 3 substituents independently selected from the group consisting of C$_{1-6}$ alkyl, C$_{3-6}$ cycloalkyl, halogen, C$_{1-6}$ haloalkyl, hydroxyl, C$_{1-6}$ alkoxy, and C$_{1-6}$ haloalkoxy. In certain embodiments, X is phenyl substituted by 1, 2, or 3 substituents independently selected from the group consisting of C$_{1-6}$ alkyl, cyclopropyl, halogen, C$_{1-3}$ haloalkyl, hydroxyl, C$_{1-3}$ alkoxy, and C$_{1-3}$ haloalkoxy. In certain embodiments, X is phenyl substituted by 1 or 2 substituents independently selected from the group consisting of C$_{1-6}$ alkyl, cyclopropyl, chloro, fluoro, C$_{1-3}$ haloalkyl, hydroxyl, C$_{1-3}$ alkoxy, and C$_{1-3}$ haloalkoxy.

In certain embodiments, X is phenyl or 5-10 membered heteroaryl, each of which is optionally substituted by 1, 2, or 3 substituents independently selected from the group consisting of C$_{1-6}$ alkyl, C$_{3-6}$ cycloalkyl, halogen, C$_{1-6}$ haloalkyl, hydroxyl, C$_{1-6}$ alkoxy, C$_{1-6}$ haloalkoxy, —O—C$_{3-6}$ cycloalkyl, —O—(C$_{1-6}$ alkylene)-OH, cyano, —N(R$^4$)(R$^5$), and C$_{6-10}$ aryl. In certain embodiments, X is a 5-6 membered heteroaryl optionally substituted by 1, 2, or 3 substituents independently selected from the group consisting of C$_{1-6}$ alkyl, C$_{3-6}$ cycloalkyl, halogen, C$_{1-6}$ haloalkyl, hydroxyl, C$_{1-6}$ alkoxy, C$_{1-6}$ haloalkoxy, —O—C$_{3-6}$ cycloalkyl, —O—(C$_{1-6}$ alkylene)-OH, cyano, —N(R$^4$)(R$^5$), and C$_{6-10}$ aryl. In certain embodiments, X is a 6-membered heteroaryl substituted by 1, 2, or 3 substituents independently selected from the group consisting of C$_{1-6}$ alkyl, C$_{3-6}$cycloalkyl, halogen, C$_{1-6}$ haloalkyl, hydroxyl, C$_{1-6}$ alkoxy, and C$_{1-6}$ haloalkoxy. In certain embodiments, X is pyridinyl, pyrimidinyl, pyrazolyl, imidazolyl, triazolyl, thiazolyl, oxazolyl, or thiadiazolyl, each of which is optionally substituted by 1, 2, or 3 substituents independently selected from the group consisting of C$_{1-6}$ alkyl, C$_{3-6}$ cycloalkyl, halogen, C$_{1-6}$ haloalkyl, hydroxyl, C$_{1-6}$alkoxy, and C$_{1-6}$ haloalkoxy.

In certain embodiments, X is pyridinyl optionally substituted by 1, 2, or 3 substituents independently selected from the group consisting of C$_{1-6}$ alkyl, C$_{3-6}$ cycloalkyl, halogen, C$_{1-6}$ haloalkyl, hydroxyl, C$_{1-6}$ alkoxy, and C$_{1-6}$ haloalkoxy. In certain embodiments, X is pyridinyl optionally substituted by 1 or 2 substituents independently selected from the group consisting of C$_{1-6}$alkyl, cyclopropyl, chloro, fluoro, C$_{1-6}$ haloalkyl, C$_{1-6}$ alkoxy, and C$_{1-6}$ haloalkoxy.

In certain embodiments, R$^1$ is halogen. In certain embodiments, R$^1$ is chloro or fluoro. In certain embodiments, R$^1$ represents independently for each occurrence halogen, C$_{1-6}$ alkyl, or C$_{1-6}$ haloalkyl. In certain embodiments, R$^1$ is halogen, and m is 1.

In certain embodiments, m is 1. In certain embodiments, m is 0.

In certain embodiments, R$^{2A}$ is —(C$_{1-6}$alkylene)-A$^2$. In certain embodiments, R$^{2A}$ is —(C$_{2-3}$ alkylene)-A$^2$. In certain embodiments, R$^{2A}$ is -(2-6 membered heteroalkylene)-A$^2$. In certain embodiments, R$^{2A}$ is —CO$_2$R$^4$. In certain embodiments, R$^{2A}$ is —(C$_{2-3}$ alkylene)-O-A$^2$.

In certain embodiments, A$^2$ is —CO$_2$R$^4$. In certain embodiments, A$^2$ is —CO$_2$H. In certain embodiments, A$^2$ is —C(O)-A$^3$. In certain embodiments, R$^{2A}$ is —(C$_{1-6}$alkylene)-A$^2$, and A$^2$ is —CO$_2$R$^4$. In certain embodiments, R$^{2A}$ is —(C$_{1-6}$ alkylene)-A$^2$, and A$^2$ is —C(O)-A$^3$.

In certain embodiments, A$^3$ comprises at least two ring nitrogen atoms. In certain embodiments, A$^3$ comprises at least two ring nitrogen atoms, and at least one ring oxygen atom.

In certain embodiments, A$^3$ is a 5-6 membered heterocyclic group optionally substituted with 1, 2, or 3 substituents independently selected from the group consisting of C$_{1-6}$ alkyl, C$_{1-6}$haloalkyl, halogen, C$_{1-6}$ alkoxy, oxo, —C(O)R$^6$, and —CO$_2$R$^7$. In certain embodiments, A$^3$ is a 5-6 membered saturated heterocyclic group optionally substituted by 1 or 2 substituents independently selected from the group consisting of C$_{1-6}$ alkyl, C$_{1-6}$ haloalkyl, C$_{3-6}$ cycloalkyl, halogen, C$_{1-6}$ alkoxy, C$_{1-6}$ haloalkoxy, oxo, —C(O)R$^6$, —CO$_2$R$^7$, —C(O)(N$^4$)(R$^5$), —N(R$^4$)C(O)(R$^6$), and —N(R$^4$)(R$^5$). In certain embodiments, A$^3$ is a 5-6 membered heterocyclic group containing at least one ring carbon atom substituted by oxo and the heterocyclic group being optionally substituted by 1 or 2 substituents independently selected from the group consisting of C$_{1-6}$ alkyl, C$_{1-6}$ haloalkyl, C$_{3-6}$ cycloalkyl, halogen, C$_{1-6}$ alkoxy, C$_{1-6}$ haloalkoxy, oxo, —C(O)R$^6$, —CO$_2$R$^7$, —C(O)(N$^4$)(R$^3$), —N(R$^4$)C(O)(R$^6$), and —N(R$^4$)(R$^5$). In certain embodiments, A$^3$ is a 5-6 membered heterocyclic group containing (i) at least one ring carbon atom substituted by oxo and (ii) at least one double bond between two ring atoms, and the heterocyclic group being optionally substituted by 1 or 2 substituents independently selected from the group consisting of C$_{1-6}$ alkyl, C$_{1-6}$ haloalkyl, C$_{3-6}$ cycloalkyl, halogen, C$_{1-6}$ alkoxy, C$_{1-6}$ haloalkoxy, oxo, —C(O)R$^6$, —CO$_2$R$^7$, —C(O)(N$^4$)(R$^5$), —N(R$^4$)C(O)(R$^6$), and —N(R$^4$)(R$^5$). In certain embodiments, A$^3$ is a 5-6 membered saturated heterocyclic group optionally substituted by 1 or 2 substituents independently selected from the group consisting of methyl, ethyl, isopropyl, trifluoromethyl, cyclopropyl, C$_{1-6}$ alkoxy, oxo, and —CO$_2$R$^7$.

In certain embodiments, A$^3$ is a 5-membered heterocyclic group. In certain embodiments, A$^3$ is a 5-6 membered heteroaromatic group comprising at least two ring nitrogen atoms, at least one unsaturated carbon atom in the ring, and the heteroaromatic group being optionally substituted by 1 or 2 substituents independently selected from the group consisting of C$_{1-6}$ alkyl, C$_{1-6}$ haloalkyl, C$_{3-6}$ cycloalkyl, halogen, C$_{1-6}$ alkoxy, C$_{1-6}$ haloalkoxy, —C(O)R$^6$, —CO$_2$R$^7$, —C(O)(N$^4$)(R$^5$), —N(R$^4$)C(O)(R$^6$), and —N(R$^4$)(R$^5$).

In certain embodiments, A$^3$ is imidazolyl; pyrazolyl; 1,2, 3-triazolyl; tetrazolyl; 1,2,4-oxadiazol-5(4H)-onyl; 1,3,4-oxadiazol-2(3H)-onyl; 1,3-dihydro-2H-imidazol-2-onyl; or 2,4-dihydro-3H-1,2,4-triazol-3-onyl; each of which is optionally substituted by 1, 2, or 3 substituents independently selected from the group consisting of C$_{1-6}$ alkyl, C$_{1-6}$ haloalkyl, C$_{3-6}$ cycloalkyl, halogen, C$_{1-6}$ alkoxy, C$_{1-6}$ haloalkoxy, oxo, —C(O)R$^6$, —CO$_2$R$^7$, —C(O)(N$^4$)(R$^5$), —N(R$^4$)C(O)(R$^6$), and —N(R$^4$)(R$^5$).

In certain embodiments, A$^3$ is one of the following:

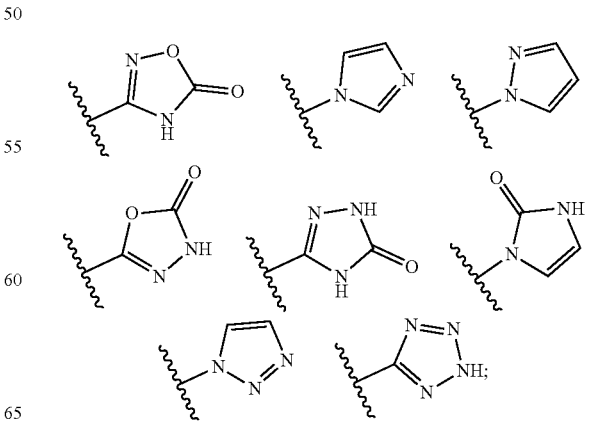

each of which is optionally substituted by 1, 2, or 3 substituents independently selected from the group consisting $C_{1-6}$ alkyl, $C_{1-6}$ haloalkyl, $C_{3-6}$ cycloalkyl, halogen, $C_{1-6}$ alkoxy, $C_{1-6}$ haloalkoxy, oxo, —C(O)R$^6$, —CO$_2$R$^7$, —C(O)(N$^4$)(R$^5$), —N(R$^4$)C(O)(R$^6$), and —N(R$^4$)(R$^5$).

In certain embodiments, A$^3$ is one of the following:

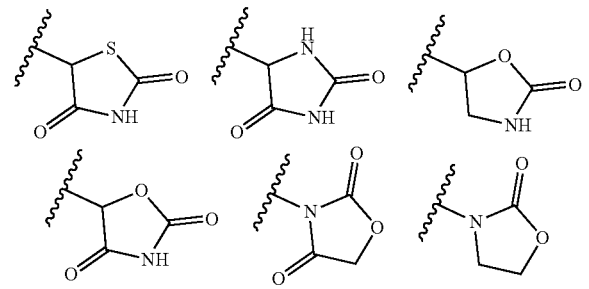

each of which is optionally substituted by 1, 2, or 3 substituents independently selected from the group consisting of $C_{1-6}$ alkyl, $C_{1-6}$ haloalkyl, $C_{3-6}$ cycloalkyl, halogen, $C_{1-6}$ alkoxy, $C_{1-6}$ haloalkoxy, oxo, —C(O)R$^6$, —CO$_2$R$^7$, —C(O)(N$^4$)(R$^5$), —N(R$^4$)C(O)(R$^6$), and —N(R$^4$)(R$^5$).

In certain embodiments, R$^2$ is methyl.

In certain embodiments, R$^3$ represents independently for each occurrence $C_{1-6}$ haloalkyl, halogen, $C_{1-6}$alkyl, $C_{1-6}$ alkoxy, or —O—($C_{1-6}$alkylene)-OH. In certain embodiments, R$^3$ is trifluoromethyl, fluoro, chloro, or methoxy. In certain embodiments, R$^3$ is trifluoromethyl.

In certain embodiments, R$^4$ and R$^5$ each represent independently for each occurrence hydrogen or $C_{1-6}$ alkyl. In certain embodiments, R$^4$ is hydrogen. In certain embodiments, R$^5$ is hydrogen.

In certain embodiments, R$^6$ represents independently for each occurrence $C_{1-6}$alkyl or $C_{3-6}$ cycloalkyl. In certain embodiments, R$^6$ is $C_{1-6}$ alkyl.

In certain embodiments, R$^7$ represents independently for each occurrence hydrogen, $C_{1-6}$ alkyl, or $C_{1-6}$ hydroxyalkyl. In certain embodiments, R$^7$ is hydrogen. In certain embodiments, R$^7$ is $C_{1-6}$ alkyl.

In certain embodiments, p is 0. In certain embodiments, p is 1.

In certain embodiments, -A$^1$-(R$^3$)$_n$ is

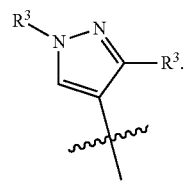

In certain embodiments, -A$^1$-(R$^3$)$_n$ is one of the following:

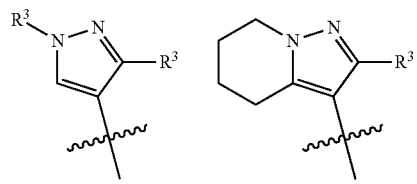

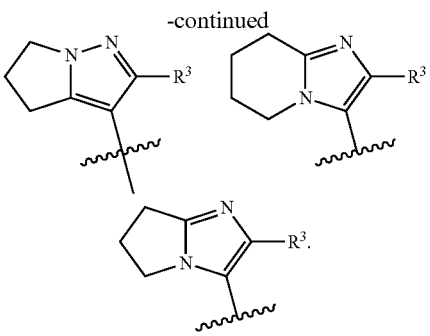

The definitions of variables in Formula I-1 above encompass multiple chemical groups. The application contemplates embodiments where, for example, i) the definition of a variable is a single chemical group selected from those chemical groups set forth above, ii) the definition of a variable is a collection of two or more of the chemical groups selected from those set forth above, and iii) the compound is defined by a combination of variables in which the variables are defined by (i) or (ii), e.g., such as where A is phenylene and R$^3$ is selected from the group consisting of $C_{1-6}$ haloalkyl, halogen, hydroxyl, and $C_{1-6}$ alkyl.

Another aspect of the invention provides a compound represented by Formula I-A:

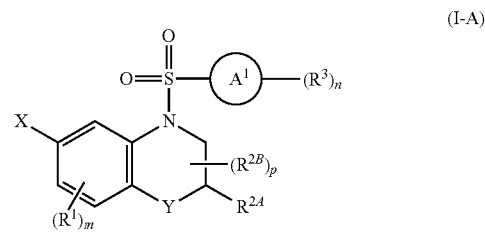

(I-A)

or a pharmaceutically acceptable salt thereof; wherein:

A$^1$ is phenylene or a 5-6 membered heteroarylene;

X is phenyl or 5-6 membered heteroaryl, each of which is optionally substituted by 1, 2, or 3 substituents independently selected from the group consisting of $C_{1-6}$ alkyl, $C_{3-6}$ cycloalkyl, halogen, $C_{1-6}$ haloalkyl, hydroxyl, $C_{1-6}$ alkoxy, $C_{1-6}$ haloalkoxy, —O—$C_{3-6}$ cycloalkyl, —O—($C_{1-6}$ alkylene)-OH, cyano, —N(R$^4$)(R$^5$), and $C_{6-10}$ aryl;

R$^1$ represents independently for each occurrence halogen, $C_{1-6}$ alkyl, or $C_{1-6}$ haloalkyl;

R$^{2A}$ is —($C_{1-6}$ alkylene)-A$^2$, —($C_{3-6}$ cycloalkylene)-A$^2$, -(2-6 membered heteroalkylene)-A$^2$, or —CO$_2$R$^4$; wherein A$^2$ is —CO$_2$R$^4$, —C(O)-A$^3$, —C(O)N(R$^4$)(R$^3$), —C(O)N(R$^4$)—($C_{1-4}$ alkylene)-CO$_2$R$^4$, —N(R$^4$)C(O)R$^7$, —N(R$^4$)C(O)A$^3$, —N(R$^4$)C(O)—($C_{1-6}$ alkylene)-CO$_2$R$^4$, —N(R$^4$)C(O)N(R$^4$)—($C_{1-6}$ alkylene)-CO$_2$R$^4$, —N(R$^4$)CO$_2$R$^6$, or A$^3$; and A$^3$ is a 5-8 membered heterocyclic group optionally substituted with 1, 2, or 3 substituents independently selected from the group consisting of $C_{1-6}$ alkyl, $C_{1-6}$ haloalkyl, $C_{3-6}$ cycloalkyl, halogen, $C_{1-6}$ alkoxy, $C_{1-6}$ haloalkoxy, oxo, —C(O)R$^6$, —CO$_2$R$^7$, and —C(O)(N$^4$)(R$^5$);

R$^{2B}$ represents independently for each occurrence $C_{1-6}$ alkyl or $C_{1-3}$ haloalkyl;

R$^3$ represents independently for each occurrence hydrogen, $C_{1-6}$ haloalkyl, halogen, hydroxyl, $C_{1-6}$ alkyl, $C_{3-6}$ cycloalkyl, $C_{1-6}$ alkoxy, $C_{1-6}$ haloalkoxy, —O—($C_{1-6}$ alkylene)-OH, or —O—($C_{1-6}$alkylene)-CO$_2$R$^4$;

$R^4$ and $R^5$ each represent independently for each occurrence hydrogen, $C_{1-6}$ alkyl, or $C_{3-6}$ cycloalkyl; or an occurrence of $R^4$ and $R^5$ attached to the same nitrogen atom are taken together with the nitrogen atom to which they are attached to form a 3-7 membered heterocyclic ring;

$R^6$ represents independently for each occurrence $C_{1-6}$ alkyl, $C_{3-6}$ cycloalkyl, or aralkyl;

$R^7$ represents independently for each occurrence hydrogen, $C_{1-6}$ alkyl, $C_{1-6}$ hydroxyalkyl, $C_{3-6}$ cycloalkyl, $C_{3-6}$ hydroxycycloalkyl, or aralkyl; m and p are independently 0, 1, or 2; and n is 1, 2, or 3.

In certain embodiments, the compound is a compound of Formula I-A.

In certain embodiments, $A^1$ is phenylene. In certain embodiments, $A^1$ is phenylene, and one occurrence of $R^3$ is attached at the meta-position on the phenyl group. In certain embodiments, $A^1$ is a 5-6 membered heteroarylene. In certain embodiments, $A^1$ is

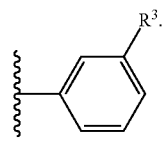

In certain embodiments, X is phenyl substituted by 1, 2, or 3 substituents independently selected from the group consisting of $C_{1-6}$ alkyl, $C_{3-6}$ cycloalkyl, halogen, $C_{1-6}$ haloalkyl, hydroxyl, $C_{1-6}$ alkoxy, $C_{1-6}$ haloalkoxy, —O—$C_{3-6}$ cycloalkyl, and —O—($C_{1-6}$ alkylene)-OH. In certain embodiments, X is phenyl substituted by 1, 2, or 3 substituents independently selected from the group consisting of $C_{1-6}$ alkyl, $C_{3-6}$ cycloalkyl, halogen, $C_{1-6}$ haloalkyl, hydroxyl, $C_{1-6}$ alkoxy, and $C_{1-6}$ haloalkoxy. In certain embodiments, X is phenyl substituted by 1, 2, or 3 substituents independently selected from the group consisting of $C_{1-6}$ alkyl, cyclopropyl, halogen, $C_{1-3}$ haloalkyl, hydroxyl, $C_{1-3}$ alkoxy, and $C_{1-3}$ haloalkoxy. In certain embodiments, X is phenyl substituted by 1 or 2 substituents independently selected from the group consisting of $C_{1-6}$ alkyl, cyclopropyl, chloro, fluoro, $C_{1-3}$ haloalkyl, hydroxyl, $C_{1-3}$ alkoxy, and $C_{1-3}$ haloalkoxy.

In certain embodiments, X is a 5-6 membered heteroaryl optionally substituted by 1, 2, or 3 substituents independently selected from the group consisting of $C_{1-6}$ alkyl, $C_{3-6}$ cycloalkyl, halogen, $C_{1-6}$ haloalkyl, hydroxyl, $C_{1-6}$ alkoxy, $C_{1-6}$ haloalkoxy, —O—$C_{3-6}$ cycloalkyl, —O—($C_{1-6}$ alkylene)-OH, cyano, —N($R^4$)$R^5$), and $C_{6-10}$ aryl. In certain embodiments, X is a 6-membered heteroaryl substituted by 1, 2, or 3 substituents independently selected from the group consisting of $C_{1-6}$ alkyl, $C_{3-6}$ cycloalkyl, halogen, $C_{1-6}$ haloalkyl, hydroxyl, $C_{1-4}$ alkoxy, and $C_{1-6}$ haloalkoxy. In certain embodiments, X is pyridinyl, pyrimidinyl, pyrazolyl, imidazolyl, triazolyl, thiazolyl, oxazolyl, or thiadiazolyl, each of which is optionally substituted by 1, 2, or 3 substituents independently selected from the group consisting of $C_{1-6}$ alkyl, $C_{3-6}$ cycloalkyl, halogen, $C_{1-6}$ haloalkyl, hydroxyl, $C_{1-6}$ alkoxy, and $C_{1-6}$ haloalkoxy. In certain embodiments, $A^3$ is a 5-6 membered saturated heterocyclic group optionally substituted by 1 or 2 substituents independently selected from the group consisting of methyl, ethyl, isopropyl, trifluoromethyl, cyclopropyl, $C_{1-6}$ alkoxy, oxo, and —$CO_2R^7$.

In certain embodiments, X is pyridinyl optionally substituted by 1, 2, or 3 substituents independently selected from the group consisting of $C_{1-6}$ alkyl, $C_{3-6}$ cycloalkyl, halogen, $C_{1-6}$ haloalkyl, hydroxyl, $C_{1-6}$ alkoxy, and $C_{1-6}$ haloalkoxy. In certain embodiments, X is pyridinyl optionally substituted by 1 or 2 substituents independently selected from the group consisting of $C_{1-6}$ alkyl, cyclopropyl, chloro, fluoro, $C_{1-6}$ haloalkyl, $C_{1-6}$ alkoxy, and $C_{1-6}$ haloalkoxy.

In certain embodiments, $R^1$ is halogen. In certain embodiments, $R^1$ is chloro or fluoro. In certain embodiments, $R^1$ represents independently for each occurrence halogen, $C_{1-6}$ alkyl, or $C_{1-6}$ haloalkyl. In certain embodiments, $R^1$ is halogen, and m is 1.

In certain embodiments, m is 1. In certain embodiments, m is 0.

In certain embodiments, $R^{2A}$ is —($C_{1-6}$alkylene)-$A^2$. In certain embodiments, $R^{2A}$ is —($C_{2-3}$ alkylene)-$A^2$. In certain embodiments, $R^{2A}$ is -(2-6 membered heteroalkylene)-$A^2$. In certain embodiments, $R^{2A}$ is —$CO_2R^4$. In certain embodiments, $R^{2A}$ is —($C_{2-3}$ alkylene)-O-$A^2$.

In certain embodiments, $A^2$ is —$CO_2R^4$. In certain embodiments, $A^2$ is —$CO_2H$. In certain embodiments, $A^2$ is —C(O)-$A^3$. In certain embodiments, $R^{2A}$ is —($C_{1-6}$alkylene)-$A^2$, and $A^2$ is —$CO_2R^4$. In certain embodiments, $R^{2A}$ is —($C_{1-6}$ alkylene)-$A^2$, and $A^2$ is —C(O)-$A^3$.

In certain embodiments, $A^3$ comprises at least two ring nitrogen atoms. In certain embodiments, $A^3$ comprises at least two ring nitrogen atoms, and at least one ring oxygen atom.

In certain embodiments, $A^3$ is a 5-6 membered heterocyclic group optionally substituted with 1, 2, or 3 substituents independently selected from the group consisting of $C_{1-6}$ alkyl, $C_{1-6}$haloalkyl, halogen, $C_{1-6}$ alkoxy, oxo, —C(O)$R^6$, and —$CO_2R^7$. In certain embodiments, $A^3$ is a 5-6 membered saturated heterocyclic group optionally substituted by 1 or 2 substituents independently selected from the group consisting of $C_{1-6}$ alkyl, $C_{1-6}$ haloalkyl, $C_{3-6}$ cycloalkyl, halogen, $C_{1-6}$ alkoxy, $C_{1-6}$ haloalkoxy, oxo, —C(O)$R^6$, —$CO_2R^7$, —C(O)(N$^4$)($R^5$), —N($R^4$)C(O)($R^6$), and —N($R^4$)($R^5$). In certain embodiments, $A^3$ is a 5-6 membered heterocyclic group containing at least one ring carbon atom substituted by oxo and the heterocyclic group being optionally substituted by 1 or 2 substituents independently selected from the group consisting of $C_{1-6}$ alkyl, $C_{1-6}$ haloalkyl, $C_{3-6}$ cycloalkyl, halogen, $C_{1-6}$ alkoxy, $C_{1-6}$ haloalkoxy, oxo, —C(O)$R^6$, —$CO_2R^7$, —C(O)(N$^4$)($R^5$), —N($R^4$)C(O)($R^6$), and —N($R^4$)($R^5$). In certain embodiments, $A^3$ is a 5-6 membered heterocyclic group containing (i) at least one ring carbon atom substituted by oxo and (ii) at least one double bond between two ring atoms, and the heterocyclic group being optionally substituted by 1 or 2 substituents independently selected from the group consisting of $C_{1-6}$ alkyl, $C_{1-6}$ haloalkyl, $C_{3-6}$ cycloalkyl, halogen, $C_{1-6}$ alkoxy, $C_{1-6}$ haloalkoxy, oxo, —C(O)$R^6$, —$CO_2R^7$, —C(O)(N$^4$)($R^3$), —N($R^4$)C(O)($R^6$), and —N($R^4$)($R^5$).

In certain embodiments, $A^3$ is a 5-membered heterocyclic group. In certain embodiments, $A^3$ is a 5-6 membered heteroaromatic group comprising at least two ring nitrogen atoms, at least one unsaturated carbon atom in the ring, and the heteroaromatic group being optionally substituted by 1 or 2 substituents independently selected from the group consisting of $C_{1-6}$ alkyl, $C_{1-6}$ haloalkyl, $C_{3-6}$ cycloalkyl, halogen, $C_{1-6}$ alkoxy, $C_{1-6}$ haloalkoxy, —C(O)$R^6$, —$CO_2R^7$, —C(O)(N$^4$)($R^5$), —N($R^4$)C(O)($R^6$), and —N($R^4$)($R^5$).

In certain embodiments, $A^3$ is imidazolyl; pyrazolyl; 1,2, 3-triazolyl; tetrazolyl; 1,2,4-oxadiazol-5(4H)-onyl; 1,3,4-oxadiazol-2(3H)-onyl; 1,3-dihydro-2H-imidazol-2-onyl; or 2,4-dihydro-3H-1,2,4-triazol-3-onyl; each of which is optionally substituted by 1, 2, or 3 substituents independently selected from the group consisting of $C_{1-6}$ alkyl, $C_{1-6}$ haloalkyl, $C_{3-6}$ cycloalkyl, halogen, $C_{1-6}$ alkoxy, $C_{1-6}$ haloalkoxy, oxo, —C(O)R$^6$, —CO$_2$R$^7$, —C(O)(N$^4$)(R$^5$), —N(R$^4$)C(O)(R$^6$), and —N(R$^4$)(R$^5$).

In certain embodiments, A$^3$ is one of the following:

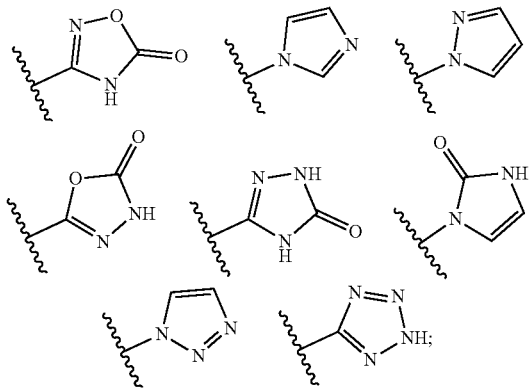

each of which is optionally substituted by 1, 2, or 3 substituents independently selected from the group consisting $C_{1-6}$ alkyl, $C_{1-6}$ haloalkyl, $C_{3-6}$ cycloalkyl, halogen, $C_{1-6}$ alkoxy, $C_{1-6}$ haloalkoxy, oxo, —C(O)R$^6$, —CO$_2$R$^7$, —C(O)(N$^4$)(R$^5$), —N(R$^4$)C(O)(R$^6$), and —N(R$^4$)(R$^5$).

In certain embodiments, A$^3$ is one of the following:

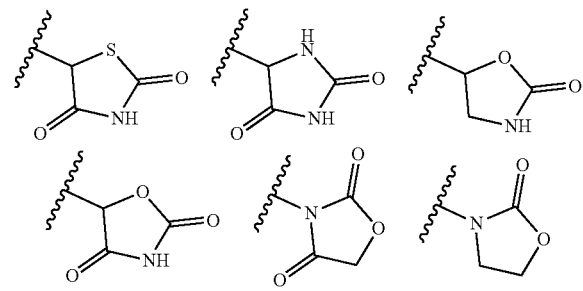

each of which is optionally substituted by 1, 2, or 3 substituents independently selected from the group consisting of $C_{1-6}$ alkyl, $C_{1-6}$ haloalkyl, $C_{3-6}$ cycloalkyl, halogen, $C_{1-6}$ alkoxy, $C_{1-6}$ haloalkoxy, oxo, —C(O)R$^6$, —CO$_2$R$^7$, —C(O)(N$^4$)(R$^5$), —N(R$^4$)C(O)(R$^6$), and —N(R$^4$)(R$^5$).

In certain embodiments, R$^2$ is methyl.

In certain embodiments, R$^3$ represents independently for each occurrence $C_{1-6}$ haloalkyl, halogen, $C_{1-6}$alkyl, $C_{1-6}$ alkoxy, or —O—($C_{1-6}$alkylene)-OH. In certain embodiments, R$^3$ is trifluoromethyl, fluoro, chloro, or methoxy. In certain embodiments, R$^3$ is trifluoromethyl.

In certain embodiments, R$^4$ and R$^5$ each represent independently for each occurrence hydrogen or $C_{1-6}$ alkyl. In certain embodiments, R$^4$ is hydrogen. In certain embodiments, R$^5$ is hydrogen.

In certain embodiments, R$^6$ represents independently for each occurrence $C_{1-6}$ alkyl or $C_{3-6}$ cycloalkyl. In certain embodiments, R$^6$ is $C_{1-6}$ alkyl.

In certain embodiments, R$^7$ represents independently for each occurrence hydrogen, $C_{1-6}$ alkyl, or $C_{1-6}$ hydroxyalkyl. In certain embodiments, R$^7$ is hydrogen. In certain embodiments, R$^7$ is $C_{1-6}$ alkyl.

In certain embodiments, p is 0. In certain embodiments, p is 1.

In certain embodiments, -A$^1$-(R$^3$)$_n$ is

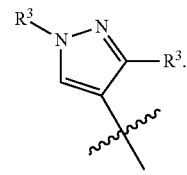

In certain embodiments, -A$^1$-(R$^3$)$_n$ is one of the following:

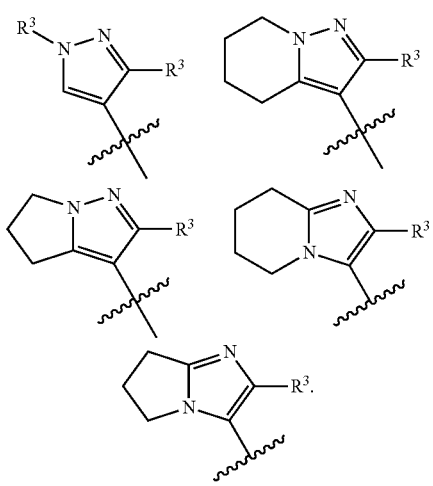

The definitions of variables in Formula I-A above encompass multiple chemical groups. The application contemplates embodiments where, for example, i) the definition of a variable is a single chemical group selected from those chemical groups set forth above, ii) the definition of a variable is a collection of two or more of the chemical groups selected from those set forth above, and iii) the compound is defined by a combination of variables in which the variables are defined by (i) or (ii), e.g., such as where A is phenylene and R$^3$ is selected from the group consisting of $C_{1-6}$ haloalkyl, halogen, hydroxyl, and $C_{1-6}$ alkyl.

Another aspect of the invention provides a compound represented by Formula I-B:

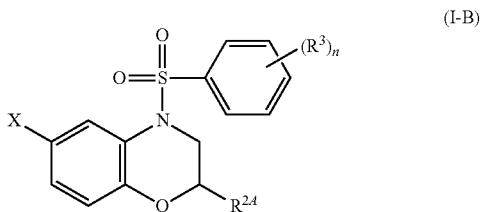

(I-B)

or a pharmaceutically acceptable salt thereof; wherein:

X is phenyl or 2-pyridinyl, each of which is substituted by 1, 2, or 3 substituents independently selected from the group consisting of chloro, fluoro, $C_{1-2}$ fluoroalkyl, $C_{1-2}$ alkoxy, and $C_{1-2}$ fluoroalkoxy;

R$^{2A}$ is —($C_{1-6}$ alkylene)-CO$_2$H or —($C_{1-6}$ alkylene)-N(R$^4$)C(O)R$^7$;

$R^3$ represents independently for each occurrence $C_{1-2}$ fluoroalkyl, chloro, fluoro, cyclopropyl, $C_{1-3}$ alkyl, $C_{1-2}$ alkoxy, or $C_{1-2}$ fluoroalkoxy;

$R^4$ is hydrogen or $C_{1-6}$ alkyl;

$R^7$ is $C_{1-6}$ alkyl, $C_{1-6}$ hydroxyalkyl, $C_{1-6}$ haloalkyl, $C_{1-6}$ hydroxyhaloalkyl, $C_{3-6}$ cycloalkyl, or $C_{3-6}$ hydroxycycloalkyl; and n is 1 or 2.

In certain embodiments, the compound is a compound of Formula I-B.

In certain embodiments, X is phenyl substituted by 1, 2, or 3 substituents independently selected from the group consisting of chloro, fluoro, $C_{1-2}$ fluoroalkyl, $C_{1-2}$ alkoxy, and $C_{1-2}$ fluoroalkoxy. In certain embodiments, X is phenyl substituted by 1, 2, or 3 substituents independently selected from the group consisting of chloro, fluoro, $C_{1-2}$ fluoroalkyl, $C_{1-2}$ alkoxy, and $C_{1-2}$ fluoroalkoxy, where at least 1 substituent is located at a meta-position on the phenyl group. In certain embodiments, X is phenyl substituted by 1, 2, or 3 substituents independently selected from the group consisting of chloro, fluoro, and $C_{1-2}$ fluoroalkoxy. In certain embodiments, X is phenyl substituted by 1, 2, or 3 substituents independently selected from the group consisting of chloro, fluoro, and $C_{1-2}$ fluoroalkoxy, where at least 1 substituent is located at a meta-position on the phenyl group. In certain embodiments, X is phenyl substituted by (a) $C_{1-2}$ alkoxy and (b) 1 or 2 substituents independently selected from the group consisting of chloro, fluoro, and $C_{1-2}$ fluoroalkyl.

In certain embodiments, $R^{2A}$ is —($C_{1-6}$ alkylene)-$CO_2H$. In certain embodiments, $R^{2A}$ is —$(CH_2)_2$—$CO_2H$. In certain embodiments, $R^{2A}$ is —$CH_2C(CH_3)_2$—$CO_2H$. In certain embodiments, $R^{2A}$ is —$(CH_2)_2$—$CO_2H$ or —$CH_2C(CH_3)_2$—$CO_2H$. In certain embodiments, $R^{2A}$ is —($C_{1-6}$ alkylene)-$N(R^4)C(O)R^7$. In certain embodiments, $R^{2A}$ is —($C_{1-6}$ alkylene)-$N(H)C(O)$—($C_{1-6}$ hydroxyhaloalkyl).

In certain embodiments, at least one occurrence of $R^3$ is attached at a meta-position on the phenyl group. In certain embodiments, $R^3$ represents independently for each occurrence $C_{1-2}$ fluoroalkyl, chloro, fluoro, $C_{1-2}$ alkoxy, or $C_{1-2}$ fluoroalkoxy. In certain embodiments, $R^3$ represents independently for each occurrence $C_{1-2}$ fluoroalkyl, chloro, or fluoro. In certain embodiments, $R^3$ is —$CF_3$. In certain embodiments, $R^3$ is —$CF_3$, which is attached at a meta-position on the phenyl group. In certain embodiments, $R^3$ is —$CF_3$, which is attached at a meta-position on the phenyl group; and n is 1.

In certain embodiments, $R^4$ is hydrogen.

In certain embodiments, $R^7$ is $C_{1-6}$ hydroxyalkyl, $C_{1-6}$ haloalkyl, or $C_{1-6}$ hydroxyhaloalkyl. In certain embodiments, $R^7$ is $C_{1-6}$ hydroxyhaloalkyl.

In certain embodiments, n is 1.

In certain embodiments, X is phenyl substituted by 1, 2, or 3 substituents independently selected from the group consisting of chloro, fluoro, and $C_{1-2}$ fluoroalkoxy, where at least 1 substituent is located at a meta-position on the phenyl group; $R^{2A}$ is —($C_{1-6}$ alkylene)-$CO_2H$; $R^3$ is —$CF_3$, which is attached at the meta-position on the phenyl group; and n is 1.

The definitions of variables in Formula I-B above encompass multiple chemical groups. The application contemplates embodiments where, for example, i) the definition of a variable is a single chemical group selected from those chemical groups set forth above, ii) the definition of a variable is a collection of two or more of the chemical groups selected from those set forth above, and iii) the compound is defined by a combination of variables in which the variables are defined by (i) or (ii).

Another aspect of the invention provides a compound represented by Formula I-C:

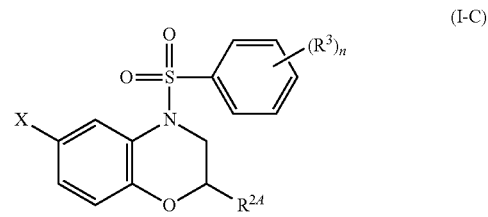

(I-C)

or a pharmaceutically acceptable salt thereof; wherein:

X is phenyl substituted by 1, 2, or 3 substituents independently selected from the group consisting of chloro, fluoro, $C_{1-2}$ fluoroalkyl, $C_{1-2}$ alkoxy, and $C_{1-2}$ fluoroalkoxy;

$R^{2A}$ is —($C_{1-3}$ alkylene)-(3-6 membered heterocycloalkylene)-($C_{0-3}$ alkylene)-$A^2$, where $A^2$ is —$CO_2R^4$ or —$N(R^4)C(O)R^7$;

$R^3$ represents independently for each occurrence $C_{1-2}$ fluoroalkyl, chloro, fluoro, cyclopropyl, $C_{1-3}$ alkyl, $C_{1-2}$ alkoxy, or $C_{1-2}$ fluoroalkoxy;

$R^4$ is hydrogen or $C_{1-6}$ alkyl;

$R^7$ is $C_{1-6}$ alkyl, $C_{1-6}$ hydroxyalkyl, $C_{1-6}$ haloalkyl, $C_{1-6}$ hydroxyhaloalkyl, $C_{3-6}$ cycloalkyl, or $C_{3-6}$ hydroxycycloalkyl; and n is 1 or 2.

In certain embodiments, the compound is a compound of Formula I-C.

In certain embodiments, X is phenyl substituted by 2 or 3 substituents independently selected from the group consisting of chloro, fluoro, $C_{1-2}$ fluoroalkyl, $C_{1-2}$ alkoxy, and $C_{1-2}$ fluoroalkoxy. In certain embodiments, X is phenyl substituted by 1, 2, or 3 substituents independently selected from the group consisting of chloro, fluoro, $C_{1-2}$ fluoroalkyl, $C_{1-2}$ alkoxy, and $C_{1-2}$ fluoroalkoxy, where at least 1 substituent is located at a meta-position on the phenyl group. In certain embodiments, X is phenyl substituted by 1, 2, or 3 substituents independently selected from the group consisting of chloro, fluoro, and $C_{1-2}$ fluoroalkoxy. In certain embodiments, X is phenyl substituted by 1, 2, or 3 substituents independently selected from the group consisting of chloro, fluoro, and $C_{1-2}$ fluoroalkoxy, where at least 1 substituent is located at a meta-position on the phenyl group. In certain embodiments, X is phenyl substituted by (a) $C_{1-2}$ alkoxy and (b) 1 or 2 substituents independently selected from the group consisting of chloro, fluoro, and $C_{1-2}$ fluoroalkyl.

In certain embodiments, $R^{2A}$ is —($C_{1-3}$ alkylene)-(4-6 membered heterocycloalkylene)-$A^2$.

In certain embodiments, $A^2$ is —$CO_2R^4$. In certain embodiments, $A^2$ is —$CO_2H$.

In certain embodiments, at least one occurrence of $R^3$ is attached at a meta-position on the phenyl group. In certain embodiments, $R^3$ represents independently for each occurrence $C_{1-2}$ fluoroalkyl, chloro, fluoro, $C_{1-2}$ alkoxy, or $C_{1-2}$ fluoroalkoxy. In certain embodiments, $R^3$ represents independently for each occurrence $C_{1-2}$ fluoroalkyl, chloro, or fluoro. In certain embodiments, $R^3$ is —$CF_3$. In certain embodiments, $R^3$ is —$CF_3$, which is attached at a meta-position on the phenyl group. In certain embodiments, $R^3$ is —$CF_3$, which is attached at a meta-position on the phenyl group; and n is 1.

In certain embodiments, $R^4$ is hydrogen.

In certain embodiments, $R^7$ is $C_{1-6}$ hydroxyalkyl, $C_{1-6}$ haloalkyl, or $C_{1-6}$ hydroxyhaloalkyl. In certain embodiments, $R^7$ is $C_{1-6}$ hydroxyhaloalkyl.

In certain embodiments, n is 1.

The definitions of variables in Formula I-C above encompass multiple chemical groups. The application contemplates embodiments where, for example, i) the definition of a variable is a single chemical group selected from those chemical groups set forth above, ii) the definition of a variable is a collection of two or more of the chemical groups selected from those set forth above, and iii) the compound is defined by a combination of variables in which the variables are defined by (i) or (ii).

Another aspect of the invention provides a compound represented by Formula II:

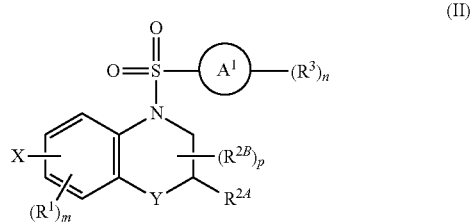

(II)

or a pharmaceutically acceptable salt thereof; wherein:

$A^1$ is phenylene, 5-6 membered heteroarylene, or 3-6 membered heterocycloalkylene;

X is phenyl or 5-10 membered heteroaryl, each of which is optionally substituted by 1, 2, 3, or 4 substituents independently selected from the group consisting of $C_{1-6}$ alkyl, $C_{3-6}$ cycloalkyl, halogen, $C_{1-6}$ haloalkyl, hydroxyl, $C_{1-6}$ alkoxy, $C_{1-6}$ haloalkoxy, —O—$C_{3-6}$ cycloalkyl, —O—($C_{1-6}$ alkylene)-OH, cyano, —N($R^4$)($R^5$), —S(O)$_2$—$R^6$, acetyl, and $C_{6-10}$ aryl;

$R^1$ represents independently for each occurrence halogen, $C_{1-6}$ alkyl, $C_{1-6}$ haloalkyl, or $C_{3-6}$ cycloalkyl;

$R^{2A}$ is —($C_{1-3}$ alkylene)-($C_{3-6}$ cycloalkenylene)-($C_{0-3}$ alkylene)-$A^2$, —($C_{1-3}$ alkylene)-($C_{3-6}$ cycloalkylene substituted by hydroxyl and $C_{1-4}$ hydroxyalkyl)-($C_{0-3}$ alkylene)-$A^2$, —($C_{1-3}$ alkylene)-(3-6 membered carbocyclylene substituted by =C($R^{10}$)$_2$)—($C_{0-3}$ alkylene)-$A^2$, or hydroxyl, wherein the cycloalkenylene, cycloalkylene, and carbocyclylene are optionally substituted with 1, 2, or 3 substituents independently selected from the group consisting of $C_{1-6}$ alkyl, $C_{1-6}$ haloalkyl, $C_{3-6}$ cycloalkyl, halogen, $C_{1-6}$ alkoxy, $C_{1-6}$ haloalkoxy, oxo, —C(O)$R^6$, —CO$_2R^7$, —C(O)($N^4$)($R^3$), —N($R^4$)C(O)($R^6$), and —N($R^4$)($R^3$); and $A^2$ is —CO$_2R^4$, —C(O)$R^6$, —C(O)N($R^4$)($R^3$), —C(O)N($R^4$)—($C_{1-4}$ alkylene)-CO$_2R^4$, or —C(O)N($R^4$)SO$_2R^4$; and $R^{2B}$ represents independently for each occurrence $C_{1-6}$ alkyl or $C_{1-3}$ haloalkyl;

$R^3$ represents independently for each occurrence hydrogen, $C_{1-6}$ haloalkyl, halogen, hydroxyl, $C_{1-6}$ alkyl, $C_{3-6}$ cycloalkyl, $C_{1-6}$ alkoxy, $C_{1-6}$ haloalkoxy, —O—($C_{1-6}$ alkylene)-OH, or —O—($C_{1-6}$ alkylene)-CO$_2R^4$; or two vicinal occurrences of $R^3$ are taken together with intervening atoms to form a 4-6 membered ring optionally substituted with 1, 2, or 3 substituents independently selected from the group consisting of $C_{1-6}$ alkyl, $C_{1-6}$ haloalkyl, $C_{3-6}$ cycloalkyl, halogen, $C_{1-6}$ alkoxy, $C_{1-6}$ haloalkoxy, —C(O)$R^6$, and —CO$_2R^7$;

$R^4$ and $R^5$ each represent independently for each occurrence hydrogen, $C_{1-6}$ alkyl, $C_{1-6}$ haloalkyl, $C_{1-6}$ hydroxylalkyl, or $C_{3-6}$ cycloalkyl; or an occurrence of $R^4$ and $R^5$ attached to the same nitrogen atom are taken together with the nitrogen atom to which they are attached to form a 3-7 membered heterocyclic ring;

$R^6$ represents independently for each occurrence $C_{1-6}$ alkyl, $C_{3-6}$ cycloalkyl, or aralkyl;

$R^7$ represents independently for each occurrence hydrogen, $C_{1-6}$ alkyl, $C_{1-6}$ hydroxyalkyl, $C_{1-6}$ haloalkyl, $C_{1-6}$ hydroxyhaloalkyl, $C_{3-6}$ cycloalkyl, $C_{3-6}$ hydroxycycloalkyl, —($C_{1-6}$ alkylene)-($C_{3-6}$ cycloalkyl), —($C_{1-6}$ alkylene)-($C_{2-4}$ alkenyl), or aralkyl;

$R^8$ and $R^9$ each represent independently for each occurrence hydrogen, halogen, or $C_{1-6}$ alkyl, or $R^8$ and $R^9$ are taken together with the carbon atom to which they are attached to form a 3-6 membered carbocyclic ring; or $R^8$ and $R^{2B}$ may taken together to form a bond when $R^{2B}$ is attached to the same carbon atom as $R^{2A}$;

$R^{10}$ represents independently for each occurrence hydrogen or $C_{1-6}$ alkyl; or two occurrences of $R^{10}$ bound to the same carbon atom are taken together with the carbon atom to which they are bound to form a 3-6 membered carbocycle;

Y is —O—, —C(O)—, —S(O)$_p$—, or —C($R^8$)($R^9$)—;

m and p each represent independently for each occurrence 0, 1, or 2; and n is 1, 2, or 3.

In certain embodiments, the compound is a compound of Formula II.

In certain embodiments, $A^1$ is phenylene or 5-6 membered heteroarylene. In certain embodiments, $A^1$ is phenylene. In certain embodiments, A is phenylene, and one occurrence of $R^3$ is attached at the meta-position on the phenyl group. In certain embodiments, $A^1$ is a 5-6 membered heteroarylene. In certain embodiments, $A^1$ is

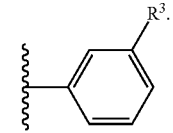

In certain embodiments, Y is —O—. In certain embodiments, Y is —O—, and $A^2$ is —CO$_2R^4$. In certain embodiments, Y is —O—, and X is attached at the 6-position of the 3,4-dihydro-2H-benzo[b][1,4]oxazinyl ring. In certain embodiments, Y is —C($R^8$)($R^9$)—. In certain embodiments, $R^8$ and $R^9$ are independently hydrogen or methyl. In certain embodiments, Y is —C($R^8$)($R^9$)—, $R^8$ and $R^9$ are independently hydrogen or methyl, and X is attached at the 7-position of the 1,2,3,4-tetrahydroquinolinyl ring.

In certain embodiments, X is phenyl substituted by 1, 2, 3, or 4 substituents independently selected from the group consisting of $C_{1-6}$ alkyl, $C_{3-6}$ cycloalkyl, halogen, $C_{1-6}$ haloalkyl, hydroxyl, $C_{1-6}$ alkoxy, $C_{1-6}$ haloalkoxy, —O—$C_{3-6}$ cycloalkyl, and —O—($C_{1-6}$ alkylene)-OH. In certain embodiments, X is phenyl substituted by 1, 2, or 3 substituents independently selected from the group consisting of $C_{1-6}$ alkyl, $C_{3-6}$ cycloalkyl, halogen, $C_{1-6}$ haloalkyl, hydroxyl, $C_{1-6}$ alkoxy, $C_{1-6}$ haloalkoxy, —O—$C_{3-6}$ cycloalkyl, and —O—($C_{1-6}$ alkylene)-OH. In certain embodiments, X is phenyl substituted by 1, 2, or 3 substituents independently selected from the group consisting of $C_{1-6}$ alkyl, $C_{3-6}$ cycloalkyl, halogen, $C_{1-6}$ haloalkyl, hydroxyl, $C_{1-6}$ alkoxy, and $C_{1-6}$ haloalkoxy. In certain embodiments, X is phenyl substituted by 1, 2, or 3 substituents independently selected from the group consisting of $C_{1-6}$ alkyl, cyclopropyl, halogen, $C_{1-3}$ haloalkyl, hydroxyl, $C_{1-3}$ alkoxy, and $C_{1-3}$ haloalkoxy. In certain embodiments, X is phenyl substituted by 1 or 2 substituents independently selected from the group consisting of $C_{1-6}$ alkyl, cyclopropyl, chloro, fluoro, $C_{1-3}$ haloalkyl, hydroxyl, $C_{1-3}$ alkoxy, and $C_{1-3}$ haloalkoxy.

In certain embodiments, X is phenyl or 5-10 membered heteroaryl, each of which is optionally substituted by 1, 2, or 3 substituents independently selected from the group consisting of $C_{1-6}$ alkyl, $C_{3-6}$ cycloalkyl, halogen, $C_{1-6}$ haloalkyl, hydroxyl, $C_{1-6}$ alkoxy, $C_{1-6}$ haloalkoxy, —O—$C_{3-6}$ cycloalkyl, —O—($C_{1-6}$ alkylene)-OH, cyano, —N($R^4$)($R^5$), and $C_{6-10}$ aryl. In certain embodiments, X is a 5-6 membered heteroaryl optionally substituted by 1, 2, or 3 substituents independently selected from the group consisting of $C_{1-6}$ alkyl, $C_{3-6}$ cycloalkyl, halogen, $C_{1-6}$ haloalkyl, hydroxyl, $C_{1-6}$ alkoxy, $C_{1-6}$ haloalkoxy, —O—$C_{3-6}$ cycloalkyl, —O—($C_{1-6}$ alkylene)-OH, cyano, —N($R^4$)($R^5$), and $C_{6-10}$ aryl. In certain embodiments, X is a 6-membered heteroaryl substituted by 1, 2, or 3 substituents independently selected from the group consisting of $C_{1-6}$ alkyl, $C_{3-6}$ cycloalkyl, halogen, $C_{1-6}$ haloalkyl, hydroxyl, $C_{1-6}$ alkoxy, and $C_{1-4}$ haloalkoxy. In certain embodiments, X is pyridinyl, pyrimidinyl, pyrazolyl, imidazolyl, triazolyl, thiazolyl, oxazolyl, or thiadiazolyl, each of which is optionally substituted by 1, 2, or 3 substituents independently selected from the group consisting of $C_{1-6}$ alkyl, $C_{3-6}$ cycloalkyl, halogen, $C_{1-6}$ haloalkyl, hydroxyl, $C_{1-6}$ alkoxy, and $C_{1-6}$ haloalkoxy. In certain embodiments, X is phenyl substituted by 1, 2, or 3 substituents independently selected from the group consisting of $C_{1-6}$ alkyl, $C_{1-6}$ cycloalkyl, halogen, $C_{1-6}$ haloalkyl, hydroxyl, $C_{1-6}$ alkoxy, and $C_{1-6}$ haloalkoxy.

In certain embodiments, X is pyridinyl optionally substituted by 1, 2, or 3 substituents independently selected from the group consisting of $C_{1-6}$ alkyl, $C_{3-6}$ cycloalkyl, halogen, $C_{1-6}$ haloalkyl, hydroxyl, $C_{1-6}$ alkoxy, and $C_{1-6}$ haloalkoxy. In certain embodiments, X is pyridinyl optionally substituted by 1 or 2 substituents independently selected from the group consisting of $C_{1-6}$ alkyl, cyclopropyl, chloro, fluoro, $C_{1-6}$ haloalkyl, $C_{1-6}$ alkoxy, and $C_{1-6}$ haloalkoxy.

In certain embodiments, $R^1$ is halogen. In certain embodiments, $R^1$ is chloro or fluoro. In certain embodiments, $R^1$ represents independently for each occurrence halogen, $C_{1-6}$ alkyl, or $C_{1-6}$ haloalkyl. In certain embodiments, $R^1$ is halogen, and m is 1.

In certain embodiments, m is 1. In certain embodiments, m is 0.

In certain embodiments, $R^{2A}$ is —($C_{1-3}$ alkylene)-($C_{3-6}$ cycloalkenylene)-($C_{3-6}$ alkylene)-$A^2$, —($C_{1-3}$ alkylene)-($C_{3-6}$ cycloalkylene substituted by hydroxyl and $C_{1-4}$ hydroxyalkyl)-($C_{3-6}$ alkylene)-$A^2$, or —($C_{1-3}$ alkylene)-(3-6 membered carbocyclylene substituted by =C($R^{10}$)$_2$)—($C_{0-3}$ alkylene)-$A^2$. In certain embodiments, $R^{2A}$ is —($C_{1-3}$ alkylene)-($C_{3-6}$ cycloalkenylene)-($C_{0-3}$ alkylene)-$A^2$. In certain embodiments, $R^{2A}$ is —($C_{0-3}$ alkylene)-($C_{3-6}$ cycloalkylene substituted by hydroxyl and $C_{1-4}$ hydroxyalkyl)-($C_{0-3}$ alkylene)-$A^2$. In certain embodiments, $R^{2A}$ is hydroxyl.

In certain embodiments, $A^2$ is —$CO_2R^4$. In certain embodiments, $A^2$ is —$CO_2H$.

In certain embodiments, $R^2$ is methyl.

In certain embodiments, $R^3$ represents independently for each occurrence $C_{1-6}$ haloalkyl, halogen, $C_{1-6}$ alkyl, $C_{1-6}$ alkoxy, or —O—($C_{1-6}$ alkylene)-OH. In certain embodiments, $R^3$ is trifluoromethyl, fluoro, chloro, or methoxy. In certain embodiments, $R^3$ is trifluoromethyl.

In certain embodiments, $R^3$ is $C_{1-6}$ haloalkyl or halogen; and n is 1.

In certain embodiments, $R^4$ and $R^5$ each represent independently for each occurrence hydrogen or $C_{1-6}$ alkyl. In certain embodiments, $R^4$ is hydrogen. In certain embodiments, $R^5$ is hydrogen.

In certain embodiments, $R^6$ represents independently for each occurrence $C_{1-6}$ alkyl or $C_{3-6}$ cycloalkyl. In certain embodiments, $R^6$ is $C_{1-6}$ alkyl.

In certain embodiments, $R^7$ represents independently for each occurrence hydrogen, $C_{1-6}$ alkyl, or $C_{1-6}$ hydroxyalkyl. In certain embodiments, $R^7$ is hydrogen. In certain embodiments, $R^7$ is $C_{1-6}$ alkyl.

In certain embodiments, p is 0. In certain embodiments, p is 1.

In certain embodiments, -$A^1$-($R^3$)$_n$ is

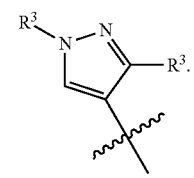

In certain embodiments, -$A^1$-($R^3$)$_n$ is one of the following:

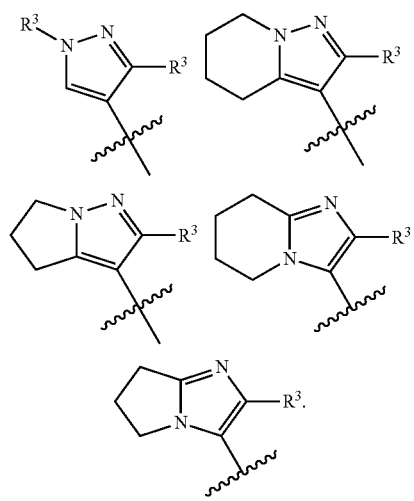

The definitions of variables in Formula II above encompass multiple chemical groups. The application contemplates embodiments where, for example, i) the definition of a variable is a single chemical group selected from those chemical groups set forth above, ii) the definition of a variable is a collection of two or more of the chemical groups selected from those set forth above, and iii) the compound is defined by a combination of variables in which the variables are defined by (i) or (ii), e.g., such as where A is phenylene and $R^3$ is selected from the group consisting of $C_{1-6}$ haloalkyl, halogen, hydroxyl, and $C_{1-6}$ alkyl.

In certain other embodiments, the compound is a compound defined by one of the following formulae where variables X and Z are as defined in Table 1, or a pharmaceutically acceptable salt thereof.

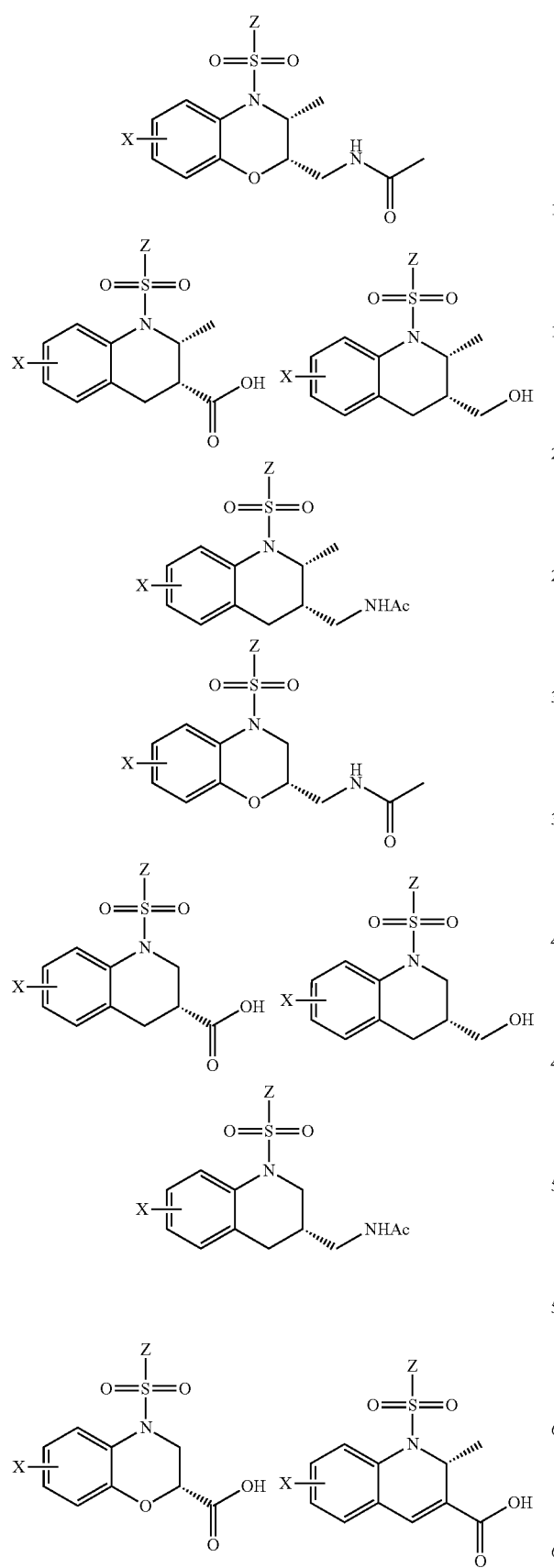
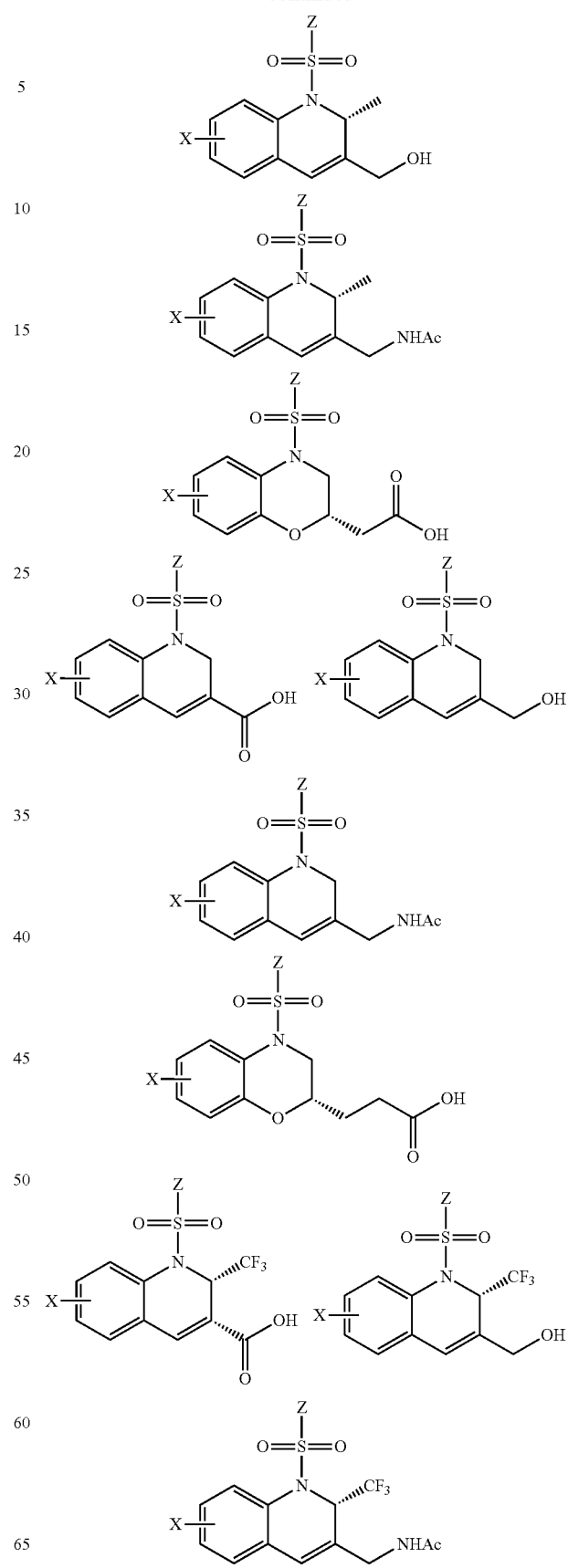

-continued
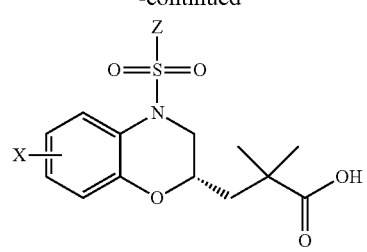
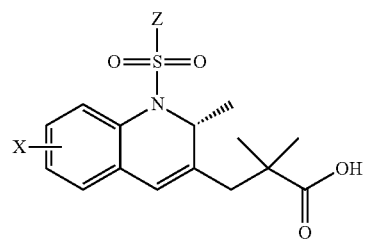
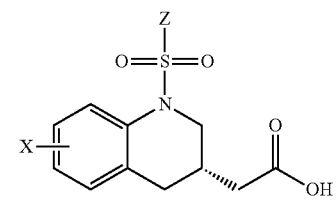
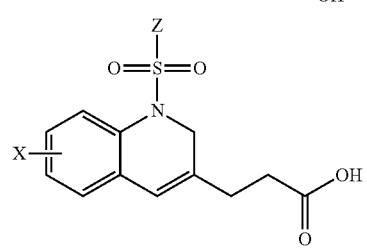
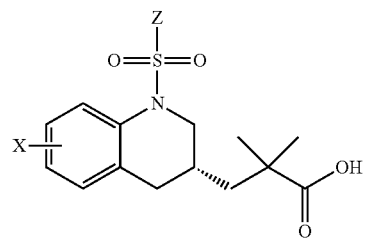
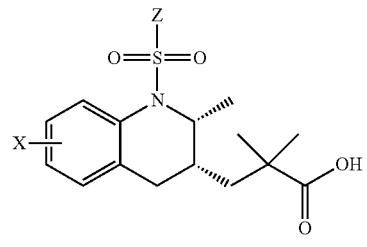
-continued
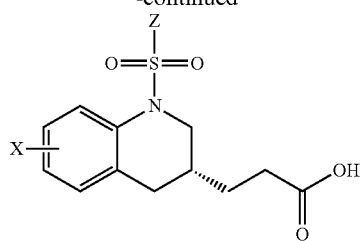
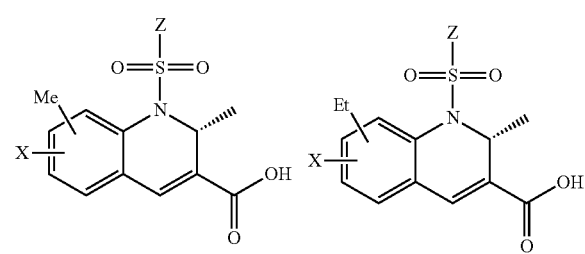
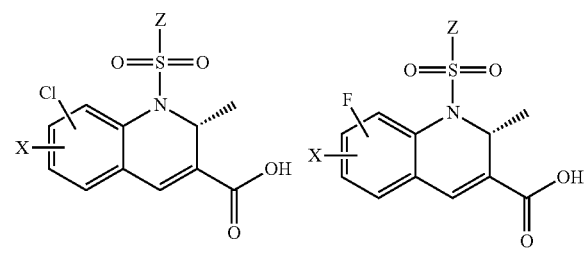
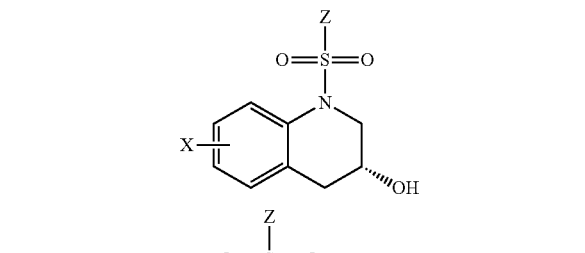
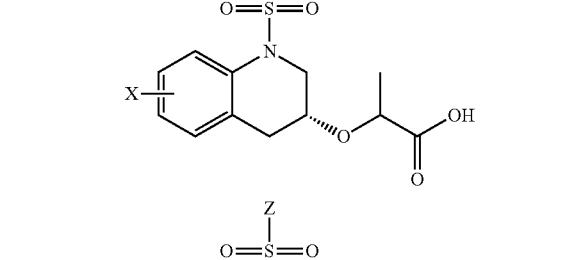
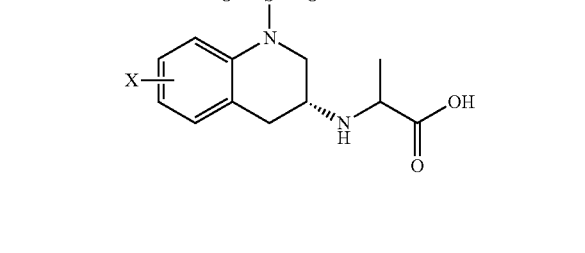
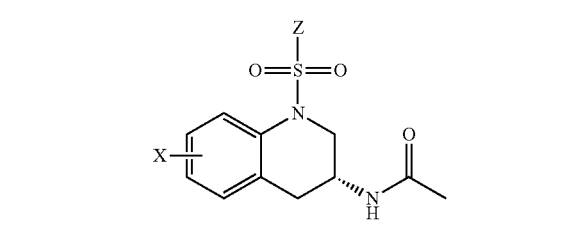

-continued
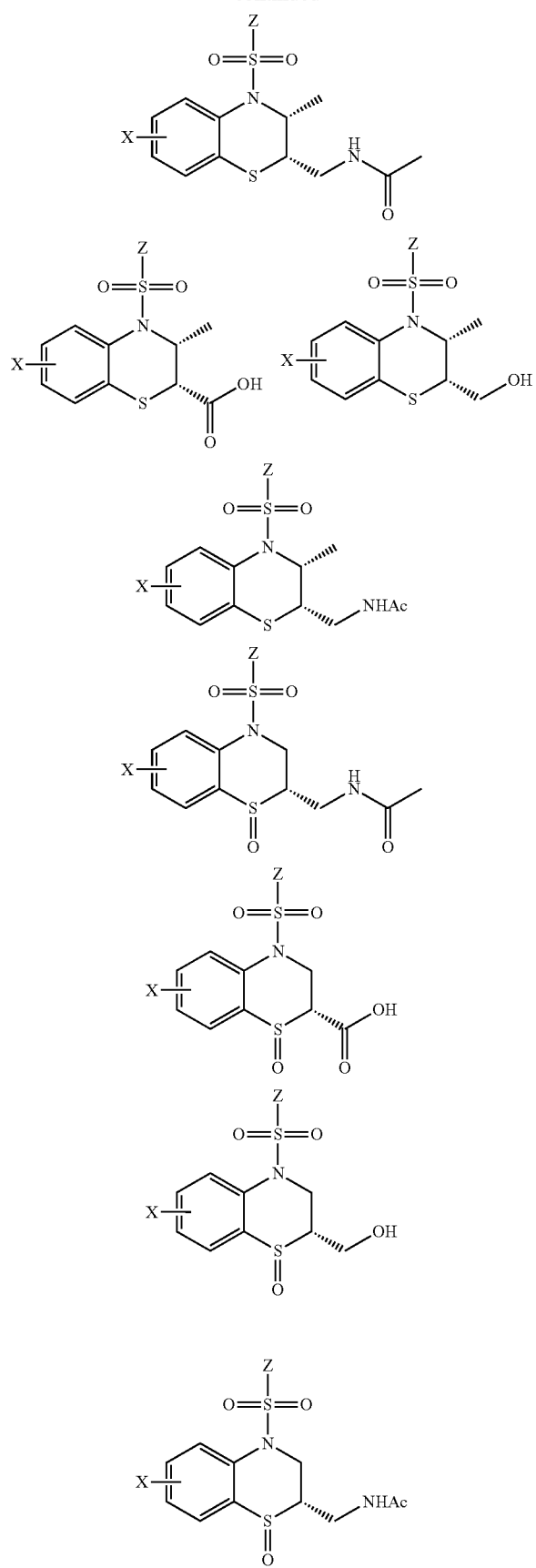
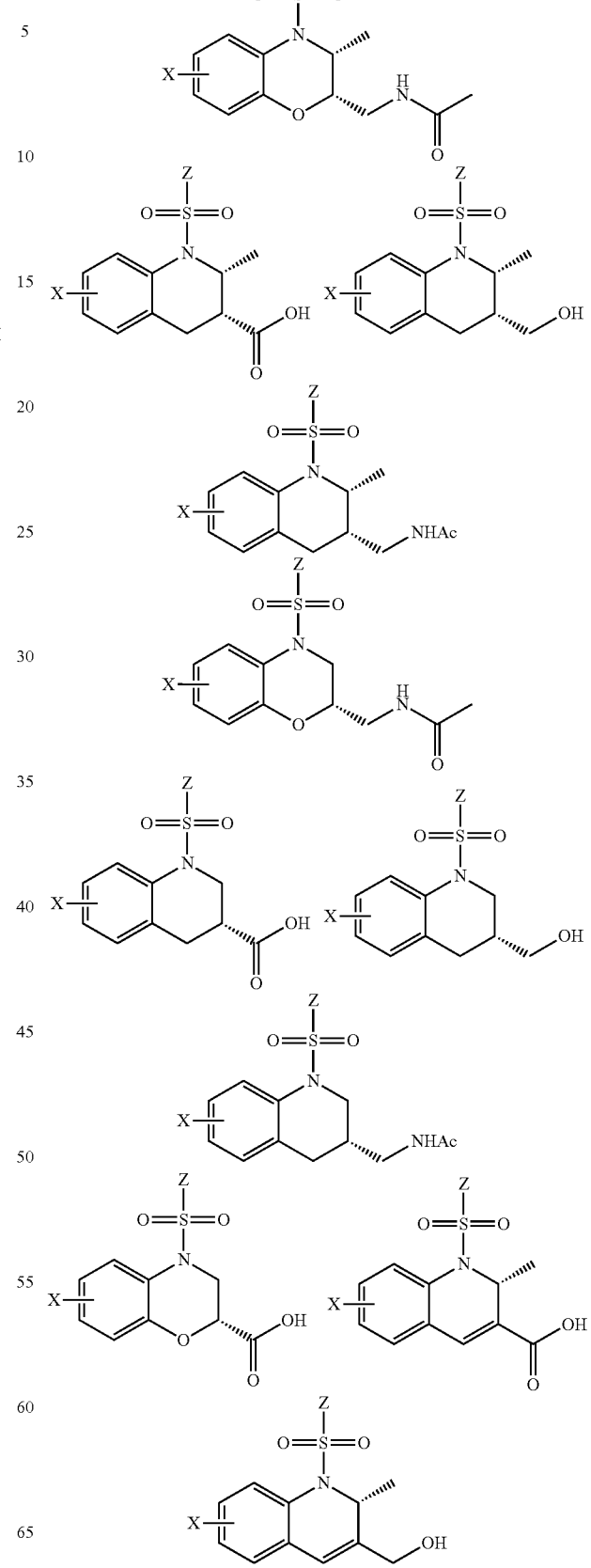

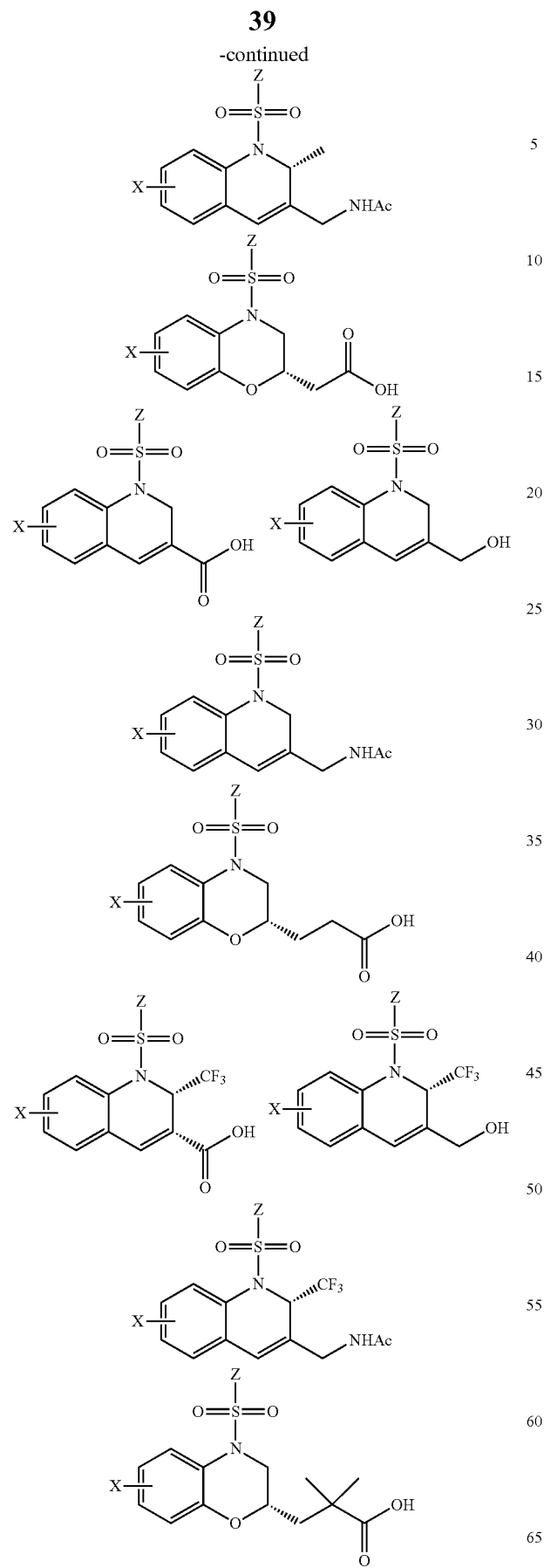
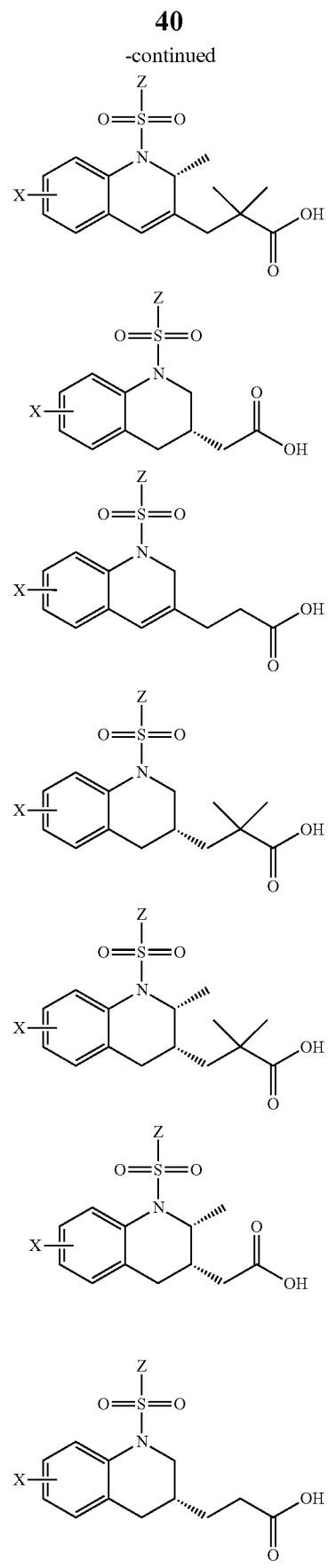

41
-continued
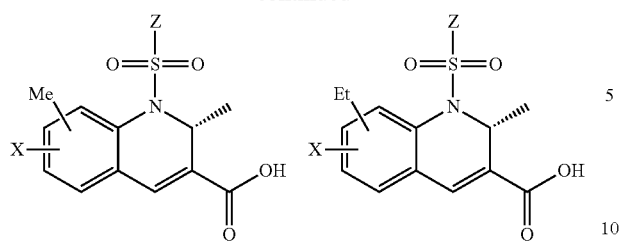
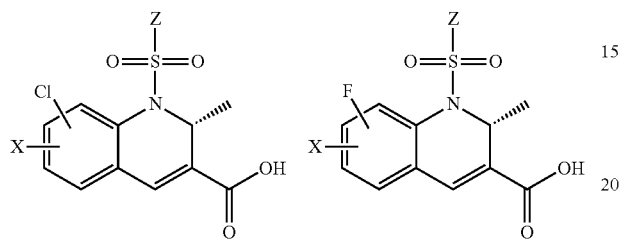
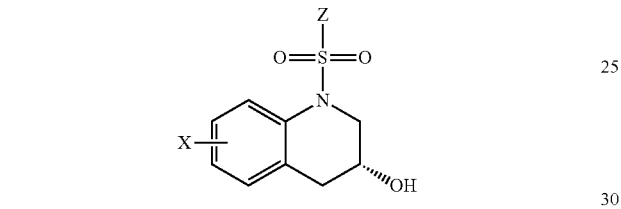
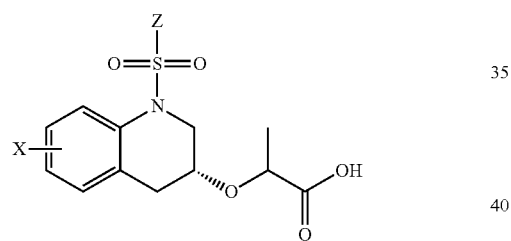
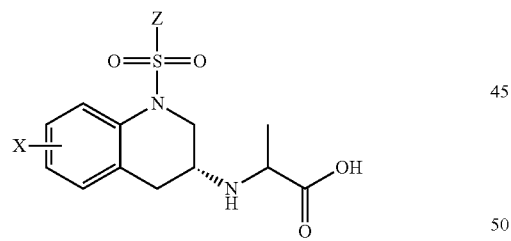
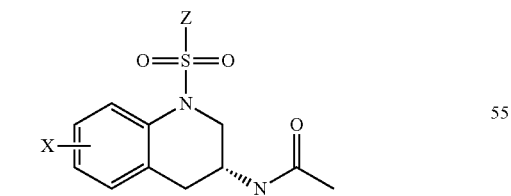
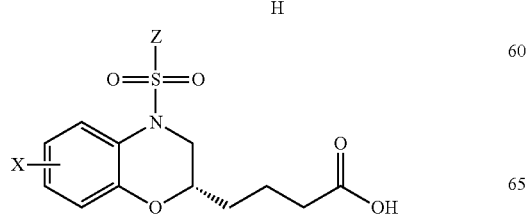
42
-continued
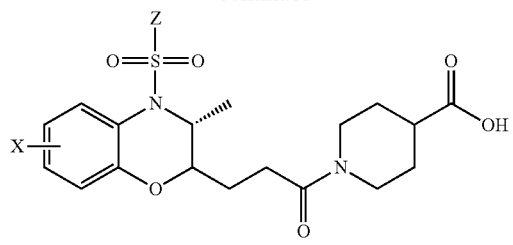
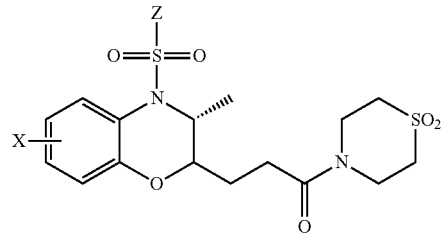
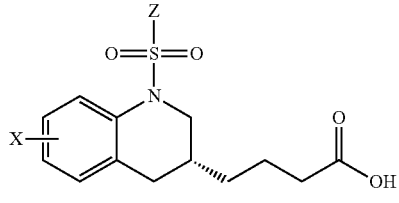
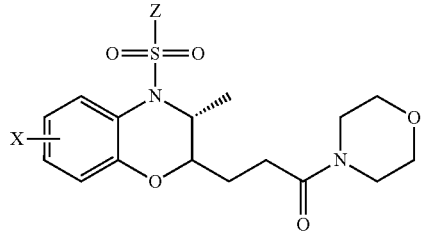
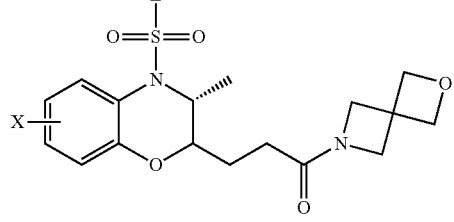
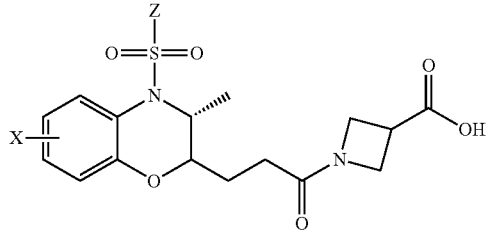
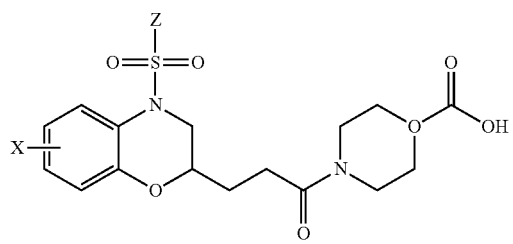

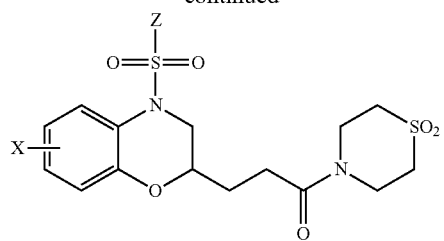
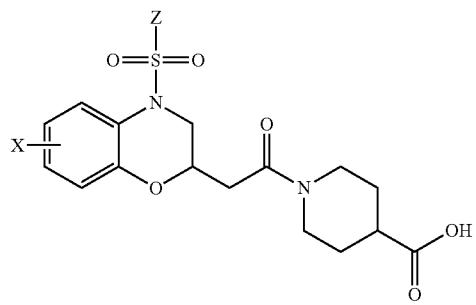
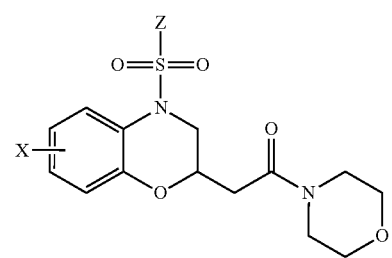
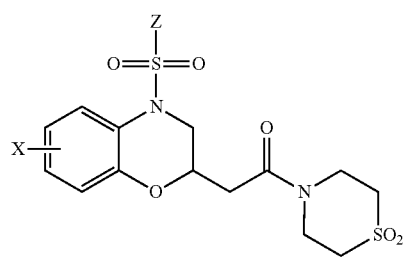
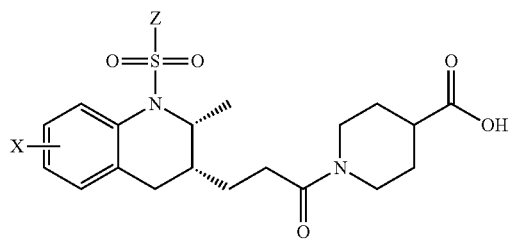
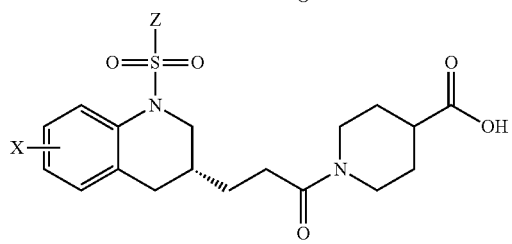
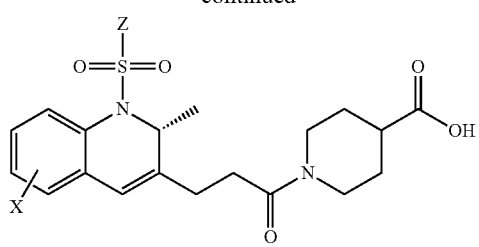
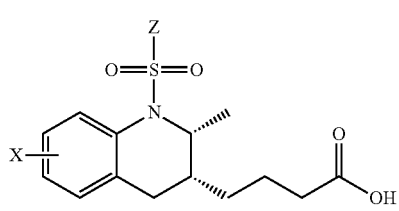
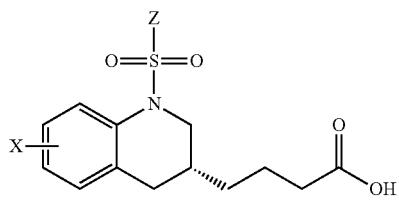
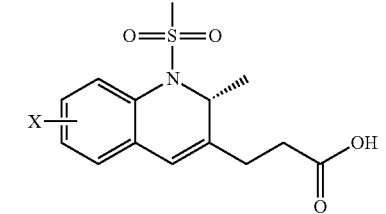
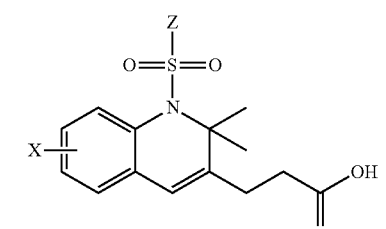
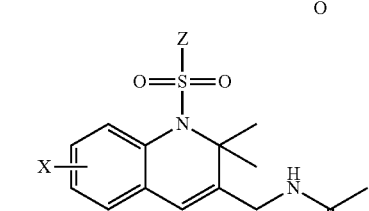
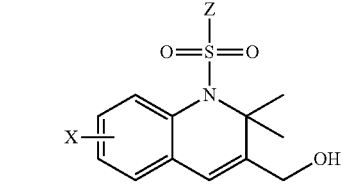

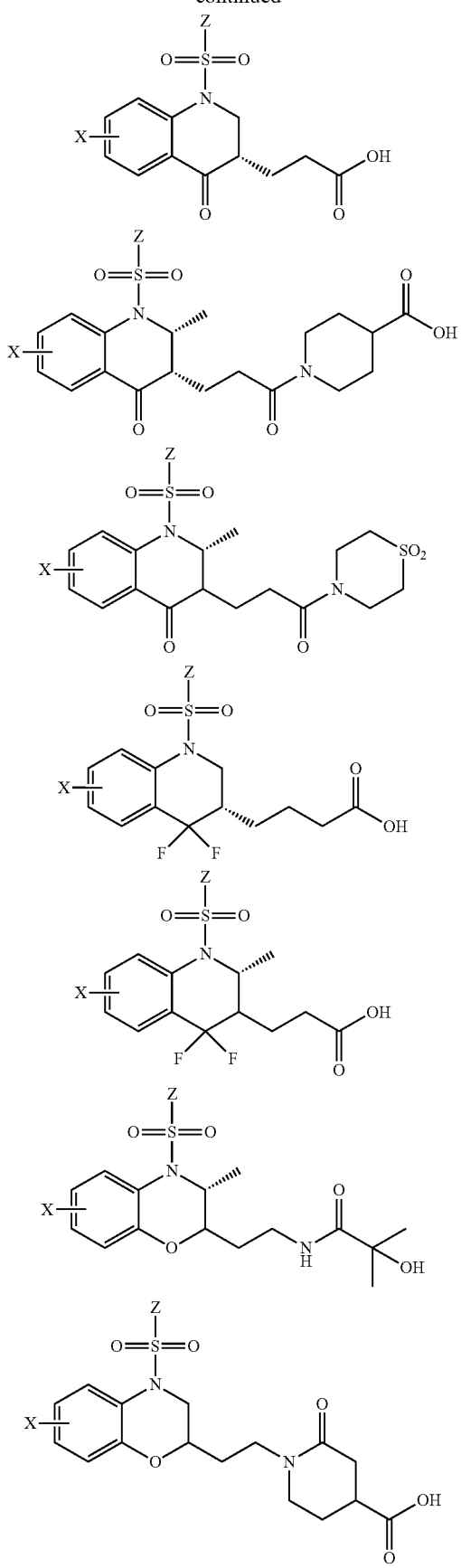
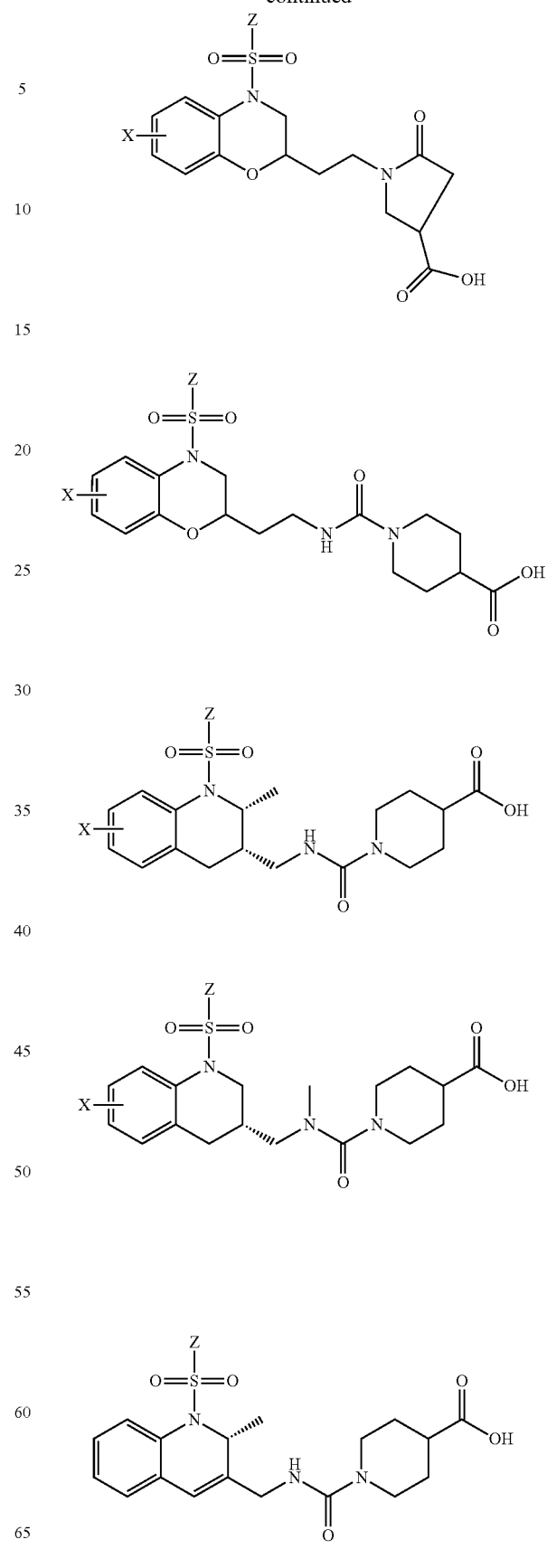

TABLE 1

| No. | X | Z |
|---|---|---|
| I-1 | 2,5-difluorophenyl | 4-fluoro-3-methoxyphenyl |
| I-2 | 2,5-difluorophenyl | 3-chlorophenyl |
| I-3 | 2,5-difluorophenyl | 3-cyclopropylphenyl |
| I-4 | 2,5-difluorophenyl | 4-fluoro-3-(trifluoromethyl)phenyl |
| I-5 | 2,5-difluorophenyl | 1-ethyl-4-chloro-1H-pyrazol-3-yl |
| I-6 | 2,5-difluorophenyl | 1-ethyl-3-ethoxy-1H-pyrazol-4-yl |
| I-7 | 2,5-difluorophenyl | 1-ethyl-3-(2-hydroxyethoxy)-1H-pyrazol-4-yl |
| I-8 | 2,5-difluorophenyl | (3R,5S)-3,5-dimethylpiperidin-1-yl |
| I-9 | 2,5-difluorophenyl | 4-methylpiperidin-1-yl |

TABLE 1-continued

| No. | X | Z |
|---|---|---|
| I-10 | 2,5-difluorophenyl | 3-(trifluoromethyl)phenyl |
| I-11 | 3-chlorophenyl | 3-(trifluoromethyl)phenyl |
| I-12 | 3-methoxyphenyl | 3-(trifluoromethyl)phenyl |
| I-13 | 3-(difluoromethoxy)phenyl | 3-(trifluoromethyl)phenyl |
| I-14 | 3,5-difluorophenyl | 3-(trifluoromethyl)phenyl |
| I-15 | 2,3-difluorophenyl | 3-(trifluoromethyl)phenyl |
| I-16 | phenyl | 3-(trifluoromethyl)phenyl |
| I-17 | 2,5-difluorophenyl | 4-fluoro-3-methoxyphenyl |
| I-18 | 3,4-difluoro-5-chlorophenyl | 3-(trifluoromethyl)phenyl |

TABLE 1-continued
| No. | X | Z |
|---|---|---|
| I-19 | 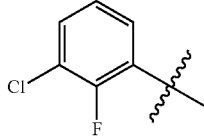 | 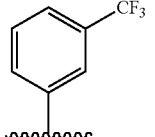 |
| I-20 | 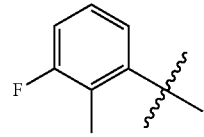 [SMILES: *c1cccc(F)c1C] | 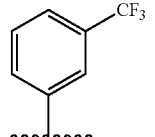 |
| I-21 | 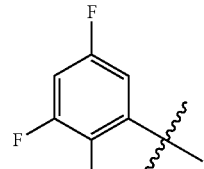 | 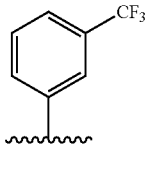 [SMILES: *c1cccc(C(F)(F)F)c1] |
| I-22 | 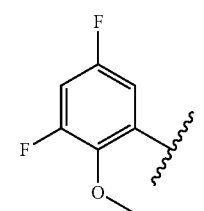 | 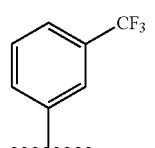 |
| I-23 | 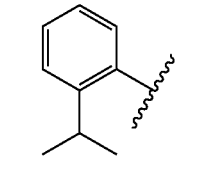 [SMILES: *c1ccccc1C(C)C] | 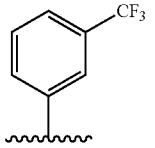 [SMILES: *c1cccc(C(F)(F)F)c1] |
| I-24 | 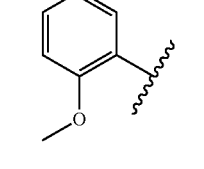 | 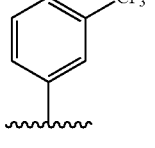 |
| I-25 | 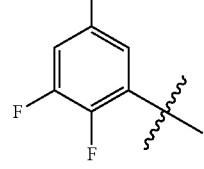 | 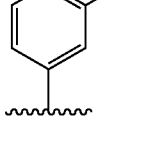 |
| I-26 | 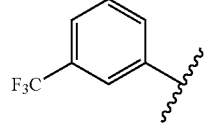 | 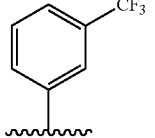 |

TABLE 1-continued

| No. | X | Z |
|---|---|---|
| I-27 | 3-F,5-CF₃-phenyl | 3-CF₃-phenyl |
| I-28 | 6-CF₃-pyridin-2-yl | 3-CF₃-phenyl |
| I-29 | 5-CF₃-pyridin-3-yl | 3-CF₃-phenyl |
| I-30 | 6-methoxy-pyridin-2-yl | 3-CF₃-phenyl |
| I-31 | 6-methoxy-pyrazin-2-yl | 3-CF₃-phenyl |
| I-32 | 6-methoxy-pyridin-2-yl | 3-CF₃-phenyl |
| I-33 | 2-Cl-3,5-diF-phenyl | 3-CF₃-phenyl |
| I-34 | 2,5-diF-phenyl | 4-F-3-OMe-phenyl |
| I-35 | 3-Cl-5-F-phenyl | 3-CF₃-phenyl |

TABLE 1-continued
| No. | X | Z |
|---|---|---|
| I-36 | 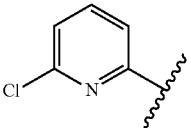 [SMILES: *c1cccc(Cl)n1] | 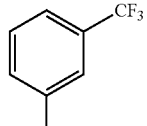 |
| I-37 | 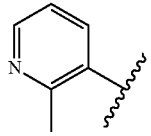 [SMILES: *c1cccnc1C] | 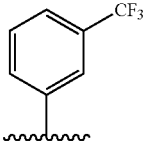 [SMILES: *c1cccc(C(F)(F)F)c1] |
| I-38 | 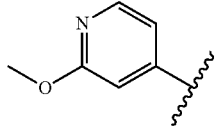 [SMILES: *c1ccnc(OC)c1] | 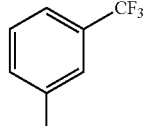 |
| I-39 | 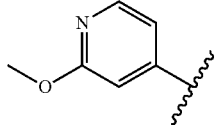 [SMILES: *c1ccnc(OC)c1] | 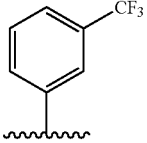 [SMILES: *c1cccc(C(F)(F)F)c1] |
| I-40 | 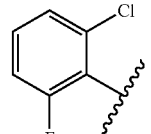 | 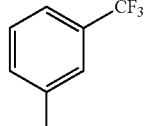 |
| I-41 | 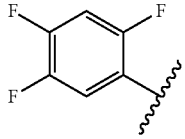 | 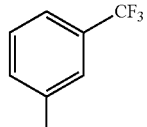 |
| I-42 | 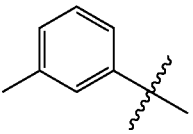 [SMILES: *c1cccc(C)c1] | 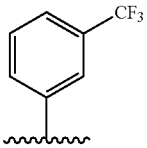 [SMILES: *c1cccc(C(F)(F)F)c1] |
| I-43 | 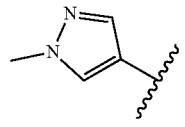 [SMILES: *c1cnn(C)c1] | 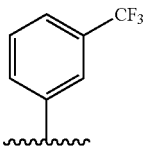 [SMILES: *c1cccc(C(F)(F)F)c1] |
| I-44 | 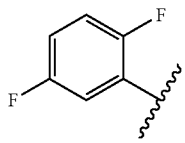 [SMILES: *c1cc(F)ccc1F] | 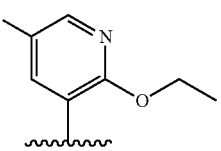 |

TABLE 1-continued

| No. | X | Z |
|---|---|---|
| I-45 | 2,5-difluorophenyl | 5-cyclopropyl-2-(2-hydroxyethoxy)pyridin-3-yl |
| I-46 | 2,5-difluorophenyl | 5-cyclopropyl-2-(2-hydroxyethoxy)pyridin-3-yl |
| I-47 | 2,5-difluorophenyl | 3-isopropylphenyl |
| I-48 | 2,5-difluorophenyl | 4-methyl-3-(trifluoromethyl)phenyl |
| I-49 | 2,5-difluorophenyl | 2-methyl-3-(trifluoromethyl)phenyl |
| I-50 | 2,5-difluorophenyl | 2-ethoxy-4,5,6,7-tetrahydropyrazolo[1,5-a]pyridin-3-yl |
| I-51 | 2,5-difluorophenyl | 5-(trifluoromethyl)pyridin-3-yl |
| I-52 | 2,5-difluorophenyl | 3-cyclopropylphenyl |
| I-53 | 2,5-difluorophenyl | 2-ethoxy-5-(trifluoromethyl)pyridin-3-yl |

TABLE 1-continued

| No. | X | Z |
|---|---|---|
| I-54 | 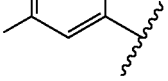 | 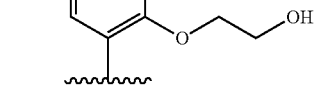 |
| I-55 | 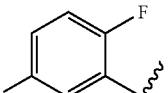 | 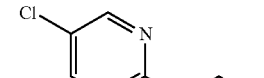 |
| I-56 | 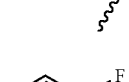 |  |
| I-57 | 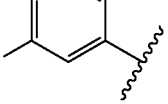 | 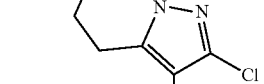 |
| I-58 | 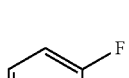 |  |
| I-59 | 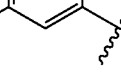 | 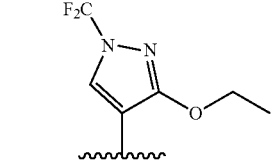 |
| I-60 | 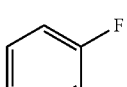 | 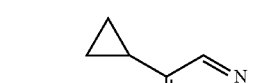 |

In certain embodiments, the compound is a compound in any one of Tables 1-8 herein or a pharmaceutically acceptable salt thereof. In certain other embodiments, the compound is a compound in any one of Tables 1, 2, 3, 4, 5, 6, 7, 8, 9, 10, 11, 12, 13, 14, 15, or 23 herein or a pharmaceutically acceptable salt thereof. In certain other embodiments, the compound is a compound in any one of Tables 2A, 3A, 6A, 9A, 10A, 14A, 15A, 16-22, or 23A herein or a pharmaceutically acceptable salt thereof. In certain embodiments, the compound is a compound in the Examples or a pharmaceutically acceptable salt thereof. In certain embodiments, the compound

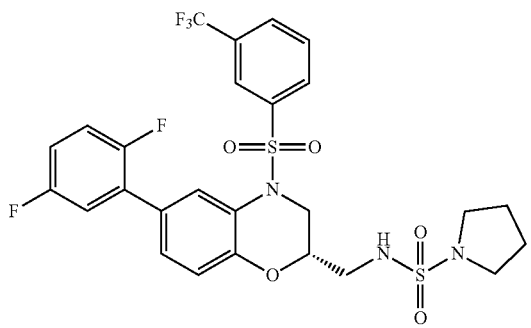 [SMILES: O=S(=O)(NC[C@H]1CN(S(=O)(=O)c2cccc(C(F)(F)F)c2)c2cc(-c3cc(F)ccc3F)ccc2O1)N1CCCC1]

or a pharmaceutically acceptable salt thereof.

Methods for preparing compounds described herein are illustrated in the following synthetic Schemes. The Schemes are given for the purpose of illustrating the invention, and are not intended to limit the scope or spirit of the invention. Starting materials shown in the Schemes can be obtained from commercial sources or be prepared based on procedures described in the literature.

The synthetic route illustrated in Scheme 1 is a general method for preparing substituted 1,2,3,4-tetrahydroquinoline compounds F and G. Reaction of aniline A with diethyl 2-(ethoxymethylene)malonate B followed by thermally induced cyclization with acid affords the substituted ethyl 4-oxo-1,4-dihydroquinoline-3-carboxylate C. Treatment of compound C with phosphoryl trichloride affords the ethyl 4-chloroquinoline-3-carboxylate D. Reduction with borane in pyridine or with transition metal-mediated hydrogenation affords the ethyl 1,2,3,4-tetrahydroquinoline-3-carboxylate E, which can be reacted with a sulphonyl chloride or sulfamoyl chloride to provide the substituted sulfonamide-tetrahydroquinoline F. The ester group of F can be hydrolyzed to afford the substituted 1,2,3,4-tetrahydroquinoline-3-carboxylic acid G. Compound G can be obtained in enanteriomerically enriched form by chiral separation techniques described in the literature for carboxylic acids.

The reaction procedures in Scheme 1 are contemplated to be amenable to preparing a wide variety of 3-substituted 1,2,3,4-tetrahydroquinoline compounds having different substituents at the R, X, and 3-positions. For example, numerous substituted anilines are known in the literature and/or are commercially available or readily prepared from nitroaromatic compounds. Furthermore, if a functional group on a molecule would not be amenable to a reaction condition described in Scheme 1, it is contemplated that the functional group can first be protected using standard protecting group chemistry and strategies, and then the protecting group is removed after completing the desired synthetic transformation. See, for example, Greene, T. W.; Wuts, P. G. M. *Protective Groups in Organic Synthesis*, 2$^{nd}$ ed.; Wiley: New York, 1991, for further description of protecting chemistry and strategies. In certain other embodiments, the ester group in compound F can be converted to another functional group using standard functional group manipulation procedures known in the art. See, for example, "Comprehensive Organic Synthesis" (B. M. Trost & I. Fleming, eds., 1991-1992).

SCHEME 1.

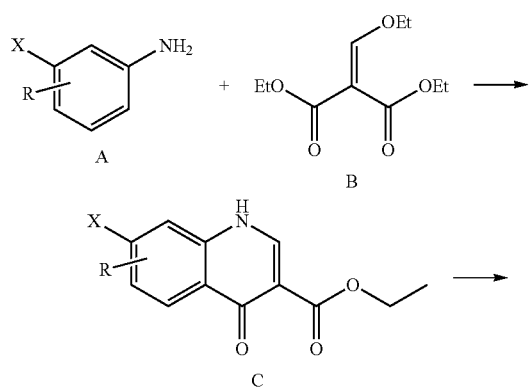

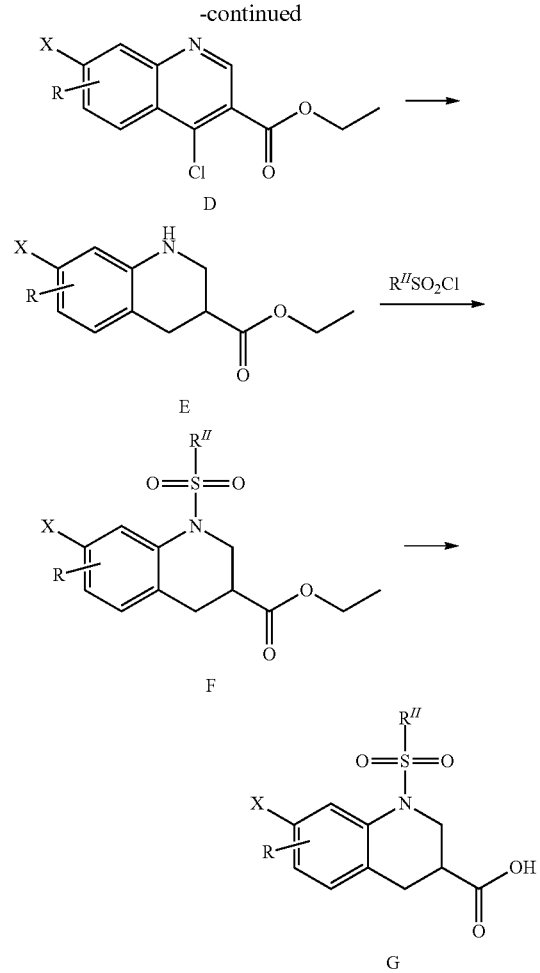

R may be, for example, hydrogen or a substituent, such as methyl or halogen; X may be, for example, phenyl or a 5-10 membered heteroaryl, each of which is optionally substituted; and R″ may be an aromatic or heteroaromatic substituent.

Scheme 2 illustrates a general method for preparing substituted 1,2,3,4-tetrahydroquinoline compound F. Condensation of a substituted 2-nitrobenzaldehyde A with diethyl malonate affords α-β-unsaturated diester B. Reduction of B with sodium borohydride affords diester C. Reduction of the nitro moiety of C with either metal-mediated hydrogenation or dissolving metal reductions (for example Zn/AcOH or Fe in HCl) affords 2-oxo-1,2,3,4-tetrahydroquinoline-3-carboxylate D. Selective reduction of the 2-keto moiety of D affords ethyl 1,2,3,4-tetrahydroquinoline-3-carboxylate E. The ester group in E can be converted to additional functional groups via the methodology described above in connection with Scheme 1.

SCHEME 2.

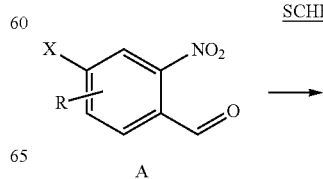

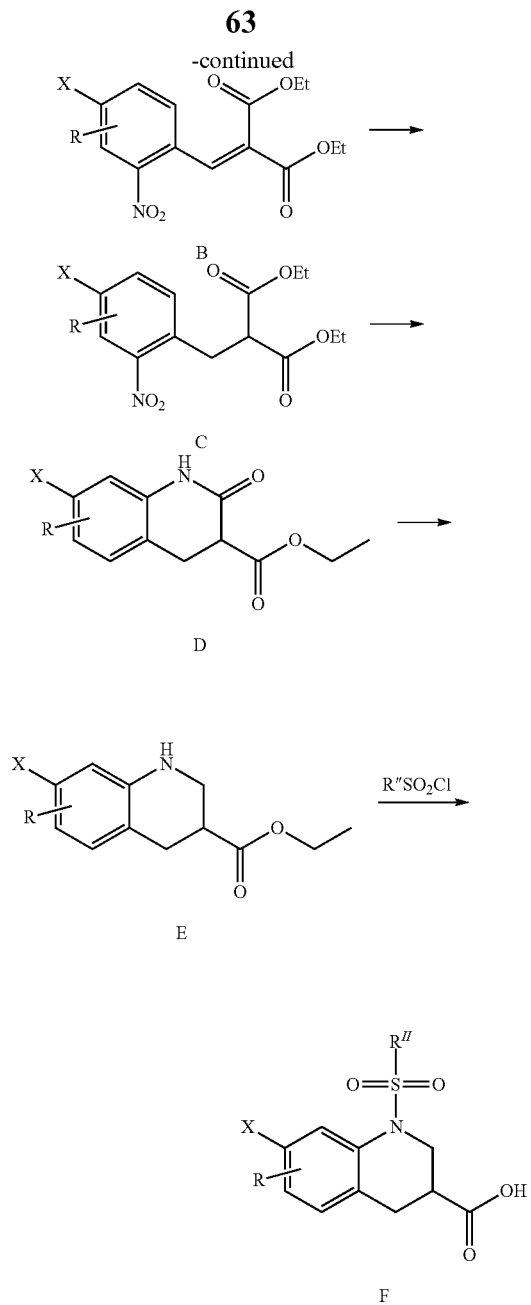

R may be, for example, hydrogen or a substituent, such as methyl or halogen; X may be, for example, phenyl or a 5-10 membered heteroaryl, each of which is optionally substituted; and R" may be an aromatic or heteroaromatic substituent.

Scheme 3 illustrates a general method for preparing substituted (R)-2-alkyl-1-(aryl or heteroaryl sulfonyl)-1,2-dihydroquinoline-3-carboxylic acids D. A tandem Michael-aldol dehydration of a substituted N-(2-formylphenyl)(aryl or heteroaryl)sulfonamide A with a 3-substituted acrylaldehyde B catalyzed by the (S)-diphenylprolinol triethyl silyl ether (see, for example, W. Wang et al., *Org. Lett.* 9: 965-968, 2007; and A. Cordova et al., *Adv. Synth. Catal.* 349: 827-832, 2007) affords substituted (R)-2-alkyl-1-(aryl or heteroaryl sulfonyl)-1,2-dihydroquinoline-3-carbaldehyde C. Oxidation (see, for example, Y. K. Bae et al. *Synlett.* 24: 1848-1850, 2013; S. J. Williams et al. in WO2011/047432) of the aldehyde in C affords substituted (R)-2-alkyl-1-(aryl or heteroaryl sulfonyl)-1,2-dihydroquinoline-3-carboxylic acid D.

SCHEME 3.

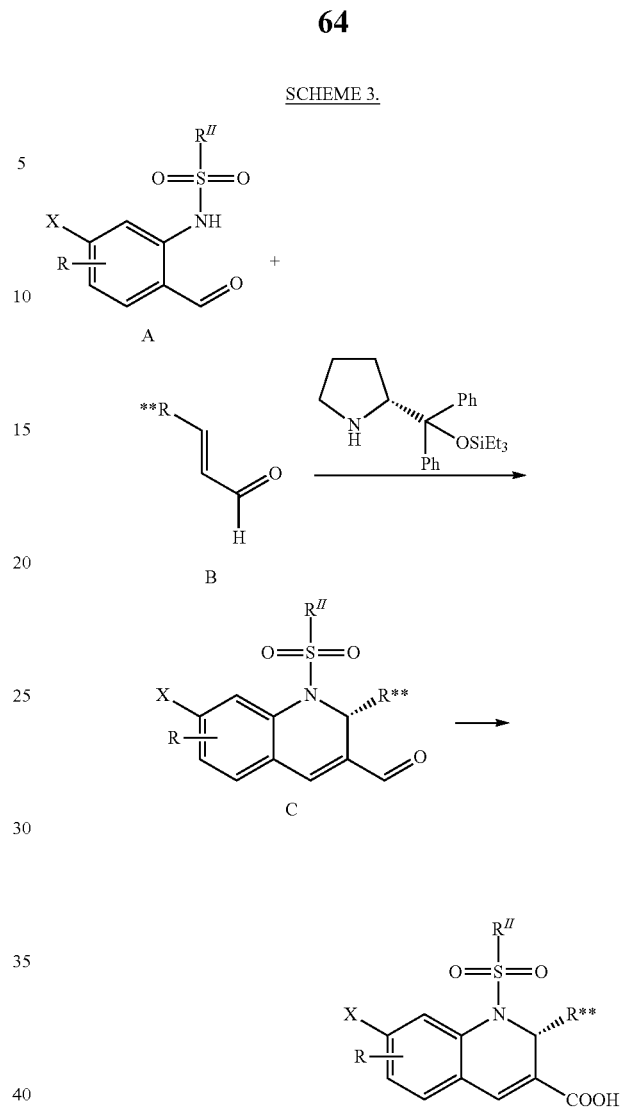

Scheme 4 illustrates a general method for preparing substituted (R)-(2-alkyl-1-(aryl or heteroaryl sulfonyl)-1,2-dihydroquinolin-3-yl)alkyl alcohol B. Reduction of the aldehyde in compound A with sodium borohydride in the presence of cerium (III) chloride (Y. Hamada et al., *Tetrahedron* 64: 11568-11579, 2008) yields compound B where R' is hydrogen. Addition of an alkyl magnesium or alkyl lithium halide in the presence of cerium (III) chloride affords the secondary alcohol B where R' is a lower alkyl (i.e., $C_{1-6}$ alkyl).

SCHEME 4.

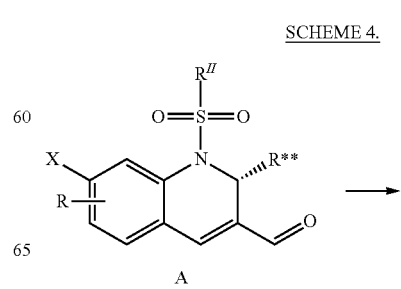

-continued

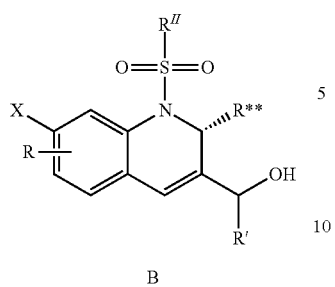

B

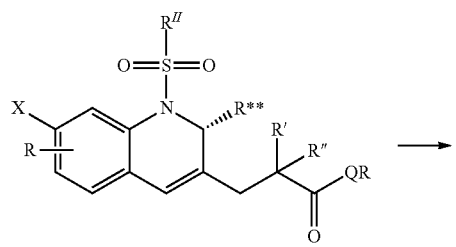

C

Scheme 5 illustrates a general procedure for preparing substituted (R)-3-(2-alkyl-1-(aryl or heteroaryl sulfonyl)-1,2-dihydroquinolin-3-yl)propanoic acid D. Treatment of allylic alcohol A with methane sulfonyl halide (or a tosyl halide or triflic anhydride may be used to activate the hydroxyl group, and alternatively the hydroxyl group may be converted to an allylic halide by methods known in the literature) affords compound B where the allylic hydroxyl is activated with a leaving group. When R' is the same as R", an ester of an appropriate substituted (or unsubstituted) acetic acid is converted to an anion with an appropriate base (e.g., LDA, lithium hexamethyldisilazide, etc.) and is alkylated with B to yield compound C where variable Q is oxygen. When R' is not the same as R", various chiral enolate chemistry methods from the literature may be used to provide a chiral acid (where variable Q may be, for example, oxygen or N(R"")). For example, the anion of an acyloxazolidinone may be utilized. Removal of the chiral auxiliary with an appropriate base (e.g., potassium carbonate, lithium hydroxide in the presence of peroxide) or an acid (for tert-butyl esters) affords (R)-3-(2-alkyl-1-(aryl or heteroaryl sulfonyl)-1,2-dihydroquinolin-3-yl)propanoic acid D.

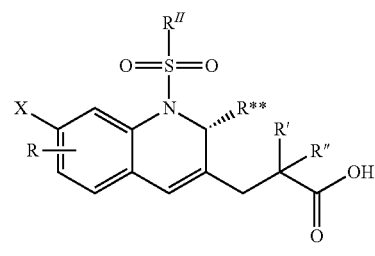

D

Scheme 6 illustrates a general procedure for preparing substituted (R)-(2-alkyl-1-(aryl or heteroarylsulfonyl)-1,2-dihydroquinolin-3-yl)alkylamines C and D. Mitsunobu reaction (D. L. Hughes et al. *Organic Reactions* 42: 1992) of allylic alcohol A with phthalamide affords substituted phthalide B. Treatment of compound B with hydrazine in an appropriate solvent (for example, ethanol or isopropanol; see, for example, H. Itoh et al. in *J. Org. Chem.* 43: 2320, 1978) affords (R)-(2-alkyl-1-(aryl or heteroarylsulfonyl)-1,2-dihydroquinolin-3-yl)alkylamine C. Reductive amination of the amine group in compound C (C. A. Maryanoff et al. *J. Org. Chem.* 61: 3849-3860, 1996) affords (R)-(2-alkyl-1-(aryl or heteroarylsulfonyl)-1,2-dihydroquinolin-3-yl)alkylamine D.

SCHEME 5.

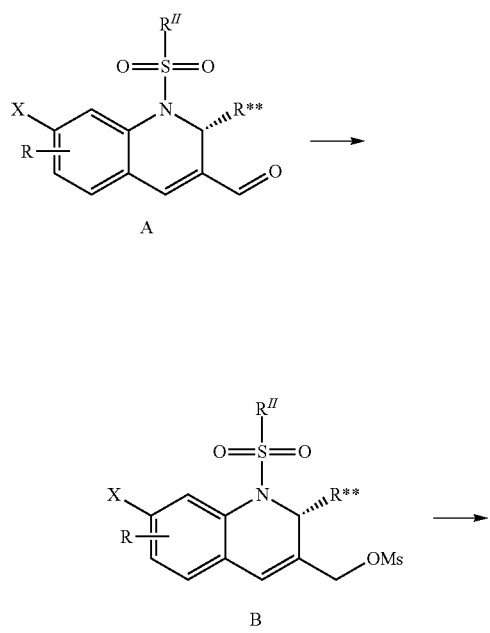

SCHEME 6.

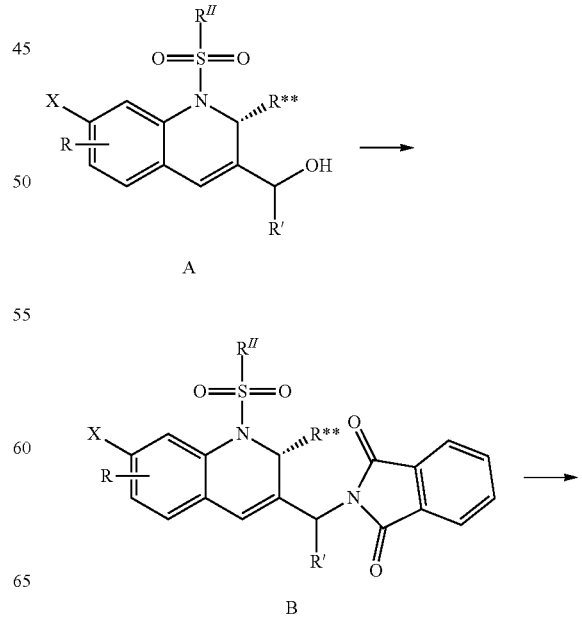

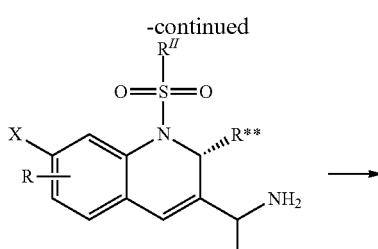

C

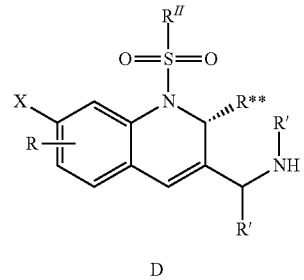

D

Scheme 7 illustrates a general procedure for preparing substituted (R)—N-((2-alkyl-1-(aryl or heteroarylsulfonyl)-1,2-dihydroquinolin-3-yl)alkyl)amide B, substituted (R)—N-((2-alkyl-1-(aryl or heteroarylsulfonyl)-1,2-dihydroquinolin-3-yl)alkyl)carbamate C, substituted (R)—N-((2-alkyl-1-(aryl or heteroarylsulfonyl)-1,2-dihydroquinolin-3-yl)alkyl)ureas or substituted (R)—N-((2-alkyl-1-(aryl or heteroarylsulfonyl)-1,2-dihydroquinolin-3-yl)alkyl)thiourea D, substituted (R)—N-((2-alkyl-1-(aryl or heteroarylsulfonyl)-1,2-dihydroquinolin-3-yl)alkyl)sulfonamide E, and substituted (R)—N-((2-alkyl-1-(aryl or heteroarylsulfonyl)-1,2-dihydroquinolin-3-yl)alkyl)sulfamide F. Reaction of substituted (R)-(2-alkyl-1-(aryl or heteroarylsulfonyl)-1,2-dihydroquinolin-3-yl)alkylamine A with an appropriate base and an acyl halide affords amide B. Alternatively, a coupling agent (e.g., a carbodiimide, PyBOP, treatment of the acid with a chloroformate to make a mixed anhydride, etc.) may be utilized to couple a wide variety of acids to form amide B. The amine A may also be coupled with a chloroformate to afford compound C; with an isocyanate, carbamoyl chloride, or isothiocyanate to afford D; with a sulfonyl halide to afford E; or with a sulfamoyl halide to afford F.

SCHEME 7.

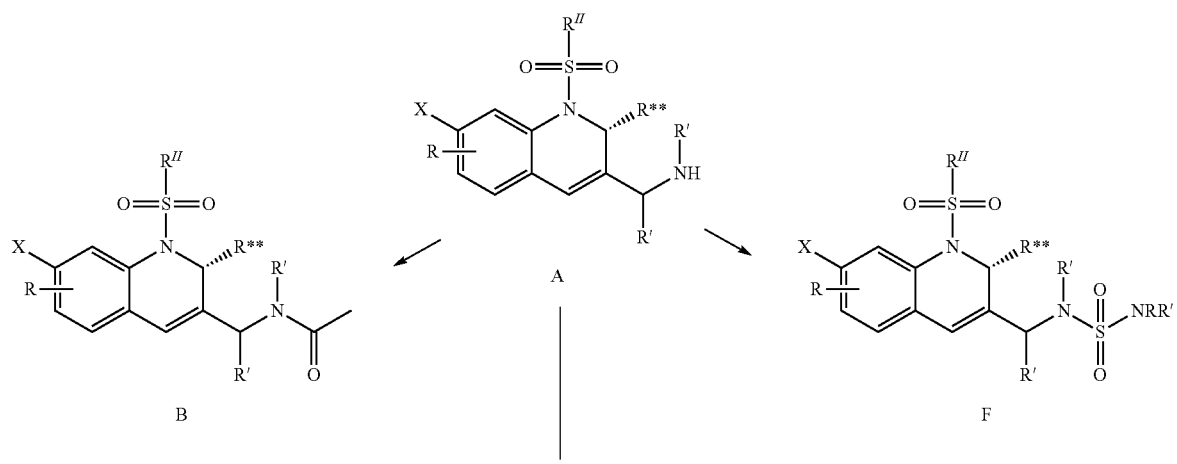

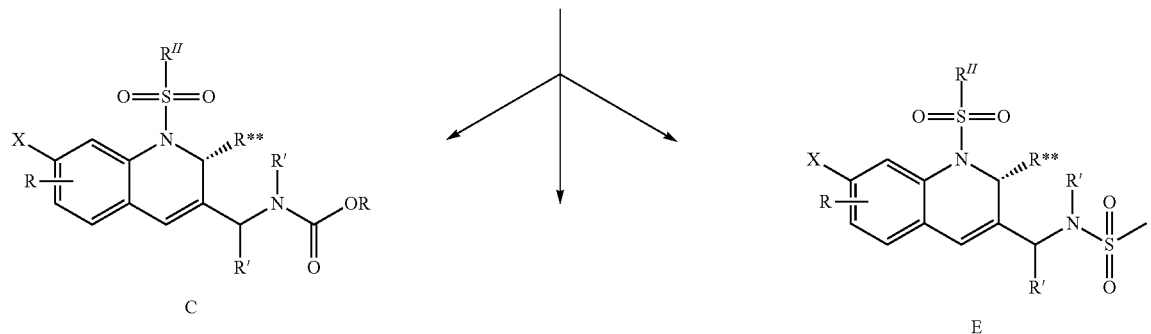

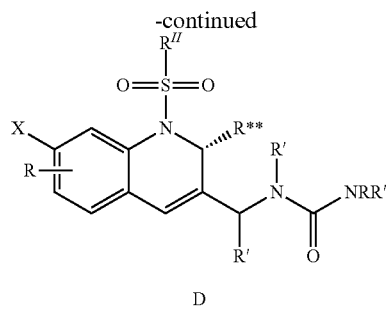

D

Scheme 8 illustrates a general method of preparing substituted cis-(2R,3)-3-substituted-2-alkyl-1-(aryl or heteroarylsulfonyl)-1,2,3,4-tetrahydroquinoline B. Hydrogenation of the substituted (R)-2-alkyl-1-(aryl or heteroarylsulfonyl)-1,2-dihydroquinoline A prepared via the above methods in the presence of a catalyst affords the substituted cis-(2R,3)-3-substituted-2-alkyl-1-(aryl or heteroarylsulfonyl)-1,2,3,4-tetrahydroquinoline B. The choice of the catalyst depends on the substituents X and R. In cases where dehalogenation or reductive removal of benzylic heteroatom is not an issue, Pd or Pt on C may be utilized. In other cases Rh and/or a heterogeneous catalyst which does not reduce these functionalities is more appropriate as is known to those skilled in the art.

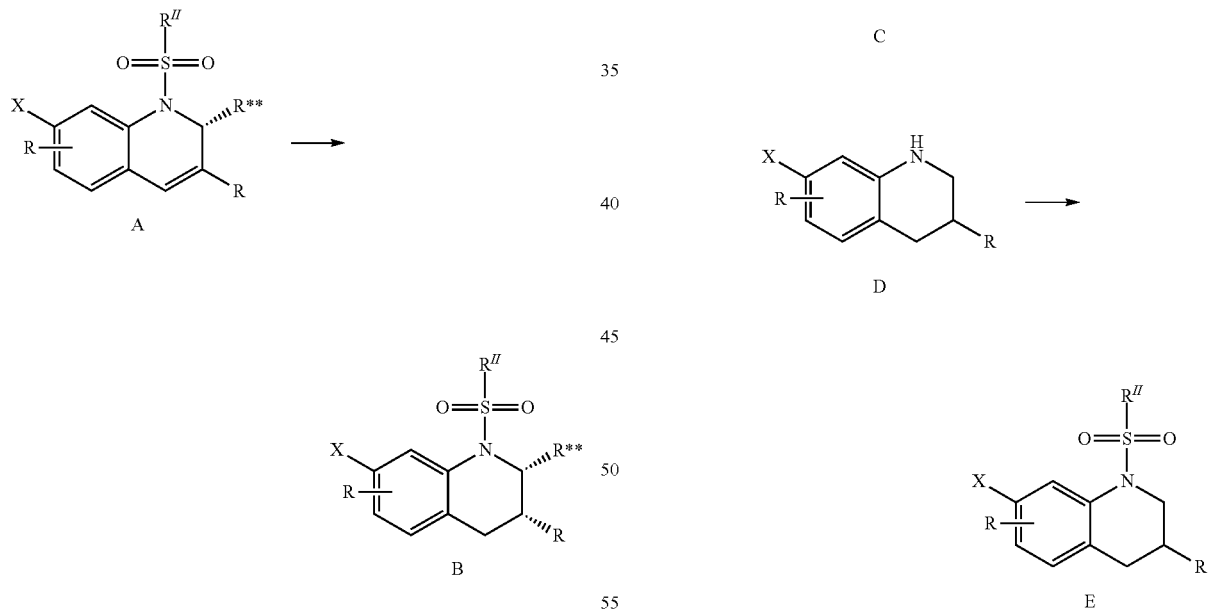

Scheme 9 is an alternative general method to prepare substituted 3-substituted-1-(aryl or heteroarylsulfonyl)-1,2,3,4-tetrahydroquinoline E. A tandem reaction combining radical and ionic cyclization of an halogenated aniline A and a substituted acrylate B affords substituted 3,4-dihydroquinolin-2-one C (N. Jiao et al. *Tetrahedron* 65: 1982-1987, 2009). Reduction of the amide group in C with a hydride (e.g., a borane or lithium aluminum hydride) affords substituted 1,2,3,4-tetrahydroquinoline D. Sulfonylation of D with a sulfonyl halide yields the substituted 3-substituted-1-(aryl or heteroarylsulfonyl)-1,2,3,4-tetrahydroquinoline E.

Scheme 10 illustrates an alternative general method to prepare chiral substituted 3-substituted-1-(aryl or heteroarylsulfonyl)-1,2,3,4-tetrahydroquinolines. Alkylation of an acylated oxazolidinedione B with a 2-nitrobenzylic halide A affords with high diastereomeric excess the 3-arylpropionamide C. Reduction of C with dissolving metal conditions affords chiral substituted 3,4-dihydroquinolin-2-one D which can be elaborated to the substituted 3-substituted-1-(aryl or heteroarylsulfonyl)-1,2,3,4-tetrahydroquinolines E and F based on procedures described above.

SCHEME 10.

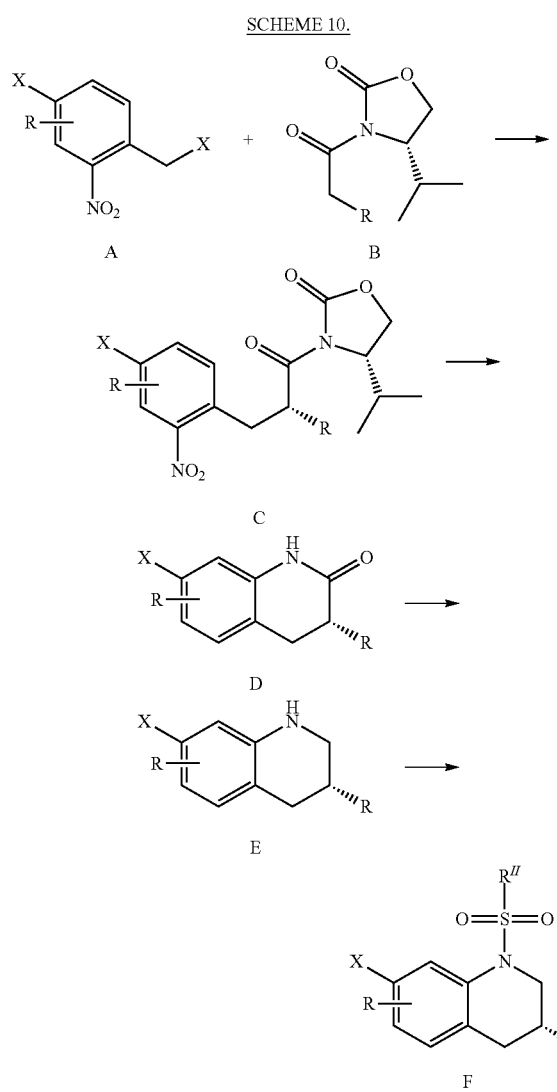

Scheme 11 illustrates an alternative general method of preparing substituted cis-2,3-disubstituted-1-(aryl or heteroarylsulfonyl)-1,2,3,4-tetrahydroquinoline E. Alkylation of β-ketoester B with 2-nitrobenzylic halide A affords substituted 2-(2-nitrobenzyl)-β-ketoester C. Reduction of C affords substituted ethyl cis-2-alkyl-1,2,3,4-tetrahydroquinoline-3-carboxylate D (R. A. Bunce et. al. *J. Heterocyclic Chem.* 44: 1059-1064, 2007). This material can be sulfonylated as described above to afford the substituted cis-2,3-disubstituted-1-(aryl or heteroarylsulfonyl)-1,2,3,4-tetrahydroquinoline E.

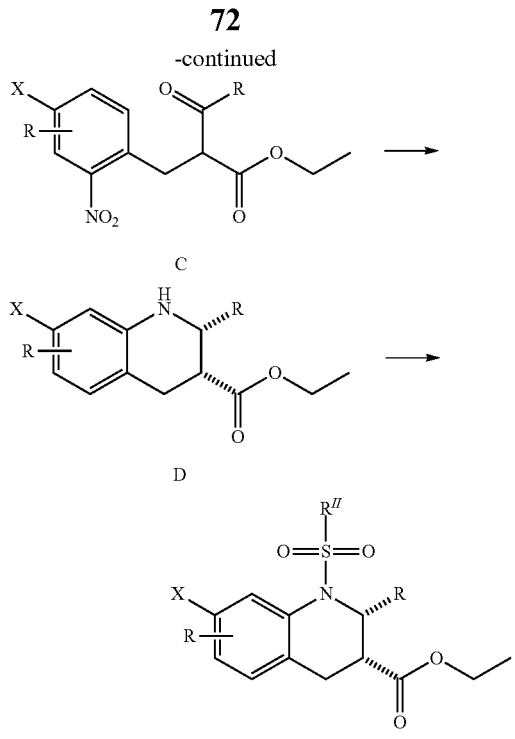

Scheme 12 illustrates a general method of preparing chiral substituted 1-(aryl or hetereoarylsulfonyl)-1,2,3,4-tetrahydroquinoline E substituted at the 3-position with an oxygen bearing group. Wittig reaction of 2-nitroaldehyde A forms α,β-unsaturated ester B, which is subjected to Os-catalyzed asymmetric dihydroxylation with the (DHQ)$_2$-PHAL ligand (see, for example, K. B. Sharpless et al. *Chem. Rev.* 94: 2483-2547, 1994) followed by treatment of the diol with thionyl chloride to form cyclic sulfite C (see, for example, K. B. Sharpless et al. *J. Am. Chem. Soc.* 110: 7538-7539, 1988). Sulfite C undergoes a one-pot cobalt chloride catalyzed reductive cyclization with sodium borohydride (see, for example, A. Sudalai et al. *Organic Letters* 11: 803-806, 2009) to form the substituted chiral 3-hydroxy-1,2,3,4-tetrahydroquinoline D. This material is sulfonylated as described above to afford chiral substituted 1-(aryl or hetereoarylsulfonyl)-3-hydroxy-1,2,3,4-tetrahydroquinoline E. The pendant hydroxyl may be alkylated (for example with 2-chloroacetic acid). When using a different, suitable ligand in the chiral osmylation, the enantiomers of C and then D and E can be produced. The hydroxyl group in E can be mesylated and displaced with azide, and the resulting azido product reduced to afford access to a wide variety of chiral 3-amino substituted-1,2,3,4-tetrahydroquinolines.

SCHEME 11.

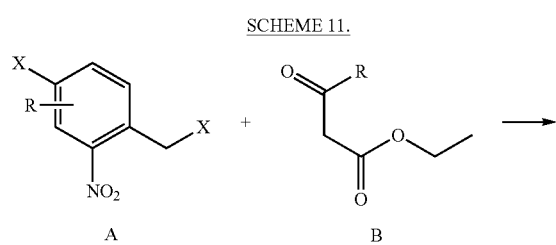

SCHEME 12.

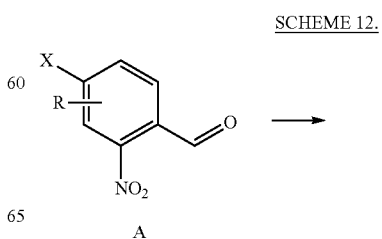

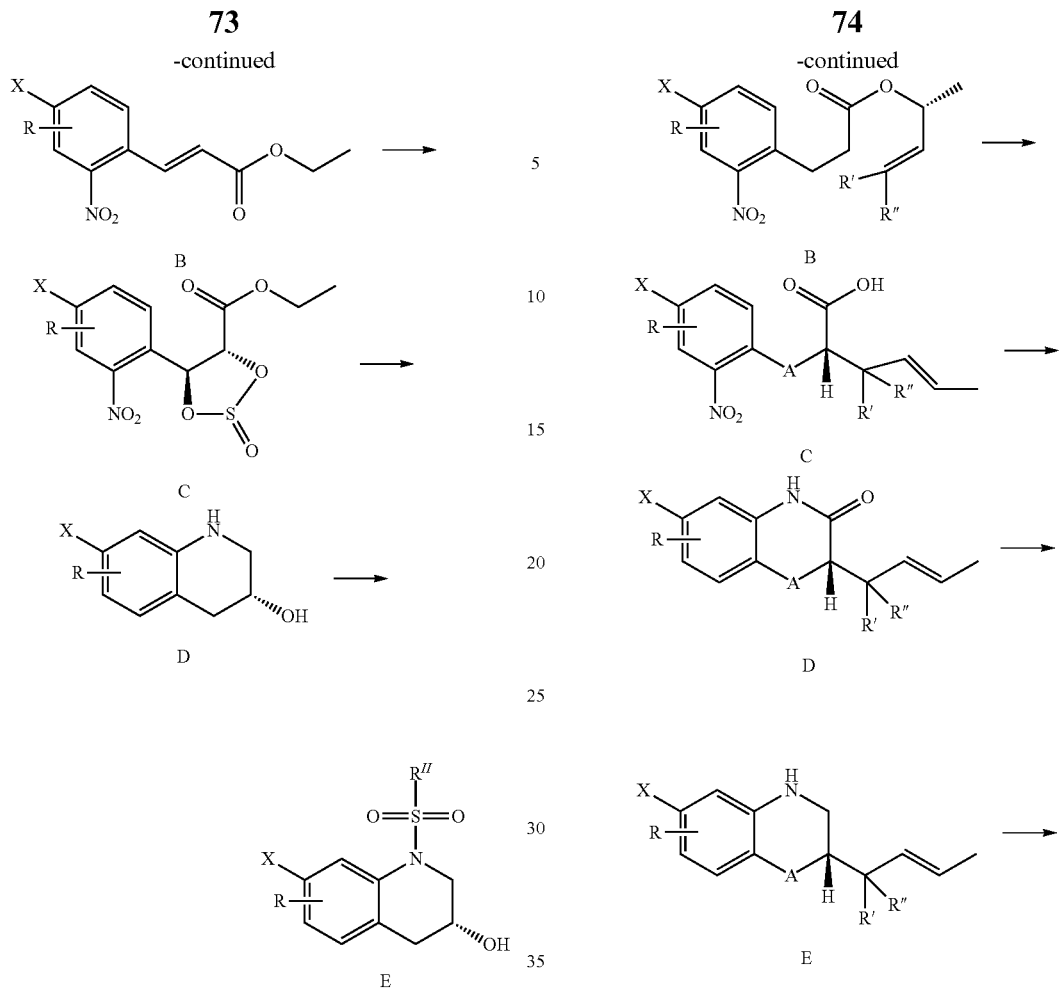

Scheme 13 illustrates a general method of forming chiral 3-substituted-1-(aryl or heteroarylsulfonyl)-1,2,3,4-tetrahydroquinolines (A is CRR') or chiral substituted benzoxazines (A is O). Esterification of the carboxylic acid A with a chiral allylic alcohol forms allylic ester B. Treatment of the enolate of ester B with TMSCl, followed by a Claisen rearrangement (see, for example, J. Kallmerten et al. *J. Org. Chem.* 52: 3889-3901, 1987) affords carboxylic acid C. Esterification of carboxylic acid C with an alcohol followed by a dissolving metal reduction affords lactam D. Reduction of lactam D with borane or lithium aluminum hydride affords tetrahydroquinoline or benzoxazine E, which is sulfonylated to afford the chiral 3-substituted-1-(aryl or heteroarylsulfonyl)-1,2,3,4-tetrahydroquinoline (A is CRR') or chiral substituted benzoxazine (A is O) F. The alkene of F, may be converted to other functional groups (for example to a COOH by oxidation).

Scheme 14 is a general method for preparing various substituted benzoxazine compounds. Reaction of aryl sulfonamide A with an epoxide provides benzoxazine B.

SCHEME 13.

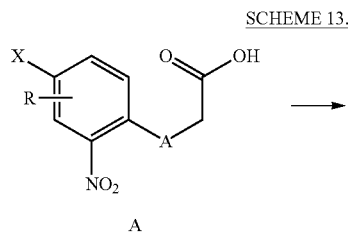

SCHEME 14.

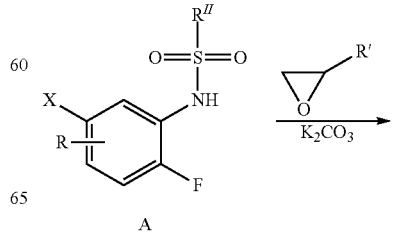

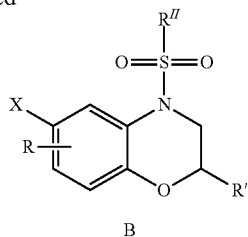

Scheme 15 is another general method for preparing various substituted benzoxazine compounds. Reaction of a 2-fluoro-nitrobenzene A with a 2-hydroxyester B provides 2-O-arylacetic acid ester C. Reduction of the nitro moiety in C with a dissolving metal in an acid forms benzoxazinone D. The amide group in benzoxazinone D can be reduced using, for example, lithium aluminum hydride (LiAlH$_4$) or a borane to provide benzoxazine E, which is treated with a sulfonyl halide and base to afford sulfonylated benzoxazine F.

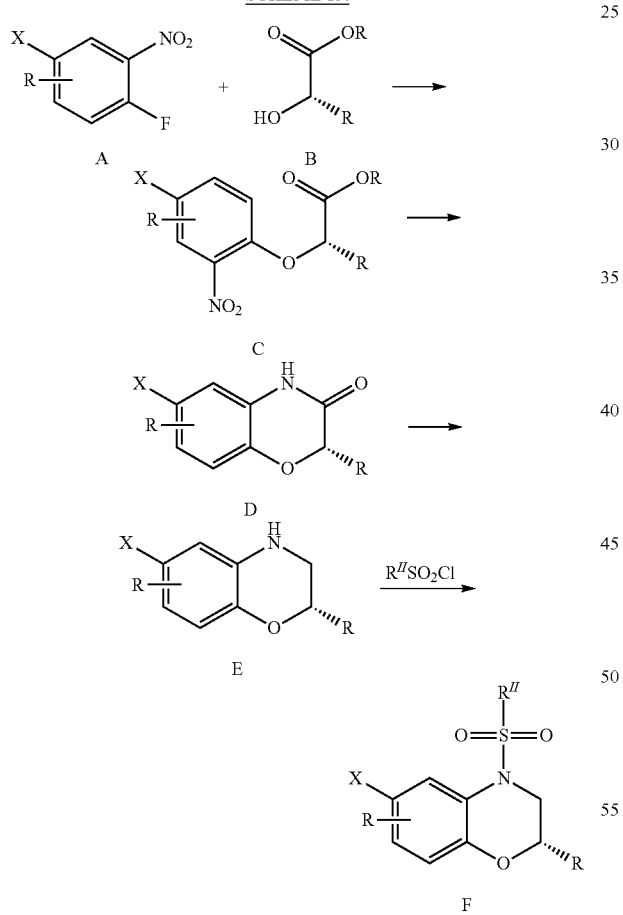

Scheme 16 is a general method for preparing various substituted benzoxazine compounds. Mitsunobu addition of sulfonamide A to chiral α-hydroxyester B affords O-aryl ether C. Treatment of compound C with DIBAL affords aldehyde D, to which vinyl magnesium bromide adds to form the anti-aminoalcohol E (see, for example, D. Gryko et al. *Tetrahedron: Asymmetry* 8: 4059-4067, 1997). Treatment of compound E with base affords benzoxazine F. The vinyl moiety in F is then converted to other alkenes via olefin metathesis chemistry which can be reduced to substituted alkanes, or oxidized to a hydroxyl group, a diol, a carboxylic acid, or other functional group.

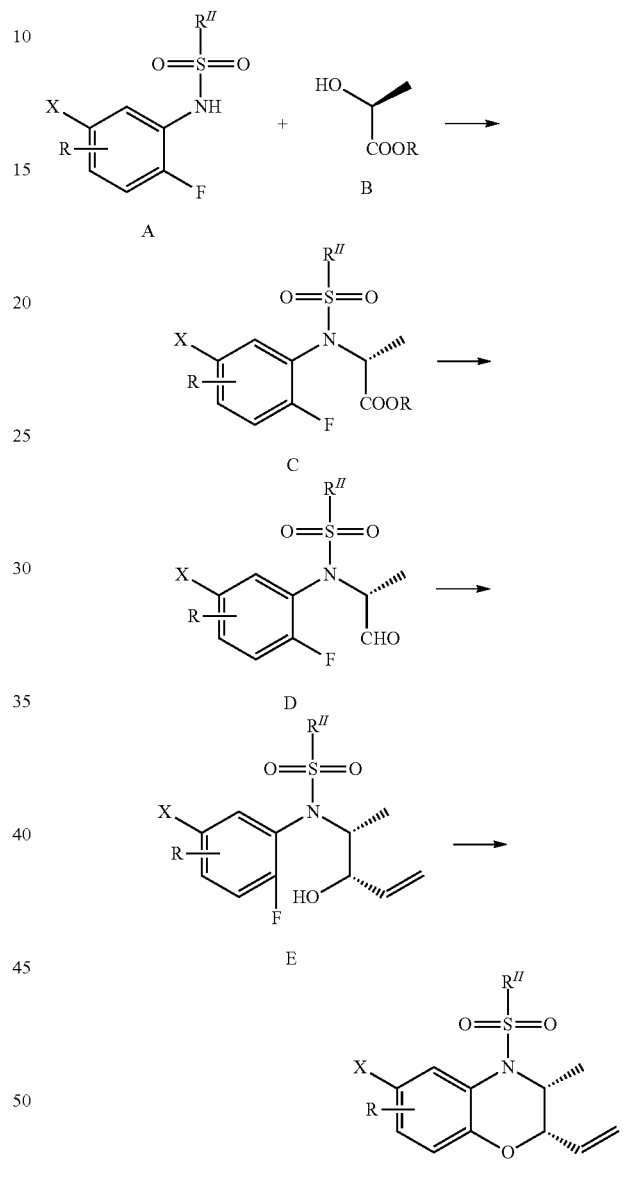

II. Therapeutic Applications of Aryl Dihydro-2H-Benzo[b][1,4]Oxazine Sulfonamide and Related Compounds It is contemplated that the aryl dihydro-2H-benzo[b][1,4]oxazine sulfonamide and related compounds described herein, such as a compound of Formula I, I-A, II, or other compounds in Section I, provide therapeutic benefits to subjects suffering from a cancer, bacterial infection, fungal infection, or immune deficiency disorder. Accordingly, one aspect of the invention provides a method of treating a disorder selected from the group consisting of cancer, bacterial infection, fungal infection, and immune deficiency disorder. The method comprises administering a therapeutically effective amount of an aryl dihydro-2H-benzo[b][1,4]oxazine sulfonamide or related compound described herein, such as a compound of Formula I, I-A, II, or other compounds in Section I, to a subject in need thereof to treat the disorder. In certain embodiments, the particular compound of Formula I, I-A, or II is a compound defined by one of the embodiments described above.

In certain embodiments, the disorder is cancer. In certain embodiments, the cancer is a solid tumor or leukemia. In certain other embodiments, the cancer is colon cancer, pancreatic cancer, breast cancer, ovarian cancer, prostate cancer, squamous cell carcinoma, basal cell carcinoma, adenocarcinoma, sweat gland carcinoma, sebaceous gland carcinoma, lung cancer, leukemia, bladder cancer, stomach cancer, cervical cancer, testicular cancer, skin cancer, rectal cancer, thyroid cancer, kidney cancer, uterus cancer, esophagus cancer, liver cancer, an acoustic neuroma, oligodendroglioma, meningioma, neuroblastoma, or retinoblastoma. In certain other embodiments, the cancer is small cell lung cancer, non-small cell lung cancer, melanoma, cancer of the central nervous system tissue, brain cancer, Hodgkin's lymphoma, non-Hodgkin's lymphoma, cutaneous T-Cell lymphoma, cutaneous B-Cell lymphoma, or diffuse large B-Cell lymphoma. In certain other embodiments, the cancer is breast cancer, colon cancer, small-cell lung cancer, non-small cell lung cancer, prostate cancer, renal cancer, ovarian cancer, leukemia, melanoma, or cancer of the central nervous system tissue. In certain other embodiments, the cancer is colon cancer, small-cell lung cancer, non-small cell lung cancer, renal cancer, ovarian cancer, renal cancer, or melanoma.

Additional exemplary cancers include fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, epithelial carcinoma, glioma, astrocytoma, medulloblastoma, and hemangioblastoma.

In certain embodiments, the cancer is a neuroblastoma, meningioma, hemangiopericytoma, multiple brain metastase, glioblastoma multiforms, glioblastoma, brain stem glioma, poor prognosis malignant brain tumor, malignant glioma, anaplastic astrocytoma, anaplastic oligodendroglioma, neuroendocrine tumor, rectal adeno carcinoma, Dukes C & D colorectal cancer, unresectable colorectal carcinoma, metastatic hepatocellular carcinoma, Kaposi's sarcoma, karotype acute myeloblastic leukemia, Hodgkin's lymphoma, non-Hodgkin's lymphoma, cutaneous T-Cell lymphoma, cutaneous B-Cell lymphoma, diffuse large B-Cell lymphoma, low grade follicular lymphoma, metastatic melanoma, localized melanoma, malignant mesothelioma, malignant pleural effusion mesothelioma syndrome, peritoneal carcinoma, papillary serous carcinoma, gynecologic sarcoma, soft tissue sarcoma, scleroderma, cutaneous vasculitis, Langerhans cell histiocytosis, leiomyosarcoma, fibrodysplasia ossificans progressive, hormone refractory prostate cancer, resected high-risk soft tissue sarcoma, unresectable hepatocellular carcinoma, Waidenstrom's macroglobulinemia, smoldering myeloma, indolent myeloma, fallopian tube cancer, androgen independent prostate cancer, androgen dependent stage IV non-metastatic prostate cancer, hormone-insensitive prostate cancer, chemotherapy-insensitive prostate cancer, papillary thyroid carcinoma, follicular thyroid carcinoma, medullary thyroid carcinoma, or leiomyoma.

In certain embodiments, the disorder is a bacterial infection. The bacterial infection can be characterized according to classifications known in the art. For example, in certain embodiments, the bacterial infection is a gram-positive bacterial infection, such as a gram-positive cocci bacterial infection or a gram-positive bacilli bacterial infection. In other embodiments, the bacterial infection is a gram-negative bacterial infection, such as a gram-negative cocci bacterial infection or a gram-negative bacilli bacterial infection. The bacterial infection can also be characterized according to whether it is caused by anaerobic or aerobic bacteria. Accordingly, in certain embodiments, the bacterial infection is an anaerobic bacterial infection. In certain other embodiments, the bacterial infection is an aerobic bacterial infection.

A variety of bacteria are contemplated to be susceptible to the tetrahydroquinoline compounds. Representative bacteria include Staphylococci species, e.g., *S. aureus*; Enterococci species, e.g., *E. faecalis* and *E. faecium*; Streptococci species, e.g., *S. pyogenes* and *S. pneumoniae; Escherichia* species, e.g., *E. coli*, including enterotoxigenic, enteropathogenic, enteroinvasive, enterohemorrhagic and enteroaggregative *E. coli* strains; *Haemophilus* species, e.g., *H. influenza*; and *Moraxella* species, e.g., *M. catarrhalis*. Other examples include *Mycobacteria* species, e.g., *M. tuberculosis, M. avian-intracellulare, M. kansasii, M. bovis, M. africanum, M. genavense, M. leprae, M. xenopi, M. simiae, M. scrofulaceum, M. malmoense, M. celatum, M. abscessus, M. chelonae, M. szulgai, M. gordonae, M. haemophilum, M. fortuni* and *M. marinum; Corynebacteria* species, e.g., *C. diphtheriae; Vibrio* species, e.g., *V. cholerae; Campylobacter* species, e.g., *C. jejuni; Helicobacter* species, e.g., *H. pylori; Pseudomonas* species, e.g., *P. aeruginosa; Legionella* species, e.g., *L. pneumophila; Treponema* species, e.g., *T. pallidum; Borrelia* species, e.g., *B. burgdorferi; Listeria* species, e.g., *L. monocytogenes; Bacillus* species, e.g., *B. cereus; Bordetella* species, e.g., *B. pertussis; Clostridium* species, e.g., *C. perfringens, C. tetani, C. difficile* and *C. botulinum; Neisseria* species, e.g., *N. meningitidis* and *N. gonorrhoeae; Chlamydia* species, e.g., *C. psittaci, C. pneumoniae* and *C. trachomatis; Rickettsia* species, e.g., *R. rickettsii* and *R. prowazekii; Shigella* species, e.g., *S. sonnei; Salmonella* species, e.g., *S. typhimurium; Yersinia* species, e.g., *Y. enterocolitica* and *Y. pseudotuberculosis; Klebsiella* species, e.g., *K. pneumoniae; Mycoplasma* species, e.g., *M. pneumoniae*; and *Trypanosoma brucei*. In certain embodiments, the compounds described herein are used to treat a subject suffering from a bacterial infection selected from the group consisting of *S. aureus, E. faecalis, E faecium, S. pyogenes, S. pneumonia*, and *P. aeruginosa*.

The antibacterial activity of compounds described herein may be evaluated using assays known in the art, such as the microbroth dilution minimum inhibition concentration (MIC) assay, as further described in National Committee for Clinical Laboratory Standards. Performance Standards for Antimicrobial Susceptibility Testing; Fourteenth Informational Supplement. NCCLS document M100-S14 {ISBN 1-56238-516-X}. This assay may be used to determine the minimum concentration of a compound necessary to prevent visible bacterial growth in a solution. In general, the drug to be tested is serially diluted into wells, and aliquots of liquid bacterial culture are added. This mixture is incubated under appropriate conditions, and then tested for growth of the bacteria. Compounds with low or no antibiotic activity (a high MIC) will allow growth at high concentrations of compound, while compounds with high antibiotic activity will allow bacterial growth only at lower concentrations (a low MIC).

The assay uses stock bacterial culture conditions appropriate for the chosen strain of bacteria. Stock cultures from the permanent stock culture collection can be stored as frozen suspensions at −70° C. Cultures may be suspended in 10% skim milk (BD) prior to snap freezing in dry ice/ethanol and then placed in a −70° C. freezer. Cultures may be maintained on Tryptic Soy Agar containing 5% Sheep Blood at room temperature (20° C.), and each culture may be recovered from frozen form and transferred an additional time before MIC testing. Fresh plates are inoculated the day before testing, incubated overnight, and checked to confirm purity and identity.

The identity and purity of the cultures recovered from the stock culture can be confirmed to rule out the possibility of contamination. The identity of the strains may be confirmed by standard microbiological methods (See, e.g., Murray et al., Manual of Clinical Microbiology, Eighth Edition. ASM Press {ISBN 1-55581-255-4}). In general, cultures are streaked onto appropriate agar plates for visualization of purity, expected colony morphology, and hemolytic patterns. Gram stains can also be utilized. The identities are confirmed using a MicroScan WalkAway 40 SI Instrument (Dade Behring, West Sacramento, Calif.). This device utilizes an automated incubator, reader, and computer to assess for identification purposes the biochemical reactions carried out by each organism. The MicroScan WalkAway can also be used to determine a preliminary MIC, which may be confirmed using the method described below.

Frozen stock cultures may be used as the initial source of organisms for performing microbroth dilution minimum inhibition concentration (MIC) testing. Stock cultures are passed on their standard growth medium for at least 1 growth cycle (18-24 hours) prior to their use. Most bacteria may be prepared directly from agar plates in 10 mL aliquots of the appropriate broth medium. Bacterial cultures are adjusted to the opacity of a 0.5 McFarland Standard (optical density value of 0.28-0.33 on a Perkin-Elmer Lambda EZ150 Spectrophotometer, Wellesley, Mass., set at a wavelength of 600 nm). The adjusted cultures are then diluted 400 fold (0.25 mL inoculum+100 mL broth) in growth media to produce a starting suspension of approximately 5×105 colony forming units (CFU)/mL. Most bacterial strains may be tested in cation adjusted Mueller Hinton Broth (CAMHB).

Test compounds ("drugs") are solubilized in a solvent suitable for the assay, such as DMSO. Drug stock solutions may be prepared on the day of testing. Microbroth dilution stock plates may be prepared in two dilution series, 64 to 0.06 µg drug/mL and 0.25 to 0.00025 µg drug/mL. For the high concentration series, 200 µL of stock solution (2 mg/mL) is added to duplicate rows of a 96-well microtiter plate. This is used as the first well in the dilution series. Serial two-fold decremental dilutions are made using a BioMek FX robot (Beckman Coulter Inc., Fullerton, Calif.) with 10 of the remaining 11 wells, each of which will contain 100 µL of the appropriate solvent/diluent. Row 12 contains solvent/diluent only and serves as the control. For the first well of the low concentration series, 200 µL of an 8 µg/mL stock are added to duplicate rows of a 96-well plate. Serial two-fold dilutions are made as described above.

Daughter 96-well plates may be spotted (3.2 µL/well) from the stock plates listed above using the BioMek FX robot and used immediately or frozen at −70° C. until use. Aerobic organisms are inoculated (100 µL volumes) into the thawed plates using the BioMek FX robot. The inoculated plates are be placed in stacks and covered with an empty plate. These plates are then incubated for 16 to 24 hours in ambient atmosphere according to CLSI guidelines (National Committee for Clinical Laboratory Standards, Methods for Dilution, Antimicrobial Tests for Bacteria that Grow Aerobically; Approved Standard-Sixth Edition. NCCLS document M7-A6 {ISBN 1-56238-486-4}).

After inoculation and incubation, the degree of bacterial growth can be estimated visually with the aid of a Test Reading Mirror (Dynex Technologies 220 16) in a darkened room with a single light shining directly through the top of the microbroth tray. The MIC is the lowest concentration of drug that prevents macroscopically visible growth under the conditions of the test.

In certain embodiments, the disorder is a fungal infection. Exemplary fungi that may be treated include, for example, *Acremonium, Absidia* (e.g., *Absidia corymbifera*), *Alternaria, Aspergillus* (e.g., *Aspergillus clavatus, Aspergillus flavus, Aspergillus fumigatus, Aspergillus nidulans, Aspergillus niger, Aspergillus terreus*, and *Aspergillus versicolor*), *Aureobasidium, Basidiobolus, Blastomyces* (e.g., *Blastomyces dermatitidis*), *Candida* (e.g., *Candida albicans, Candida glabrata, Candida guilliermondii, Candida kefyr, Candida krusei, Candida lusitaniae, Candida parapsilosis, Candida pseudotropicalis, Candida stellatoidea, Candida tropicalis, Candida utilis, Candida lipolytica, Candida famata* and *Candida rugosa*), *Cephalosporium, Chaetomium, Chrysosporium, Cladosporium* (e.g., *Cladosporium carrionii* and *Cladosporium trichloides*), *Coccidioides* (e.g., *Coccidioides immitis*), *Conidiobolus, Coprinus, Corynespora, Cryptococcus* (e.g., *Cryptococcus neoformans*), *Curvularia, Cunninghamella* (e.g., *Cunninghamella elegans*), *Exophiala* (e.g., *Exophiala dermatitidis* and *Exophiala spinifera*), *Epidermophyton* (e.g., *Epidermophyton floccosum*), *Fonsecaea* (e.g., *Fonsecaea pedrosoi*), *Fusarium* (e.g., *Fusarium solani*), *Geotrichum* (e.g., *Geotrichum candiddum* and *Geotrichum clavatum*), *Hendersonula, Histoplasma, Leptosphaeria, Loboa, Madurella, Malassezia* (e.g., *Malasseziaf furfur*), *Microsporum* (e.g., *Microsporum canis* and *Microsporum gypseum*), *Mycocentrospora, Mucor, Neotestudina, Paecilomyces, Paracoccidioides* (e.g., *Paracoccidioides brasiliensis*), *Penicillium* (e.g., *Penicillium marneffei*), *Phialophora, Pneumocystis* (e.g., *Pneumocystis carinii*), *Pseudallescheria* (e.g., *Pseudallescheria boydii*), *Rhinosporidium, Rhizomucor, Rhizopus* (e.g., *Rhizopus microsporus* var. *rhizopodiformis* and *Rhizopus oryzae*), *Saccharomyces* (e.g., *Saccharomyces cerevisiae*), *Scopulariopsis, Sporothrix* (e.g., *Sporothrix schenckii*), *Trichophyton* (e.g., *Trichophyton mentagrophytes* and *Trichophyton rubrum*), *Trichosporon* (e.g., *Trichosporon asahii, Trichosporon beigelii* and *Trichosporon cutaneum*), and *Wangiella*.

In certain embodiments, the disorder is an immune deficiency disorder. Exemplary immune deficiency disorders include, for example, a human immunodeficiency viral infection, a patient with a deficient immune system due to chemotherapy, or a patient recovering from surgery who has a deficient immune system.

In certain embodiments, the subject is a human.

Another aspect of the invention provides for the use of a compound described herein (such as a compound of Formula I, I-A, II, or other compounds in Section I) in the manufacture of a medicament. In certain embodiments, the medicament is for treating a disorder described herein, such as cancer.

Another aspect of the invention provides for the use of a compound described herein (such as a compound of Formula I, I-A, II, or other compounds in Section I) for treating a medical disorder, such a medical disorder described herein (e.g., cancer).

Further, it is contemplated that aryl dihydro-2H-benzo[b][1,4]oxazine sulfonamide and related compounds described herein, such as a compound of Formula I, I-A, II, or other compounds in Section I, can promote the activity of RORγ. Accordingly, another aspect of the invention provides a method of promoting the activity of RORγ. The method comprises exposing a RORγ to an effective amount of an aryl dihydro-2H-benzo[b][1,4]oxazine sulfonamide or related compound described herein, such as a compound of Formula I, I-A, IL, or other compounds in Section I, to promote RORγ activity. In certain embodiments, the particular compound of Formula I, I-A, or II is the compound defined by one of the embodiments described above. Promoting the activity of RORγ means to increase the activity of RORγ. In certain embodiments, exposing a RORγ to an effective amount of an aryl dihydro-2H-benzo[b][1,4]oxazine sulfonamide or related compound described herein (such as a compound of Formula I, I-A, II, or other compounds in Section I) results in an increase in RORγ activity of at least 5%, 10%, 20%, or 50% relative to the activity of RORγ under substantially the same conditions but without the presence of the aryl dihydro-2H-benzo[b][1,4]oxazine sulfonamide or related compound.

Further, it is contemplated that aryl dihydro-2H-benzo[b][1,4]oxazine sulfonamide and related compounds described herein, such as a compound of Formula I, I-A, II, or other compounds in Section I, can increase the amount of interleukin-17 (IL-17) in a subject. IL-17 is a cytokine that affects numerous biological functions. Accordingly, another aspect of the invention provides a method of increasing the amount of IL-17 in a subject. The method comprises administering to a subject an effective amount of an aryl dihydro-2H-benzo[b][1,4]oxazine sulfonamide or related compound described herein, such as a compound of Formula I, I-A, IL, or other compounds in Section I, to increase the amount of IL-17 in the subject. In certain embodiments, the particular compound of Formula I, I-A, or II is the compound defined by one of the embodiments described above.

In certain embodiments, the subject is a human. In certain embodiments, administering the compound increases the amount of IL-17 produced by Th-17 cells in the subject. A change in the amount of IL-17 produced by, for example, Th-17 cells can be measured using procedures described in the literature, such as an ELISA assay or intracellular staining assay.

Further, it is contemplated that aryl dihydro-2H-benzo[b][1,4]oxazine sulfonamide and related compounds described herein, such as a compound of Formula I, I-A, II, or other compounds in Section I, may increase the synthesis of IL-17 in a subject. Accordingly, another aspect of the invention provides a method of increasing the synthesis of IL-17 in a subject. The method comprises administering to a subject an effective amount of a compound described herein, e.g., a compound of Formula I, I-A, II, or other compounds in Section I, to increase the synthesis of IL-17 in the subject. In certain embodiments, the particular compound of Formula I, I-A, or II is a compound defined by one of the embodiments described above.

Adoptive Cellular Therapy

RORγ agonist compounds described herein may also be used in adoptive cellular therapy to treat various medical disorders, such as cancer, bacterial infections, fungal infections, and immune disorders. Cells, e.g., lymphocyte cells or dendritic cells, are exposed ex vivo to an RORγ agonist compound herein, and then the treated cells are administered to a patient. In adoptive cellular transfer, cells are obtained from a source (typically the patient in need of treatment), cultured ex vivo with an agent, and then the resulting cells are administered to the patient in need of therapy. The culturing typically subjects the cells to conditions whereby the cells increase in number (i.e., expansion) and/or acquire features providing improved therapeutic benefit. General features of the adoptive cellular therapy methods and compositions are described below, along with more specific embodiments of the lymphocyte cells, dendritic cells, and procedures for isolating and culturing cells.

Accordingly, one aspect of the invention provides a method of delivering to a patient a RORγ agonist treated cell selected from the group consisting of a lymphocyte cell and dendritic cell. The method comprises administering to a patient in need thereof a pharmaceutical composition comprising said cell that has been exposed ex vivo to an agonist of RORγ described herein, such as a compound of Formula I, I-A, or II. The method may further comprise a culturing step. In such embodiments, the method further comprises culturing a cell (i.e., the lymphocyte cell or dendritic cell) with an agonist of RORγ to provide the cell that has been exposed ex vivo to the agonist of RORγ. The culturing may comprise exposing the cell to a cytokine (e.g., IL-1β, IL-2, IL-6, IL-7, IL-1β, IL-12, IL-15, IL-18, IL-21, IL-23, or transforming growth factor beta). During the culturing step, the cell may be exposed to an antigen associated with a medical disorder. Although not to be bound by theory, cells having an receptor specific to an antigen associated with a medical disorder can provide a more effective therapy than cells lacking such a receptor. Accordingly, in certain embodiments, the culturing step comprises exposing the cell to an antigen associated with a medical disorder. The antigen may be an antigen presenting cell. Alternatively, the antigen may comprise cancer tissue. Further, as described below, the cell may be genetically altered to express a receptor specific to an antigen associated with a medical disorder.

The cell may be autologous or allogenic. Autologous cells are cells obtained from the patient whom will receive the cell exposed ex vivo to an agonist of RORγ. As such, in certain embodiments, the method may further comprise obtaining a cell from said patient, for use in the culturing step. Alternatively, the cells may be allogenic, i.e., obtained from a subject that produces cells allogenic to cells of the patient. In such embodiments, the method may further comprise obtaining a cell from a subject that produces cells allogenic to lymphocyte cells of the patient, for use in the culturing step.

In certain embodiments, the cell is a lymphocyte cell. Lymphocyte cells can be obtained from human or animal tissues according to procedures described in the literature. In certain embodiments, the lymphocyte cell is obtained from blood, cancer tissue, bone marrow, the spleen, a lymph node, or the thymus. In certain other embodiments, the lymphocyte cell is obtained from a population of peripheral blood mononuclear cells, such as human peripheral blood mononuclear cells. In certain other embodiments, the lymphocyte cell is obtained from a lymph node in proximity to a tumor or site of infection. In certain other embodiments, the lymphocyte cell is obtained from cancer tissue. In yet other embodiments, the lymphocyte cell is a tumor-infiltrating-lymphocyte cell.

Cells can be characterized according to the presence of a receptor for an antigen specific for a medical disorder. In certain embodiments, the cell expresses a receptor for an antigen specific for a medical disorder. As indicate above, such cells may provide more effective therapies for treating disease since the cells are more likely to target tissue specific to the disease to be treated. In certain embodiments, the medical disorder is a cancer, bacterial infection, fungal infection, or immune disorder. In yet other embodiments, the cell may express a receptor that, while not specific for a medical disorder, has utility in enhancing cell efficacy in treating the disorder.

Various types of lymphocyte cells have been described in the literature for use in adoptive cellular transfer. In certain embodiments, the lymphocyte cell is a T cell. In certain other embodiments, the lymphocyte cell is a $CD8^+$ T cell, $CD4^+$ T cell, or $T_H17$ cell. In certain other embodiments, the lymphocyte cell is a $CD8^+$ T cell, $CD4^+$ T cell, or a combination thereof. In certain other embodiments, the lymphocyte cell is a natural killer cell. In certain other embodiments, the lymphocyte cell is a Tc17 cell, natural killer T cell, or $\gamma\delta$ T cell. In yet other embodiments, the lymphocyte cell is a genetically altered lymphocyte cell.

Cells may be administered to the patient according to procedures described in the literature. In certain embodiments, the administering comprises injecting into the patient the pharmaceutical composition. The injecting may be intravenous injection or injection directly into diseased tissue, such as a tumor. In yet other embodiments, the injecting may be subcutaneous injection into the patient.

The therapeutic method embraces combination therapies, such as administering (i) an agent that enhances the efficacy of the cell exposed to the agonist of ROR$\gamma$ and/or (ii) an agent having independent efficacy in treating the target medical disorder.

Another aspect of the invention provides a method of preparing a population of cells that have been exposed ex vivo to an agonist of ROR$\gamma$ described herein, where the cells are lymphocyte cells and/or dendritic cells. The method comprises exposing a population of cells selected from the group consisting of lymphocyte cells and dendritic cells ex vivo to an agonist of ROR$\gamma$ described herein to thereby provide said population of cells that have been exposed ex vivo to an agonist of ROR$\gamma$. The population of cells may be used in therapeutic methods described herein. The exposing step may comprise culturing a population of cells with the agonist of ROR$\gamma$ for a duration of time sufficient to increase the number of cells in the population. The culturing may comprise exposing the cell to a cytokine (e.g., IL-1$\beta$, IL-2, IL-6, IL-7, IL-1$\beta$, IL-12, IL-15, IL-18, IL-21, IL-23, or transforming growth factor beta). Further during the culturing step, the cell may optionally be exposed to an antigen associated with a medical disorder. Accordingly, in certain embodiments, the culturing step comprises exposing the cell to an antigen associated with a medical disorder. The antigen may be an antigen presenting cell. Alternatively, the antigen may comprise cancer tissue. The cell may be autologous or allogenic. Autologous cells are cells obtained from the patient whom will receive the cell exposed ex vivo to an agonist of ROR$\gamma$. As such, in certain embodiments, the method may further comprise obtaining a cell (i.e., a lymphocyte or dendritic cell) from said patient for use in the culturing step. Alternatively, the cells may be allogenic, i.e., obtained from subject that produces cells allogenic to cells of the patient. In such embodiments, the method may further comprise obtaining a cell from a subject that produces cells allogenic to cells of the patient, for use in the culturing step. In certain embodiments, the cell is a lymphocyte cell. Lymphocyte cells can be obtained from human or animal tissues according to procedures described in the literature. In certain embodiments, the lymphocyte cell is obtained from blood, cancer tissue, bone marrow, the spleen, a lymph node, or the thymus. In certain other embodiments, the lymphocyte cell is obtained from a population of peripheral blood mononuclear cells, such as human peripheral blood mononuclear cells. In certain other embodiments, the lymphocyte cell is obtained from a lymph node in proximity to a tumor or site of infection. In certain other embodiments, the lymphocyte cell is obtained from cancer tissue. In yet other embodiments, the lymphocyte cell is a tumor-infiltrating-lymphocyte cell.

Cells can be characterized according to the presence of a receptor for an antigen specific for a medical disorder. In certain embodiments, the cell expresses a receptor for an antigen specific for a medical disorder. As indicated above, such cells may provide more effective therapies for treating disease since the cells is more likely to target tissue specific to the disease to be treated. In certain embodiments, the medical disorder is a cancer, bacterial infection, fungal infection, or immune disorder. In yet other embodiments, the cell may express a receptor that, while not specific for a medical disorder, has utility in enhancing cell efficacy in treating the disorder.

As described above, various types of lymphocyte cells have been described in the literature for use in adoptive cellular transfer. In certain embodiments, the lymphocyte cell is a T cell. In certain other embodiments, the lymphocyte cell is a $CD8^+$ T cell, $CD4^+$ T cell, or $T_H17$ cell. In certain other embodiments, the lymphocyte cell is a $CD8^+$ T cell, $CD4^+$ T cell, or a combination thereof. In certain other embodiments, the lymphocyte cell is a natural killer cell. In certain other embodiments, the lymphocyte cell is a Tc17, natural killer T cell, or $\gamma\delta$ T cell. In yet other embodiments, the lymphocyte cell is a genetically altered lymphocyte cell.

Another aspect of the invention provides a method of treating a medical disorder. The method comprises administering to a patient in need thereof a cell that has been exposed ex vivo to an agonist of ROR$\gamma$ described herein to treat the medical disorder, wherein the cell is a lymphocyte cell or dendritic cell. The medical disorder can be, for example, a cancer, bacterial infection, fungal infection, or immune disorder. Additional exemplary medical disorders are described above, and in certain embodiments, the medical disorder is a cancer selected from the group consisting of a solid tumor, lymphoma, and leukemia. In certain other embodiments, the medical disorder is a cancer selected from the group consisting of ovarian cancer, melanoma, colorectal cancer, lung cancer, breast cancer, prostate cancer, pancreatic cancer, renal cell carcinoma, leukemia, a B-cell lymphoma, and non-Hodgkin lymphoma.

Another aspect of the invention provides a population of lymphocyte cells that have been exposed ex vivo to an agonist of ROR$\gamma$ described herein. The population may be characterized by the presence and/or quantity of particular types of cells in the population. For example, in certain embodiments, the population comprises one or more of the following: T cells and natural killer cells. In certain other embodiments, a majority of lymphocyte cells in the population are T cells. In certain other embodiments, a majority of lymphocyte cells in the population are $CD8^+$ T cells, $CD4^+$ T cells, $T_H17$ cells, or a combination thereof. In yet other embodiments, a majority of lymphocyte cells in the population are natural killer cells. In yet other embodiments, a single type of lymphocyte cell (e.g., a T cell, $CD8^+$ T cell, $CD4^+$ T cell, $T_H17$ cell, Tc17 cell, natural killer T cell, or $\gamma\delta$ T cell) comprises at least 60%, 70% 80%, 90% or 95% of the cells in the population. In yet other embodiments, the population is characterized by: (i) a majority of lymphocyte cells in the population are T cells, (ii) a majority of lymphocyte cells in the population are CD8+ T cells, CD4+ T cells, $T_H17$ cells, or a combination thereof, (iii) a majority of lymphocyte cells in the population are Tc17 cells, (iv) a majority of lymphocyte cells in the population are natural killer cells, or (v) a majority of lymphocyte cells in the population are natural killer T cells, γδ T cells, or a combination thereof. In yet other embodiments, a majority of lymphocyte cells in the population are CD8+ T cells, CD4+ T cells, or a combination thereof. In yet other embodiments, the population is characterized by a majority of lymphocyte cells in the population are Tc17 cells, CD4+Th0 T lymphocyte cells, Th17-polarized CD4+ T lymphocyte cells, CD8+ Tc17 T lymphocyte cells, or a combination thereof.

In each of the above aspects and embodiments, lymphocyte cells may be characterized according to whether they are a tumor infiltrating lymphocyte, naïve T lymphocyte, memory T lymphocyte, effector T lymphocyte, CD8+ T cell, CD4+ T cell, CD4+/CD8+ double positive T lymphocyte, CD28+CD8+ T cell, or $T_H17$ cell. CD8+ T cells can be separated into naïve CD8+ T cells, memory CD8+ T cells, and effector CD8+ T cells, according to cell surface antigens characteristic to each type of cell. Whether a cell or cell population is positive for a particular cell surface marker can be determined by flow cytometry using staining with a specific antibody for the surface marker and an isotype matched control antibody. A cell population negative for a marker refers to the absence of significant staining of the cell population with the specific antibody above the isotype control, and positive refers to uniform staining of the cell population above the isotype control. For instance, CD4+ T helper cells can be sorted into naïve, central memory, and effector cells by identifying cell populations that have cell surface antigens. In certain embodiments, central memory CD4+ T cells are CD62L positive and CD45RO positive. In certain embodiments, effector CD4+ T cells are CD62L and CD45RO negative. In yet other embodiments, the lymphocyte cell is a Th1 cell, Tc1 cell, Th0 cell, or Tc0 cell. In certain embodiments, the lymphocyte cell is a CD8+ T cell, which is optionally further characterized according to the whether the CD8+ T cell is a naïve CD8+ T cell, a memory CD8+ T cell, or an effector CD8+ T cell. In certain embodiments, the lymphocyte cell is a memory CD8+ T cell, which may be further characterized according to whether the cell is CD62L positive or CD45RO positive. In certain other embodiments, the lymphocyte cell is an effector CD8+ T cell, which may be further characterized according to whether the cell is CD62L negative or CD45RO negative. In yet other embodiments, the lymphocyte cell is a CD4+ Th0 T lymphocyte, Th17-polarized CD4+ T lymphocyte, or CD8+ Tc17 T lymphocyte. In still other embodiments, the lymphocyte cell is a memory T cell present in CD62L+ or CD62L− subsets of CD8+ peripheral blood lymphocytes. In certain embodiments, the central memory T cells may be CD45RO+, CD62L+, CD8+ T cells. In certain embodiments, effector T cells are negative for CD62L, CCR7, CD28, and CD127, and positive for granzyme B and perforin.

T cells can be characterized according to identity of a T cell receptor located on the surface of the T cell. The T cell receptor is a disulfide-linked membrane-anchored heterodimer that normally consists of highly variable alpha (α) and beta (β) chains expressed as part of a complex with the invariant CD3 chain molecules. T cells expressing this receptor are referred to as α:β (or αβ) T cells. A minority of T cells express an alternate receptor, formed by variable gamma (γ) and delta (δ) chains, and such T cells are referred as γδ T cells. One subtype of T cells is natural killer T (NKT) cells. NKT cells are a heterogeneous group of T cells that share properties of both T cells and natural killer NK cells. Many NKT cells recognize the non-polymorphic CD1d molecule, an antigen-presenting molecule that binds self- and foreign lipids and glycolipids. Other subtypes of T cells include, for example, CD8+ T cells, CD4+ T cells, Tc17 cells, natural killer T cells, and γδ T cells. Still other subtypes of T cells include, for example, CD4− CD8− T cells and CD28+CD8+ T cells.

Preferably the lymphocyte cell comprises a receptor specific for an antigen of a medical condition. The receptor can be the endogenous lymphocyte cell receptor, i.e., the antigen-specific lymphocyte cell receptor that is endogenous (i.e., native to) the lymphocyte. In such instances, the lymphocyte comprising the endogenous lymphocyte cell receptor can be a lymphocyte cell that was isolated from the patient, which is known to express the particular medical condition-specific antigen. Alternatively, the lymphocyte comprising the endogenous lymphocyte cell receptor can be a lymphocyte cell that was isolated from a subject that produces allogenic lymphocyte cells (i.e., lymphocyte cells that are histocompatible with the patient that will receive the lymphocyte cells). In certain embodiments, the subject from which lymphocyte cells are obtained may be immunized prior to obtaining the lymphocyte cells, so that the lymphocyte cells to be administered to the patient will have specificity for the medical disorder to be treated.

The antigen of a disease recognized by the endogenous lymphocyte cell receptor can be any antigen which is characteristic of the disease. For example, the antigen may be, for example, a tumor antigen, such as gp100, MART-1, TRP-1, TRP-2, tyrosinase, NY-ESO-1, MAGE-1, or MAGE-3.

Lymphocyte cells may also be characterized according to the presence of a phenotypic marker of activation for tumor reactivity, such as the presence of 4-1BBL. Populations of lymphocyte cells enriched for such a phenotypic marker may provide therapeutic advantages. Lymphocyte cells may also be characterized according to the level of expression of the RORγ. In certain embodiments, the lymphocyte cell may be induced to express or engineered to express RORγ, thereby increasing the amount of RORγ.

The lymphocyte cell may be a genetically modified lymphocyte cell, such as a genetically modified lymphocyte cell described in, for example, International Patent Application Publication No. WO 2012/129514, which is hereby incorporated by reference. Genetic modification of the lymphocyte may improve the efficacy of therapy by promoting the viability and/or function of transferred lymphocyte cells, provide a genetic marker to permit selection and/or evaluation of in vivo survival or migration, or may incorporate functions that improve the safety of immunotherapy, for example, by making the cell susceptible to negative selection in vivo. The lymphocyte may be genetically modified so that the lymphocyte cell expresses certain proteins, such as a survival cytokine (e.g., granulocyte-macrophage colony-stimulating factor) and/or receptor for an antigen (e.g., a tumor antigen).

Accordingly, in embodiments, lymphocyte cells are modified with chimeric antigen receptors (CAR). The CARs may comprise a single-chain antibody fragment (scFv) that is derived from the variable heavy (VH) and variable light (VL) chains of a monoclonal antibody (mAb) linked to the TCR CD3+ chain that mediates T-cell activation and cytotoxicity. Costimulatory signals can also be provided through the CAR by fusing the costimulatory domain of CD28 or 4-1 BB to the CD3+ chain. CARs are specific for cell surface molecules independent from HLA, thus overcoming the limitations of TCR-recognition including HLA-restriction and low levels of HLA-expression on tumor cells.

III. Combination Therapy

Another aspect of the invention provides for combination therapy. Aryl dihydro-2H-benzo[b][1,4]oxazine sulfonamide and related compounds (e.g., a compound of Formula I, I-A, IL, or other compounds in Section I) or their pharmaceutically acceptable salts may be used in combination with additional therapeutic agents to treat medical disorders, such as a cancer, bacterial infection, fungal infection, and immune deficiency disorder.

Exemplary therapeutic agents that may be used as part of a combination therapy in treating cancer, include, for example, mitomycin, tretinoin, ribomustin, gemcitabine, vincristine, etoposide, cladribine, mitobronitol, methotrexate, doxorubicin, carboquone, pentostatin, nitracrine, zinostatin, cetrorelix, letrozole, raltitrexed, daunorubicin, fadrozole, fotemustine, thymalfasin, sobuzoxane, nedaplatin, cytarabine, bicalutamide, vinorelbine, vesnarinone, aminoglutethimide, amsacrine, proglumide, elliptinium acetate, ketanserin, doxifluridine, etretinate, isotretinoin, streptozocin, nimustine, vindesine, flutamide, drogenil, butocin, carmofur, razoxane, sizofilan, carboplatin, mitolactol, tegafur, ifosfamide, prednimustine, picibanil, levamisole, teniposide, improsulfan, enocitabine, lisuride, oxymetholone, tamoxifen, progesterone, mepitiostane, epitiostanol, formestane, interferon-alpha, interferon-2 alpha, interferon-beta, interferon-gamma, colony stimulating factor-1, colony stimulating factor-2, denileukin diftitox, interleukin-2, and leutinizing hormone releasing factor.

An additional class of agents that may be used as part of a combination therapy in treating cancer is immune checkpoint inhibitors (also referred to as immune checkpoint blockers). Immune checkpoint inhibitors are a class of therapeutic agents that have the effect of blocking immune checkpoints. See, for example, Pardoll in *Nature Reviews Cancer* (2012) vol. 12, pages 252-264. Exemplary immune checkpoint inhibitors include agents that inhibit one or more of (i) cytotoxic T-lymphocyte-associated antigen 4 (CTLA4), (ii) programmed cell death protein 1 (PD1), (iii) PDL1, (iv) LAB3, (v) B7-H3, (vi) B7-H4, and (vii) TIM3. The CTLA4 inhibitor Ipilumumab has been approved by the United States Food and Drug Administration for treating melanoma.

Yet other agents that may be used as part of a combination therapy in treating cancer are monoclonal antibody agents that target non-checkpoint targets (e.g., herceptin) and non-cytoxic agents (e.g., tyrosine-kinase inhibitors).

Accordingly, another aspect of the invention provides a method of treating cancer in a patient, where the method comprises administering to the patient in need thereof (i) a therapeutically effective amount of a RORγ agonist compound described herein and (ii) a second anti-cancer agent, in order to treat the cancer, where the second therapeutic agent may be one of the additional therapeutic agents described above (e.g., mitomycin, tretinoin, ribomustin, gemcitabine, an immune checkpoint inhibitor, or a monoclonal antibody agent that targets non-checkpoint targets) or one of the following:

an inhibitor selected from an ALK Inhibitor, an ATR Inhibitor, an A2A Antagonist, a Base Excision Repair Inhibitor, a Bcr-Abl Tyrosine Kinase Inhibitor, a Bruton's Tyrosine Kinase Inhibitor, a CDC7 Inhibitor, a CHK1 Inhibitor, a Cyclin-Dependent Kinase Inhibitor, a DNA-PK Inhibitor, an Inhibitor of both DNA-PK and mTOR, a DNMT1 Inhibitor, a DNMT1 Inhibitor plus 2-chloro-deoxyadenosine, an HDAC Inhibitor, a Hedgehog Signaling Pathway Inhibitor, an IDO Inhibitor, a JAK Inhibitor, a mTOR Inhibitor, a MEK Inhibitor, a MELK Inhibitor, a MTH1 Inhibitor, a PARP Inhibitor, a Phosphoinositide 3-Kinase Inhibitor, an Inhibitor of both PARP1 and DHODH, a Proteasome Inhibitor, a Topoisomerase-II Inhibitor, a Tyrosine Kinase Inhibitor, a VEGFR Inhibitor, and a WEE1 Inhibitor;

an agonist of OX40, CD137, CD40, GITR, CD27, HVEM, TNFRSF25, or ICOS;

a therapeutic antibody targeting one of the following: CD20, CD30, CD33, CD52, EpCAM, CEA, gpA33, a mucin, TAG-72, CAIX, PSMA, a folate-binding protein, a ganglioside, Le, VEGF, VEGFR, VEGFR2, integrin αVβ3, integrin α5β1, EGFR, ERBB2, ERBB3, MET, IGF1R, EPHA3, TRAILR1, TRAILR2, RANKL, FAP, tenascin, CD19, KIR, NKG2A, CD47, CEACAM1, c-MET, VISTA, CD73, CD38, BAFF, interleukin-1 beta, B4GALNT1, interleukin-6, and interleukin-6 receptor;

a cytokine selected from IL-12, IL-15, GM-CSF, and G-CSF;

a therapeutic agent selected from sipuleucel-T, aldesleukin (a human recombinant interleukin-2 product having the chemical name des-alanyl-1, serine-125 human interleukin-2), dabrafenib (a kinase inhibitor having the chemical name N-{3-[5-(2-aminopyrimidin-4-yl)-2-tert-butyl-1,3-thiazol-4-yl]-2-fluorophenyl}-2,6-difluorobenzenesulfonamide), vemurafenib (a kinase inhibitor having the chemical name propane-1-sulfonic acid {3-[5-(4-chlorophenyl)-1H-pyrrolo[2,3-b]pyridine-3-carbonyl]-2,4-difluoro-phenyl}-amide), and 2-chloro-deoxyadenosine; or a placental growth factor, an antibody-drug conjugate, an oncolytic virus, or an anti-cancer vaccine.

In certain embodiments, the second anti-cancer agent is an ALK Inhibitor. In certain embodiments, the second anti-cancer agent is an ALK Inhibitor comprising ceritinib or crizotinib. In certain embodiments, the second anti-cancer agent is an ATR Inhibitor. In certain embodiments, the second anti-cancer agent is an ATR Inhibitor comprising AZD6738 or VX-970. In certain embodiments, the second anti-cancer agent is an A2A Antagonist. In certain embodiments, the second anti-cancer agent is a Base Excision Repair Inhibitor comprising methoxyamine. In certain embodiments, the second anti-cancer agent is a Base Excision Repair Inhibitor, such as methoxyamine. In certain embodiments, the second anti-cancer agent is a Bcr-Abl Tyrosine Kinase Inhibitor. In certain embodiments, the second anti-cancer agent is a Bcr-Abl Tyrosine Kinase Inhibitor comprising dasatinib or nilotinib. In certain embodiments, the second anti-cancer agent is a Bruton's Tyrosine Kinase Inhibitor. In certain embodiments, the second anti-cancer agent is a Bruton's Tyrosine Kinase Inhibitor comprising ibrutinib. In certain embodiments, the second anti-cancer agent is a CDC7 Inhibitor. In certain embodiments, the second anti-cancer agent is a CDC7 Inhibitor comprising RXDX-103 or AS-141.

In certain embodiments, the second anti-cancer agent is a CHK1 Inhibitor. In certain embodiments, the second anti-cancer agent is a CHK1 Inhibitor comprising MK-8776, ARRY-575, or SAR-020106. In certain embodiments, the second anti-cancer agent is a Cyclin-Dependent Kinase Inhibitor. In certain embodiments, the second anti-cancer agent is a Cyclin-Dependent Kinase Inhibitor comprising palbociclib. In certain embodiments, the second anti-cancer agent is a DNA-PK Inhibitor. In certain embodiments, the second anti-cancer agent is a DNA-PK Inhibitor comprising MSC2490484A. In certain embodiments, the second anti-cancer agent is Inhibitor of both DNA-PK and mTOR. In certain embodiments, the second anti-cancer agent comprises CC-115.

In certain embodiments, the second anti-cancer agent is a DNMT1 Inhibitor. In certain embodiments, the second anti-cancer agent is a DNMT1 Inhibitor comprising decitabine, RX-3117, guadecitabine, NUC-8000, or azacytidine. In certain embodiments, the second anti-cancer agent comprises a DNMT1 Inhibitor and 2-chloro-deoxyadenosine. In certain embodiments, the second anti-cancer agent comprises ASTX-727.

In certain embodiments, the second anti-cancer agent is a HDAC Inhibitor. In certain embodiments, the second anti-cancer agent is a HDAC Inhibitor comprising OBP-801, CHR-3996, etinostate, resminostate, pracinostat, CG-200745, panobinostat, romidepsin, mocetinostat, belinostat, AR-42, ricolinostat, KA-3000, or ACY-241.

In certain embodiments, the second anti-cancer agent is a Hedgehog Signaling Pathway Inhibitor. In certain embodiments, the second anti-cancer agent is a Hedgehog Signaling Pathway Inhibitor comprising sonidegib or vismodegib. In certain embodiments, the second anti-cancer agent is an IDO Inhibitor. In certain embodiments, the second anti-cancer agent is an IDO Inhibitor comprising INCB024360. In certain embodiments, the second anti-cancer agent is a JAK Inhibitor. In certain embodiments, the second anti-cancer agent is a JAK Inhibitor comprising ruxolitinib or tofacitinib. In certain embodiments, the second anti-cancer agent is a mTOR Inhibitor. In certain embodiments, the second anti-cancer agent is a mTOR Inhibitor comprising everolimus or temsirolimus. In certain embodiments, the second anti-cancer agent is a MEK Inhibitor. In certain embodiments, the second anti-cancer agent is a MEK Inhibitor comprising cobimetinib or trametinib. In certain embodiments, the second anti-cancer agent is a MELK Inhibitor. In certain embodiments, the second anti-cancer agent is a MELK Inhibitor comprising ARN-7016, APTO-500, or OTS-167. In certain embodiments, the second anti-cancer agent is a MTH1 Inhibitor. In certain embodiments, the second anti-cancer agent is a MTH1 Inhibitor comprising (S)-crizotinib, TH287, or TH588.

In certain embodiments, the second anti-cancer agent is a PARP Inhibitor. In certain embodiments, the second anti-cancer agent is a PARP Inhibitor comprising MP-124, olaparib, BGB-290, talazoparib, veliparib, niraparib, E7449, rucaparb, or ABT-767. In certain embodiments, the second anti-cancer agent is a Phosphoinositide 3-Kinase Inhibitor. In certain embodiments, the second anti-cancer agent is a Phosphoinositide 3-Kinase Inhibitor comprising idelalisib. In certain embodiments, the second anti-cancer agent is an inhibitor of both PARP1 and DHODH (i.e., an agent that inhibits both poly ADP ribose polymerase 1 and dihydroorotate dehydrogenase).

In certain embodiments, the second anti-cancer agent is a Proteasome Inhibitor. In certain embodiments, the second anti-cancer agent is a Proteasome Inhibitor comprising bortezomib or carfilzomib. In certain embodiments, the second anti-cancer agent is a Topoisomerase-II Inhibitor. In certain embodiments, the second anti-cancer agent is a Topoisomerase-II Inhibitor comprising vosaroxin.

In certain embodiments, the second anti-cancer agent is a Tyrosine Kinase Inhibitor. In certain embodiments, the second anti-cancer agent is a Tyrosine Kinase Inhibitor comprising bosutinib, cabozantinib, imatinib or ponatinib. In certain embodiments, the second anti-cancer agent is a VEGFR Inhibitor. In certain embodiments, the second anti-cancer agent is a VEGFR Inhibitor comprising regorafenib. In certain embodiments, the second anti-cancer agent is a WEE1 Inhibitor. In certain embodiments, the second anti-cancer agent is a WEE1 Inhibitor comprising AZD1775.

In certain embodiments, the second anti-cancer agent is an agonist of OX40, CD137, CD40, GITR, CD27, HVEM, TNFRSF25, or ICOS. In certain embodiments, the second anti-cancer agent is a therapeutic antibody selected from the group consisting of rituximab, ibritumomab tiuxetan, tositumomab, obinutuzumab, ofatumumab, brentuximab vedotin, gemtuzumab ozogamicin, alemtuzumab, IGN101, adecatumumab, labetuzumab, huA33, pemtumomab, oregovomab, minetumomab, cG250, J591, Movl8, farletuzumab, 3F8, ch14.18, KW-2871, hu3S193, 1gN311, bevacizumab, IM-2C6, pazopanib, sorafenib, axitinib, CDP791, lenvatinib, ramucirumab, etaracizumab, volociximab, cetuximab, panitumumab, nimotuzumab, 806, afatinib, erlotinib, gefitinib, osimertinib, vandetanib, trastuzumab, pertuzumab, MM-121, AMG 102, METMAB, SCH 900105, AVE1642, IMC-A12, MK-0646, R1507, CP 751871, KB004, IIIA-4, mapatumumab, HGS-ETR2, CS-1008, denosumab, sibrotuzumab, F19, 81C6, MEDI551, lirilumab, MEDI9447, daratumumab, belimumab, canakinumab, dinutuximab, siltuximab, and tocilizumab.

In certain embodiments, the second anti-cancer agent is a placental growth factor. In certain embodiments, the second anti-cancer agent is a placental growth factor comprising ziv-aflibercept. In certain embodiments, the second anti-cancer agent is an antibody-drug conjugate. In certain embodiments, the second anti-cancer agent is an antibody-drug conjugate selected from the group consisting of brentoxumab vedotin and trastuzumab emtransine.

In certain embodiments, the second anti-cancer agent is an oncolytic virus. In certain embodiments, the second anti-cancer agent is the oncolytic virus talimogene laherparepvec. In certain embodiments, the second anti-cancer agent is an anti-cancer vaccine. In certain embodiments, the second anti-cancer agent is an anti-cancer vaccine selected from the group consistent of a GM-CSF tumor vaccine, a STING/GM-CSF tumor vaccine, and NY-ESO-1. In certain embodiments, the second anti-cancer agent is a cytokine selected from IL-12, IL-15, GM-CSF, and G-CSF.

In certain embodiments, the second anti-cancer agent is a therapeutic agent selected from sipuleucel-T, aldesleukin (a human recombinant interleukin-2 product having the chemical name des-alanyl-1, serine-125 human interleukin-2), dabrafenib (a kinase inhibitor having the chemical name N-{3-[5-(2-aminopyrimidin-4-yl)-2-tert-butyl-1,3-thiazol-4-yl]-2-fluorophenyl}-2,6-difluorobenzenesulfonamide), vemurafenib (a kinase inhibitor having the chemical name propane-1-sulfonic acid {3-[5-(4-chlorophenyl)-1H-pyrrolo[2,3-b]pyridine-3-carbonyl]-2,4-difluoro-phenyl}-amide), and 2-chloro-deoxyadenosine.

Exemplary therapeutic agents that may be used as part of a combination therapy in treating a bacterial infection, include, for example, amoxicillin, azithromycin, cefazolin, ceftriaxone, cefuroxime, cephalexin, ciprofloxacin, clindamycin, doxycycline, levofloxacin, linezolid, metronidazole, moxifloxacin, and penicillin.

Exemplary therapeutic agents that may be used as part of a combination therapy in treating a fungal infection, include, for example, 2-phenylphenol; 8-hydroxyquinoline sulfate; acibenzolar-S-methyl; aldimorph; amidoflumet; ampropylfos; ampropylfos-potassium; andoprim; anilazine; azaconazole; azoxystrobin; benalaxyl; benodanil; benomyl; benthiavalicarb-isopropyl; benzamacril; benzamacril-isobutyl; bilanafos; binapacryl; biphenyl; bitertanol; blasticidin-S; bromuconazole; butylamine; calcium polysulphide; capsimycin; captafol; captan; carbendazim; carboxin; carpropamid; carvone; chinomethionat; chlobenthiazone; chlorfenazole; chloroneb; chlorothalonil; chlozolinate; clozylacon; cyazofamid; cyflufenamid; cymoxanil; cyproconazole; cyprodinil; cyprofuram; Dagger G; debacarb; dichlofluanid; dichlone; dichlorophen; diclocymet; diclomezine; dicloran; diethofencarb; difenoconazole; diflumetorim; dimethirimol; dimethomorph; dimoxystrobin; diniconazole; diniconazole-M; dinocap; diphenylamine; dipyrithione; ditalimfos; dithianon; dodine; drazoxolon; edifenphos; epoxiconazole; ethaboxam; ethirimol; etridiazole; famoxadone; fenamidone; fenapanil; fenarimol; fenbuconazole; fenfuram; fenhexamid; fenitropan; fenoxanil; fenpiclonil; fenpropidin; fenpropimorph; ferbam; fluazinam; flubenzimine; fludioxonil; flumetover; flumorph; fluoromide; fluoxastrobin; fluquinconazole; flurprimidol; flusilazole; flusulphamide, hexaconazole; hymexazole; imazalil; imibenconazole; iminoctadine triacetate; iminoctadine tris(albesil); iodocarb; ipconazole; iprobenfos; iprodione; iprovalicarb; irumamycin; isoprothiolane; isovaledione; kasugamycin; kresoxim-methyl; oxyfenthiin; paclobutrazole; pefurazoate; penconazole; pencycuron; phosdiphen; phthalide; picoxystrobin; piperalin; polyoxins; polyoxorim; probenazole; prochloraz; procymidone; propamocarb; propanosine-sodium; propiconazole; propineb; proquinazid; prothioconazole; pyraclostrobin; pyrazophos; pyrifenox; pyrimethanil; pyroquilon; pyroxyfur; pyrrolenitrine; tetraconazole; thiabendazole; thicyofen; thifluzamide; thiophanate-methyl; thiram; tioxymid; tricyclazole; tridemorph; trifloxystrobin; triflumizole; triforine; triticonazole; uniconazole; validamycin A; vinclozolin; zineb; ziram; and zoxamide.

The amount of aryl dihydro-2H-benzo[b][1,4]oxazine sulfonamide or related compound (e.g., a compound of Formula I, I-A, II, or other compounds in Section I) and additional therapeutic agent and the relative timing of administration may be selected in order to achieve a desired combined therapeutic effect. For example, when administering a combination therapy to a patient in need of such administration, the therapeutic agents in the combination, or a pharmaceutical composition or compositions comprising the therapeutic agents, may be administered in any order such as, for example, sequentially, concurrently, together, simultaneously and the like. Further, for example, an aryl dihydro-2H-benzo[b][1,4]oxazine sulfonamide or related compound (e.g., a compound of any one of Formula I, I-A, IL, or other compounds in Section I) may be administered during a time when the additional therapeutic agent(s) exerts its prophylactic or therapeutic effect, or vice versa.

The doses and dosage regimen of the active ingredients used in the combination therapy may be determined by an attending clinician. In certain embodiments, the aryl dihydro-2H-benzo[b][1,4]oxazine sulfonamide or related compound (e.g., a compound of any one of Formula I, I-A, II, or other compounds in Section I) and the additional therapeutic agent(s) are administered in doses commonly employed when such agents are used as monotherapy for treating the disorder. In other embodiments, the aryl dihydro-2H-benzo[b][1,4]oxazine sulfonamide or related compound (e.g., a compound of any one of Formula I, I-A, IL, or other compounds in Section I) and the additional therapeutic agent(s) are administered in doses lower than the doses commonly employed when such agents are used as monotherapy for treating the disorder. In certain embodiments, the aryl dihydro-2H-benzo[b][1,4]oxazine sulfonamide or related compound (e.g., a compound of any one of Formula I, I-A, II, or other compounds in Section I) and the additional therapeutic agent(s) are present in the same composition, which is suitable for oral administration.

In certain embodiments, the aryl dihydro-2H-benzo[b][1,4]oxazine sulfonamide or related compound (e.g., a compound of any one of Formula I, I-A, II, or other compounds in Section I) and the additional therapeutic agent(s) may act additively or synergistically. A synergistic combination may allow the use of lower dosages of one or more agents and/or less frequent administration of one or more agents of a combination therapy. A lower dosage or less frequent administration of one or more agents may lower toxicity of the therapy without reducing the efficacy of the therapy.

Another aspect of this invention is a kit comprising a therapeutically effective amount of the aryl dihydro-2H-benzo[b][1,4]oxazine sulfonamide or related compound (e.g., a compound of any one of Formula I, I-A, II, or other compounds in Section I), a pharmaceutically acceptable carrier, vehicle or diluent, and optionally at least one additional therapeutic agent listed above.

IV. Pharmaceutical Compositions and Dosing Considerations

As indicated above, the invention provides pharmaceutical compositions, which comprise a therapeutically-effective amount of one or more of the compounds described above, formulated together with one or more pharmaceutically acceptable carriers (additives) and/or diluents. The pharmaceutical compositions may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, trouches and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof, (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Preferably, the compounds are administered at about 0.01 mg/kg to about 200 mg/kg, more preferably at about 0.1 mg/kg to about 100 mg/kg, even more preferably at about 0.5 mg/kg to about 50 mg/kg. When the compounds described herein are co-administered with another agent (e.g., as sensitizing agents), the effective amount may be less than when the agent is used alone.

If desired, the effective daily dose of the active compound may be administered as two, three, four, five, six or more sub-doses administered separately at appropriate intervals throughout the day, optionally, in unit dosage forms. Preferred dosing is one administration per day.

The invention further provides a unit dosage form (such as a tablet or capsule) comprising an aryl dihydro-2H-benzo[b][1,4]oxazine sulfonamide or related compound described herein in a therapeutically effective amount for the treatment of a medical disorder described herein.

EXAMPLES

The invention now being generally described, will be more readily understood by reference to the following examples, which are included merely for purposes of illustration of certain aspects and embodiments of the present invention, and are not intended to limit the invention. Starting materials described herein can be obtained from commercial sources or may be readily prepared from commercially available materials using transformations known to those of skill in the art.

Example 1—Synthesis of (S)-3-(6-(2,3-difluorophenyl)-4-((3-(trifluoromethyl)phenyl)sulfonyl)-3,4-dihydro-2H-benzo[b][1,4]oxazin-2-yl)propanoic acid

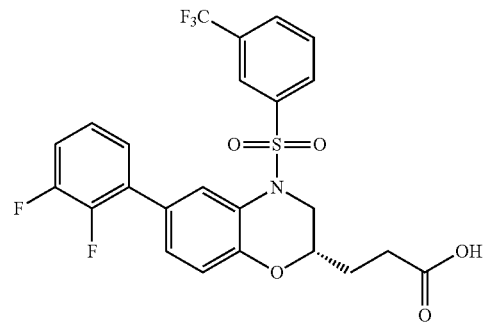 [SMILES: O=C(O)CC[C@H]1CN(S(=O)(=O)c2cccc(C(F)(F)F)c2)c2cc(-c3cccc(F)c3F)ccc2O1]

Part I—Synthesis of dimethyl (R)-2-hydroxypentanedioate

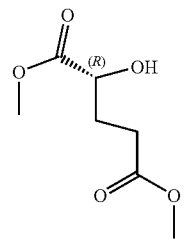

To a mixture of (2R)-5-oxotetrahydro-2-furancarboxylic acid (25 g, 192 mmol) in methanol (300 mL) was added concentrated hydrogen chloride (0.5 mL) and the mixture was refluxed overnight. Then, the reaction mixture was cooled to ambient temperature, and solid sodium bicarbonate was added and resultant mixture slurried for 20 minutes. The mixture was filtered and concentrated to obtain dimethyl (R)-2-hydroxypentanedioate (34.7 g, 100%).

Part II—Synthesis of dimethyl (S)-2-(4-bromo-2-nitrophenoxy)pentanedioate

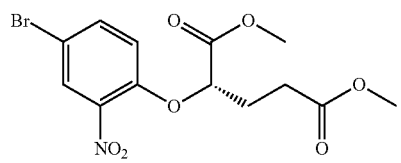 [SMILES: COC(=O)CC[C@H](Oc1ccc(Br)cc1[N+](=O)[O-])C(=O)OC]

To a solution of dimethyl (R)-2-hydroxypentanedioate (33.8 g, 192 mmol), 4-bromo-2-nitrophenol (50.2 g, 230 mmol), and triphenylphosphine (60.4 g, 230 mmol) in dichloromethane (300 mL) with activated molecular sieves at 0° C. was added a solution of diisopropyl azodicarboxylate (45.4 mL, 230 mmol) in dichloromethane (50 mL) dropwise. The reaction mixture was stirred at 0° C. for 20 minutes, then stirred at ambient temperature overnight. Next, the reaction mixture was concentrated, triphenylphosphine oxide was removed by running the residue through a large pad of silica, eluting with dichloromethane (~6 L). The eluted material was a mixture of the title compound and a small amount of residual phenol. The eluted material was redissolved in ethyl acetate, washed four times with 1M sodium hydroxide, washed with brine, dried (Na$_2$SO$_4$), and concentrated to yield dimethyl (S)-2-(4-bromo-2-nitrophenoxy)pentanedioate (62.84 g, 87%) as a clear oil.

Part III—Synthesis of methyl (S)-3-(6-bromo-3-oxo-3,4-dihydro-2H-benzo[b][1,4]oxazin-2-yl)propanoate

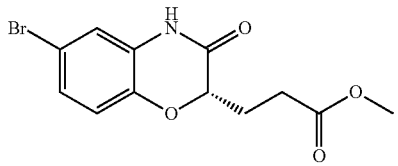 [SMILES: COC(=O)CC[C@@H]1Oc2ccc(Br)cc2NC1=O]

In a flask equipped with a mechanical stirrer was charged dimethyl (S)-2-(4-bromo-2-nitrophenoxy)pentanedioate (62.84 g, 167 mmol), acetic acid (500 mL), followed by powdered iron (46.7 g, 835 mmol) at ambient temperature. Heated to 60° C. for two hours. Filtered hot through a pad of Celite, washing with ethyl acetate (900 mL). The filtrates were washed three times with water, washed with brine, dried (Na$_2$SO$_4$) and concentrated to yield methyl (S)-3-(6-bromo-3-oxo-3,4-dihydro-2H-benzo[b][1,4]oxazin-2-yl) propanoate (48.06 g, 92%) as a white solid.

Part IV—Synthesis of methyl (S)-3-(6-bromo-3,4-dihydro-2H-benzo[b][1,4]oxazin-2-yl)propanoate

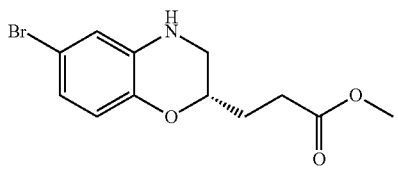 [SMILES: COC(=O)CC[C@H]1CNc2cc(Br)ccc2O1]

To methyl (S)-3-(6-bromo-3-oxo-3,4-dihydro-2H-benzo[b][1,4]oxazin-2-yl)propanoate (24.46 g, 77.9 mmol) in anhydrous tetrahydrofuran (200 mL) at 0° C. was added borane-methyl sulfide complex (19.5 mL, 195 mmol) dropwise. The reaction mixture was heated to 50° C. for one hour. Then, the reaction mixture was cooled to 0° C., and next carefully quenched by adding methanol (150 mL). The resulting mixture was heated to 60° C. for one hour and then concentrated to provide a residue. The residue was partitioned between water and ethyl acetate. The organic layer was washed with brine, dried (Na$_2$SO$_4$) and concentrated to provide a mixture. The mixture was purified by column chromatography eluting with a gradient of 5-50% ethyl acetate in hexanes to yield methyl (S)-3-(6-bromo-3,4-dihydro-2H-benzo[b][1,4]oxazin-2-yl)propanoate (17.97 g, 77%) as a white solid.

Part V—Synthesis of (S)-methyl 3-(6-bromo-4-((3-(trifluoromethyl)phenyl)sulfonyl)-3,4-dihydro-2H-benzo[b][1,4]oxazin-2-yl)propanoate

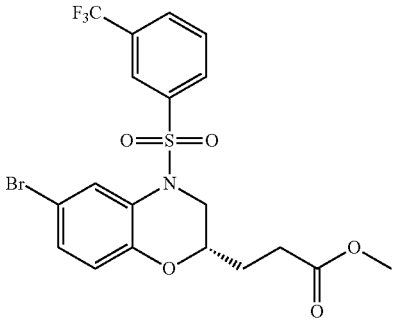 [SMILES: COC(=O)CC[C@H]1CN(S(=O)(=O)c2cccc(C(F)(F)F)c2)c2cc(Br)ccc2O1]

To a solution of methyl (S)-3-(6-bromo-3,4-dihydro-2H-benzo[b][1,4]oxazin-2-yl)propanoate (10.0 g, 33.3 mmol) in pyridine (60 mL) was added 3-(trifluoromethyl)benzenesulfonyl chloride (8.96 g, 36.6 mmol). The mixture was heated at 50° C. for four hours, then cooled, and next concentrated to provide a residue. The residue was partitioned between ethyl acetate and 1N HCl. The organic layer was washed twice with 1N HCl, brine, and dried (Na$_2$SO$_4$) to produce a solution. To the solution, activated charcoal was added, then the mixture was slurried, and next filtered through Celite. The filtrate was concentrated onto a small amount of silica and the residue was purified via MPLC eluting with a gradient of ethyl acetate in hexanes. The major UV component was concentrated to afford (S)-methyl 3-(6-bromo-4-((3-(trifluoromethyl)phenyl)sulfonyl)-3,4-dihydro-2H-benzo[b][1,4]oxazin-2-yl)propanoate (14.75 g, 87%).

Part VI—Synthesis of methyl (S)-3-(6-(2,3-difluorophenyl)-4-((3-(trifluoromethyl)phenyl)sulfonyl)-3,4-dihydro-2H-benzo[b][1,4]oxazin-2-yl)propanoate

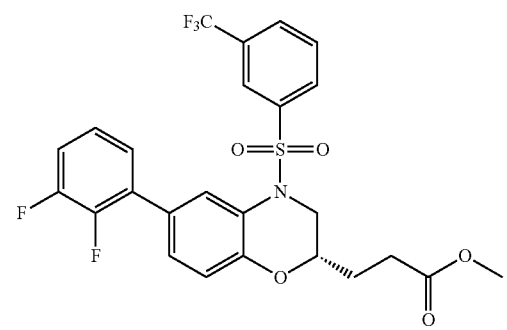 [SMILES: COC(=O)CC[C@H]1CN(S(=O)(=O)c2cccc(C(F)(F)F)c2)c2cc(-c3cccc(F)c3F)ccc2O1]

A stirred mixture of (S)-methyl 3-(6-bromo-4-((3-(trifluoromethyl)phenyl)-sulfonyl)-3,4-dihydro-2H-benzo[b][1,4] oxazin-2-yl)propanoate (200 mg, 0.39 mmol), toluene (5 mL), sodium carbonate (125 mg, 1.17 mmol), ethanol (1 mL), water (1 mL), (2,3-difluoro-phenyl)boronic acid (124.7 mg, 0.79 mmol), tetrakis(triphenylphosphine)palladium (46 mg, 0.04 mmol) was heated three hours at 90° C. Then, the mixture was cooled, and partitioned between ethyl acetate and water. The organic layer was dried (Na$_2$SO$_4$) and concentrated to provide a residue. The residue was purified by MPLC eluting with 25% ethyl acetate in petroleum ether to afford methyl (S)-3-(6-(2,3-difluorophenyl)-4-((3-(trifluoromethyl)phenyl)sulfonyl)-3,4-dihydro-2H-benzo[b][1,4]oxazin-2-yl)propanoate (185 mg, 87%) as a yellow oil.

Part VII—Synthesis of (S)-3-(6-(2,3-difluorophenyl)-4-((3-(trifluoromethyl)phenyl)sulfonyl)-3,4-dihydro-2H-benzo[b][1,4]oxazin-2-yl)propanoic acid

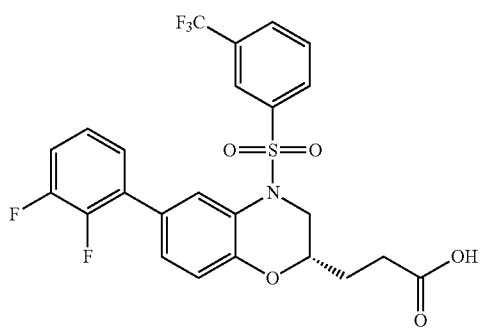 [SMILES: O=C(O)CC[C@H]1CN(S(=O)(=O)c2cccc(C(F)(F)F)c2)c2cc(-c3cccc(F)c3F)ccc2O1]

A mixture of methyl (S)-3-(6-(2,3-difluorophenyl)-4-((3-(trifluoromethyl)phenyl)sulfonyl)-3,4-dihydro-2H-benzo[b][1,4]oxazin-2-yl)propanoate (185 mg, 0.34 mmol), tetrahydrofuran (6 mL), lithium hydroxide (86 mg, 2.05 mmol), and water (2 mL) was stirred for four hours at room temperature. Then, the mixture was concentrated, and the resulting residue was dissolved in water (5 mL). To the aqueous mixture was added 1M hydrogen chloride to adjust the pH to 1. Then, the mixture was extracted with three times with dichloromethane. The combined organic layers were dried ($Na_2SO_4$) and concentrated. The resulting residue was purified by Prep-HPLC eluting with a gradient of 56-70% acetonitrile in water with 0.05% trifluoroacetic acid to afford (S)-3-(6-(2,3-difluorophenyl)-4-((3-(trifluoromethyl)phenyl)sulfonyl)-3,4-dihydro-2H-benzo[b][1,4]oxazin-2-yl) propanoic acid (56.4 mg, 31%) as a white solid. $^1$H-NMR (400 MHz, $CDCl_3$) δ 7.97 (s, 2H), 7.81-7.90 (m, 2H), 7.61 (m, 1H), 7.29 (m, 1H), 7.02-7.20 (m, 3H), 6.92 (d, J=8.4 Hz, 1H), 4.39 (dd, J=2.4 Hz, 14.4 Hz, 1H), 3.67 (m, 1H), 3.30 (m, 1H), 2.54-2.65 (m, 2H), 1.85-2.02 (m, 2H). (ES, m/z): $(M+H)^+$ 528.

Example 2—Preparation of Additional Aryl Sulfonyl-3,4-dihydro-2H-benzo[b][1,4]oxazin-2-yl)propanoic Acids Compounds in Tables 2 and 2A were prepared based on experimental procedures described in Example 1 and the detailed description. $^1$H NMR data for exemplary compounds is provided in Table 2B.

TABLE 2

| Compd No. | Structure | Name | Observed m/z |
|---|---|---|---|
| 2A | ![structure] | (S)-3-(6-(2-chlorophenyl)-4-((3-(trifluoromethyl)phenyl)-sulfonyl)-3,4-dihydro-2H-benzo[b][1,4]oxazin-2-yl)propanoic acid | 526 $(M + H)^+$ |
| 2B | ![structure] | (S)-3-(6-(4-chlorophenyl)-4-((3-(trifluoromethyl)phenyl)-sulfonyl)-3,4-dihydro-2H-benzo[b][1,4]oxazin-2-yl)propanoic acid | 526 $(M + H)^+$ |

TABLE 2-continued

| Compd No. | Structure | Name | Observed m/z |
|---|---|---|---|
| 2C | 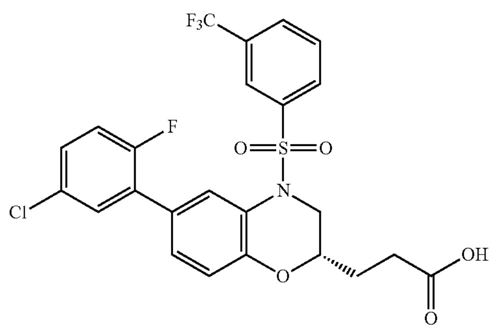 | (S)-3-(6-(5-chloro-2-fluorophenyl)-4-((3-(trifluoromethyl)phenyl)-sulfonyl)-3,4-dihydro-2H-benzo[b][1,4]oxazin-2-yl)propanoic acid | 544 (M + H)+ |
| 2D | 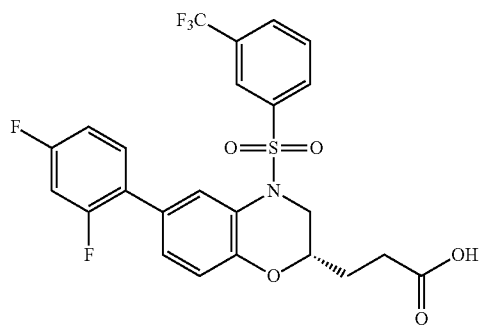 [SMILES: O=C(O)CC[C@H]1CN(S(=O)(=O)c2cccc(C(F)(F)F)c2)c2cc(-c3ccc(F)cc3F)ccc2O1] | (S)-3-(6-(2,4-difluorophenyl)-4-((3-(trifluoromethyl)phenyl)-sulfonyl)-3,4-dihydro-2H-benzo[b][1,4]oxazin-2-yl)propanoic acid | 528 (M + H)+ |
| 2E | 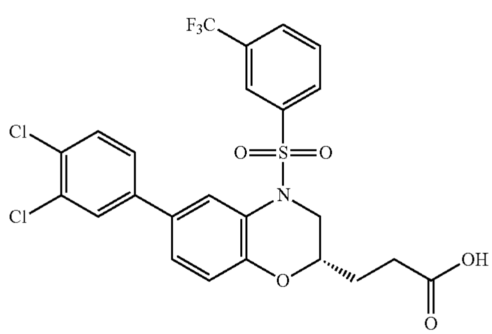 [SMILES: O=C(O)CC[C@H]1CN(S(=O)(=O)c2cccc(C(F)(F)F)c2)c2cc(-c3ccc(Cl)c(Cl)c3)ccc2O1] | (S)-3-(6-(3,4-dichlorophenyl)-4-((3-(trifluoromethyl)phenyl)-sulfonyl)-3,4-dihydro-2H-benzo[b][1,4]oxazin-2-yl)propanoic acid | 560 (M + H)+ |
| 2F | 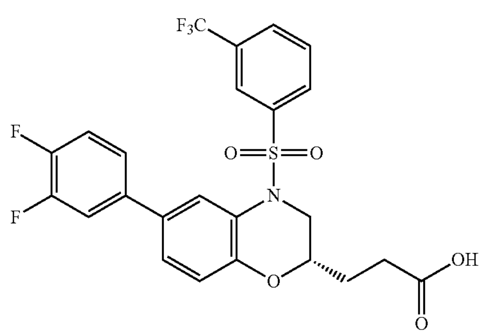 [SMILES: O=C(O)CC[C@H]1CN(S(=O)(=O)c2cccc(C(F)(F)F)c2)c2cc(-c3ccc(F)c(F)c3)ccc2O1] | (S)-3-(6-(3,4-difluorophenyl)-4-((3-(trifluoromethyl)phenyl)-sulfonyl)-3,4-dihydro-2H-benzo[b][1,4]oxazin-2-yl)propanoic acid | 528 (M + H)+ |

TABLE 2-continued

| Compd No. | Structure | Name | Observed m/z |
|---|---|---|---|
| 2G | 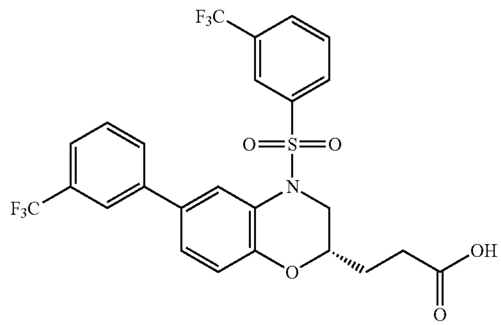 | (S)-3-(6-(3-(trifluoromethyl)phenyl)-4-((3-(trifluoromethyl)phenyl)-sulfonyl)-3,4-dihydro-2H-benzo[b][1,4]oxazin-2-yl)propanoic acid | 560 (M + H)+ |
| 2H | 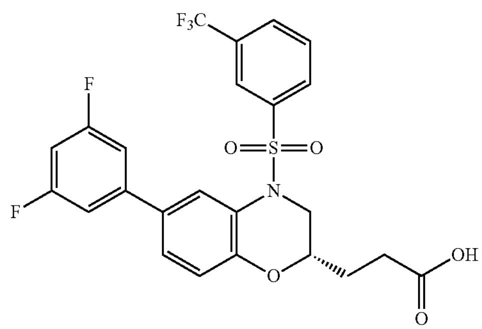 [SMILES: O=C(O)CC[C@H]1CN(S(=O)(=O)c2cccc(C(F)(F)F)c2)c2cc(-c3cc(F)cc(F)c3)ccc2O1] | (S)-3-(6-(3,5-difluorophenyl)-4-((3-(trifluoromethyl)phenyl)-sulfonyl)-3,4-dihydro-2H-benzo[b][1,4]oxazin-2-yl)propanoic acid | 528 (M + H)+ |
| 2I | 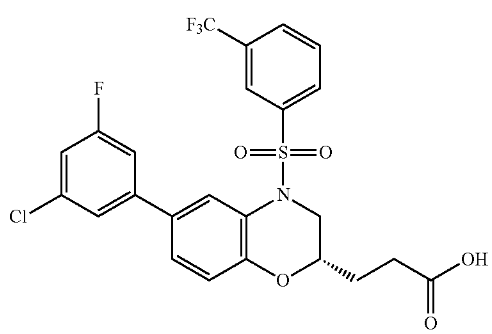 [SMILES: O=C(O)CC[C@H]1CN(S(=O)(=O)c2cccc(C(F)(F)F)c2)c2cc(-c3cc(F)cc(Cl)c3)ccc2O1] | (S)-3-(6-(3-chloro-5-fluorophenyl)-4-((3-(trifluoromethyl)phenyl)sulfonyl)-3,4-dihydro-2H-benzo[b][1,4]-oxazin-2-yl)propanoic acid | 544 (M + H)+ |
| 2J | 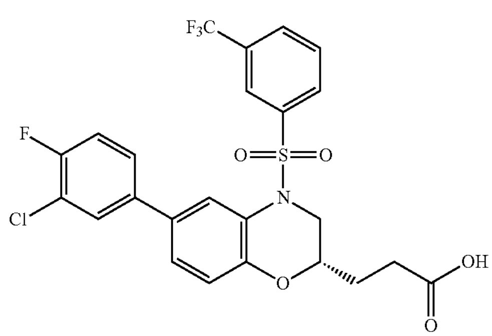 [SMILES: O=C(O)CC[C@H]1CN(S(=O)(=O)c2cccc(C(F)(F)F)c2)c2cc(-c3ccc(F)c(Cl)c3)ccc2O1] | (S)-3-(6-(3-chloro-4-fluorophenyl)-4-((3-(trifluoromethyl)phenyl)-sulfonyl)-3,4-dihydro-2H-benzo[b][1,4]oxazin-2-yl)propanoic acid | 544 (M + H)+ |

TABLE 2-continued

| Compd No. | Structure | Name | Observed m/z |
|---|---|---|---|
| 2K | 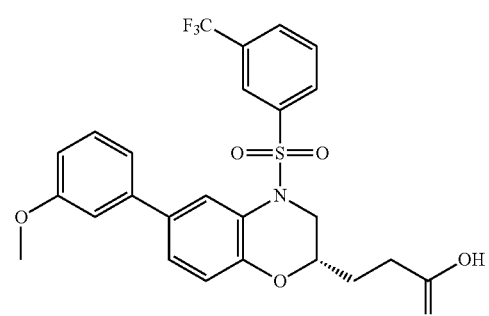 | (S)-3-(6-(3-methoxyphenyl)-4-((3-(trifluoromethyl)phenyl)-sulfonyl)-3,4-dihydro-2H-benzo[b][1,4]oxazin-2-yl)propanoic acid | 522 (M + H)+ |
| 2L | 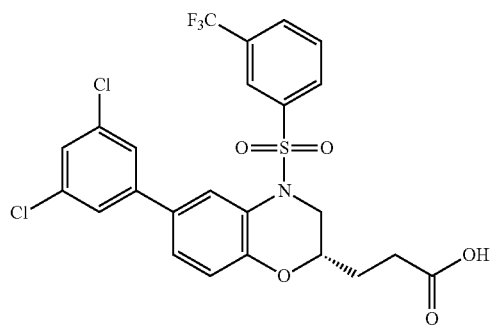 [SMILES: O=C(O)CC[C@H]1CN(S(=O)(=O)c2cccc(C(F)(F)F)c2)c2cc(-c3cc(Cl)cc(Cl)c3)ccc2O1] | (S)-3-(6-(3,5-dichlorophenyl)-4-((3-(trifluoromethyl)phenyl)-sulfonyl)-3,4-dihydro-2H-benzo[b][1,4]oxazin-2-yl)propanoic acid | 582 (M + Na)− |
| 2M | 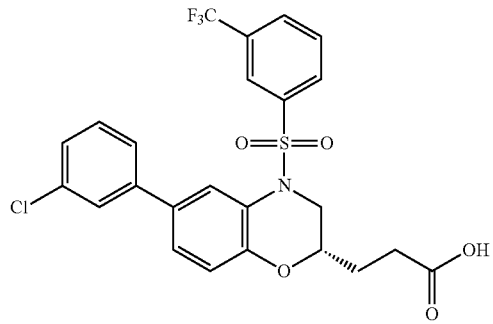 | (S)-3-(6-(3-chlorophenyl)-4-((3-(trifluoromethyl)phenyl)-sulfonyl)-3,4-dihydro-2H-benzo[b][1,4]oxazin-2-yl)propanoic acid | 526 (M + H)+ |
| 2N | 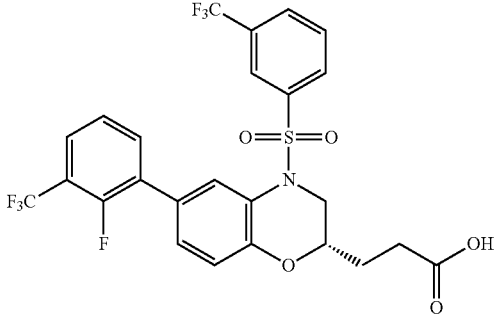 | (S)-3-(6-(2-fluoro-3-(trifluoromethyl)phenyl)-4-((3-(trifluoromethyl)phenyl)-sulfonyl)-3,4-dihydro-2H-benzo[b][1,4]oxazin-2-yl)propanoic acid | 578 (M + H)+ |

TABLE 2-continued

| Compd No. | Structure | Name | Observed m/z |
|---|---|---|---|
| 2O | 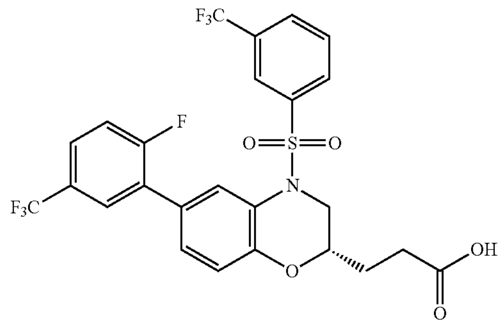 | (S)-3-(6-(2-fluoro-5-(trifluoromethyl)phenyl)-4-((3-(trifluoromethyl)phenyl)-sulfonyl)-3,4-dihydro-2H-benzo[b][1,4]oxazin-2-yl)propanoic acid | 578 (M + H)+ |
| 2P | 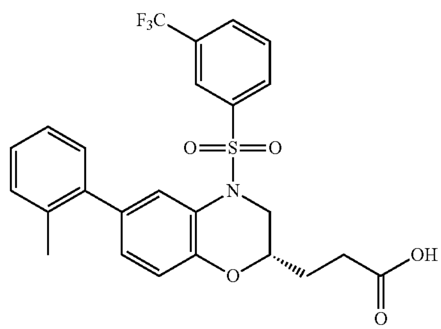 [SMILES: Cc1ccccc1-c1ccc2c(c1)N(S(=O)(=O)c1cccc(C(F)(F)F)c1)C[C@H](CCC(=O)O)O2] | (S)-3-(6-(o-tolyl)-4-((3-(trifluoromethyl)phenyl)-sulfonyl)-3,4-dihydro-2H-benzo[b][1,4]oxazin-2-yl)propanoic acid | 528 (M + Na)+ |
| 2Q | 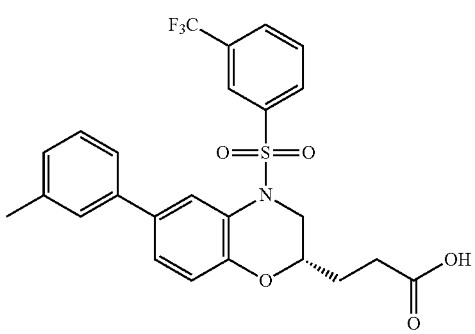 | (S)-3-(6-(m-tolyl)-4-((3-(trifluoromethyl)phenyl)-sulfonyl)-3,4-dihydro-2H-benzo[b][1,4]oxazin-2-yl)propanoic acid | 506 (M + H)+ |
| 2R | 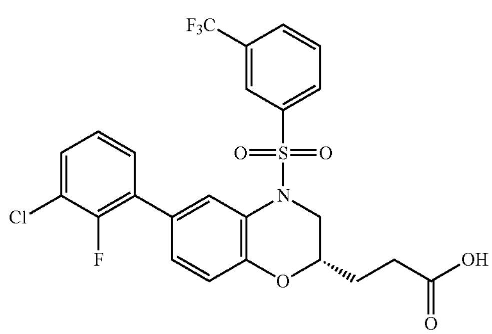 | (S)-3-(6-(3-chloro-2-fluorophenyl)-4-((3-(trifluoromethyl)phenyl)-sulfonyl)-3,4-dihydro-2H-benzo[b][1,4]oxazin-2-yl)propanoic acid | 566 (M + Na)+ |

TABLE 2-continued

| Compd No. | Structure | Name | Observed m/z |
|---|---|---|---|
| 2S | 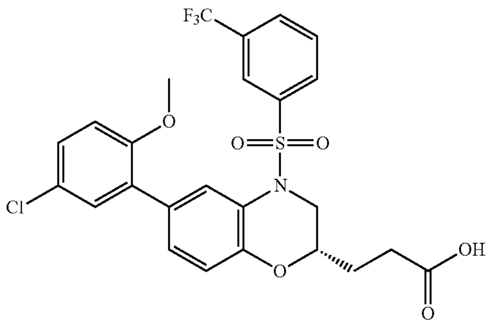 [SMILES: COc1ccc(Cl)cc1-c1ccc2c(c1)N(S(=O)(=O)c1cccc(C(F)(F)F)c1)C[C@H](CCC(=O)O)O2] | (S)-3-(6-(5-chloro-2-methoxyphenyl)-4-((3-(trifluoromethyl)phenyl)-sulfonyl)-3,4-dihydro-2H-benzo[b][1,4]oxazin-2-yl)propanoic acid | 578 (M + Na)+ |
| 2T | 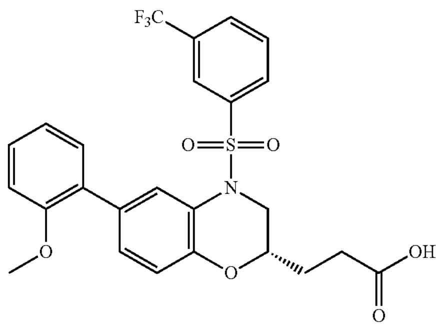 [SMILES: COc1ccccc1-c1ccc2c(c1)N(S(=O)(=O)c1cccc(C(F)(F)F)c1)C[C@H](CCC(=O)O)O2] | (S)-3-(6-(2-methoxyphenyl)-4-((3-(trifluoromethyl)phenyl)-sulfonyl)-3,4-dihydro-2H-benzo[b][1,4]oxazin-2-yl)propanoic acid | 544 (M + Na)+ |
| 2U | 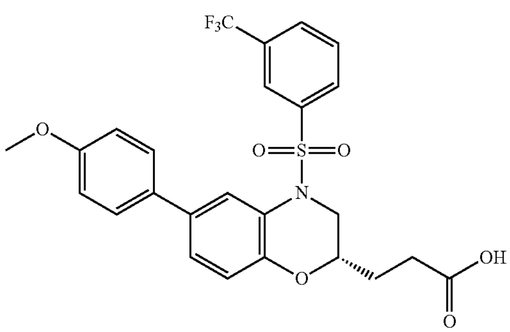 [SMILES: COc1ccc(-c2ccc3c(c2)N(S(=O)(=O)c2cccc(C(F)(F)F)c2)C[C@H](CCC(=O)O)O3)cc1] | (S)-3-(6-(4-methoxyphenyl)-4-((3-(trifluoromethyl)phenyl)-sulfonyl)-3,4-dihydro-2H-benzo[b][1,4]oxazin-2-yl)propanoic acid | 522 (M + H)+ |
| 2V | 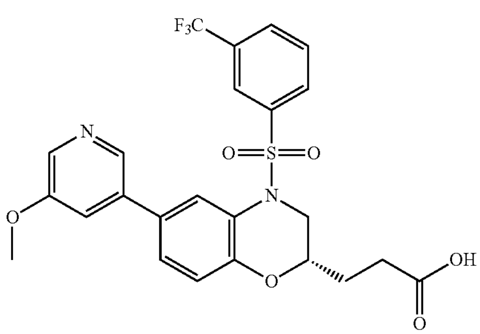 | (S)-3-(6-(5-methoxypyridin-3-yl)-4-((3-(trifluoromethyl)-phenyl)sulfonyl)-3,4-dihydro-2H-benzo[b][1,4]oxazin-2-yl)propanoic acid | 523 (M + H)+ |

TABLE 2-continued

| Compd No. | Structure | Name | Observed m/z |
|---|---|---|---|
| 2W | 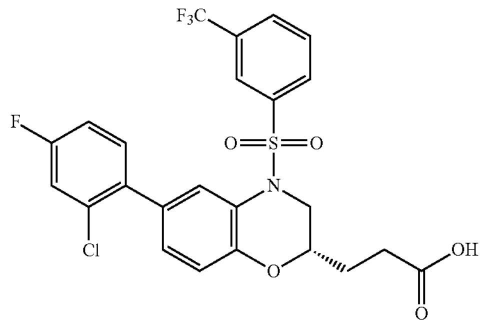 [SMILES: O=C(O)CC[C@H]1CN(S(=O)(=O)c2cccc(C(F)(F)F)c2)c2cc(-c3ccc(F)cc3Cl)ccc2O1] | (S)-3-(6-(2-chloro-4-fluorophenyl)-4-((3-(trifluoromethyl)phenyl)-sulfonyl)-3,4-dihydro-2H-benzo[b][1,4]oxazin-2-yl)propanoic acid | 566 (M + Na)+ |
| 2X | 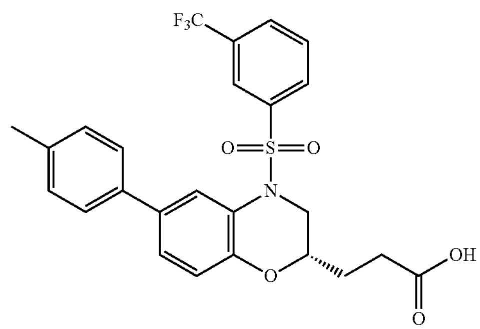 [SMILES: Cc1ccc(-c2ccc3c(c2)N(S(=O)(=O)c2cccc(C(F)(F)F)c2)C[C@H](CCC(=O)O)O3)cc1] | (S)-3-(6-(p-tolyl)-4-((3-(trifluoromethyl)phenyl)-sulfonyl)-3,4-dihydro-2H-benzo[b][1,4]oxazin-2-yl)propanoic acid | 506 (M + H)+ |
| 2Y | 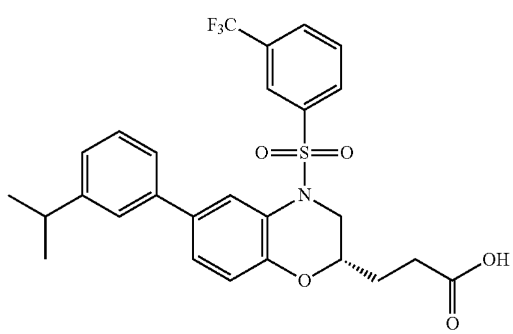 [SMILES: CC(C)c1cccc(-c2ccc3c(c2)N(S(=O)(=O)c2cccc(C(F)(F)F)c2)C[C@H](CCC(=O)O)O3)c1] | (S)-3-(6-(3-isopropylphenyl)-4-((3-(trifluoromethyl)phenyl)-sulfonyl)-3,4-dihydro-2H-benzo[b][1,4]oxazin-2-yl)propanoic acid | 534 (M + H)+ |
| 2Z | 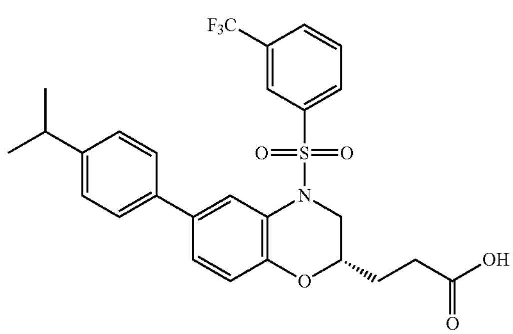 [SMILES: CC(C)c1ccc(-c2ccc3c(c2)N(S(=O)(=O)c2cccc(C(F)(F)F)c2)C[C@H](CCC(=O)O)O3)cc1] | (S)-3-(6-(4-isopropylphenyl)-4-((3-(trifluoromethyl)phenyl)-sulfonyl)-3,4-dihydro-2H-benzo[b][1,4]oxazin-2-yl)propanoic acid | 534 (M + H)+ |

TABLE 2-continued

| Compd No. | Structure | Name | Observed m/z |
|---|---|---|---|
| 2AA | 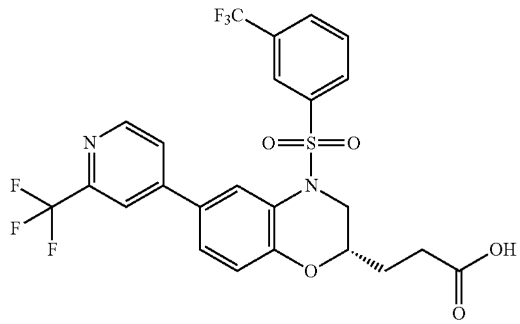 [SMILES: O=C(O)CC[C@H]1CN(S(=O)(=O)c2cccc(C(F)(F)F)c2)c2cc(-c3ccnc(C(F)(F)F)c3)ccc2O1] | (S)-3-(4-((3-(trifluoromethyl)-phenyl)sulfonyl)-6-(2-(trifluoromethyl)pyridin-4-yl)-3,4-dihydro-2H-benzo[b][1,4]oxazin-2-yl)propanoic acid | 561 (M + H)+ |
| 2AB | 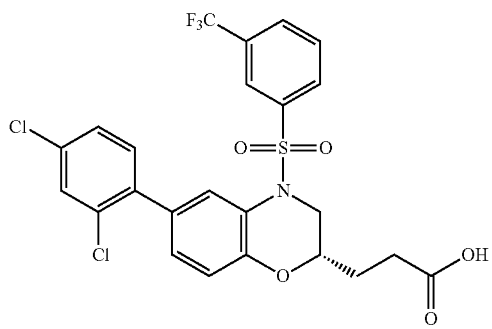 [SMILES: O=C(O)CC[C@H]1CN(S(=O)(=O)c2cccc(C(F)(F)F)c2)c2cc(-c3ccc(Cl)cc3Cl)ccc2O1] | (S)-3-(6-(2,4-dichlorophenyl)-4-((3-(trifluoromethyl)phenyl)-sulfonyl)-3,4-dihydro-2H-benzo[b][1,4]oxazin-2-yl)propanoic acid | 584 (M + Na)+ |
| 2AC | 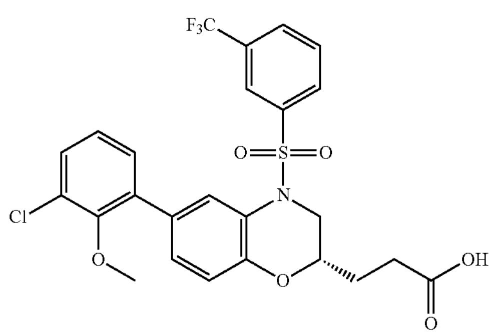 [SMILES: COc1c(Cl)cccc1-c1ccc2c(c1)N(S(=O)(=O)c1cccc(C(F)(F)F)c1)C[C@H](CCC(=O)O)O2] | (S)-3-(6-(3-chloro-2-methoxy-phenyl)-4-((3-(trifluoromethyl)-phenyl)sulfonyl)-3,4-dihydro-2H-benzo[b][1,4]oxazin-2-yl)propanoic acid | 578 (M + Na)+ |
| 2AD | 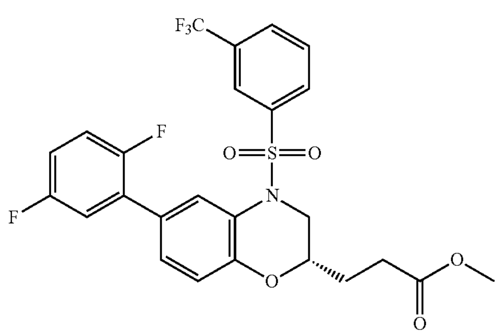 [SMILES: COC(=O)CC[C@H]1CN(S(=O)(=O)c2cccc(C(F)(F)F)c2)c2cc(-c3cc(F)ccc3F)ccc2O1] | (S)-3-(6-(2,5-difluorophenyl)-4-((3-(trifluoromethyl)-phenyl)sulfonyl)-3,4-dihydro-2H-benzo[b][1,4]oxazin-2-yl)propanoic acid | 550 (M + Na)+ |

TABLE 2-continued

| Compd No. | Structure | Name | Observed m/z |
|---|---|---|---|
| 2AE | 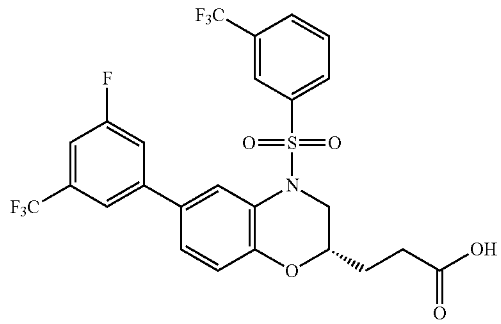 | (S)-3-(6-(3-fluoro-5-(trifluoromethyl)phenyl)-4-((3-(trifluoromethyl)phenyl)-sulfonyl)-3,4-dihydro-2H-benzo[b][1,4]oxazin-2-yl)propanoic acid | 576 (M − H)⁻ |
| 2AF | 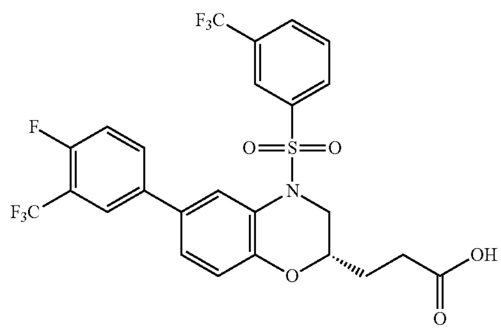 [SMILES: O=C(O)CC[C@H]1CN(S(=O)(=O)c2cccc(C(F)(F)F)c2)c2cc(-c3ccc(F)c(C(F)(F)F)c3)ccc2O1] | (S)-3-(6-(4-fluoro-3-(trifluoromethyl)phenyl)-4-((3-(trifluoromethyl)phenyl)-sulfonyl)-3,4-dihydro-2H-benzo[b][1,4]oxazin-2-yl)propanoic acid | 576 (M − H)⁻ |
| 2AG | 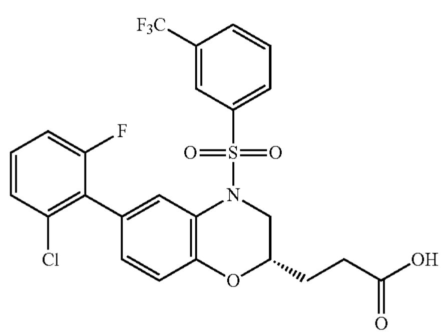 [SMILES: O=C(O)CC[C@H]1CN(S(=O)(=O)c2cccc(C(F)(F)F)c2)c2cc(-c3c(F)cccc3Cl)ccc2O1] | (S)-3-(6-(2-chloro-6-fluoro-phenyl)-4-((3-(trifluoromethyl)-phenyl)sulfonyl)-3,4-dihydro-2H-benzo[b][1,4]oxazin-2-yl)propanoic acid | 544 (M + H)⁺ |
| 2AH | 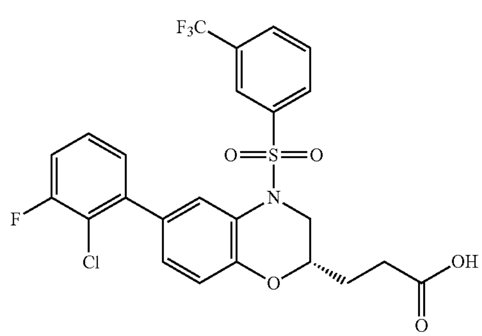 [SMILES: O=C(O)CC[C@H]1CN(S(=O)(=O)c2cccc(C(F)(F)F)c2)c2cc(-c3cccc(F)c3Cl)ccc2O1] | (S)-3-(6-(2-chloro-3-fluoro-phenyl)-4-((3-(trifluoromethyl)-phenyl)sulfonyl)-3,4-dihydro-2H-benzo[b][1,4]oxazin-2-yl)propanoic acid | 566 (M + Na)⁺ |

TABLE 2-continued

| Compd No. | Structure | Name | Observed m/z |
|---|---|---|---|
| 2AI | 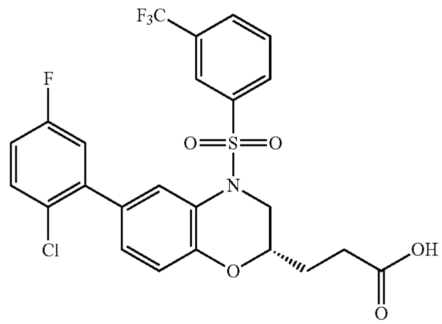 [SMILES: O=C(O)CC[C@H]1CN(S(=O)(=O)c2cccc(C(F)(F)F)c2)c2cc(-c3cc(F)ccc3Cl)ccc2O1] | (S)-3-(6-(2-chloro-5-fluorophenyl)-4-((3-(trifluoromethyl)phenyl)sulfonyl)-3,4-dihydro-2H-benzo[b][1,4]oxazin-2-yl)propanoic acid | 566 (M + Na)+ |
| 2AJ | 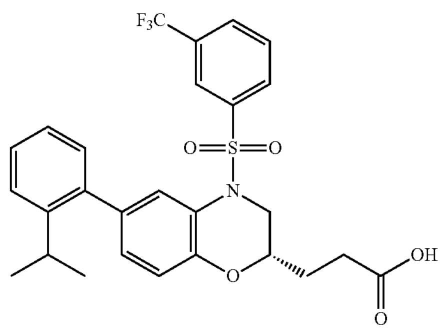 [SMILES: CC(C)c1ccccc1-c1ccc2c(c1)N(S(=O)(=O)c1cccc(C(F)(F)F)c1)C[C@H](CCC(=O)O)O2] | (S)-3-(6-(2-isopropylphenyl)-4-((3-(trifluoromethyl)phenyl)sulfonyl)-3,4-dihydro-2H-benzo[b][1,4]oxazin-2-yl)propanoic acid | 534 (M + H)+ |
| 2AK | 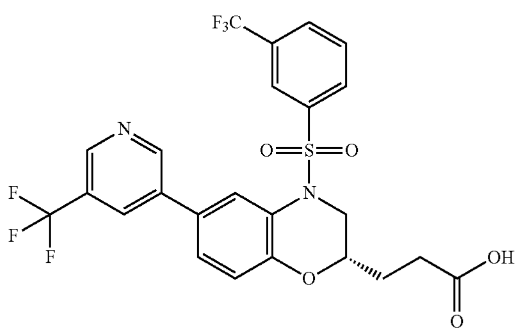 [SMILES: O=C(O)CC[C@H]1CN(S(=O)(=O)c2cccc(C(F)(F)F)c2)c2cc(-c3cncc(C(F)(F)F)c3)ccc2O1] | (S)-3-(4-((3-(trifluoromethyl)phenyl)sulfonyl)-6-(5-(trifluoromethyl)pyridin-3-yl)-3,4-dihydro-2H-benzo[b][1,4]oxazin-2-yl)propanoic acid | 561 (M + H)+ |
| 2AL | 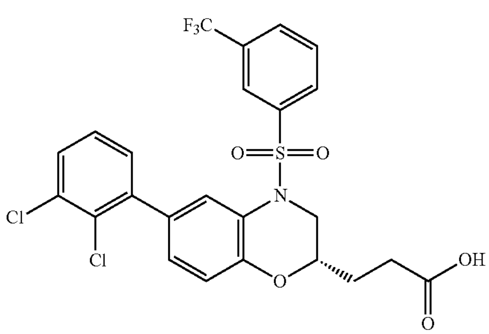 | (S)-3-(6-(2,3-dichlorophenyl)-4-((3-(trifluoromethyl)phenyl)sulfonyl)-3,4-dihydro-2H-benzo[b][1,4]oxazin-2-yl)propanoic acid | 582 (M + Na)− |

TABLE 2-continued

| Compd No. | Structure | Name | Observed m/z |
|---|---|---|---|
| 2AM | 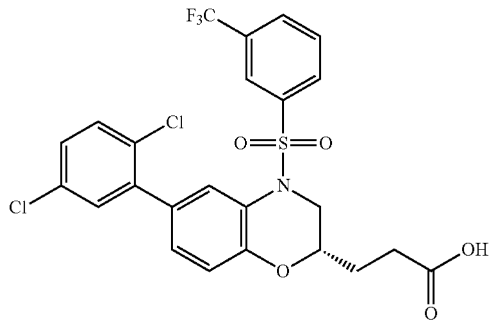 [SMILES: O=C(O)CC[C@H]1CN(S(=O)(=O)c2cccc(C(F)(F)F)c2)c2cc(-c3cc(Cl)ccc3Cl)ccc2O1] | (S)-3-(6-(2,5-dichlorophenyl)-4-((3-(trifluoromethyl)phenyl)-sulfonyl)-3,4-dihydro-2H-benzo[b][1,4]oxazin-2-yl)propanoic acid | 582 (M + H)⁻ |
| 2AN | 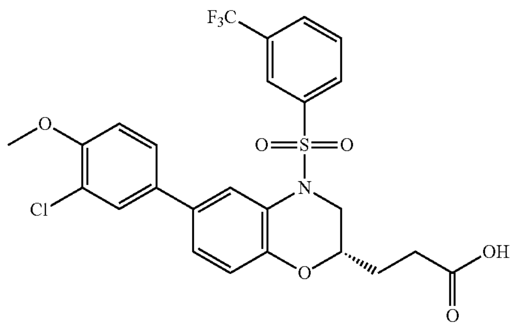 [SMILES: COc1ccc(-c2ccc3c(c2)N(S(=O)(=O)c2cccc(C(F)(F)F)c2)C[C@H](CCC(=O)O)O3)cc1Cl] | (S)-3-(6-(3-chloro-4-methoxyphenyl)-4-((3-(trifluoromethyl)phenyl)-sulfonyl)-3,4-dihydro-2H-benzo[b][1,4]oxazin-2-yl)propanoic acid | 578 (M + Na)⁺ |
| 2AO | 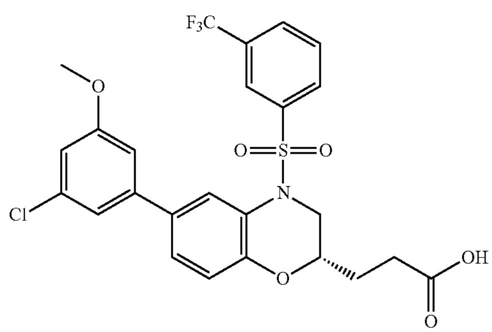 [SMILES: COc1cc(Cl)cc(-c2ccc3c(c2)N(S(=O)(=O)c2cccc(C(F)(F)F)c2)C[C@H](CCC(=O)O)O3)c1] | (S)-3-(6-(3-chloro-5-methoxyphenyl)-4-((3-(trifluoromethyl)phenyl)-sulfonyl)-3,4-dihydro-2H-benzo[b][1,4]oxazin-2-yl)propanoic acid | 556 (M + H)⁺ |
| 2AP | 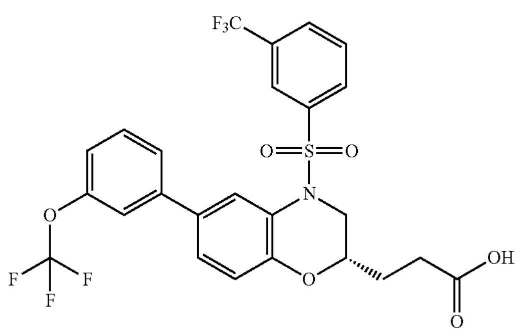 [SMILES: O=C(O)CC[C@H]1CN(S(=O)(=O)c2cccc(C(F)(F)F)c2)c2cc(-c3cccc(OC(F)(F)F)c3)ccc2O1] | (S)-3-(6-(3-(trifluoromethoxy)-phenyl)-4-((3-(trifluoromethyl)-phenyl)sulfonyl)-3,4-dihydro-2H-benzo[b][1,4]oxazin-2-yl)propanoic acid | 576 (M + H)⁺ |

TABLE 2-continued

| Compd No. | Structure | Name | Observed m/z |
|---|---|---|---|
| 2AQ | 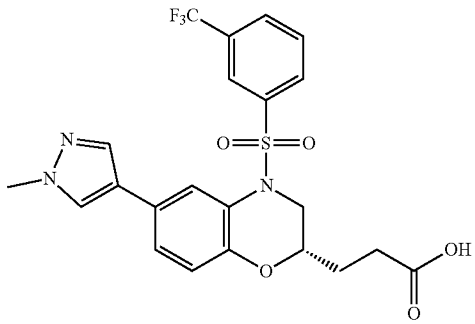 [SMILES: Cn1cc(-c2ccc3c(c2)N(S(=O)(=O)c2cccc(C(F)(F)F)c2)C[C@H](CCC(=O)O)O3)cn1] | (S)-3-(6-(1-methyl-1H-pyrazol-4-yl)-4-((3-(trifluoromethyl)-phenyl)sulfonyl)-3,4-dihydro-2H-benzo[b][1,4]oxazin-2-yl)propanoic acid | 496 (M + H)+ |
| 2AR | 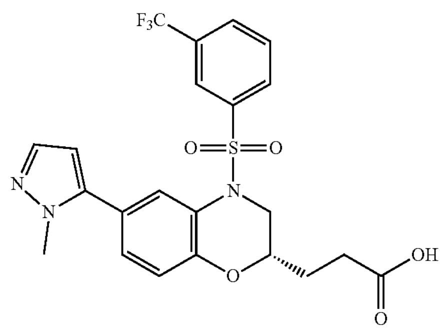 [SMILES: Cn1nccc1-c1ccc2c(c1)N(S(=O)(=O)c1cccc(C(F)(F)F)c1)C[C@H](CCC(=O)O)O2] | (S)-3-(6-(1-methyl-1H-pyrazol-5-yl)-4-((3-(trifluoromethyl)-phenyl)sulfonyl)-3,4-dihydro-2H-benzo[b][1,4]oxazin-2-yl)propanoic acid | 496 (M + H)+ |
| 2AS | 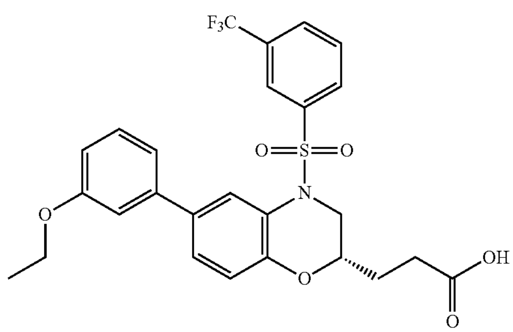 [SMILES: CCOc1cccc(-c2ccc3c(c2)N(S(=O)(=O)c2cccc(C(F)(F)F)c2)C[C@H](CCC(=O)O)O3)c1] | (S)-3-(6-(3-ethoxyphenyl)-4-((3-(trifluoromethyl)phenyl)-sulfonyl)-3,4-dihydro-2H-benzo[b][1,4]-oxazin-2-yl)propanoic acid | 536 (M + H)+ |
| 2AT | 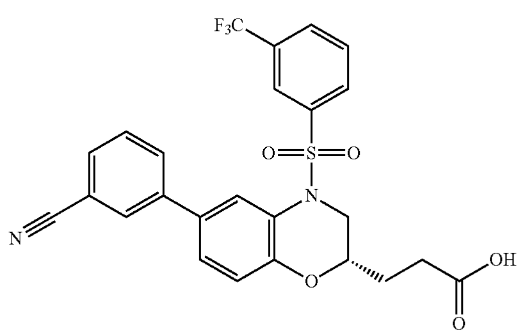 [SMILES: N#Cc1cccc(-c2ccc3c(c2)N(S(=O)(=O)c2cccc(C(F)(F)F)c2)C[C@H](CCC(=O)O)O3)c1] | (S)-3-(6-(3-cyanophenyl)-4-((3-(trifluoromethyl)phenyl)-sulfonyl)-3,4-dihydro-2H-benzo[b][1,4]oxazin-2-yl)propanoic acid | 539 (M + Na)+ |

TABLE 2-continued

| Compd No. | Structure | Name | Observed m/z |
|---|---|---|---|
| 2AU | 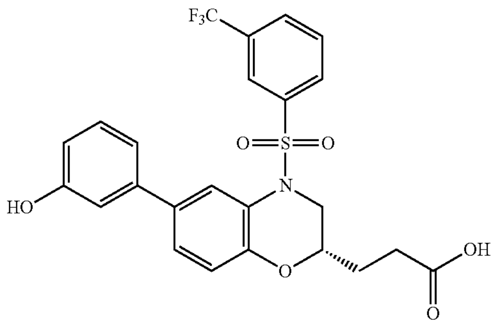 [SMILES: O=C(O)CC[C@H]1CN(S(=O)(=O)c2cccc(C(F)(F)F)c2)c2cc(-c3cccc(O)c3)ccc2O1] | (S)-3-(6-(3-hydroxyphenyl)-4-((3-(trifluoromethyl)phenyl)-sulfonyl)-3,4-dihydro-2H-benzo[b][1,4]oxazin-2-yl)propanoic acid | 525 $(M + NH_4)^+$ |
| 2AV | 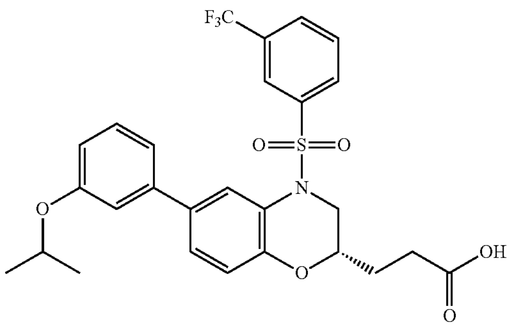 [SMILES: CC(C)Oc1cccc(-c2ccc3c(c2)N(S(=O)(=O)c2cccc(C(F)(F)F)c2)C[C@H](CCC(=O)O)O3)c1] | (S)-3-(6-(3-isopropoxyphenyl)-4-((3-(trifluoromethyl)phenyl)-sulfonyl)-3,4-dihydro-2H-benzo[b][1,4]oxazin-2-yl)propanoic acid | 550 $(M + H)^+$ |
| 2AW | 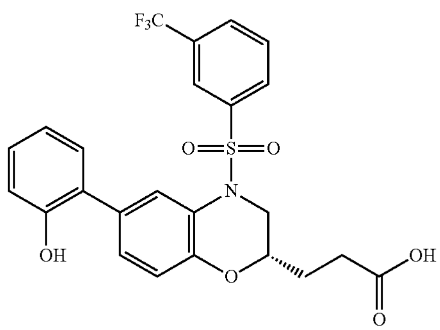 [SMILES: O=C(O)CC[C@H]1CN(S(=O)(=O)c2cccc(C(F)(F)F)c2)c2cc(-c3ccccc3O)ccc2O1] | (S)-3-(6-(2-hydroxyphenyl)-4-((3-(trifluoromethyl)phenyl)-sulfonyl)-3,4-dihydro-2H-benzo[b][1,4]oxazin-2-yl)propanoic acid | 530 $(M + Na)^+$ |
| 2AX | 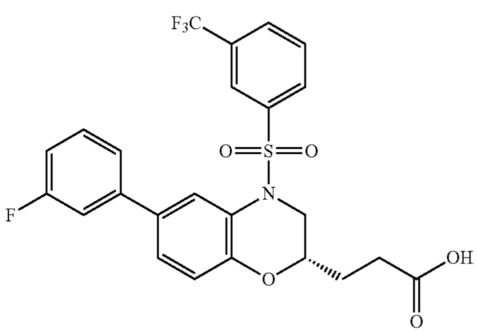 [SMILES: O=C(O)CC[C@H]1CN(S(=O)(=O)c2cccc(C(F)(F)F)c2)c2cc(-c3cccc(F)c3)ccc2O1] | (S)-3-(6-(3-fluorophenyl)-4-((3-(trifluoromethyl)phenyl)-sulfonyl)-3,4-dihydro-2H-benzo[b][1,4]oxazin-2-yl)propanoic acid | 532 $(M + Na)^+$ |

TABLE 2-continued

| Compd No. | Structure | Name | Observed m/z |
|---|---|---|---|
| 2AY | 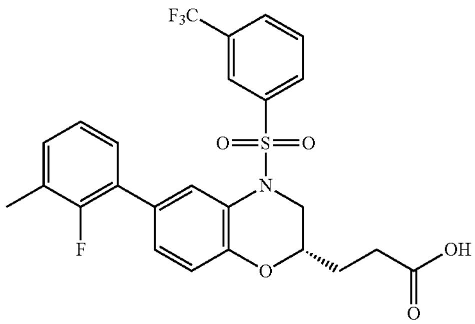 | (S)-3-(6-(2-fluoro-3-methyl-phenyl)-4-((3-(trifluoro-methyl)phenyl)sulfonyl)-3,4-dihydro-2H-benzo[b][1,4]-oxazin-2-yl)propanoic acid | 524 (M + H)+ |
| 2AZ | 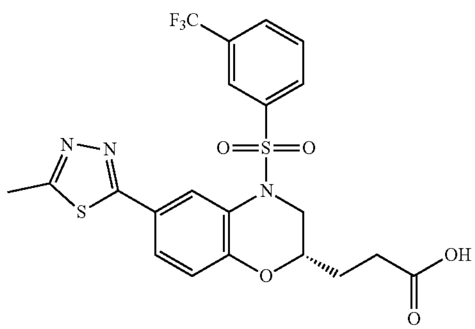 [SMILES: Cc1nnc(-c2ccc3c(c2)N(S(=O)(=O)c2cccc(C(F)(F)F)c2)C[C@H](CCC(=O)O)O3)s1] | (S)-3-(6-(5-methyl-1,3,4-thiadiazol-2-yl)-4-((3-(trifluoromethyl)phenyl)-sulfonyl)-3,4-dihydro-2H-benzo[b][1,4]oxazin-2-yl)propanoic acid | 514 (M + H)+ |
| 2BA | 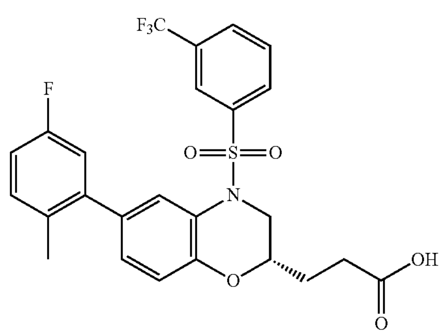 [SMILES: Cc1ccc(F)cc1-c1ccc2c(c1)N(S(=O)(=O)c1cccc(C(F)(F)F)c1)C[C@H](CCC(=O)O)O2] | (S)-3-(6-(5-fluoro-2-methylphenyl)-4-((3-(trifluoromethyl)phenyl)sulfonyl)-3,4-dihydro-2H-benzo[b][1,4]oxazin-2-yl)propanoic acid | 524 (M + H)+ |
| 2BC | 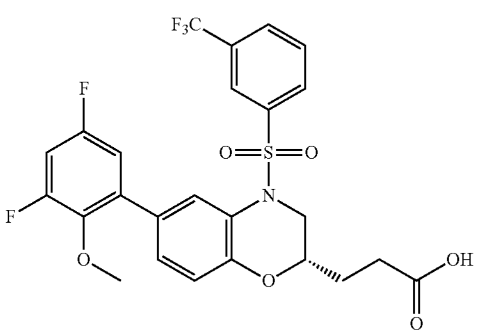 | (S)-3-(6-(3,5-difluoro-2-methoxyphenyl)-4-((3-(trifluoromethyl)phenyl)-sulfonyl)-3,4-dihydro-2H-benzo[b][1,4]oxazin-2-yl)propanoic acid | 558 (M + H)+ |

TABLE 2-continued

| Compd No. | Structure | Name | Observed m/z |
|---|---|---|---|
| 2BD | 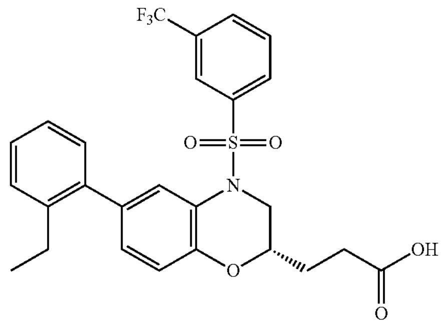 | (S)-3-(6-(2-ethylphenyl)-4-((3-(trifluoromethyl)phenyl)sulfonyl)-3,4-dihydro-2H-benzo[b][1,4]oxazin-2-yl)propanoic acid | 520 (M + H)+ |
| 2BE | 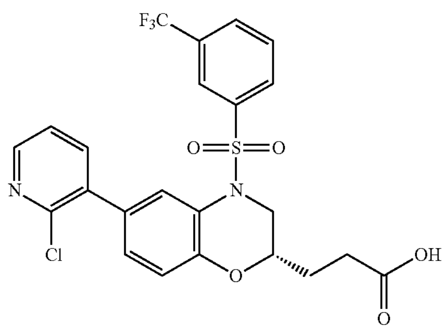 | (S)-3-(6-(2-chloropyridin-3-yl)-4-((3-(trifluoromethyl)phenyl)-sulfonyl)-3,4-dihydro-2H-benzo[b][1,4]oxazin-2-yl)propanoic acid | 527 (M + H)+ |
| 2BF | 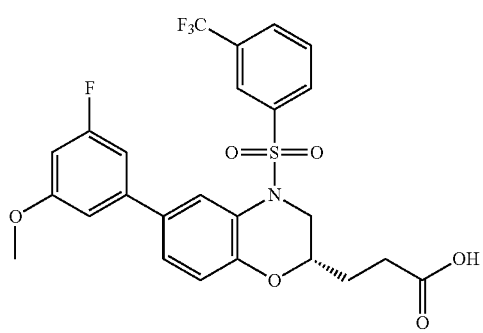 | (S)-3-(6-(3-fluoro-5-methoxyphenyl)-4-((3-(trifluoromethyl)-phenyl)sulfonyl)-3,4-dihydro-2H-benzo[b][1,4]oxazin-2-yl)propanoic acid | 540 (M + H)+ |
| 2BG | 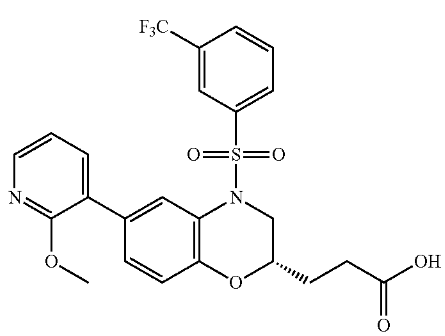 [SMILES: COc1ncccc1-c1ccc2c(c1)N(S(=O)(=O)c1cccc(C(F)(F)F)c1)C[C@H](CCC(=O)O)O2] | (S)-3-(6-(2-methoxypyridin-3-yl)-4-((3-(trifluoromethyl)-phenyl)sulfonyl)-3,4-dihydro-2H-benzo[b][1,4]oxazin-2-yl)propanoic acid | 523 (M + H)+ |

TABLE 2-continued

| Compd No. | Structure | Name | Observed m/z |
|---|---|---|---|
| 2BH | 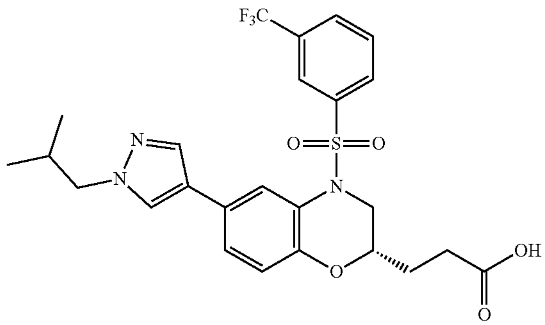 [SMILES: CC(C)Cn1cc(-c2ccc3c(c2)N(S(=O)(=O)c2cccc(C(F)(F)F)c2)C[C@H](CCC(=O)O)O3)cn1] | (S)-3-(6-(1-isobutyl-1H-pyrazol-4-yl)-4-((3-(trifluoromethyl)phenyl)sulfonyl)-3,4-dihydro-2H-benzo[b][1,4]oxazin-2-yl)propanoic acid | 538 (M + H)+ |
| 2BI | 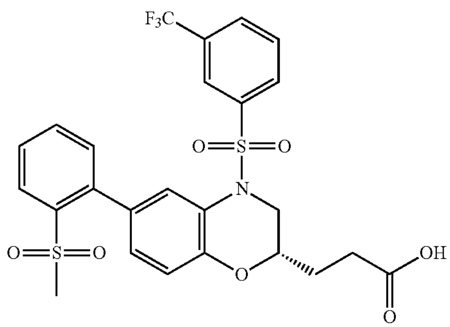 [SMILES: CS(=O)(=O)c1ccccc1-c1ccc2c(c1)N(S(=O)(=O)c1cccc(C(F)(F)F)c1)C[C@H](CCC(=O)O)O2] | (S)-3-(6-(2-(methylsulfonyl)phenyl)-4-((3-(trifluoromethyl)phenyl)sulfonyl)-3,4-dihydro-2H-benzo[b][1,4]oxazin-2-yl)propanoic acid | 570 (M + H)+ |
| 2BJ | 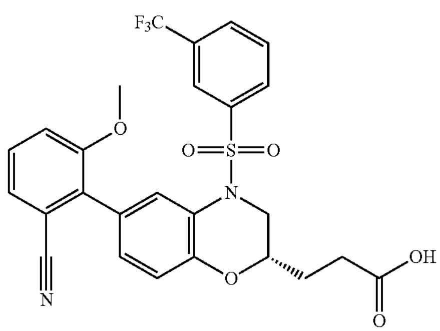 [SMILES: COc1cccc(C#N)c1-c1ccc2c(c1)N(S(=O)(=O)c1cccc(C(F)(F)F)c1)C[C@H](CCC(=O)O)O2] | (S)-3-(6-(2-cyano-6-methoxyphenyl)-4-((3-(trifluoromethyl)phenyl)sulfonyl)-3,4-dihydro-2H-benzo[b][1,4]oxazin-2-yl)propanoic acid | 547 (M + H)+ |
| 2BK | 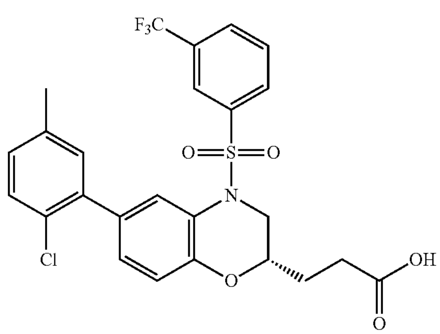 | (S)-3-(6-(2-chloro-5-methylphenyl)-4-((3-(trifluoromethyl)phenyl)sulfonyl)-3,4-dihydro-2H-benzo[b][1,4]oxazin-2-yl)propanoic acid | 540 (M + H)+ |

TABLE 2-continued

| Compd No. | Structure | Name | Observed m/z |
|---|---|---|---|
| 2BL | 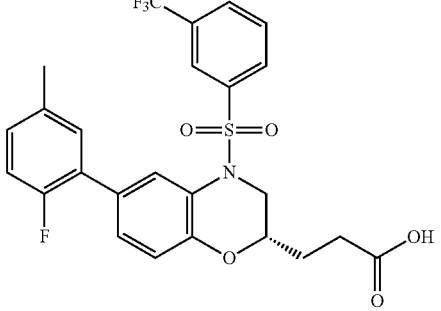 | (S)-3-(6-(2-fluoro-5-methyl-phenyl)-4-((3-(trifluoromethyl)-phenyl)sulfonyl)-3,4-dihydro-2H-benzo[b][1,4]oxazin-2-yl)propanoic acid | 524 (M + H)+ |
| 2BM | 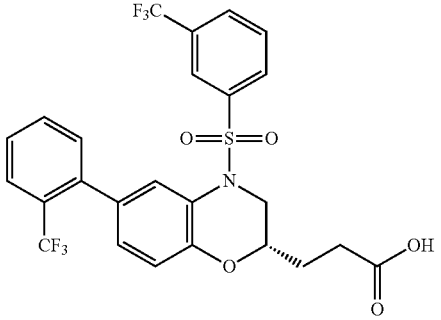 | (S)-3-(6-(2-(trifluoromethyl)-phenyl)-4-((3-(trifluoromethyl)-phenyl)sulfonyl)-3,4-dihydro-2H-benzo[b][1,4]oxazin-2-yl)propanoic acid | 560 (M + H)+ |
| 2BN | 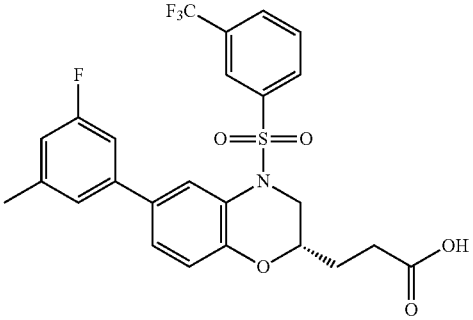 | (S)-3-(6-(3-fluoro-5-methyl-phenyl)-4-((3-(trifluoromethyl)-phenyl)sulfonyl)-3,4-dihydro-2H-benzo[b][1,4]oxazin-2-yl)propanoic acid | 524 (M + H)+ |
| 2BO | 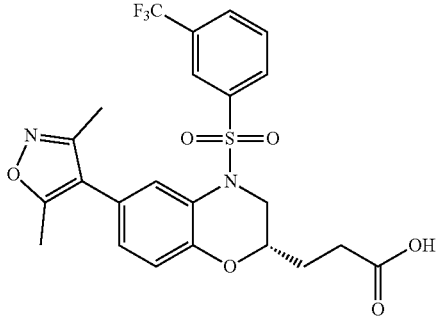 [SMILES: Cc1noc(C)c1-c1ccc2c(c1)N(S(=O)(=O)c1cccc(C(F)(F)F)c1)C[C@H](CCC(=O)O)O2] | (S)-3-(6-(3,5-dimethylisoxazol-4-yl)-4-((3-(trifluoromethyl)-phenyl)sulfonyl)-3,4-dihydro-2H-benzo[b][1,4]oxazin-2-yl)propanoic acid | 511 (M + H)+ |

TABLE 2A

| Compd No. | Structure | Name | Observed m/z |
|---|---|---|---|
| 2BP | 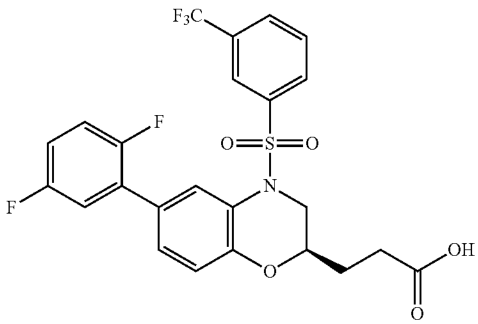 [SMILES: O=C(O)CC[C@@H]1CN(S(=O)(=O)c2cccc(C(F)(F)F)c2)c2cc(-c3cc(F)ccc3F)ccc2O1] | (R)-3-(6-(2,5-difluorophenyl)-4-((3-(trifluoromethyl)phenyl)-sulfonyl)-3,4-dihydro-2H-benzo[b][1,4]oxazin-2-yl)propanoic acid | 528 (M + H)+ |
| 2BQ | 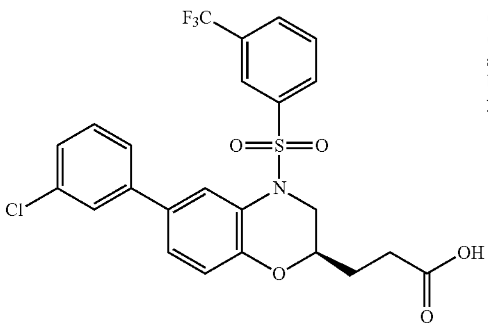 | (R)-3-(6-(3-chlorophenyl)-4-((3-(trifluoromethyl)phenyl)-sulfonyl)-3,4-dihydro-2H-benzo[b][1,4]oxazin-2-yl)propanoic acid | 526 (M + H)+ |
| 2BR | 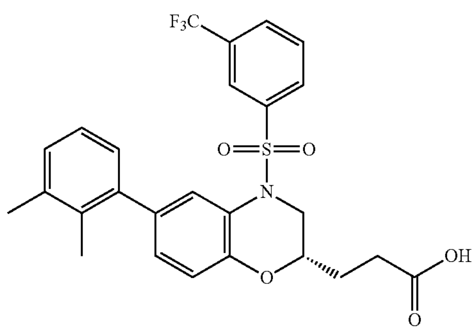 [SMILES: Cc1cccc(-c2ccc3c(c2)N(S(=O)(=O)c2cccc(C(F)(F)F)c2)C[C@H](CCC(=O)O)O3)c1C] | (S)-3-(6-(2,3-dimethylphenyl)-4-((3-(trifluoromethyl)phenyl)-sulfonyl)-3,4-dihydro-2H-benzo[b][1,4]oxazin-2-yl)propanoic acid | 520 (M + H)+ |

TABLE 2B

| Compd No. | Physical Characterization Data |
|---|---|
| 2I | $^1$H NMR (300 MHz, CD$_3$OD-d$_4$) δ 8.06-7.96 (m, 3H), 7.93 (s, 1H), 7.80 (t, J = 7.9 Hz, 1H), 7.47-7.38 (m, 2H), 7.30 (dt, J = 9.9, 2.0 Hz, 1H), 7.20 (dt, J = 8.5, 2.1 Hz, 1H), 6.96 (d, J = 8.6 Hz, 1H), 4.46 (dd, J = 14.5, 2.4 Hz, 1H), 3.46 (m, 1H), 3.28 (m, 1H), 2.44 (q, J = 7.0 Hz, 2H), 1.92 (m, 1H), 1.84 (m, 1H). |
| 2J | $^1$H NMR (300 MHz, CD$_3$OD-d$_4$) δ 8.02-7.98 (m, 3H), 7.92 (s, 1H), 7.79 (t, J = 7.9 Hz, 1H), 7.66 (dd, J = 7.0, 2.3 Hz, 1H), 7.56-7.52 (m, 1H), 7.41-7.29 (m, 2H), 6.93 (d, J = 8.5 Hz, 1H), 4.45 (dd, J = 14.5, 2.4 Hz, 1H), 3.46-3.42 (m, 1H), 3.32-3.25 (m, 1H), 2.53-2.34 (m, 2H), 1.94-1.90 (m, 1H), 1.90-1.78 (m, 1H). |
| 2K | $^1$H NMR (300 MHz, CD$_3$OD-d$_4$) δ 8.03 (t, J = 2.4, 1H), 7.99 (t, J = 8.4, 16.8 Hz, 2H), 7.93 (s, 1H), 7.78 (t, J = 7.6, 15.6 Hz, 1H), 7.39-7.35 (m, 2H), 7.15 (m, 1H), 7.11 (m, 1H), 6.94-6.90 (m, 2H), 4.45 (dd, J = 14.4, 2.4 Hz, 1H), 3.88 (s, 3H), 3.47 (m, 1H), 3.29 (m, 1H), 2.53-2.35 (m, 2H), 1.93 (m, 1H), 1.81 (m, 1H). |
| 2L | $^1$H NMR (300 MHz, CD$_3$OD-d$_4$) δ 8.04-7.93 (m, 3H), 7.82 (s, 1H), 7.80 (t, J = 7.9 Hz, 1H), 7.53 (d, J = 2.0 Hz, 2H), 7.46-7.37 (m, 2H), 6.96 (d, J = 8.6 Hz, 1H), 4.46 (dd, J = 14.5, 2.4 Hz, 1H), 3.48-3.43 (m, 1H), 3.33-3.24 (m, 1H), 2.49-2.37 (m, 2H), 1.96-1.78 (m, 2H). |
| 2M | $^1$H NMR (300 MHz, CD$_3$OD-d$_4$) δ 8.07-7.89 (m, 4H), 7.78 (t, J = 7.9 Hz, 1H), 7.60-7.30 (m, 5H), 6.93 (d, J = 8.6 Hz, 1H), 4.45 (dd, J = 14.3, 2.3 Hz, 1H), 3.46 (s, 1H), 3.27 (d, J = 10.0 Hz, 1H), 2.43 (td, J = 7.1, 3.8 Hz, 2H), 1.93-1.73 (m, 2H) |
| 2N | $^1$H NMR (300 MHz, CDCl$_3$) δ 8.07-8.00 (m, 2H), 7.92-7.86 (m, 2H), 7.68-7.60 (m, 3H), 7.35-7.28 (m, 2H), 6.95-6.93 (m, 1H), 4.40 (dd, J = 14.5, 2.4 Hz, 1H), 3.66-3.64 (m, 1H), 3.33-3.27 (m, 1H), 2.67-2.54 (m, 2H), 2.03-1.79 (m, 2H). |

TABLE 2B-continued

| Compd No. | Physical Characterization Data |
|---|---|
| 2O | $^1$H NMR (300 MHz, CDCl$_3$) δ 8.09 (s, 2H), 7.93-7.86 (m, 1H), 7.69-7.61 (m, 1H), 7.32-7.27 (m, 2H), 6.96-6.93 (m, 1H), 4.40 (dd, J = 14.5, 2.4 Hz, 1H), 3.70-3.66 (m, 1H), 3.33-3.27 (m, 1H), 2.65-2.54 (m, 2H), 2.03-1.85 (m, 2H). |
| 2P | $^1$H NMR (300 MHz, CD$_3$OD-d$_4$) δ 8.04-7.96 (m, 2H), 7.83-7.77 (m, 2H), 7.73 (s, 1H), 7.30-7.16 (m, 4H), 7.05 (dd, 1H), 6.87 (d, 1H), 4.44 (dd, 1H), 3.43 (m, 1H), 3.28 (m, 1H), 2.44 (m, 2H), 2.30 (s, 3H), 1.91 (m, 1H), 1.79 (m, 1H). |
| 2Q | $^1$H NMR (300 MHz, CD$_3$OD-d$_4$) δ 7.99 (s, 1H), 7.99-7.95 (m, 2H), 7.91 (s, 1H), 7.78 (m, 1H), 7.37-7.29 (m, 4H), 7.16 (m, 1H), 6.88 (d, 1H), 4.45 (dd, 1H), 3.45 (m, 1H), 3.28 (m, 1H), 2.43 (m, 2H), 2.42 (s, 3H), 1.92 (m, 1H), 1.79 (m, 1H). |
| 2R | $^1$H NMR (300 MHz, CD$_3$OD-d$_4$) δ 8.07-7.92 (m, 4H), 7.80 (t, J = 7.9 Hz, 1H), 7.48 (m, 1H), 7.43-7.39 (m, 1H), 7.34-7.22 (m, 2H), 6.95 (d, J = 8.5 Hz, 1H), 4.49 (dd, J = 14.5, 2.4 Hz, 1H), 3.52 (m, 1H), 3.31 (m, 1H), 2.55-2.37 (m, 2H), 1.93 (m, 1H), 1.84 (m, 1H). |
| 2S | $^1$H NMR (300 MHz, CD$_3$OD-d$_4$) δ 8.05-8.01 (m, 2H), 7.96 (t, J = 8.0 Hz, 2H), 7.78 (t, J = 8.0 Hz, 1H), 7.34-7.28 (m, 2H), 7.22 (dd, J = 2.4, 8.8 Hz, 1H), 6.86 (d, J = 8.4 Hz, 1H), 4.47 (dd, J = 2.0, 14.4 Hz, 1H), 3.86 (s, 3H), 3.45 (ddd, J = 2.5, 4.7, 10.1 Hz, 1H), 3.28 (dd, J = 10.1, 14.4 Hz, 1H), 2.52-2.35 (m, 2H), 1.98-1.73 (m, 2H). |
| 2T | $^1$H NMR (300 MHz, CD$_3$OD-d$_4$) δ 8.07-8.00 (m, 2H), 7.96 (d, J = 8.4 Hz, 2H), 7.78 (t, J = 7.8 Hz, 1H), 7.39-7.31 (m, 2H), 7.25 (m, 1H), 7.10 (d, J = 8.0 Hz, 1H), 7.06 (M, 1H), 4.47 (dd, J = 2.4, 14.4 Hz, 1H), 3.86 (s, 3H), 3.46 (ddd, J = 10.2, 4.6, 2.5 Hz, 1H), 3.28 (dd, J = 14.5, 10.1 Hz, 1H), 2.54-2.35 (m, 2H), 1.98-1.73 (m, 2H). |
| 2U | $^1$H NMR (300 MHz, CD$_3$OD-d$_4$) δ 8.01-7.97 (m, 3H), 7.93 (s, 1H), 7.78 (t, J = 7.8 Hz, 1H), 7.56-7.47 (m, 2H), 7.34 (dd, J = 8.5, 2.2 Hz, 1H), 7.06-6.98 (m, 2H), 6.88 (d, J = 8.5 Hz, 1H), 4.45 (dd, J = 14.4, 2.4 Hz, 1H), 3.86 (s, 3H), 3.45 (dddd, J = 10.2, 7.2, 4.4, 2.3 Hz, 1H), 3.29 (dd, J = 14.4, 10.0 Hz, 1H), 2.49-2.39 (m, 2H), 1.98-1.75 (m, 2H). |
| 2V | $^1$H NMR (300 MHz, CD$_3$OD-d$_4$) δ 8.34 (s, 1H), 8.22 (s, 1H), 8.06 (s, 1H), 8.02-7.94 (m, 2H), 7.89 (s, 1H), 7.77 (m, 1H), 7.55 (s, 1H), 7.44 (m, 1H), 6.95 (d, 1H), 4.44 (dd, 1H), 3.44 (m, 1H), 3.28 (m, 1H), 2.41 (m, 2H), 1.95-1.70 (m, 2H). |
| 2W | $^1$H NMR (300 MHz, CD$_3$OD-d$_4$) δ 8.06-7.92 (m, 2H), 7.88-7.82 (m, 2H), 7.78 (t, J = 7.9 Hz, 1H), 7.45-7.25 (m, 2H), 7.15 (ddd, J = 18.3, 8.4, 2.4 Hz, 2H), 6.89 (d, J = 8.5 Hz, 1H), 4.46 (dd, J = 14.5, 2.4 Hz, 1H), 3.44 (tdd, J = 10.3, 4.5, 2.4 Hz, 1H), 3.25 (d, J = 10.1 Hz, 1H), 2.52-2.35 (m, 2H), 1.95-1.70 (m, 2H). |
| 2X | $^1$H NMR (300 MHz, CD$_3$OD-d$_4$) δ 8.00 (s, 1H), 7.99-7.94 (m, 2H), 7.91 (s, 1H), 7.76 (m, 1H), 7.45 (d, 2H), 7.36 (m, 1H), 7.26 (d, 2H), 6.87 (d, 1H), 4.44 (dd, 1H), 3.45 (m, 1H), 3.27 (m, 1H), 2.43 (m, 2H), 2.38 (s, 3H), 1.88 (m, 1H), 1.78 (m, 1H). |
| 2Y | $^1$H NMR (300 MHz, CD$_3$OD-d$_4$) δ 8.00 (s, 1H), 7.99-7.94 (m, 2H), 7.91 (s, 1H), 7.77 (m, 1H), 7.41-7.21 (m, 5H), 6.89 (d, 1H), 4.45 (dd, 1H), 3.45 (m, 1H), 3.29 (m, 1H), 2.98 (m, 1H), 2.43 (m, 2H), 1.91 (m, 1H), 1.81 (m, 1H), 1.31 (d, 6H). |
| 2Z | $^1$H NMR (300 MHz, CD$_3$OD-d$_4$) δ 8.01 (s, 1H), 8.00-7.94 (m, 2H), 7.91 (s, 1H), 7.76 (m, 1H), 7.48 (d, 2H), 7.36-7.30 (m, 3H), 6.87 (d, 1H), 4.44 (dd, 1H), 3.46 (m, 1H), 3.29 (m, 1H), 2.95 (m, 1H), 2.41 (m, 2H), 1.89 (m, 1H), 1.81 (m, 1H), 1.29 (d, 6H). |
| 2AA | $^1$H NMR (300 MHz, CD$_3$OD-d$_4$) δ 8.74 (d, 1H), 8.22 (s, 1H), 8.01-7.89 (m, 5H), 7.79 (m, 1H), 7.61 (dd, 1H), 7.01 (d, 1H), 4.44 (dd, 1H), 3.46 (m, 1H), 3.31 (m, 1H), 2.45 (m, 2H), 1.92 (m, 1H), 1.81 (m, 1H). |
| 2AB | $^1$H NMR (300 MHz, CD$_3$OD-d$_4$) δ 8.03-7.95 (m, 2H), 7.86 (s, 1H), 7.78 (m, 1H), 7.57 (s, 1H), 7.42-7.33 (m, 2H), 7.15 (m, 1H), 6.89 (d, 1H), 4.45 (dd, 1H), 3.43 (m, 1H), 3.26 (m, 1H), 2.41 (m, 2H), 1.95-1.74 (m, 2H). |
| 2AC | $^1$H NMR (300 MHz, CD$_3$OD-d$_4$) δ 8.06-7.93 (m, 3H), 7.91-7.86 (m, 1H), 7.78 (t, J = 7.9 Hz, 1H), 7.40 (dd, J = 7.9, 1.6 Hz, 1H), 7.34-7.24 (m, 2H), 7.17 (t, J = 7.8 Hz, 1H), 6.90 (d, J = 8.5 Hz, 1H), 4.44 (dd, J = 14.5, 2.4 Hz, 1H), 3.54 (s, 3H), 3.51-3.44 (m, 1H), 3.29-3.21 (m, 1H), 2.53-2.34 (m, 2H), 1.98-1.73 (m, 2H). |
| 2AD | $^1$H NMR (300 MHz, CDCl$_3$) δ 8.02 (s, 2H), 7.91-7. 84 (m, 1H), 7.67-7.63 (m, 1H), 7.28-7.26 (m, 1H), 7.16-7.10 (m, 2H), 7.05-6.99 (m, 1H), 6.92 (d, J = 8.4 Hz, 1H), 4.39 (dd, J = 2.4 Hz, 14.4 Hz, 1H), 3.64-3.69 (m, 1H), 3.27-3.33 (m 1H), 2.54-2.65 (m, 2H), 1.85-2.02 (m, 2H). |
| 2AE | $^1$H NMR (300 MHz, CDCl$_3$) δ 8.02-8.01 (m, 2H), 7.89-7.87 (m, 2H), 7.68-7.64 (m, 1H), 7.58 (s, 1H), 7.46-7.44 (m, 1H), 7.36-7.28 (m, 2H), 6.96-6.94 (m, 1H), 4.35 (dd, J = 14.5, 2.4 Hz, 2H), 3.70-3.66 (m, 1H), 3.33-3.27 (m, 1H), 2.65-2.54 (m, 2H), 2.03-1.85 (m, 2H). |
| 2AF | $^1$H NMR (300 MHz, CDCl$_3$) δ 8.02-8.01 (m, 2H), 7.89-7.87 (m, 2H), 7.68-7.64 (m, 1H), 7.58 (s, 1H), 7.45 (m, 1H), 7.36-7.28 (m, 2H), 6.95 (m, 1H), 4.35 (dd, J = 14.5, 2.4 Hz, 1H), 3.68 (m, 1H), 3.30 (m, 1H), 2.65-2.54 (m, 2H), 2.03-1.85 (m, 2H). |
| 2AG | $^1$H NMR (300 MHz, CDCl$_3$) δ 7.98 (s, 1H), 7.94-7.81 (m, 3H), 7.54-7.64 (m, 1H), 7.30-7.34 (m, 2H), 7.16-7.07 (m, 2H), 6.91 (d, J = 8.4 Hz, 1H), 4.43 (dd, J = 14.3, 2.4 Hz, 1H), 3.59-3.62 (m, 1H), 3.26-3.32 (m, 1H), 2.55-2.61 (m, 2H), 1.98-2.02 (m, 1H), 1.81-1.97 (m, 1H). |
| 2AH | $^1$H NMR (300 MHz, CDCl$_3$) δ 7.98 (s, 1H), 7.92-7.85 (m, 3H), 7.65 (m, 1H), 7.30 (m, 1H), 7.20-7.14 (m, 3H), 6.92 (d, J = 8.4 Hz, 1H), 4.42 (dd, J = 14.3, 2.4 Hz, 1H), 3.64 (m, 1H), 3.30 (m, 1H), 2.65-2.56 (m, 2H), 2.03-1.82 (m, 2H). |
| 2AI | $^1$H NMR (300 MHz, CDCl$_3$) δ 7.99 (s, 1H), 7.93-7.85 (m, 3H), 7.65 (m, 1H), 7.30 (m, 1H), 7.20-7.14 (m, 3H), 6.92 (d, J = 8.4 Hz, 1H), 4.42 (dd, J = 14.3, 2.4 Hz, 1H), 3.64 (m, 1H), 3.30 (m, 1H), 2.65-2.56 (m, 2H), 2.03-1.82 (m, 2H). |
| 2AJ | $^1$H NMR (300 MHz, CD$_3$OD-d$_4$) δ 8.04-7.96 (m, 2H), 7.81-7.76 (m, 2H), 7.68 (s, 1H), 7.41-7.02 (m, 5H), 6.87 (d, 1H), 4.44 (dd, 1H), 3.40 (m, 1H), 3.28 (m, 1H), 3.11 (m, 1H), 2.41 (m, 2H), 1.95-1.73 (m, 2H), 1.22-1.14 (m, 6H). |
| 2AK | $^1$H NMR (300 MHz, CD$_3$OD-d$_4$) δ 9.04 (s, 1H), 8.83 (s, 1H), 8.27 (s, 1H), 8.10 (s, 1H), 8.01-7.92 (m, 3H), 7.77 (m, 1H), 7.48 (dd, 1H), 7.00 (d, 1H), 4.45 (dd, 1H), 3.45 (m, 1H), 3.28 (m, 1H), 2.38 (m, 2H), 1.95-1.75 (m, 2H). |
| 2AL | $^1$H NMR (300 MHz, CD$_3$OD-d$_4$) δ 8.06-7.93 (m, 3H), 7.87 (m, 1H), 7.78 (t, J = 7.9 Hz, 1H), 7.40 (dd, J = 7.9, 1.6 Hz, 1H), 7.34-7.24 (m, 2H), 7.17 (t, J = 7.8 Hz, 1H), 6.90 (d, J = 8.5 Hz, |

TABLE 2B-continued

| Compd No. | Physical Characterization Data |
| --- | --- |
| | 1H), 4.44 (dd, J = 14.5, 2.4 Hz, 1H), 3.54 (s, 3H), 3.51-3.44 (m, 1H), 3.29-3.21 (m, 1H), 2.53-2.34 (m, 2H), 1.98-1.73 (m, 2H). |
| 2AM | $^1$H NMR (300 MHz, CD$_3$OD-d$_4$) δ 7.93-7.82 (m, 2H), 7.68-7.57 (m, 2H), 7.58-7.47 (m, 2H), 7.41-7.25 (m, 2H), 7.04 (m, 1H), 6.68-6.51 (m, 3H), 4.28 (s, 2H), 3.82 (s, 2H), 3.20 (q, J = 7.4 Hz, 2H), 1.21 (t, J = 7.4 Hz, 3H). |
| 2AN | $^1$H NMR (300 MHz, CD$_3$OD-d$_4$) δ 8.01-7.99 (t, J = 8.8 Hz, 3H), 7.92 (s, 1H), 7.89 (t, J = 8.0 Hz, 1H), 7.54 (d, J = 2.0 Hz, 1H), 7.52-7.49 (dd, J = 2.4, 8.8 Hz, 1H), 7.33 (dd, J = 2.0, 8.8 Hz, 1H), 7.17 (d, J = 8.4 Hz, 1H), 6.90 (d, J = 8.4 Hz, 1H), 4.45 (dd, J = 2.4, 14.8 Hz, 1H), 3.95 (s, 3H), 3.45-3.42 (m, 3H), 3.27 (m, 1H), 2.49-2.37 (m, 2H), 1.93 (m, 1H), 1.87 (m, 1H). |
| 2AO | $^1$H NMR (300 MHz, CD$_3$OD-d$_4$) δ 8.02-7.95 (m, 3H), 7.92 (s, 1H), 7.80 (t, J = 7.9 Hz, 1H), 7.40 (dd, J = 2.2, 8.6 Hz, 1H), 7.15 (t, J = 1.7 Hz, 1H), 7.05 (t, J = 1.8 Hz, 1H), 6.99-6.90 (m, 2H), 4.46 (dd, J = 2.4, 14.8 Hz, 1H), 3.89 (s, 3H), 3.45 (s, 1H), 3.28 (m, 1H), 2.44 (m, 2H), 1.97-1.76 (m, 2H). |
| 2AP | $^1$H NMR (300 MHz, CD$_3$OD-d$_4$) δ 8.07-7.91 (m, 4H), 7.79 (t, J = 7.9 Hz, 1H), 7.63-7.51 (m, 2H) 7.47-7.36 (m, 2H), 7.27 (d, J = 7.6 Hz, 1H), 6.95 (d, J = 8.4 Hz, 1H), 4.46 (dd, J = 14.5, 2.4 Hz, 1H), 3.52-3.46 (m, 1H), 3.33-3.24 (m, 1H), 2.50-2.40 (m, 2H), 1.99-1.79 (m, 2H). |
| 2AQ | $^1$H NMR (300 MHz, CD$_3$OD-d$_4$) δ 8.00-7.96 (t, J = 9.4 Hz, 3H), 7.92 (s, 2H), 7.79 (t, J = 5.8 Hz, 2H), 7.30 (d, J = 10.4 Hz, 1H), 7.84 (d, J = 8.8 Hz, 1H), 4.42 (d, J = 16.0 Hz, 1H), 3.95 (s, 3H), 3.48-3.37 (m, 1H), 3.29 (m, 1H), 2.48-2.35 (m, 2H), 1.90 (m, 1H), 1.78 (m, 1H). |
| 2AR | $^1$H NMR (300 MHz, CD$_3$OD-d$_4$) δ 8.02 (t, J = 7.2 Hz, 1H), 7.94-7.88 (m, 2H), 7.82 (t, J = 7.9 Hz, 1H), 7.54 (d, J = 2.0 Hz, 1H), 7.27 (dd, J = 8.5, 2.1 Hz, 1H), 6.98 (d, J = 8.5 Hz, 1H), 6.38 (d, J = 2.0 Hz, 1H), 4.45 (dd, J = 14.5, 2.3 Hz, 1H), 3.92 (s, 3H), 3.55-3.40 (m, 1H), 3.27 (m, 1H), 2.54-2.35 (m, 2H), 2.02-1.72 (m, 2H). |
| 2AS | $^1$H NMR (300 MHz, CDCl$_3$) δ 8.06-8.01 (m, 2H), 7.88-7.84 (m, 2H), 7.62 (m, 1H), 7.38-7.33 (m, 2H), 7.17-7.11 (m, 2H), 6.91-6.88 (m, 2H), 4.37 (dd, J = 14.4, 2.4 Hz, 1H), 4.15-4.10 (m, 2H), 3.58-3.57 (m, 1H), 3.31-3.25 (m, 1H), 2.60-2.56 (m, 2H), 1.97-1.84 (m, 2H), 1.49-1.46 (m, 3H), 1.28 (s, 1H). |
| 2AT | $^1$H NMR (300 MHz, CD$_3$OD-d$_4$) δ 8.05 (s, 1H), 8.02-7.87 (m, 5H), 7.77 (m, 1H), 7.69 (m, 1H), 7.64 (m, 1H), 7.43 (m, 1H), 6.95 (d, 1H), 4.44 (dd, 1H), 3.45 (m, 1H), 3.29 (m, 1H), 2.42 (m, 2H), 1.90 (m, 1H), 1.79 (m, 1H). |
| 2AU | $^1$H NMR (300 MHz, CD$_3$OD-d$_4$) δ 8.02 (s, 1H), 8.01-7.95 (m, 2H), 7.88 (s, 1H), 7.77 (m, 1H), 7.34 (dd, 1H), 7.26 (m, 1H), 7.06-7.03 (m, 2H), 6.88 (d, 1H), 6.75 (m, 1H), 4.44 (dd, 1H), 3.43 (m, 1H), 3.28 (m, 1H), 2.39 (m, 2H), 1.95-1.75 (m, 2H). |
| 2AV | $^1$H NMR (300 MHz, CD$_3$OD-d$_4$) δ 8.00 (s, 1H), 7.99-7.95 (m, 2H), 7.91 (s, 1H), 7.77 (m, 1H), 7.36-7.30 (m, 2H), 7.12-7.05 (m, 2H), 6.88 (d, 2H), 4.66 (m, 1H), 4.44 (dd, 1H), 3.46 (m, 1H), 3.28 (m, 1H), 2.42 (m, 2H), 1.92 (m, 1H), 1.79 (m, 1H), 1.36 (d, 6H). |
| 2AW | $^1$H NMR (300 MHz, CD$_3$OD-d$_4$) δ 8.07 (s, 1H), 8.06 (m, 1H), 7.98 (s, 1H), 7.93 (d, 1H), 7.75 (m, 1H), 7.28-7.12 (m, 3H), 6.92-6.89 (m, 2H), 6.81 (d, 1H), 4.45 (dd, 1H), 3.27 (dd, 1H), 2.38 (m, 2H), 1.94-1.83 (m, 2H). |
| 2AX | $^1$H NMR (300 MHz, CD$_3$OD-d$_4$) δ 8.06-7.89 (m, 4H), 7.78 (t, J = 7.9 Hz, 1H), 7.46 (m, 1H), 7.42-7.36 (m, 2H), 7.29 (m, 1H), 7.07 (m, 1H), 6.92 (d, J = 8.5 Hz, 1H), 4.44 (dd, J = 14.5, 2.4 Hz, 1H), 3.45 (m, 1H), 3.30-3.23 (m, 1H), 2.52-2.34 (m, 2H), 1.92 (m, 1H), 1.78 (m, 1H). |
| 2AY | $^1$H NMR (300 MHz, CD$_3$OD-d$_4$) δ 8.04-7.93 (m, 4H), 7.77 (m, 1H), 7.28-7.10 (m, 4H), 6.88 (d, 1H), 4.45 (dd, 1H), 3.52 (m, 1H), 3.29 (m, 1H), 2.44 (m, 2H), 2.34 (s, 3H), 1.91 (m, 1H), 1.82 (m, 1H). |
| 2AZ | $^1$H NMR (300 MHz, CDCl$_3$) δ 8.29 (s, 1H), 8.04 (s, 1H), 7.90-7.87 (m, 2H), 7.78 (m, 1H), 7.60 (m, 1H), 6.94 (d, J = 8.4 Hz, 1H), 4.38 (dd, J = 14.4, 2.4 Hz, 1H), 3.65-3.62 (m, 1H), 3.30-3.24 (m, 1H), 2.85 (s, 3H), 2.63-2.56 (m, 2H), 1.97-1.84 (m, 2H). |
| 2BA | $^1$H NMR (300 MHz, CD$_3$OD-d$_4$) δ 8.06-7.95 (m, 2H), 7.87-7.78 (m, 2H), 7.74 (d, J = 2.1 Hz, 1H), 7.29 (m, 1H), 7.07 (dd, J = 8.4, 2.1 Hz, 1H), 7.00 (m, 1H), 6.95-6.87 (m, 2H), 4.45 (dd, J = 14.5, 2.4 Hz, 1H), 3.44 (m, 1H), 3.27 (m, 1H), 2.53-2.34 (m, 2H), 2.27 (s, 3H), 1.91 (m, 1H), 1.80 (m, 1H). |
| 2BC | $^1$H NMR (300 MHz, CD$_3$OD-d$_4$) δ 8.09-7.95 (m, 3H), 7.90 (d, J = 2.0 Hz, 1H), 7.79 (t, J = 7.9 Hz, 1H), 7.28 (dd, J = 8.5, 2.1 Hz, 1H), 7.06-6.98 (m, 1H), 6.97-6.88 (m, 2H), 4.45 (dd, J = 14.5, 2.4 Hz, 1H), 3.72 (d, J = 1.0 Hz, 3H), 3.49 (m, 1H), 3.26 (m, 1H), 2.53-2.35 (m, 2H), 1.92 (m, 1H), 1.78 (m, 1H). |
| 2BD | $^1$H NMR (300 MHz, CD$_3$OD-d$_4$) δ 8.05-7.94 (m, 2H), 7.83-7.75 (m, 2H), 7.71 (d, J = 2.1 Hz, 1H), 7.35-7.17 (m, 3H), 7.14 (m, 1H), 7.03 (dd, J = 8.4, 2.1 Hz, 1H), 6.88 (d, J = 8.4 Hz, 1H), 4.44 (dd, J = 14.4, 2.3 Hz, 1H), 3.40 (dddd, J = 10.3, 7.3, 4.3, 2.3 Hz, 1H), 3.25 (m, 1H), 2.73-2.55 (m, J = 6.5 Hz, 2H), 2.42 (q, J = 7.0 Hz, 2H), 1.96-1.72 (m, 2H), 1.10 (t, J = 7.6 Hz, 3H). |
| 2BE | $^1$H NMR (300 MHz, CD$_3$OD-d$_4$) δ 8.06-7.74 (m, 6H), 7.48 (dd, J = 7.6, 4.8 Hz, 1H), 7.20 (dd, J = 8.5, 2.1 Hz, 1H), 6.93 (d, J = 8.5 Hz, 1H), 4.46 (dd, J = 14.6, 2.4 Hz, 1H), 3.46 (m, 1H), 3.25 (m, 1H), 2.52-2.34 (m, 2H), 1.92 (m, 1H), 1.77 (m, 1H). |
| 2BF | $^1$H NMR (300 MHz, CD$_3$OD-d$_4$) δ 8.04-7.93 (m, 3H), 7.90 (t, J = 1.8 Hz, 1H), 7.77 (t, J = 7.9 Hz, 1H), 7.37 (dd, J = 8.5, 2.2 Hz, 1H), 6.95-6.79 (m, 3H), 6.68 (dt, J = 10.8, 2.3 Hz, 1H), 4.43 (dd, J = 14.5, 2.4 Hz, 1H), 3.86 (s, 3H), 3.44 (dddd, J = 10.3, 7.3, 4.5, 2.4 Hz, 1H), 3.25 (d, J = 10.0 Hz, 1H), 2.51-2.32 (m, 2H), 1.89 (m, 1H), 1.77 (m, 1H). |
| 2BP | $^1$H NMR (300 MHz, CD$_3$OD-d$_4$) δ 8.05-7.90 (m, 4H), 7.77 (t, J = 7.9 Hz, 1H), 7.33-7.16 (m, 3H), 7.09 (m, 1H), 6.92 (dd, J = 8.5, 1.3 Hz, 1H), 4.47 (dd, J = 14.4, 2.4 Hz, 1H), 3.51 (m, 1H), 3.26 (m, 1H), 2.53-2.35 (m, 2H), 1.92 (m, 1H), 1.79 (m, 1H). |

TABLE 2B-continued

| Compd No. | Physical Characterization Data |
| --- | --- |
| 2BQ | $^1$H NMR (300 MHz, CD$_3$OD-d$_4$) δ 8.07-7.89 (m, 4H), 7.78 (t, J = 7.9 Hz, 1H), 7.60-7.30 (m, 5H), 6.93 (d, J = 8.6 Hz, 1H), 4.45 (dd, J = 14.3, 2.3 Hz, 1H), 3.46 (s, 1H), 3.27 (d, J = 10.0 Hz, 1H), 2.43 (td, J = 7.1, 3.8 Hz, 2H), 1.93-1.73 (m, 2H). |

Example 3—Synthesis of (S)-3-(4-((3-(trifluoromethyl)phenyl)sulfonyl)-6-(4-(trifluoromethyl)pyridin-2-yl)-3,4-dihydro-2H-benzo[b][1,4]oxazin-2-yl)propanoic acid

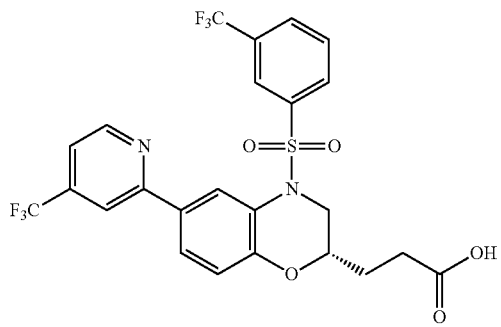

Part I—Synthesis of methyl (S)-3-(6-(4,4,5,5-tetramethyl-1,3,2-dioxaborolan-2-yl)-3,4-dihydro-2H-benzo[b][1,4]oxazin-2-yl)propanoate

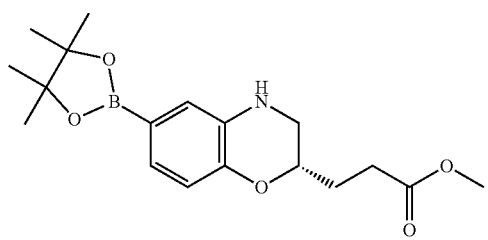

A mixture of methyl (S)-3-(6-bromo-3,4-dihydro-2H-benzo[b][1,4]oxazin-2-yl)propanoate (5 g, 16.7 mmol), ethylene glycol dimethyl ether (50 mL), potassium acetate (6.55 g, 66.7 mmol), 4,4,5,5-tetramethyl-2-(tetramethyl-1,3,2-dioxaborolan-2-yl)-1,3,2-dioxaborolane (8.5 g, 33.5 mmol), and [1,1'-bis(diphenylphosphino)ferrocene] dichloropalladium (II) complex with dichloromethane (1.22 g, 1.67 mmol) was stirred for three hours at 90° C. Then, the mixture was concentrated, and the resulting residue was purified by MPLC eluting with a gradient of 16% ethyl acetate in petroleum ether to afford methyl (S)-3-(6-(4,4,5,5-tetramethyl-1,3,2-dioxaborolan-2-yl)-3,4-dihydro-2H-benzo[b][1,4]oxazin-2-yl)propanoate (7.0 g) as a yellow oil.

Part II—Synthesis of methyl (S)-3-(6-(4,4,5,5-tetramethyl-1,3,2-dioxaborolan-2-yl)-4-((3-(trifluoromethyl)phenyl)sulfonyl)-3,4-dihydro-2H-benzo[b][1,4]oxazin-2-yl)propanoate

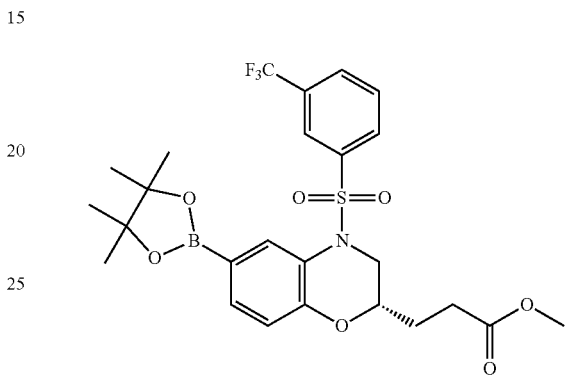

A mixture of methyl (S)-3-(6-(4,4,5,5-tetramethyl-1,3,2-dioxaborolan-2-yl)-3,4-dihydro-2H-benzo[b][1,4]oxazin-2-yl)propanoate (1 g, 2.88 mmol), pyridine (10 mL), 3-(trifluoromethyl)benzene-1-sulfonyl chloride (1.05 g, 4.29 mmol), and 4-dimethylaminopyridine (170 mg, 1.39 mmol) was stirred overnight at room temperature. Then, the mixture was concentrated and the resulting residue was purified via MPLC eluting with 33% ethyl acetate in petroleum ether to afford methyl (S)-3-(6-(4,4,5,5-tetramethyl-1,3,2-dioxaborolan-2-yl)-4-((3-(trifluoromethyl)phenyl)sulfonyl)-3,4-dihydro-2H-benzo[b][1,4]oxazin-2-yl)propanoate (1.2 g, 75%) as a yellow oil.

Part III—Synthesis of methyl (S)-3-(4-((3-(trifluoromethyl)phenyl)sulfonyl)-6-(4-(trifluoromethyl)pyridin-2-yl)-3,4-dihydro-2H-benzo[b][1,4]oxazin-2-yl)propanoate

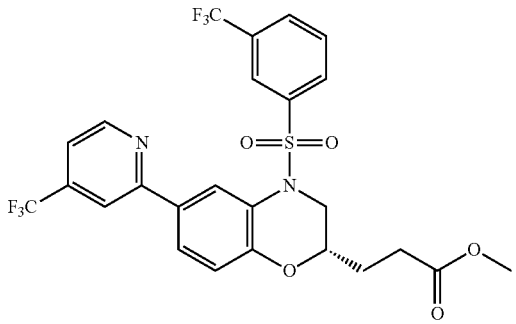 [SMILES: COC(=O)CC[C@H]1CN(S(=O)(=O)c2cccc(C(F)(F)F)c2)c2cc(-c3cc(C(F)(F)F)ccn3)ccc2O1]

A mixture of methyl (S)-3-(6-(4,4,5,5-tetramethyl-1,3,2-dioxaborolan-2-yl)-4-((3-(trifluoromethyl)phenyl)sulfonyl)-3,4-dihydro-2H-benzo[b][1,4]oxazin-2-yl)propanoate (150 mg, 0.27 mmol), 2-chloro-4-(trifluoromethyl)pyridine (73.4 mg, 0.40 mmol), tetrakis(triphenylphosphine)palladium (15.6 mg, 0.01 mmol), sodium carbonate (85.9 mg), toluene (3 mL), ethanol (1 mL), and water (1 mL) was stirred for two hours at 90° C. Then, the mixture was partitioned between ethyl acetate and water. The organic layer was concentrated and the resulting residue was purified via MPLC eluting with 33% ethyl acetate in petroleum ether to afford methyl (S)-3-(4-((3-(trifluoromethyl)phenyl)sulfonyl)-6-(4-(trifluoromethyl)pyridin-2-yl)-3,4-dihydro-2H-benzo[b][1,4]oxazin-2-yl)propanoate (130 mg, 84%) as a white solid.

Part IV—Synthesis of (S)-3-(4-((3-(trifluoromethyl)phenyl)sulfonyl)-6-(4-(trifluoromethyl)pyridin-2-yl)-3,4-dihydro-2H-benzo[b][1,4]oxazin-2-yl)propanoic acid

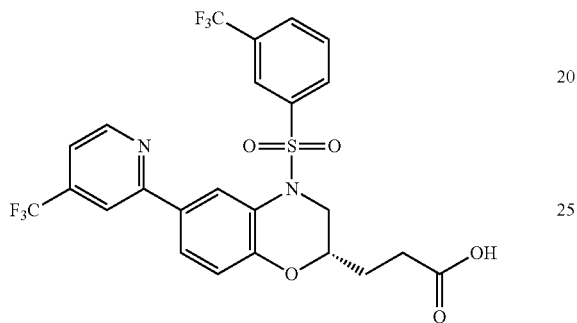

Based on the procedure in Example 1, Part VII, (S)-3-(4-((3-(trifluoromethyl)phenyl)sulfonyl)-6-(4-(trifluoromethyl)pyridin-2-yl)-3,4-dihydro-2H-benzo[b][1,4]oxazin-2-yl)propanoic acid was prepared. $^1$H-NMR (400 MHz, CD$_3$OD) δ 8.89 (d, J=5.1 Hz, 1H), 8.59 (d, J=2.2 Hz, 1H), 8.08-7.95 (m, 4H), 7.88-7.74 (m, 2H), 7.61 (dd, J=5.0, 1.3 Hz, 1H), 7.00 (d, J=8.6 Hz, 1H), 4.48 (dd, J=14.4, 2.4 Hz, 1H), 3.57 (m, 1H), 3.36 (m, 1H), 2.54-2.38 (m, 2H), 2.01-1.78 (m, 2H). (ES, m/z): (M+H)$^+$ 561.

Example 4—Preparation of Additional Aryl Sulfonyl-3,4-dihydro-2H-benzo[b][1,4]oxazin-2-yl)propanoic Acids Compounds in Tables 3 and 3A were prepared based on experimental procedures described in Example 3 and the detailed description. $^1$H NMR data for exemplary compounds is provided in Table 3B.

TABLE 3

| Compd No. | Structure | Name | Observed m/z |
|---|---|---|---|
| 4A | 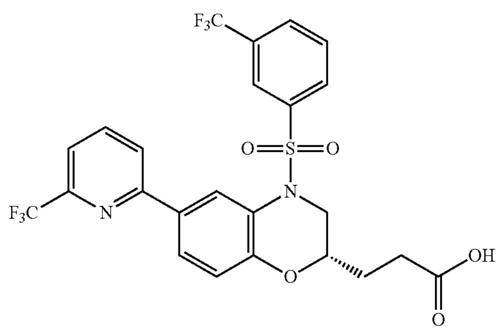 [SMILES: O=C(O)CC[C@H]1CN(S(=O)(=O)c2cccc(C(F)(F)F)c2)c2cc(-c3cccc(C(F)(F)F)n3)ccc2O1] | (S)-3-(4-((3-(trifluoromethyl)phenyl)sulfonyl)-6-(6-(trifluoromethyl)pyridin-2-yl)-3,4-dihydro-2H-benzo[b][1,4]oxazin-2-yl)propanoic acid | 561 (M + H)$^+$ |
| 4B | 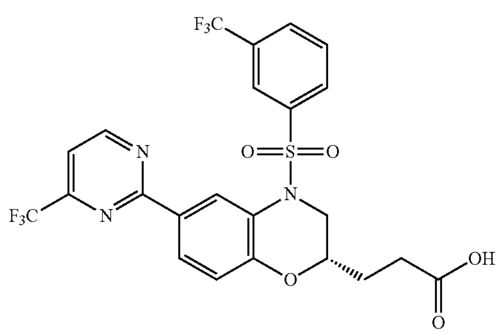 [SMILES: O=C(O)CC[C@H]1CN(S(=O)(=O)c2cccc(C(F)(F)F)c2)c2cc(-c3nccc(C(F)(F)F)n3)ccc2O1] | (S)-3-(4-((3-(trifluoromethyl)phenyl)sulfonyl)-6-(4-(trifluoromethyl)pyrimidin-2-yl)-3,4-dihydro-2H-benzo[b][1,4]oxazin-2-yl)propanoic acid | 562 (M + H)$^+$ |

TABLE 3-continued

| Compd No. | Structure | Name | Observed m/z |
|---|---|---|---|
| 4C | 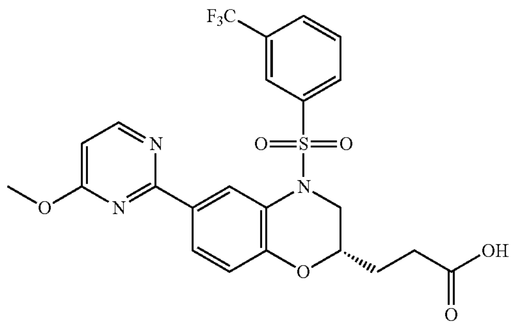 [SMILES: COc1ccnc(-c2ccc3c(c2)N(S(=O)(=O)c2cccc(C(F)(F)F)c2)C[C@H](CCC(=O)O)O3)n1] | (S)-3-(6-(4-methoxypyrimidin-2-yl)-4-((3-(trifluoromethyl)-phenyl)sulfonyl)-3,4-dihydro-2H-benzo[b][1,4]oxazin-2-yl)propanoic acid | 524 (M + H)+ |
| 4D | 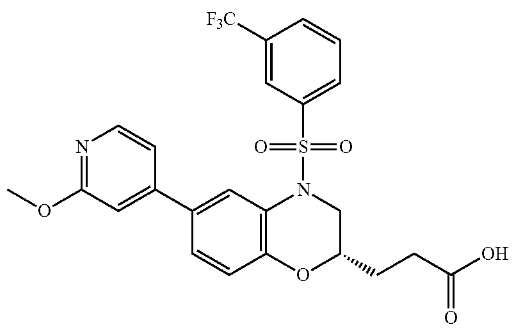 [SMILES: COc1cc(-c2ccc3c(c2)N(S(=O)(=O)c2cccc(C(F)(F)F)c2)C[C@H](CCC(=O)O)O3)ccn1] | (S)-3-(6-(2-methoxypyridin-4-yl)-4-((3-(trifluoromethyl)-phenyl)sulfonyl)-3,4-dihydro-2H-benzo[b][1,4]oxazin-2-yl)propanoic acid | 523 (M + H)+ |
| 4E | 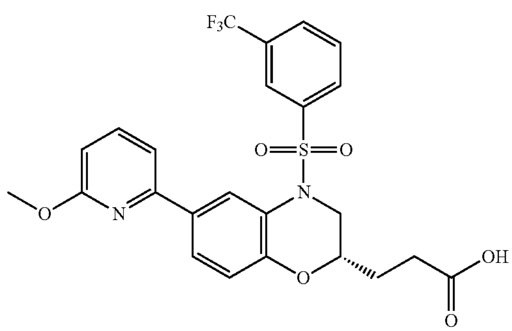 [SMILES: COc1cccc(-c2ccc3c(c2)N(S(=O)(=O)c2cccc(C(F)(F)F)c2)C[C@H](CCC(=O)O)O3)n1] | (S)-3-(6-(6-methoxypyridin-2-yl)-4-((3-(trifluoromethyl)-phenyl)sulfonyl)-3,4-dihydro-2H-benzo[b][1,4]oxazin-2-yl)propanoic acid | 523 (M + H)+ |
| 4F | 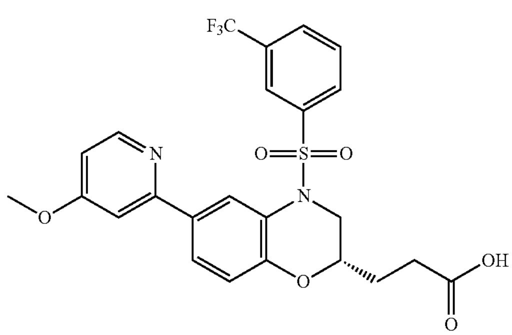 [SMILES: COc1ccnc(-c2ccc3c(c2)N(S(=O)(=O)c2cccc(C(F)(F)F)c2)C[C@H](CCC(=O)O)O3)c1] | (S)-3-(6-(4-methoxypyridin-2-yl)-4-((3-(trifluoromethyl)-phenyl)sulfonyl)-3,4-dihydro-2H-benzo[b][1,4]oxazin-2-yl)propanoic acid | 523 (M + H)+ |

TABLE 3-continued

| Compd No. | Structure | Name | Observed m/z |
|---|---|---|---|
| 4G | 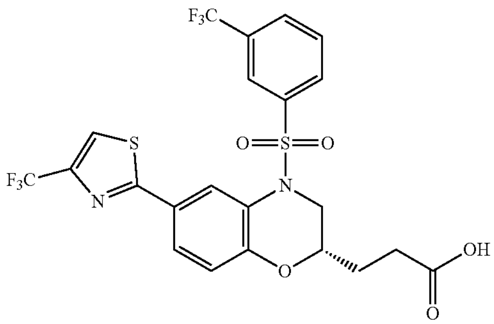 [SMILES: O=C(O)CC[C@H]1CN(S(=O)(=O)c2cccc(C(F)(F)F)c2)c2cc(-c3nc(C(F)(F)F)cs3)ccc2O1] | (S)-3-(4-((3-(trifluoromethyl)phenyl)sulfonyl)-6-(4-(trifluoromethyl)thiazol-2-yl)-3,4-dihydro-2H-benzo[b][1,4]oxazin-2-yl)propanoic acid | 567 (M + H)+ |
| 4H | 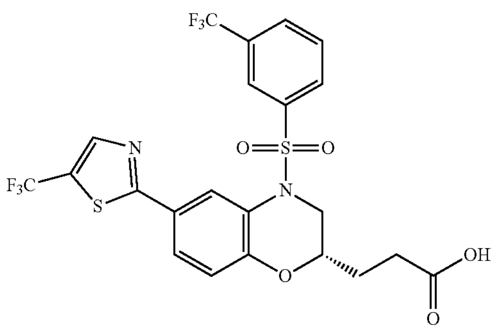 [SMILES: O=C(O)CC[C@H]1CN(S(=O)(=O)c2cccc(C(F)(F)F)c2)c2cc(-c3ncc(C(F)(F)F)s3)ccc2O1] | (S)-3-(4-((3-(trifluoromethyl)phenyl)sulfonyl)-6-(5-(trifluoromethyl)thiazol-2-yl)-3,4-dihydro-2H-benzo[b][1,4]oxazin-2-yl)propanoic acid | 567 (M + H)+ |
| 4I | 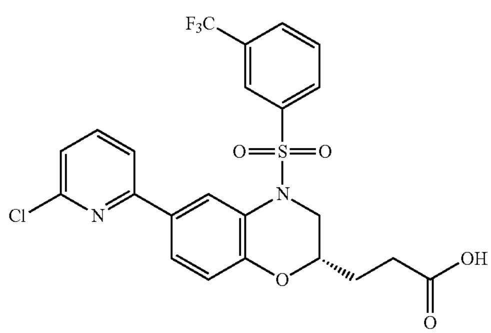 [SMILES: O=C(O)CC[C@H]1CN(S(=O)(=O)c2cccc(C(F)(F)F)c2)c2cc(-c3cccc(Cl)n3)ccc2O1] | (S)-3-(6-(6-chloropyridin-2-yl)-4-((3-(trifluoromethyl)phenyl)sulfonyl)-3,4-dihydro-2H-benzo[b][1,4]oxazin-2-yl)propanoic acid | 527 (M + H)+ |
| 4J | 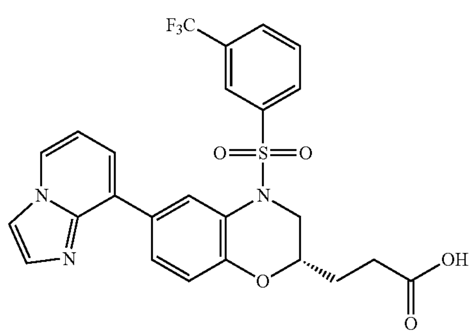 [SMILES: O=C(O)CC[C@H]1CN(S(=O)(=O)c2cccc(C(F)(F)F)c2)c2cc(-c3cccn4ccnc34)ccc2O1] | (S)-3-(6-(imidazo[1,2-a]pyridin-8-yl)-4-((3-(trifluoromethyl)phenyl)sulfonyl)-3,4-dihydro-2H-benzo[b][1,4]oxazin-2-yl)propanoic acid | 532 G-616 (M + H)+ |

| Compd No. | Structure | Name | Observed m/z |
|---|---|---|---|
| 4K | 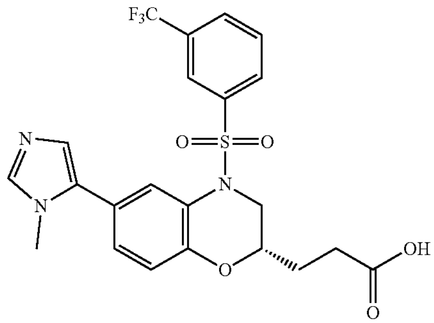 [SMILES: Cn1cncc1-c1ccc2c(c1)N(S(=O)(=O)c1cccc(C(F)(F)F)c1)C[C@H](CCC(=O)O)O2] | (S)-3-(6-(1-methyl-1H-imidazol-5-yl)-4-((3-(trifluoromethyl)-phenyl)sulfonyl)-3,4-dihydro-2H-benzo[b][1,4]oxazin-2-yl)propanoic acid | 496 (M + H)+ |
| 4L | 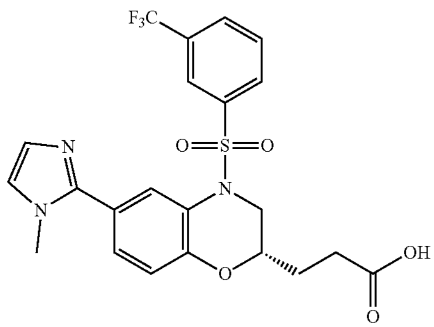 [SMILES: Cn1ccnc1-c1ccc2c(c1)N(S(=O)(=O)c1cccc(C(F)(F)F)c1)C[C@H](CCC(=O)O)O2] | (S)-3-(6-(1-methyl-1H-imidazol-2-yl)-4-((3-(trifluoromethyl)-phenyl)sulfonyl)-3,4-dihydro-2H-benzo[b][1,4]oxazin-2-yl)propanoic acid | 496 (M + H)+ |
| 4M | 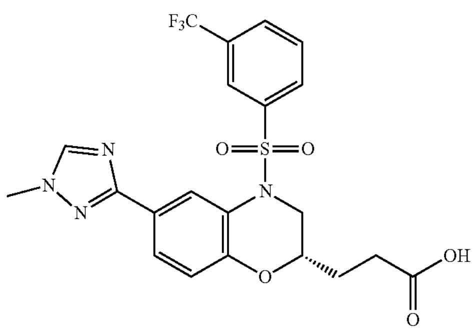 [SMILES: Cn1cnc(-c2ccc3c(c2)N(S(=O)(=O)c2cccc(C(F)(F)F)c2)C[C@H](CCC(=O)O)O3)n1] | (S)-3-(6-(1-methyl-1H-1,2,4-triazol-3-yl)-4-((3-(trifluoromethyl)phenyl)sulfonyl)-3,4-dihydro-2H-benzo[b][1,4]-oxazin-2-yl)propanoic acid | 497 (M + H)+ |
| 4N | 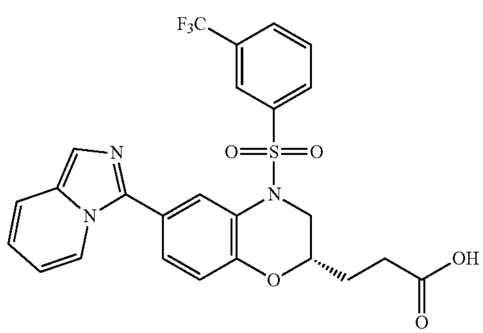 [SMILES: O=C(O)CC[C@H]1CN(S(=O)(=O)c2cccc(C(F)(F)F)c2)c2cc(-c3ncc4ccccn34)ccc2O1] | (S)-3-(6-(imidazo[1,5-a]pyridin-3-yl)-4-((3-(trifluoromethyl)-phenyl)sulfonyl)-3,4-dihydro-2H-benzo[b][1,4]oxazin-2-yl)propanoic acid | 532 (M + H)+ |

TABLE 3-continued

| Compd No. | Structure | Name | Observed m/z |
|---|---|---|---|
| 4O | 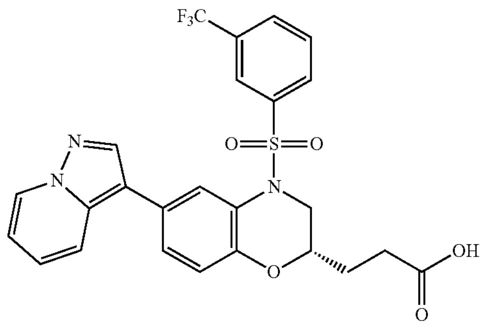 [SMILES: O=C(O)CC[C@H]1CN(S(=O)(=O)c2cccc(C(F)(F)F)c2)c2cc(-c3cnn4ccccc34)ccc2O1] | (S)-3-(6-(pyrazolo[1,5-a]pyridin-3-yl)-4-((3-(trifluoromethyl)-phenyl)sulfonyl)-3,4-dihydro-2H-benzo[b][1,4]oxazin-2-yl)propanoic acid | 532 (M + H)+ |
| 4P | 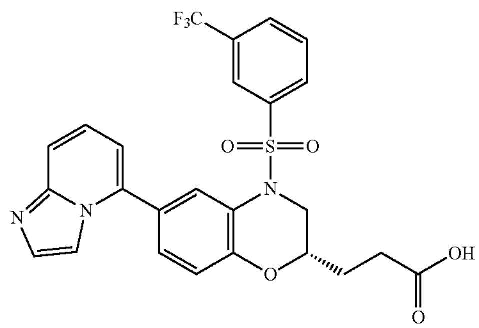 [SMILES: O=C(O)CC[C@H]1CN(S(=O)(=O)c2cccc(C(F)(F)F)c2)c2cc(-c3cccc4nccn34)ccc2O1] | (S)-3-(6-(imidazo[1,2-a]pyridin-5-yl)-4-((3-(trifluoromethyl)-phenyl)sulfonyl)-3,4-dihydro-2H-benzo[b][1,4]oxazin-2-yl)propanoic acid | 532 (M + H)+ |
| 4Q | 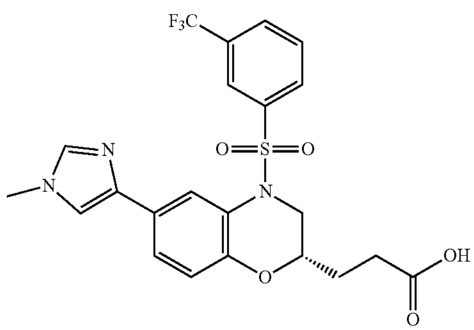 | (S)-3-(6-(1-methyl-1H-imidazol-4-yl)-4-((3-(trifluoromethyl)-phenyl)sulfonyl)-3,4-dihydro-2H-benzo[b][1,4]oxazin-2-yl)propanoic acid | 496 (M + H)+ |
| 4R | 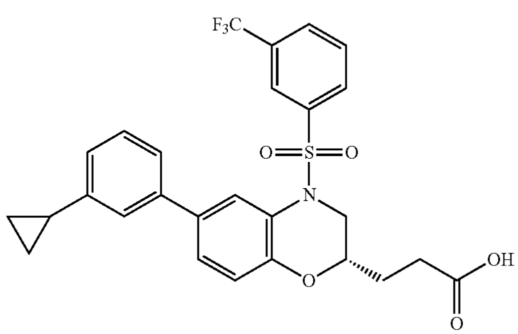 [SMILES: O=C(O)CC[C@H]1CN(S(=O)(=O)c2cccc(C(F)(F)F)c2)c2cc(-c3cccc(C4CC4)c3)ccc2O1] | (S)-3-(6-(3-cyclopropylphenyl)-4-((3-(trifluoromethyl)phenyl)-sulfonyl)-3,4-dihydro-2H-benzo[b][1,4]oxazin-2-yl)propanoic acid | 532 (M + H)+ |

TABLE 3-continued

| Compd No. | Structure | Name | Observed m/z |
|---|---|---|---|
| 4S | 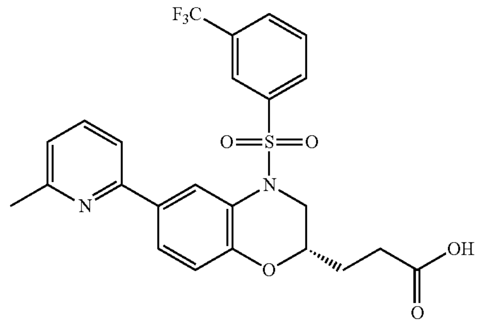 [SMILES: Cc1cccc(-c2ccc3c(c2)N(S(=O)(=O)c2cccc(C(F)(F)F)c2)C[C@H](CCC(=O)O)O3)n1] | (S)-3-(6-(6-methylpyridin-2-yl)-4-((3-(trifluoromethyl)phenyl)-sulfonyl)-3,4-dihydro-2H-benzo[b][1,4]oxazin-2-yl)propanoic acid | 507 (M + H)+ |
| 4T | 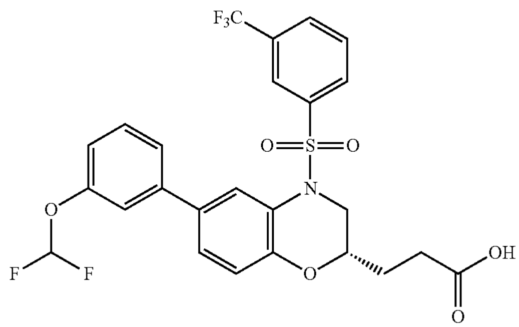 [SMILES: O=C(O)CC[C@H]1CN(S(=O)(=O)c2cccc(C(F)(F)F)c2)c2cc(-c3cccc(OC(F)F)c3)ccc2O1] | (S)-3-(6-(3-(difluoromethoxy)-phenyl)-4-((3-(trifluoromethyl)-phenyl)sulfonyl)-3,4-dihydro-2H-benzo[b][1,4]oxazin-2-yl)propanoic acid | 580 (M + Na)+ |
| 4U | 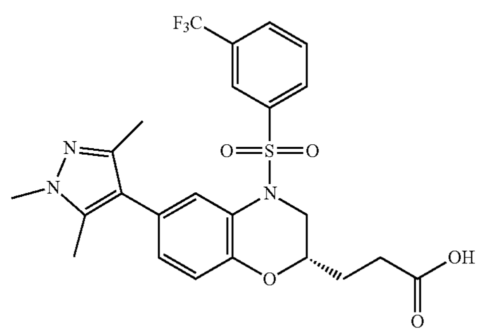 [SMILES: Cc1nn(C)c(C)c1-c1ccc2c(c1)N(S(=O)(=O)c1cccc(C(F)(F)F)c1)C[C@H](CCC(=O)O)O2] | (S)-3-(4-((3-(trifluoromethyl)-phenyl)sulfonyl)-6-(1,3,5-trimethyl-1H-pyrazol-4-yl)-3,4-dihydro-2H-benzo[b][1,4]-oxazin-2-yl)propanoic acid | 524 (M + H)+ |
| 4V | 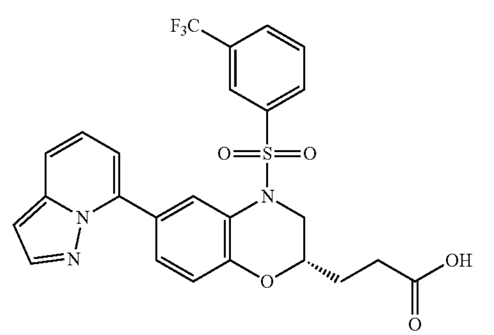 [SMILES: O=C(O)CC[C@H]1CN(S(=O)(=O)c2cccc(C(F)(F)F)c2)c2cc(-c3cccc4ccnn34)ccc2O1] | (S)-3-(6-(pyrazolo[1,5-a]-pyridin-7-yl)-4-((3-(trifluoro-methyl)-phenyl)sulfonyl)-3,4-dihydro-2H-benzo[b][1,4]-oxazin-2-yl)propanoic acid | 532 (M + H)+ |

TABLE 3-continued

| Compd No. | Structure | Name | Observed m/z |
|---|---|---|---|
| 4W | 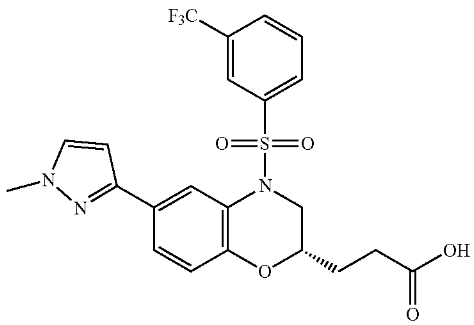 [SMILES: Cn1ccc(-c2ccc3c(c2)N(S(=O)(=O)c2cccc(C(F)(F)F)c2)C[C@H](CCC(=O)O)O3)n1] | (S)-3-(6-(1-methyl-1H-pyrazol-3-yl)-4-((3-(trifluoromethyl)phenyl)sulfonyl)-3,4-dihydro-2H-benzo[b][1,4]oxazin-2-yl)propanoic acid | 496 (M + H)+ |
| 4X | 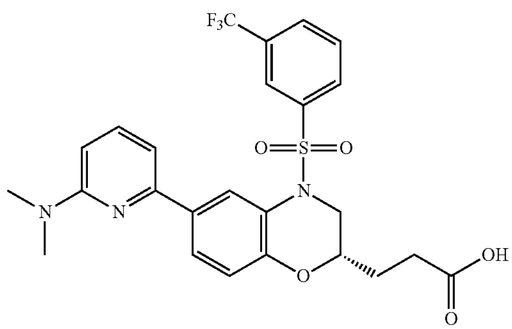 [SMILES: CN(C)c1cccc(-c2ccc3c(c2)N(S(=O)(=O)c2cccc(C(F)(F)F)c2)C[C@H](CCC(=O)O)O3)n1] | (S)-3-(6-(6-(dimethylamino)pyridin-2-yl)-4-((3-(trifluoromethyl)phenyl)sulfonyl)-3,4-dihydro-2H-benzo[b][1,4]-oxazin-2-yl)propanoic acid | 536 (M + H)+ |
| 4Y | 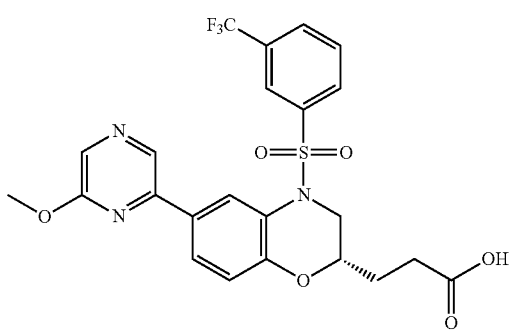 [SMILES: COc1cncc(-c2ccc3c(c2)N(S(=O)(=O)c2cccc(C(F)(F)F)c2)C[C@H](CCC(=O)O)O3)n1] | (S)-3-(6-(6-methoxypyrazin-2-yl)-4-((3-(trifluoromethyl)phenyl)sulfonyl)-3,4-dihydro-2H-benzo[b][1,4]oxazin-2-yl)propanoic acid | 524 (M + H)+ |
| 4Z | 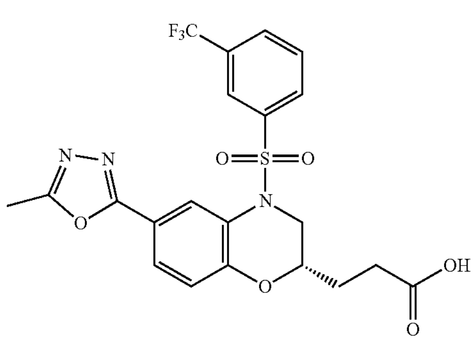 [SMILES: Cc1nnc(-c2ccc3c(c2)N(S(=O)(=O)c2cccc(C(F)(F)F)c2)C[C@H](CCC(=O)O)O3)o1] | (S)-3-(6-(5-methyl-1,3,4-oxadiazol-2-yl)-4-((3-(trifluoromethyl)phenyl)sulfonyl)-3,4-dihydro-2H-benzo[b][1,4]-oxazin-2-yl)propanoic acid | 498 (M + H)+ |

TABLE 3-continued

| Compd No. | Structure | Name | Observed m/z |
|---|---|---|---|
| 4AA | 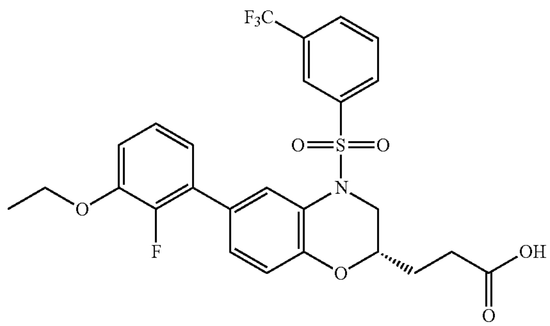 [SMILES: CCOc1cccc(-c2ccc3c(c2)N(S(=O)(=O)c2cccc(C(F)(F)F)c2)C[C@H](CCC(=O)O)O3)c1F] | (S)-3-(6-(3-ethoxy-2-fluorophenyl)-4-((3-(trifluoromethyl)phenyl)sulfonyl)-3,4-dihydro-2H-benzo[b][1,4]oxazin-2-yl)propanoic acid | 554 (M + H)+ |
| 4AB | 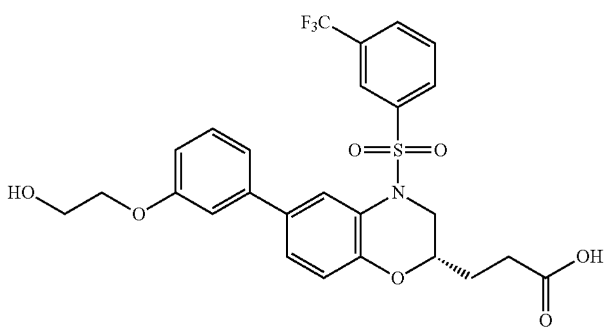 [SMILES: O=C(O)CC[C@H]1CN(S(=O)(=O)c2cccc(C(F)(F)F)c2)c2cc(-c3cccc(OCCO)c3)ccc2O1] | (S)-3-(6-(3-(2-hydroxyethoxy)phenyl)-4-((3-(trifluoromethyl)phenyl)-sulfonyl)-3,4-dihydro-2H-benzo[b][1,4]oxazin-2-yl)propanoic acid | 552 (M + H)+ |
| 4AC | 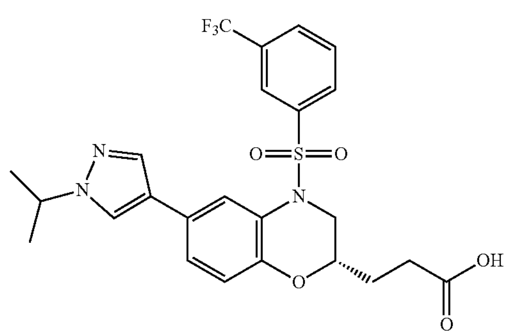 [SMILES: CC(C)n1cc(-c2ccc3c(c2)N(S(=O)(=O)c2cccc(C(F)(F)F)c2)C[C@H](CCC(=O)O)O3)cn1] | (S)-3-(6-(1-isopropyl-1H-pyrazol-4-yl)-4-((3-(trifluoromethyl)phenyl)sulfonyl)-3,4-dihydro-2H-benzo[b][1,4]oxazin-2-yl)propanoic acid | 524 (M + H)+ |
| 4AD | 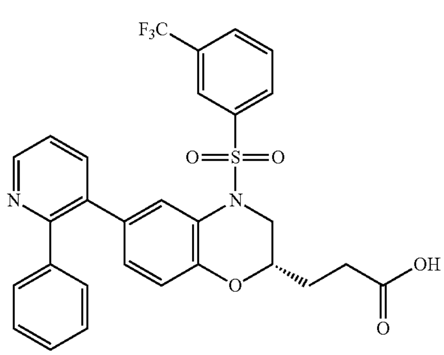 [SMILES: O=C(O)CC[C@H]1CN(S(=O)(=O)c2cccc(C(F)(F)F)c2)c2cc(-c3cccnc3-c3ccccc3)ccc2O1] | (S)-3-(6-(2-phenylpyridin-3-yl)-4-((3-(trifluoromethyl)-phenyl)sulfonyl)-3,4-dihydro-2H-benzo[b][1,4]oxazin-2-yl)propanoic acid | 569 (M + H)+ |

TABLE 3-continued

| Compd No. | Structure | Name | Observed m/z |
|---|---|---|---|
| 4AE | 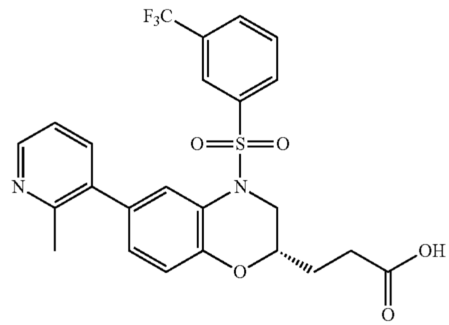 [SMILES: Cc1ncccc1-c1ccc2c(c1)N(S(=O)(=O)c1cccc(C(F)(F)F)c1)C[C@H](CCC(=O)O)O2] | (S)-3-(6-(2-methylpyridin-3-yl)-4-((3-(trifluoromethyl)phenyl)sulfonyl)-3,4-dihydro-2H-benzo[b][1,4]oxazin-2-yl)propanoic acid | 507 (M + H)+ |
| 4AF | 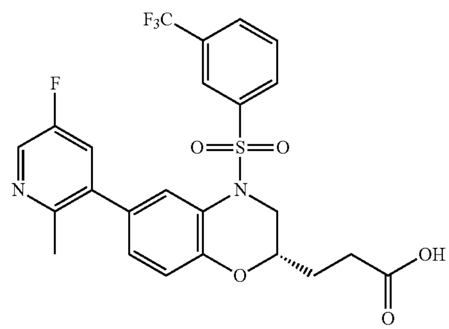 [SMILES: Cc1ncc(F)cc1-c1ccc2c(c1)N(S(=O)(=O)c1cccc(C(F)(F)F)c1)C[C@H](CCC(=O)O)O2] | (S)-3-(6-(5-fluoro-2-methylpyridin-3-yl)-4-((3-(trifluoromethyl)phenyl)sulfonyl)-3,4-dihydro-2H-benzo[b][1,4]oxazin-2-yl)propanoic acid | 525 (M + H)+ |
| 4AG | 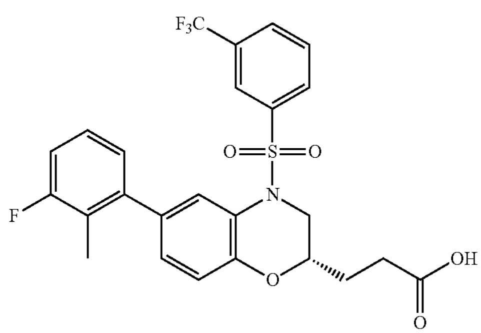 [SMILES: Cc1c(F)cccc1-c1ccc2c(c1)N(S(=O)(=O)c1cccc(C(F)(F)F)c1)C[C@H](CCC(=O)O)O2] | (S)-3-(6-(3-fluoro-2-methylphenyl)-4-((3-(trifluoromethyl)phenyl)sulfonyl)-3,4-dihydro-2H-benzo[b][1,4]oxazin-2-yl)propanoic acid | 546 (M + Na)+ |
| 4AH | 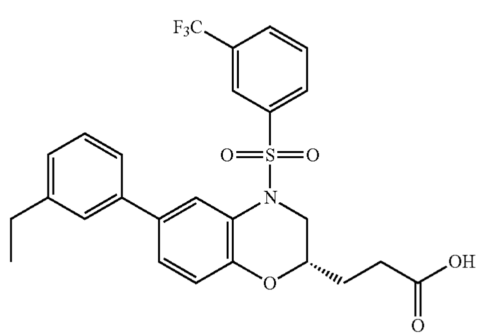 | (S)-3-(6-(3-ethylphenyl)-4-((3-(trifluoromethyl)phenyl)sulfonyl)-3,4-dihydro-2H-benzo[b][1,4]oxazin-2-yl)propanoic acid | 520 (M + H)+ |

TABLE 3-continued

| Compd No. | Structure | Name | Observed m/z |
|---|---|---|---|
| 4AI | 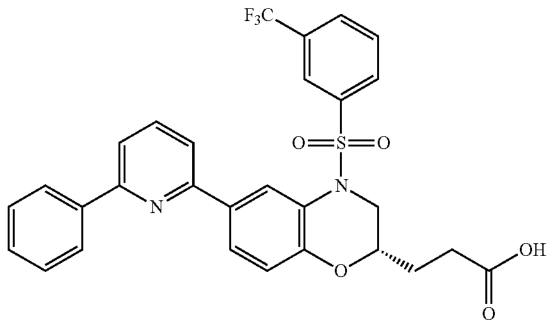 [SMILES: O=C(O)CC[C@H]1CN(S(=O)(=O)c2cccc(C(F)(F)F)c2)c2cc(-c3cccc(-c4ccccc4)n3)ccc2O1] | (S)-3-(6-(6-phenylpyridin-2-yl)-4-((3-(trifluoromethyl)phenyl)sulfonyl)-3,4-dihydro-2H-benzo[b][1,4]oxazin-2-yl)propanoic acid | 569 (M + H)+ |
| 4AJ | 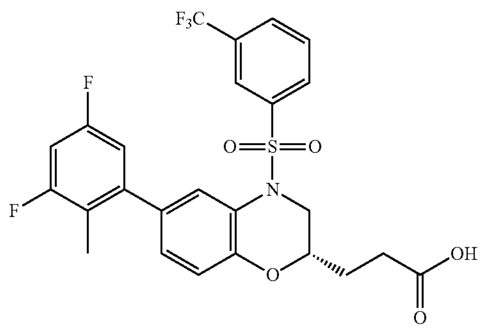 [SMILES: O=C(O)CC[C@H]1CN(S(=O)(=O)c2cccc(C(F)(F)F)c2)c2cc(-c3cc(F)cc(F)c3F)ccc2O1] | (S)-3-(6-(3,5-difluoro-2-methylphenyl)-4-((3-(trifluoromethyl)phenyl)sulfonyl)-3,4-dihydro-2H-benzo[b][1,4]oxazin-2-yl)propanoic acid | 542 (M + H)+ |
| 4AK | 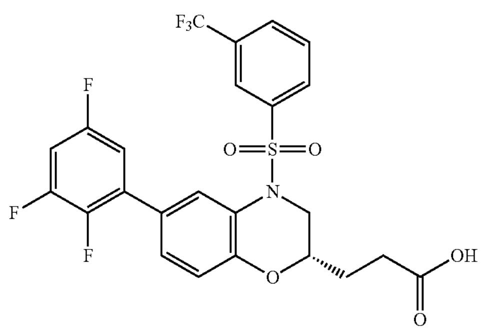 | (S)-3-(4-((3-(trifluoromethyl)phenyl)sulfonyl)-6-(2,3,5-trifluorophenyl)-3,4-dihydro-2H-benzo[b][1,4]oxazin-2-yl)propanoic acid | 546 (M + H)+ |
| 4AL | 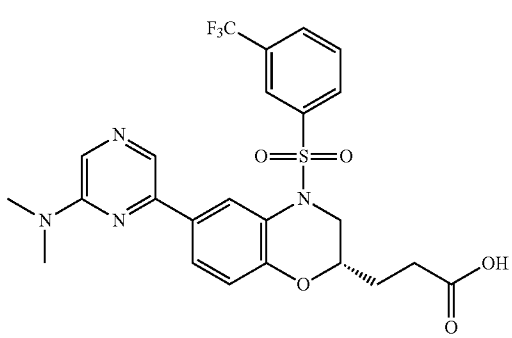 [SMILES: CN(C)c1cncc(-c2ccc3c(c2)N(S(=O)(=O)c2cccc(C(F)(F)F)c2)C[C@H](CCC(=O)O)O3)n1] | (S)-3-(6-(6-(dimethylamino)pyrazin-2-yl)-4-((3-(trifluoromethyl)phenyl)sulfonyl)-3,4-dihydro-2H-benzo[b][1,4]oxazin-2-yl)propanoic acid | 537 (M + H)+ |

TABLE 3-continued

| Compd No. | Structure | Name | Observed m/z |
|---|---|---|---|
| 4AM | 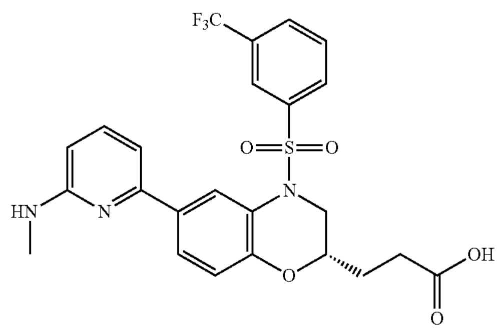 [SMILES: CNc1cccc(-c2ccc3c(c2)N(S(=O)(=O)c2cccc(C(F)(F)F)c2)C[C@H](CCC(=O)O)O3)n1] | (S)-3-(6-(6-(methylamino)-pyridin-2-yl)-4-((3-(trifluoromethyl)phenyl)-sulfonyl)-3,4-dihydro-2H-benzo[b][1,4]oxazin-2-yl)propanoic acid | 522 (M + H)+ |
| 4AN | 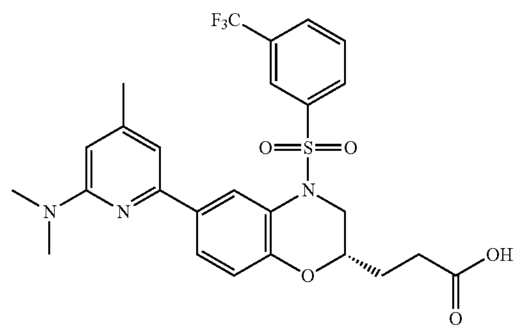 [SMILES: Cc1cc(-c2ccc3c(c2)N(S(=O)(=O)c2cccc(C(F)(F)F)c2)C[C@H](CCC(=O)O)O3)nc(N(C)C)c1] | (S)-3-(6-(6-(dimethylamino)-4-methylpyridin-2-yl)-4-((3-(trifluoromethyl)phenyl)sulfonyl)-3,4-dihydro-2H-benzo[b][1,4]oxazin-2-yl)propanoic acid | 550 (M + H)+ |
| 4AO | 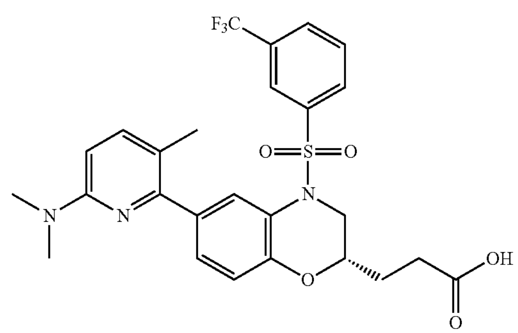 [SMILES: Cc1ccc(N(C)C)nc1-c1ccc2c(c1)N(S(=O)(=O)c1cccc(C(F)(F)F)c1)C[C@H](CCC(=O)O)O2] | (S)-3-(6-(6-(dimethylamino)-3-methylpyridin-2-yl)-4-((3-(trifluoromethyl)phenyl)sulfonyl)-3,4-dihydro-2H-benzo[b][1,4]oxazin-2-yl)propanoic acid | 550 (M + H)+ |
| 4AP | 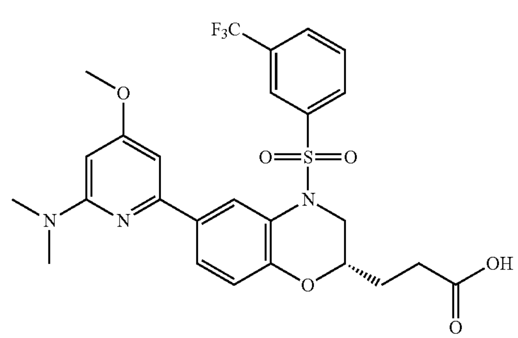 [SMILES: COc1cc(-c2ccc3c(c2)N(S(=O)(=O)c2cccc(C(F)(F)F)c2)C[C@H](CCC(=O)O)O3)nc(N(C)C)c1] | (S)-3-(6-(6-(dimethylamino)-4-methoxypyridin-2-yl)-4-((3-(trifluoromethyl)phenyl)sulfonyl)-3,4-dihydro-2H-benzo[b][1,4]oxazin-2-yl)propanoic acid | 566 (M + H)+ |

TABLE 3-continued

| Compd No. | Structure | Name | Observed m/z |
|---|---|---|---|
| 4AQ | 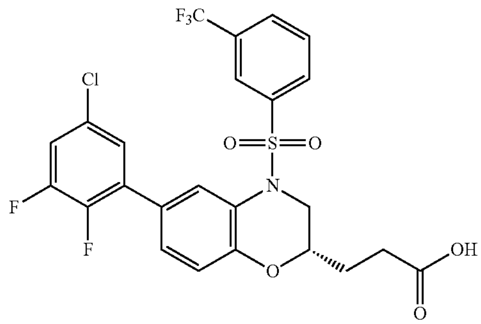 | (S)-3-(6-(5-chloro-2,3-difluorophenyl)-4-((3-(trifluoromethyl)phenyl)sulfonyl)-3,4-dihydro-2H-benzo[b][1,4]oxazin-2-yl)propanoic acid | 562 (M + H)+ |
| 4AR | 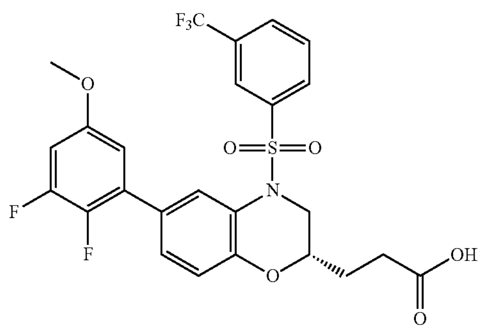 | (S)-3-(6-(2,3-difluoro-5-methoxyphenyl)-4-((3-(trifluoromethyl)phenyl)sulfonyl)-3,4-dihydro-2H-benzo[b][1,4]oxazin-2-yl)propanoic acid | 558 (M + H)+ |
| 4AS | 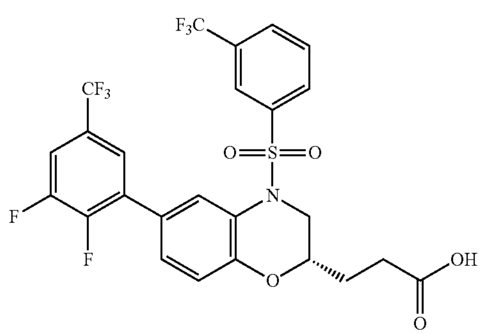 [SMILES: O=C(O)CC[C@H]1CN(S(=O)(=O)c2cccc(C(F)(F)F)c2)c2cc(-c3cc(C(F)(F)F)cc(F)c3F)ccc2O1] | (S)-3-(6-(2,3-difluoro-5-(trifluoromethyl)phenyl)-4-((3-(trifluoromethyl)phenyl)-sulfonyl)-3,4-dihydro-2H-benzo[b][1,4]oxazin-2-yl)propanoic acid | 596 (M + H)+ |
| 4AT | 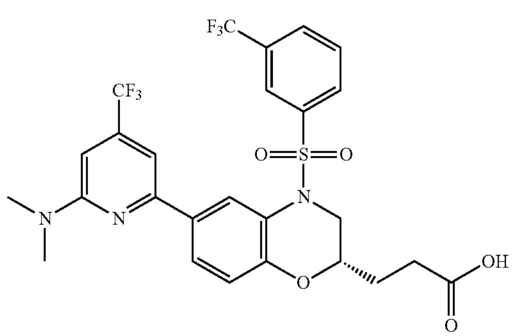 [SMILES: CN(C)c1cc(C(F)(F)F)cc(-c2ccc3c(c2)N(S(=O)(=O)c2cccc(C(F)(F)F)c2)C[C@H](CCC(=O)O)O3)n1] | (S)-3-(6-(6-(dimethylamino)-4-(trifluoromethyl)pyridin-2-yl)-4-((3-(trifluoromethyl)phenyl)-sulfonyl)-3,4-dihydro-2H-benzo[b][1,4]oxazin-2-yl)propanoic acid | 604 (M + H)+ |

TABLE 3-continued

| Compd No. | Structure | Name | Observed m/z |
|---|---|---|---|
| 4AU | 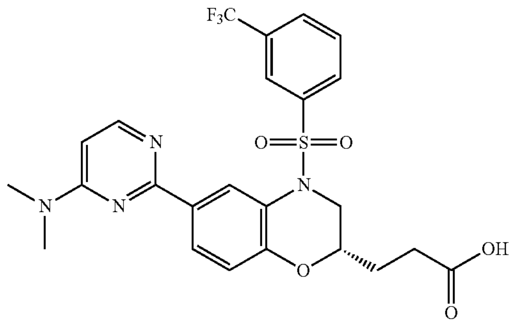 [SMILES: CN(C)c1ccnc(-c2ccc3c(c2)N(S(=O)(=O)c2cccc(C(F)(F)F)c2)C[C@H](CCC(=O)O)O3)n1] | (S)-3-(6-(4-(dimethylamino)-pyrimidin-2-yl)-4-((3-(trifluoromethyl)phenyl)-sulfonyl)-3,4-dihydro-2H-benzo[b][1,4]oxazin-2-yl)propanoic acid | 537 (M + H)+ |
| 4AV | 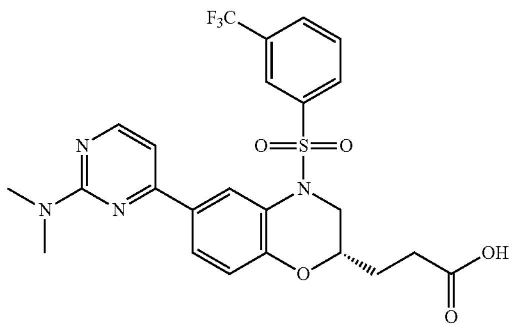 [SMILES: CN(C)c1nccc(-c2ccc3c(c2)N(S(=O)(=O)c2cccc(C(F)(F)F)c2)C[C@H](CCC(=O)O)O3)n1] | (S)-3-(6-(2-(dimethylamino)-pyrimidin-4-yl)-4-((3-(trifluoromethyl)phenyl)-sulfonyl)-3,4-dihydro-2H-benzo[b][1,4]oxazin-2-yl)propanoic acid | 537 (M + H)+ |
| 4AX | 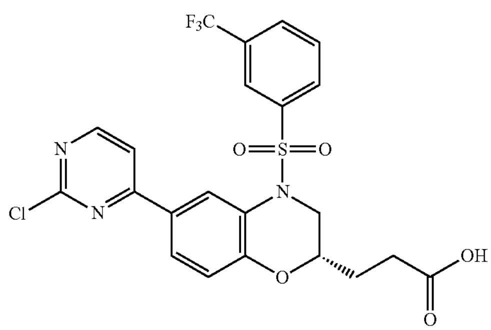 [SMILES: O=C(O)CC[C@H]1CN(S(=O)(=O)c2cccc(C(F)(F)F)c2)c2cc(-c3ccnc(Cl)n3)ccc2O1] | (S)-3-(6-(2-chloropyrimidin-4-yl)-4-((3-(trifluoromethyl)-phenyl)sulfonyl)-3,4-dihydro-2H-benzo[b][1,4]oxazin-2-yl)propanoic acid | 528 (M + H)+ |
| 4AY | 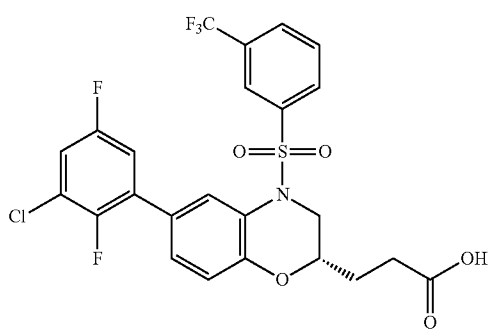 [SMILES: O=C(O)CC[C@H]1CN(S(=O)(=O)c2cccc(C(F)(F)F)c2)c2cc(-c3cc(F)cc(Cl)c3F)ccc2O1] | (S)-3-(6-(3-chloro-2,5-difluorophenyl)-4-((3-(trifluoromethyl)phenyl)-sulfonyl)-3,4-dihydro-2H-benzo[b][1,4]oxazin-2-yl)propanoic acid | 562 (M + H)+ |

TABLE 3-continued

| Compd No. | Structure | Name | Observed m/z |
|---|---|---|---|
| 4AZ | 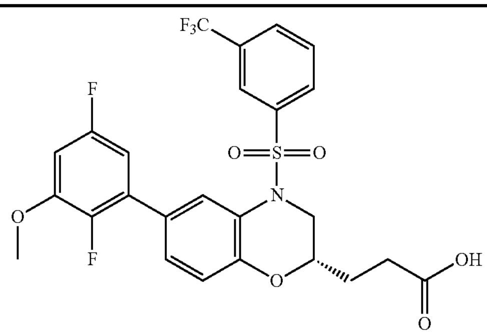 | (S)-3-(6-(2,5-difluoro-3-methoxyphenyl)-4-((3-(trifluoromethyl)phenyl)-sulfonyl)-3,4-dihydro-2H-benzo[b][1,4]oxazin-2-yl)propanoic acid | 558 (M + H)+ |

TABLE 3A

| Compd No. | Structure | Name | Observed m/z |
|---|---|---|---|
| 4BB | 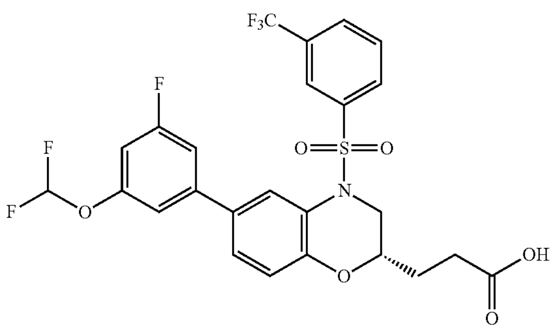 [SMILES: O=C(O)CC[C@H]1CN(S(=O)(=O)c2cccc(C(F)(F)F)c2)c2cc(-c3cc(F)cc(OC(F)F)c3)ccc2O1] | (S)-3-(6-(3-(difluoromethoxy)-5-fluorophenyl)-4-((3-(trifluoromethyl)phenyl)sulfonyl)-3,4-dihydro-2H-benzo[b][1,4]oxazin-2-yl)propanoic acid | 574 (M − H)− |
| 4BC | 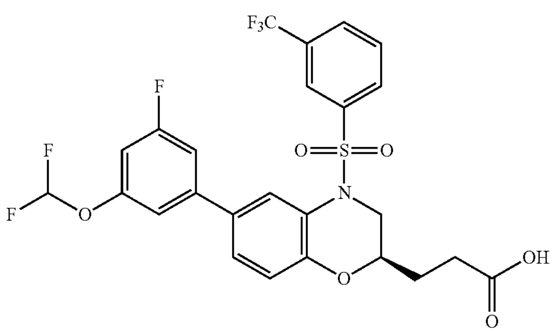 [SMILES: O=C(O)CC[C@@H]1CN(S(=O)(=O)c2cccc(C(F)(F)F)c2)c2cc(-c3cc(F)cc(OC(F)F)c3)ccc2O1] | (R)-3-(6-(3-(difluoromethoxy)-5-fluorophenyl)-4-((3-(trifluoromethyl)phenyl)sulfonyl)-3,4-dihydro-2H-benzo[b][1,4]oxazin-2-yl)propanoic acid | 574 (M − H)− |
| 4BD | 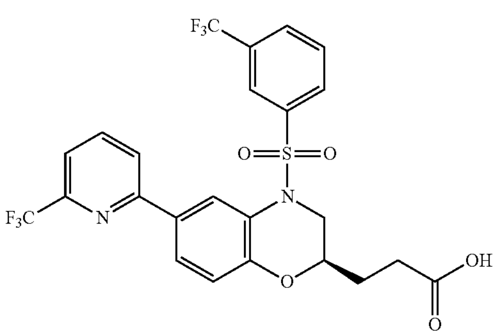 [SMILES: O=C(O)CC[C@@H]1CN(S(=O)(=O)c2cccc(C(F)(F)F)c2)c2cc(-c3cccc(C(F)(F)F)n3)ccc2O1] | (S)-3-(4-((3-(trifluoromethyl)-phenyl)sulfonyl)-6-(6-(trifluoromethyl)pyridin-2-yl)-3,4-dihydro-2H-benzo[b][1,4]oxazin-2-yl)propanoic acid | 559 (M − H)− |

TABLE 3A-continued

| Compd No. | Structure | Name | Observed m/z |
|---|---|---|---|
| 4BE | 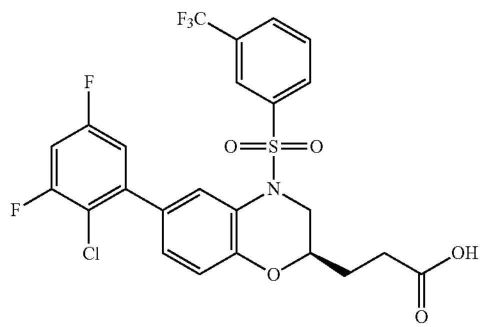 [SMILES: O=C(O)CC[C@@H]1CN(S(=O)(=O)c2cccc(C(F)(F)F)c2)c2cc(-c3cc(F)cc(F)c3Cl)ccc2O1] | (R)-3-(6-(2-chloro-3,5-difluoro-phenyl)-4-((3-(trifluoromethyl)-phenyl)sulfonyl)-3,4-dihydro-2H-benzo[b][1,4]oxazin-2-yl)propanoic acid | 560 (M − H)⁻ |

TABLE 3B

| Compd No. | Physical Characterization Data |
|---|---|
| 4A | $^1$H NMR (300 MHz, CD$_3$OD-d$_4$) δ 8.60 (d, J = 2.1 Hz, 1H), 8.10-8.06 (m, 4H), 8.02 (s, 1H), 7.97 (m, 1H), 7.87 (dd, J = 8.6, 2.2 Hz, 1H), 7.78 (t, J = 7.9 Hz, 1H), 7.73-7.69 (m, 1H), 6.98 (d, J = 8.6 Hz, 1H), 4.48 (dd, J = 14.3, 2.4 Hz, 1H), 3.63 (dddd, J = 10.6, 7.5, 4.6, 2.6 Hz, 1H), 3.42-3.34 (m, 1H), 2.57-2.39 (m, 2H), 2.08-1.79 (m, 2H). |
| 4G | $^1$H NMR (300 MHz, CD$_3$OD-d$_4$) δ 8.44 (d, J = 2.0 Hz, 1H), 8.14 (s, 1H), 8.09-7.97 (m, 3H), 7.85-7.72 (m, 2H), 7.00-6.98 (d, J = 8.0 Hz, 1H), 4.48 (dd, J = 14.4, 2.4 Hz, 1H), 3.58 (m, 1H), 3.37 (m, 1H), 2.46 (m, 2H), 2.02-1.91 (m, 1H), 1.90-1.80 (m, 1H). |
| 4H | $^1$H NMR (300 MHz, CD$_3$OD-d$_4$) δ 8.49 (d, J = 2.1 Hz, 1H), 8.26 (s, 1H), 8.09-7.97 (m, 3H), 7.85-7.72 (m, 2H), 7.00 (d, J = 8.6 Hz, 1H), 4.48 (dd, J = 14.4, 2.4 Hz, 1H), 3.57 (m, 1H), 3.42-3.34 (m, 1H), 2.55-2.37 (m, 2H), 1.95 (m, 1H), 1.82 (m, 1H). |
| 4I | $^1$H NMR (300 MHz, CD$_3$OD-d$_4$) δ 8.39 (s, 1H), 8.34 (s, 1H), 7.91-7.84 (m, 3H), 7.74-7.71 (m, 1H), 7.67-7.63 (m, 2H), 7.27 (m, 1H), 6.94 (m, 1H), 4.38 (dd, J = 14.3, 2.4 Hz, 1H), 3.63 (m, 1H), 3.28 (m, 1H), 2.61-2.54 (m, 2H), 2.03-1.83 (m, 2H). |
| 4J | $^1$H NMR (300 MHz, CD$_3$OD-d$_4$) δ 8.83 (d, J = 6.8 Hz, 1H), 8.35 (s, 1H), 8.18 (s, 1H), 8.12-8.00 (m, 3H), 7.98-7.93 (m, 2H), 7.82 (t, J = 7.8 Hz, 1H), 7.61 (t, J = 7.0 Hz, 1H), 7.49 (d, J = 10.4 Hz, 1H), 7.12 (d, J = 8.4 Hz, 1H), 4.50 (d, J = 16.8 Hz, 1H), 3.57 (m, 1H), 3.35 (m, 1H), 2.52-2.43 (m, 2H), 1.95 (m, 1H), 1.86 (m, 1H). |
| 4K | $^1$H NMR (300 MHz, CD$_3$OD-d$_4$) δ 8.94 (s, 1H), 8.04-8.02 (m, 3H), 7.90 (s, 1H), 7.83 (t, J = 8.0 Hz, 1H), 7.64 (s, 1H), 7.35 (d, J = 10.4 Hz, 1H), 7.06 (d, J = 8.4 Hz, 1H), 4.45 (d, J = 16.8 Hz, 1H), 3.93 (s, 3H), 3.43 (m, 1H), 3.30 (m, 1H), 2.49-2.37 (m, 2H), 1.92 (m, 1H), 1.81 (m, 1H). |
| 4L | $^1$H NMR (300 MHz, CD$_3$OD-d$_4$) δ 8.23 (s, 1H), 8.22-8.05 (m, 2H), 7.96 (s, 1H), 7.84 (t, J = 8.0 Hz, 1H), 7.67 (d, J = 16.0 Hz, 2H), 7.53 (d, J = 10.8 Hz, 1H), 7.16 (d, J = 8.4 Hz, 1H), 4.47 (d, J = 17.2 Hz, 1H), 3.99 (s, 3H), 3.46 (m, 1H), 3.29 (m, 1H), 2.49-2.40 (m, 2H), 1.94 (m, 1H), 1.84 (m, 1H). |
| 4M | $^1$H NMR (300 MHz, CD$_3$OD-d$_4$) δ 8.57-8.47 (m, 2H), 8.01 (d, J = 7.9 Hz, 1H), 7.95 (d, J = 7.7 Hz, 2H), 7.80-7.69 (m, 2H), 6.91 (d, J = 8.5 Hz, 1H), 4.43 (dd, J = 14.5, 2.4 Hz, 1H), 4.00 (s, 3H), 3.50 (m, 1H), 3.28-3.20 (m, 1H), 2.52-2.33 (m, 2H), 1.97-1.72 (m, 2H). |
| 4N | $^1$H NMR (300 MHz, CD$_3$OD-d$_4$) δ 8.74 (d, J = 6.9 Hz, 1H), 8.19-8.10 (m, 2H), 8.09-7.98 (m, 4H), 7.95 (d, J = 1.8 Hz, 1H), 7.81 (t, J = 7.9 Hz, 1H), 7.55 (m, 1H), 7.48 (dd, J = 8.5, 2.1 Hz, 1H), 7.13 (d, J = 8.5 Hz, 1H), 4.43 (dd, J = 14.6, 2.4 Hz, 1H), 3.46 (m, 1H), 3.34 (m, 1H), 2.53-2.35 (m, 2H), 1.93 (m, 1H), 1.87-1.75 (m, 1H). |
| 4O | $^1$H NMR (300 MHz, CD$_3$OD-d$_4$) δ 8.61-8.53 (m, 1H), 8.16 (s, 1H), 8.04 (d, J = 2.1 Hz, 1H), 8.02-7.91 (m, 4H), 7.78 (t, J = 7.9 Hz, 1H), 7.44-7.29 (m, 2H), 7.00-6.90 (m, 2H), 4.43 (dd, J = 14.3, 2.3 Hz, 1H), 3.46-3.32 (m, 2H), 2.52-2.33 (m, 2H), 1.96-1.72 (m, 2H). |
| 4P | $^1$H NMR (300 MHz, CD$_3$OD-d$_4$) δ 8.20-8.17 (m, 2H), 8.13-8.04 (m, 4H), 7.98-7.95 (m, 2H), 7.85 (t, J = 7.8 Hz, 1H), 7.57-7.51 (m, 2H), 7.17 (d, J = 8.4 Hz, 1H), 4.45 (d, J = 12.4 Hz, 1H), 3.55-3.51 (m, 1H), 3.35 (m, 1H), 2.50-2.45 (m, 2H), 1.95 (m, 1H), 1.86 (m, 1H). |
| 4Q | $^1$H NMR (300 MHz, CD$_3$OD-d$_4$) δ 8.95 (s, 1H), 8.21 (s, 1H), 8.05-7.99 (m, 2H), 7.88 (d, J = 7.2 Hz, 2H), 7.82 (t, J = 8.0 Hz 1H), 7.48 (d, J = 10.8 Hz, 1H), 7.02 (d, J = 8.8 Hz, 1H), 4.46 (d, J = 16.8 Hz, 1H), 4.01 (s, 3H), 3.42-3.45 (m, 1H), 3.32-3.28 (m, 1H), 2.47-2.37 (m, 2H), 1.96-1.86 (m, 1H), 1.85-1.78 (m, 1H). |

TABLE 3B-continued

| Compd No. | Physical Characterization Data |
|---|---|
| 4R | $^1$H NMR (300 MHz, CD$_3$OD-d$_4$) δ 7.99 (s, 1H), 7.99-7.95 (m, 2H), 7.91 (s, 1H), 7.77 (m, 1H), 7.37-7.25 (m, 4H), 7.03 (m, 1H), 6.88 (d, 1H), 4.45 (dd, 1H), 3.46 (m, 1H), 3.29 (m, 1H), 2.43 (m, 2H), 2.03-1.85 (m, 3H), 1.04-0.98 (m, 2H), 0.76-0.72 (m, 2H). |
| 4S | $^1$H NMR (300 MHz, CD$_3$OD-d$_4$) δ 8.42-8.36 (m, 2H), 8.06-7.95 (m, 4H), 7.99 (s, 1H), 7.82-7.70 (m, 3H), 7.01 (d, 1H), 4.45 (dd, 1H), 3.46 (m, 1H), 3.29 (m, 1H), 2.43 (m, 2H), 1.92 (m, 1H), 1.81 (m, 1H). |
| 4T | $^1$H NMR (300 MHz, CD$_3$OD-d$_4$) δ 8.05-7.95 (m, 3H), 7.93 (s, 1H), 7.77 (m, 1H), 7.54-7.47 (m, 3H), 7.42 (s, 1H), 7.13 (m, 1H), 6.93 (t, 1H), 6.92 (d, 1H), 4.46 (dd, 1H), 3.57 (m, 1H), 3.29 (m, 1H), 2.43 (m, 2H), 1.92 (m, 1H), 1.81 (m, 1H). |
| 4U | $^1$H NMR (300 MHz, CD$_3$OD-d$_4$) δ 8.40 (d, J = 2.0 Hz, 1H), 8.01 (dd, J = 13.3, 7.7 Hz, 1H), 7.96 (d, J = 8.0 Hz, 2H), 7.86-7.77 (m, 1H), 7.71 (d, J = 2.1 Hz, 1H), 7.08 (dd, J = 8.4, 2.1 Hz, 1H), 6.94 (d, J = 8.4 Hz, 1H), 4.44 (dd, J = 14.6, 2.3 Hz, 1H), 3.41 (dddd, J = 10.2, 7.2, 4.5, 2.4 Hz, 1H), 3.28 (dd, J = 14.5, 10.1 Hz, 1H), 2.53-2.28 (m, 5H), 1.97-1.73 (m, 2H). |
| 4V | $^1$H NMR (300 MHz, CD$_3$OD-d$_4$) δ 8.45 (s, 1H), 8.15-8.12 (m, 2H), 8.00-7.98 (m, 2H), 7.79 (t, J = 8.0 Hz, 1H), 7.68 (d, J = 12.0 Hz, 1H), 7.61 (d, J = 10.8 Hz, 1H), 7.30 (t, J = 7.8 Hz, 1H), 7.00 (d, J = 8.4 Hz, 1H), 6.92 (d, J = 6.8 Hz, 1H), 6.71 (s, 1H), 4.50 (d, J = 16.8 Hz, 1H), 3.56 (m, 1H), 3.38-3.32 (m, 1H), 2.52-2.43 (m, 2H), 1.99-1.82 (m, 2H). |
| 4W | $^1$H NMR (300 MHz, CD$_3$OD-d$_4$) δ 8.22 (s, 1H), 8.02-7.94 (m, 3H), 7.79 (t, J = 8.0 Hz, 1H), 7.62 (s, 1H), 7.52 (d, J = 10.8 Hz, 1H), 6.87 (d, J = 8.8 Hz, 1H), 6.56 (s, 1H), 4.44 (d, J = 14.4 Hz, 1H), 3.96 (s, 3H), 3.43 (m, 1H), 3.30-3.28 (m, 1H), 2.48-2.35 (m, 2H), 1.90 (m, 1H), 1.79 (m, 1H) |
| 4X | $^1$H NMR (300 MHz, CD$_3$OD-d$_4$) δ 8.33 (s, 1H), 8.07-7.78 (m, 5H), 7.62 (m, 1H), 7.09-7.02 (m, 3H), 4.45 (dd, J = 14.3, 2.4 Hz, 1H), 3.48 (m, 1H), 3.46-3.33 (m, 6H), 3.30 (m, 1H), 2.51-2.40 (m, 2H), 1.93 (m, 1H), 1.84 (m, 1H). |
| 4Y | $^1$H NMR (300 MHz, CD$_3$OD-d$_4$) δ 8.66-8.60 (m, 2H), 8.13 (s, 1H), 8.04 (m, 1H), 7.99-7.97 (m, 2H), 7.87-7.86 (m, 1H), 7.79 (m, 1H), 6.98 (d, J = 8.8 Hz, 1H), 4.50 (dd, J = 14.3, 2.4 Hz, 1H), 4.12 (s, 1H), 3.56 (m, 1H), 3.35 (m, 1H), 2.52-2.42 (m, 2H), 1.99-1.81 (m, 2H). |
| 4Z | $^1$H NMR (300 MHz, CD$_3$OD-d$_4$) δ 8.48 (s, 1H), 8.05-7.96 (m, 3H), 7.83-7.77 (m, 2H), 7.04 (d, J = 8.8 Hz, 1H), 4.49 (dd, J = 14.4, 2.4 Hz, 1H), 3.53 (m, 1H), 3.34 (m, 1H), 2.65 (s, 3H), 2.48-2.43 (m, 2H), 1.96-1.81 (m, 2H). |
| 4AA | $^1$H NMR (300 MHz, CD$_3$OD-d$_4$) δ 8.04-7.95 (m, 4H), 7.79 (m, 1H), 7.28 (m, 1H), 7.17 (m, 1H), 7.12 (m, 1H), 7.00 (m, 1H), 6.91 (d, J = 8.8 Hz, 1H), 4.50 (dd, J = 14.4, 2.4 Hz, 1H), 4.20-4.15 (m, 2H), 3.51 (m, 1H), 3.29 (m, 1H), 2.45 (m, 2H), 1.94 (m, 1H), 1.83 (m, 1H), 1.49-1.46 (m, 3H). |
| 4AB | $^1$H NMR (300 MHz, CD$_3$OD-d$_4$) δ 8.04 (d, J = 2.0 Hz, 1H), 8.04 (t, J = 8.0 Hz, 2H), 7.92 (s, 1H), 7.79 (t, J = 7.9 Hz, 1H), 7.43-7.33 (m, 2H), 7.17 (dt, J = 4.1, 1.6 Hz, 2H), 6.97 (m, 1H), 6.91 (d, J = 8.4 Hz, 1H), 4.46 (dd, J = 14.4, 2.4 Hz, 1H), 4.14 (t, J = 4.7 Hz, 2H), 3.93 (t, J = 4.7 Hz, 2H), 3.51-3.40 (m, 1H), 3.33-3.24 (m, 1H), 2.44 (q, J = 7.1 Hz, 2H), 1.98-1.74 (m, 2H). |
| 4AC | $^1$H NMR (300 MHz, CD$_3$OD-d$_4$) δ 8.03-7.90 (m, 5H), 7.82-7.73 (m, 2H), 7.32 (dd, J = 8.5, 2.1 Hz, 1H), 6.84 (d, J = 8.5 Hz, 1H), 4.59 (m, 1H), 4.43 (dd, J = 14.3, 2.3 Hz, 1H), 3.40 (ddd, J = 10.2, 4.5, 2.4 Hz, 1H), 3.26 (dd, J = 14.4, 10.1 Hz, 1H), 2.42 (q, J = 7.4 Hz, 2H), 1.88 (m, 1H), 1.80 (m, 1H), 1.56 (d, J = 6.7 Hz, 6H). |
| 4AD | $^1$H NMR (300 MHz, CD$_3$OD-d$_4$) δ 8.78 (dd, J = 5.5, 1.5 Hz, 1H), 8.44 (dd, J = 8.0, 1.5 Hz, 1H), 8.06-7.92 (m, 2H), 7.84-7.75 (m, 3H), 7.72 (d, J = 2.1 Hz, 1H), 7.56-7.43 (m, 5H), 7.02 (dd, J = 8.5, 2.2 Hz, 1H), 6.84 (d, J = 8.5 Hz, 1H), 4.36 (dd, J = 14.3, 2.1 Hz, 1H), 3.25 (m, 1H), 3.16 (m, 1H), 2.38 (q, J = 7.2 Hz, 2H), 1.93-1.68 (m, 2H). |
| 4AE | $^1$H NMR (300 MHz, CD$_3$OD-d$_4$) δ 8.68 (dd, J = 5.8, 1.6 Hz, 1H), 8.39 (dd, J = 7.8, 1.5 Hz, 1H), 8.09-7.96 (m, 2H), 7.97-7.90 (m, 2H), 7.88-7.76 (m, 2H), 7.24 (dd, J = 8.5, 2.2 Hz, 1H), 7.03 (d, J = 8.5 Hz, 1H), 4.43 (dd, J = 14.6, 2.4 Hz, 1H), 3.42 (m, 1H), 3.24 (m, 1H), 2.76 (s, 3H), 2.51-2.33 (m, 2H), 1.91 (m, 1H), 1.77 (m, 1H). |
| 4AF | $^1$H NMR (300 MHz, CD$_3$OD-d$_4$) δ 8.51 (d, J = 2.7 Hz, 1H), 8.06-7.96 (m, 2H), 7.89-7.71 (m, 4H), 7.18 (dd, J = 8.5, 2.1 Hz, 1H), 6.99 (d, J = 8.5 Hz, 1H), 4.44 (dd, J = 14.5, 2.4 Hz, 1H), 3.48-3.37 (m, 1H), 3.29-3.21 (m, 1H), 2.57 (s, 3H), 2.52-2.33 (m, 2H), 1.97-1.87 (m, 1H), 1.85-1.74 (m, 1H). |
| 4AG | $^1$H NMR (300 MHz, CD$_3$OD-d$_4$) δ 8.07-7.89 (m, 2H), 7.86-7.76 (m, 2H), 7.72 (d, J = 2.0 Hz, 1H), 7.23 (q, J = 7.5 Hz, 1H), 7.10-6.98 (m, 3H), 6.89 (dd, J = 8.4, 1.4 Hz, 1H), 4.44 (dd, J = 14.5, 2.3 Hz, 1H), 3.43 (m, 1H), 3.25 (m, 1H), 2.52-2.32 (m, 2H), 2.19 (d, J = 2.4 Hz, 3H), 1.97-1.72 (m, 2H). |
| 4AH | $^1$H NMR (300 MHz, CD$_3$OD-d$_4$) δ 8.03-7.89 (m, 4H), 7.77 (t, J = 7.9 Hz, 1H), 7.41-7.30 (m, 4H), 7.18 (dt, J = 6.2, 1.9 Hz, 1H), 6.89 (d, J = 8.5 Hz, 1H), 4.44 (dd, J = 14.4, 2.4 Hz, 1H), 3.44 (m, 1H), 3.27 (m, 1H), 2.72 (q, |

TABLE 3B-continued

| Compd No. | Physical Characterization Data |
|---|---|
| | J = 7.6 Hz, 2H), 2.42 (q, J = 7.3 Hz, 2H), 1.97-1.74 (m, 2H), 1.29 (t, J = 7.6 Hz, 3H). |
| 4AI | $^1$H NMR (300 MHz, CD$_3$OD-d$_4$) δ 8.69-8.63 (m, 1H), 8.17-7.86 (m, 9H), 7.76 (t, J = 7.9 Hz, 1H), 7.55 (dt, J = 13.5, 7.0 Hz, 3H), 7.01 (d, J = 8.5 Hz, 1H), 4.49 (dd, J = 14.5, 2.4 Hz, 1H), 3.53 (ddt, J = 10.6, 5.1, 2.9 Hz, 1H), 3.37-3.31 (m, 1H), 2.56-2.37 (m, 2H), 2.01-1.77 (m, 2H). |
| 4AJ | $^1$H NMR (300 MHz, CD$_3$OD-d$_4$) δ 8.04-7.88 (m, 4H), 7.77 (t, J = 7.9 Hz, 1H), 7.30 (t, J = 8.7 Hz, 1H), 7.23 (m, 1H), 6.98 (t, J = 10.1 Hz, 1H), 6.89 (dd, J = 8.5, 1.1 Hz, 1H), 4.45 (dd, J = 14.5, 2.4 Hz, 1H), 3.47 (m, 1H), 3.26 (m, 1H), 2.52-2.33 (m, 2H), 2.29 (s, 3H), 1.91 (m, 1H), 1.78 (m, 1H). |
| 4AK | $^1$H NMR (300 MHz, CD$_3$OD-d$_4$) δ 8.07-7.92 (m, 4H), 7.80 (t, J = 7.9 Hz, 1H), 7.33 (dt, J = 8.5, 1.7 Hz, 1H), 7.24-7.04 (m, 2H), 6.97 (d, J = 8.6 Hz, 1H), 4.49 (dd, J = 14.5, 2.4 Hz, 1H), 3.54 (ddd, J = 10.4, 4.8, 2.7 Hz, 1H), 3.30 (d, J = 9.9 Hz, 1H), 2.46 (q, J = 6.9 Hz, 2H), 2.01-1.76 (m, 2H). |
| 4AL | $^1$H NMR (300 MHz, CD$_3$OD-d$_4$) δ 8.67 (s, 1H), 8.24 (s, 1H), 8.05-7.95 (m, 4H), 7.83-7.76 (m, 2H), 6.96 (d, J = 8.4 Hz, 1H), 4.51 (dd, J = 14.4, 2.4 Hz, 1H), 3.59-3.52 (m, 1H), 3.34 (m, 1H), 3.30-3.28 (m, 6H), 2.52-2.42 (m, 2H), 1.99-1.81 (m, 2H). |
| 4AM | $^1$H NMR (300 MHz, CD$_3$OD-d$_4$) δ 8.21 (dd, J = 2.5, 1.0 Hz, 1H), 8.07-7.96 (m, 3H), 7.91 (s, 1H), 7.78 (t, J = 7.9 Hz, 1H), 7.55 (dd, J = 8.6, 2.3 Hz, 1H), 7.12-6.98 (m, 3H), 4.45 (dd, J = 14.7, 2.4 Hz, 1H), 3.47-3.36 (m, 1H), 3.28-3.21 (m, 1H), 3.10 (s, 3H), 2.50-2.32 (m, 2H), 1.91 (m, 1H), 1.80 (m, 1H). |
| 4AN | $^1$H NMR (300 MHz, CD$_3$OD-d$_4$) δ 8.04 (s, 1H), 7.98 (s, 1H), 7.87-7.80 (m, 2H), 7.65 (m, 1H), 7.51 (m, 1H), 6.90 (d, J = 8.1 Hz, 1H), 6.71 (s, 1H), 6.56 (s, 1H), 4.21 (m, 1H), 3.44 (m, 1H), 3.36 (s, 6H), 3.23-3.15 (m, 1H), 2.51-2.38 (m, 5H), 1.88-1.72 (m, 2H). |
| 4AO | $^1$H NMR (300 MHz, CD$_3$OD-d$_4$) δ 8.09 (d, J = 8.0 Hz, 1H), 8.04 (d, J = 8.0 Hz, 1H), 7.99-7.95 (m, 2H), 7.91 (s, 1H). 7.85 (t, J = 7.8 Hz, 1H), 7.35 (d, J = 8.8 Hz, 1H), 7.26 (d, J = 9.6 Hz, 1H), 7.09 (d, J = 8.4 Hz, 1H), 4.47 (d, J = 17.2 Hz, 1H), 3.52-3.48 (m, 1H), 3.33-3.29 (m, 6H), 3.28 (s, 1H), 2.48-2.43 (m, 2H), 2.24 (s, 3H), 1.97-1.90 (m, 1H), 1.89-1.80 (m, 1H). |
| 4AP | $^1$H NMR (300 MHz, CD$_3$OD-d$_4$) δ 8.22 (s, 1H), 8.01 (dd, J = 19.8, 9.7 Hz, 3H), 7.79 (t, J = 7.9 Hz, 1H), 7.56 (dd, J = 8.6, 2.3 Hz, 1H), 7.03 (d, J = 8.6 Hz, 1H), 6.69 (d, J = 2.1 Hz, 1H), 6.38 (s, 1H), 4.45 (dd, J = 14.4, 2.2 Hz, 1H), 4.06 (s, 3H), 3.58-3.36 (m, 1H), 3.33 (s, 6H), 3.28-3.06 (m, 1H), 2.43 (td, J = 7.2, 3.1 Hz, 2H), 1.98-1.74 (m, 2H). |
| 4AQ | $^1$H NMR (300 MHz, CD$_3$OD-d$_4$) δ 8.05-7.89 (m, 4H), 7.78 (t, J = 7.9 Hz, 1H), 7.43-7.25 (m, 3H), 6.95 (d, J = 8.6 Hz, 1H), 4.46 (dd, J = 14.4, 2.4 Hz, 1H), 3.52 (ddd, J = 10.1, 4.7, 2.7 Hz, 1H), 3.27 (d, J = 10.0 Hz, 1H), 2.44 (q, J = 6.9 Hz, 2H), 1.98-1.74 (m, 2H). |
| 4AR | $^1$H NMR (300 MHz, CD$_3$OD-d$_4$) δ 8.04-7.94 (m, 4H), 7.80 (t, J = 8.0 Hz, 1H), 7.31 (d, J = 8.8 Hz 1H), 6.94 (d, J = 8.8 Hz, 1H), 6.94-6.86 (m, 1H), 6.79-6.76 (m, 1H), 4.44 (d, J = 30 Hz, 1H), 3.85 (s, 3H), 3.54-3.50 (m, 1H), 3.33-3.28 (m, 1H), 2.48-2.43 (m, 2H), 1.96-1.89 (m, 1H), 1.87-1.80 (m, 1H). |
| 4AS | $^1$H NMR (300 MHz, CD$_3$OD-d$_4$) δ 8.06-8.04 (m, 2H), 8.01 (m, 1H), 7.97 (m, 1H), 7.82 (m, 1H), 7.74 (m, 1H), 7.64 (m, 1H), 7.02 (m, 1H), 7.36 (d, J = 8.4 Hz, 1H), 4.50 (dd, J = 14.4, 2.4 Hz, 1H), 3.55-3.52 (m, 1H), 3.33-3.30 (m, 1H), 2.53-2.40 (m, 2H), 1.99-1.86 (m, 2H). |
| 4AT | $^1$H NMR (300 MHz, CD$_3$OD-d$_4$) δ 8.67 (d, J = 2.1 Hz, 1H), 8.07-7.93 (m, 3H), 7.83-7.73 (m, 2H), 7.17 (s, 1H), 6.93 (d, J = 8.6 Hz, 1H), 6.75 (s, 1H), 4.48 (dd, J = 14.3, 2.3 Hz, 1H), 3.57 (d, J = 8.6 Hz, 1H), 3.37 (s, 1H), 3.25 (s, 6H), 2.56-2.39 (m, 2H), 1.90 (ddt, J = 41.0, 14.4, 6.8 Hz, 2H). |
| 4AU | $^1$H NMR (300 MHz, CD$_3$OD-d$_4$) δ 8.81 (d, J = 7.5 Hz, 1H), 8.14 (d, J = 2.2 Hz, 1H), 8.09-7.96 (m, 2H), 7.97-7.83 (m, 2H), 7.81 (d, J = 7.9 Hz, 1H), 7.08 (d, J = 8.7 Hz, 1H), 6.95 (d, J = 7.5 Hz, 1H), 4.49 (dd, J = 14.6, 2.4 Hz, 1H), 3.61-3.43 (m, 4H), 3.38-3.29 (m, 4H), 2.45 (td, J = 7.1, 2.7 Hz, 2H), 1.99-1.72 (m, 2H). |
| 4AV | $^1$H NMR (300 MHz, CD$_3$OD-d$_4$) δ 8.78 (d, J = 2.1 Hz, 1H), 8.28 (d, J = 6.1 Hz, 1H), 8.07-7.88 (m, 4H), 7.77 (t, J = 7.9 Hz, 1H), 7.26 (d, J = 6.2 Hz, 1H), 6.98 (d, J = 8.7 Hz, 1H), 4.47 (dd, J = 14.5, 2.5 Hz, 1H), 3.55 (ddt, J = 12.4, 7.5, 2.4 Hz, 1H), 3.35 (s, 6H), 3.32 (d, J = 5.6 Hz, 1H), 2.62-2.34 (m, 2H), 1.98-1.68 (m, 2H). |
| 4AX | $^1$H NMR (300 MHz, CD$_3$OD-d$_4$) δ 8.67 (s, 1H), 8.67-8.61 (m, 2H), 8.08-7.83 (m, 5H), 7.78 (t, J = 7.8 Hz, 1H), 6.99 (d, J = 8.7 Hz, 1H), 4.45 (dd, J = 14.5, 2.5 Hz, 1H), 3.59 (dddd, J = 10.3, 7.4, 4.5, 2.5 Hz, 1H), 3.35 (d, J = 9.7 Hz, 1H), 2.54-2.35 (m, 2H), 1.95 (m, 1H), 1.84 (m, 1H). |
| 4AY | $^1$H NMR (300 MHz, CD$_3$OD-d$_4$) δ 8.05-7.88 (m, 4H), 7.78 (t, J = 7.9 Hz, 1H), 7.31 (ddd, J = 15.1, 8.5, 2.4 Hz, 2H), 7.23-7.11 (m, 1H), 6.94 (d, J = 8.5 Hz, 1H), 4.47 (dd, J = 14.5, 2.4 Hz, 1H), 3.54-3.42 (m, 1H), 3.27 (d, J = 10.3 Hz, 1H), 2.52-2.34 (m, 2H), 1.97-1.73 (m, 2H). |
| 4AZ | $^1$H NMR (300 MHz, CD$_3$OD-d$_4$) δ 8.03-7.94 (m, 4H), 7.79 (m, 1H), 7.28 (m, 1H), 6.96-6.92 (m, 2H), 6.74 (m, 1H), 4.50 (dd, J = 14.4, 2.4 Hz, 1H), 3.95 (s, 3H), 3.53-3.49 (m, 1H), 3.29 (m, 1H), 2.48-2.43 (m, 2H), 1.96-1.79 (m, 2H). |

TABLE 3B-continued

| Compd No. | Physical Characterization Data |
|---|---|
| 4BB | $^1$H NMR (300 MHz, CD$_3$OD-d$_4$) δ 8.07-7.89 (m, 4H), 7.78 (t, J = 7.9 Hz, 1H), 7.41 (dd, J = 8.6, 2.2 Hz, 1H), 7.29-6.66 (m, 5H), 4.45 (dd, J = 14.5, 2.3 Hz, 1H), 3.53-3.41 (m, 2H), 2.44 (dt, J = 10.7, 5.3 Hz, 2H), 1.85 (dp, J = 21.4, 7.1 Hz, 2H). |
| 4BC | $^1$H NMR (300 MHz, CD$_3$OD-d$_4$) δ 8.07-7.89 (m, 4H), 7.78 (t, J = 7.9 Hz, 1H), 7.41 (dd, J = 8.6, 2.2 Hz, 1H), 7.29-6.66 (m, 5H), 4.45 (dd, J = 14.5, 2.3 Hz, 1H), 3.53-3.41 (m, 2H), 2.44 (dt, J = 10.7, 5.3 Hz, 2H), 1.85 (dp, J = 21.4, 7.1 Hz, 2H). |
| 4BD | $^1$H NMR (300 MHz, CD$_3$OD-d$_4$) δ 8.59 (d, J = 2.1 Hz, 1H), 8.12-7.92 (m, 5H), 7.91-7.65 (m, 3H), 6.97 (d, J = 8.6 Hz, 1H), 4.47 (dd, J = 14.3, 2.4 Hz, 1H), 3.61 (s, 2H), 3.43-3.31 (m, 1H), 2.47 (dt, J = 10.3, 5.4 Hz, 2H), 1.97-1.80 (m, 2H). |
| 4BE | $^1$H NMR (300 MHz, CD$_3$OD-d$_4$) δ 8.08-7.74 (m, 5H), 7.26-7.12 (m, 2H), 7.09-6.90 (m, 2H), 4.47 (dd, J = 14.4, 2.3 Hz, 1H), 3.47 (s, 2H), 2.44 (td, J = 7.2, 3.5 Hz, 2H), 1.85 (dp, J = 21.8, 7.3 Hz, 2H). |

Example 5—Synthesis of (S)-3-(6-(3-chlorophenyl)-4-((4-fluoro-3-methoxyphenyl)sulfonyl)-3,4-dihydro-2H-benzo[b][1,4]oxazin-2-yl)propanoic acid

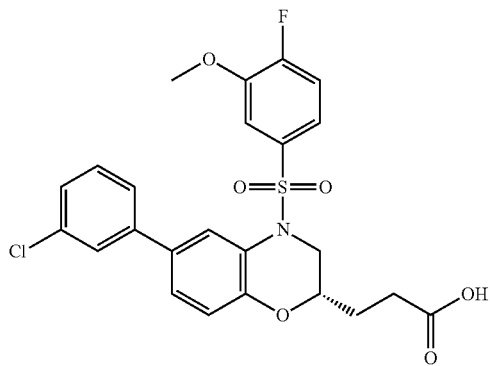 [SMILES: COc1cc(S(=O)(=O)N2C[C@H](CCC(=O)O)Oc3ccc(-c4cccc(Cl)c4)cc32)ccc1F]

Part I—Synthesis of methyl (S)-3-(6-(3-chlorophenyl)-3,4-dihydro-2H-benzo[b][1,4]oxazin-2-yl)propanoate

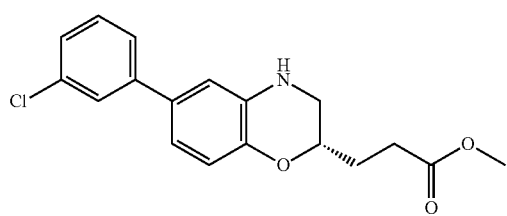 [SMILES: COC(=O)CC[C@H]1CNc2cc(-c3cccc(Cl)c3)ccc2O1]

A mixture of (3-chlorophenyl)boronic acid (4.99 g, 31.91 mmol), methyl (S)-3-(6-bromo-3,4-dihydro-2H-benzo[b][1,4]oxazin-2-yl)propanoate (4.8 g, 15.99 mmol), tetrakis(triphenylphosphine)palladium (1.8 g, 1.56 mmol), sodium carbonate (5.1 g, 48.12 mmol), toluene (100 mL), methanol (10 mL), and water (10 mL) was stirred overnight at 80° C. Then, the mixture was partitioned between ethyl acetate and water. The organic layer was dried (Na$_2$SO$_4$) and concentrated. The resulting residue was purified via MPLC eluting with a gradient of 10-20% ethyl acetate in petroleum ether to afford methyl (S)-3-(6-(3-chlorophenyl)-3,4-dihydro-2H-benzo[b][1,4]oxazin-2-yl)propanoate (2.2 g, 41%) as a white solid.

Part II—Synthesis of methyl (S)-3-(6-(3-chlorophenyl)-4-((4-fluoro-3-methoxyphenyl)sulfonyl)-3,4-dihydro-2H-benzo[b][1,4]oxazin-2-yl)propanoate

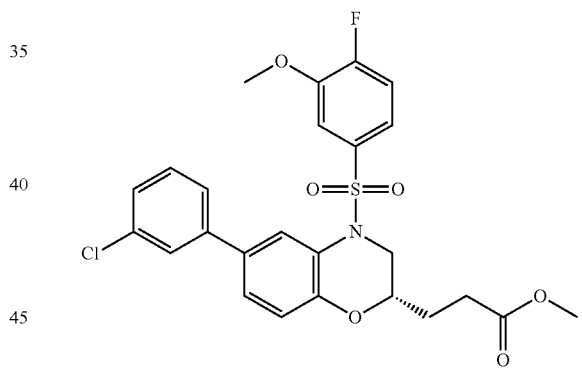

A mixture of methyl (S)-3-(6-(3-chlorophenyl)-3,4-dihydro-2H-benzo[b][1,4]oxazin-2-yl)propanoate (200 mg, 0.60 mmol), 4-fluoro-3-methoxybenzene-1-sulfonyl chloride (406 mg, 1.81 mmol), pyridine (237 mg, 3.00 mmol), and dichloromethane (20 mL) was stirred overnight at room temperature. Then, the pH value of the solution was adjusted to 3-4 with 1M hydrogen chloride. Next, the resulting solution was extracted three times with dichloromethane. The combined organic layers were dried (Na$_2$SO$_4$), and concentrated. The resulting residue was purified via MPLC eluting with a gradient of 10-20% ethyl acetate in petroleum ether to afford methyl (S)-3-(6-(3-chlorophenyl)-4-((4-fluoro-3-methoxyphenyl)sulfonyl)-3,4-dihydro-2H-benzo[b][1,4]oxazin-2-yl)propanoate (250 mg, 80%) as a light yellow oil.

Part III—Synthesis of (S)-3-(6-(3-chlorophenyl)-4-((4-fluoro-3-methoxyphenyl)sulfonyl)-3,4-dihydro-2H-benzo[b][1,4]oxazin-2-yl)propanoic acid

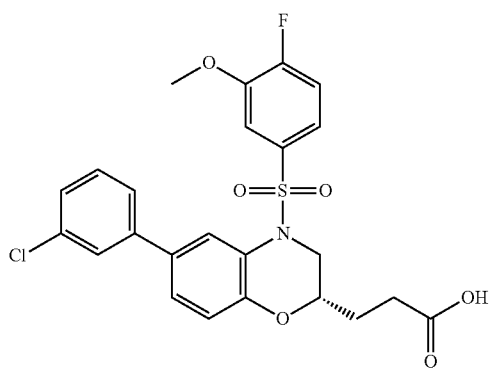 [SMILES: COc1cc(S(=O)(=O)N2C[C@H](CCC(=O)O)Oc3ccc(-c4cccc(Cl)c4)cc32)ccc1F]

Based on the procedure in Example 1, Part VII, (S)-3-(6-(3-chlorophenyl)-4-((4-fluoro-3-methoxyphenyl)sulfonyl)-3,4-dihydro-2H-benzo[b][1,4]oxazin-2-yl)propanoic acid was prepared. $^1$H-NMR (400 MHz, CD$_3$OD) δ 8.10 (s, 1H), 7.60 (m, 1H), 7.56 (d, J=8.0H4z, 1H), 7.47-7.41 (m, 2H), 7.37-7.26 (m, 3H), 7.21 (d, J=8.0 Hz, 1H), 6.96 (d, J=8.0 Hz, 1H), 4.42 (dd, J=14.4 Hz, 2.4 Hz, 1H), 3.72 (s, 3H), 3.43 (m, 1H), 3.23 (dd, J=14.4 Hz, 2.4 Hz, 1H), 2.46 (t, J=7.2 Hz, 2H), 1.95-1.75 (m, 2H). (ES, m/z): (M+Na)$^+$ 527.95.

Example 6—Preparation of Additional Aryl and Heteroaryl Sulfonyl-3,4-dihydro-2H-benzo[b][1,4]oxazin-2-yl)propanoic Acids Compounds in Table 4 were prepared based on experimental procedures described in Examples 5 and 24 and the detailed description. $^1$H NMR data for exemplary compounds from Table 4 is provided in Table 4A.

TABLE 4

| Compd. No. | Structure | Name | Observed m/z |
|---|---|---|---|
| 6A | 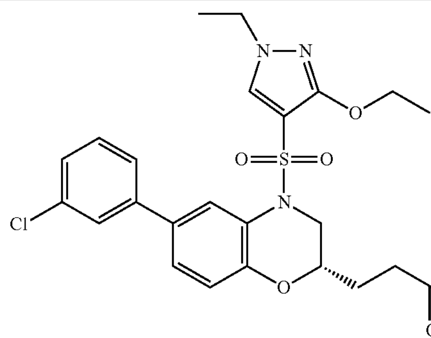 | (S)-3-(6-(3-chlorophenyl)-4-((3-ethoxy-1-ethyl-1H-pyrazol-4-yl)sulfonyl)-3,4-dihydro-2H-benzo[b][1,4]oxazin-2-yl)propanoic acid | 520(M + H)$^+$ |
| 6B | 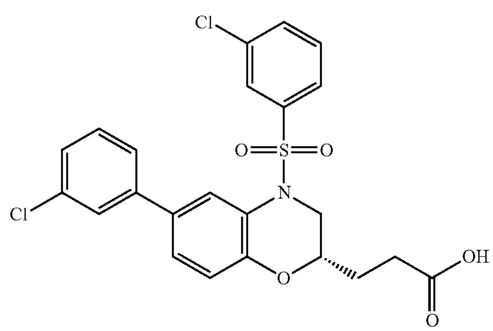 [SMILES: O=C(O)CC[C@H]1CN(S(=O)(=O)c2cccc(Cl)c2)c2cc(-c3cccc(Cl)c3)ccc2O1] | (S)-3-(6-(3-chlorophenyl)-4-((3-chlorophenyl)sulfonyl)-3,4-dihydro-2H-benzo[b][1,4]oxazin-2-yl)propanoic acid | 492 (M + H)$^+$ |
| 6C | 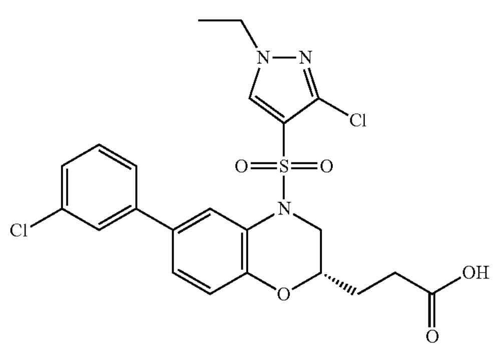 [SMILES: CCn1cc(S(=O)(=O)N2C[C@H](CCC(=O)O)Oc3ccc(-c4cccc(Cl)c4)cc32)c(Cl)n1] | (S)-3-(4-((3-chloro-1-ethyl-1H-pyrazol-4-yl)sulfonyl)-6-(3-chlorophenyl)-3,4-dihydro-2H-benzo[b][1,4]oxazin-2-yl)propanoic acid | 510 (M + H)$^+$ |

TABLE 4-continued

| Compd. No. | Structure | Name | Observed m/z |
|---|---|---|---|
| 6D | 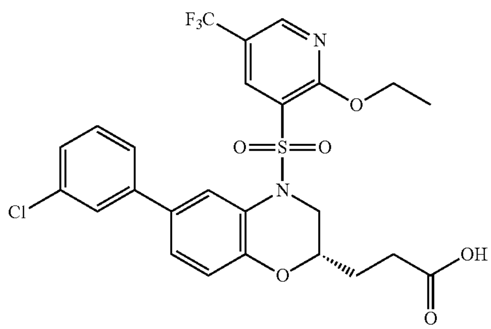 [SMILES: CCOc1ncc(C(F)(F)F)cc1S(=O)(=O)N1C[C@H](CCC(=O)O)Oc2ccc(-c3cccc(Cl)c3)cc21] | (S)-3-(6-(3-chlorophenyl)-4-((2-ethoxy-5-(trifluoromethyl)-pyridin-3-yl)sulfonyl)-3,4-dihydro-2H-benzo[b][1,4]-oxazin-2-yl)propanoic acid | 571 (M + H)+ |
| 6E | 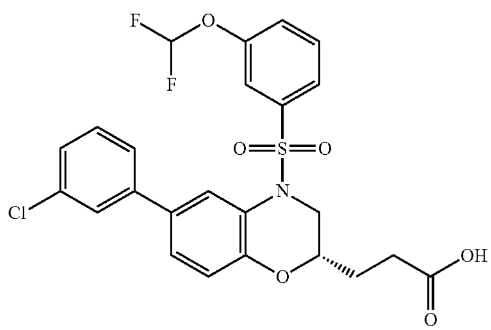 [SMILES: O=C(O)CC[C@H]1CN(S(=O)(=O)c2cccc(OC(F)F)c2)c2cc(-c3cccc(Cl)c3)ccc2O1] | (S)-3-(6-(3-chlorophenyl)-4-((3-(difluoromethoxy)phenyl)sulfonyl)-3,4-dihydro-2H-benzo[b][1,4]-oxazin-2-yl)propanoic acid | 524 (M + H)+ |
| 6F | 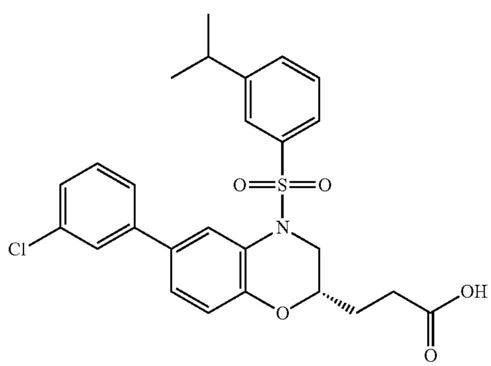 [SMILES: CC(C)c1cccc(S(=O)(=O)N2C[C@H](CCC(=O)O)Oc3ccc(-c4cccc(Cl)c4)cc32)c1] | (S)-3-(6-(3-chlorophenyl)-4-((3-isopropylphenyl)sulfonyl)-3,4-dihydro-2H-benzo[b][1,4]oxazin-2-yl)propanoic acid | 500 (M + H)+ |
| 6G | 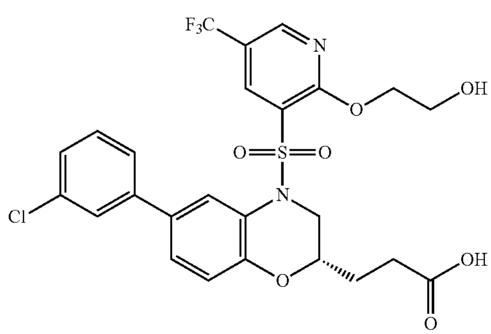 [SMILES: O=C(O)CC[C@H]1CN(S(=O)(=O)c2cc(C(F)(F)F)cnc2OCCO)c2cc(-c3cccc(Cl)c3)ccc2O1] | (S)-3-(6-(3-chlorophenyl)-4-((2-(2-hydroxyethoxy-5-(trifluoromethyl)-pyridin-3-yl)sulfonyl)-3,4-dihydro-2H-benzo[b][1,4]oxazin-2-yl)propanoic acid | 587 (M + H)+ |

TABLE 4-continued

| Compd. No. | Structure | Name | Observed m/z |
|---|---|---|---|
| 6H | 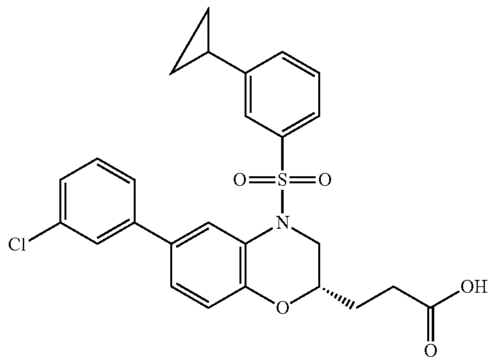 [SMILES: O=C(O)CC[C@H]1CN(S(=O)(=O)c2cccc(C3CC3)c2)c2cc(-c3cccc(Cl)c3)ccc2O1] | (S)-3-(6-(3-chlorophenyl)-4-((3-cyclopropylphenyl)sulfonyl)-3,4-dihydro-2H-benzo[b][1,4]oxazin-2-yl)propanoic acid | 498 (M + H)+ |
| 6I | 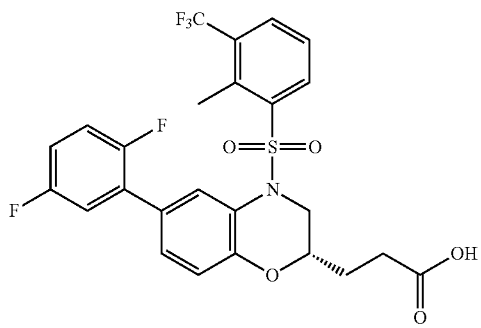 [SMILES: Cc1c(C(F)(F)F)cccc1S(=O)(=O)N1C[C@H](CCC(=O)O)Oc2ccc(-c3cc(F)ccc3F)cc21] | (S)-3-(6-(2,5-difluorophenyl)-4-((2-methyl-3-(trifluoromethyl)phenyl)-sulfonyl)-3,4-dihydro-2H-benzo[b][1,4]oxazin-2-yl)propanoic acid | 564 (M + Na)+ |
| 6J | 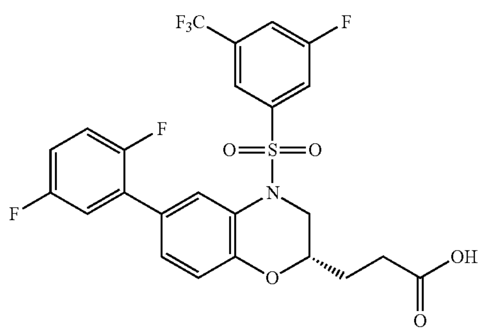 [SMILES: O=C(O)CC[C@H]1CN(S(=O)(=O)c2cc(F)cc(C(F)(F)F)c2)c2cc(-c3cc(F)ccc3F)ccc2O1] | (S)-3-(6-(2,5-difluorophenyl)-4-((3-fluoro-5-(trifluoromethyl)phenyl)-sulfonyl)-3,4-dihydro-2H-benzo[b][1,4]oxazin-2-yl)propanoic acid | 546 (M + H)+ |
| 6K | 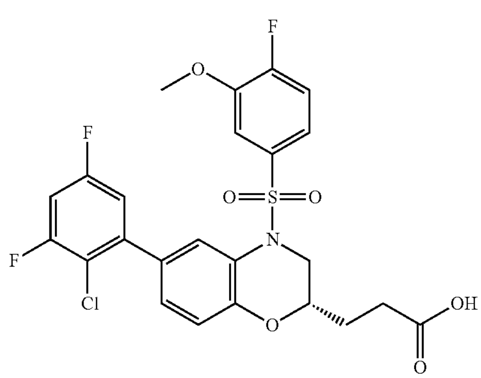 [SMILES: COc1cc(S(=O)(=O)N2C[C@H](CCC(=O)O)Oc3ccc(-c4cc(F)cc(F)c4Cl)cc32)ccc1F] | (S)-3-(6-(2-chloro-3,5-difluorophenyl)-4-((4-fluoro-3-methoxyphenyl)sulfonyl)-3,4-dihydro-2H-benzo[b][1,4]oxazin-2-yl)propanoic acid | 542 (M + H)+ |

TABLE 4-continued

| Compd. No. | Structure | Name | Observed m/z |
|---|---|---|---|
| 6L | 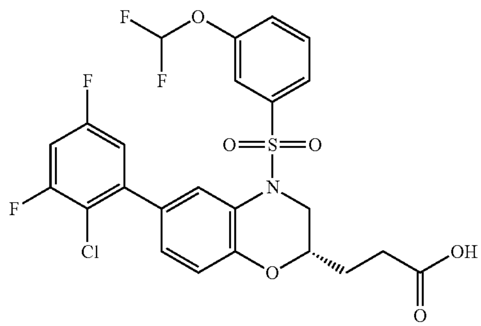 [SMILES: O=C(O)CC[C@H]1CN(S(=O)(=O)c2cccc(OC(F)F)c2)c2cc(-c3cc(F)cc(F)c3Cl)ccc2O1] | (S)-3-(6-(2-chloro-3,5-difluorophenyl)-4-((3-(difluoromethoxy)phenyl)sulfonyl)-3,4-dihydro-2H-benzo[b][1,4]oxazin-2-yl)propanoic acid | 560 (M − H)⁻ |

TABLE 4A

| Compd No. | Physical Characterization Data |
|---|---|
| 6A | ¹H NMR (300 MHz, CD₃OD-d₄) δ 7.97 (s, 2H), 7.55-7.31 (m, 5H), 6.96 (d, J = 8.4 Hz, 1H), 4.35 (dd, J = 14.4 Hz, J = 2.4 Hz, 1H), 4.15-4.07 (m, 2H), 4.40-3.99 (m, 2H), 3.94-3.93 (m, 1H), 3.29-3.23 (m, 1H), 2.57-2.53 (m, 2H), 1.98-1.89 (m, 2H), 1.38 (t, J = 7.2 Hz, 3H), 1.16 (t, J = 7.2 Hz, 3H). |
| 6B | ¹H NMR (300 MHz, CD₃OD-d₄) δ 8.02 (d, J = 2.4 Hz, 1H), 7.70-7.64 (m, 3H), 7.59-7.52 (m, 3H), 7.47-7.34 (m, 3H), 6.95 (d, J = 8.8 Hz, 1H), 4.42 (dd, J = 14.4 Hz, 2.4 Hz, 1H), 3.49-3.47 (m, 1H), 3.33-3.24 (m, 1H), 2.48-2.44 (m, 2H), 1.94-1.82 (m, 2H). |
| 6C | ¹H NMR (300 MHz, CD₃OD-d₄) δ 8.25 (s, 1H), 7.97 (s, 1H), 7.56 (s, 1H), 7.51 (m, 1H), 7.45-7.33 (m, 3H), 6.98 (d, J = 8.8 Hz, 1H), 4.40 (dd, J = 14.4 Hz, J = 2.4 Hz, 1H), 4.19-4.14 (m, 2H), 3.85 (m, 1H), 3.27 (m, 1H), 2.55 (t, J = 7.2 Hz, 2H), 2.03-1.86 (m, 2H), 1.43 (t, J = 7.2 Hz, 3H). |
| 6D | ¹H NMR (300 MHz, CD₃OD-d₄) δ 8.74 (s, 1H), 8.62 (s, 1H), 7.75 (s, 1H), 7.50 (s, 1H), 7.41-7.32 (m, 4H), 7.01 (d, J = 8.8 Hz, 1H), 4.47-4.42 (m, 2H), 4.29 (d, J = 14.0 Hz, 1H), 3.95 (m, 1H), 3.46 (m, 1H), 2.58-2.46 (m, 2H), 2.02-1.90 (m, 2H), 1.15 (t, J = 7.2 Hz, 3H). |
| 6E | ¹H NMR (300 MHz, CD₃OD-d₄) δ 8.05 (s, 1H), 7.62-7.53 (m, 4H), 7.50-7.34 (m, 5H), 6.94 (d, J = 8.8 Hz, 1H), 6.86 (t, J = 7.8 Hz, 1H), 4.41 (d, J = 14.4 Hz, 1H), 3.41-3.38 (m, 1H), 3.20 (m, 1H), 2.50-2.38 (m, 2H), 1.95-1.76 (m, 2H). |
| 6F | ¹H NMR (300 MHz, CD₃OD-d₄) δ 8.07 (s, 1H), 7.60-7.34 (m, 9H), 6.91 (d, J = 8.8 Hz, 1H), 4.38 (dd, J = 14.4 Hz, 2.4 Hz, 1H), 3.34-3.18 (m, 2H), 2.91 (t, J = 7.2 Hz, 1H), 2.45-2.35 (m, 2H), 1.87-1.78 (m, 2H), 1.15-1.10 (m, 6H). |
| 6G | ¹H NMR (300 MHz, CD₃OD-d₄) δ 8.75 (s, 1H), 8.65 (s, 1H), 7.62 (d, J = 2.0 Hz, 1H), 7.48 (s, 1H), 7.39-7.38 (m, 2H), 7.33-7.30 (m, 2H), 7.01 (d, J = 8.4 Hz, 1H), 4.60 (m, 1H), 4.49 (m, 1H), 4.42 (dd, J = 14.4 Hz, 2.4 Hz, 1H), 4.07 (m, 1H), 3.75-3.72 (m, 2H), 3.60 (dd, J = 14.4 Hz, 2.4 Hz, 1H), 2.56 (t, J = 7.2 Hz, 2H), 2.06-1.92 (m, 2H). |
| 6H | ¹H NMR (300 MHz, CD₃OD-d₄) δ 8.05 (s, 1H), 7.60-7.35 (m, 8H), 7.21 (s, 1H), 6.93 (d, J = 8.4 Hz, 1H), 4.38 (dd, J = 14.4 Hz, 2.4 Hz, 1H), 3.22 (m, 1H), 3.20 (dd, J = 14.4 Hz, 2.4 Hz, 1H), 2.45-2.39 (m, 2H), 1.96-1.79 (m, 3H), 0.99-0.96 (m, 2H), 0.62-0.59 (m, 1H), 0.46-0.42 (m, 1H). |
| 6I | ¹H NMR (300 MHz, CD₃OD-d₄) δ 8.27 (d, J = 8.1 Hz, 1H), 7.99 (d, J = 7.9 Hz, 1H), 7.60 (t, J = 8.0 Hz, 1H), 7.47 (m, 1H), 7.29 (m, 1H), 7.20-6.98 (m, 4H), 4.25 (dd, J = 14.3, 2.4 Hz, 1H), 3.8 (m, 1H), 3.38 (m, 1H), 2.61 (d, J = 1.8 Hz, 3H), 2.49 (t, J = 7.2 Hz, 2H), 2.02-1.83 (m, 2H). |
| 6J | ¹H NMR (300 MHz, CD₃OD-d₄) δ 8.02 (s, 1H), 7.86-7.79 (m, 3H), 7.32 (m, 1H), 7.24 (m, 1H), 7.13 (m, 1H), 6.97 (d, J = 8.4 Hz, 1H), 4.51 (dd, J = 14.4, 2.4 Hz, 1H), 3.62 (m, 1H), 3.35 (m, 1H), 2.51-2.47 (m, 2H), 1.98-1.86 (m, 1H), 1.82 (m, 1H). |
| 6K | ¹H NMR (300 MHz, CD₃OD-d₄) δ 7.96 (d, J = 2.1 Hz, 1H), 7.39-7.11 (m, 5H), 7.07 (m, 1H), 6.97 (d, J = 8.5 Hz, 1H), 4.41 (dd, J = 14.5, 2.3 Hz, 1H), 3.72 (s, 3H), 3.36 (m, 1H), 3.23 (m, 1H), 2.45 (t, J = 7.0 Hz, 2H), 2.03-1.62 (m, 2H). |
| 6L | ¹H NMR (300 MHz, CD₃OD-d₄) δ 7.90 (m, 1H), 7.63-7.51 (m, 2H), 7.47-7.39 (m, 2H), 7.25-7.11 (m, 2H), 7.10-6.64 (m, 3H), 4.40 (dd, J = 14.6, 2.3 Hz, 1H), 3.41 (tdt, J = 7.2, 4.2, 2.3 Hz, 1H), 3.23 (ddd, J = 14.7, 9.9, 1.9 Hz, 1H), 2.43 (td, J = 7.1, 3.2 Hz, 2H), 1.96-1.70 (m, 2H). |

Example 7—Synthesis of (S)-3-(7-cloro-6-(3-chlorophenyl-4-((3-(trifluoromethyl)phenyl)sulfonyl)-3,4-dihydro-2H-benzo[b][1,4]oxazin-2-yl)propanoic acid

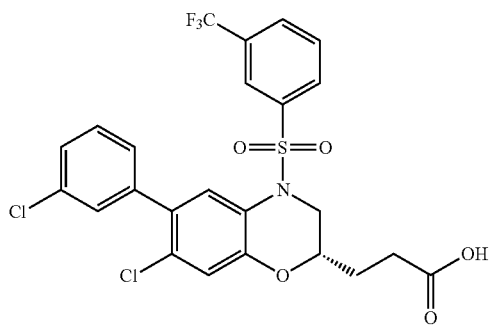 [SMILES: O=C(O)CC[C@H]1CN(S(=O)(=O)c2cccc(C(F)(F)F)c2)c2cc(-c3cccc(Cl)c3)c(Cl)cc2O1]

Part I—Synthesis of 4-Bromo-5-chloro-2-nitrophenol

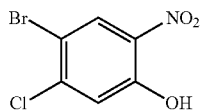

A solution of 65% nitric acid (3.6 mL, 52 mmol) in acetic acid (9.8 mL) was added dropwise to a stirred solution of 4-bromo-3-chlorophenol (10.13 g, 48.83 mmol) in acetic acid (16.3 mL) and the mixture was stirred for one hour at room temperature. Next, ice water was added to the reaction mixture, and the resulting mixture was extracted three times with dichloromethane. The combined organic layers were concentrated, and the resulting residue was purified by MPLC eluting with a gradient of 10-33% ethyl acetate in petroleum ether to afford 4-bromo-5-chloro-2-nitrophenol (10.58 g, 86%) as a red solid.

Part II—Synthesis of (S)-Dimethyl 2-(4-bromo-5-chloro-2-nitrophenoxy)pentanedioate

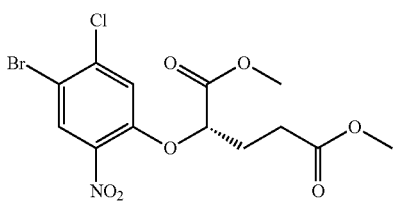 [SMILES: COC(=O)CC[C@H](Oc1cc(Cl)c(Br)cc1[N+](=O)[O-])C(=O)OC]

To a stirred solution of 1,5-dimethyl (2R)-2-hydroxypentanedioate (5.80 g, 32.9 mmol), 4-bromo-5-chloro-2-nitrophenol (9.97 g, 39.5 mmol), dichloromethane (160 mL), and triphenyl phosphine (12.9 g, 49.2 mmol) at 0° C. was added dropwise diisopropyl azodicarboxylate (7.4 mL, 39 mmol). The mixture was stirred overnight at room temperature and then diluted with saturated sodium bicarbonate (500 mL). The mixture was extracted three times with dichloromethane. The organic layers were combined and concentrated. The resulting residue was purified by MPLC eluting with a gradient of 10-66% ethyl acetate in petroleum ether to afford (S)-dimethyl 2-(4-bromo-5-chloro-2-nitrophenoxy)pentanedioate (20.06 g) as a yellow solid.

Part III—Synthesis of (S)-Methyl 3-(6-bromo-7-chloro-3-oxo-3,4-dihydro-2H-benzo[b][1,4]oxazin-2-yl)propanoate

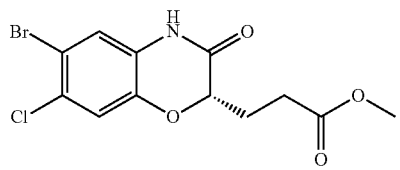 [SMILES: COC(=O)CC[C@@H]1Oc2cc(Cl)c(Br)cc2NC1=O]

A mixture of (S)-dimethyl 2-(4-bromo-5-chloro-2-nitrophenoxy)pentanedioate (13.5 g, 32.9 mmol), acetic acid (100 mL), and iron powder (15.0 g, 0.27 mol) was stirred for one hour at 100° C. The mixture was filtered, and the filtrate was concentrated. The resulting residue was diluted with saturated sodium bicarbonate, and extracted three times with dichloromethane. The combined organic layers were concentrated and the resulting residue was purified by MPLC eluting with a gradient of 20-50% ethyl acetate in petroleum ether to afford (S)-methyl 3-(6-bromo-7-chloro-3-oxo-3,4-dihydro-2H-benzo[b][1,4]oxazin-2-yl)propanoate (11.5 g) as a light brown solid.

Part IV—Synthesis of methyl (S)-3-(6-bromo-7-chloro-3,4-dihydro-2H-benzo[b][1,4]oxazin-2-yl)propanoate

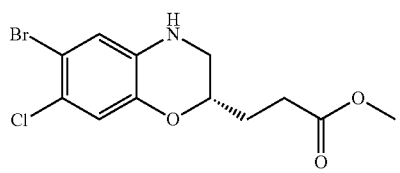 [SMILES: COC(=O)CC[C@H]1CNc2cc(Br)c(Cl)cc2O1]

A 10M solution of borane dimethyl sulfide in THF (4.3 mL, 43 mmol) was added dropwise to a solution of (S)-methyl 3-(6-bromo-7-chloro-3-oxo-3,4-dihydro-2H-benzo[b][1,4]oxazin-2-yl)propanoate (11.5 g, 33 mmol) in tetrahydrofuran (100 mL). The solution was stirred overnight at room temperature, and then quenched by the slow addition of methanol (100 mL). The resulting mixture was concentrated, diluted with saturated sodium bicarbonate, and extracted three times with ethyl acetate. The combined organic layers were concentrated, and the resulting residue was purified MPLC eluting with a gradient of 20-50% ethyl acetate in petroleum ether to afford (S)-methyl 3-(6-bromo-7-chloro-3,4-dihydro-2H-benzo[b][1,4]-oxazin-2-yl)propanoate (15.0 g) as a pink solid Part V—Synthesis of methyl (S)-3-(6-bromo-7-chloro-4-((3-(trifluoromethyl)phenyl)sulfonyl)-3,4-dihydro-2H-benzo[b][1,4]oxazin-2-yl)propanoate

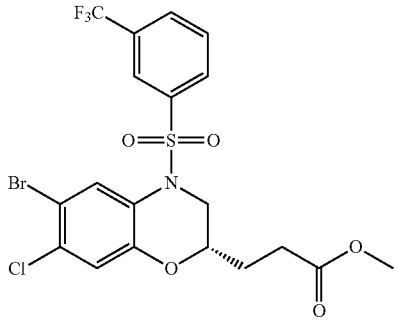 [SMILES: COC(=O)CC[C@H]1CN(S(=O)(=O)c2cccc(C(F)(F)F)c2)c2cc(Br)c(Cl)cc2O1]

A mixture of methyl (S)-3-(6-bromo-7-chloro-3,4-dihydro-2H-benzo[b][1,4]oxazin-2-yl)propanoate (1 g, 2.99 mmol), dichloromethane (15 mL), pyridine (1.2 g, 15.2 mmol), 3-(trifluoromethyl)benzene-1-sulfonyl chloride (880 mg, 3.60 mmol), and 4-dimethylaminopyridine (0.18 g) was stirred overnight at room temperature. Then, the mixture was diluted with dichloromethane, and was washed twice with 1M hydrogen chloride. The organic layer was dried (Na$_2$SO$_4$) and concentrated. The resulting residue was purified via MPLC eluting with 20% ethyl acetate in petroleum ether to afford methyl (S)-3-(6-bromo-7-chloro-4-((3-(trifluoromethyl)phenyl)sulfonyl)-3,4-dihydro-2H-benzo[b][1,4]oxazin-2-yl)propanoate (1.0 g, 62%) as a solid.

Part VI—Synthesis of methyl (S)-3-(7-chloro-6-(3-chlorophenyl)-4-((3-(trifluoromethyl)phenyl)sulfonyl)-3,4-dihydro-2H-benzo[b][1,4]oxazin-2-yl)propanoate

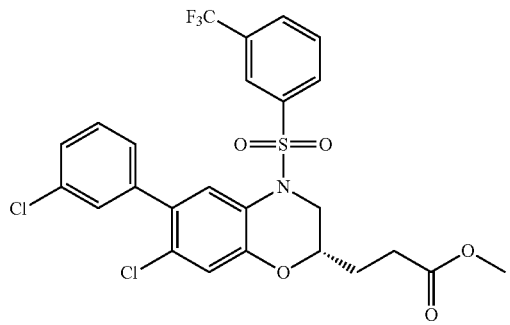 [SMILES: COC(=O)CC[C@H]1CN(S(=O)(=O)c2cccc(C(F)(F)F)c2)c2cc(-c3cccc(Cl)c3)c(Cl)cc2O1]

A mixture of methyl (S)-3-(6-bromo-7-chloro-4-((3-(trifluoromethyl)phenyl)sulfonyl)-3,4-dihydro-2H-benzo[b][1,4]oxazin-2-yl)propanoate (150 mg, 0.28 mmol), (3-chlorophenyl)boronic acid (65 mg, 0.42 mmol), sodium carbonate (88 mg, 0.83 mmol), tetrakis(triphenylphosphine)palladium (32 mg, 0.03 mmol), toluene (6 mL), methanol (2 mL), and water (2 mL) was stirred for three hours at 90° C. Then, the mixture was diluted with water and was extracted twice with ethyl acetate. The combined organic layers were dried (Na$_2$SO$_4$) and concentrated. The resulting residue was purified via MPLC eluting with 25% ethyl acetate in petroleum ether to afford methyl (S)-3-(7-chloro-6-(3-chlorophenyl)-4-((3-(trifluoromethyl)phenyl)sulfonyl)-3,4-dihydro-2H-benzo[b][1,4]oxazin-2-yl)propanoate (100 mg, 63%) as a colorless oil.

Part VII—Synthesis of (S)-3-(7-chloro-6-(3-chlorophenyl)-4-((3-(trifluoromethyl)phenyl)sulfonyl)-3,4-dihydro-2H-benzo[b][1,4]oxazin-2-yl)propanoic acid

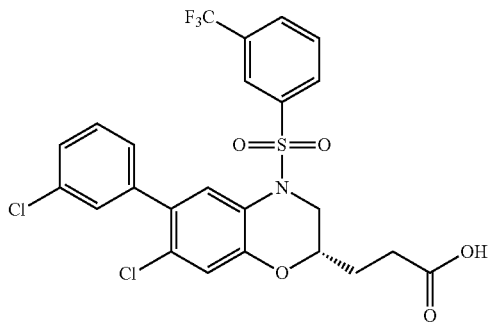 [SMILES: O=C(O)CC[C@H]1CN(S(=O)(=O)c2cccc(C(F)(F)F)c2)c2cc(-c3cccc(Cl)c3)c(Cl)cc2O1]

Based on the procedure in Example 1, Part VII, (S)-3-(7-chloro-6-(3-chlorophenyl)-4-((3-(trifluoromethyl)phenyl)sulfonyl)-3,4-dihydro-2H-benzo[b][1,4]oxazin-2-yl)propanoic acid was prepared. $^1$H-NMR (400 MHz, CD$_3$OD) δ 8.01 (dd, J=7.5, 1.7 Hz, 2H), 7.93 (s, 1H), 7.74-7.87 (m, 2H), 7.37-7.48 (m, 3H), 7.32 (m, 1H), 7.02 (s, 1H), 4.44 (dd, J=14.5, 2.3 Hz, 1H), 3.56-3.42 (m, 1H), 3.26 (m, 1H), 2.34-2.53 (m, 2H), 1.71-1.98 (m, 2H). (ES, m/z): (M+H)$^+$ 560.

Example 8—Synthesis of (S)-3-(6-(3-chlorophenyl)-8-fluoro-4-((3-(trifluoromethyl)phenyl)sulfonyl)-3,4-dihydro-2H-benzo[b][1,4]oxazin-2-yl)propanoic acid

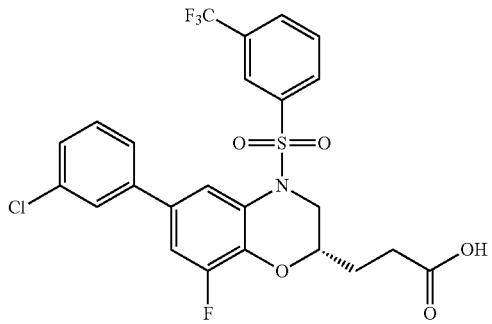 [SMILES: O=C(O)CC[C@H]1CN(S(=O)(=O)c2cccc(C(F)(F)F)c2)c2cc(-c3cccc(Cl)c3)cc(F)c2O1]

Based on the procedure in Example 7, utilizing 4-bromo-2-fluoro-6-nitrophenol as the phenol starting material, (S)-3-(6-(3-chlorophenyl)-8-fluoro-4-((3-(trifluoromethyl)phenyl)sulfonyl)-3,4-dihydro-2H-benzo[b][1,4]oxazin-2-yl)propanoic acid was prepared. $^1$H-NMR (400 MHz, CD$_3$OD) δ 8.02 (m, 3H), 7.85-7.80 (m, 2H), 7.58 (s, 1H), 7.52 (d, J=8.0 Hz, 1H), 7.45 (d, J=24.0 Hz, 1H), 7.39 (d, J=8.0 Hz, 1H), 7.29 (d, J=12.0 Hz, 1H), 4.51 (dd, J=14.6, 2.3 Hz, 1H), 3.56 (m, 1H), 3.35 (m, 1H), 2.48 (td, J=7.2, 5.4 Hz, 2H), 1.96 (m, 1H), 1.85 (m, 1H). (ES, m/z): (M+H)$^+$ 544.

Example 9—Synthesis of (S)-1-(3-(6-(3-chlorophenyl)-8-fluoro-4-((3-(trifluoromethyl)phenyl)sulfonyl)-3,4-dihydro-2H-benzo[b][1,4]oxazin-2-yl)propanoyl)piperidine-4-carboxylic acid

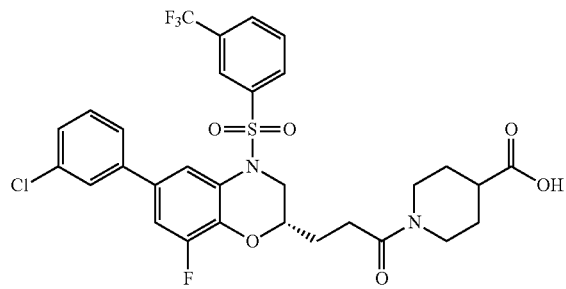 [SMILES: O=C(O)C1CCN(C(=O)CC[C@H]2CN(S(=O)(=O)c3cccc(C(F)(F)F)c3)c3cc(-c4cccc(Cl)c4)cc(F)c3O2)CC1]

Part I—Synthesis of methyl (S)-1-(3-(6-(3-chlorophenyl)-8-fluoro-4-((3-(trifluoromethyl)-phenyl)sulfonyl)-3,4-dihydro-2H-benzo[b][1,4]oxazin-2-yl)propanoyl)piperidine-4-carboxylate

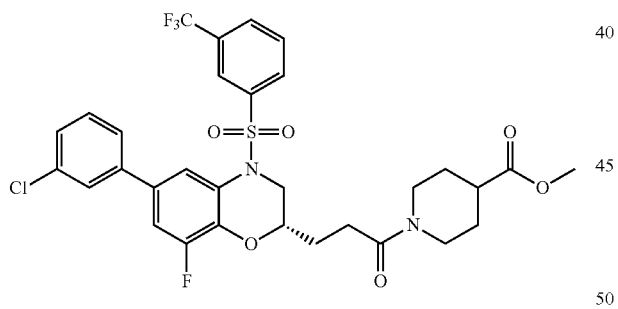

A mixture of (S)-3-(6-(3-chlorophenyl)-8-fluoro-4-((3-(trifluoromethyl)phenyl)sulfonyl)-3,4-dihydro-2H-benzo[b][1,4]oxazin-2-yl)propanoic acid (200 mg, 0.37 mmol), DMF (3 mL), methyl piperidine-4-carboxylate (79 mg, 0.55 mmol), N,N-diisopropylethyl amine (71.2 mg, 0.55 mmol), and HATU (210 mg, 0.55 mmol) was stirred for two hours at room temperature. The resulting mixture was concentrated, and the residue was purified by MPLC eluting with 50% ethyl acetate in petroleum ether to afford methyl (S)-1-(3-(6-(3-chlorophenyl)-8-fluoro-4-((3-(trifluoromethyl)-phenyl)sulfonyl)-3,4-dihydro-2H-benzo[b][1,4]oxazin-2-yl)propanoyl)piperidine-4-carboxylate (200 mg, 81%) as an oil.

Part II—Synthesis of (S)-1-(3-(6-(3-chlorophenyl)-8fluoro-4-((3-(trifluoromethyl)phenyl)sulfonyl)-3,4-dihydro-2H-benzo[b][1,4]oxazin-2-yl)propanoyl)piperidine-4-carboxylicacid

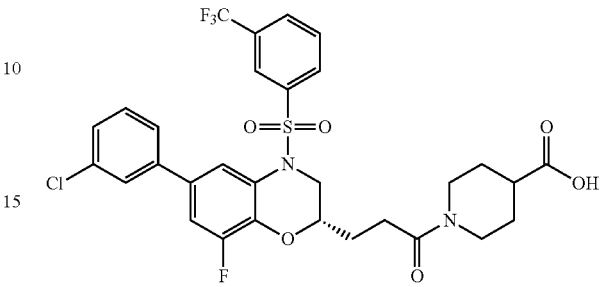

Based on the procedure in Example 1, Part VII, (S)-1-(3-(6-(3-chlorophenyl)-8-fluoro-4-((3-(trifluoromethyl)phenyl)sulfonyl)-3,4-dihydro-2H-benzo[b][1,4]oxazin-2-yl)propanoyl)piperidine-4-carboxylic acid was prepared. $^{1}$H-NMR (400 MHz, CD$_3$OD) δ 8.04 (m, 3H), 7.84-7.80 (m, 2H), 7.58 (s, 1H), 7.53-7.40 (m, 3H), 7.33 (m, 1H), 4.53 (dd, J=14.6, 2.4 Hz, 1H), 4.36 (dd, J=13.1, 5.3 Hz, 1H), 3.93 (dd, J=13.9, 4.9 Hz, 1H), 3.59 (d, J=9.8 Hz, 1H), 3.39 (m, 1H), 3.19 (m, 1H), 2.90 (m, 1H), 2.60 (qd, J=11.4, 10.2, 4.5 Hz, 3H), 2.08-1.79 (m, 4H), 1.72-1.48 (m, 2H). (ES, m/z): (M+Na)$^+$ 655.

Example 10—Synthesis of (S)-4-(6-(2,5-difluorophenyl)-4-((3-(trifluoromethyl)phenyl)sulfonyl)-3,4-dihydro-2H-benzo[b][1,4]oxazin-2-yl)-2-methylbutan-2-ol

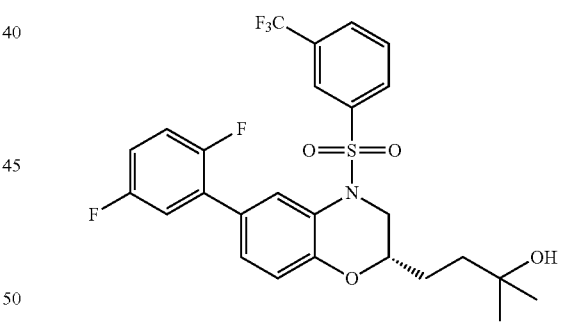

A 1M solution of methyl magnesium bromide (1.8 mL, 1.8 mmol) in THF was added dropwise to a stirred solution of methyl (S)-3-(6-(2,5-difluorophenyl)-4-((3-(trifluoromethyl)phenyl)sulfonyl)-3,4-dihydro-2H-benzo[b][1,4]oxazin-2-yl)propanoate (100 mg, 0.18 mmol) in tetrahydrofuran (10 mL) at 0° C. The mixture was stirred overnight at room temperature and then concentrated. The resulting residue was purified by Prep-HPLC eluting with a gradient of 53-83% acetonitrile in water with 0.05% trifluoroacetic acid to afford (S)-4-(6-(2,5-difluorophenyl)-4-((3-(trifluoromethyl)phenyl)sulfonyl)-3,4-dihydro-2H-benzo[b][1,4]oxazin-2-yl)-2-methylbutan-2-ol (27.1 mg, 27%) as a white solid. $^{1}$H-NMR (400 MHz, CD$_3$OD) δ 8.03-7.92 (m, 4H), 7.76 (t, J=8.0 Hz, 1H), 7.31-7.14 (m, 3H), 7.08 (ddt, J=9.0, 7.1, 3.4 Hz, 1H), 6.90 (d, J=8.5 Hz, 1H), 4.43 (dd, J=13.9, 1.9 Hz, 1H), 3.34 (ddd, J=9.9, 5.6, 2.1 Hz, 1H), 3.28-3.18 (m, 1H), 1.69-1.52 (m, 3H), 1.42 (m, 1H), 1.18 (s, 6H). (ES, m/z): (M+H)⁺ 542.

Example 11—Synthesis of (S)-5-(2-(6-(2,5-difluorophenyl)-4-((3-(trifluoromethyl)phenyl)sulfonyl)-3,4-dihydro-2H-benzo[b][1,4]oxazin-2-yl)ethyl)-1,3,4-oxadiazol-2(3H)-one

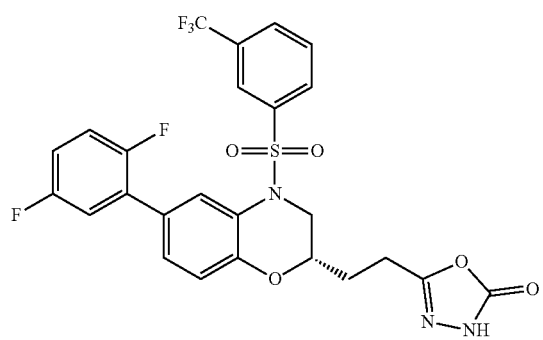 [SMILES: O=c1[nH]nc(CC[C@H]2CN(S(=O)(=O)c3cccc(C(F)(F)F)c3)c3cc(-c4cc(F)ccc4F)ccc3O2)o1]

Part I—Synthesis of (S)-3-(6-(2,5-difluorophenyl)-4-((3-(trifluoromethyl)phenyl)sulfonyl)-3,4-dihydro-2H-benzo[b][1,4]oxazin-2-yl)propanehydrazide

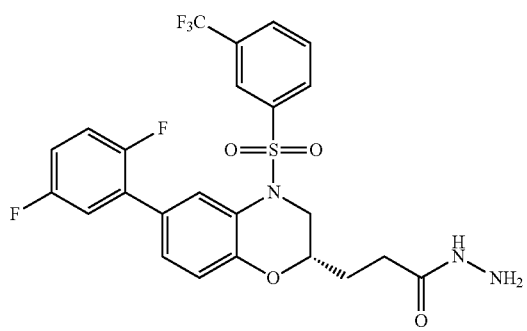 [SMILES: NNC(=O)CC[C@H]1CN(S(=O)(=O)c2cccc(C(F)(F)F)c2)c2cc(-c3cc(F)ccc3F)ccc2O1]

A mixture of methyl (S)-3-(6-(2,5-difluorophenyl)-4-((3-(trifluoromethyl)phenyl)sulfonyl)-3,4-dihydro-2H-benzo[b][1,4]oxazin-2-yl)propanoate (150 mg, 0.28 mmol), hydrazine hydrate (280 mg), and methanol (10 mL) was stirred overnight at 50° C. Then, the mixture was concentrated and the residue was purified via MPLC eluting with 25% ethyl acetate in petroleum ether to afford (S)-3-(6-(2,5-difluorophenyl)-4-((3-(trifluoromethyl)phenyl)sulfonyl)-3,4-dihydro-2H-benzo[b][1,4]oxazin-2-yl)propanehydrazide (130 mg, 87%) as an oil.

Part II—Synthesis of (S)-5-(2-(6-(2,5-difluorophenyl)-4-((3-(trifluoromethyl)phenyl)sulfonyl)-3,4-dihydro-2H-benzo[b][1,4]oxazin-2-yl)ethyl)-1,3,4-oxadiazol-2(3H)-one

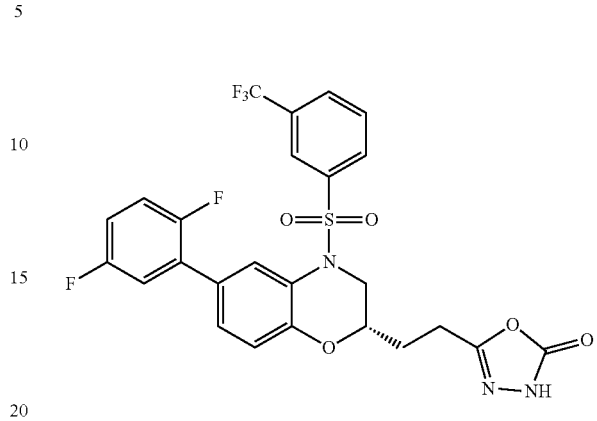

To a solution of (S)-3-(6-(2,5-difluorophenyl)-4-((3-(trifluoromethyl)phenyl)sulfonyl)-3,4-dihydro-2H-benzo[b][1,4]oxazin-2-yl)propanehydrazide (130 mg, 0.24 mmol), tetrahydrofuran (10 mL) and N,N-diisopropylethylamine (6 mg, 0.05 mmol) was added a solution of triphosgene (35 mg) in tetrahydrofuran (1 mL) dropwise at 0° C. The mixture was stirred for two hours at room temperature and then concentrated. The resulting residue was purified by Prep-HPLC eluting with a gradient of 49-79% acetonitrile in water with 0.05% trifluoroacetic acid to afford (S)-5-(2-(6-(2,5-difluorophenyl)-4-((3-(trifluoromethyl)phenyl)sulfonyl)-3,4-dihydro-2H-benzo[b][1,4]oxazin-2-yl)ethyl)-1,3,4-oxadiazol-2(3H)-one (19.8 mg, 15%) as a solid. ¹H-NMR (400 MHz, CD₃OD) δ 8.06-7.98 (m, 2H), 7.97 (d, J=8.1 Hz, 1H), 7.91 (s, 1H), 7.78 (t, J=7.9 Hz, 1H), 7.29 (m, 1H), 7.25-7.16 (m, 2H), 7.11 (td, J=8.7, 4.2 Hz, 1H), 6.92 (d, J=8.5 Hz, 1H), 4.47 (dd, J=14.4, 2.4 Hz, 1H), 3.51 (s, 1H), 3.35 (m, 1H), 2.73 (t, J=7.2 Hz, 2H), 2.02 (m, 1H), 1.90 (m, 1H). (ES, m/z): (M+H)⁺ 568.

Example 12—Synthesis of tert-butyl (S)-(2-(6-(2,5-difluorophenyl)-4-((3-(trifluoromethyl)phenyl)sulfonyl)-3,4-dihydro-2H-benzo[b][1,4]oxazin-2-yl)ethyl)carbamate

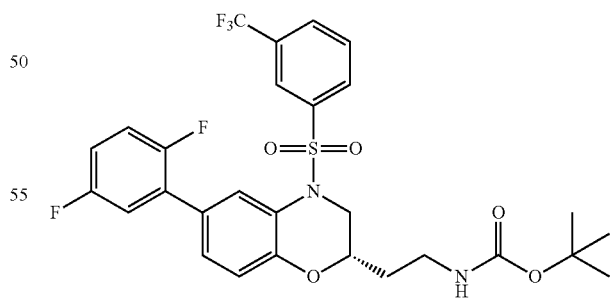

A mixture of (S)-3-(6-(2,5-difluorophenyl)-4-((3-(trifluoromethyl)-phenyl)sulfonyl)-3,4-dihydro-2H-benzo[b][1,4]oxazin-2-yl)propanoic acid (150 mg, 0.28 mmol), toluene (10 mL), tert-butanol (5 mL), triethylamine (43 mg, 0.42 mmol), and diphenylphosphoryl azide (102 mg, 0.37 mmol) was stirred for two hours at room temperature. Then, the mixture was warmed to 60° C. for one additional hour, then heated at 100° C. overnight. Next, the mixture was cooled, and then diluted with saturated sodium bicarbonate. The resulting mixture was extracted twice with ethyl acetate. The combined organic layers were dried (Na₂SO₄) and concentrated. The resulting residue was purified by MPLC eluting with 33% ethyl acetate in petroleum ether to afford tert-butyl (S)-(2-(6-(2,5-difluorophenyl)-4-((3-(trifluoromethyl)phenyl)sulfonyl)-3,4-dihydro-2H-benzo[b][1,4]oxazin-2-yl)ethyl)carbamate (54.9 mg, 32%) as a white solid. ¹H-NMR (400 MHz, CD₃OD) δ 8.06 (d, J=8.0 Hz, 1H), 8.04-7.97 (m, 3H), 7.80 (t, J=7.9 Hz, 1H), 7.33-7.16 (m, 3H), 7.12 (m, 1H), 6.94 (d, J=8.5 Hz, 1H), 4.46 (dd, J=14.2, 2.5 Hz, 1H), 3.59 (m, 1H), 3.37 (m, 1H), 3.29-3.11 (m, 2H), 1.86-1.69 (m, 2H), 1.47 (s, 9H). (ES, m/z): (M+H)⁺ 599.

Example 13—Synthesis of (S—N-(2-(6-(2,5-difluorophenyl)-4-((3-(trifluoromethyl)phenyl)sulfonyl)-3,4-dihydro-2H-benzo[b][1,4]oxazin-2-yl)ethyl)acetamide

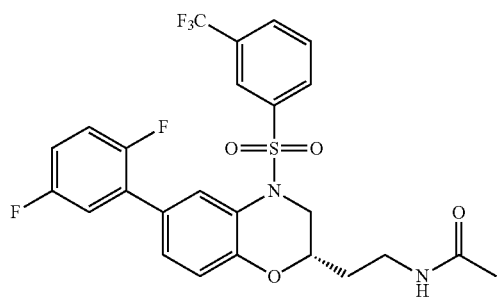 [SMILES: CC(=O)NCC[C@H]1CN(S(=O)(=O)c2cccc(C(F)(F)F)c2)c2cc(-c3cc(F)ccc3F)ccc2O1]

A mixture of (S)-2-(6-(2,5-difluorophenyl)-4-((3-(trifluoromethyl)phenyl)sulfonyl)-3,4-dihydro-2H-benzo[b][1,4]oxazin-2-yl)ethan-1-amine (100 mg, 0.20 mmol), dichloromethane (5 mL), acetyl chloride (23 mg, 0.3 mmol), and triethyl amine (61 mg, 0.60 mmol) was stirred for 30 minutes at room temperature. Then, the mixture was partitioned between brine and dichloromethane. The organic layer was dried (Na₂SO₄) and concentrated. The resulting residue was purified by Prep-HPLC eluting with a gradient of 58-88% acetonitrile in water with 0.1% trifluoroacetic acid to afford (S)—N-(2-(6-(2,5-difluorophenyl)-4-((3-(trifluoromethyl)phenyl)sulfonyl)-3,4-dihydro-2H-benzo[b][1,4]oxazin-2-yl)ethyl)acetamide (80 mg, 74%) as a white solid. ¹H-NMR (400 MHz, CD₃OD) δ 8.10-7.97 (m, 4H), 7.80 (t, J=8.1 Hz, 1H), 7.36-7.19 (m, 3H), 7.10 (m, 1H), 6.96 (d, J=8.6 Hz, 1H), 4.47 (dd, J=14.4, 2.5 Hz, 1H), 3.59 (m, 1H), 3.40-3.34 (m, 2H), 3.27 (m, 1H), 1.95 (s, 3H), 1.86 (m, 1H), 1.75 (m, 1H). (ES, m/z): (M+H)⁺ 541.

Example 14—Synthesis of (S)-2-((6-(2,5-difluorophenyl)-4-((3-(trifluoromethyl)phenyl)sulfonyl)-3,4-dihydro-2H-benzo[b][1,4]oxazin-2-yl)methyl)isoindoline-1,3-dione

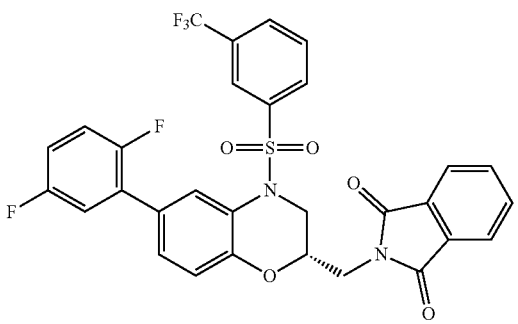 [SMILES: O=C1c2ccccc2C(=O)N1C[C@H]1CN(S(=O)(=O)c2cccc(C(F)(F)F)c2)c2cc(-c3cc(F)ccc3F)ccc2O1]

Part I—Synthesis of methyl (2S)-2-(4-bromo-2-nitro-phenoxy)-3-[tert-butyl(diphenyl)silyl]oxy-propanoate

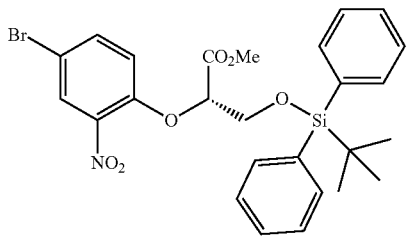 [SMILES: COC(=O)[C@H](CO[Si](c1ccccc1)(c1ccccc1)C(C)(C)C)Oc1ccc(Br)cc1[N+](=O)[O-]]

To a solution of (2R)-3-[tert-butyl(diphenyl)silyl]oxy-2-hydroxy-propanoate (28.6 g, 79.8 mmol) [see, for example, Goubert, Marlene et al. in *Tetrahedron*, 63 (34), 8255-8266; 2007], 4-bromo-2-nitrophenol (22.5 g, 103 mmol), and triphenylphosphine (27.1 g, 103 mmol) in THF (400 mL) at 0° C. was added diisopropyl azodicarboxylate (20.5 mL, 104 mmol). The reaction mixture was allowed to warm to room temperature, and stirred overnight. Then, the reaction mixture was concentrated, and the resulting residue was dissolved in methyl tert-butyl ether (400 mL). To this solution was slowly added hexanes (500 mL), and the solution became cloudy. Next, the solution was allowed to crystallize overnight and the mixture was filtered. The filtrate was concentrated and the resulting residue was purified by filtering through a pad of silica gel eluting with 25% ethyl acetate in hexanes to afford methyl (2S)-2-(4-bromo-2-nitrophenoxy)-3-[tert-butyl(diphenyl)silyl]oxy-propanoate (47.5 g, 91%).

Part II—Synthesis of (2S)-6-bromo-2-[[tert-butyl (diphenyl)silyl]oxymethyl]-4H-1,4-benzoxazin-3-one

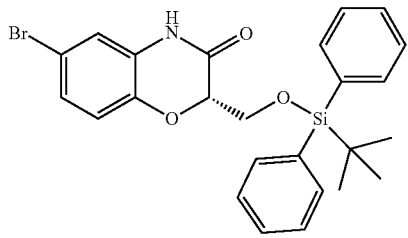 [SMILES: CC(C)(C)[Si](OC[C@@H]1Oc2ccc(Br)cc2NC1=O)(c1ccccc1)c1ccccc1]

Methyl (2S)-2-(4-bromo-2-nitro-phenoxy)-3-[tert-butyl (diphenyl)silyl]oxy-propanoate (44.6 g, 79.8 mmol) was dissolved in acetic acid (300 mL) and powdered iron (22.55 g, 404 mmol) was added. The mixture was heated to 70° C. overnight. Then, the mixture was filtered through a pad of Celite, and the material was rinsed with ethyl acetate. The combined filtrates were then partitioned between ethyl acetate and water, and the organic phase was washed a second time with water, then washed with brine, and concentrated to provide (2S)-6-bromo-2-[[tert-butyl(diphenyl) silyl]oxymethyl]-4H-1,4-benzoxazin-3-one.

Part III—Synthesis of [(2R)-6-bromo-3,4-dihydro-2H-1,4-benzoxazin-2-yl]methoxy-tert-butyl-diphenyl-silane

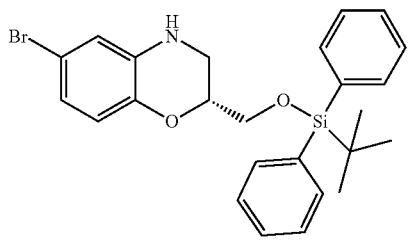 [SMILES: CC(C)(C)[Si](OC[C@H]1CNc2cc(Br)ccc2O1)(c1ccccc1)c1ccccc1]

A 10M solution of borane-methyl sulfide complex in THF (32 mL, 320 mmol) was added dropwise to a solution of (2S)-6-bromo-2-[[tert-butyl(diphenyl)silyl]oxymethyl]-4H-1,4-benzoxazin-3-one (39.62 g, 79.8 mmol) in THF (350 mL) at 0° C. The mixture was then stirred at 60° C. for 2.5 hours, and subsequently quenched by adding methanol (1 mL). The resulting mixture was refluxed for ten minutes. Then, the mixture was concentrated, and the resulting residue was purified by filtering through a plug of silica gel with 50% methyl tert-butyl ether and hexanes to afford [(2R)-6-bromo-3,4-dihydro-2H-1,4-benzoxazin-2-yl]methoxy-tert-butyl-diphenyl-silane (33.0 g, 73%) as an orange oil.

Part IV—Synthesis of (R)-(6-bromo-3,4-dihydro-2H-benzo[b][1,4]oxazin-2-yl)methanol

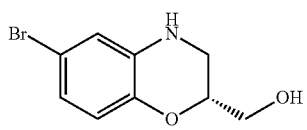 [SMILES: OC[C@H]1CNc2cc(Br)ccc2O1]

A solution of [(2R)-6-bromo-3,4-dihydro-2H-1,4-benzoxazin-2-yl]methoxy-tert-butyl-diphenyl-silane (12.9 g, 26.7 mmol), tetrabutylammonium fluoride (7.84 g, 30 mmol), methyl tert-butyl ether (200 mL) and THF (50 mL) was stirred at room temperature overnight. Next, saturated ammonium chloride was added, and the resulting mixture extracted twice with methyl tert-butyl ether. The combined organic layers were washed with water, brine, dried (Na$_2$SO$_4$), and concentrated. The resulting residue was purified via MPLC, eluting with a gradient of 0-100% ethyl acetate in hexanes to afford (R)-(6-bromo-3,4-dihydro-2H-benzo[b][1,4]oxazin-2-yl)methanol (3.99 g, 56%) as a solid.

Part V—Synthesis of (R)-2-((6-bromo-3,4-dihydro-2H-benzo[b][1,4]oxazin-2-yl)methyl)isoindoline-1,3-dione

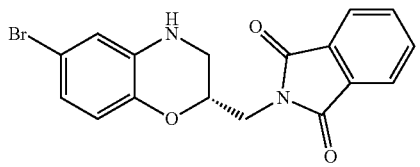 [SMILES: O=C1c2ccccc2C(=O)N1C[C@H]1CNc2cc(Br)ccc2O1]

Diisopropyl azodicarboxylate (4.11 g, 20.3 mmol) was added to a stirred solution of (R)-(6-bromo-3,4-dihydro-2H-benzo[b][1,4]oxazin-2-yl)methanol (3.99 g, 16.4 mmol), phthalimide (3.00 g, 20.4 mmol), triphenylphosphine (200 mL), and THF (50 mL) at 0° C. The mixture was stirred at room temperature for two hours. Then, the mixture was concentrated and the resulting residue was purified via MPLC, eluting with a gradient of adding 0-20% methyl tert-butyl ether to a 1:1 mixture of hexanes and dichloromethane to afford (R)-2-((6-bromo-3,4-dihydro-2H-benzo [b][1,4]oxazin-2-yl)methyl)isoindoline-1,3-dione (5.08 g, 83%) as a solid.

Part VI—Synthesis of (S)-2-((6-bromo-4-((3-(trifluoromethyl)phenyl)sulfonyl)-3,4-dihydro-2H-benzo [b][1,4]oxazin-2-yl)methyl)isoindoline-1,3-dione

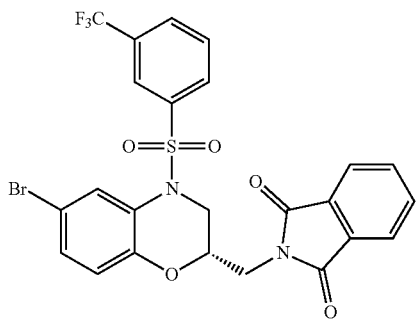 [SMILES: O=C1c2ccccc2C(=O)N1C[C@H]1CN(S(=O)(=O)c2cccc(C(F)(F)F)c2)c2cc(Br)ccc2O1]

A mixture of (R)-2-((6-bromo-3,4-dihydro-2H-benzo[b] [1,4]oxazin-2-yl)methyl)isoindoline-1,3-dione (1.29 g, 3.46 mmol), 3-(trifluoromethyl)benzenesulfonyl chloride (1.01 g, 4.15 mmol), in pyridine (10 mL) was heated at 60° C. Then, the mixture was concentrated and resulting material purified by MPLC eluting with a 0-100% gradient of ethyl acetate in hexanes to afford (S)-2-((6-bromo-4-((3-(trifluoromethyl)

phenyl)sulfonyl)-3,4-dihydro-2H-benzo[b][1,4]oxazin-2-yl)
methyl)isoindoline-1,3-dione (2.0 g) as an oil.

Part VII—Synthesis of (S)-2-((6-(2,5-difluorophe-
nyl)-4-((3-(trifluoromethyl)phenyl)sulfonyl)-3,4-
dihydro-2H-benzo[b][1,4]oxazin-2-yl)methyl)isoin-
doline-1,3-dione

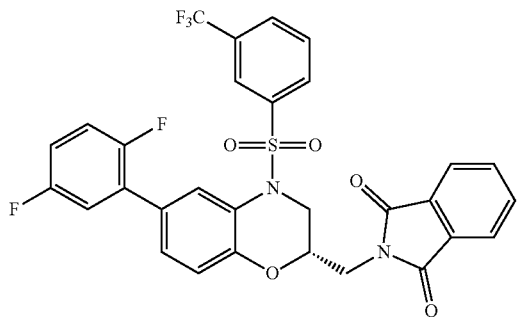 [SMILES: O=C1c2ccccc2C(=O)N1C[C@H]1CN(S(=O)(=O)c2cccc(C(F)(F)F)c2)c2cc(-c3cc(F)ccc3F)ccc2O1]

A mixture of (S)-2-((6-bromo-4-((3-(trifluoromethyl)phe-
nyl)sulfonyl)-3,4-dihydro-2H-benzo[b][1,4]oxazin-2-yl)
methyl)isoindoline-1,3-dione (2.0 g, 3.44 mmol), (2,5-dif-
luorophenyl)boronic acid (0.81 g, 5.16 mmol), potassium
carbonate (0.95 g, 6.88 mmol), dioxane (2 mL), water (0.5
mL) and [1,1'-bis(diphenylphosphino)ferrocene] dichlo-
ropalladium (II) complex with dichloromethane (0.26 g,
0.34 mmol) was heated at 80° C. overnight. Then, the
mixture was partitioned between ethyl acetate and brine. The
organic layer was dried ($Na_2SO_4$) and concentrated. The
resulting residue was purified via MPLC eluting with a
gradient of 0-50% ethyl acetate in hexanes to afford (S)-2-
((6-(2,5-difluorophenyl)-4-((3-(trifluoromethyl)phenyl)
sulfonyl)-3,4-dihydro-2H-benzo[b][1,4]oxazin-2-yl)
methyl)isoindoline-1,3-dione (1.43 g, 68%).

Example 15—Synthesis of ((S)-(6-(2,5-difluorophe-
nyl)-4-((3-(trifluoromethyl)phenyl)sulfonyl)-3,4-
dihydro-2H-benzo[b][1,4]oxazin-2-yl)methanamine

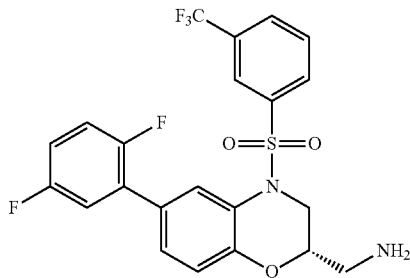 [SMILES: NC[C@H]1CN(S(=O)(=O)c2cccc(C(F)(F)F)c2)c2cc(-c3cc(F)ccc3F)ccc2O1]

A mixture of (S)-2-((6-(2,5-difluorophenyl)-4-((3-(trif-
luoromethyl)phenyl)sulfonyl)-3,4-dihydro-2H-benzo[b][1,
4]oxazin-2-yl)methyl)isoindoline-1,3-dione (1.43 g, 2.33
mmol), hydrazine (0.73 mL, 23.2 mmol), and ethanol (30
mL) was heated at 80° C. for three hours. Then, the mixture
was cooled and filtered. The filtrate was concentrated and
the residue was purified via MPLC eluting with a gradient of
0-5% methanol in dichloromethane to afford ((S)-(6-(2,5-
difluorophenyl)-4-((3-(trifluoromethyl)phenyl)sulfonyl)-3,
4-dihydro-2H-benzo[b][1,4]oxazin-2-yl)methanamine.

Example 16—Synthesis of (S)—N-((6-(2,5-difluo-
rophenyl)-4-((3-(trifluoromethyl)phenyl)sulfonyl)-3,
4-dihydro-2H-benzo[b][1,4]oxazin-2-yl)methyl)
morpholine-4-carboxamide

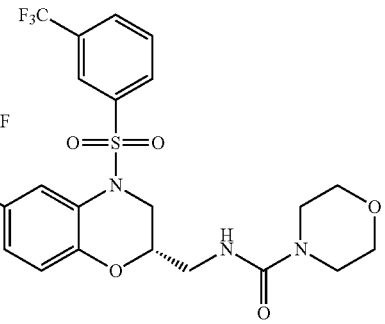

A mixture of ((S)-(6-(2,5-difluorophenyl)-4-((3-(trifluo-
romethyl)phenyl)sulfonyl)-3,4-dihydro-2H-benzo[b][1,4]
oxazin-2-yl)methanamine (50 mg, 0.10 mmol), N,N-diiso-
propylethylamine (30 mg, 0.21 mmol), and morpholine-4-
carbonyl chloride (20 mg, 0.12 mmol) in THF (0.5 mL) was
stirred at room temperature overnight. Then, the mixture
was concentrated and purified via Prep-HPLC eluting with
a gradient of acetonitrile in water with 0.05% trifluoroacetic
acid to afford (S)—N-((6-(2,5-difluorophenyl)-4-((3-(trif-
luoromethyl)phenyl)sulfonyl)-3,4-dihydro-2H-benzo[b][1,
4]oxazin-2-yl)methyl)morpholine-4-carboxamide (16 mg,
26%) as a white solid.

Example 17—Synthesis of (S)—N-((6-(2,5-difluo-
rophenyl)-4-((3-(trifluoromethyl)phenyl)sulfonyl)-3,
4-dihydro-2H-benzo[b][1,4]oxazin-2-yl)methyl)-2-
hydroxy-2-methylpropanamide

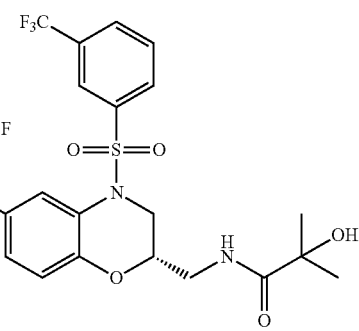

A mixture of ((S)-(6-(2,5-difluorophenyl)-4-((3-(trifluo-
romethyl)phenyl)sulfonyl)-3,4-dihydro-2H-benzo[b][1,4]
oxazin-2-yl)methanamine (100 mg, 0.21 mmol), N,N-diiso-
propylethylamine (80 mg, 0.62 mmol), 2-hydroxy-2-
methylpropanoic acid (30 mg, 0.31 mmol), and
benzotriazol-1-yl-oxytripyrrolidinophosphonium hexafluo-
rophosphate (160 mg, 0.31 mmol) in DMF (1.0 mL) was
stirred at room temperature for two hours. Then, the mixture
was concentrated and purified via Prep-HPLC eluting with
a gradient of acetonitrile in water with 0.05% trifluoroacetic
acid to afford (S)—N-((6-(2,5-difluorophenyl)-4-((3-(trif-
luoromethyl)phenyl)sulfonyl)-3,4-dihydro-2H-benzo[b][1, 4]oxazin-2-yl)methyl)-2-hydroxy-2-methylpropanamide (55 mg, 47%) as a white solid.

Example 18—Synthesis of 1-(((S)-6-(2,5-difluorophenyl)-4-((3-(trifluoromethyl)phenyl)sulfonyl)-3,4-dihydro-2H-benzo[b][1,4]oxazin-2-yl)methyl)-5-oxopyrrolidine-3-carboxylic acid

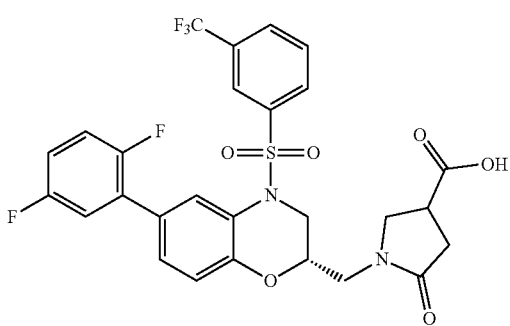 [SMILES: O=C(O)C1CC(=O)N(C[C@H]2CN(S(=O)(=O)c3cccc(C(F)(F)F)c3)c3cc(-c4cc(F)ccc4F)ccc3O2)C1]

A mixture of ((S)-(6-(2,5-difluorophenyl)-4-((3-(trifluoromethyl)phenyl)sulfonyl)-3,4-dihydro-2H-benzo[b][1,4]oxazin-2-yl)methanamine (100 mg, 0.21 mmol), dimethyl itaconate (33 mg, 0.21 mmol), and methanol (1 mL) was heated at 70° C. for two days. The mixture was cooled, and 2M sodium hydroxide (0.5 mL, 1.0 mmol) was added and the mixture was stirred an additional three hours. The mixture was concentrated and purified via Prep-HPLC eluting with a gradient of acetonitrile in water with 0.05% trifluoroacetic acid to afford 1-(((S)-6-(2,5-difluorophenyl)-4-((3-(trifluoromethyl)phenyl)sulfonyl)-3,4-dihydro-2H-benzo[b][1,4]oxazin-2-yl)methyl)-5-oxopyrrolidine-3-carboxylic acid (40 mg, 34%) as a white solid.

Example 19 and 20—Synthesis of (R)-3-((S)-6-(2,5-difluorophenyl)-4-((3-(trifluoromethyl)phenyl)sulfonyl)-3,4-dihydro-2H-benzo[b][1,4]oxazin-2-yl)-2-methylpropanoic acid and (S)-3-((S)-6-(2,5-difluorophenyl)-4-((3-(trifluoromethyl)phenyl)sulfonyl)-3,4-dihydro-2H-benzo[b][1,4]oxazin-2-yl)-2-methylpropanoic acid (19)

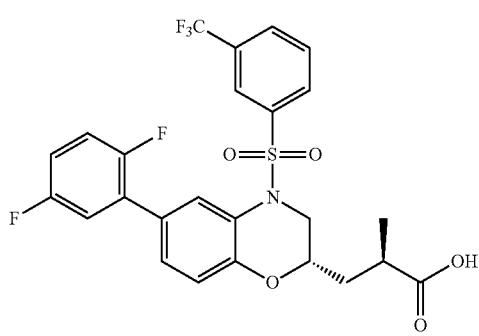

(20)

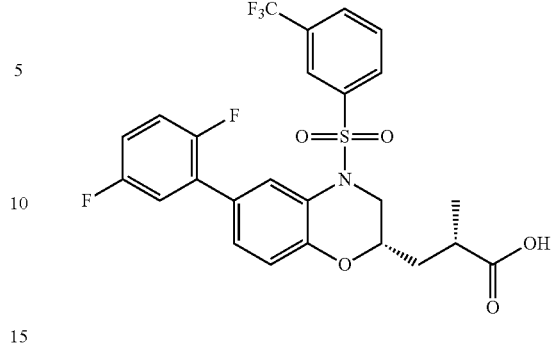

A 2M solution of sodium hexamethyldisilazide (0.56 mL, 1.12 mmol) in dioxane was added to a stirred solution of methyl (S)-3-(6-(2,5-difluorophenyl)-4-((3-(trifluoromethyl)phenyl)sulfonyl)-3,4-dihydro-2H-benzo[b][1,4]oxazin-2-yl)propanoate (150 mg, 0.28 mmol) in dioxane (5.0 mL) at −78° C. The mixture was stirred for one hour at −78° C., and then iodomethane (0.18 mL) was added dropwise to the reaction mixture. Next, the reaction mixture was stirred for 2.5 hours at −78° C. and then allowed to warm to −20° C. Then, a saturated ammonium chloride solution was added to the reaction mixture, and the resulting mixture was extracted three times with dichloromethane. The combined organic layers were dried (Na$_2$SO$_4$) and concentrated. The resulting residue was purified by MPLC eluting with a gradient of 0-25% ethyl acetate in petroleum ether to afford each of the diastereomers of the methyl esters of the title compounds. The two methyl esters were each separately hydrolyzed by the procedure within Example 1, Part VII to afford the title compounds. $^1$H-NMR (400 MHz, CD$_3$OD) δ 8.08-7.95 (m, 3H), 7.89 (s, 1H), 7.80 (t, J=15.6 Hz, 1H), 7.31 (d, J=12 Hz, 1H), 7.28-7.20 (m, 2H), 7.11 (m, 1H), 6.93 (d, J=8.8 Hz, 1H), 4.44 (d, J=17.2 Hz, 1H), 3.49-3.40 (m, 1H), 3.27 (m, 1H), 2.68 (m, 1H), 1.91 (m, 1H), 1.60 (m, 1H), 1.19 (d, J=7.2 Hz, 3H). (ES, m/z): (M+H)$^+$ 542 and $^1$H-NMR (400 MHz, CD$_3$OD) δ 8.05-7.95 (m, 4H), 7.81 (t, J=12 Hz, 1H), 7.34 (d, J=12 Hz, 1H), 7.27-7.23 (m, 2H), 7.13 (m, 1H), 6.93 (d, J=8.8 Hz, 1H), 4.48 (d, J=16.8 Hz, 1H), 3.50 (m, 1H), 3.31 (m, 1H), 2.64 (m, 1H), 1.97 (m, 1H), 1.65 (m, 1H), 1.10 (d, J=6.8 Hz, 3H). (ES, m/z): (M+H)$^+$ 542.

Example 21—Preparation of Additional Substituted 4-(aryl sulfonyl)-3,4-dihydro-2H-benzo[b][1,4]oxazin-2-yl) Compounds Compounds in Table 5 were prepared based on experimental procedures described in Examples 1, 3, and 24 and the detailed description utilizing (R)-6-oxotetrahydro-2H-pyran-2-carboxylic acid as the starting lactone. $^1$H NMR data for compounds from Table 5 is provided in Table 5A.

TABLE 5

| Compd No. | Structure | Name | Observed m/z |
|---|---|---|---|
| 21A | 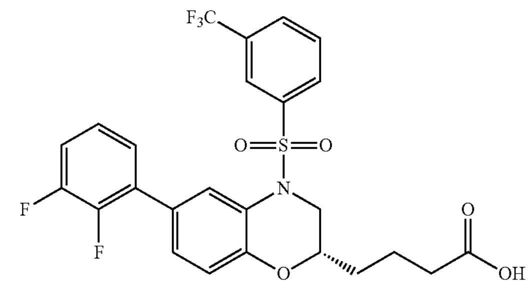 [SMILES: O=C(O)CCC[C@H]1CN(S(=O)(=O)c2cccc(C(F)(F)F)c2)c2cc(-c3cccc(F)c3F)ccc2O1] | (S)-4-(6-(2,3-difluorophenyl)-4-((3-(trifluoromethyl)phenyl)-sulfonyl)-3,4-dihydro-2H-benzo[b][1,4]oxazin-2-yl)butanoic acid | 542 (M + H)+ |
| 21B | 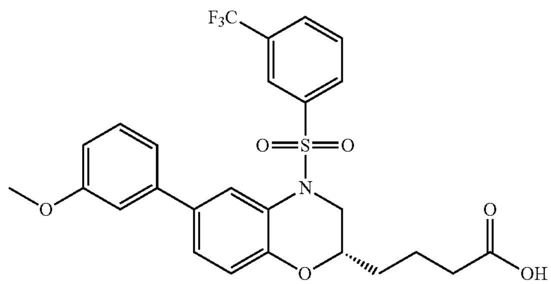 [SMILES: COc1cccc(-c2ccc3c(c2)N(S(=O)(=O)c2cccc(C(F)(F)F)c2)C[C@H](CCCC(=O)O)O3)c1] | (S)-4-(6-(3-methoxyphenyl)-4-((3-(trifluoromethyl)phenyl)sulfonyl)-3,4-dihydro-2H-benzo[b][1,4]-oxazin-2-yl)butanoic acid | 536 (M + H)+ |
| 21C | 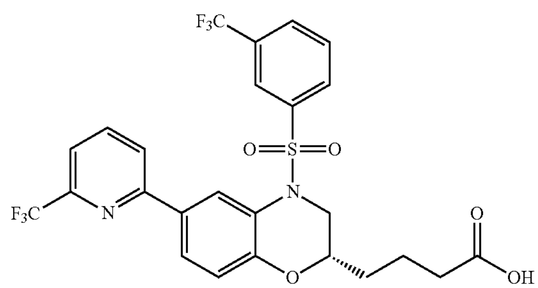 [SMILES: O=C(O)CCC[C@H]1CN(S(=O)(=O)c2cccc(C(F)(F)F)c2)c2cc(-c3cccc(C(F)(F)F)n3)ccc2O1] | (S)-4-(4-((3-(trifluoromethyl)-phenyl)sulfonyl)-6-(6-(trifluoromethyl)pyridin-2-yl)-3,4-dihydro-2H-benzo[b][1,4]oxazin-2-yl)butanoic acid | 575 (M + H)+ |
| 21D | 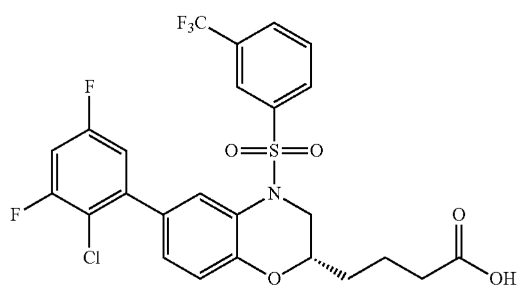 [SMILES: O=C(O)CCC[C@H]1CN(S(=O)(=O)c2cccc(C(F)(F)F)c2)c2cc(-c3cc(F)cc(F)c3Cl)ccc2O1] | (S)-4-(6-(2-chloro-3,5-difluorophenyl)-4-((3-(trifluoromethyl)phenyl)sulfonyl)-3,4-dihydro-2H-benzo[b][1,4]-oxazin-2-yl)butanoic acid | 598 (M + Na)+ |

TABLE 5A

| Compd No. | [1] Physical Characterization Data |
|---|---|
| 21A | $^1$H NMR (300 MHz, CD$_3$OD-d$_4$) δ 8.02-7.99 (m, 4H), 7.80 (t, J = 8.0 Hz, 1H), 7.33-7.22 (m, 4H), 6.95 (d, J = 8.8 Hz, 1H), 4.44 (dd, J = 14.4 Hz, 2.4 Hz, 1H), 3.50-3.40 (m, 1H), 3.33-3.24 (m, 1H), 2.33-2.29 (m, 2H), 1.80-1.65 (m, 4H). |
| 21B | $^1$H NMR (300 MHz, CD$_3$OD-d$_4$) δ 8.04-7.97 (m, 4H), 7.81-7.77 (m, 1H), 7.40-7.35 (m, 2H), 7.17-7.11 (m, 2H), 6.94 = 6.90 (m, 2H), 4.41 (dd, J = 14.4 Hz, 2.4 Hz, 1H), 3.88 (s, 3H), 3.36-3.25 (m, 2H), 2.30 (t, J = 7.2 Hz, 2H), 1.79-1.62 (m, 4H). |
| 21C | $^1$H NMR (300 MHz, CD$_3$OD-d$_4$) δ 8.59 (s, 1H), 8.10-8.05 (m, 4H), 8.01-7.99 (m, 1H), 7.89-7.86 (m, 1H), 7.80-7.76 (m, 1H), 7.73-7.68 (m, 1H), 6.98 (d, J = 8.4 Hz, 1H), 4.44 (dd, J = 14.4 Hz, 2.4 Hz, 1H), 3.54-3.52 (m, 1H), 3.38-3.33 (m, 1H), 2.34-2.31 (m, 2H), 1.85-1.63 (m, 4H). |

TABLE 5A-continued

| Compd No. | [1] Physical Characterization Data |
|---|---|
| 21D | $^1$H NMR (300 MHz, CD$_3$OD-d$_4$) δ 8.03-8.01 (m, 2H), 7.95-7.91 (m, 2H), 7.83-7.80 (m, 1H), 7.22-7.17 (m, 2H), 7.07-7.03 (m, 1H), 6.95 (d, J = 8.4 Hz, 1H), 4.44 (dd, J = 14.0 Hz, J = 2.0 Hz, 1H), 3.41-3.26 (m, 2H), 2.34-2.29 (m, 2H), 1.82-1.59 (m, 4H). |

Example 22—Preparation of Additional Substituted 4-(aryl sulfonyl)-3,4-dihydro-2H-benzo[b][1,4]oxazin-2-yl) Compounds Compounds in Tables 6 and 6A were prepared based on experimental procedures described in Examples 1, 3, 7,8, and 24 and the detailed description. $^1$H NMR data for exemplary compounds is provided in Table 6B.

TABLE 6

| Compd No. | Structure | Name | Observed m/z |
|---|---|---|---|
| 22A | 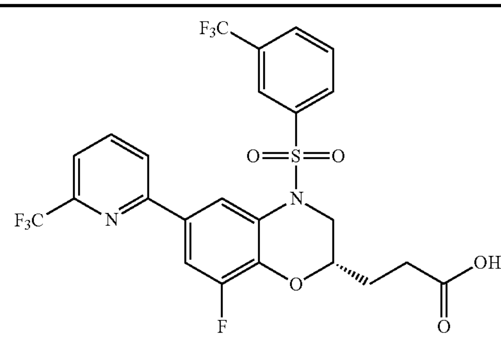 | (S)-3-(8-fluoro-4-((3-(trifluoromethyl)phenyl)-sulfonyl)-6-(6-(trifluoromethyl)pyridin-2-yl)-3,4-dihydro-2H-benzo[b][1,4]oxazin-2-yl)propanoic acid | 579 (M + H)$^+$ |
| 22B | 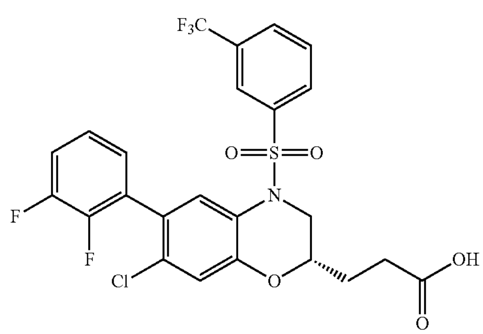 [SMILES: O=C(O)CC[C@H]1CN(S(=O)(=O)c2cccc(C(F)(F)F)c2)c2cc(-c3cccc(F)c3F)c(Cl)cc2O1] | (S)-3-(7-chloro-6-(2,3-difluorophenyl)-4-((3-(trifluoromethyl)phenyl)sulfonyl)-3,4-dihydro-2H-benzo[b][1,4]-oxazin-2-yl)propanoic acid | 562 (M + H)$^+$ |
| 22C | 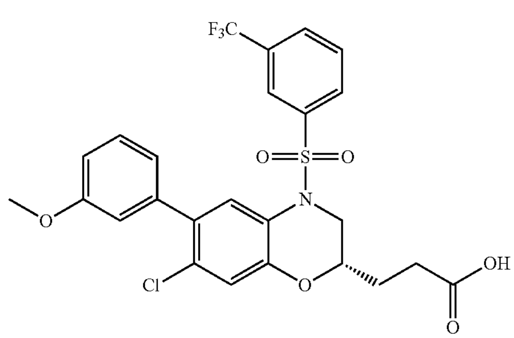 [SMILES: COc1cccc(-c2cc3c(cc2Cl)O[C@@H](CCC(=O)O)CN3S(=O)(=O)c2cccc(C(F)(F)F)c2)c1] | (S)-3-(7-chloro-6-(3-methoxyphenyl)-4-((3-(trifluoromethyl)phenyl)sulfonyl)-3,4-dihydro-2H-benzo[b][1,4]-oxazin-2-yl)propanoic acid | 556 (M + H)$^+$ |

TABLE 6-continued

| Compd No. | Structure | Name | Observed m/z |
|---|---|---|---|
| 22D | 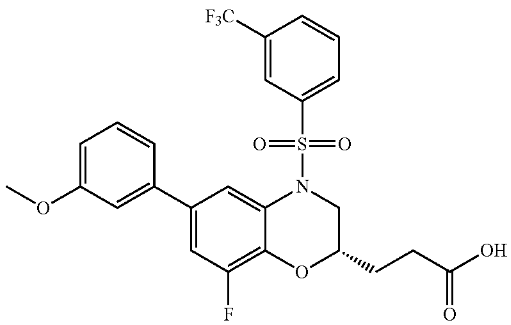 [SMILES: COc1cccc(-c2cc(F)c3c(c2)N(S(=O)(=O)c2cccc(C(F)(F)F)c2)C[C@H](CCC(=O)O)O3)c1] | (S)-3-(8-fluoro-6-(3-methoxyphenyl)-4-((3-(trifluoromethyl)phenyl)sulfonyl)-3,4-dihydro-2H-benzo[b][1,4]-oxazin-2-yl)propanoic acid | 540 (M + H)+ |
| 22E | 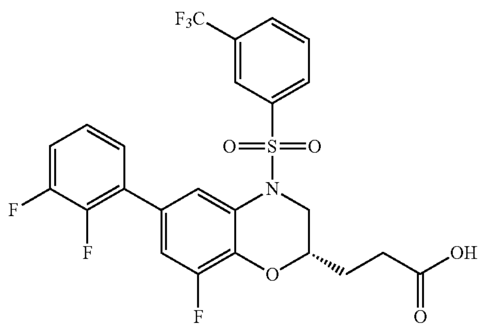 [SMILES: O=C(O)CC[C@H]1CN(S(=O)(=O)c2cccc(C(F)(F)F)c2)c2cc(-c3cccc(F)c3F)cc(F)c2O1] | (S)-3-(6-(2,3-difluorophenyl)-8-fluoro-4-((3-(trifluoromethyl)phenyl)sulfonyl)-3,4-dihydro-2H-benzo[b][1,4]-oxazin-2-yl)propanoic acid | 546 (M + H)+ |
| 22F | 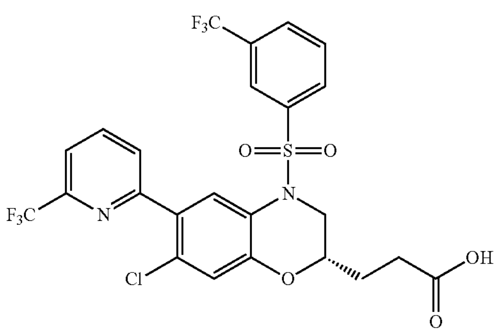 [SMILES: O=C(O)CC[C@H]1CN(S(=O)(=O)c2cccc(C(F)(F)F)c2)c2cc(-c3cccc(C(F)(F)F)n3)c(Cl)cc2O1] | (S)-3-(7-chloro-4-((3-(trifluoromethyl)phenyl)sulfonyl)-6-(6-(trifluoromethyl)pyridin-2-yl)-3,4-dihydro-2H-benzo[b][1,4]-oxazin-2-yl)propanoic acid | 595 (M + H)+ |
| 22G | 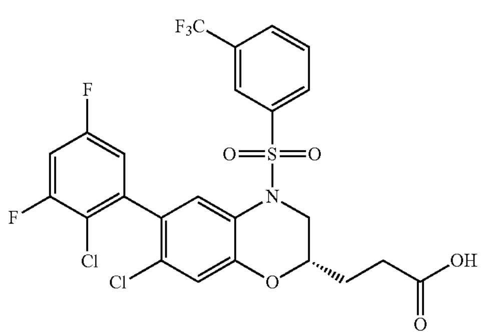 | (S)-3-(7-chloro-6-(2-chloro-3,5-difluorophenyl)-4-((3-(trifluoromethyl)phenyl)sulfonyl)-3,4-dihydro-2H-benzo[b][1,4]-oxazin-2-yl)propanoic acid | 596 (M + H)+ |

TABLE 6A

| Compd No. | Structure | Name | Observed m/z |
|---|---|---|---|
| 22H | 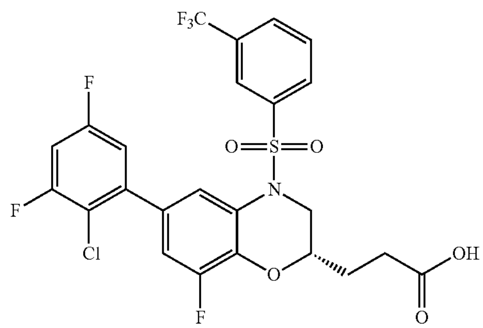 [SMILES: O=C(O)CC[C@H]1CN(S(=O)(=O)c2cccc(C(F)(F)F)c2)c2cc(-c3cc(F)cc(F)c3Cl)cc(F)c2O1] | (S)-3-(6-(2-chloro-3,5-difluorophenyl)-8-fluoro-4-((3-(trifluoromethyl)phenyl)sulfonyl)-3,4-dihydro-2H-benzo[b][1,4]oxazin-2-yl)propanoic acid | 580 (M + H)⁺ |
| 22I | 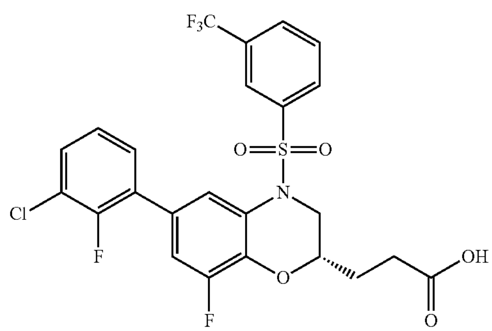 [SMILES: O=C(O)CC[C@H]1CN(S(=O)(=O)c2cccc(C(F)(F)F)c2)c2cc(-c3cccc(Cl)c3F)cc(F)c2O1] | (S)-3-(6-(3-chloro-2-fluorophenyl)-8-fluoro-4-((3-(trifluoromethyl)phenyl)sulfonyl)-3,4-dihydro-2H-benzo[b][1,4]-oxazin-2-yl)propanoic acid | 562 (M + H)⁺ |
| 22J | 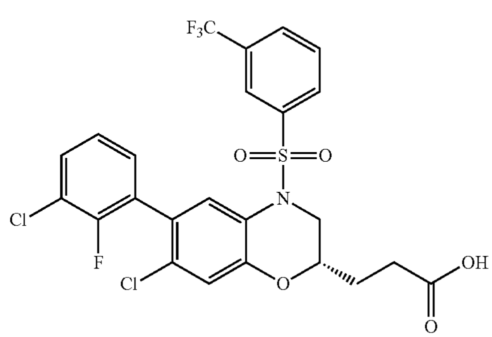 [SMILES: O=C(O)CC[C@H]1CN(S(=O)(=O)c2cccc(C(F)(F)F)c2)c2cc(-c3cccc(Cl)c3F)c(Cl)cc2O1] | (S)-3-(7-chloro-6-(3-chloro-2-fluorophenyl)-4-((3-(trifluoromethyl)phenyl)sulfonyl)-3,4-dihydro-2H-benzo[b][1,4]oxazin-2-yl)propanoic acid | 576 (M − H)⁻ |
| 22K | 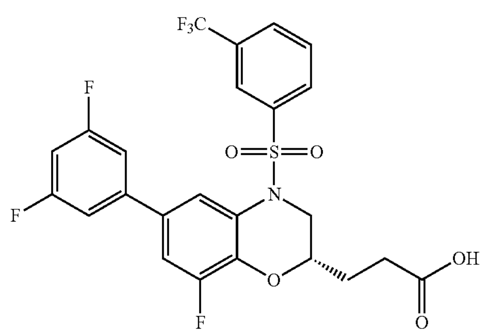 [SMILES: O=C(O)CC[C@H]1CN(S(=O)(=O)c2cccc(C(F)(F)F)c2)c2cc(-c3cc(F)cc(F)c3)cc(F)c2O1] | (S)-3-(6-(3,5-difluorophenyl)-8-fluoro-4-((3-(trifluoromethyl)phenyl)sulfonyl)-3,4-dihydro-2H-benzo[b][1,4]oxazin-2-yl)propanoic acid | 544 (M − H)⁻ |

TABLE 6A-continued

| Compd No. | Structure | Name | Observed m/z |
|---|---|---|---|
| 22L | 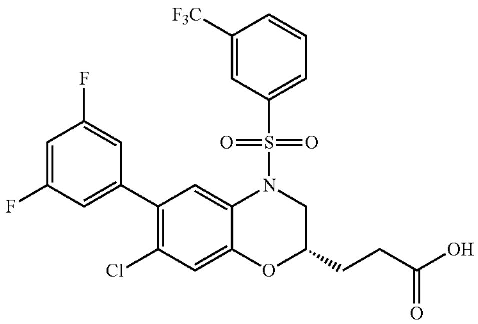 [SMILES: O=C(O)CC[C@H]1CN(S(=O)(=O)c2cccc(C(F)(F)F)c2)c2cc(-c3cc(F)cc(F)c3)c(Cl)cc2O1] | (S)-3-(7-chloro-6-(3,5-difluorophenyl)-4-((3-(trifluoromethyl)phenyl)sulfonyl)-3,4-dihydro-2H-benzo[b][1,4]oxazin-2-yl)propanoic acid | 560 (M − H)⁻ |
| 22M | 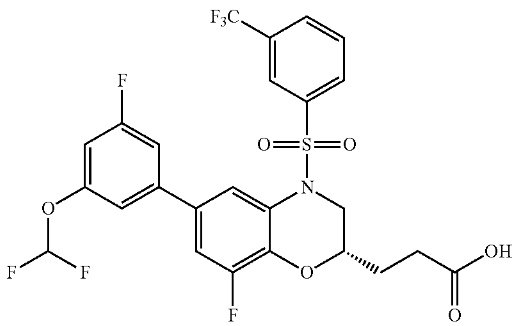 [SMILES: O=C(O)CC[C@H]1CN(S(=O)(=O)c2cccc(C(F)(F)F)c2)c2cc(-c3cc(F)cc(OC(F)F)c3)cc(F)c2O1] | (S)-3-(6-(3-(difluoromethoxy)-5-fluorophenyl)-8-fluoro-4-((3-(trifluoromethyl)phenyl)sulfonyl)-3,4-dihydro-2H-benzo[b][1,4]-oxazin-2-yl)propanoic acid | 594 (M + H)⁺ |
| 22N | 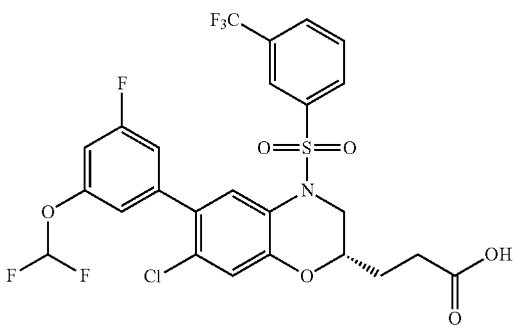 [SMILES: O=C(O)CC[C@H]1CN(S(=O)(=O)c2cccc(C(F)(F)F)c2)c2cc(-c3cc(F)cc(OC(F)F)c3)c(Cl)cc2O1] | (S)-3-(7-chloro-6-(3-(difluoromethoxy)-5-fluorophenyl)-4-((3-(trifluoromethyl)phenyl)sulfonyl)-3,4-dihydro-2H-benzo[b][1,4]-oxazin-2-yl)propanoic acid | 576 (M − H)⁻ |

TABLE 6B

| Compd No. | Physical Characterization Data |
|---|---|
| 22A | $^1$H NMR (300 MHz, CD$_3$OD-d$_4$) δ 8.43 (t, J = 1.7 Hz, 1H), 8.15-8.05 (m, 4H), 8.00 (d, J = 8.1 Hz, 1H), 7.85-7.71 (m, 3H), 4.53 (dd, J = 14.4, 2.4 Hz, 1H), 3.72 (s, 1H), 3.43 (dd, J = 14.4, 9.5 Hz, 1H), 2.51 (m, 2H), 2.08-1.85 (m, 2H). |
| 22B | $^1$H NMR (300 MHz, CD$_3$OD-d$_4$) δ 8.00 (m, 2H), 7.90 (s, 1H), 7.82-7.77 (m, 2H), 7.38-7.20 (m, 2H), 7.10 (m, 1H), 7.02 (s, 1H), 4.45 (dd, J = 14.5, 2.3 Hz, 1H), 3.48 (m, 1H), 3.30 (m, 1H), 2.42 (m, 2H), 1.95-1.76 (m, 2H). |
| 22C | $^1$H NMR (300 MHz, CD$_3$OD-d$_4$) δ 8.05-7.98 (m, 2H), 7.93 (s, 1H), 7.87-7.77 (m, 2H), 7.38 (t, J = 7.9 Hz, 1H), 7.03-6.93 (m, 4H), 4.45 (dd, J = 14.5, 2.4 Hz, 1H), 3.86 (s, 3H), 3.53-3.44 (m, 1H), 3.31-3.24 (m, 1H), 2.52-2.37 (m, 2H), 1.98-1.86 (m, 1H), 1.89-1.75 (m, 1H). |
| 22D | $^1$H NMR (300 MHz, CD$_3$OD-d$_4$) δ 8.05-7.98 (m, 3H), 7.85-7.79 (m, 2H), 7.40-7.36 (m, 1H), 7.27 (dq, J = 11.4, 2.0 Hz, 1H), 7.15-7.09 (m, 2H), 6.96-6.94 (m, 1H), 4.52 (dd, J = 14.6, 2.3 Hz, 1H), 3.88 (s, 3H), 3.58-3.50 (m, 1H), 3.42-3.33 (m, 1H), 2.57-2.38 (m, 2H), 2.04-1.79 (m, 2H). |
| 22E | $^1$H NMR (300 MHz, CD$_3$OD-d$_4$) δ 8.08-8.00 (m, 3H), 7.84-7.81 (m, 2H), 7.32-7.19 (m, 4H), 4.54 (dd, J = 14.6, 2.4 Hz, 1H), 3.62 (m, 1H), 3.44-3.35 (m, 1H), 2.54-2.40 (m, 2H), 2.08-1.81 (m, 2H). |
| 22F | $^1$H NMR (300 MHz, CD$_3$OD-d$_4$) δ 8.09 (s, 1H), 8.04-7.91 (m, 3H), 7.80 (t, J = 7.9 Hz, 1H), 7.04 (s, 1H), 4.39 (dd, J = 14.6, 2.4 Hz, 1H), 3.44-3.31 (m, 2H), 3.28 (s, 2H), 3.28-3.16 (m, 1H), 2.48-2.30 (m, 2H), 1.95-1.83 (m, 1H), 1.83-1.70 (m, 1H). |

TABLE 6B-continued

| Compd No. | Physical Characterization Data |
|---|---|
| 22G | $^1$H NMR (300 MHz, CD$_3$OD-d$_4$) δ 8.06-7.68 (m, 5H), 7.30-7.20 (m, 1H), 7.06-6.93 (m, 2H), 4.52-4.39 (m, 1H), 3.56-3.36 (m, 1H), 3.29-3.21 (m, 1H), 2.50-2.32 (m, 2H), 1.96-1.85 (m, 1H), 1.84-1.73 (m, 1H). |
| 22H | $^1$H NMR (300 MHz, CD$_3$OD-d$_4$) δ 8.08 (d, J = 7.6 Hz 1H), 8.02 (d, J = 8.0 Hz 1H), 7.96 (s, 1H), 7.84 (t, J = 8.0 Hz 1H), 7.72 (s, 1H), 7.23 (t, J = 10.2 Hz 1H), 7.13-7.06 (m, 2H), 4.54 (d, J = 17.2 Hz, 1H), 3.58-3.55 (m, 1H), 3.40-3.35 (m, 1H), 2.51-2.46 (m, 2H), 2.01-1.90 (m, 1H), 1.88-1.84 (m, 1H). |
| 22I | $^1$H NMR (300 MHz, CD$_3$OD-d$_4$) δ 8.10-7.96 (m, 3H), 7.83 (d, J = 7.0 Hz, 2H), 7.56-7.35 (m, 2H), 7.33-7.14 (m, 2H), 4.53 (d, J = 14.5 Hz, 1H), 3.45-3.33 (m, 2H), 2.48 (s, 2H), 1.96 (s, 2H). |
| 22J | $^1$H NMR (300 MHz, CD$_3$OD-d$_4$) δ 8.01 (d, J = 8.2 Hz, 2H), 7.92 (s, 1H), 7.87-7.76 (m, 2H), 7.56 (td, J = 6.6, 3.5 Hz, 1H), 7.32-7.23 (m, 2H), 7.05 (s, 1H), 4.46 (dd, J = 14.4, 2.4 Hz, 1H), 3.50 (s, 1H), 3.35 (s, 1H), 2.44 (td, J = 7.1, 3.3 Hz, 2H), 1.98-1.77 (m, 2H). |
| 22K | $^1$H NMR (300 MHz, CD$_3$OD-d$_4$) δ 8.08-7.96 (m, 3H), 7.89-7.75 (m, 2H), 7.33 (dd, J = 11.5, 2.1 Hz, 1H), 7.26-7.14 (m, 2H), 6.96 (tt, J = 9.1, 2.4 Hz, 1H), 4.50 (dd, J = 14.6, 2.4 Hz, 1H), 3.55 (q, J = 7.0 Hz, 1H), 3.43-3.32 (m, H), 2.46 (td, J = 7.2, 3.0 Hz, 2H), 2.04-1.78 (m, 2H). |
| 22L | $^1$H NMR (300 MHz, CD$_3$OD-d$_4$) δ 8.02-8.00 (m, 2H), 7.94 (s, 1H), 7.83 (m, 1H), 7.79 (s, 1H), 7.04 (s, 2H), 7.03-6.99 (m, 2H), 4.88 (dd, 1H), 3.55-3.42 (m, 2H), 2.49-2.40 (m, 2H), 1.94-1.82 (m, 2H). |
| 22M | $^1$H NMR (300 MHz, CD$_3$OD-d$_4$) δ 8.08-7.96 (m, 3H), 7.89-7.75 (m, 2H), 7.49-6.65 (m, 5H), 4.50 (dd, J = 14.6, 2.3 Hz, 1H), 3.43-3.32 (m, 2H), 2.46 (td, J = 7.2, 3.0 Hz, 2H), 2.02-1.81 (m, 2H). |
| 22N | $^1$H NMR (300 MHz, CD$_3$OD-d$_4$) δ 8.06-7.91 (m, 3H), 7.88-7.77 (m, 2H), 7.25-6.69 (m, 5H), 4.50-4.39 (m, 1H), 3.50 (s, 1H), 3.34 (s, 1H), 2.43 (s, 2H), 1.94-1.76 (m, 2H). |

Example 23—Preparation of Additional Substituted 4-(aryl sulfonyl)-3,4-dihydro-2H-benzo[b][1,4]oxazin-2-yl) Compounds Compounds in Table 7 below were prepared based on experimental procedures described in Examples 1, 3, 7, 8, and 9 and the detailed description. $^1$H NMR data for exemplary compounds from Table 7 is provided in Table 7A.

TABLE 7

| Compd No. | Structure | Name | Observed m/z |
|---|---|---|---|
| 23A | 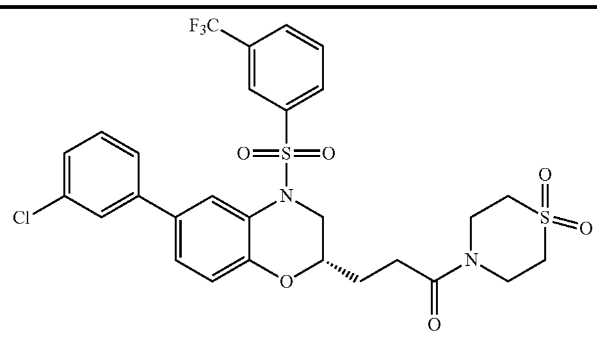 | (S)-3-(6-(3-chlorophenyl)-4-((3-(trifluoromethyl)phenyl)sulfonyl)-3,4-dihydro-2H-benzo[b][1,4]-oxazin-2-yl)-1-(1,1-dioxidothio-morpholino)propan-1-one | 643 (M + H)$^+$ |
| 23B | 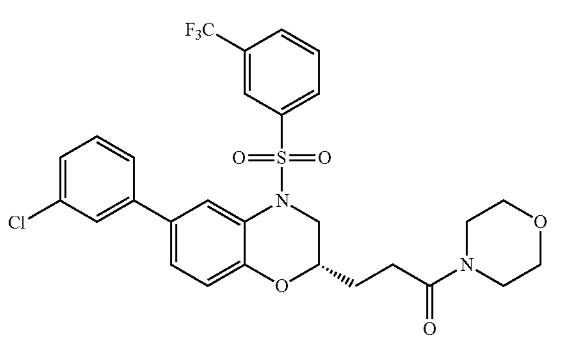 [SMILES: O=C(CC[C@H]1CN(S(=O)(=O)c2cccc(C(F)(F)F)c2)c2cc(-c3cccc(Cl)c3)ccc2O1)N1CCOCC1] | (S)-3-(6-(3-chlorophenyl)-4-((3-(trifluoromethyl)phenyl)sulfonyl)-3,4-dihydro-2H-benzo[b][1,4]-oxazin-2-yl)-1-morpholino-propan-1-one | 595 (M + H)$^+$ |

TABLE 7-continued

| Compd No. | Structure | Name | Observed m/z |
|---|---|---|---|
| 23C | 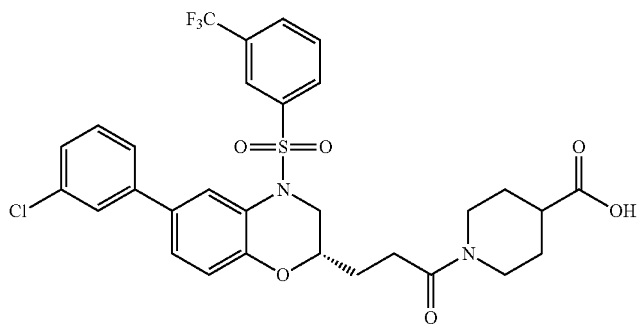 [SMILES: O=C(O)C1CCN(C(=O)CC[C@H]2CN(S(=O)(=O)c3cccc(C(F)(F)F)c3)c3cc(-c4cccc(Cl)c4)ccc3O2)CC1] | (S)-1-(3-(6-(3-chlorophenyl)-4-((3-(trifluoromethyl)phenyl)-sulfonyl)-3,4-dihydro-2H-benzo[b][1,4]oxazin-2-yl)propanoyl)piperidine-4-carboxylic acid | 637 (M + H)+ |
| 23D | 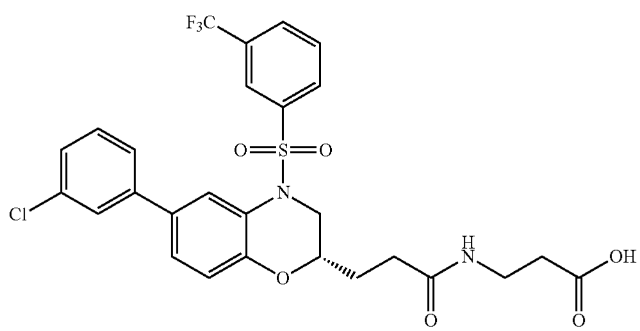 [SMILES: O=C(O)CCNC(=O)CC[C@H]1CN(S(=O)(=O)c2cccc(C(F)(F)F)c2)c2cc(-c3cccc(Cl)c3)ccc2O1] | (S)-3-(3-(6-(3-chlorophenyl)-4-((3-(trifluoromethyl)phenyl)-sulfonyl)-3,4-dihydro-2H-benzo[b][1,4]oxazin-2-yl)propanamido)propanoic acid | 597 (M + H)+ |
| 23E | 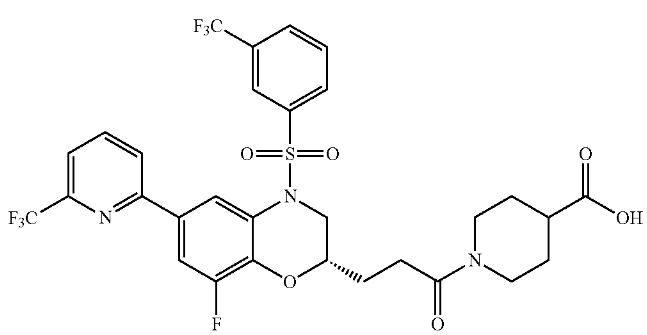 [SMILES: O=C(O)C1CCN(C(=O)CC[C@H]2CN(S(=O)(=O)c3cccc(C(F)(F)F)c3)c3cc(-c4cccc(C(F)(F)F)n4)cc(F)c3O2)CC1] | (S)-1-(3-(8-fluoro-4-((3-(trifluoromethyl)phenyl)sulfonyl)-6-(6-(trifluoromethyl)pyridin-2-yl)-3,4-dihydro-2H-benzo[b][1,4]oxazin-2-yl)propanoyl)piperidine-4-carboxylic acid | 690 (M + H)+ |
| 23F | 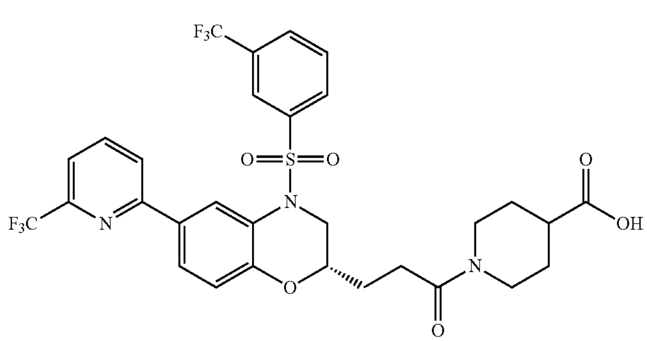 [SMILES: O=C(O)C1CCN(C(=O)CC[C@H]2CN(S(=O)(=O)c3cccc(C(F)(F)F)c3)c3cc(-c4cccc(C(F)(F)F)n4)ccc3O2)CC1] | (S)-1-(3-(4-((3-(trifluoromethyl)-phenyl)sulfonyl)-6-(6-(trifluoro-methyl)pyridin-2-yl)-3,4-dihydro-2H-benzo[b][1,4]oxazin-2-yl)propanoyl)piperidine-4-carboxylic acid | 672 (M + H)+ |

TABLE 7-continued

| Compd No. | Structure | Name | Observed m/z |
|---|---|---|---|
| 23G | 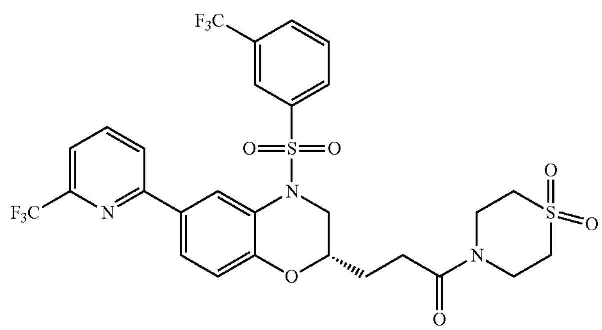 [SMILES: O=C(CC[C@H]1CN(S(=O)(=O)c2cccc(C(F)(F)F)c2)c2cc(-c3cccc(C(F)(F)F)n3)ccc2O1)N1CCS(=O)(=O)CC1] | (S)-1-(1,1-dioxidothio-morpholino)-3-(4-((3-(trifluoro-methyl)phenyl)sulfonyl)-6-(6-(trifluoromethyl)pyridin-2-yl)-3,4-dihydro-2H-benzo[b][1,4]-oxazin-2-yl)propan-1-one | 678 (M + H)+ |
| 23H | 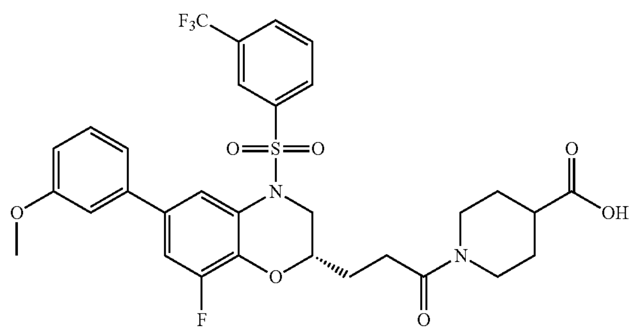 [SMILES: COc1cccc(-c2cc(F)c3c(c2)N(S(=O)(=O)c2cccc(C(F)(F)F)c2)C[C@H](CCC(=O)N2CCC(C(=O)O)CC2)O3)c1] | (S)-1-(3-(8-fluoro-6-(3-methoxyphenyl)-4-((3-(trifluoromethyl)phenyl)sulfonyl)-3,4-dihydro-2H-benzo[b][1,4]oxazin-2-yl)propanoyl)piperidine-4-carboxylic acid | 651 (M + H)+ |
| 23I | 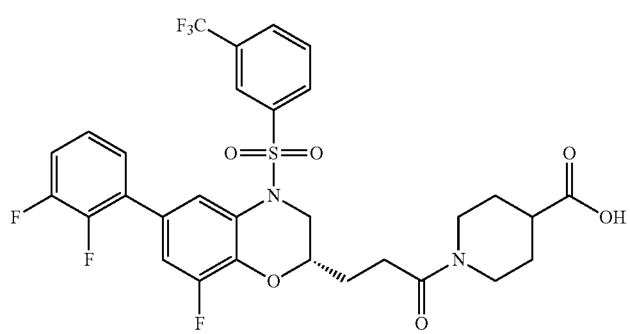 [SMILES: O=C(O)C1CCN(C(=O)CC[C@H]2CN(S(=O)(=O)c3cccc(C(F)(F)F)c3)c3cc(-c4cccc(F)c4F)cc(F)c3O2)CC1] | (S)-1-(3-(6-(2,3-difluorophenyl)-8-fluoro-4-((3-(trifluoromethyl)phenyl)sulfonyl)-3,4-dihydro-2H-benzo[b][1,4]oxazin-2-yl)propanoyl)piperidine-4-carboxylic acid | 657 (M + H)+ |
| 23J | 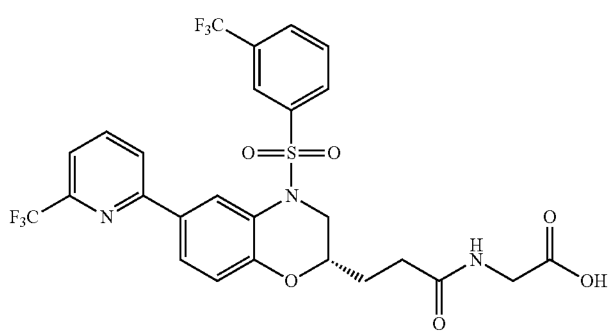 [SMILES: O=C(O)CNC(=O)CC[C@H]1CN(S(=O)(=O)c2cccc(C(F)(F)F)c2)c2cc(-c3cccc(C(F)(F)F)n3)ccc2O1] | (S)-(3-(4-((3-(trifluoromethyl)-phenyl)sulfonyl)-6-(6-(trifluoromethyl)pyridin-2-yl)-3,4-dihydro-2H-benzo[b][1,4]oxazin-2-yl)propanoyl)glycine | 618 (M + H)+ |

TABLE 7-continued

| Compd No. | Structure | Name | Observed m/z |
|---|---|---|---|
| 23K | 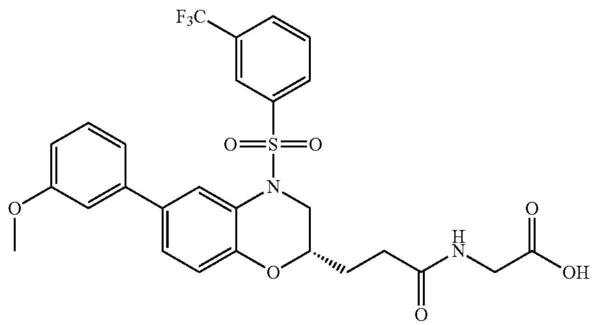 [SMILES: COc1cccc(-c2ccc3c(c2)N(S(=O)(=O)c2cccc(C(F)(F)F)c2)C[C@H](CCC(=O)NCC(=O)O)O3)c1] | (S)-(3-(6-(3-methoxyphenyl)-4-((3-(trifluoromethyl)-phenyl)sulfonyl)-3,4-dihydro-2H-benzo[b][1,4]oxazin-2-yl)propanoyl)glycine | 579 (M + H)+ |
| 23L | 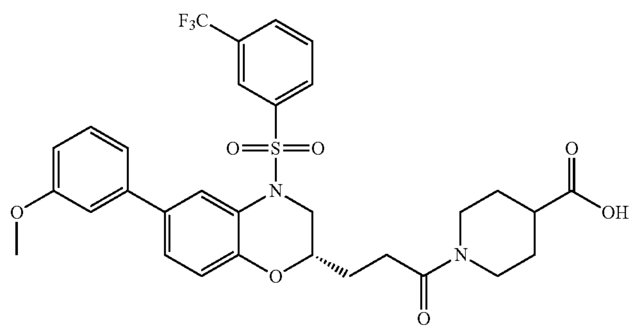 [SMILES: COc1cccc(-c2ccc3c(c2)N(S(=O)(=O)c2cccc(C(F)(F)F)c2)C[C@H](CCC(=O)N2CCC(C(=O)O)CC2)O3)c1] | (S)-1-(3-(6-(3-methoxyphenyl)-4-((3-(trifluoromethyl)-phenyl)sulfonyl)-3,4-dihydro-2H-benzo[b][1,4]oxazin-2-yl)propanoyl)piperidine-4-carboxylic acid | 633 (M + H)+ |
| 23M | 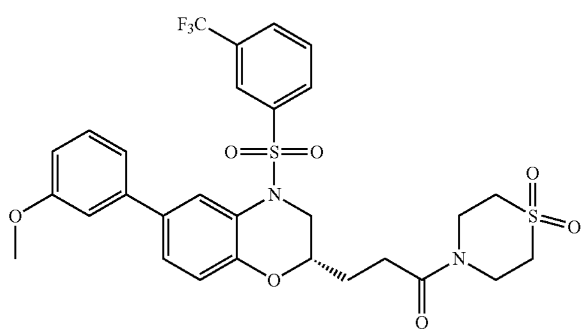 [SMILES: COc1cccc(-c2ccc3c(c2)N(S(=O)(=O)c2cccc(C(F)(F)F)c2)C[C@H](CCC(=O)N2CCS(=O)(=O)CC2)O3)c1] | (S)-1-(1,1-dioxidothio-morpholino)-3-(6-(3-methoxyphenyl)-4-((3-(trifluoromethyl)phenyl)sulfonyl)-3,4-dihydro-2H-benzo[b][1,4]-oxazin-2-yl)propan-1-one | 639 (M + H)+ |
| 23N | 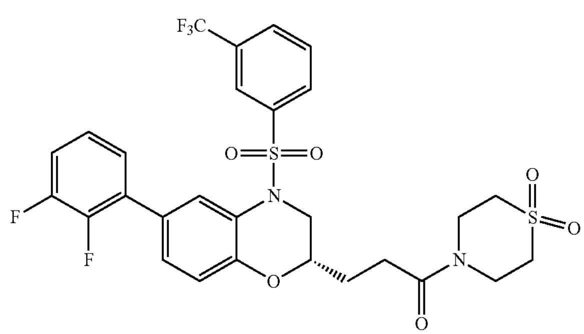 [SMILES: O=C(CC[C@H]1CN(S(=O)(=O)c2cccc(C(F)(F)F)c2)c2cc(-c3cccc(F)c3F)ccc2O1)N1CCS(=O)(=O)CC1] | (S)-3-(6-(2,3-difluorophenyl)-4-((3-(trifluoromethyl)-phenyl)sulfonyl)-3,4-dihydro-2H-benzo[b][1,4]oxazin-2-yl)-1-(1,1-dioxidothiomorpholino)propan-1-one | 645 (M + H)+ |

TABLE 7-continued

| Compd No. | Structure | Name | Observed m/z |
|---|---|---|---|
| 23O | 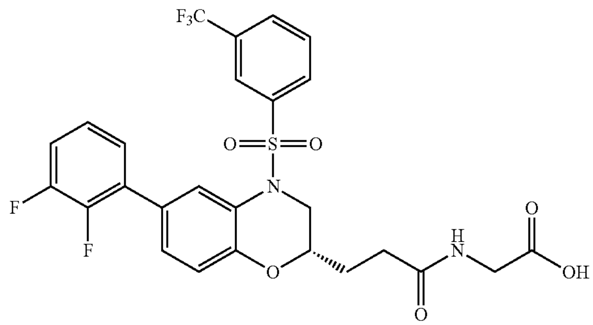 [SMILES: O=C(O)CNC(=O)CC[C@H]1CN(S(=O)(=O)c2cccc(C(F)(F)F)c2)c2cc(-c3cccc(F)c3F)ccc2O1] | (S)-(3-(6-(2,3-difluorophenyl)-4-((3-(trifluoromethyl)-phenyl)sulfonyl)-3,4-dihydro-2H-benzo[b][1,4]oxazin-2-yl)propanoyl)glycine | 585 (M + H)+ |
| 23P | 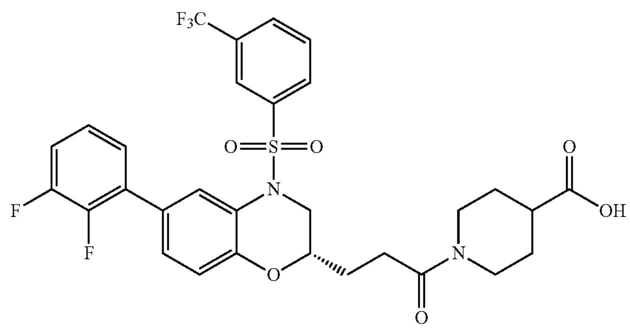 [SMILES: O=C(O)C1CCN(C(=O)CC[C@H]2CN(S(=O)(=O)c3cccc(C(F)(F)F)c3)c3cc(-c4cccc(F)c4F)ccc3O2)CC1] | (S)-1-(3-(6-(2,3-difluorophenyl)-4-((3-(trifluoromethyl)-phenyl)sulfonyl)-3,4-dihydro-2H-benzo[b][1,4]oxazin-2-yl)propanoyl)piperidine-4-carboxylic acid | 639 (M + H)+ |
| 23Q | 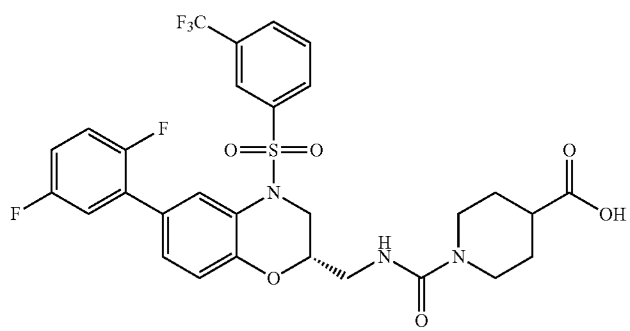 [SMILES: O=C(O)C1CCN(C(=O)NC[C@H]2CN(S(=O)(=O)c3cccc(C(F)(F)F)c3)c3cc(-c4cc(F)ccc4F)ccc3O2)CC1] | (S)-1-(((6-(2,5-difluorophenyl)-4-((3-(trifluoromethyl)-phenyl)sulfonyl)-3,4-dihydro-2H-benzo[b][1,4]oxazin-2-yl)methyl)carbamoyl)piperidine-4-carboxylic acid | 640 (M + H)+ |
| 23R | 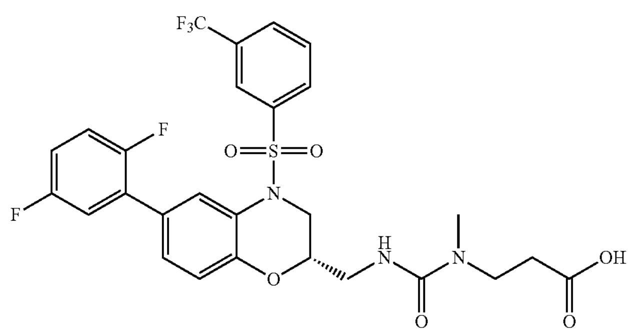 [SMILES: CN(CCC(=O)O)C(=O)NC[C@H]1CN(S(=O)(=O)c2cccc(C(F)(F)F)c2)c2cc(-c3cc(F)ccc3F)ccc2O1] | (S)-3-(3-((6-(2,5-difluorophenyl)-4-((3-(trifluoromethyl)phenyl)-sulfonyl)-3,4-dihydro-2H-benzo[b][1,4]oxazin-2-yl)methyl)-1-methylureido)propanoic acid | 614 (M + H)+ |

TABLE 7-continued

| Compd No. | Structure | Name | Observed m/z |
|---|---|---|---|
| 23S | 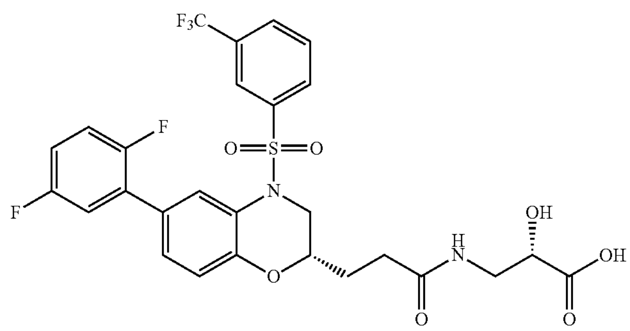 [SMILES: O=C(CC[C@H]1CN(S(=O)(=O)c2cccc(C(F)(F)F)c2)c2cc(-c3cc(F)ccc3F)ccc2O1)NC[C@H](O)C(=O)O] | (S)-3-(3-((S)-6-(2,5-difluoro-phenyl)-4-((3-(trifluoromethyl)-phenyl)sulfonyl)-3,4-dihydro-2H-benzo[b][1,4]oxazin-2-yl)propanamido)-2-hydroxypropanoic acid | 615 (M + H)+ |
| 23T | 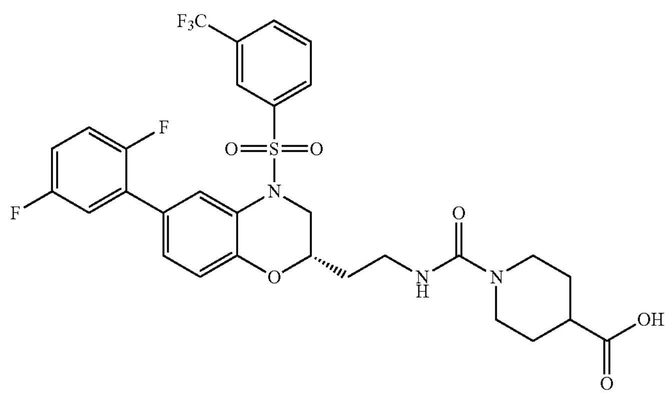 [SMILES: O=C(O)C1CCN(C(=O)NCC[C@H]2CN(S(=O)(=O)c3cccc(C(F)(F)F)c3)c3cc(-c4cc(F)ccc4F)ccc3O2)CC1] | (S)-1-((2-(6-(2,5-difluorophenyl)-4-((3-(trifluoromethyl)phenyl)-sulfonyl)-3,4-dihydro-2H-benzo[b][1,4]oxazin-2-yl)ethyl)carbamoyl)piperidine-4-carboxylic acid | 654 (M + H)+ |
| 23U | 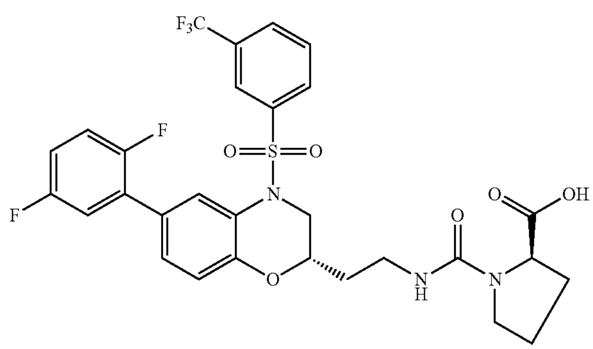 [SMILES: O=C(O)[C@H]1CCCN1C(=O)NCC[C@H]1CN(S(=O)(=O)c2cccc(C(F)(F)F)c2)c2cc(-c3cc(F)ccc3F)ccc2O1] | ((2-((S)-6-(2,5-difluorophenyl)-4-((3-(trifluoromethyl)phenyl)-sulfonyl)-3,4-dihydro-2H-benzo[b][1,4]oxazin-2-yl)ethyl)carbamoyl)-D-proline | 640 (M + H)+ |
| 23V | 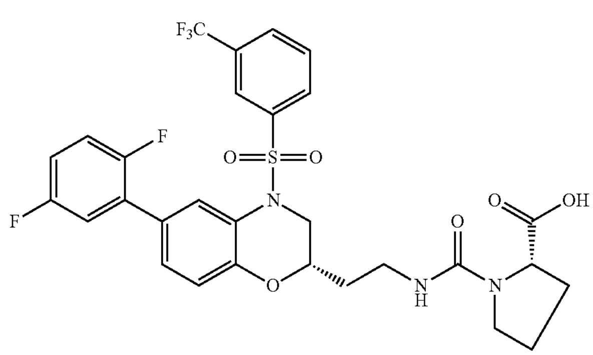 [SMILES: O=C(O)[C@@H]1CCCN1C(=O)NCC[C@H]1CN(S(=O)(=O)c2cccc(C(F)(F)F)c2)c2cc(-c3cc(F)ccc3F)ccc2O1] | ((2-((S)-6-(2,5-difluorophenyl)-4-((3-(trifluoromethyl)phenyl)-sulfonyl)-3,4-dihydro-2H-benzo[b][1,4]oxazin-2-yl)ethyl)carbamoyl)-L-proline | 640 (M + H)+ |

TABLE 7-continued

| Compd No. | Structure | Name | Observed m/z |
|---|---|---|---|
| 23W | 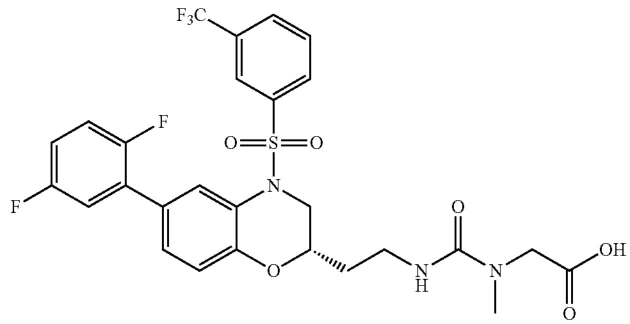 [SMILES: CN(CC(=O)O)C(=O)NCC[C@H]1CN(S(=O)(=O)c2cccc(C(F)(F)F)c2)c2cc(-c3cc(F)ccc3F)ccc2O1] | (S)-N-((2-(6-(2,5-difluorophenyl)-4-((3-(trifluoromethyl)phenyl)-sulfonyl)-3,4-dihydro-2H-benzo[b][1,4]oxazin-2-yl)ethyl)carbamoyl)-N-methylglycine | 614 (M + H)+ |
| 23X | 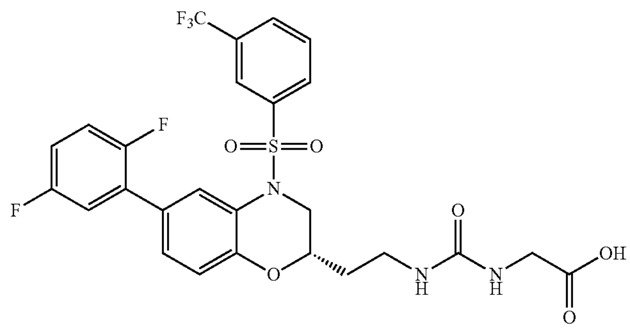 [SMILES: O=C(O)CNC(=O)NCC[C@H]1CN(S(=O)(=O)c2cccc(C(F)(F)F)c2)c2cc(-c3cc(F)ccc3F)ccc2O1] | (S)-((2-(6-(2,5-difluorophenyl)-4-((3-(trifluoromethyl)phenyl)-sulfonyl)-3,4-dihydro-2H-benzo[b][1,4]oxazin-2-yl)ethyl)carbamoyl)glycine | 600 (M + H)+ |
| 23Y | 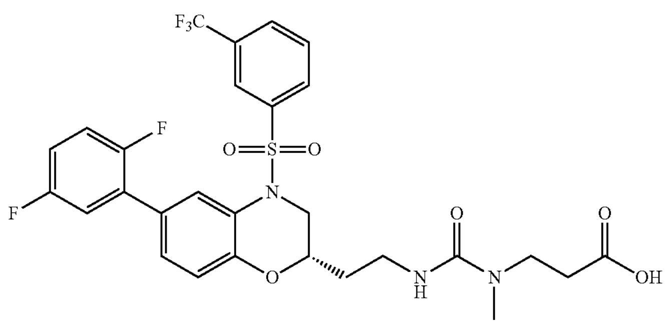 [SMILES: CN(CCC(=O)O)C(=O)NCC[C@H]1CN(S(=O)(=O)c2cccc(C(F)(F)F)c2)c2cc(-c3cc(F)ccc3F)ccc2O1] | (S)-3-(3-(2-(6-(2,5-difluoro-phenyl)-4-((3-(trifluoromethyl)-phenyl)sulfonyl)-3,4-dihydro-2H-benzo[b][1,4]oxazin-2-yl)ethyl)-1-methylureido)propanoic acid | 628 (M + H)+ |
| 23Z | 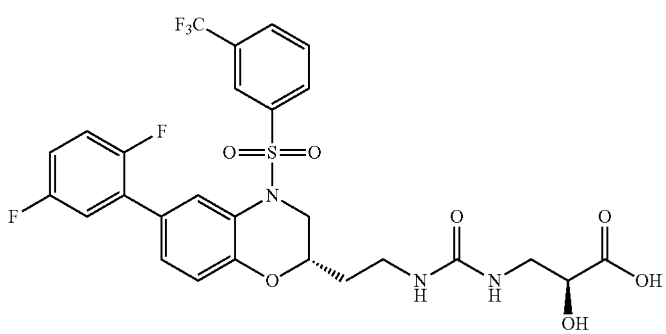 [SMILES: O=C(NCC[C@H]1CN(S(=O)(=O)c2cccc(C(F)(F)F)c2)c2cc(-c3cc(F)ccc3F)ccc2O1)NC[C@H](O)C(=O)O] | (S)-3-(3-(2-((S)-6-(2,5-difluorophenyl)-4-((3-(trifluoro-methyl)phenyl)sulfonyl)-3,4-dihydro-2H-benzo[b][1,4]oxazin-2-yl)ethyl)ureido)-2-hydroxypropanoic acid | 630 (M + H)+ |

TABLE 7A

| Compd No. | $^1$H NMR Data |
|---|---|
| 23E | $^1$H NMR (300 MHz, CD$_3$OD-d$_4$) δ 8.42 (s, 1H), 8.13-8.08 (m, 4H), 8.01-7.99 (d, J = 8.0 Hz, 1H), 7.84-7.70 (m, 3H), 4.56 (dd, J = 14.4, 2.4 Hz, 1H), 4.37 (dq, J = 9.6, 4.4 Hz, 1H), 3.97-3.93 (m, 1H), 3.77 (q, J = 8.9, 6.7 Hz, 1H), 3.45 (m, 1H), 3.27-3.16 (m, 1H), 2.89-2.88 (m, 1H), 2.62 (m, 3H), 2.07-1.90 (m, 4H), 1.72-1.61 (m, 2H). |

TABLE 7A-continued

| Compd No. | ¹H NMR Data |
|---|---|
| 23F | ¹H NMR (300 MHz, CD₃OD-d₄) δ 8.59 (d, J = 2.1 Hz, 1H), 8.06 (td, J = 6.4, 5.6, 3.5 Hz, 4H), 7.97 (d, J = 7.9 Hz, 1H), 7.91-7.64 (m, 3H), 6.98 (d, J = 8.6 Hz, 1H), 4.55-4.42 (m, 1H), 4.36 (d, J = 13.6 Hz, 1H), 3.93 (d, J = 14.4 Hz, 1H), 3.67 (s, 1H), 3.45-3.35 (m, 1H), 3.20 (t, J = 12.9 Hz, 1H), 2.88 (t, J = 11.7 Hz, 1H), 2.59 (q, J = 9.1, 7.6 Hz, 3H), 2.10-1.78 (m, 4H), 1.57 (dd, J = 26.3, 13.0 Hz, 2H). |
| 23G | ¹H NMR (400 MHz, CD₃OD-d₄) δ 8.57 (d, J = 2.1 Hz, 1H), 8.10-8.01 (m, 4H), 7.96 (d, J = 7.5 Hz, 1H), 7.84 (dd, J = 8.6, 2.2 Hz, 1H), 7.80-7.64 (m, 2H), 6.97 (d, J = 8.6 Hz, 1H), 4.48 (dd, J = 14.3, 2.5 Hz, 1H), 4.10-3.95 (m, 4H), 3.77-3.66 (m, 1H), 3.38 (dd, J = 14.3, 9.6 Hz, 1H), 3.18 (q, J = 6.1 Hz, 2H), 3.10 (s, 2H), 2.66 (t, J = 7.2 Hz, 2H), 2.07-1.94 (m, 1H), 1.86 (dq, J = 14.5, 6.9 Hz, 1H). |
| 23H | ¹H NMR (400 MHz, CD₃OD-d₄) δ 8.06-7.98 (m, 3H), 7.87-7.76 (m, 2H), 7.38 (t, J = 8.0 Hz, 1H), 7.30-7.22 (m, 1H), 7.18-7.07 (m, 2H), 6.95 (dd, J = 8.3, 2.5 Hz, 1H), 4.57-4.48 (dd, J = 1.2 Hz, J = 2 Hz 1H), 4.36 (m, 1H), 3.88 (m, 4H), 3.60 (m, 1H), 3.44-3.33 (m, 1H), 3.20 (t, J = 12.4 Hz, 1H), 2.88 (t, J = 12.8 Hz, 1H), 2.58 (m, 3H), 2.06-1.85 (m, 4H), 1.64-1.58 (m, 2H). |
| 23I | ¹H NMR (400 MHz, CD₃OD-d₄) δ 8.09-8.01 (m, 3H), 7.84-7.80 (d, J = 6.8 Hz, 2H), 7.31-7.17 (m, 4H), 4.58-4.51 (m, 1H), 4.39-4.34 (dd, J = 4, 13.2 Hz, 1H), 3.96-3.92 (dd, J = 3.6, 13.6 Hz, 1H), 3.66 (s, 1H), 3.44-3.35 (m, 1H), 3.20 (m, 1H), 2.96-2.83 (m, 1H), 2.61 (dq, J = 16.1, 7.8 Hz, 3H), 2.10-1.81 (m, 4H), 1.73-1.49 (m, 2H). |
| 23J | ¹H NMR (400 MHz, CD₃OD-d₄) δ 8.57 (d, J = 2.1 Hz, 1H), 8.11-8.06 (m, 1H), 8.06-8.02 (m, 2H), 8.01 (s, 1H), 7.97-7.93 (m, 1H), 7.84 (dd, J = 8.6, 2.1 Hz, 1H), 7.76 (t, J = 7.9 Hz, 1H), 7.71-7.64 (m, 1H), 6.96 (d, J = 8.6 Hz, 1H), 4.47 (dd, J = 14.3, 2.5 Hz, 1H), 3.98-3.83 (m, 2H), 3.65 (dddd, J = 10.2, 7.3, 4.5, 2.5 Hz, 1H), 3.41-3.33 (m, 1H), 2.53-2.34 (m, 2H), 2.06-1.81 (m, 2H). |
| 23K | ¹H NMR (400 MHz, CD₃OD-d₄) δ 8.04-7.88 (m, 4H), 7.77 (t, J = 1.9 Hz, 1H), 7.39-7.30 (m, 2H), 7.16-7.05 (m, 2H), 6.94-6.86 (m, 2H), 4.45 (dd, J = 14.4, 2.5 Hz, 1H), 3.98-3.82 (m, 5H), 3.54-3.43 (m, 1H), 3.27 (d, J = 10.0 Hz, 1H), 2.50-2.30 (m, 2H), 2.00-1.76 (m, 2H). |
| 23L | ¹H NMR (400 MHz, CD₃OD-d₄) δ 8.04-7.90 (m, 4H), 7.76 (t, J = 7.9 Hz, 1H), 7.40-7.30 (m, 2H), 7.16-7.05 (m, 2H), 6.94-6.86 (m, 2H), 4.50-4.41 (m, 1H), 4.34 (d, J = 13.4 Hz, 1H), 3.86 (s, 4H), 3.48 (d, J = 7.7 Hz, 1H), 3.23-3.12 (m, 1H), 2.86 (t, J = 12.3 Hz, 1H), 2.64-2.49 (m, 3H), 2.00-1.87 (m, 3H), 1.80 (dt, J = 14.3, 7.1 Hz, 1H), 1.67-1.46 (m, 2H). |
| 23M | ¹H NMR (400 MHz, CD₃OD-d₄) δ 8.03-7.92 (m, 4H), 7.76 (t, J = 7.9 Hz, 1H), 7.40-7.30 (m, 2H), 7.16-7.05 (m, 2H), 6.95-6.86 (m, 2H), 4.46 (dd, J = 14.4, 2.4 Hz, 1H), 4.07 (s, 1H), 3.98 (s, 3H), 3.86 (s, 3H), 3.54 (d, J = 8.5 Hz, 1H), 3.19-3.07 (m, 5H), 2.63 (t, J = 7.2 Hz, 2H), 2.01-1.90 (m, 1H), 1.81 (dq, J = 14.4, 6.9 Hz, 1H). |
| 23N | ¹H NMR (400 MHz, CD₃OD-d₄) δ 8.05-7.93 (m, 4H), 7.77 (t, J = 7.8 Hz, 1H), 7.33-7.17 (m, 4H), 6.93 (d, J = 8.5 Hz, 2H), 4.49 (dd, J = 14.4, 2.5 Hz, 1H), 4.08 (s, 1H), 4.00 (q, J = 12.1, 9.7 Hz, 3H), 3.61 (dddd, J = 10.5, 8.1, 4.1, 2.4 Hz, 1H), 3.39-3.32 (m, 1H), 3.22-3.05 (m, 4H), 2.64 (t, J = 7.1 Hz, 2H), 2.06-1.92 (m, 1H), 1.90-1.76 (m, 1H). |
| 23O | ¹H NMR (400 MHz, CD₃OD-d₄) δ 8.07-7.89 (m, 4H), 7.78 (t, J = 7.9 Hz, 1H), 7.32-7.17 (m, 4H), 6.93 (d, J = 8.5 Hz, 1H), 4.48 (dd, J = 14.4, 2.5 Hz, 1H), 3.98-3.83 (m, 2H), 3.55 (dddd, J = 10.2, 7.3, 4.5, 2.5 Hz, 1H), 3.31 (m, 1H), 2.51-2.32 (m, 2H), 2.02-1.78 (m, 2H). |
| 23P | ¹H NMR (400 MHz, CD₃OD-d₄) δ 8.06-7.92 (m, 4H), 7.77 (t, J = 8.0 Hz, 1H), 7.33-7.19 (m, 4H), 6.93 (d, J = 8.5 Hz, 1H), 4.48 (dt, J = 14.4, 1.9 Hz, 1H), 4.35 (d, J = 13.4 Hz, 1H), 3.91 (d, J = 13.9 Hz, 1H), 3.60-3.49 (m, 1H), 3.31 (s, 1H), 3.23-3.12 (m, 1H), 2.93-2.80 (m, 1H), 2.65-2.50 (m, 3H), 1.95 (ddq, J = 15.4, 8.0, 4.2 Hz, 3H), 1.81 (dt, J = 14.3, 7.2 Hz, 1H), 1.59 (dddd, J = 25.3, 21.2, 12.6, 8.6 Hz, 2H). |
| 23T | ¹H NMR (400 MHz, CD₃OD-d₄) δ 8.10-8.03 (m, 1H), 8.03-7.92 (m, 3H), 7.77 (t, J = 7.9 Hz, 1H), 7.32-7.15 (m, 3H), 7.15-7.04 (m, 1H), 6.92 (d, J = 8.5 Hz, 1H), 4.45 (dd, J = 14.4, 2.5 Hz, 1H), 3.92 (t, J = 12.8 Hz, 2H), 3.59 (dd, J = 10.2, 3.8 Hz, 1H), 3.35 (d, J = 9.1 Hz, 2H), 3.32-3.21 (m, 1H), 2.95-2.89 (m, 2H), 2.54 (ddt, J = 11.0, 7.0, 4.0 Hz, 1H), 1.92-1.74 (m, 4H), 1.59 (qd, J = 11.3, 4.0 Hz, 2H). |
| 23U | ¹H NMR (400 MHz, CD₃OD-d₄) δ 8.13 (m, 1H), 8.03-7.88 (m, 3H), 7.82 (t, J = 8.0 Hz, 1H), 7.29-7.15 (m, 3H), 7.09 (m, 1H), 6.92 (d, J = 8.5 Hz, 1H), 4.52-4.35 (m, 2H), 3.68 (m, 1H), 3.43 (td, J = 8.6, 7.6, 5.1 Hz, 1H), 3.38-3.32 (m, 4H), 2.24 (td, J = 9.1, 8.4, 4.5 Hz, 1H), 2.04 (h, J = 4.9, 4.0 Hz, 3H), 1.87 (ddd, J = 14.5, 7.3, 4.4 Hz, 1H), 1.71 (m, 1H). |
| 23V | ¹H NMR (400 MHz, CD₃OD-d₄) δ 8.09 (d, J = 7.9 Hz, 1H), 8.04-7.96 (m, 3H), 7.81 (t, J = 7.9 Hz, 1H), 7.34-7.17 (m, 3H), 7.16-7.07 (m, 1H), 6.95 (d, J = 8.5 Hz, 1H), 4.51-4.36 (m, 2H), 3.71-3.60 (m, 1H), 3.52-3.44 (m, 1H), 3.42-3.34 (m, 3H), 3.30-3.20 (m, 1H), 2.33-2.21 (m, 1H), 2.12-1.98 (m, 3H), 1.93-1.83 (m, 1H), 1.82-1.72 (m, 1H). |
| 23W | ¹H NMR (400 MHz, CD₃OD-d₄) δ 8.09 (d, J = 7.9 Hz, 1H), 8.05-7.91 (m, 3H), 7.85-7.73 (m, 1H), 7.31-7.25 (m, 1H), 7.25-7.16 (m, 2H), 7.14-7.06 (m, 1H), 6.97-6.86 (m, 1H), 4.50-4.39 (m, 1H), 4.05 (d, J = 5.3 Hz, 1H), 3.67-3.55 (m, 1H), 3.39-3.33 (m, 3H), 3.29-3.20 (m, 1H), 2.95 (s, 3H), 1.94-1.80 (m, 1H), 1.80-1.66 (m, 1H). |
| 23X | ¹H NMR (400 MHz, CD₃OD-d₄) δ 8.06 (d, J = 7.9 Hz, 1H), 8.04-7.88 (m, 3H), 7.80 (t, J = 7.9 Hz, 1H), 7.30-7.13 (m, 3H), 7.14-7.05 (m, 1H), 6.92 (d, J = 8.5 Hz, 1H), 4.45 (dd, J = 14.4, 2.4 Hz, 1H), 3.84 (d, J = 1.6 Hz, 2H), 3.62-3.52 (m, 1H), 3.36-3.30 (m, 2H), 3.24-3.15 (m, 1H), 1.85-1.75 (m, 1H), 1.76-1.64 (m, 1H). |
| 23Y | ¹H NMR (400 MHz, CD₃OD-d₄) δ 8.06 (d, J = 7.9 Hz, 1H), 8.02-7.89 (m, 3H), 7.78 (t, J = 7.9 Hz, 1H), 7.32-7.15 (m, 3H), 7.10 (dq, J = 8.5, 4.3, 3.9 Hz, 1H), 6.93 (d, J = 8.6 Hz, |

TABLE 7A-continued

| Compd No. | ¹H NMR Data |
|---|---|
| | 1H), 4.45 (dd, J = 14.4, 2.5 Hz, 1H), 3.57 (dtd, J = 21.8, 7.0, 6.0, 2.4 Hz, 3H), 3.37 (s, 2H), 3.25 (m, 1H), 2.89 (s, 3H), 2.55 (t, J = 6.9 Hz, 2H), 1.90-1.66 (m, 2H). |
| 23Z | ¹H NMR (400 MHz, CD₃OD-d₄) δ 8.08 (d, J = 7.9 Hz, 1H), 8.02-7.95 (m, 2H), 7.93 (s, 1H), 7.81 (t, J = 7.8 Hz, 1H), 7.30-7.15 (m, 3H), 7.09 (tt, J = 9.0, 3.4 Hz, 1H), 6.93 (d, J = 8.6 Hz, 1H), 4.46 (dd, J = 14.4, 2.4 Hz, 1H), 4.20 (s, 1H), 3.64-3.51 (m, 2H), 3.37 (dd, J = 22.4, 8.5 Hz, 2H), 3.29-3.13 (m, 2H), 1.75 (ddq, J = 34.7, 13.9, 6.6 Hz, 2H). |

Example 24—Synthesis of (S)-3-(6-(2-chloro-3,5-difluorophenyl)-4-((3-(trifluoromethyl)phenyl)sulfonyl)-3,4-dihydro-2H-benzo[b][1,4]oxazin-2-yl)propanoic acid

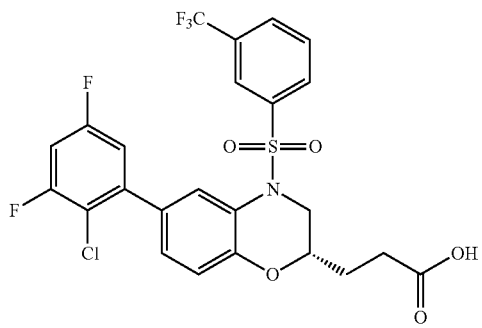 [SMILES: O=C(O)CC[C@H]1CN(S(=O)(=O)c2cccc(C(F)(F)F)c2)c2cc(-c3cc(F)cc(F)c3Cl)ccc2O1]

Part I—Synthesis of 2-chloro-3,5-difluorophenyl trifluoromethanesulfonate

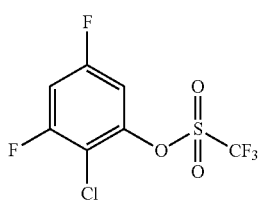 [SMILES: O=S(=O)(Oc1cc(F)cc(F)c1Cl)C(F)(F)F]

A solution of trifluoromethanesulfonic anhydride (570 mg, 2.02 mmol) in dichloromethane (5 mL) was added dropwise to a stirred mixture of chloro-3,5-difluorophenol (300 mg, 1.82 mmol) in dichloromethane (10 mL) at 0° C. The mixture was stirred for an additional three hours at room temperature. Then, 1N Hydrochloric acid was added to the reaction mixture and the resulting mixture was extracted three times with dichloromethane. The combined organic layers were dried (Na₂SO₄) and concentrated. The resulting residue was purified via MPLC eluting with 25% ethyl acetate in petroleum ether to afford 2-chloro-3,5-difluorophenyl trifluoromethanesulfonate (270 mg, 50%) as a yellow oil.

Part II—Synthesis of methyl (S)-3-(6-(2-chloro-3,5-difluorophenyl)-4-((3-(trifluoromethyl)phenyl)sulfonyl)-3,4-dihydro-2H-benzo[b][1,4]oxazin-2-yl)propanoate A mixture of methyl (S)-3-(6-(4,4,5,5-tetramethyl-1,3,2-dioxaborolan-2-yl)-4-((3-(trifluoromethyl)phenyl)sulfonyl)-3,4-dihydro-2H-benzo[b][1,4]oxazin-2-yl)propanoate (703 mg, 1.27 mmol), 2-chloro-3,5-difluorophenyl trifluoromethanesulfonate (250 mg, 0.84 mmol), tetrakis(triphenylphosphine)palladium (146 mg, 0.13 mmol), sodium carbonate (290 mg, 2.7 mmol), toluene (9 mL), ethanol (3 mL), and water (3 mL) was stirred for three hours at 90° C. Then, the resulting mixture was concentrated, and the resulting residue was purified via MPLC eluting with 33% ethyl acetate in petroleum ether to afford methyl (S)-3-(6-(2-chloro-3,5-difluorophenyl)-4-((3-(trifluoromethyl)phenyl)sulfonyl)-3,4-dihydro-2H-benzo[b][1,4]oxazin-2-yl)propanoate (150 mg, 31%) as a yellow oil.

Part III—Synthesis of (S)-3-(6-(2-chloro-3,5-difluorophenyl)-4-((3-(trifluoromethyl)phenyl)sulfonyl)-3,4-dihydro-2H-benzo[b][1,4]oxazin-2-yl)propanoic acid

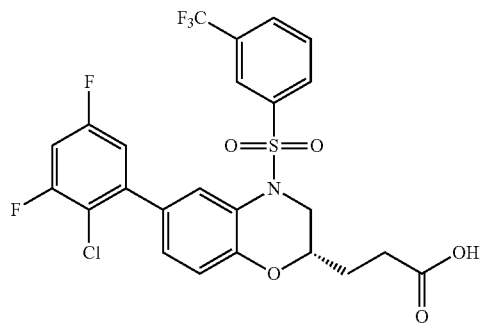 [SMILES: O=C(O)CC[C@H]1CN(S(=O)(=O)c2cccc(C(F)(F)F)c2)c2cc(-c3cc(F)cc(F)c3Cl)ccc2O1]

Based on the procedure in Example 1, Part VII, (S)-3-(6-(2-chloro-3,5-difluorophenyl)-4-((3-(trifluoromethyl)phenyl)sulfonyl)-3,4-dihydro-2H-benzo[b][1,4]oxazin-2-yl)propanoic acid was prepared. $^1$H-NMR (400 MHz, CD$_3$OD) δ 8.02 (d, J=7.8 Hz, 1H), 7.97 (m, 1H), 7.85-7.92 (m, 2H), 7.79 (t, J=7.9 Hz, 1H), 7.18 (m, 2H), 7.03 (dt, J=9.0, 2.3 Hz, 1H), 6.93 (d, J=8.5 Hz, 1H), 4.46 (dd, J=14.5, 2.4 Hz, 1H), 3.46 (m, 1H), 3.27 (m, 1H), 2.32-2.54 (m, 2H), 1.74-1.97 (m, 2H). (ES, m/z): (M+H)$^+$ 562.

Example 25—Synthesis of (S)-3-(6-(4-methyloxazol-2-yl)-4-((3-(trifluoromethyl)phenyl)sulfonyl)-3,4-dihydro-2H-benzo[b][1,4]oxazin-2-yl)propanoic acid

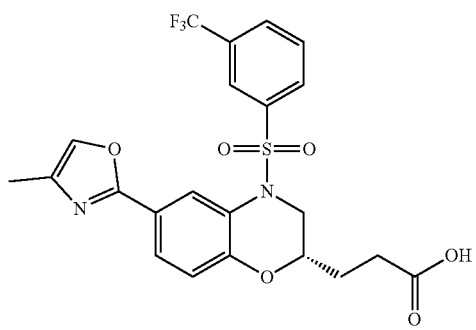 [SMILES: Cc1coc(-c2ccc3c(c2)N(S(=O)(=O)c2cccc(C(F)(F)F)c2)C[C@H](CCC(=O)O)O3)n1]

Part I—Synthesis of 4-methyl-2-(tributylstannyl)oxazole

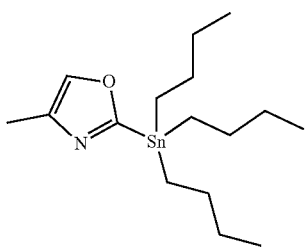 [SMILES: CCC[CH2][Sn]([CH2]CCC)([CH2]CCC)[c]1nc(C)co1]

A 2.5 M solution of n-butyl lithium in THF (0.96 mL) was added dropwise to a solution of 4-methyl-1,3-oxazole (200 mg, 2.41 mmol) in ether (4 mL) at −78° C. The mixture was stirred for an hour at −78° C. and a solution of tributylchlorostannane (510.8 mg, 2.41 mmol) in ether (2 mL) was added. The mixture was stirred for an hour at −78° C. and then allowed to warm to room temperature. Then, the mixture was filtered, and the filtrate was concentrated to afford 4-methyl-2-(tributylstannyl)oxazole (550 mg, 61%) as a yellow oil.

Part II—Synthesis of methyl (S)-3-(6-(4-methyloxazol-2-yl)-4-((3-(trifluoromethyl)phenyl)sulfonyl)-3,4-dihydro-2H-benzo[b][1,4]oxazin-2-yl)propanoate

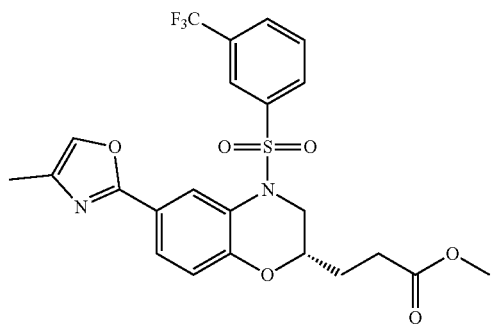

A mixture of 4-methyl-2-(tributylstannyl)oxazole (588.6 mg, 1.58 mmol), dioxane (5 mL), (S)-methyl 3-(6-bromo-4-((3-(trifluoromethyl)phenyl)sulfonyl)-3,4-dihydro-2H-benzo[b][1,4]oxazin-2-yl)propanoate (200 mg, 0.39 mmol), and tetrakis(triphenylphosphine)-palladium (22.8 mg, 0.02 mmol) was stirred overnight at 120° C. Then, the mixture was concentrated, and the residue was purified via MPLC eluting with 33% ethyl acetate in petroleum ether to afford methyl (S)-3-(6-(4-methyloxazol-2-yl)-4-((3-(trifluoromethyl)phenyl)sulfonyl)-3,4-dihydro-2H-benzo[b][1,4]oxazin-2-yl)propanoate (100 mg, 50%) as a yellow oil.

Part III—Synthesis of (S)-3-(6-(4-methyloxazol-2-yl)-4-((3-(trifluoromethyl)phenyl) sulfonyl)-3,4-dihydro-2H-benzo[b][1,4]oxazin-2-yl)propanoic acid

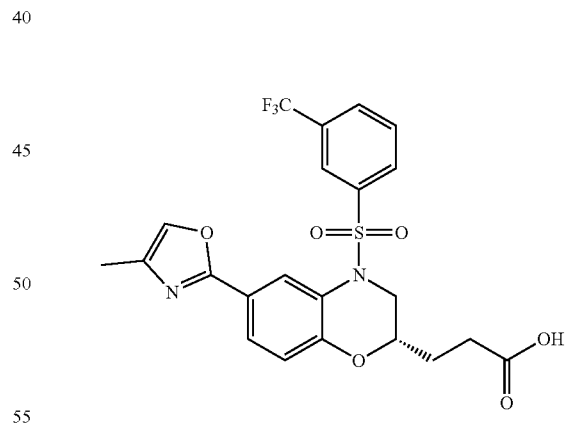

Based on the procedure in Example 1, Part VII, (S)-3-(6-(4-methyloxazol-2-yl)-4-((3-(trifluoromethyl)phenyl)sulfonyl)-3,4-dihydro-2H-benzo[b][1,4]oxazin-2-yl)propanoic acid was prepared. $^1$H-NMR (400 MHz, CD$_3$OD) δ 8.43 (t, J=2.1 Hz, 1H), 8.06-7.92 (m, 3H), 7.83-7.62 (m, 3H), 6.94 (dd, J=8.7, 2.1 Hz, 1H), 4.44 (dt, J=14.5, 2.0 Hz, 1H), 3.51 (m, 1H), 3.27 (m, 1H), 2.43 (td, J=7.2, 3.4 Hz, 2H), 2.23 (t, J=1.5 Hz, 3H), 2.00-1.70 (m, 2H). (ES, m/z): (M+H)$^+$ 497.

Example 26—Synthesis of (S)-3-(6-(5-methyloxazol-2-yl)-4-((3-(trifluoromethyl)phenyl)sulfonyl)-3,4-dihydro-2H-benzo[b][1,4]oxazin-2-yl)propanoic acid

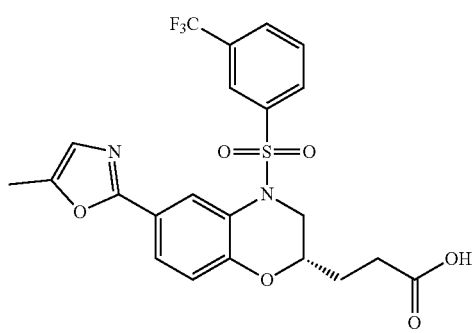 [SMILES: Cc1cnc(-c2ccc3c(c2)N(S(=O)(=O)c2cccc(C(F)(F)F)c2)C[C@H](CCC(=O)O)O3)o1]

Based on the procedure in Example 25, utilizing 4-methyl-1,3-oxazole as the starting material, (S)-3-(6-(5-methyloxazol-2-yl)-4-((3-(trifluoromethyl)phenyl)sulfonyl)-3,4-dihydro-2H-benzo[b][1,4]oxazin-2-yl)propanoic acid was prepared. $^1$H-NMR (400 MHz, CD$_3$OD) δ 8.40 (s, 1H), 8.02 (d, 1H), 7.98 (d, 1H), 7.97 (s, 1H), 7.78 (t, 1H), 7.68 (d, 1H), 6.94 (d, 1H), 6.88 (s, 1H), 4.44 (dd, 1H), 3.52 (m, 1H), 3.30 (m, 1H), 2.43 (s, 3H), 2.42 (m, 2H), 1.82-1.95 (m, 2H). (ES, m/z): (M+H)$^+$ 497.

Example 27—Synthesis of (S)-2-(6-(2,5-difluorophenyl)-4-((3-(trifluoromethyl)phenyl)sulfonyl)-3,4-dihydro-2H-benzo[b][1,4]oxazin-2-yl)ethan-1-amine

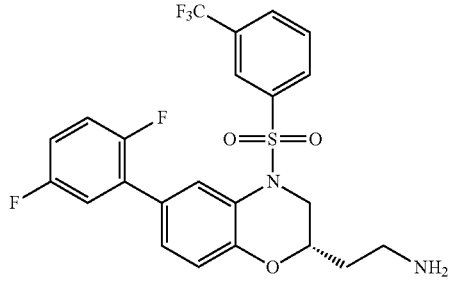 [SMILES: NCC[C@H]1CN(S(=O)(=O)c2cccc(C(F)(F)F)c2)c2cc(-c3cc(F)ccc3F)ccc2O1]

A solution of tert-butyl (S)-(2-(6-(2,5-difluorophenyl)-4-((3-(trifluoromethyl)phenyl)sulfonyl)-3,4-dihydro-2H-benzo[b][1,4]oxazin-2-yl)ethyl)carbamate (80 mg, 0.13 mmol), dichloromethane (3 mL), and trifluoroacetic acid (0.5 mL) was stirred for one hour at room temperature. Then, the mixture was diluted with saturated sodium bicarbonate and next extracted twice with ethyl acetate. The combined organic layers were dried (Na$_2$SO$_4$) and concentrated. The resulting residue was purified by Prep-HPLC eluting with a gradient of 50-80% acetonitrile in water with 0.1% trifluoroacetic acid to afford (S)-2-(6-(2,5-difluorophenyl)-4-((3-(trifluoromethyl)phenyl)sulfonyl)-3,4-dihydro-2H-benzo[b][1,4]oxazin-2-yl)ethan-1-amine (21.4 mg, 32%) as a white solid. $^1$H-NMR (400 MHz, CD$_3$OD) δ 8.10-7.98 (m, 2H), 7.95 (d, J=7.9 Hz, 1H), 7.91 (s, 1H), 7.80 (t, J=7.9 Hz, 1H), 7.27 (n, 1H), 7.23-7.05 (m, 3H), 6.92 (d, J=8.5 Hz, 1H), 4.45 (dd, J=14.4, 2.4 Hz, 1H), 3.84 (m, 1H), 3.57 (m, 1H), 3.26-3.14 (m, 2H), 1.88-1.62 (m, 2H). (ES, m/z): (M+H)$^+$ 449.

Example 28—Preparation of Additional Substituted 4-(aryl sulfonyl)-3,4-dihydro-2H-benzo[b][1,4]oxazin-2-yl) Compounds Compounds in Table 8 were prepared based on experimental procedures described in Examples 1, 3, 5, 11, and 24 and the detailed description. $^1$H NMR data for exemplary compounds from Table 8 is provided in Table 8A.

TABLE 8

| Compd No. | Structure | Name | Observed m/z |
|---|---|---|---|
| 28A | 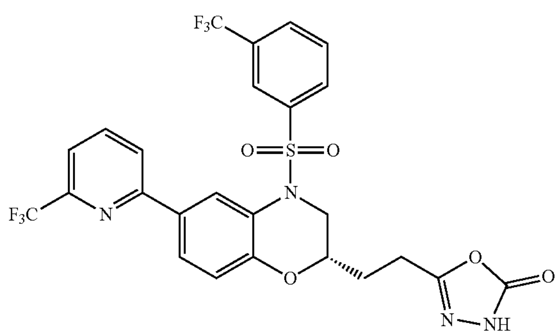 [SMILES: O=c1[nH]nc(CC[C@H]2CN(S(=O)(=O)c3cccc(C(F)(F)F)c3)c3cc(-c4cccc(C(F)(F)F)n4)ccc3O2)o1] | (S)-5-(2-(4-((3-(trifluoromethyl)phenyl)sulfonyl)-6-(6-(trifluoromethyl)pyridin-2-yl)-3,4-dihydro-2H-benzo[b][1,4]oxazin-2-yl)ethyl)-1,3,4-oxadiazol-2(3H)-one | 601 (M + H)$^+$ |

TABLE 8-continued

| Compd No. | Structure | Name | Observed m/z |
|---|---|---|---|
| 28B | 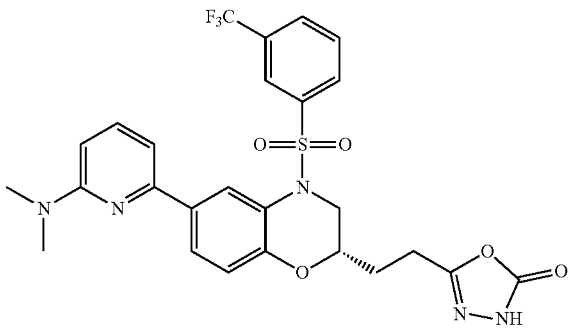 [SMILES: CN(C)c1cccc(-c2ccc3c(c2)N(S(=O)(=O)c2cccc(C(F)(F)F)c2)C[C@H](CCc2n[nH]c(=O)o2)O3)n1] | (S)-5-(2-(6-(6-(dimethylamino)-pyridin-2-yl)-4-((3-(trifluoromethyl)phenyl)sulfonyl)-3,4-dihydro-2H-benzo[b][1,4]oxazin-2-yl)ethyl)-1,3,4-oxadiazol-2(3H)-one | 576 (M + H)+ |
| 28C | 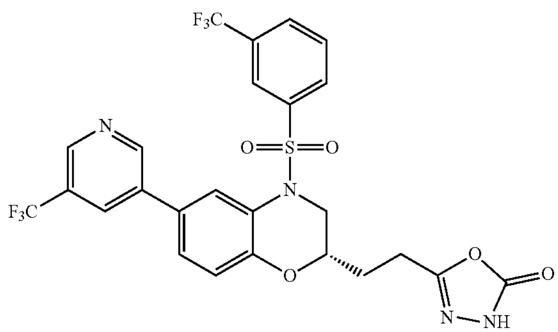 [SMILES: O=c1[nH]nc(CC[C@H]2CN(S(=O)(=O)c3cccc(C(F)(F)F)c3)c3cc(-c4cncc(C(F)(F)F)c4)ccc3O2)o1] | (S)-5-(2-(4-((3-(trifluoromethyl)phenyl)sulfonyl)-6-(5-(trifluoromethyl)pyridin-3-yl)-3,4-dihydro-2H-benzo[b][1,4]oxazin-2-yl)ethyl)-1,3,4-oxadiazol-2(3H)-one | 601 (M + H)+ |
| 28D | 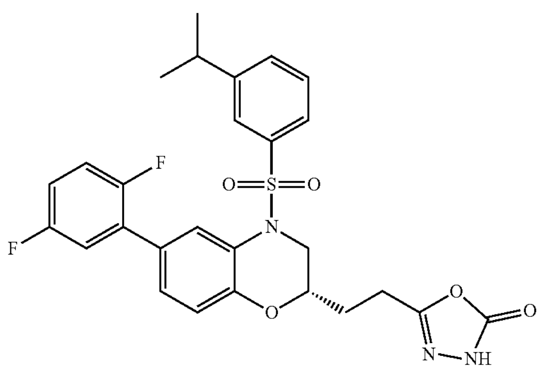 [SMILES: CC(C)c1cccc(S(=O)(=O)N2C[C@H](CCc3n[nH]c(=O)o3)Oc3ccc(-c4cc(F)ccc4F)cc32)c1] | (S)-5-(2-(6-(2,5-difluorophenyl)-4-((3-isopropylphenyl)sulfonyl)-3,4-dihydro-2H-benzo[b][1,4]-oxazin-2-yl)ethyl)-1,3,4-oxadiazol-2(3H)-one | 542 (M + H)+ |
| 28E | 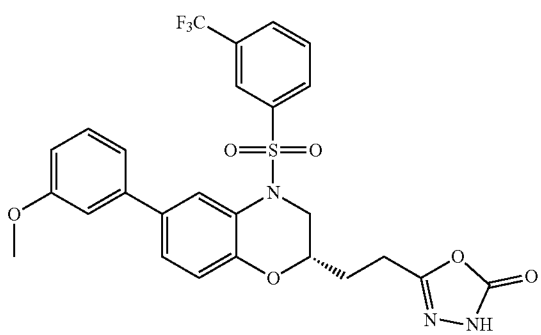 [SMILES: COc1cccc(-c2ccc3c(c2)N(S(=O)(=O)c2cccc(C(F)(F)F)c2)C[C@H](CCc2n[nH]c(=O)o2)O3)c1] | (S)-5-(2-(6-(3-methoxyphenyl)-4-((3-(trifluoromethyl)phenyl)-sulfonyl)-3,4-dihydro-2H-benzo[b][1,4]oxazin-2-yl)ethyl)-1,3,4-oxadiazol-2(3H)-one | 562 (M + H)+ |

TABLE 8-continued

| Compd No. | Structure | Name | Observed m/z |
|---|---|---|---|
| 28F | 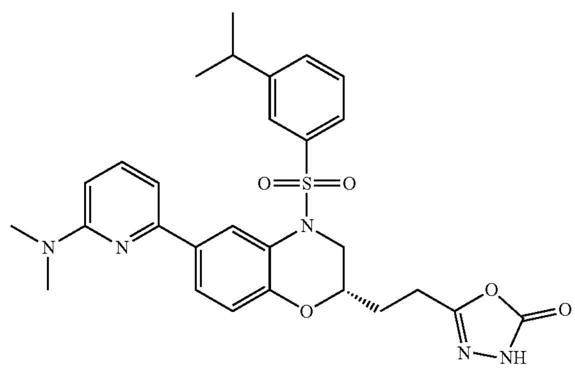 [SMILES: CC(C)c1cccc(S(=O)(=O)N2C[C@H](CCc3n[nH]c(=O)o3)Oc3ccc(-c4cccc(N(C)C)n4)cc32)c1] | (S)-5-(2-(6-(6-(dimethylamino)-pyridin-2-yl)-4-((3-isopropyl-phenyl)sulfonyl)-3,4-dihydro-2H-benzo[b][1,4]oxazin-2-yl)ethyl)-1,3,4-oxadiazol-2(3H)-one | 550 (M + H)+ |
| 28G | 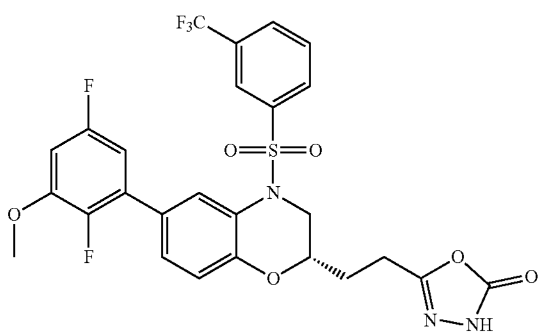 [SMILES: COc1cc(F)cc(-c2ccc3c(c2)N(S(=O)(=O)c2cccc(C(F)(F)F)c2)C[C@H](CCc2n[nH]c(=O)o2)O3)c1F] | (S)-5-(2-(6-(2,5-difluoro-3-methoxyphenyl)-4-((3-(trifluoromethyl)phenyl)sulfonyl)-3,4-dihydro-2H-benzo[b][1,4]-oxazin-2-yl)ethyl)-1,3,4-oxadiazol-2(3H)-one | 598 (M + H)+ |
| 28H | 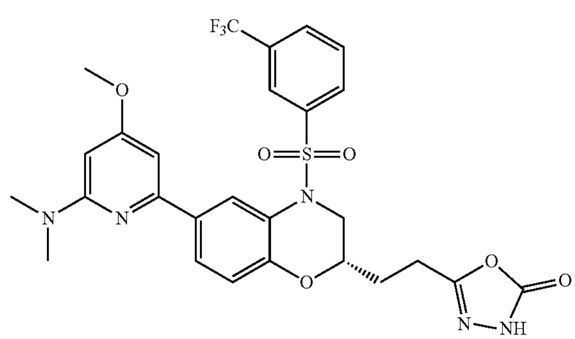 [SMILES: COc1cc(-c2ccc3c(c2)N(S(=O)(=O)c2cccc(C(F)(F)F)c2)C[C@H](CCc2n[nH]c(=O)o2)O3)nc(N(C)C)c1] | (S)-5-(2-(6-(6-(dimethylamino)-4-methoxypyridin-2-yl)-4-((3-(trifluoromethyl)phenyl)sulfonyl)-3,4-dihydro-2H-benzo[b][1,4]-oxazin-2-yl)ethyl)-1,3,4-oxadiazol-2(3H)-one | 606 (M + H)+ |
| 28I | 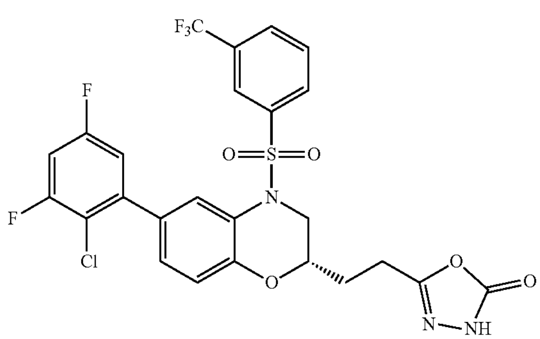 [SMILES: O=c1[nH]nc(CC[C@H]2CN(S(=O)(=O)c3cccc(C(F)(F)F)c3)c3cc(-c4cc(F)cc(F)c4Cl)ccc3O2)o1] | (S)-5-(2-(6-(2-chloro-3,5-difluorophenyl)-4-((3-(trifluoromethyl)phenyl)sulfonyl)-3,4-dihydro-2H-benzo[b][1,4]oxazin-2-yl)ethyl)-1,3,4-oxadiazol-2(3H)-one | 624 (M + Na)+ |

TABLE 8-continued

| Compd No. | Structure | Name | Observed m/z |
|---|---|---|---|
| 28J | 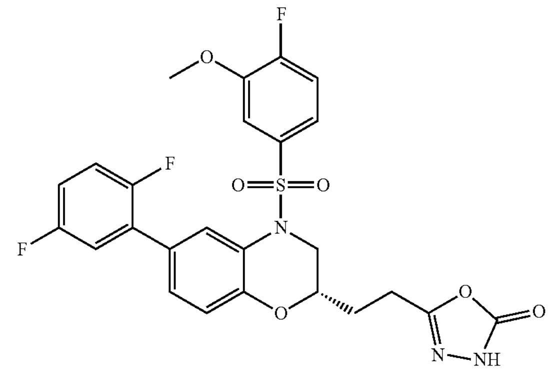 [SMILES: COc1cc(S(=O)(=O)N2C[C@H](CCc3n[nH]c(=O)o3)Oc3ccc(-c4cc(F)ccc4F)cc32)ccc1F] | (S)-5-(2-(6-(2,5-difluorophenyl)-4-((4-fluoro-3-methoxyphenyl)-sulfonyl)-3,4-dihydro-2H-benzo[b][1,4]oxazin-2-yl)ethyl)-1,3,4-oxadiazol-2(3H)-one | 548 (M + H)+ |
| 28K | 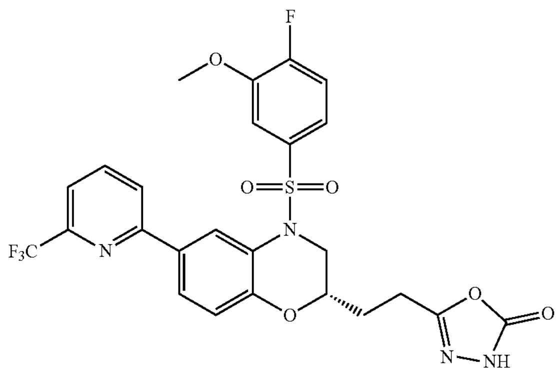 [SMILES: COc1cc(S(=O)(=O)N2C[C@H](CCc3n[nH]c(=O)o3)Oc3ccc(-c4cccc(C(F)(F)F)n4)cc32)ccc1F] | (S)-5-(2-(4-((4-fluoro-3-methoxyphenyl)sulfonyl)-6-(6-(trifluoromethyl)pyridin-2-yl)-3,4-dihydro-2H-benzo[b][1,4]oxazin-2-yl)ethyl)-1,3,4-oxadiazol-2(3H)-one | 581 (M + H)+ |

TABLE 8A

| Compd No. | $^1$H NMR Data |
|---|---|
| 28A | $^1$H NMR (300 MHz, CD$_3$OD-d$_4$) δ 8.57 (s, 1H), 8.08-7.94 (m, 5H), 7.74 (dd, 1H), 7.68 (m, 1H), 7.67 (s, 1H), 6.94 (d, 1H), 4.45 (dd, 1H), 3.63 (m, 1H), 3.60 (dd, 1H), 2.75 (m, 2H), 2.04 (m, 1H), 1.94 (m, 1H). |
| 28B | $^1$H NMR (300 MHz, CD$_3$OD-d$_4$) δ 8.30 (d, J = 2.2 Hz, 1H), 8.05 (dd, J = 8.0, 1.7 Hz, 1H), 7.99 (dd, J = 8.0, 1.8 Hz, 1H), 7.95 (d, J = 1.7 Hz, 1H), 7.90 (d, J = 9.0, 7.3 Hz, 1H), 7.78 (t, J = 7.9 Hz, 1H), 7.61 (dd, J = 8.6, 2.2 Hz, 1H), 7.09-6.97 (m, 3H), 4.44 (dd, J = 14.5, 2.3 Hz, 1H), 3.46 (ddq, J = 10.8, 6.1, 2.3 Hz, 1H), 3.36 (m, 1H), 2.72 (t, J = 7.2 Hz, 2H), 2.00 (ddt, J = 11.4, 7.6, 3.8 Hz, 1H), 1.89 (m, 1H). |
| 28C | $^1$H NMR (300 MHz, CD$_3$OD-d$_4$) δ 9.05 (s, 1H), 8.86 (s, 1H), 8.29 (s, 1H), 8.12 (s, 1H), 8.05-7.95 (m, 2H), 7.91 (s, 1H), 7.79 (t, 1H), 7.53 (d, 1H), 7.00 (d, 1H), 4.45 (dd, 1H), 3.48 (m, 1H), 3.37-3.30 (m, 2H), 2.72 (m, 2H), 2.03 (m, 1H), 1.87 (m, 1H). |
| 28D | $^1$H NMR (300 MHz, CD$_3$OD-d$_4$) δ 8.05 (s, 1H), 7.58 (d, 1H), 7.56-7.44 (m, 2H), 7.36 (s, 1H), 7.31-7.09 (m, 4H), 6.89 (d, 1H), 4.35 (dd, 1H), 3.22 (m, 2H), 2.86 (m, 1H), 2.70 (m, 2H), 1.94 (m, 1H), 1.85 (m, 1H), 1.10-1.05 (m, 6H). |
| 28E | $^1$H NMR (300 MHz, CD$_3$OD-d$_4$) δ 8.01 (s, 1H), 8.00-7.95 (m, 2H), 7.89 (s, 1H), 7.78 (m, 1H), 7.40-7.35 (m, 2H), 7.14 (d, 1H), 7.09 (s, 1H), 6.92-6.87 (m, 2H), 4.43 (dd, 1H), 3.45 (m, 1H), 3.32 (m, 1H), 2.72 (m, 2H), 2.00 (m, 1H), 1.88 (m, 1H). |
| 28F | $^1$H NMR (300 MHz, CD$_3$OD-d$_4$) δ 8.40 (s, 1H), 7.95 (t, 1H), 7.60-7.44 (m, 4H), 7.40 (s, 1H), 7.09-6.98 (m, 3H), 4.34 (dd, 1H), 3.34 (s, 6H), 3.30-3.18 (m, 2H), 2.89 (m, 1H), 2.68 (m, 2H), 1.93 (m, 1H), 1.83 (m, 1H). |
| 28G | $^1$H NMR (300 MHz, CD$_3$OD-d$_4$) δ 8.05-7.93 (m, 4H), 7.82-7.78 (m, 1H), 7.31-7.28 (m, 1H), 6.97-6.91 (m, 2H), 6.74 (m, 1H), 4.51 (dd, J = 14.3, 2.4 Hz, 1H), 3.95 (s, 3H), 3.52-3.39 (m, 2H), 2.77-2.73 (m, 2H), 2.06-1.88 (m, 2H). |
| 28H | $^1$H NMR (300 MHz, CD$_3$OD-d$_4$) δ 8.22 (s, 1H), 8.09-7.91 (m, 3H), 7.78 (t, J = 7.9 Hz, 1H), 7.56 (d, J = 8.5 Hz, 1H), 7.04-6.97 (m, 1H), 6.68 (d, J = 2.1 Hz, 1H), 6.36 (s, 1H), 4.44 (dd, J = 14.5, 2.3 Hz, 1H), 4.04 (s, 3H), 3.44 (t, J = 9.7 Hz, 2H), 3.35 (d, J = 9.9 Hz, 6H), 2.72 (t, J = 7.2 Hz, 2H), 2.07-1.82 (m, 2H). |

TABLE 8A-continued

| Compd No. | ¹H NMR Data |
|---|---|
| 28I | ¹H NMR (300 MHz, CD$_3$OD-d$_4$) δ 8.05 (d, J = 8.0 Hz, 1H), 7.98 (d, J = 7.7 Hz, 1H), 7.93-7.85 (m, 2H), 7.80 (t, J = 7.9 Hz, 1H), 7.18 (ddd, J = 9.5, 6.7, 2.5 Hz, 2H), 7.04 (ddd, J = 8.9, 2.9, 1.7 Hz, 1H), 6.93 (d, J = 8.5 Hz, 1H), 4.47 (dd, J = 14.3, 2.3 Hz, 1H), 3.54-3.43 (m, 1H), 3.36 (d, J = 10.1 Hz, 1H), 2.74 (t, J = 7.2 Hz, 2H), 2.10-1.82 (m, 2H). |
| 28J | ¹H NMR (300 MHz, CD$_3$OD-d$_4$) δ 8.06 (s, 1H), 7.38-7.08 (m, 7H), 6.93 (d, 1H), 4.41 (dd, 1H), 3.66 (s, 3H), 3.41 (m, 1H), 3.28 (m, 1H), 2.73 (m, 2H), 2.01 (m, 1H), 1.88 (m, 1H). |
| 28K | ¹H NMR (300 MHz, CD$_3$OD-d$_4$) δ 8.64 (s, 1H), 8.10-8.09 (m, 2H), 7.89 (dd, 1H), 7.72 (m, 1H), 7.43 (m, 1H), 7.30-7.24 (m, 2H), 6.98 (d, 1H), 4.43 (dd, 1H), 3.71 (s, 3H), 3.55 (m, 1H), 3.33 (m, 1H), 2.78 (m, 2H), 2.05 (m, 1H), 1.95 (m, 1H). |

Example 29—Synthesis of (S)—N-(2-(6-(2,5-difluorophenyl)-4-((3-(trifluoromethyl)phenyl)sulfonyl)-3,4-dihydro-2H-benzo[b][1,4]oxazin-2-yl)ethyl)-2-hydroxy-2-methylpropanamide

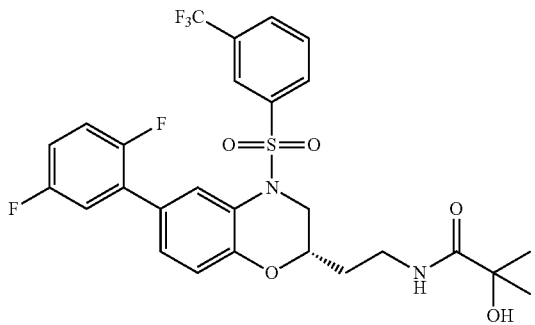 [SMILES: CC(C)(O)C(=O)NCC[C@H]1CN(S(=O)(=O)c2cccc(C(F)(F)F)c2)c2cc(-c3cc(F)ccc3F)ccc2O1]

A solution of (S)-2-(6-(2,5-difluorophenyl)-4-((3-(trifluoromethyl)phenyl) sulfonyl)-3,4-dihydro-2H-benzo[b][1,4]oxazin-2-yl)ethan-1-amine (100 mg, 0.20 mmol), 2-hydroxy-2-methylpropanoic acid (30 mg, 0.29 mmol), 1-[bis(dimethylamino) methylene]-1H-1,2,3-triazolo[4,5-b]pyridinium 3-oxid hexafluorophosphate (150 mg, 0.39 mmol), diisopropylethylamine (50 mg, 0.39 mmol), and dichloromethane (15 mL) was stirred for three hours at room temperature. Then, the mixture was concentrated, and the residue was purified by Prep-HPLC eluting with a gradient of 50-80% acetonitrile in water with 0.1% trifluoroacetic acid to afford (S)—N-(2-(6-(2,5-difluorophenyl)-4-((3-(trifluoromethyl)phenyl) sulfonyl)-3,4-dihydro-2H-benzo[b][1,4]oxazin-2-yl)ethyl)-2-hydroxy-2-methylpropanamide (56 mg, 48%) as a white solid. ¹H-NMR (400 MHz, CD$_3$OD) δ 8.09 (dd, J=7.8, 1.5 Hz, 1H), 8.04-7.96 (m, 3H), 7.82 (t, J=8.1 Hz, 1H), 7.34-7.17 (m, 3H), 7.12 (m, 1H), 6.98 (d, J=8.5 Hz, 1H), 4.48 (dd, J=14.3, 2.5 Hz, 1H), 3.65 (tdd, J=8.0, 4.3, 2.4 Hz, 1H), 3.41-3.32 (m, 3H), 1.96-1.73 (m, 2H), 1.37 (d, J=4.9 Hz, 6H). (ES, m/z): (M+H)$^+$ 585.

Example 30—Preparation of Additional Substituted 4-((aryl or heteroaryl)-sulfonyl)-3,4-dihydro-2H-benzo[b][1,4]oxazin-2-yl) Compounds Compounds in Tables 9 and 9A were prepared based on experimental procedures described in Examples 12, 13, 17, and 29 and the detailed description.

TABLE 9

| Compd No. | Structure | Name | Observed m/z |
|---|---|---|---|
| 30A | 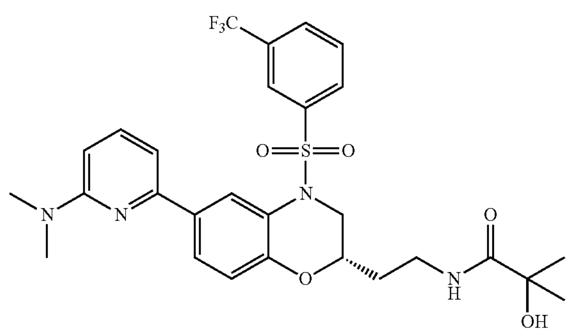 [SMILES: CN(C)c1cccc(-c2ccc3c(c2)N(S(=O)(=O)c2cccc(C(F)(F)F)c2)C[C@H](CCNC(=O)C(C)(C)O)O3)n1] | (S)-N-(2-(6-(6-(dimethylamino)-pyridin-2-yl)-4-((3-(trifluoromethyl)phenyl)sulfonyl)-3,4-dihydro-2H-benzo[b][1,4]-oxazin-2-yl)ethyl)-2-hydroxy-2-methylpropanamide | 593 (M + H)$^+$ |

TABLE 9-continued

| Compd No. | Structure | Name | Observed m/z |
|---|---|---|---|
| 30B | 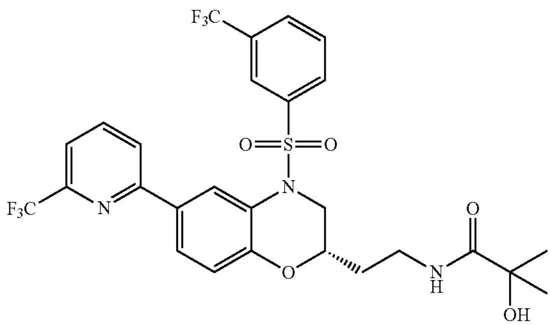 [SMILES: CC(C)(O)C(=O)NCC[C@H]1CN(S(=O)(=O)c2cccc(C(F)(F)F)c2)c2cc(-c3cccc(C(F)(F)F)n3)ccc2O1] | (S)-2-hydroxy-2-methyl-N-(2-(4-((3-(trifluoromethyl)phenyl)-sulfonyl)-6-(6-(trifluoromethyl)-pyridin-2-yl)-3,4-dihydro-2H-benzo[b][1,4]oxazin-2-yl)ethyl)propanamide | 618 (M + H)+ |
| 30C | 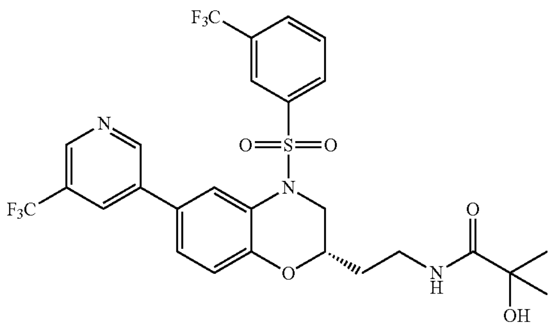 [SMILES: CC(C)(O)C(=O)NCC[C@H]1CN(S(=O)(=O)c2cccc(C(F)(F)F)c2)c2cc(-c3cncc(C(F)(F)F)c3)ccc2O1] | (S)-2-hydroxy-2-methyl-N-(2-(4-((3-(trifluoromethyl)-phenyl)sulfonyl)-6-(5-(trifluoromethyl)pyridin-3-yl)-3,4-dihydro-2H-benzo[b][1,4]oxazin-2-yl)ethyl)propanamide | 618 (M + H)+ |
| 30D | 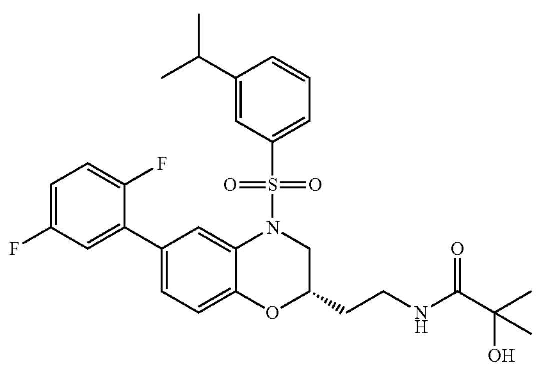 [SMILES: CC(C)c1cccc(S(=O)(=O)N2C[C@H](CCNC(=O)C(C)(C)O)Oc3ccc(-c4cc(F)ccc4F)cc32)c1] | (S)-N-(2-(6-(2,5-difluoro-phenyl)-4-((3-isopropylphenyl)-sulfonyl)-3,4-dihydro-2H-benzo[b][1,4]oxazin-2-yl)ethyl)-2-hydroxy-2-methylpropanamide | 559 (M + H)+ |
| 30E | 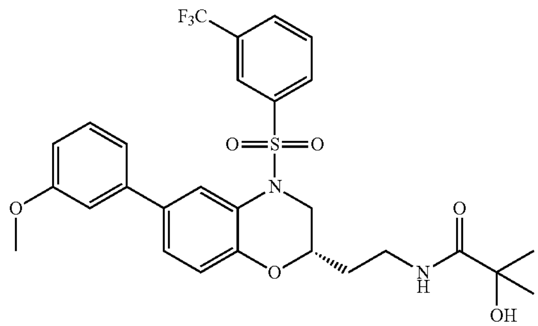 [SMILES: COc1cccc(-c2ccc3c(c2)N(S(=O)(=O)c2cccc(C(F)(F)F)c2)C[C@H](CCNC(=O)C(C)(C)O)O3)c1] | (S)-2-hydroxy-N-(2-(6-(3-methoxyphenyl)-4-((3-(trifluoromethyl)phenyl)sulfonyl)-3,4-dihydro-2H-benzo[6][1,4]oxazin-2-yl)ethyl)-2-methylpropanamide | 579 (M + H)+ |

TABLE 9-continued

| Compd No. | Structure | Name | Observed m/z |
|---|---|---|---|
| 30F | 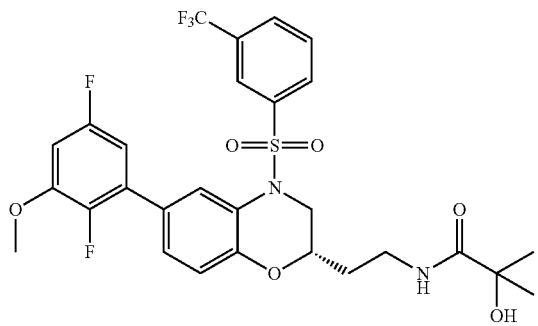 [SMILES: COc1cc(F)cc(-c2ccc3c(c2)N(S(=O)(=O)c2cccc(C(F)(F)F)c2)C[C@H](CCNC(=O)C(C)(C)O)O3)c1F] | (S)-N-(2-(6-(2,5-difluoro-3-methoxyphenyl)-4-((3-(trifluoromethyl)phenyl)sulfonyl)-3,4-dihydro-2H-benzo[b][1,4]oxazin-2-yl)ethyl)-2-hydroxy-2-methylpropanamide | 615 (M + H)+ |
| 30G | 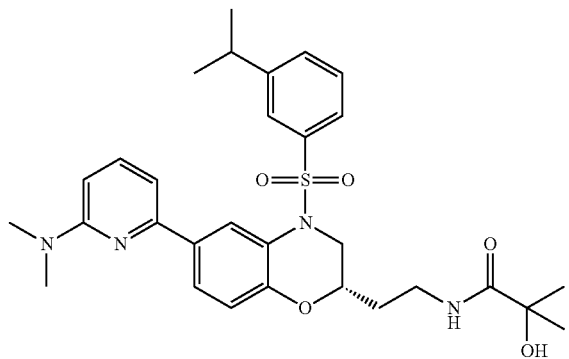 [SMILES: CC(C)c1cccc(S(=O)(=O)N2C[C@H](CCNC(=O)C(C)(C)O)Oc3ccc(-c4cccc(N(C)C)n4)cc32)c1] | (S)-N-(2-(6-(6-(dimethylamino)-pyridin-2-yl)-4-((3-isopropyl-phenyl)sulfonyl)-3,4-dihydro-2H-benzo[b][1,4]oxazin-2-yl)ethyl)-2-hydroxy-2-methylpropanamide | 567 (M + H)+ |
| 30H | 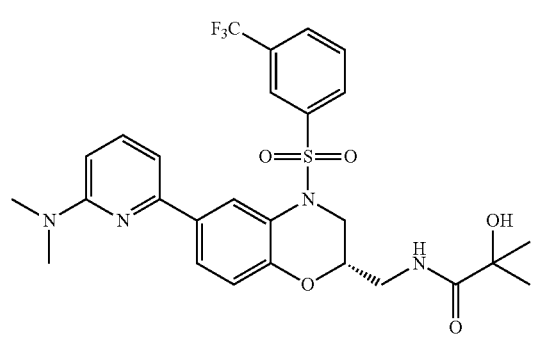 [SMILES: CN(C)c1cccc(-c2ccc3c(c2)N(S(=O)(=O)c2cccc(C(F)(F)F)c2)C[C@H](CNC(=O)C(C)(C)O)O3)n1] | (S)-N-((6-(6-(dimethylamino)-pyridin-2-yl)-4-((3-(trifluoromethyl)phenyl)sulfonyl)-3,4-dihydro-2H-benzo[b][1,4]oxazin-2-yl)methyl)-2-hydroxy-2-methylpropanamide | 579 (M + H)+ |
| 30I | 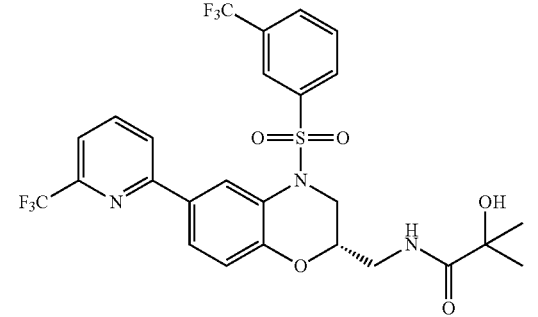 [SMILES: CC(C)(O)C(=O)NC[C@H]1CN(S(=O)(=O)c2cccc(C(F)(F)F)c2)c2cc(-c3cccc(C(F)(F)F)n3)ccc2O1] | (S)-2-hydroxy-2-methyl-N-((4-((3-(trifluoromethyl)phenyl)-sulfonyl)-6-(6-(trifluoromethyl)-pyridin-2-yl)-3,4-dihydro-2H-benzo[b][1,4]oxazin-2-yl)methyl)propanamide | 604 (M + H)+ |

TABLE 9-continued

| Compd No. | Structure | Name | Observed m/z |
|---|---|---|---|
| 30J | 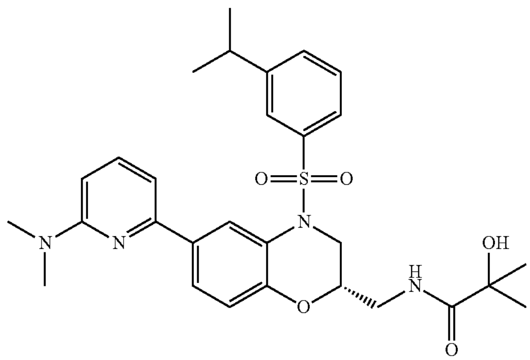 [SMILES: CC(C)c1cccc(S(=O)(=O)N2C[C@H](CNC(=O)C(C)(C)O)Oc3ccc(-c4cccc(N(C)C)n4)cc32)c1] | (S)-N-((6-(6-(dimethylamino)-pyridin-2-yl)-4-((3-isopropylphenyl)sulfonyl)-3,4-dihydro-2H-benzo[b][1,4]oxazin-2-yl)methyl)-2-hydroxy-2-methylpropanamide | 553 (M + H)+ |
| 30K | 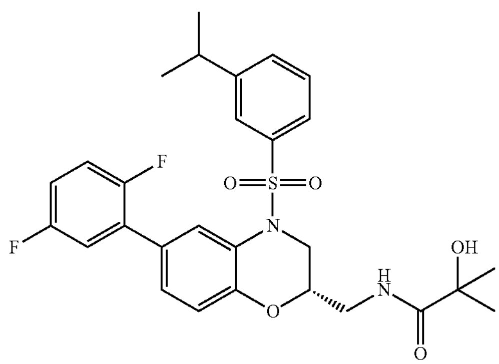 [SMILES: CC(C)c1cccc(S(=O)(=O)N2C[C@H](CNC(=O)C(C)(C)O)Oc3ccc(-c4cc(F)ccc4F)cc32)c1] | (S)-N-((6-(2,5-difluorophenyl)-4-((3-isopropylphenyl)sulfonyl)-3,4-dihydro-2H-benzo[b][1,4]oxazin-2-yl)methyl)-2-hydroxy-2-methylpropanamide | 545 (M + H)+ |
| 30L | 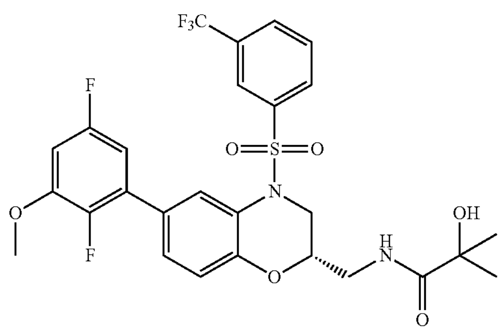 [SMILES: COc1cc(F)cc(-c2ccc3c(c2)N(S(=O)(=O)c2cccc(C(F)(F)F)c2)C[C@H](CNC(=O)C(C)(C)O)O3)c1F] | (S)-N-((6-(2,5-difluoro-3-methoxyphenyl)-4-((3-(trifluoromethyl)phenyl)sulfonyl)-3,4-dihydro-2H-benzo[b][1,4]oxazin-2-yl)methyl)-2-hydroxy-2-methylpropanamide | 601 (M + H)+ |
| 30M | 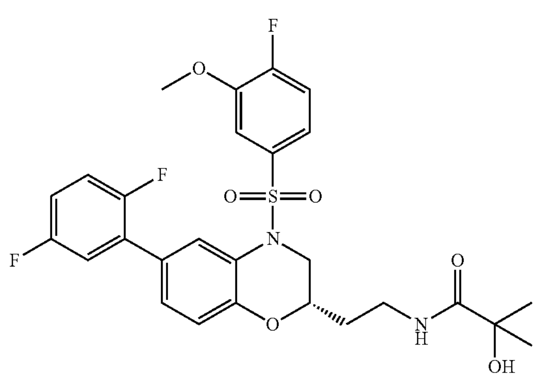 [SMILES: COc1cc(S(=O)(=O)N2C[C@H](CCNC(=O)C(C)(C)O)Oc3ccc(-c4cc(F)ccc4F)cc32)ccc1F] | (S)-N-(2-(6-(2,5-difluorophenyl)-4-((4-fluoro-3-methoxyphenyl)sulfonyl)-3,4-dihydro-2H-benzo[b][1,4]oxazin-2-yl)ethyl)-2-hydroxy-2-methylpropanamide | 565 (M + H)+ |

TABLE 9-continued

| Compd No. | Structure | Name | Observed m/z |
|---|---|---|---|
| 30N | 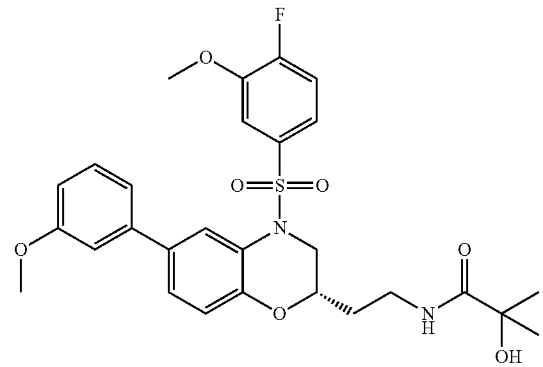 [SMILES: COc1cccc(-c2ccc3c(c2)N(S(=O)(=O)c2ccc(F)c(OC)c2)C[C@H](CCNC(=O)C(C)(C)O)O3)c1] | (S)-N-(2-(4-((4-fluoro-3-methoxyphenyl)sulfonyl)-6-(3-methoxyphenyl)-3,4-dihydro-2H-benzo[b][1,4]oxazin-2-yl)ethyl)-2-hydroxy-2-methylpropanamide | 559 (M + H)+ |
| 30O | 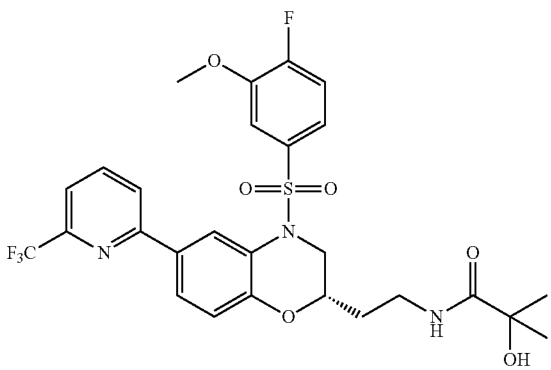 [SMILES: COc1cc(S(=O)(=O)N2C[C@H](CCNC(=O)C(C)(C)O)Oc3ccc(-c4cccc(C(F)(F)F)n4)cc32)ccc1F] | (S)-N-(2-(4-((4-fluoro-3-methoxyphenyl)sulfonyl)-6-(6-(trifluoromethyl)pyridin-2-yl)-3,4-dihydro-2H-benzo[b][1,4]-oxazin-2-yl)ethyl)-2-hydroxy-2-methylpropanamide | 598 (M + H)+ |
| 30P | 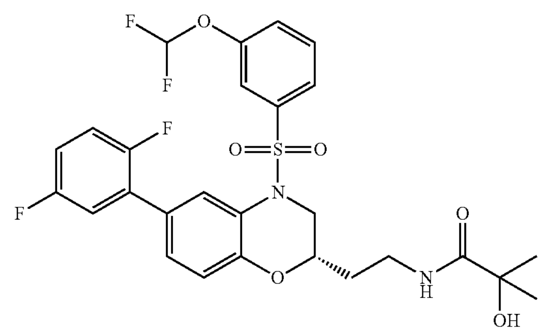 [SMILES: CC(C)(O)C(=O)NCC[C@H]1CN(S(=O)(=O)c2cccc(OC(F)F)c2)c2cc(-c3cc(F)ccc3F)ccc2O1] | (S)-N-(2-(4-((3-(difluoro-methoxy)phenyl)sulfonyl)-6-(2,5-difluorophenyl)-3,4-dihydro-2H-benzo[b][1,4]oxazin-2-yl)ethyl)-2-hydroxy-2-methylpropanamide | 583 (M + H)+ |
| 30Q | 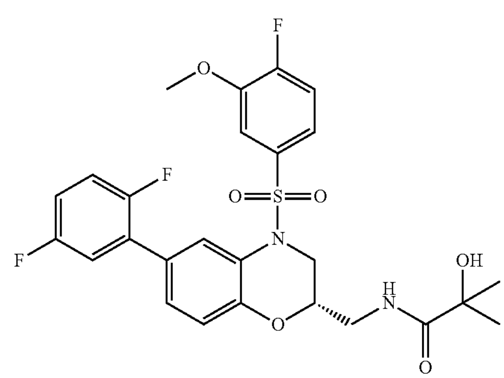 [SMILES: COc1cc(S(=O)(=O)N2C[C@H](CNC(=O)C(C)(C)O)Oc3ccc(-c4cc(F)ccc4F)cc32)ccc1F] | (S)-N-((6-(2,5-difluorophenyl)-4-((4-fluoro-3-methoxyphenyl)-sulfonyl)-3,4-dihydro-2H-benzo[b][1,4]oxazin-2-yl)methyl)-2-hydroxy-2-methylpropanamide | 551 (M + H)+ |

TABLE 9-continued

| Compd No. | Structure | Name | Observed m/z |
|---|---|---|---|
| 30R | 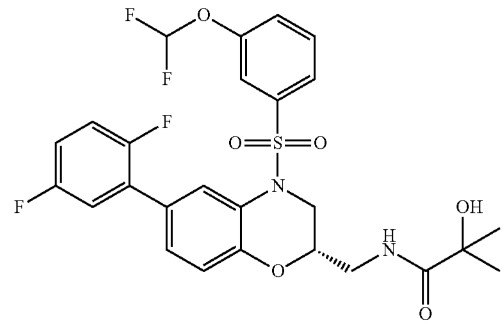 [SMILES: CC(C)(O)C(=O)NC[C@H]1CN(S(=O)(=O)c2cccc(OC(F)F)c2)c2cc(-c3cc(F)ccc3F)ccc2O1] | (S)-N-((4-((3-(difluoromethoxy)-phenyl)sulfonyl)-6-(2,5-difluorophenyl)-3,4-dihydro-2H-benzo[b][1,4]oxazin-2-yl)methyl)-2-hydroxy-2-methylpropanamide | 569 (M + H)+ |
| 30S | 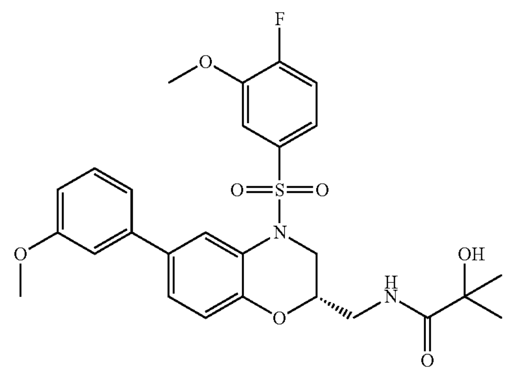 [SMILES: COc1cccc(-c2ccc3c(c2)N(S(=O)(=O)c2ccc(F)c(OC)c2)C[C@H](CNC(=O)C(C)(C)O)O3)c1] | (S)-N-((4-((4-fluoro-3-methoxyphenyl)sulfonyl)-6-(3-methoxyphenyl)-3,4-dihydro-2H-benzo[b][1,4]oxazin-2-yl)methyl)-2-hydroxy-2-methylpropanamide | 545 (M + H)+ |
| 30T | 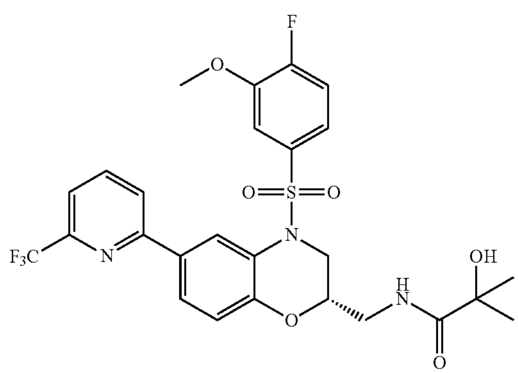 [SMILES: COc1cc(S(=O)(=O)N2C[C@H](CNC(=O)C(C)(C)O)Oc3ccc(-c4cccc(C(F)(F)F)n4)cc32)ccc1F] | (S)-N-((4-((4-fluoro-3-methoxyphenyl)sulfonyl)-6-(6-(trifluoromethyl)pyridin-2-yl)-3,4-dihydro-2H-benzo[b][1,4]oxazin-2-yl)methyl)-2-hydroxy-2-methylpropanamide | 584 (M + H)+ |
| 30U | 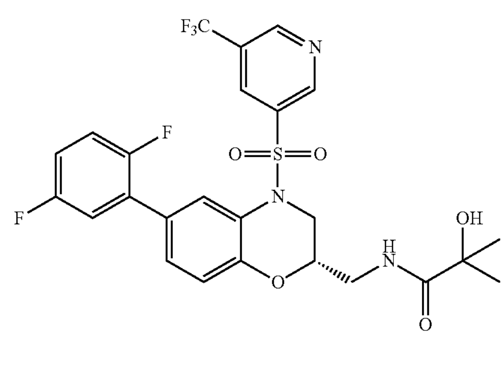 [SMILES: CC(C)(O)C(=O)NC[C@H]1CN(S(=O)(=O)c2cncc(C(F)(F)F)c2)c2cc(-c3cc(F)ccc3F)ccc2O1] | (S)-N-((6-(2,5-difluorophenyl)-4-((5-(trifluoromethyl)pyridin-3-yl)sulfonyl)-3,4-dihydro-2H-benzo[b][1,4]oxazin-2-yl)methyl)-2-hydroxy-2-methylpropanamide | 572 (M + H)+ |

TABLE 9-continued

| Compd No. | Structure | Name | Observed m/z |
|---|---|---|---|
| 30V | 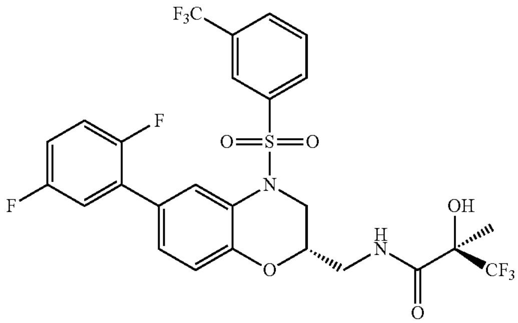 [SMILES: C[C@@](O)(C(=O)NC[C@H]1CN(S(=O)(=O)c2cccc(C(F)(F)F)c2)c2cc(-c3cc(F)ccc3F)ccc2O1)C(F)(F)F] | (R)-N-(((S)-6-(2,5-difluorophenyl)-4-((3-(trifluoromethyl)phenyl)sulfonyl)-3,4-dihydro-2H-benzo[b][1,4]oxazin-2-yl)methyl)-3,3,3-trifluoro-2-hydroxy-2-methylpropanamide | 625 (M + H)+ |
| 30W | 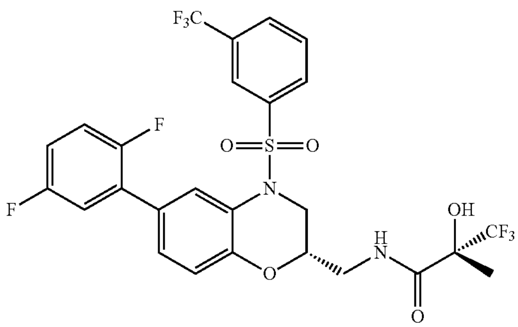 [SMILES: C[C@](O)(C(=O)NC[C@H]1CN(S(=O)(=O)c2cccc(C(F)(F)F)c2)c2cc(-c3cc(F)ccc3F)ccc2O1)C(F)(F)F] | (S)-N-(((S)-6-(2,5-difluorophenyl)-4-((3-(trifluoromethyl)phenyl)sulfonyl)-3,4-dihydro-2H-benzo[b][1,4]oxazin-2-yl)methyl)-3,3,3-trifluoro-2-hydroxy-2-methylpropanamide | 625 (M + H)+ |
| 30X | 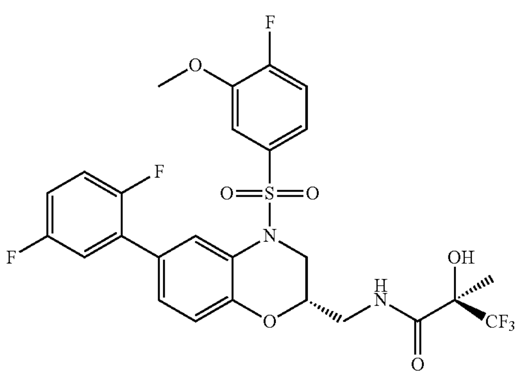 [SMILES: COc1cc(S(=O)(=O)N2C[C@H](CNC(=O)[C@@](C)(O)C(F)(F)F)Oc3ccc(-c4cc(F)ccc4F)cc32)ccc1F] | (R)-N-(((S)-6-(2,5-difluorophenyl)-4-((4-fluoro-3-methoxyphenyl)sulfonyl)-3,4-dihydro-2H-benzo[b][1,4]oxazin-2-yl)methyl)-3,3,3-trifluoro-2-hydroxy-2-methylpropanamide | 605 (M + H)+ |
| 30Y | 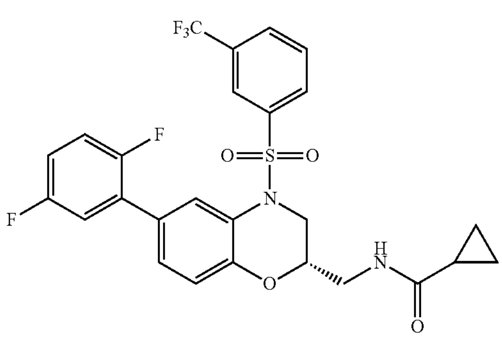 [SMILES: O=C(NC[C@H]1CN(S(=O)(=O)c2cccc(C(F)(F)F)c2)c2cc(-c3cc(F)ccc3F)ccc2O1)C1CC1] | (S)-N-((6-(2,5-difluorophenyl)-4-((3-(trifluoromethyl)phenyl)sulfonyl)-3,4-dihydro-2H-benzo[b][1,4]oxazin-2-yl)methyl)cyclopropanecarboxamide | 553 (M + H)+ |

TABLE 9-continued

| Compd No. | Structure | Name | Observed m/z |
|---|---|---|---|
| 30Z | 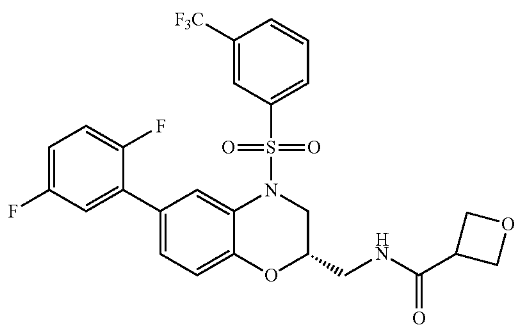 [SMILES: O=C(NC[C@H]1CN(S(=O)(=O)c2cccc(C(F)(F)F)c2)c2cc(-c3cc(F)ccc3F)ccc2O1)C1COC1] | (S)-N-((6-(2,5-difluorophenyl)-4-((3-(trifluoromethyl)phenyl)-sulfonyl)-3,4-dihydro-2H-benzo[b][1,4]oxazin-2-yl)methyl)oxetane-3-carboxamide | 569 (M + H)+ |
| 30AA | 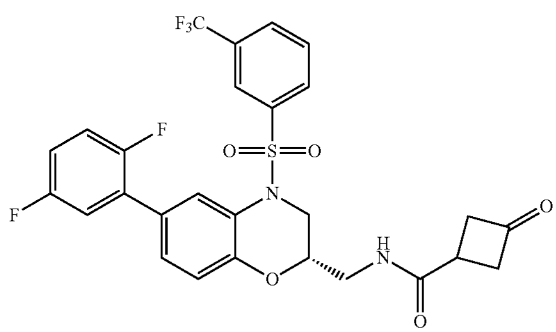 [SMILES: O=C1CC(C(=O)NC[C@H]2CN(S(=O)(=O)c3cccc(C(F)(F)F)c3)c3cc(-c4cc(F)ccc4F)ccc3O2)C1] | (S)-N-((6-(2,5-difluorophenyl)-4-((3-(trifluoromethyl)phenyl)-sulfonyl)-3,4-dihydro-2H-benzo[b][1,4]oxazin-2-yl)methyl)-3-oxocyclobutane-1-carboxamide | 581 (M + H)+ |
| 30AB | 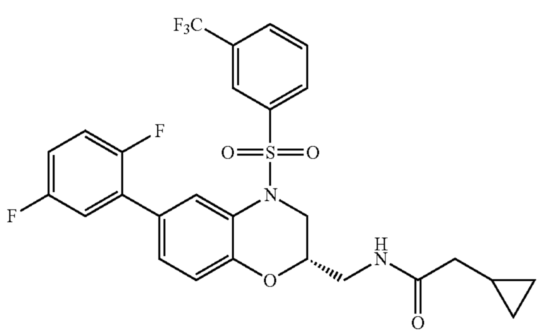 [SMILES: O=C(CC1CC1)NC[C@H]1CN(S(=O)(=O)c2cccc(C(F)(F)F)c2)c2cc(-c3cc(F)ccc3F)ccc2O1] | (S)-2-cyclopropyl-N-((6-(2,5-difluorophenyl)-4-((3-(trifluoromethyl)phenyl)sulfonyl)-3,4-dihydro-2H-benzo[b][1,4]oxazin-2-yl)methyl)acetamide | 567 (M + H)+ |
| 30AC | 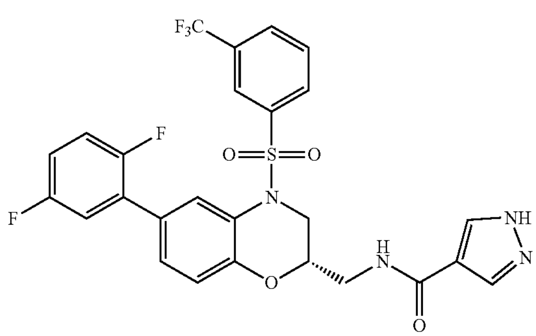 | (S)-N-((6-(2,5-difluorophenyl)-4-((3-(trifluoromethyl)phenyl)-sulfonyl)-3,4-dihydro-2H-benzo[b][1,4]oxazin-2-yl)methyl)-1H-pyrazole-4-carboxamide | 579 (M + H)+ |

TABLE 9-continued

| Compd No. | Structure | Name | Observed m/z |
|---|---|---|---|
| 30AD | 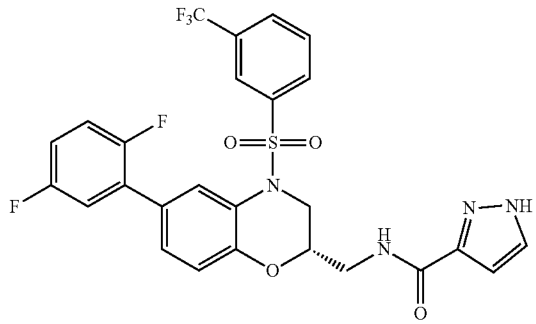 [SMILES: O=C(NC[C@H]1CN(S(=O)(=O)c2cccc(C(F)(F)F)c2)c2cc(-c3cc(F)ccc3F)ccc2O1)c1cn[nH]c1] | (S)-N-((6-(2,5-difluorophenyl)-4-((3-(trifluoromethyl)phenyl)-sulfonyl)-3,4-dihydro-2H-benzo[b][1,4]oxazin-2-yl)methyl)-1H-pyrazole-3-carboxamide | 579 (M + H)+ |
| 30AE | 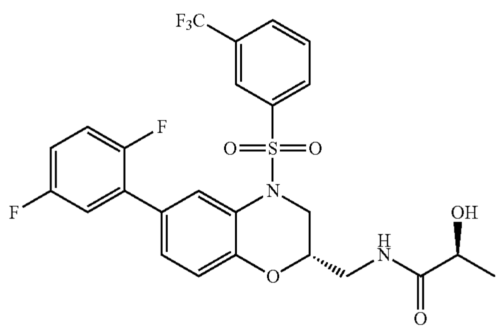 [SMILES: C[C@H](O)C(=O)NC[C@H]1CN(S(=O)(=O)c2cccc(C(F)(F)F)c2)c2cc(-c3cc(F)ccc3F)ccc2O1] | (S)-N-(((S)-6-(2,5-difluorophenyl)-4-((3-(trifluoromethyl)-phenyl)sulfonyl)-3,4-dihydro-2H-benzo[b][1,4]oxazin-2-yl)-methyl)-2-hydroxypropanamide | 557 (M + H)+ |
| 30AF | 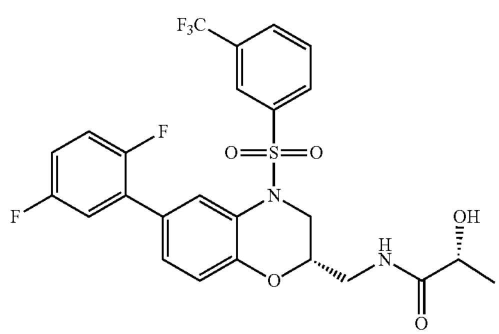 [SMILES: C[C@@H](O)C(=O)NC[C@H]1CN(S(=O)(=O)c2cccc(C(F)(F)F)c2)c2cc(-c3cc(F)ccc3F)ccc2O1] | (R)-N-(((S)-6-(2,5-difluorophenyl)-4-((3-(trifluoromethyl)-phenyl)sulfonyl)-3,4-dihydro-2H-benzo[b][1,4]oxazin-2-yl)-methyl)-2-hydroxypropanamide | 557 (M + H)+ |
| 30AG | 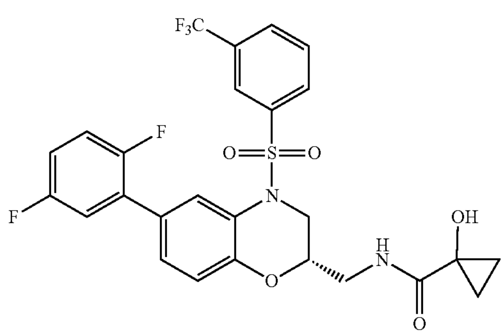 [SMILES: O=C(NC[C@H]1CN(S(=O)(=O)c2cccc(C(F)(F)F)c2)c2cc(-c3cc(F)ccc3F)ccc2O1)C1(O)CC1] | (S)-N-((6-(2,5-difluorophenyl)-4-((3-(trifluoromethyl)phenyl)-sulfonyl)-3,4-dihydro-2H-benzo[b][1,4]oxazin-2-yl)methyl)-1-hydroxycyclopropane-1-carboxamide | 569 (M + H)+ |

TABLE 9-continued

| Compd No. | Structure | Name | Observed m/z |
|---|---|---|---|
| 30AH | 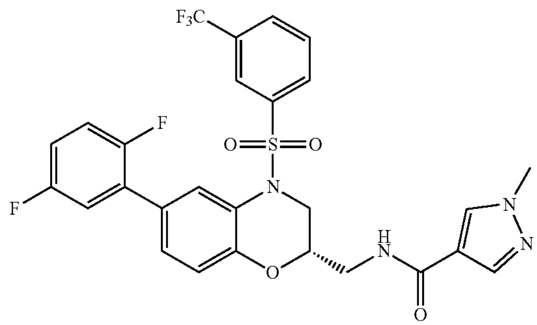 [SMILES: Cn1cc(C(=O)NC[C@H]2CN(S(=O)(=O)c3cccc(C(F)(F)F)c3)c3cc(-c4cc(F)ccc4F)ccc3O2)cn1] | (S)-N-((6-(2,5-difluorophenyl)-4-((3-(trifluoromethyl)phenyl)-sulfonyl)-3,4-dihydro-2H-benzo[b][1,4]oxazin-2-yl)methyl)-1-methyl-1H-pyrazole-4-carboxamide | 593 (M + H)+ |
| 30AI | 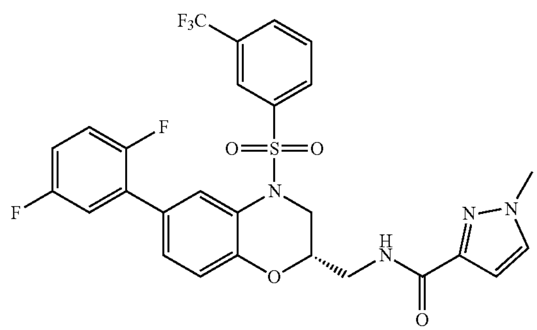 [SMILES: Cn1ccc(C(=O)NC[C@H]2CN(S(=O)(=O)c3cccc(C(F)(F)F)c3)c3cc(-c4cc(F)ccc4F)ccc3O2)n1] | (S)-N-((6-(2,5-difluorophenyl)-4-((3-(trifluoromethyl)phenyl)-sulfonyl)-3,4-dihydro-2H-benzo[b][1,4]oxazin-2-yl)methyl)-1-methyl-1H-pyrazole-3-carboxamide | 593 (M + H)+ |
| 30AJ | 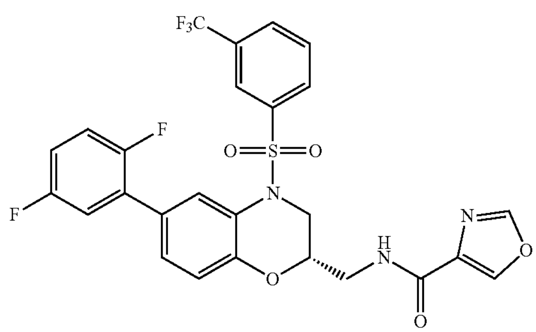 [SMILES: O=C(NC[C@H]1CN(S(=O)(=O)c2cccc(C(F)(F)F)c2)c2cc(-c3cc(F)ccc3F)ccc2O1)c1cnco1] | (S)-N-((6-(2,5-difluorophenyl)-4-((3-(trifluoromethyl)phenyl)-sulfonyl)-3,4-dihydro-2H-benzo[b][1,4]oxazin-2-yl)methyl)oxazole-4-carboxamide | 580 (M + H)+ |
| 30AK | 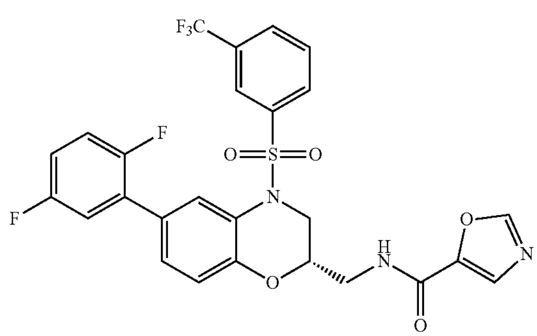 | (S)-N-((6-(2,5-difluorophenyl)-4-((3-(trifluoromethyl)phenyl)-sulfonyl)-3,4-dihydro-2H-benzo[b][1,4]oxazin-2-yl)methyl)oxazole-5-carboxamide | 580 (M + H)+ |

TABLE 9-continued

| Compd No. | Structure | Name | Observed m/z |
|---|---|---|---|
| 30AL | 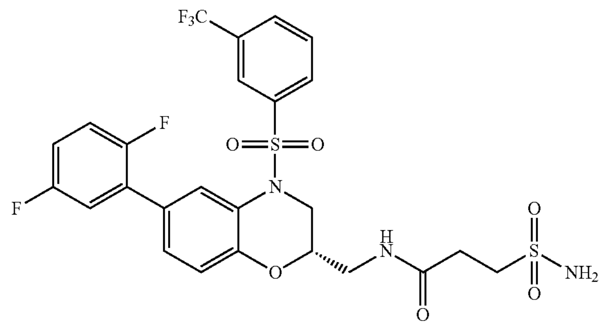 [SMILES: NS(=O)(=O)CCC(=O)NC[C@H]1CN(S(=O)(=O)c2cccc(C(F)(F)F)c2)c2cc(-c3cc(F)ccc3F)ccc2O1] | (S)-N-((6-(2,5-difluorophenyl)-4-((3-(trifluoromethyl)phenyl)-sulfonyl)-3,4-dihydro-2H-benzo[b][1,4]oxazin-2-yl)methyl)-3-sulfamoyl-propanamide | 620 (M + H)+ |
| 30AM | 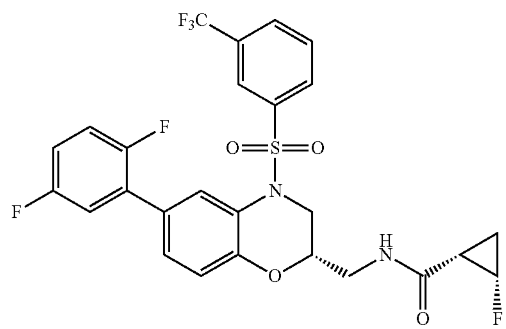 [SMILES: O=C(NC[C@H]1CN(S(=O)(=O)c2cccc(C(F)(F)F)c2)c2cc(-c3cc(F)ccc3F)ccc2O1)[C@@H]1C[C@@H]1F] | (1S,2S)-N-(((S)-6-(2,5-difluoro-phenyl)-4-((3-(trifluoromethyl)-phenyl)sulfonyl)-3,4-dihydro-2H-benzo[b][1,4]oxazin-2-yl)methyl)-2-fluorocyclo-propane-1-carboxamide | 571 (M + H)+ |
| 30AN | 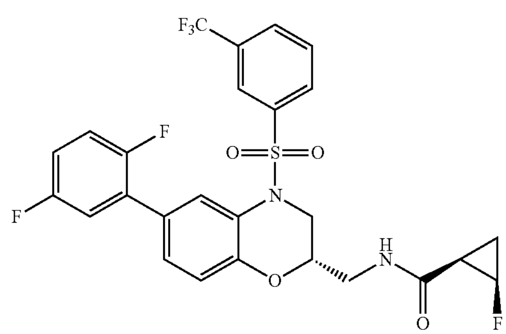 [SMILES: O=C(NC[C@H]1CN(S(=O)(=O)c2cccc(C(F)(F)F)c2)c2cc(-c3cc(F)ccc3F)ccc2O1)[C@H]1C[C@H]1F] | (1R,2R)-N-(((S)-6-(2,5-difluoro-phenyl)-4-((3-(trifluoromethyl)-phenyl)sulfonyl)-3,4-dihydro-2H-benzo[b][1,4]oxazin-2-yl)methyl)-2-fluorocyclo-propane-1-carboxamide | 571 (M + H)+ |
| 30AO | 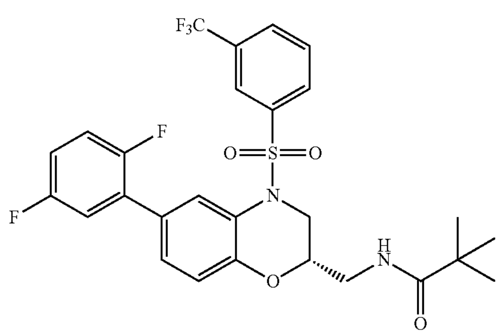 [SMILES: CC(C)(C)C(=O)NC[C@H]1CN(S(=O)(=O)c2cccc(C(F)(F)F)c2)c2cc(-c3cc(F)ccc3F)ccc2O1] | (S)-N-((6-(2,5-difluorophenyl)-4-((3-(trifluoromethyl)phenyl)-sulfonyl)-3,4-dihydro-2H-benzo[b][1,4]oxazin-2-yl)methyl)pivalamide | 569 (M + H)+ |

TABLE 9-continued

| Compd No. | Structure | Name | Observed m/z |
|---|---|---|---|
| 30AP | 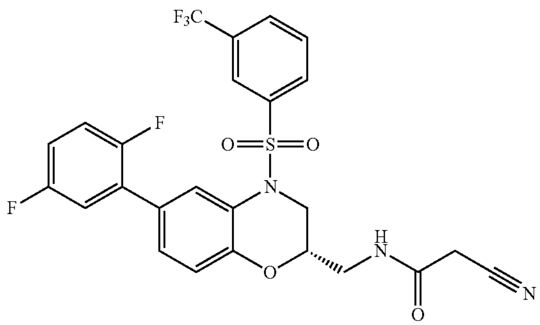 [SMILES: N#CCC(=O)NC[C@H]1CN(S(=O)(=O)c2cccc(C(F)(F)F)c2)c2cc(-c3cc(F)ccc3F)ccc2O1] | (S)-2-cyano-N-((6-(2,5-difluoro-phenyl)-4-((3-(trifluoromethyl)-phenyl)sulfonyl)-3,4-dihydro-2H-benzo[b][1,4]oxazin-2-yl)methyl)acetamide | 552 (M + H)+ |
| 30AQ | 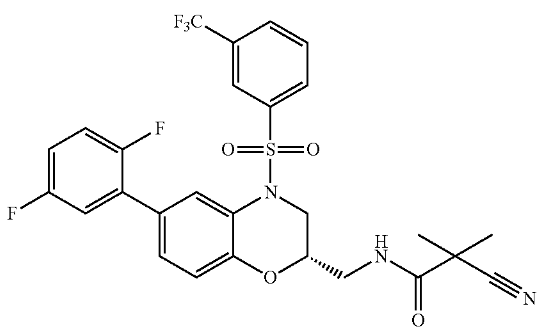 [SMILES: CC(C)(C#N)C(=O)NC[C@H]1CN(S(=O)(=O)c2cccc(C(F)(F)F)c2)c2cc(-c3cc(F)ccc3F)ccc2O1] | (S)-2-cyano-N-((6-(2,5-difluoro-phenyl)-4-((3-(trifluoromethyl)-phenyl)sulfonyl)-3,4-dihydro-2H-benzo[b][1,4]oxazin-2-yl)methyl)-2-methylpropanamide | 580 (M + H)+ |
| 30AR | 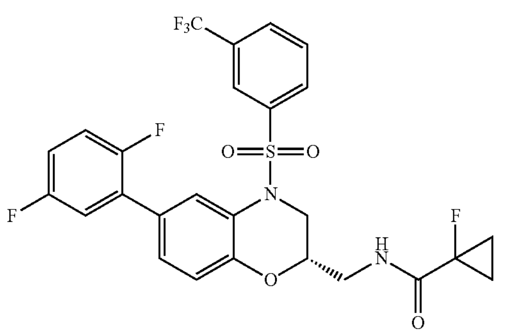 [SMILES: O=C(NC[C@H]1CN(S(=O)(=O)c2cccc(C(F)(F)F)c2)c2cc(-c3cc(F)ccc3F)ccc2O1)C1(F)CC1] | (S)-N-((6-(2,5-difluorophenyl)-4-((3-(trifluoromethyl)phenyl)-sulfonyl)-3,4-dihydro-2H-benzo[b][1,4]oxazin-2-yl)-methyl)-1-fluorocyclopropane-1-carboxamide | 571 (M + H)+ |
| 30AS | 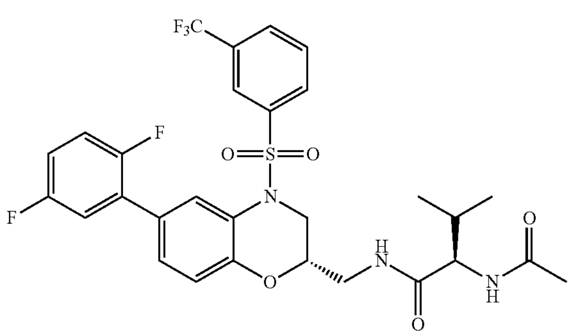 [SMILES: CC(=O)N[C@@H](C(=O)NC[C@H]1CN(S(=O)(=O)c2cccc(C(F)(F)F)c2)c2cc(-c3cc(F)ccc3F)ccc2O1)C(C)C] | (R)-2-acetamido-N-((S)-6-(2,5-difluorophenyl)-4-((3-(trifluoro-methyl)phenyl)sulfonyl)-3,4-dihydro-2H-benzo[b][1,4]-oxazin-2-yl)methyl)-3-methylbutanamide | 626 (M + H)+ |

TABLE 9-continued

| Compd No. | Structure | Name | Observed m/z |
|---|---|---|---|
| 30AT | 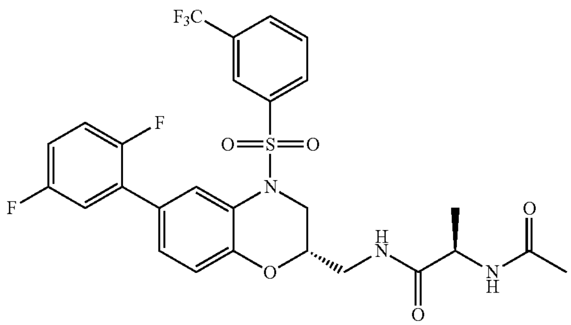 [SMILES: CC(=O)N[C@H](C)C(=O)NC[C@H]1CN(S(=O)(=O)c2cccc(C(F)(F)F)c2)c2cc(-c3cc(F)ccc3F)ccc2O1] | (R)-2-acetamido-N-(((S)-6-(2,5-difluorophenyl)-4-((3-(trifluoromethyl)phenyl)sulfonyl)-3,4-dihydro-2H-benzo[b][1,4]-oxazin-2-yl)methyl)propanamide | 598 (M + H)+ |
| 30AU | 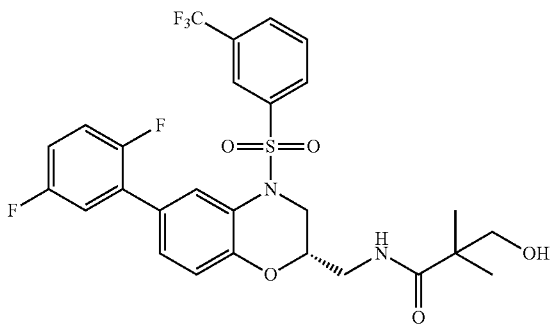 [SMILES: CC(C)(CO)C(=O)NC[C@H]1CN(S(=O)(=O)c2cccc(C(F)(F)F)c2)c2cc(-c3cc(F)ccc3F)ccc2O1] | (S)-N-((6-(2,5-difluorophenyl)-4-((3-(trifluoromethyl)phenyl)-sulfonyl)-3,4-dihydro-2H-benzo[b][1,4]oxazin-2-yl)methyl)-3-hydroxy-2,2-dimethylpropanamide | 585 (M + H)+ |
| 30AV | 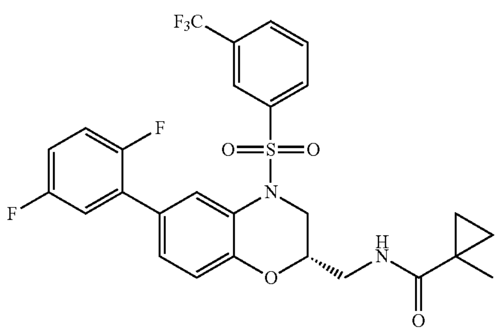 [SMILES: CC1(C(=O)NC[C@H]2CN(S(=O)(=O)c3cccc(C(F)(F)F)c3)c3cc(-c4cc(F)ccc4F)ccc3O2)CC1] | (S)-N-((6-(2,5-difluorophenyl)-4-((3-(trifluoromethyl)phenyl)-sulfonyl)-3,4-dihydro-2H-benzo[b][1,4]oxazin-2-yl)methyl)-1-methylcyclopropane-1-carboxamide | 567 (M + H)+ |
| 30AW | 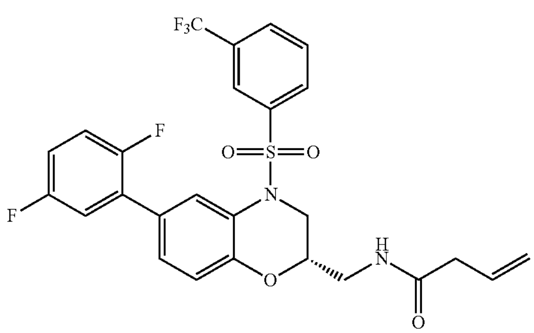 [SMILES: C=CCC(=O)NC[C@H]1CN(S(=O)(=O)c2cccc(C(F)(F)F)c2)c2cc(-c3cc(F)ccc3F)ccc2O1] | (S)-N-((6-(2,5-difluorophenyl)-4-((3-(trifluoromethyl)phenyl)-sulfonyl)-3,4-dihydro-2H-benzo[b][1,4]oxazin-2-yl)methyl)but-3-enamide | 553 (M + H)+ |

TABLE 9-continued

| Compd No. | Structure | Name | Observed m/z |
|---|---|---|---|
| 30AX | 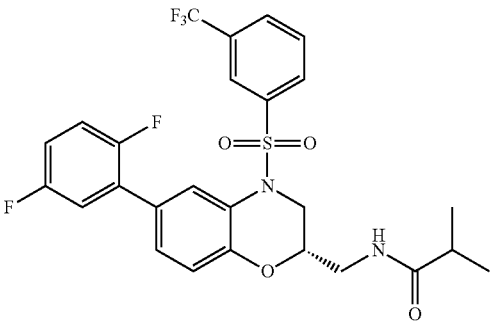 | (S)-N-((6-(2,5-difluorophenyl)-4-((3-(trifluoromethyl)phenyl)-sulfonyl)-3,4-dihydro-2H-benzo[b][1,4]oxazin-2-yl)methyl)isobutyramide | 555 (M + H)+ |
| 30AY | 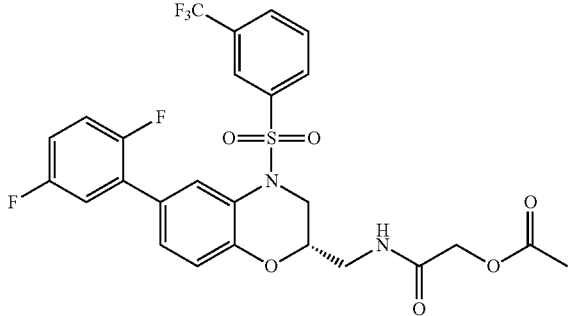 [SMILES: CC(=O)OCC(=O)NC[C@H]1CN(S(=O)(=O)c2cccc(C(F)(F)F)c2)c2cc(-c3cc(F)ccc3F)ccc2O1] | (S)-2-(((6-(2,5-difluorophenyl)-4-((3-(trifluoromethyl)phenyl)-sulfonyl)-3,4-dihydro-2H-benzo[b][1,4]oxazin-2-yl)methyl)amino)-2-oxoethyl acetate | 585 (M + H)+ |
| 30AZ | 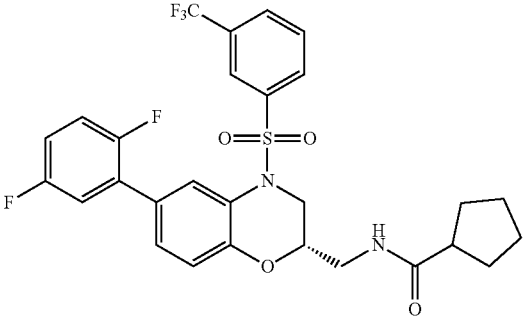 [SMILES: O=C(NC[C@H]1CN(S(=O)(=O)c2cccc(C(F)(F)F)c2)c2cc(-c3cc(F)ccc3F)ccc2O1)C1CCCC1] | (S)-N-((6-(2,5-difluorophenyl)-4-((3-(trifluoromethyl)phenyl)-sulfonyl)-3,4-dihydro-2H-benzo-[b][1,4]oxazin-2-yl)methyl)-cyclopentanecarboxamide | 581 (M + H)+ |
| 30BA | 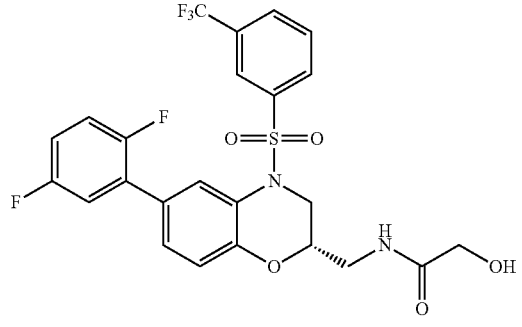 [SMILES: O=C(CO)NC[C@H]1CN(S(=O)(=O)c2cccc(C(F)(F)F)c2)c2cc(-c3cc(F)ccc3F)ccc2O1] | (S)-N-((6-(2,5-difluorophenyl)-4-((3-(trifluoromethyl)phenyl)-sulfonyl)-3,4-dihydro-2H-benzo[b][1,4]oxazin-2-yl)methyl)-2-hydroxyacetamide | 543 (M + H)+ |

TABLE 9-continued

| Compd No. | Structure | Name | Observed m/z |
|---|---|---|---|
| 30BB | 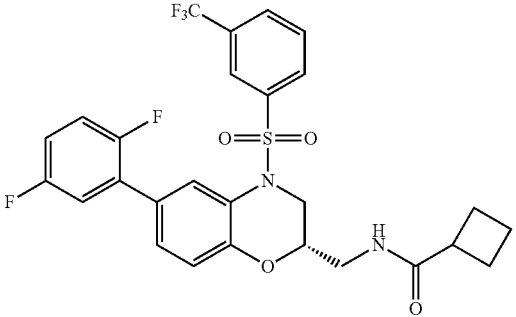 [SMILES: O=C(NC[C@H]1CN(S(=O)(=O)c2cccc(C(F)(F)F)c2)c2cc(-c3cc(F)ccc3F)ccc2O1)C1CCC1] | (S)-N-((6-(2,5-difluorophenyl)-4-((3-(trifluoromethyl)phenyl)-sulfonyl)-3,4-dihydro-2H-benzo-[b][1,4]oxazin-2-yl)methyl)-cyclobutanecarboxamide | 567 (M + H)+ |
| 30BC | 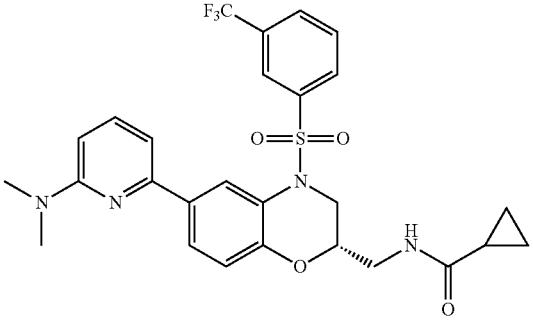 [SMILES: CN(C)c1cccc(-c2ccc3c(c2)N(S(=O)(=O)c2cccc(C(F)(F)F)c2)C[C@H](CNC(=O)C2CC2)O3)n1] | (S)-N-((6-(6-(dimethylamino)-pyridin-2-yl)-4-((3-(trifluoro-methyl)phenyl)sulfonyl)-3,4-dihydro-2H-benzo[b][1,4]-oxazin-2-yl)methyl)cyclo-propanecarboxamide | 561 (M + H)+ |
| 30BD | 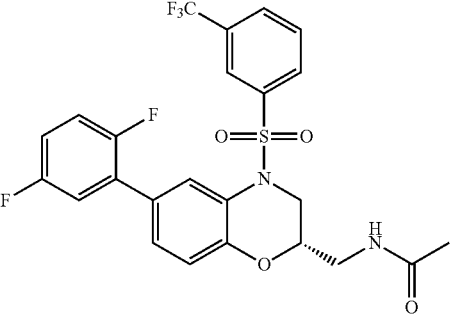 [SMILES: CC(=O)NC[C@H]1CN(S(=O)(=O)c2cccc(C(F)(F)F)c2)c2cc(-c3cc(F)ccc3F)ccc2O1] | (S)-N-((6-(2,5-difluorophenyl)-4-((3-(trifluoromethyl)phenyl)-sulfonyl)-3,4-dihydro-2H-benzo[b][1,4]oxazin-2-yl)methyl)acetamide | 527 (M + H)+ |
| 30BE | 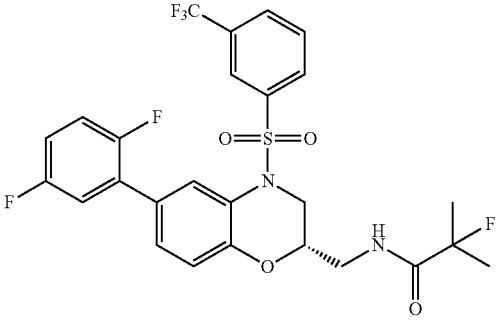 [SMILES: CC(C)(F)C(=O)NC[C@H]1CN(S(=O)(=O)c2cccc(C(F)(F)F)c2)c2cc(-c3cc(F)ccc3F)ccc2O1] | (S)-N-((6-(2,5-difluorophenyl)-4-((3-(trifluoromethyl)phenyl)-sulfonyl)-3,4-dihydro-2H-benzo[b][1,4]oxazin-2-yl)methyl)-2-fluoro-2-methylpropanamide | 573 (M + H)+ |

TABLE 9-continued

| Compd No. | Name | Observed m/z |
|---|---|---|
| 30BF | (R)-N-(((S)-6-(2,5-difluoro-3-methoxyphenyl)-4-((3-(trifluoromethyl)phenyl)sulfonyl)-3,4-dihydro-2H-benzo[b][1,4]-oxazin-2-yl)methyl)-3,3,3-trifluoro-2-hydroxy-2-methylpropanamide | 655 (M + H)+ |
| 30BG | (S)-3-sulfamoyl-N-((4-((3-(trifluoromethyl)phenyl)-sulfonyl)-6-(6-(trifluoromethyl)pyridin-2-yl)-3,4-dihydro-2H-benzo[b][1,4]-oxazin-2-yl)methyl)-propanamide | 653 (M + H)+ |
| 30BH | (S)-2-cyano-N-((4-((3-(trifluoromethyl)phenyl)-sulfonyl)-6-(6-(trifluoromethyl)pyridin-2-yl)-3,4-dihydro-2H-benzo[b][1,4]-oxazin-2-yl)methyl)acetamide | 585 (M + H)+ |
| 30BI | (S)-3-hydroxy-2,2-dimethyl-N-((4-((3-(trifluoromethyl)-phenyl)sulfonyl)-6-(6-(trifluoromethyl)pyridin-2-yl)-3,4-dihydro-2H-benzo[b][1,4]-oxazin-2-yl)methyl)-propanamide | 618 (M + H)+ |

TABLE 9A

| Compd No. | Structure | Name | Observed m/z |
|---|---|---|---|
| 30BJ | 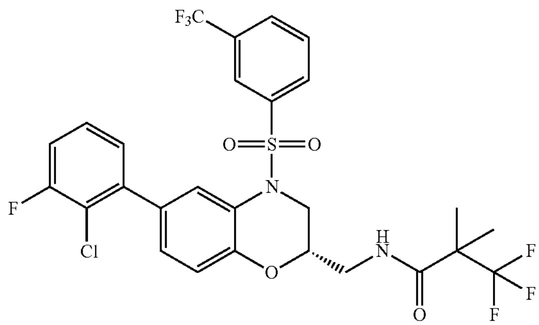 [SMILES: CC(C)(C(=O)NC[C@H]1CN(S(=O)(=O)c2cccc(C(F)(F)F)c2)c2cc(-c3cccc(F)c3Cl)ccc2O1)C(F)(F)F] | (S)-N-((6-(2-chloro-3-fluoro-phenyl)-4-((3-(trifluoromethyl)-phenyl)sulfonyl)-3,4-dihydro-2H-benzo[b][1,4]oxazin-2-yl)methyl)-3,3,3-trifluoro-2,2-dimethylpropanamide | 639 (M + H)+ |
| 30BK | 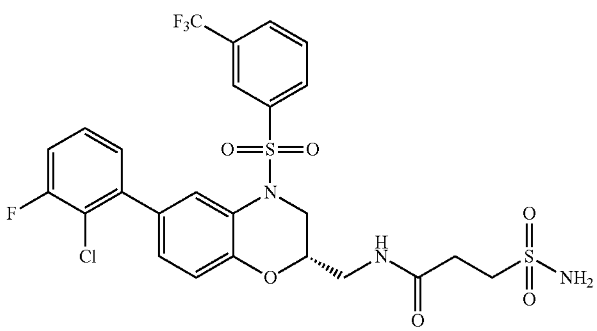 [SMILES: NS(=O)(=O)CCC(=O)NC[C@H]1CN(S(=O)(=O)c2cccc(C(F)(F)F)c2)c2cc(-c3cccc(F)c3Cl)ccc2O1] | (S)-N-((6-(2-chloro-3-fluoro-phenyl)-4-((3-(trifluoromethyl)-phenyl)sulfonyl)-3,4-dihydro-2H-benzo[b][1,4]oxazin-2-yl)methyl)-3-sulfamoylpropanamide | 636 (M + H)+ |
| 30BL | 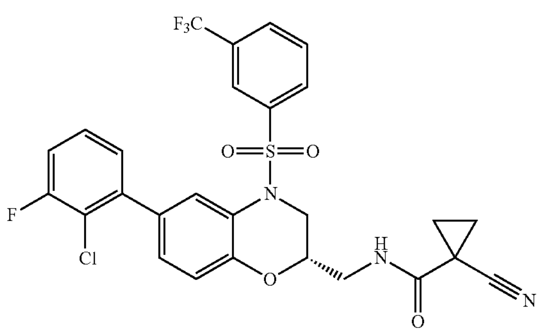 [SMILES: N#CC1(C(=O)NC[C@H]2CN(S(=O)(=O)c3cccc(C(F)(F)F)c3)c3cc(-c4cccc(F)c4Cl)ccc3O2)CC1] | (S)-N-((6-(2-chloro-3-fluoro-phenyl)-4-((3-(trifluoromethyl)-phenyl)sulfonyl)-3,4-dihydro-2H-benzo[b][1,4]oxazin-2-yl)methyl)-1-cyanocyclo-propane-1-carboxamide | 594 (M + H)+ |
| 30BM | 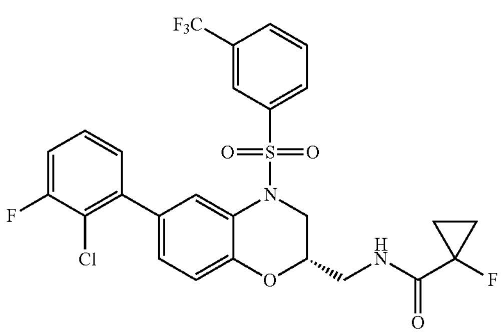 [SMILES: O=C(NC[C@H]1CN(S(=O)(=O)c2cccc(C(F)(F)F)c2)c2cc(-c3cccc(F)c3Cl)ccc2O1)C1(F)CC1] | (S)-N-((6-(2-chloro-3-fluoro-phenyl)-4-((3-(trifluoromethyl)-phenyl)sulfonyl)-3,4-dihydro-2H-benzo[b][1,4]oxazin-2-yl)methyl)-1-fluorocyclo-propane-1-carboxamide | 587 (M + H)+ |

TABLE 9A-continued

| Compd No. | Structure | Name | Observed m/z |
|---|---|---|---|
| 30BN | 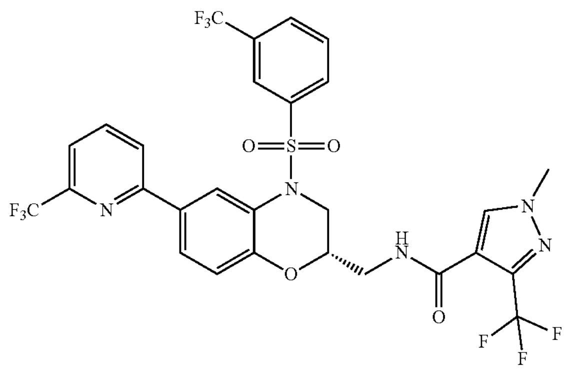 [SMILES: Cn1cc(C(=O)NC[C@H]2CN(S(=O)(=O)c3cccc(C(F)(F)F)c3)c3cc(-c4cccc(C(F)(F)F)n4)ccc3O2)c(C(F)(F)F)n1] | (S)-1-methyl-3-(trifluoro-methyl)-N-((4-((3-(trifluoro-methyl)phenyl)sulfonyl)-6-(6-(trifluoromethyl)pyridin-2-yl)-3,4-dihydro-2H-benzo[b][1,4]-oxazin-2-yl)methyl)-1H-pyrazole-4-carboxamide | 694 (M + H)+ |
| 30BO | 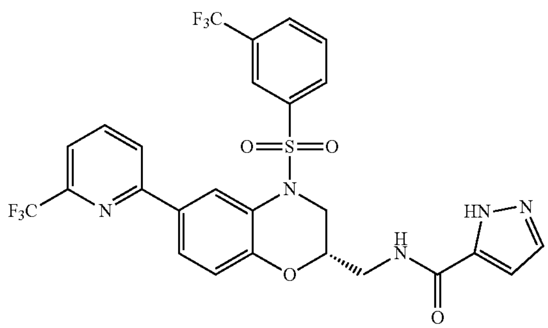 [SMILES: O=C(NC[C@H]1CN(S(=O)(=O)c2cccc(C(F)(F)F)c2)c2cc(-c3cccc(C(F)(F)F)n3)ccc2O1)c1ccn[nH]1] | (S)-N-((4-((3-(trifluoromethyl)-phenyl)sulfonyl)-6-(6-(trifluoromethyl)pyridin-2-yl)-3,4-dihydro-2H-benzo[b][1,4]-oxazin-2-yl)methyl)-1H-pyrazole-5-carboxamide | 612 (M + H)+ |
| 30BP | 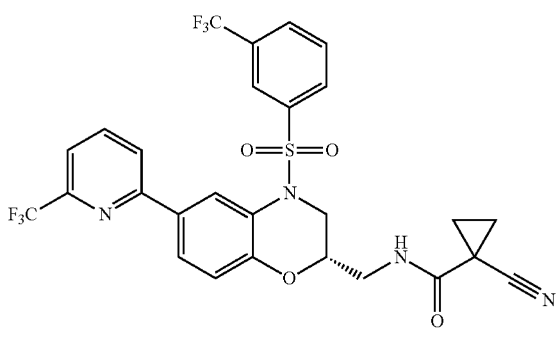 [SMILES: N#CC1(C(=O)NC[C@H]2CN(S(=O)(=O)c3cccc(C(F)(F)F)c3)c3cc(-c4cccc(C(F)(F)F)n4)ccc3O2)CC1] | (S)-1-cyano-N-((4-((3-(trifluoromethyl)phenyl)sulfonyl)-6-(6-(trifluoromethyl)pyridin-2-yl)-3,4-dihydro-2H-benzo[b][1,4]oxazin-2-yl)methyl)cyclopropane-1-carboxamide | 611 (M + H)+ |
| 30BQ | 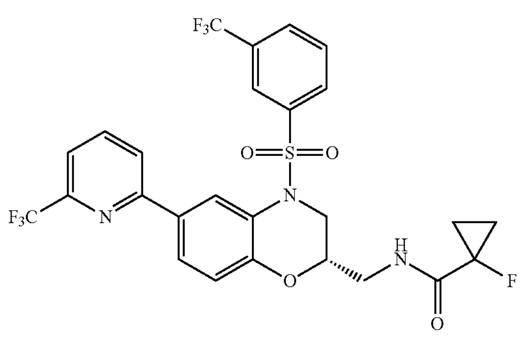 [SMILES: O=C(NC[C@H]1CN(S(=O)(=O)c2cccc(C(F)(F)F)c2)c2cc(-c3cccc(C(F)(F)F)n3)ccc2O1)C1(F)CC1] | (S)-1-fluoro-N-((4-((3-(trifluoro-methyl)phenyl)sulfonyl)-6-(6-(trifluoromethyl)pyridin-2-yl)-3,4-dihydro-2H-benzo[b][1,4]-oxazin-2-yl)methyl)cyclo-propane-1-carboxamide | 604 (M + H)+ |

TABLE 9A-continued

| Compd No. | Structure | Name | Observed m/z |
|---|---|---|---|
| 30BR | 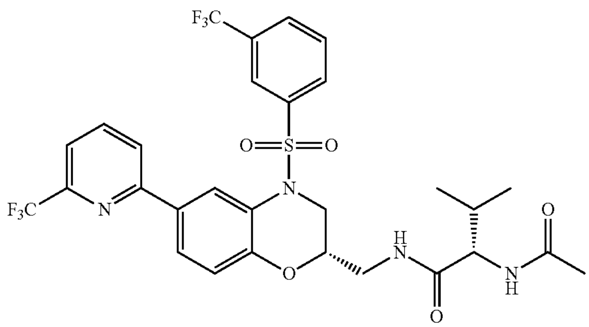 [SMILES: CC(=O)N[C@H](C(=O)NC[C@H]1CN(S(=O)(=O)c2cccc(C(F)(F)F)c2)c2cc(-c3cccc(C(F)(F)F)n3)ccc2O1)C(C)C] | (S)-2-acetamido-3-methyl-N-(((S)-4-((3-(trifluoromethyl)-phenyl)sulfonyl)-6-(6-(trifluoro-methyl)pyridin-2-yl)-3,4-dihydro-2H-benzo[b][1,4]-oxazin-2-yl)methyl)butanamide | 659 (M + H)+ |
| 30BS | 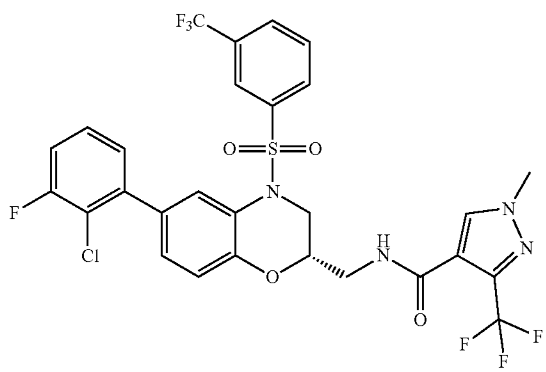 [SMILES: Cn1cc(C(=O)NC[C@H]2CN(S(=O)(=O)c3cccc(C(F)(F)F)c3)c3cc(-c4cccc(F)c4Cl)ccc3O2)c(C(F)(F)F)n1] | (S)-N-((6-(2-chloro-3-fluoro-phenyl)-4-((3-(trifluoromethyl)-phenyl)sulfonyl)-3,4-dihydro-2H-benzo[b][1,4]oxazin-2-yl)methyl)-1-methyl-3-(trifluoromethyl)-1H-pyrazole-4-carboxamide | 677 (M + H)+ |
| 30BT | 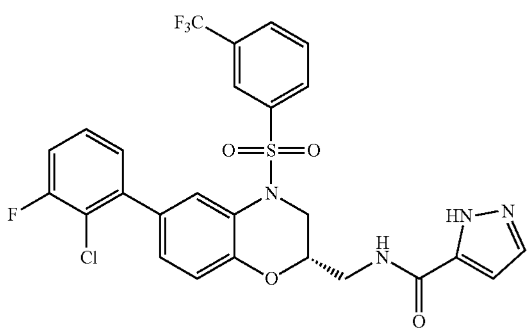 | (S)-N-((6-(2-chloro-3-fluoro-phenyl)-4-((3-(trifluoromethyl)-phenyl)sulfonyl)-3,4-dihydro-2H-benzo[b][1,4]oxazin-2-yl)methyl)-1H-pyrazole-5-carboxamide | 595 (M + H)+ |
| 30BU | 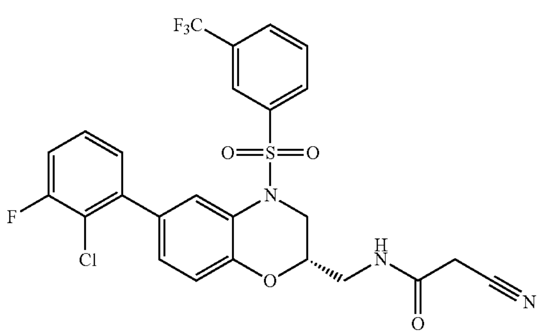 [SMILES: N#CCC(=O)NC[C@H]1CN(S(=O)(=O)c2cccc(C(F)(F)F)c2)c2cc(-c3cccc(F)c3Cl)ccc2O1] | (S)-N-((6-(2-chloro-3-fluoro-phenyl)-4-((3-(trifluoromethyl)-phenyl)sulfonyl)-3,4-dihydro-2H-benzo[b][1,4]oxazin-2-yl)methyl)-2-cyanoacetamide | 568 (M + H)+ |

TABLE 9A-continued

| Compd No. | Structure | Name | Observed m/z |
|---|---|---|---|
| 30BV | 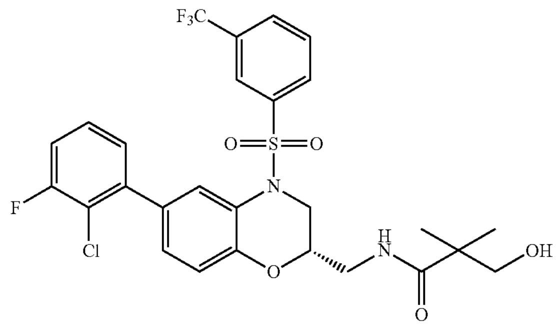 [SMILES: CC(C)(CO)C(=O)NC[C@H]1CN(S(=O)(=O)c2cccc(C(F)(F)F)c2)c2cc(-c3cccc(F)c3Cl)ccc2O1] | (S)-N-((6-(2-chloro-3-fluorophenyl)-4-((3-(trifluoromethyl)phenyl)sulfonyl)-3,4-dihydro-2H-benzo[b][1,4]oxazin-2-yl)methyl)-3-hydroxy-2,2-dimethylpropanamide | 602 (M + H)+ |
| 30BW | 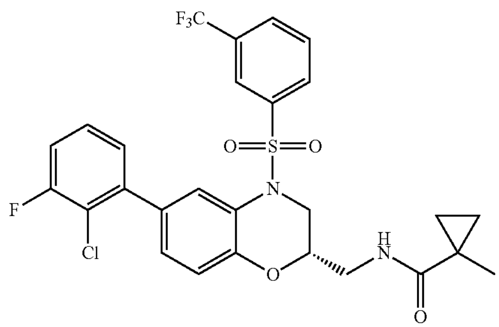 [SMILES: CC1(C(=O)NC[C@H]2CN(S(=O)(=O)c3cccc(C(F)(F)F)c3)c3cc(-c4cccc(F)c4Cl)ccc3O2)CC1] | (S)-N-((6-(2-chloro-3-fluorophenyl)-4-((3-(trifluoromethyl)phenyl)sulfonyl)-3,4-dihydro-2H-benzo[b][1,4]oxazin-2-yl)methyl)-1-methylcyclopropane-1-carboxamide | 583 (M + H)+ |
| 30BX | 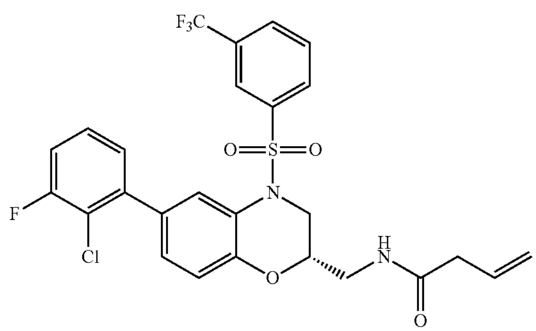 [SMILES: C=CCC(=O)NC[C@H]1CN(S(=O)(=O)c2cccc(C(F)(F)F)c2)c2cc(-c3cccc(F)c3Cl)ccc2O1] | (S)-N-((6-(2-chloro-3-fluorophenyl)-4-((3-(trifluoromethyl)phenyl)sulfonyl)-3,4-dihydro-2H-benzo[b][1,4]-oxazin-2-yl)methyl)but-3-enamide | 569 (M + H)+ |
| 30BY | 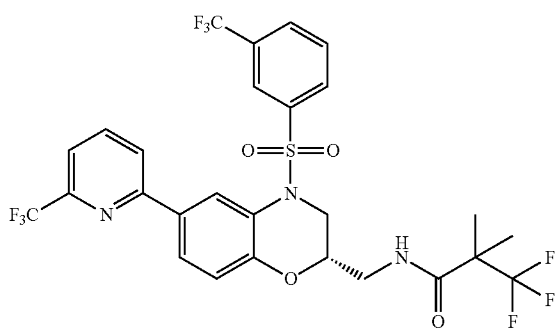 [SMILES: CC(C)(C(=O)NC[C@H]1CN(S(=O)(=O)c2cccc(C(F)(F)F)c2)c2cc(-c3cccc(C(F)(F)F)n3)ccc2O1)C(F)(F)F] | (S)-3,3,3-trifluoro-2,2-dimethyl-N-((4-((3-(trifluoromethyl)phenyl)sulfonyl)-6-(6-(trifluoromethyl)pyridin-2-yl)-3,4-dihydro-2H-benzo[b][1,4]-oxazin-2-yl)methyl)propanamide | 656 (M + H)+ |

TABLE 9A-continued

| Compd No. | Structure | Name | Observed m/z |
|---|---|---|---|
| 30BZ | 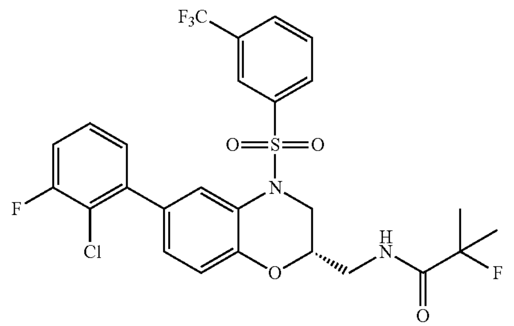 [SMILES: CC(C)(F)C(=O)NC[C@H]1CN(S(=O)(=O)c2cccc(C(F)(F)F)c2)c2cc(-c3cccc(F)c3Cl)ccc2O1] | (S)-N-((6-(2-chloro-3-fluoro-phenyl)-4-((3-(trifluoromethyl)-phenyl)sulfonyl)-3,4-dihydro-2H-benzo[b][1,4]oxazin-2-yl)methyl)-2-fluoro-2-methylpropanamide | 589 (M + H)+ |
| 30CA | 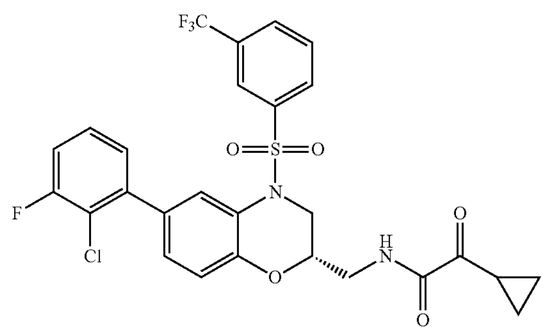 [SMILES: O=C(NC[C@H]1CN(S(=O)(=O)c2cccc(C(F)(F)F)c2)c2cc(-c3cccc(F)c3Cl)ccc2O1)C(=O)C1CC1] | (S)-N-((6-(2-chloro-3-fluoro-phenyl)-4-((3-(trifluoromethyl)-phenyl)sulfonyl)-3,4-dihydro-2H-benzo[b][1,4]oxazin-2-yl)methyl)-2-cyclopropyl-2-oxoacetamide | 597 (M + H)+ |
| 30CB | 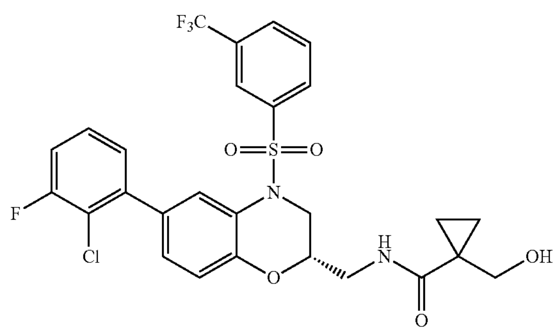 [SMILES: O=C(NC[C@H]1CN(S(=O)(=O)c2cccc(C(F)(F)F)c2)c2cc(-c3cccc(F)c3Cl)ccc2O1)C1(CO)CC1] | (S)-N-((6-(2-chloro-3-fluoro-phenyl)-4-((3-(trifluoromethyl)-phenyl)sulfonyl)-3,4-dihydro-2H-benzo[b][1,4]oxazin-2-yl)methyl)-1-(hydroxymethyl)-cyclopropane-1-carboxamide | 599 (M + H)+ |
| 30CC | 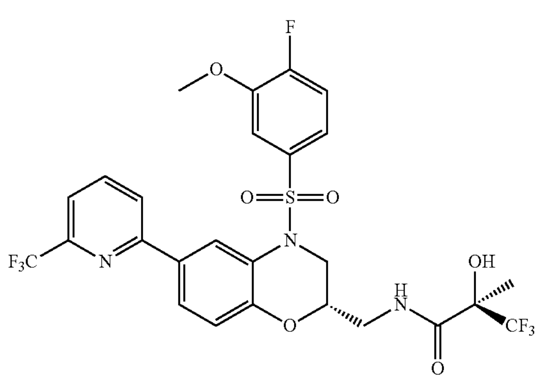 [SMILES: COc1cc(S(=O)(=O)N2C[C@H](CNC(=O)[C@@](C)(O)C(F)(F)F)Oc3ccc(-c4cccc(C(F)(F)F)n4)cc32)ccc1F] | (R)-3,3,3-trifluoro-N-(((S)-4-((4-fluoro-3-methoxyphenyl)-sulfonyl)-6-(6-(trifluoromethyl)-pyridin-2-yl)-3,4-dihydro-2H-benzo[b][1,4]oxazin-2-yl)methyl)-2-hydroxy-2-methylpropanamide | 638 (M + H)+ |

TABLE 9A-continued

| Compd No. | Structure | Name | Observed m/z |
|---|---|---|---|
| 30CD | 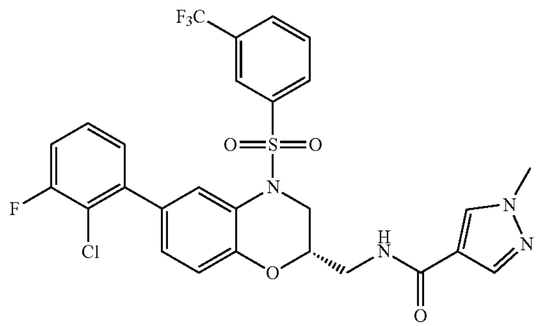 [SMILES: Cn1cc(C(=O)NC[C@H]2CN(S(=O)(=O)c3cccc(C(F)(F)F)c3)c3cc(-c4cccc(F)c4Cl)ccc3O2)cn1] | (S)-N-((6-(2-chloro-3-fluoro-phenyl)-4-((3-(trifluoromethyl)-phenyl)sulfonyl)-3,4-dihydro-2H-benzo[b][1,4]oxazin-2-yl)methyl)-1-methyl-1H-pyrazole-4-carboxamide | 609 (M + H)+ |
| 30CE | 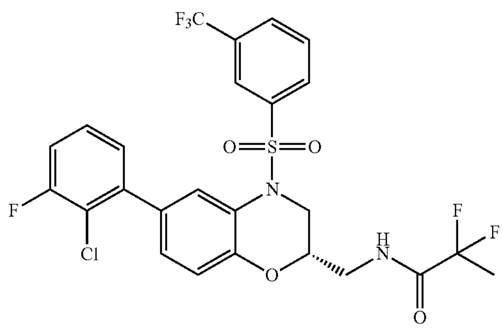 [SMILES: CC(F)(F)C(=O)NC[C@H]1CN(S(=O)(=O)c2cccc(C(F)(F)F)c2)c2cc(-c3cccc(F)c3Cl)ccc2O1] | (S)-N-((6-(2-chloro-3-fluoro-phenyl)-4-((3-(trifluoromethyl)-phenyl)sulfonyl)-3,4-dihydro-2H-benzo[b][1,4]oxazin-2-yl)methyl)-2,2-difluoro-propanamide | 593 (M + H)+ |
| 30CF | 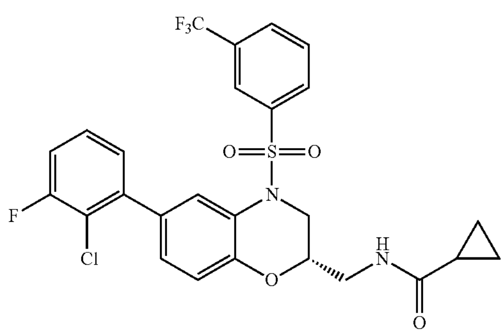 [SMILES: O=C(NC[C@H]1CN(S(=O)(=O)c2cccc(C(F)(F)F)c2)c2cc(-c3cccc(F)c3Cl)ccc2O1)C1CC1] | (S)-N-((6-(2-chloro-3-fluoro-phenyl)-4-((3-(trifluoromethyl)-phenyl)sulfonyl)-3,4-dihydro-2H-benzo[b][1,4]oxazin-2-yl)methyl)cyclopropanecarbox-amide | 569 (M + H)+ |
| 30CG | 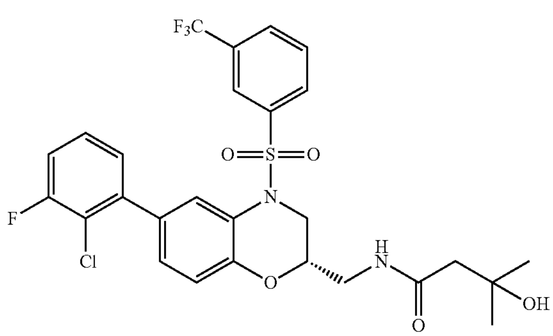 [SMILES: CC(C)(O)CC(=O)NC[C@H]1CN(S(=O)(=O)c2cccc(C(F)(F)F)c2)c2cc(-c3cccc(F)c3Cl)ccc2O1] | (S)-N-((6-(2-chloro-3-fluoro-phenyl)-4-((3-(trifluoromethyl)-phenyl)sulfonyl)-3,4-dihydro-2H-benzo[b][1,4]oxazin-2-yl)methyl)-3-hydroxy-3-methylbutanamide | 601 (M + H)+ |

TABLE 9A-continued

| Compd No. | Structure | Name | Observed m/z |
|---|---|---|---|
| 30CH | 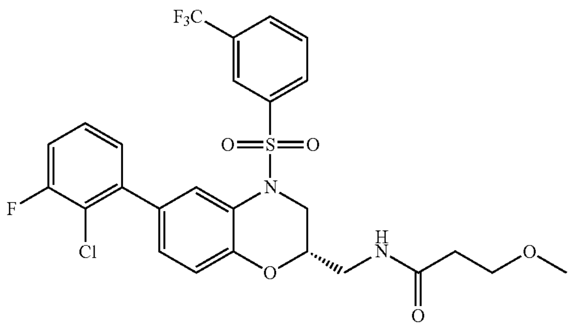 [SMILES: COCCC(=O)NC[C@H]1CN(S(=O)(=O)c2cccc(C(F)(F)F)c2)c2cc(-c3cccc(F)c3Cl)ccc2O1] | (S)-N-((6-(2-chloro-3-fluorophenyl)-4-((3-(trifluoromethyl)phenyl)sulfonyl)-3,4-dihydro-2H-benzo[b][1,4]oxazin-2-yl)methyl)-3-methoxypropanamide | 587 (M + H)+ |
| 30CI | 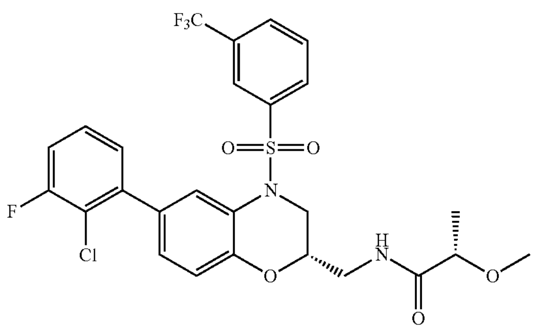 [SMILES: CO[C@@H](C)C(=O)NC[C@H]1CN(S(=O)(=O)c2cccc(C(F)(F)F)c2)c2cc(-c3cccc(F)c3Cl)ccc2O1] | (S)-N-(((S)-6-(2-chloro-3-fluorophenyl)-4-((3-(trifluoromethyl)phenyl)sulfonyl)-3,4-dihydro-2H-benzo[b][1,4]-oxazin-2-yl)methyl)-2-methoxypropanamide | 587 (M + H)+ |
| 30CJ | 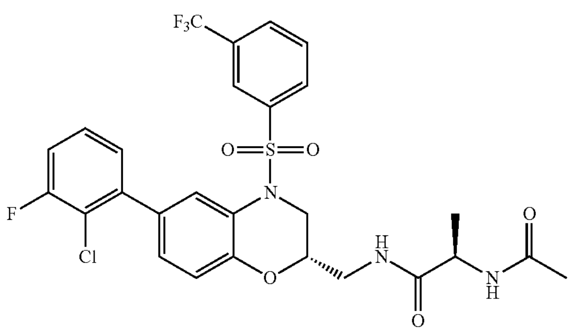 [SMILES: CC(=O)N[C@H](C)C(=O)NC[C@H]1CN(S(=O)(=O)c2cccc(C(F)(F)F)c2)c2cc(-c3cccc(F)c3Cl)ccc2O1] | (R)-2-acetamido-N-(((S)-6-(2-chloro-3-fluorophenyl)-4-((3-(trifluoromethyl)phenyl)sulfonyl)-3,4-dihydro-2H-benzo[b][1,4]oxazin-2-yl)methyl)propanamide | 614 (M + H)+ |
| 30CK | 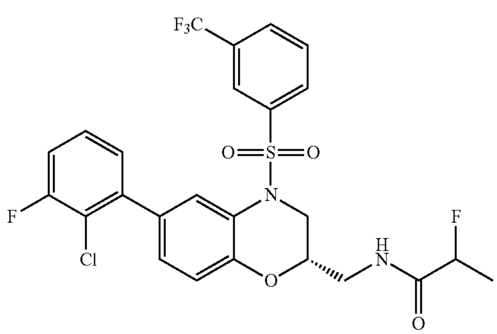 [SMILES: CC(F)C(=O)NC[C@H]1CN(S(=O)(=O)c2cccc(C(F)(F)F)c2)c2cc(-c3cccc(F)c3Cl)ccc2O1] | N-(((S)-6-(2-chloro-3-fluorophenyl)-4-((3-(trifluoromethyl)phenyl)sulfonyl)-3,4-dihydro-2H-benzo[b][1,4]oxazin-2-yl)methyl)-2-fluoropropanamide | 575 (M + H)+ |

TABLE 9A-continued

| Compd No. | Structure | Name | Observed m/z |
|---|---|---|---|
| 30CL | 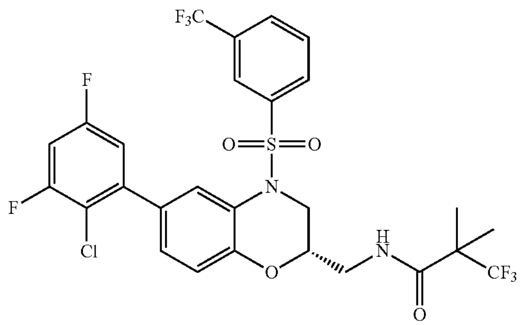 [SMILES: CC(C)(C(=O)NC[C@H]1CN(S(=O)(=O)c2cccc(C(F)(F)F)c2)c2cc(-c3cc(F)cc(F)c3Cl)ccc2O1)C(F)(F)F] | (S)-N-((6-(2-chloro-3,5-difluoro-phenyl)-4-((3-(trifluoromethyl)-phenyl)sulfonyl)-3,4-dihydro-2H-benzo[b][1,4]oxazin-2-yl)methyl)-3,3,3-trifluoro-2,2-dimethylpropanamide | 657 (M + H)+ |
| 30CM | 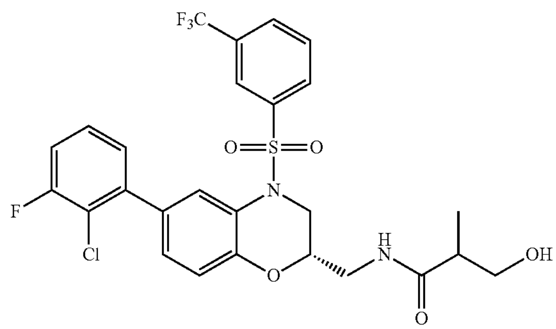 [SMILES: CC(CO)C(=O)NC[C@H]1CN(S(=O)(=O)c2cccc(C(F)(F)F)c2)c2cc(-c3cccc(F)c3Cl)ccc2O1] | N-(((S)-6-(2-chloro-3-fluoro-phenyl)-4-((3-(trifluoromethyl)-phenyl)sulfonyl)-3,4-dihydro-2H-benzo[b][1,4]oxazin-2-yl)methyl)-3-hydroxy-2-methylpropanamide | 587 (M + H)+ |
| 30CN | 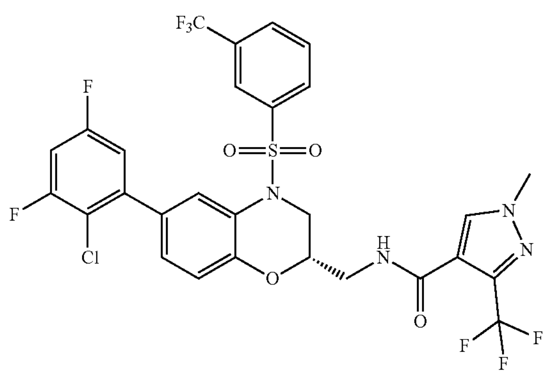 [SMILES: Cn1cc(C(=O)NC[C@H]2CN(S(=O)(=O)c3cccc(C(F)(F)F)c3)c3cc(-c4cc(F)cc(F)c4Cl)ccc3O2)c(C(F)(F)F)n1] | (S)-N-((6-(2-chloro-3,5-di-fluorophenyl)-4-((3-(trifluoro-methyl)phenyl)sulfonyl)-3,4-dihydro-2H-benzo[b][1,4]-oxazin-2-yl)methyl)-1-methyl-3-(trifluoromethyl)-1H-pyrazole-4-carboxamide | 695 (M + H)+ |
| 30CO | 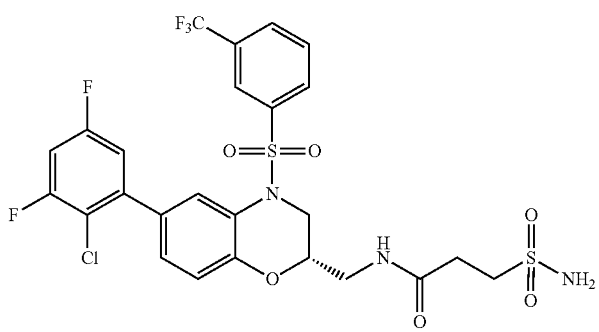 [SMILES: NS(=O)(=O)CCC(=O)NC[C@H]1CN(S(=O)(=O)c2cccc(C(F)(F)F)c2)c2cc(-c3cc(F)cc(F)c3Cl)ccc2O1] | (S)-N-((6-(2-chloro-3,5-di-fluorophenyl)-4-((3-(trifluoro-methyl)-phenyl)sulfonyl)-3,4-dihydro-2H-benzo[b][1,4]-oxazin-2-yl)methyl)-3-sulfamoylpropanamide | 654 (M + H)+ |

TABLE 9A-continued

| Compd No. | Name | Observed m/z |
|---|---|---|
| 30CP | (S)-N-((6-(2-chloro-3,5-difluorophenyl)-4-((3-(trifluoromethyl)phenyl)sulfonyl)-3,4-dihydro-2H-benzo[b][1,4]-oxazin-2-yl)methyl)-1H-pyrazole-5-carboxamide | 613 (M + H)+ |
| 30CQ | (S)-N-((6-(2-chloro-3,5-difluorophenyl)-4-((3-(trifluoromethyl)phenyl)sulfonyl)-3,4-dihydro-2H-benzo[b][1,4]-oxazin-2-yl)methyl)-2-fluoro-2-methylpropanamide | 607 (M + H)+ |
| 30CR | (S)-N-(6-(2-chloro-3,5-difluorophenyl)-4-((3-(trifluoromethyl)phenyl)sulfonyl)-3,4-dihydro-2H-benzo[b][1,4]-oxazin-2-yl)methyl)but-3-enamide | 587 (M + H)+ |
| 30CS | (S)-N-((6-(2-chloro-3,5-difluorophenyl)-4-((3-(trifluoromethyl)phenyl)sulfonyl)-3,4-dihydro-2H-benzo[b][1,4]-oxazin-2-yl)methyl)-2-fluoro-2-methylpropanamide | 607 (M + H)+ |

TABLE 9A-continued

| Compd No. | Structure | Name | Observed m/z |
|---|---|---|---|
| 30CT | 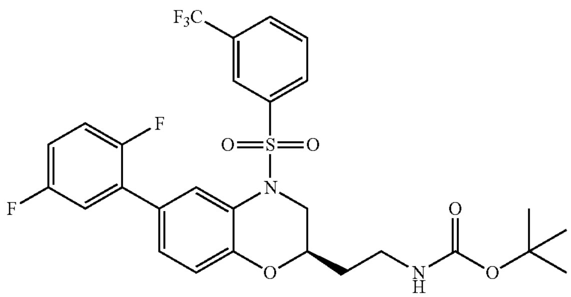 [SMILES: CC(C)(C)OC(=O)NCC[C@@H]1CN(S(=O)(=O)c2cccc(C(F)(F)F)c2)c2cc(-c3cc(F)ccc3F)ccc2O1] | tert-butyl (R)-(2-(6-(2,5-di-fluorophenyl)-4-((3-(trifluoro-methyl)phenyl)sulfonyl)-3,4-dihydro-2H-benzo[b][1,4]-oxazin-2-yl)ethyl)carbamate | 599 (M + H)+ |
| 30CU | 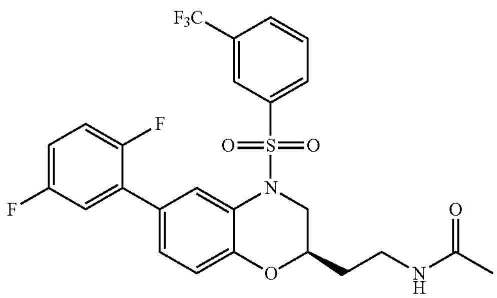 [SMILES: CC(=O)NCC[C@@H]1CN(S(=O)(=O)c2cccc(C(F)(F)F)c2)c2cc(-c3cc(F)ccc3F)ccc2O1] | (R)-N-(2-(6-(2,5-difluoro-phenyl)-4-((3-(trifluoromethyl)-phenyl)sulfonyl)-3,4-dihydro-2H-benzo[b][1,4]oxazin-2-yl)ethyl)acetamide | 541 (M + H)+ |
| 30CV | 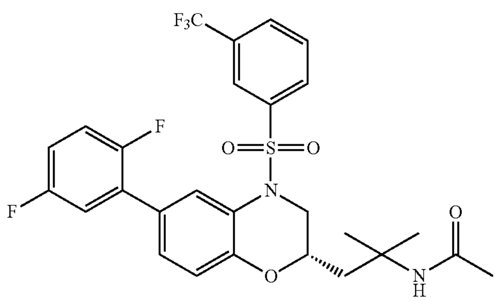 [SMILES: CC(=O)NC(C)(C)C[C@H]1CN(S(=O)(=O)c2cccc(C(F)(F)F)c2)c2cc(-c3cc(F)ccc3F)ccc2O1] | (S)-N-(1-(6-(2,5-difluoro-phenyl)-4-((3-(trifluoromethyl)-phenyl)sulfonyl)-3,4-dihydro-2H-benzo[b][1,4]oxazin-2-yl)-2-methylpropan-2-yl)acetamide | 569 (M + H)+ |
| 30CW | 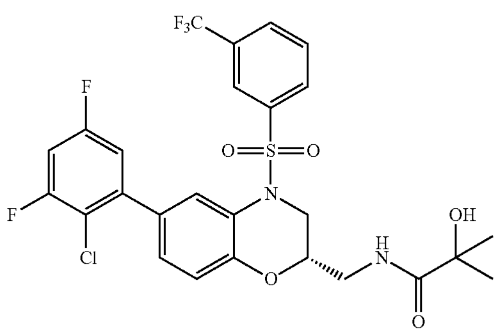 [SMILES: CC(C)(O)C(=O)NC[C@H]1CN(S(=O)(=O)c2cccc(C(F)(F)F)c2)c2cc(-c3cc(F)cc(F)c3Cl)ccc2O1] | (S)-N-((6-(2-chloro-3,5-difluorophenyl)-4-((3-(trifluoromethyl)phenyl)-sulfonyl)-3,4-dihydro-2H-benzo[b][1,4]oxazin-2-yl)methyl)-2-hydroxy-2-methylpropanamide | 605 (M + H)+ |
| 30CX | 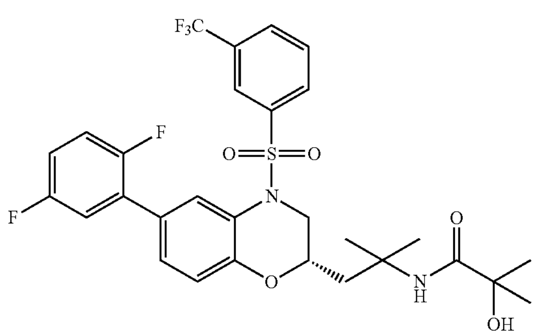 [SMILES: CC(C)(C[C@H]1CN(S(=O)(=O)c2cccc(C(F)(F)F)c2)c2cc(-c3cc(F)ccc3F)ccc2O1)NC(=O)C(C)(C)O] | (S)-N-(1-(6-(2,5-difluoro-phenyl)-4-((3-(trifluoromethyl)-phenyl)sulfonyl)-3,4-dihydro-2H-benzo[b][1,4]oxazin-2-yl)-2-methylpropan-2-yl)-2-hydroxy-2-methylpropanamide | 613 (M + H)+ |

TABLE 9A-continued

| Compd No. | Structure | Name | Observed m/z |
|---|---|---|---|
| 30CY | 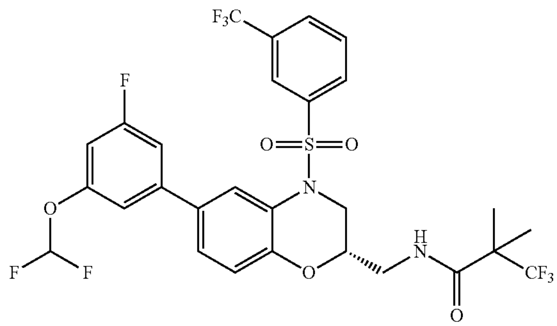 [SMILES: CC(C)(C(=O)NC[C@H]1CN(S(=O)(=O)c2cccc(C(F)(F)F)c2)c2cc(-c3cc(F)cc(OC(F)F)c3)ccc2O1)C(F)(F)F] | (S)-N-((6-(3-(difluoromethoxy)-5-fluorophenyl)-4-((3-(trifluoromethyl)phenyl)sulfonyl)-3,4-dihydro-2H-benzo[b][1,4]-oxazin-2-yl)methyl)-3,3,3-trifluoro-2,2-dimethyl-propanamide | 671 (M + H)+ |
| 30CZ | 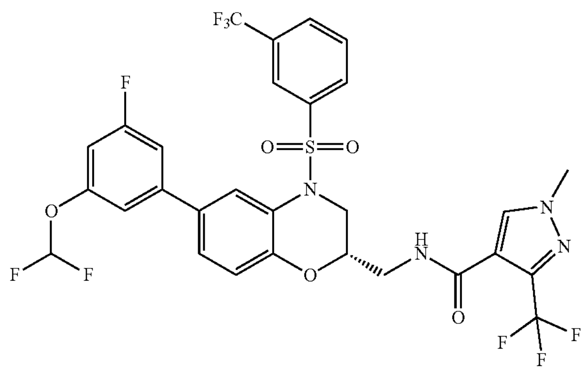 [SMILES: Cn1cc(C(=O)NC[C@H]2CN(S(=O)(=O)c3cccc(C(F)(F)F)c3)c3cc(-c4cc(F)cc(OC(F)F)c4)ccc3O2)c(C(F)(F)F)n1] | (S)-N-((6-(3-(difluoromethoxy)-5-fluorophenyl)-4-((3-(trifluoromethyl)phenyl)sulfonyl)-3,4-dihydro-2H-benzo[b][1,4]-oxazin-2-yl)methyl)-1-methyl-3-(trifluoromethyl)-1H-pyrazole-4-carboxamide | 709 (M + H)+ |
| 30DA | 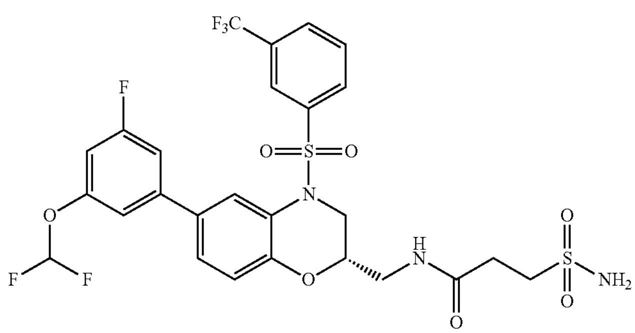 [SMILES: NS(=O)(=O)CCC(=O)NC[C@H]1CN(S(=O)(=O)c2cccc(C(F)(F)F)c2)c2cc(-c3cc(F)cc(OC(F)F)c3)ccc2O1] | (S)-N-((6-(3-(difluoromethoxy)-5-fluorophenyl)-4-((3-(trifluoromethyl)phenyl)sulfonyl)-3,4-dihydro-2H-benzo[b][1,4]-oxazin-2-yl)methyl)-3-sulfamoylpropanamide | 668 (M + H)+ |
| 30DB | 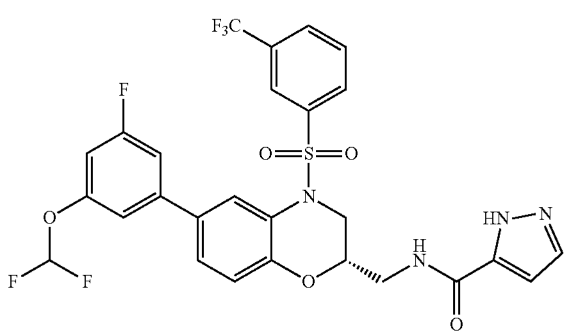 [SMILES: O=C(NC[C@H]1CN(S(=O)(=O)c2cccc(C(F)(F)F)c2)c2cc(-c3cc(F)cc(OC(F)F)c3)ccc2O1)c1ccn[nH]1] | (S)-N-((6-(3-(difluoromethoxy)-5-fluorophenyl)-4-((3-(trifluoromethyl)phenyl)sulfonyl)-3,4-dihydro-2H-benzo[b][1,4]oxazin-2-yl)methyl)-1H-pyrazole-5-carboxamide | 627 (M + H)+ |

TABLE 9A-continued

| Compd No. | Structure | Name | Observed m/z |
|---|---|---|---|
| 30DC | 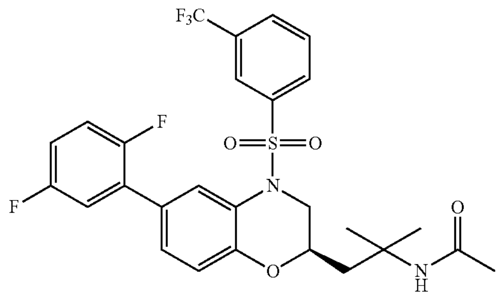 [SMILES: CC(=O)NC(C)(C)C[C@@H]1CN(S(=O)(=O)c2cccc(C(F)(F)F)c2)c2cc(-c3cc(F)ccc3F)ccc2O1] | (R)-N-(1-(6-(2,5-difluoro-phenyl)-4-((3-(trifluoromethyl)-phenyl)sulfonyl)-3,4-dihydro-2H-benzo[b][1,4]oxazin-2-yl)-2-methylpropan-2-yl)acetamide | 569 (M + H)+ |
| 30DD | 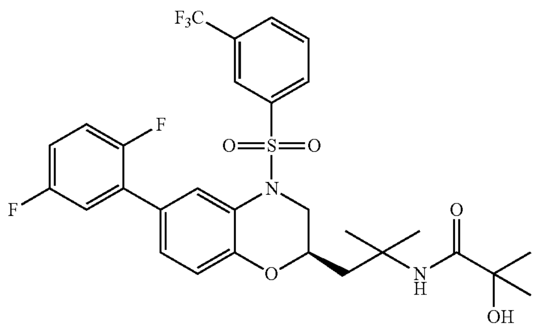 [SMILES: CC(C)(C[C@@H]1CN(S(=O)(=O)c2cccc(C(F)(F)F)c2)c2cc(-c3cc(F)ccc3F)ccc2O1)NC(=O)C(C)(C)O] | (R)-N-(1-(6-(2,5-difluoro-phenyl)-4-((3-(trifluoromethyl)-phenyl)sulfonyl)-3,4-dihydro-2H-benzo[b][1,4]oxazin-2-yl)-2-methylpropan-2-yl)-2-hydroxy-2-methylpropanamide | 613 (M + H)+ |
| 30DE | 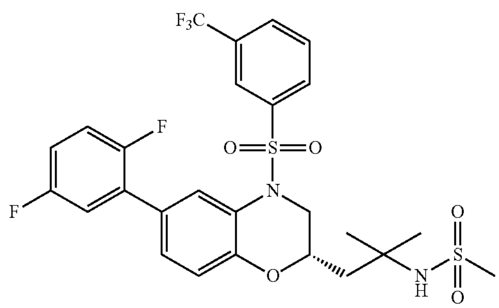 [SMILES: CC(C)(C[C@H]1CN(S(=O)(=O)c2cccc(C(F)(F)F)c2)c2cc(-c3cc(F)ccc3F)ccc2O1)NS(C)(=O)=O] | (S)-N-(1-(6-(2,5-difluoro-phenyl)-4-((3-(trifluoromethyl)-phenyl)sulfonyl)-3,4-dihydro-2H-benzo[b][1,4]oxazin-2-yl)-2-methylpropan-2-yl)methane-sulfonamide | 605 (M + H)+ |
| 30DF | 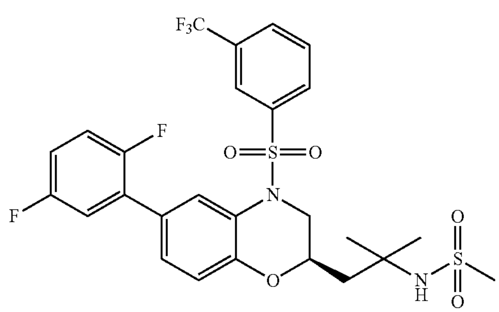 [SMILES: CC(C)(C[C@@H]1CN(S(=O)(=O)c2cccc(C(F)(F)F)c2)c2cc(-c3cc(F)ccc3F)ccc2O1)NS(C)(=O)=O] | (R)-N-(1-(6-(2,5-difluoro-phenyl)-4-((3-(trifluoromethyl)-phenyl)sulfonyl)-3,4-dihydro-2H-benzo[b][1,4]oxazin-2-yl)-2-methylpropan-2-yl)methane-sulfonamide | 605 (M + H)+ |
| 30DG | 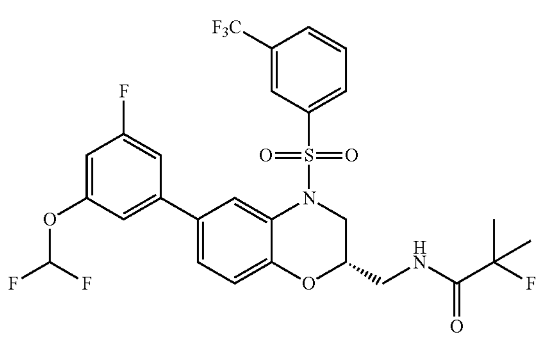 [SMILES: CC(C)(F)C(=O)NC[C@H]1CN(S(=O)(=O)c2cccc(C(F)(F)F)c2)c2cc(-c3cc(F)cc(OC(F)F)c3)ccc2O1] | (S)-N-((6-(3-(difluoromethoxy)-5-fluorophenyl)-4-((3-(trifluoro-methyl)phenyl)sulfonyl)-3,4-dihydro-2H-benzo[b][1,4]-oxazin-2-yl)methyl)-2-fluoro-2-methylpropanamide | 621 (M + H)+ |

TABLE 9A-continued

| Compd No. | Structure | Name | Observed m/z |
|---|---|---|---|
| 30DH | 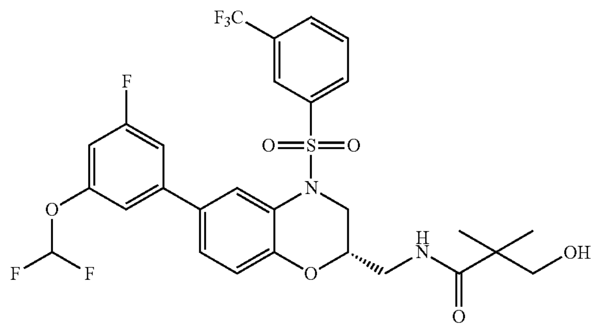 [SMILES: CC(C)(CO)C(=O)NC[C@H]1CN(S(=O)(=O)c2cccc(C(F)(F)F)c2)c2cc(-c3cc(F)cc(OC(F)F)c3)ccc2O1] | (S)-N-((6-(3-(difluoromethoxy)-5-fluorophenyl)-4-((3-(trifluoromethyl)phenyl)sulfonyl)-3,4-dihydro-2H-benzo[b][1,4]oxazin-2-yl)methyl)-3-hydroxy-2,2-dimethylpropanamide | 633 (M + H)+ |
| 30DI | 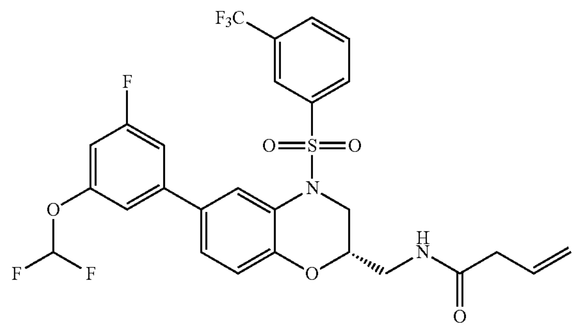 [SMILES: C=CCC(=O)NC[C@H]1CN(S(=O)(=O)c2cccc(C(F)(F)F)c2)c2cc(-c3cc(F)cc(OC(F)F)c3)ccc2O1] | (S)-N-((6-(3-(difluoromethoxy)-5-fluorophenyl)-4-((3-(trifluoromethyl)phenyl)sulfonyl)-3,4-dihydro-2H-benzo[b][1,4]oxazin-2-yl)methyl)but-3-enamide | 601 (M + H)+ |
| 30DJ | 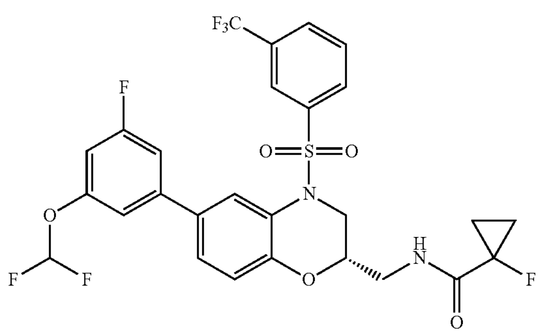 [SMILES: O=C(NC[C@H]1CN(S(=O)(=O)c2cccc(C(F)(F)F)c2)c2cc(-c3cc(F)cc(OC(F)F)c3)ccc2O1)C1(F)CC1] | (S)-N-((6-(3-(difluoromethoxy)-5-fluorophenyl)-4-((3-(trifluoromethyl)phenyl)sulfonyl)-3,4-dihydro-2H-benzo[b][1,4]oxazin-2-yl)methyl)-1-fluorocyclopropane-1-carboxamide | 619 (M + H)+ |
| 30DK | 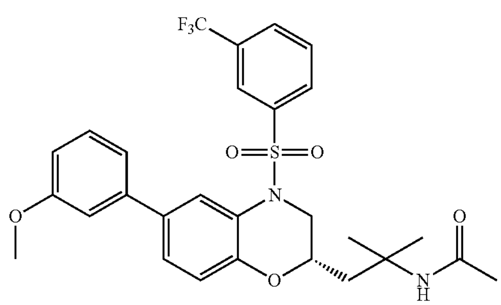 [SMILES: COc1cccc(-c2ccc3c(c2)N(S(=O)(=O)c2cccc(C(F)(F)F)c2)C[C@H](CC(C)(C)NC(C)=O)O3)c1] | (S)-N-(1-(6-(3-methoxyphenyl)-4-((3-(trifluoromethyl)phenyl)-sulfonyl)-3,4-dihydro-2H-benzo[b][1,4]oxazin-2-yl)-2-methylpropan-2-yl)acetamide | 563 (M + H)+ |

Example 31—Synthesis of (S)-3-(6-(2,5-difluorophenyl)-4-((3-(trifluoromethyl)phenyl)sulfonyl)-3,4-dihydro-2H-benzo[b][1,4]oxazin-2-yl)-2,2-dimethylpropanoic acid

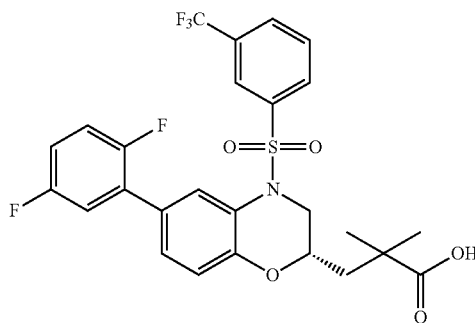

Part I—Synthesis of methyl (S)-3-(6-(2,5-difluorophenyl)-4-((3-(trifluoromethyl)phenyl)sulfonyl)-3,4-dihydro-2H-benzo[b][1,4]oxazin-2-yl)-2,2-dimethylpropanoate

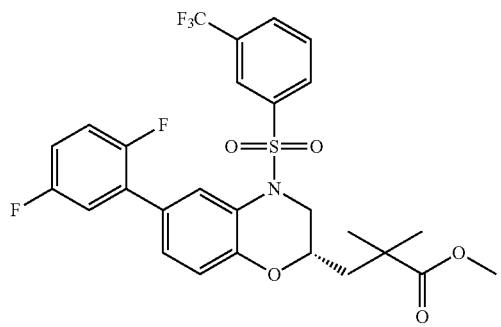 [SMILES: COC(=O)C(C)(C)C[C@H]1CN(S(=O)(=O)c2cccc(C(F)(F)F)c2)c2cc(-c3cc(F)ccc3F)ccc2O1]

A solution of sodium bis(trimethylsilyl)amide (747 mg, 4.08 mmol) in THF (1.5 mL) was added to a stirred solution of methyl 3-((S)-6-(2,5-difluorophenyl)-4-((3-(trifluoromethyl)phenyl)sulfonyl)-3,4-dihydro-2H-benzo[b][1,4]oxazin-2-yl)-2-methylpropanoate (286 mg, 0.51 mmol) in THF (20 mL) at −78° C. The mixture was stirred for one hour at −78° C. and iodomethane (1.14 mL) was then added at −78° C. The resulting mixture was allowed to warm slowly during 2.5 hours to −20° C. Then, the mixture was then stirred overnight at room temperature. Next, the reaction was quenched by the addition of saturated ammonium chloride to the reaction mixture and then the resulting mixture was extracted three times with dichloromethane. The combined organic layers were dried (Na$_2$SO$_4$) and concentrated. The resulting residue was purified by MPLC eluting with a gradient of 0-25% ethyl acetate in petroleum ether to afford methyl (S)-3-(6-(2,5-difluorophenyl)-4-((3-(trifluoromethyl)phenyl)sulfonyl)-3,4-dihydro-2H-benzo[b][1,4]oxazin-2-yl)-2,2-dimethylpropanoate (150 mg, 51%) as a light yellow oil.

Part II—Synthesis of (S)-3-(6-(2,5-difluorophenyl)-4-((3-(trifluoromethyl)phenyl)sulfonyl)-3,4-dihydro-2H-benzo[b][1,4]oxazin-2-yl)-2,2-dimethylpropanoic acid

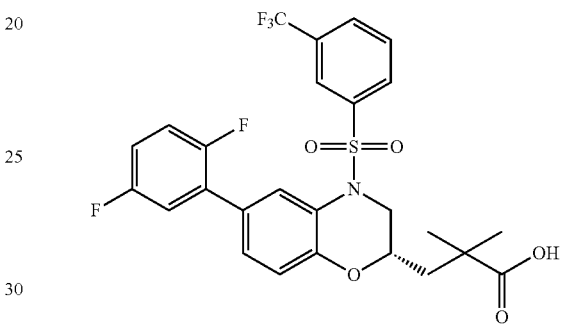

Based on the procedure in Example 1, Part VII, (S)-3-(6-(2,5-difluorophenyl)-4-((3-(trifluoromethyl)phenyl)sulfonyl)-3,4-dihydro-2H-benzo[b][1,4]oxazin-2-yl)-2,2-dimethylpropanoic acid was prepared. $^1$H-NMR (400 MHz, CD$_3$OD) δ 8.07 (m, 1H), 8.02 (d, J=16.0 Hz, 2H), 7.92 (s, 1H), 7.80 (t, J=6.1 Hz, 1H), 7.32-7.21 (m, 3H), 7.12 (m, 1H), 6.88 (d, J=8.4 Hz, 1H), 4.45 (d, J=16.8 Hz, 1H), 3.52 (m, 1H), 3.28 (m, 1H), 1.87-1.77 (m, 2H), 1.32 (d, J=9.2 Hz, 6H). (ES, m/z): (M+H)$^+$ 556.

Example 32—Preparation of Additional Substituted 4-(aryl sulfonyl)-3,4-dihydro-2H-benzo[b][1,4]oxazin-2-yl) Compounds Compounds in Tables 10 and 10A were prepared based on experimental procedures described in Examples 1, 3, 5, 21, 24, 31, and 52 and the detailed description. $^1$H NMR data for exemplary compounds is provided in Table 10B.

TABLE 10

| Compd No. | Structure | Name | Observed m/z |
|---|---|---|---|
| 32A | 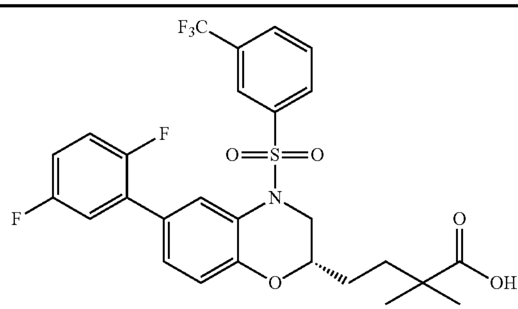 | (S)-4-(6-(2,5-difluorophenyl)-4-((3-(trifluoromethyl)phenyl)-sulfonyl)-3,4-dihydro-2H-benzo[b][1,4]oxazin-2-yl)-2,2-dimethylbutanoic acid | 592 (M + Na)$^+$ |

TABLE 10-continued

| Compd No. | Structure | Name | Observed m/z |
|---|---|---|---|
| 32B | 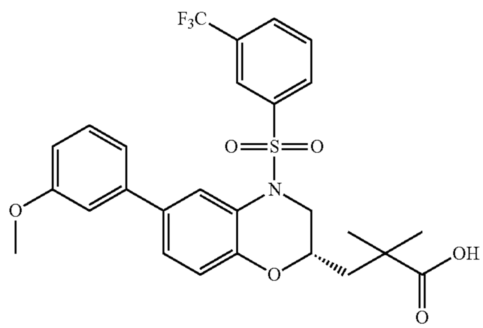 [SMILES: COc1cccc(-c2ccc3c(c2)N(S(=O)(=O)c2cccc(C(F)(F)F)c2)C[C@H](CC(C)(C)C(=O)O)O3)c1] | (S)-3-(6-(3-methoxyphenyl)-4-((3-(trifluoromethyl)phenyl)sulfonyl)-3,4-dihydro-2H-benzo[b][1,4]oxazin-2-yl)-2,2-dimethylpropanoic acid | 550 (M + H)+ |
| 32C | 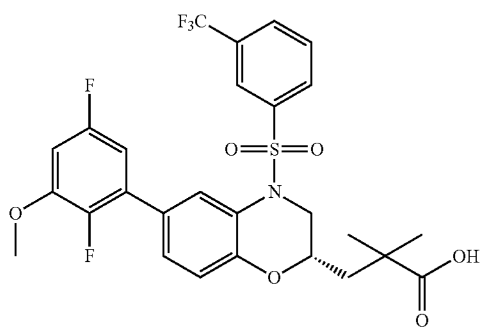 [SMILES: COc1cc(F)cc(-c2ccc3c(c2)N(S(=O)(=O)c2cccc(C(F)(F)F)c2)C[C@H](CC(C)(C)C(=O)O)O3)c1F] | (S)-3-(6-(2,5-difluoro-3-methoxyphenyl)-4-((3-(trifluoromethyl)phenyl)sulfonyl)-3,4-dihydro-2H-benzo[b][1,4]oxazin-2-yl)-2,2-dimethylpropanoic acid | 586 (M + H)+ |
| 32D | 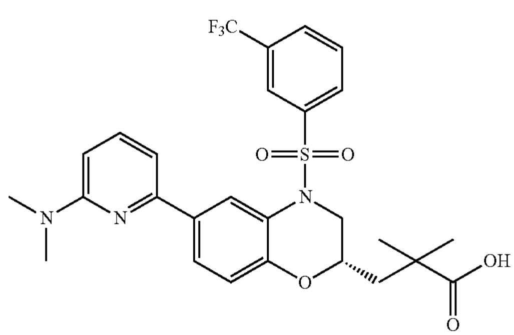 [SMILES: CN(C)c1cccc(-c2ccc3c(c2)N(S(=O)(=O)c2cccc(C(F)(F)F)c2)C[C@H](CC(C)(C)C(=O)O)O3)n1] | (S)-3-(6-(6-(dimethylamino)-pyridin-2-yl)-4-((3-(trifluoromethyl)phenyl)sulfonyl)-3,4-dihydro-2H-benzo[b][1,4]oxazin-2-yl)-2,2-dimethylpropanoic acid | 564 (M + H)+ |
| 32E | 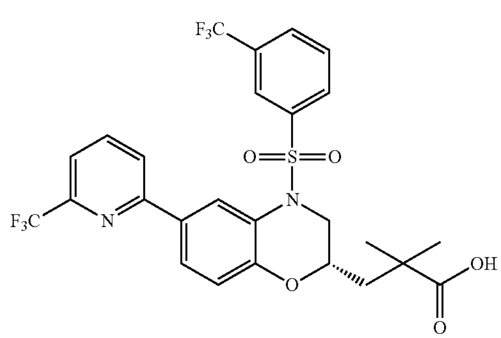 [SMILES: CC(C)(C[C@H]1CN(S(=O)(=O)c2cccc(C(F)(F)F)c2)c2cc(-c3cccc(C(F)(F)F)n3)ccc2O1)C(=O)O] | (S)-2,2-dimethyl-3-(4-((3-(trifluoromethyl)phenyl)sulfonyl)-6-(6-(trifluoromethyl)pyridin-2-yl)-3,4-dihydro-2H-benzo[b][1,4]oxazin-2-yl)propanoic acid | 589 (M + H)+ |

TABLE 10-continued

| Compd No. | Structure | Name | Observed m/z |
|---|---|---|---|
| 32F | 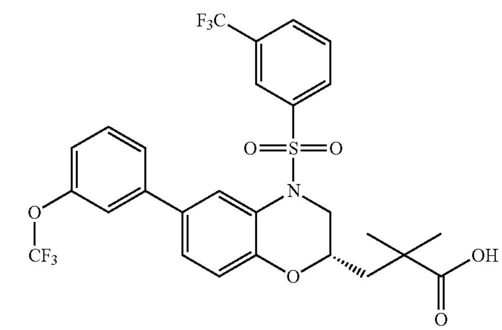 [SMILES: CC(C)(C[C@H]1CN(S(=O)(=O)c2cccc(C(F)(F)F)c2)c2cc(-c3cccc(OC(F)(F)F)c3)ccc2O1)C(=O)O] | (S)-2,2-dimethyl-3-(6-(3-(trifluoromethoxy)phenyl)-4-((3-(trifluoromethyl)phenyl)sulfonyl)-3,4-dihydro-2H-benzo[b][1,4]oxazin-2-yl)propanoic acid | 626 (M + Na)+ |
| 32G | 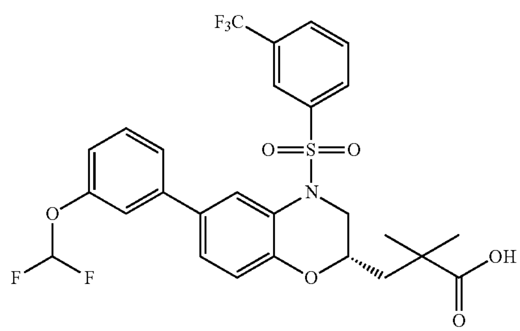 [SMILES: CC(C)(C[C@H]1CN(S(=O)(=O)c2cccc(C(F)(F)F)c2)c2cc(-c3cccc(OC(F)F)c3)ccc2O1)C(=O)O] | (S)-3-(6-(3-(difluoromethoxy)-phenyl)-4-((3-(trifluoromethyl)-phenyl)sulfonyl)-3,4-dihydro-2H-benzo[b][1,4]oxazin-2-yl)-2,2-dimethylpropanoic acid | 608 (M + Na)+ |
| 32H | 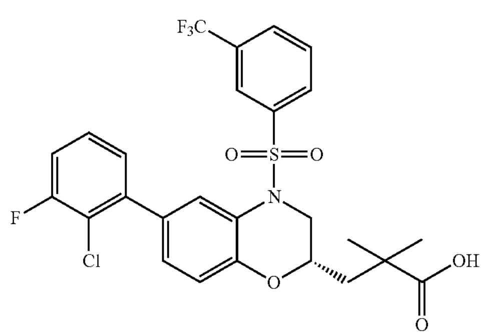 [SMILES: CC(C)(C[C@H]1CN(S(=O)(=O)c2cccc(C(F)(F)F)c2)c2cc(-c3cccc(F)c3Cl)ccc2O1)C(=O)O] | (S)-3-(6-(2-chloro-3-fluorophenyl)-4-((3-(trifluoromethyl)phenyl)sulfonyl)-3,4-dihydro-2H-benzo[b][1,4]oxazin-2-yl)-2,2-dimethylpropanoic acid | 594 (M + Na)+ |
| 32I | 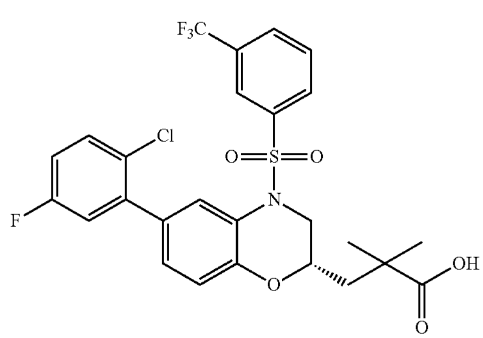 | (S)-3-(6-(2-chloro-5-fluorophenyl)-4-((3-(trifluoromethyl)phenyl)sulfonyl)-3,4-dihydro-2H-benzo[b][1,4]oxazin-2-yl)-2,2-dimethylpropanoic acid | 594 (M + Na)+ |

TABLE 10-continued

| Compd No. | Structure | Name | Observed m/z |
|---|---|---|---|
| 32J | 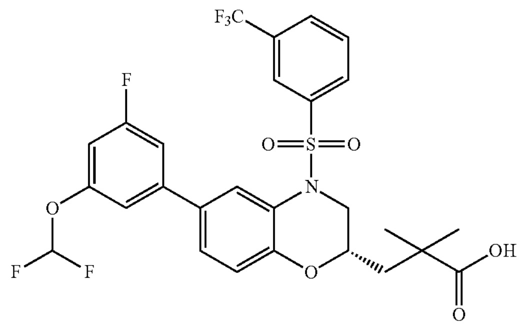 [SMILES: CC(C)(C[C@H]1CN(S(=O)(=O)c2cccc(C(F)(F)F)c2)c2cc(-c3cc(F)cc(OC(F)F)c3)ccc2O1)C(=O)O] | (S)-3-(6-(3-(difluoromethoxy)-5-fluorophenyl)-4-((3-(trifluoromethyl)phenyl)sulfonyl)-3,4-dihydro-2H-benzo[b][1,4]oxazin-2-yl)-2,2-dimethylpropanoic acid | 626 (M + Na)+ |
| 32K | 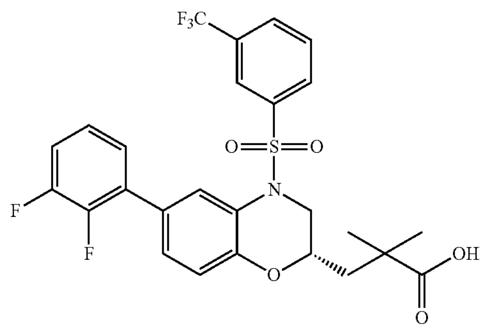 [SMILES: CC(C)(C[C@H]1CN(S(=O)(=O)c2cccc(C(F)(F)F)c2)c2cc(-c3cccc(F)c3F)ccc2O1)C(=O)O] | (S)-3-(6-(2,3-difluorophenyl)-4-((3-(trifluoromethyl)phenyl)sulfonyl)-3,4-dihydro-2H-benzo[b][1,4]oxazin-2-yl)-2,2-dimethylpropanoic acid | 578 (M + Na)+ |
| 32L | 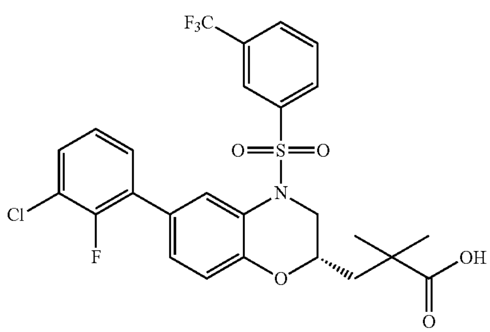 | (S)-3-(6-(3-chloro-2-fluorophenyl)-4-((3-(trifluoromethyl)phenyl)sulfonyl)-3,4-dihydro-2H-benzo[b][1,4]oxazin-2-yl)-2,2-dimethylpropanoic acid | 594 (M + Na)+ |
| 32M | 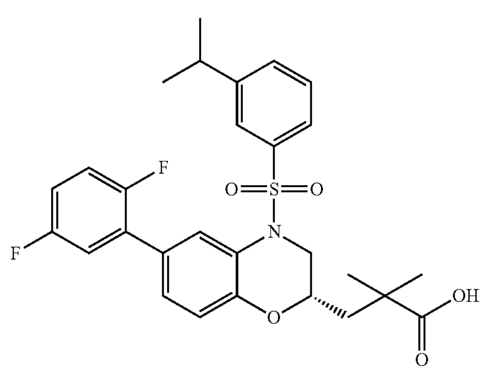 [SMILES: CC(C)c1cccc(S(=O)(=O)N2C[C@H](CC(C)(C)C(=O)O)Oc3ccc(-c4cc(F)ccc4F)cc32)c1] | (S)-3-(6-(2,5-difluorophenyl)-4-((3-isopropylphenyl)sulfonyl)-3,4-dihydro-2H-benzo[b][1,4]oxazin-2-yl)-2,2-dimethylpropanoic acid | 552 (M + Na)+ |

TABLE 10-continued

| Compd No. | Structure | Name | Observed m/z |
|---|---|---|---|
| 32N | 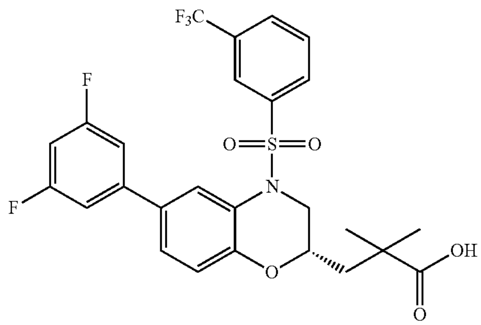 [SMILES: CC(C)(C[C@H]1CN(S(=O)(=O)c2cccc(C(F)(F)F)c2)c2cc(-c3cc(F)cc(F)c3)ccc2O1)C(=O)O] | (S)-3-(6-(3,5-difluorophenyl)-4-((3-(trifluoromethyl)phenyl)-sulfonyl)-3,4-dihydro-2H-benzo[b][1,4]oxazin-2-yl)-2,2-dimethylpropanoic acid | 578 (M + Na)+ |
| 32O | 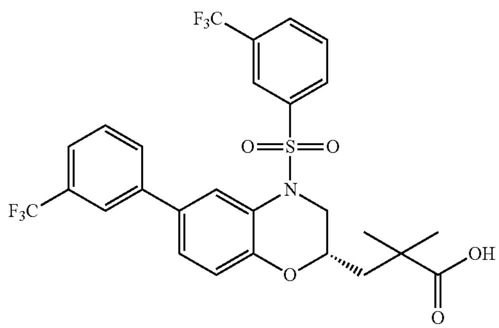 [SMILES: CC(C)(C[C@H]1CN(S(=O)(=O)c2cccc(C(F)(F)F)c2)c2cc(-c3cccc(C(F)(F)F)c3)ccc2O1)C(=O)O] | (S)-2,2-dimethyl-3-(6-(3-(trifluoromethyl)phenyl)-4-((3-(trifluoromethyl)phenyl)sulfonyl)-3,4-dihydro-2H-benzo[b][1,4]oxazin-2-yl)propanoic acid | 610 (M + Na)+ |
| 32P | 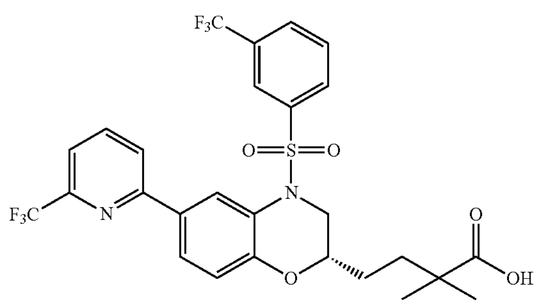 [SMILES: CC(C)(CC[C@H]1CN(S(=O)(=O)c2cccc(C(F)(F)F)c2)c2cc(-c3cccc(C(F)(F)F)n3)ccc2O1)C(=O)O] | (S)-2,2-dimethyl-4-(4-((3-(trifluoromethyl)phenyl)sulfonyl)-6-(6-(trifluoromethyl)pyridin-2-yl)-3,4-dihydro-2H-benzo[b][1,4]oxazin-2-yl)butanoic acid | 603 (M + H)+ |
| 32Q | 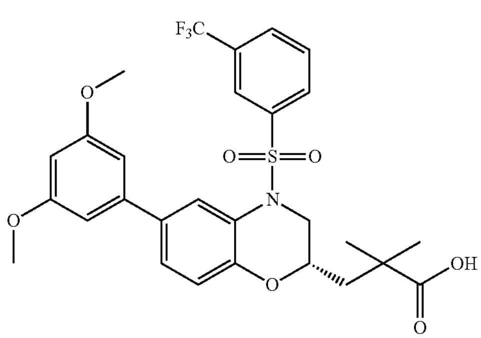 [SMILES: COc1cc(OC)cc(-c2ccc3c(c2)N(S(=O)(=O)c2cccc(C(F)(F)F)c2)C[C@H](CC(C)(C)C(=O)O)O3)c1] | (S)-3-(6-(3,5-dimethoxyphenyl)-4-((3-(trifluoromethyl)phenyl)-sulfonyl)-3,4-dihydro-2H-benzo[b][1,4]oxazin-2-yl)-2,2-dimethylpropanoic acid | 580 (M + H)+ |

TABLE 10-continued

| Compd No. | Structure | Name | Observed m/z |
|---|---|---|---|
| 32R | 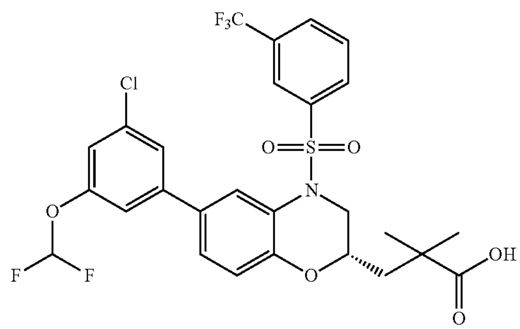 [SMILES: CC(C)(C[C@H]1CN(S(=O)(=O)c2cccc(C(F)(F)F)c2)c2cc(-c3cc(Cl)cc(OC(F)F)c3)ccc2O1)C(=O)O] | (S)-3-(6-(3-chloro-5-(difluoro-methoxy)phenyl)-4-((3-(trifluoro-methyl)phenyl)sulfonyl)-3,4-dihydro-2H-benzo[b][1,4]oxazin-2-yl)-2,2-dimethylpropanoic acid | 642 (M + Na)+ |
| 32S | 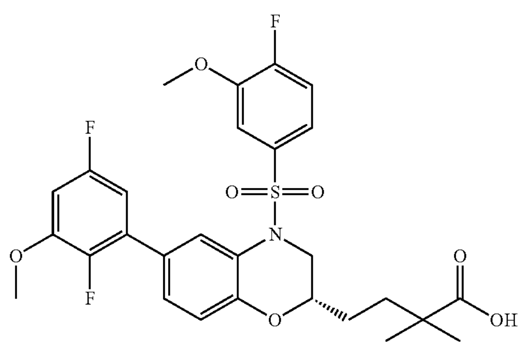 [SMILES: COc1cc(S(=O)(=O)N2C[C@H](CCC(C)(C)C(=O)O)Oc3ccc(-c4cc(F)cc(OC)c4F)cc32)ccc1F] | (S)-4-(6-(2,5-difluoro-3-methoxyphenyl)-4-((4-fluoro-3-methoxyphenyl)sulfonyl)-3,4-dihydro-2H-benzo[b][1,4]oxazin-2-yl)-2,2-dimethylbutanoic acid | 580 (M + H)+ |
| 32T | 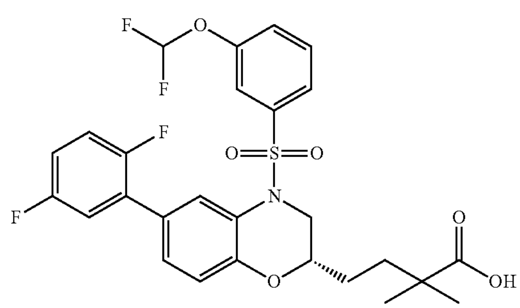 [SMILES: CC(C)(CC[C@H]1CN(S(=O)(=O)c2cccc(OC(F)F)c2)c2cc(-c3cc(F)ccc3F)ccc2O1)C(=O)O] | (S)-4-(4-((3-(difluoro-methoxy)phenyl)sulfonyl)-6-(2,5-difluorophenyl)-3,4-dihydro-2H-benzo[b][1,4]oxazin-2-yl)-2,2-dimethylbutanoic acid | 590 (M + Na)+ |
| 32U | 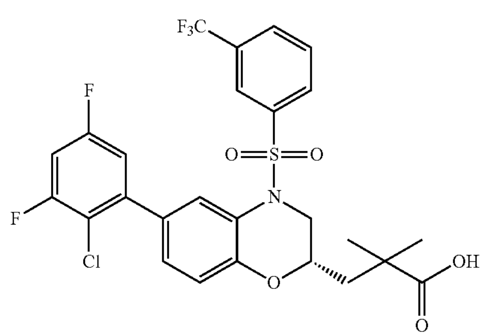 | (S)-3-(6-(2-chloro-3,5-difluoro-phenyl)-4-((3-(trifluoromethyl)-phenyl)sulfonyl)-3,4-dihydro-2H-benzo[b][1,4]oxazin-2-yl)-2,2-dimethylpropanoic acid | 612 (M + Na)+ |

TABLE 10A

| Compd No. | Structure | Name | Observed m/z |
|---|---|---|---|
| 32V | 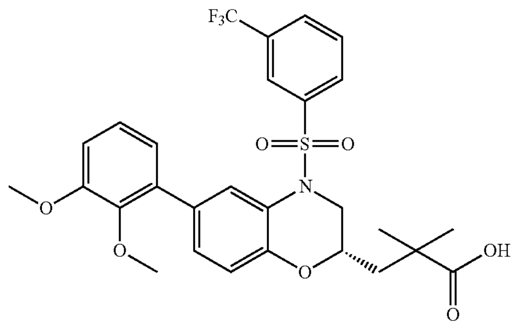 [SMILES: COc1cccc(-c2ccc3c(c2)N(S(=O)(=O)c2cccc(C(F)(F)F)c2)C[C@H](CC(C)(C)C(=O)O)O3)c1OC] | (S)-3-(6-(2,3-dimethoxyphenyl)-4-((3-(trifluoromethyl)phenyl)-sulfonyl)-3,4-dihydro-2H-benzo[b][1,4]oxazin-2-yl)-2,2-dimethylpropanoic acid | 602 (M + Na)+ |
| 32W | 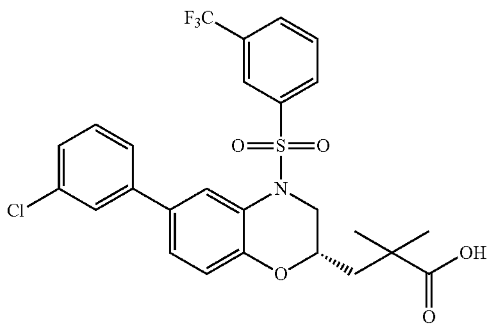 [SMILES: CC(C)(C[C@H]1CN(S(=O)(=O)c2cccc(C(F)(F)F)c2)c2cc(-c3cccc(Cl)c3)ccc2O1)C(=O)O] | (S)-3-(6-(3-chlorophenyl)-4-((3-(trifluoromethyl)phenyl)sulfonyl)-3,4-dihydro-2H-benzo[b][1,4]-oxazin-2-yl)-2,2-dimethyl-propanoic acid | 576 (M + Na)+ |
| 32X | 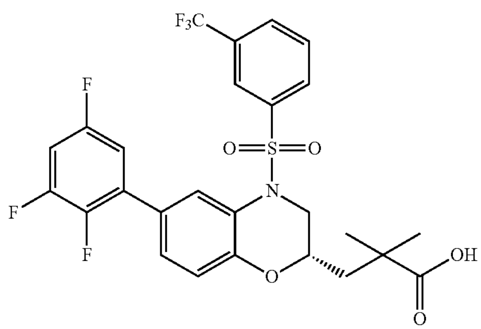 [SMILES: CC(C)(C[C@H]1CN(S(=O)(=O)c2cccc(C(F)(F)F)c2)c2cc(-c3cc(F)cc(F)c3F)ccc2O1)C(=O)O] | (S)-2,2-dimethyl-3-(4-((3-(trifluoromethyl)phenyl)sulfonyl)-6-(2,3,5-trifluorophenyl)-3,4-dihydro-2H-benzo[b][1,4]oxazin-2-yl)propanoic acid | 596 (M + Na)+ |
| 32Y | 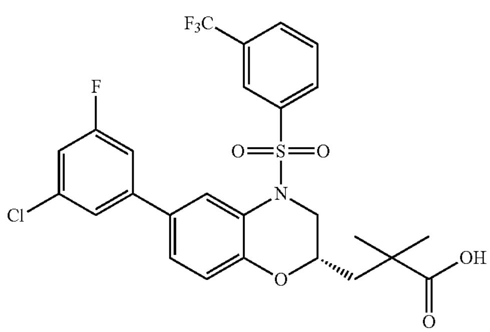 [SMILES: CC(C)(C[C@H]1CN(S(=O)(=O)c2cccc(C(F)(F)F)c2)c2cc(-c3cc(F)cc(Cl)c3)ccc2O1)C(=O)O] | (S)-3-(6-(3-chloro-5-fluoro-phenyl)-4-((3-(trifluoromethyl)-phenyl)sulfonyl)-3,4-dihydro-2H-benzo[b][1,4]oxazin-2-yl)-2,2-dimethylpropanoic acid | 594 (M + Na)+ |

TABLE 10A-continued

| Compd No. | Structure | Name | Observed m/z |
|---|---|---|---|
| 32Z | 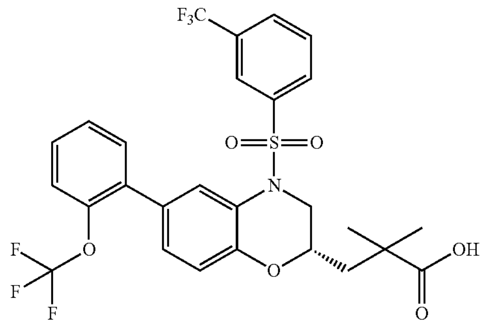 [SMILES: CC(C)(C[C@H]1CN(S(=O)(=O)c2cccc(C(F)(F)F)c2)c2cc(-c3ccccc3OC(F)(F)F)ccc2O1)C(=O)O] | (S)-2,2-dimethyl-3-(6-(2-(trifluoromethoxy)phenyl)-4-((3-(trifluoromethyl)phenyl)sulfonyl)-3,4-dihydro-2H-benzo[b][1,4]-oxazin-2-yl)propanoic acid | 626 (M + Na)+ |
| 32AA | 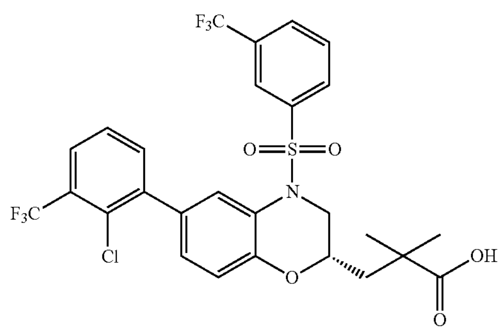 [SMILES: CC(C)(C[C@H]1CN(S(=O)(=O)c2cccc(C(F)(F)F)c2)c2cc(-c3cccc(C(F)(F)F)c3Cl)ccc2O1)C(=O)O] | (S)-3-(6-(2-chloro-3-(trifluoromethyl)phenyl)-4-((3-(trifluoromethyl)phenyl)sulfonyl)-3,4-dihydro-2H-benzo[b][1,4]-oxazin-2-yl)-2,2-dimethyl-propanoic acid | 644 (M + Na)+ |
| 32AB | 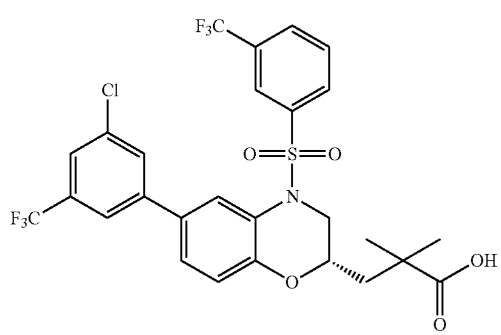 [SMILES: CC(C)(C[C@H]1CN(S(=O)(=O)c2cccc(C(F)(F)F)c2)c2cc(-c3cc(Cl)cc(C(F)(F)F)c3)ccc2O1)C(=O)O] | (S)-3-(6-(3-chloro-5-(trifluoromethyl)phenyl)-4-((3-(trifluoromethyl)phenyl)sulfonyl)-3,4-dihydro-2H-benzo[b][1,4]oxazin-2-yl)-2,2-dimethylpropanoic acid | 644 (M + Na)+ |
| 32AC | 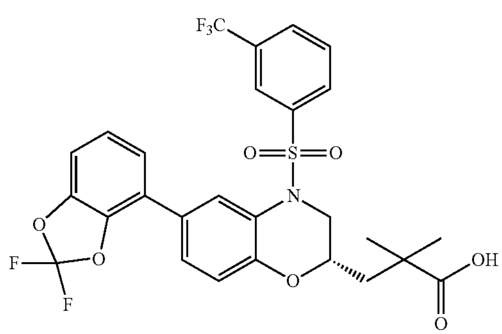 [SMILES: CC(C)(C[C@H]1CN(S(=O)(=O)c2cccc(C(F)(F)F)c2)c2cc(-c3cccc4c3OC(F)(F)O4)ccc2O1)C(=O)O] | (S)-3-(6-(2,2-difluorobenzo[d]-[1,3]dioxol-4-yl)-4-((3-(trifluoromethyl)phenyl)sulfonyl)-3,4-dihydro-2H-benzo[b][1,4]oxazin-2-yl)-2,2-dimethylpropanoic acid | 622 (M + Na)+ |

TABLE 10A-continued

| Compd No. | Structure | Name | Observed m/z |
|---|---|---|---|
| 32AD | 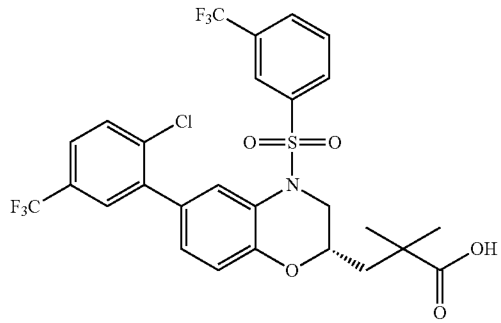 [SMILES: CC(C)(C[C@H]1CN(S(=O)(=O)c2cccc(C(F)(F)F)c2)c2cc(-c3cc(C(F)(F)F)ccc3Cl)ccc2O1)C(=O)O] | (S)-3-(6-(2-chloro-5-(trifluoromethyl)phenyl)-4-((3-(trifluoromethyl)phenyl)sulfonyl)-3,4-dihydro-2H-benzo[b][1,4]oxazin-2-yl)-2,2-dimethylpropanoic acid | 644 (M + Na)+ |
| 32AE | 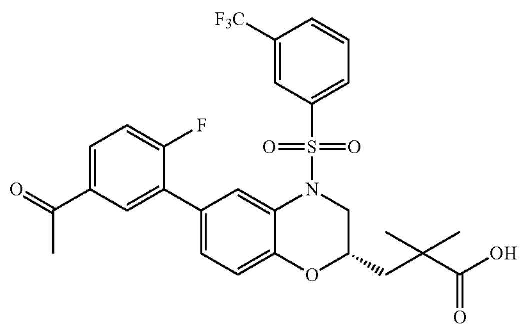 [SMILES: CC(=O)c1ccc(F)c(-c2ccc3c(c2)N(S(=O)(=O)c2cccc(C(F)(F)F)c2)C[C@H](CC(C)(C)C(=O)O)O3)c1] | (S)-3-(6-(5-acetyl-2-fluoro-phenyl)-4-((3-(trifluoromethyl)-phenyl)sulfonyl)-3,4-dihydro-2H-benzo[b][1,4]oxazin-2-yl)-2,2-dimethylpropanoic acid | 602 (M + Na)+ |
| 32AF | 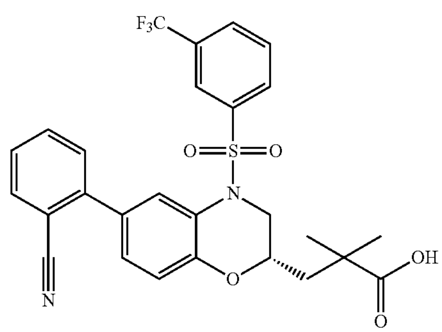 [SMILES: CC(C)(C[C@H]1CN(S(=O)(=O)c2cccc(C(F)(F)F)c2)c2cc(-c3ccccc3C#N)ccc2O1)C(=O)O] | (S)-3-(6-(2-cyanophenyl)-4-((3-(trifluoromethyl)phenyl)sulfonyl)-3,4-dihydro-2H-benzo[b][1,4]-oxazin-2-yl)-2,2-dimethyl-propanoic acid | 567 (M + Na)+ |
| 32AG | 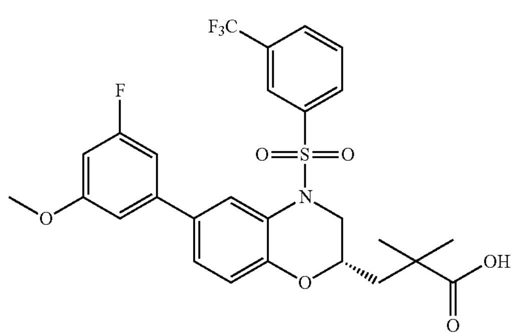 [SMILES: COc1cc(F)cc(-c2ccc3c(c2)N(S(=O)(=O)c2cccc(C(F)(F)F)c2)C[C@H](CC(C)(C)C(=O)O)O3)c1] | (S)-3-(6-(3-fluoro-5-methoxy-phenyl)-4-((3-(trifluoromethyl)-phenyl)sulfonyl)-3,4-dihydro-2H-benzo[b][1,4]oxazin-2-yl)-2,2-dimethylpropanoic acid | 590 (M + Na)+ |

TABLE 10A-continued

| Compd No. | Structure | Name | Observed m/z |
|---|---|---|---|
| 32AH | 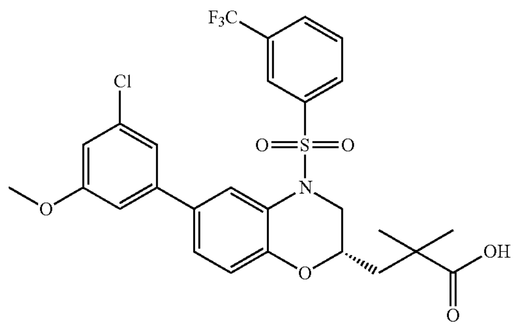 | (S)-3-(6-(3-chloro-5-methoxy-phenyl)-4-((3-(trifluoromethyl)-phenyl)sulfonyl)-3,4-dihydro-2H-benzo[b][1,4]oxazin-2-yl)-2,2-dimethylpropanoic acid | 606 (M + Na)+ |
| 32AI | 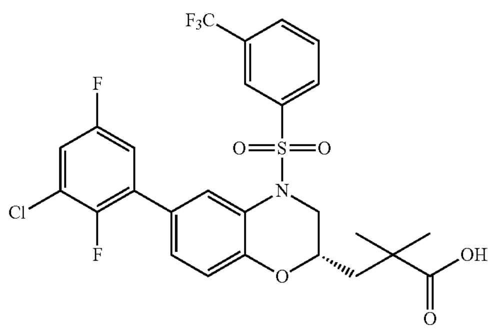 [SMILES: CC(C)(C[C@H]1CN(S(=O)(=O)c2cccc(C(F)(F)F)c2)c2cc(-c3cc(F)cc(Cl)c3F)ccc2O1)C(=O)O] | (S)-3-(6-(3-chloro-2,5-difluoro-phenyl)-4-((3-(trifluoromethyl)-phenyl)sulfonyl)-3,4-dihydro-2H-benzo[b][1,4]oxazin-2-yl)-2,2-dimethylpropanoic acid | 612 (M + Na)+ |
| 32AJ | 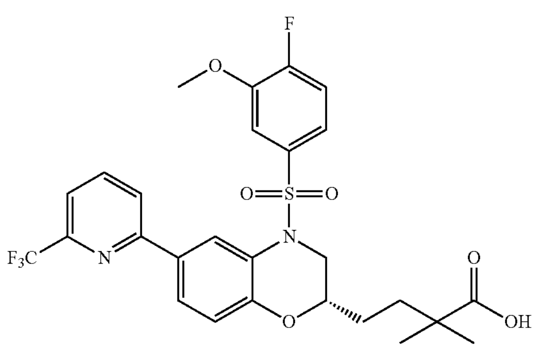 [SMILES: COc1cc(S(=O)(=O)N2C[C@H](CCC(C)(C)C(=O)O)Oc3ccc(-c4cccc(C(F)(F)F)n4)cc32)ccc1F] | (S)-4-(4-((4-fluoro-3-methoxy-phenyl)sulfonyl)-6-(6-(trifluoro-methyl)pyridin-2-yl)-3,4-dihydro-2H-benzo[b][1,4]oxazin-2-yl)-2,2-dimethylbutanoic acid | 583 (M + H)+ |
| 32AK | 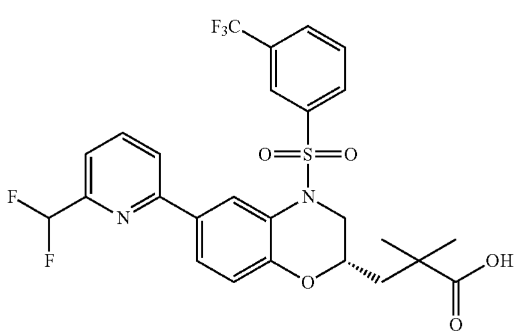 [SMILES: CC(C)(C[C@H]1CN(S(=O)(=O)c2cccc(C(F)(F)F)c2)c2cc(-c3cccc(C(F)F)n3)ccc2O1)C(=O)O] | (S)-3-(6-(6-(difluoromethyl)-pyridin-2-yl)-4-((3-(trifluoro-methyl)phenyl)sulfonyl)-3,4-dihydro-2H-benzo[b][1,4]oxazin-2-yl)-2,2-dimethylpropanoic acid | 571 (M + H)+ |

TABLE 10A-continued

| Compd No. | Structure | Name | Observed m/z |
|---|---|---|---|
| 32AL | 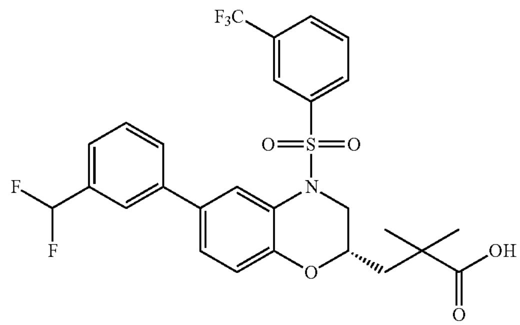 [SMILES: CC(C)(C[C@H]1CN(S(=O)(=O)c2cccc(C(F)(F)F)c2)c2cc(-c3cccc(C(F)F)c3)ccc2O1)C(=O)O] | (S)-3-(6-(3-(difluoromethyl)-phenyl)-4-((3-(trifluoromethyl)-phenyl)sulfonyl)-3,4-dihydro-2H-benzo[b][1,4]oxazin-2-yl)-2,2-dimethylpropanoic acid | 592 (M + Na)+ |
| 32AM | 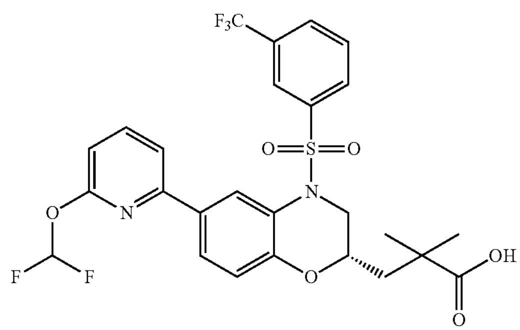 [SMILES: CC(C)(C[C@H]1CN(S(=O)(=O)c2cccc(C(F)(F)F)c2)c2cc(-c3cccc(OC(F)F)n3)ccc2O1)C(=O)O] | (S)-3-(6-(6-(difluoromethoxy)-pyridin-2-yl)-4-((3-(trifluoromethyl)phenyl)sulfonyl)-3,4-dihydro-2H-benzo[b][1,4]oxazin-2-yl)-2,2-dimethylpropanoic acid | 587 (M + H)+ |
| 32AN | 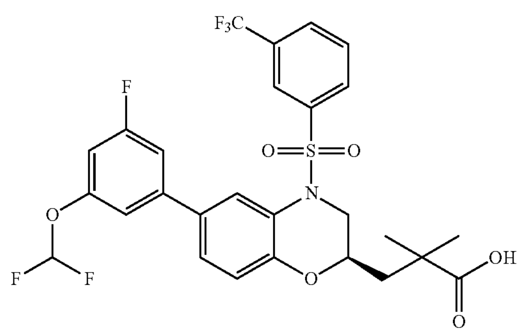 [SMILES: CC(C)(C[C@@H]1CN(S(=O)(=O)c2cccc(C(F)(F)F)c2)c2cc(-c3cc(F)cc(OC(F)F)c3)ccc2O1)C(=O)O] | (R)-3-(6-(3-(difluoromethoxy)-5-fluorophenyl)-4-((3-(trifluoromethyl)phenyl)sulfonyl)-3,4-dihydro-2H-benzo[b][1,4]oxazin-2-yl)-2,2-dimethylpropanoic acid | 602 (M − H)− |
| 32AO | 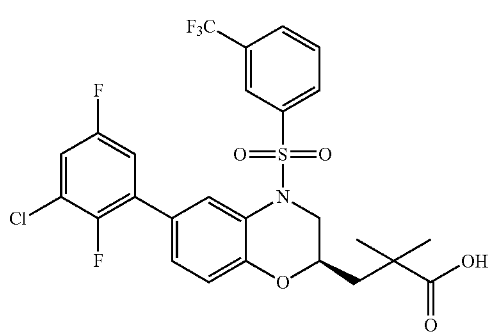 [SMILES: CC(C)(C[C@@H]1CN(S(=O)(=O)c2cccc(C(F)(F)F)c2)c2cc(-c3cc(F)cc(Cl)c3F)ccc2O1)C(=O)O] | (R)-3-(6-(3-chloro-2,5-difluoro-phenyl)-4-((3-(trifluoromethyl)-phenyl)sulfonyl)-3,4-dihydro-2H-benzo[b][1,4]oxazin-2-yl)-2,2-dimethylpropanoic acid | 588 (M − H)− |

TABLE 10A-continued

| Compd No. | Structure | Name | Observed m/z |
|---|---|---|---|
| 32AP | 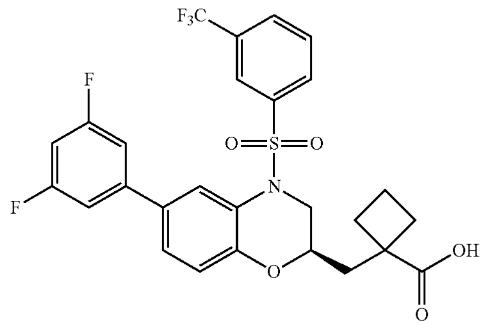 [SMILES: O=C(O)C1(C[C@@H]2CN(S(=O)(=O)c3cccc(C(F)(F)F)c3)c3cc(-c4cc(F)cc(F)c4)ccc3O2)CCC1] | (R)-1-((6-(3,5-difluorophenyl)-4-((3-(trifluoromethyl)phenyl)-sulfonyl)-3,4-dihydro-2H-benzo[b][1,4]oxazin-2-yl)methyl)cyclobutane-1-carboxylic acid | 568 (M + H)+ |
| 32AQ | 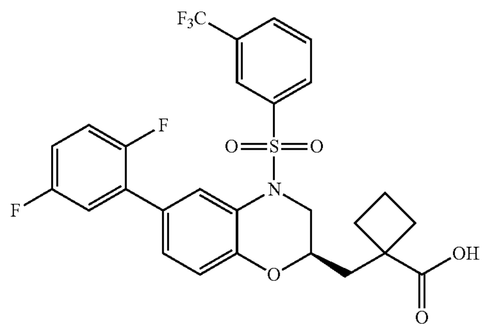 [SMILES: O=C(O)C1(C[C@@H]2CN(S(=O)(=O)c3cccc(C(F)(F)F)c3)c3cc(-c4cc(F)ccc4F)ccc3O2)CCC1] | (R)-1-((6-(2,5-difluorophenyl)-4-((3-(trifluoromethyl)phenyl)-sulfonyl)-3,4-dihydro-2H-benzo[b][1,4]oxazin-2-yl)methyl)cyclobutane-1-carboxylic acid | 568 (M + H)+ |
| 32AR | 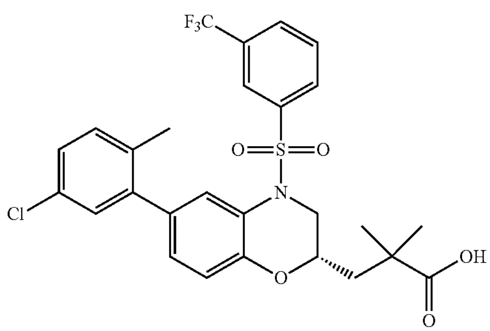 [SMILES: Cc1ccc(Cl)cc1-c1ccc2c(c1)N(S(=O)(=O)c1cccc(C(F)(F)F)c1)C[C@H](CC(C)(C)C(=O)O)O2] | (S)-3-(6-(5-chloro-2-methyl-phenyl)-4-((3-(trifluoromethyl)-phenyl)sulfonyl)-3,4-dihydro-2H-benzo[b][1,4]oxazin-2-yl)-2,2-dimethylpropanoic acid | 590 (M + Na)+ |
| 32AS | 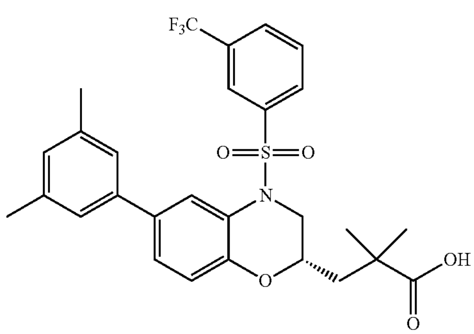 | (S)-3-(6-(3,5-dimethylphenyl)-4-((3-(trifluoromethyl)phenyl)-sulfonyl)-3,4-dihydro-2H-benzo[b][1,4]oxazin-2-yl)-2,2-dimethylpropanoic acid | 570 (M + Na)+ |

TABLE 10A-continued

| Compd No. | Structure | Name | Observed m/z |
|---|---|---|---|
| 32AT | 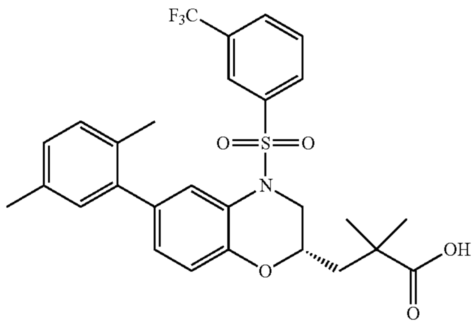 [SMILES: Cc1ccc(C)c(-c2ccc3c(c2)N(S(=O)(=O)c2cccc(C(F)(F)F)c2)C[C@H](CC(C)(C)C(=O)O)O3)c1] | (S)-3-(6-(2,5-dimethylphenyl)-4-((3-(trifluoromethyl)phenyl)-sulfonyl)-3,4-dihydro-2H-benzo[b][1,4]oxazin-2-yl)-2,2-dimethylpropanoic acid | 570 (M + Na)+ |
| 32AU | 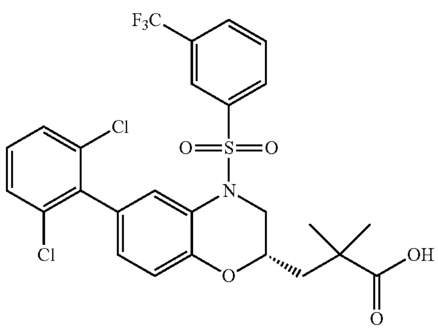 [SMILES: CC(C)(C[C@H]1CN(S(=O)(=O)c2cccc(C(F)(F)F)c2)c2cc(-c3c(Cl)cccc3Cl)ccc2O1)C(=O)O] | (S)-3-(6-(2,6-dichlorophenyl)-4-((3-(trifluoromethyl)phenyl)-sulfonyl)-3,4-dihydro-2H-benzo[b][1,4]oxazin-2-yl)-2,2-dimethylpropanoic acid | 610 (M + Na)+ |
| 32AV | 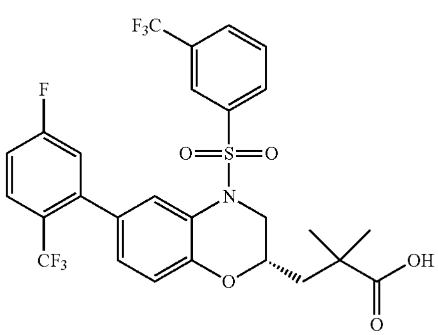 [SMILES: CC(C)(C[C@H]1CN(S(=O)(=O)c2cccc(C(F)(F)F)c2)c2cc(-c3cc(F)ccc3C(F)(F)F)ccc2O1)C(=O)O] | (S)-3-(6-(5-fluoro-2-(trifluoro-methyl)phenyl)-4-((3-(trifluoro-methyl)phenyl)sulfonyl)-3,4-dihydro-2H-benzo[b][1,4]oxazin-2-yl)-2,2-dimethylpropanoic acid | 628 (M + Na)+ |
| 32AW | 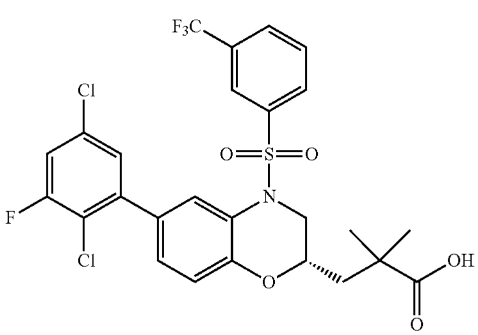 [SMILES: CC(C)(C[C@H]1CN(S(=O)(=O)c2cccc(C(F)(F)F)c2)c2cc(-c3cc(Cl)cc(F)c3Cl)ccc2O1)C(=O)O] | (S)-3-(6-(2,5-dichloro-3-fluoro-phenyl)-4-((3-(trifluoromethyl)-phenyl)sulfonyl)-3,4-dihydro-2H-benzo[b][1,4]oxazin-2-yl)-2,2-dimethylpropanoic acid | 628 (M + Na)+ |

TABLE 10A-continued

| Compd No. | Structure | Name | Observed m/z |
|---|---|---|---|
| 32AX | 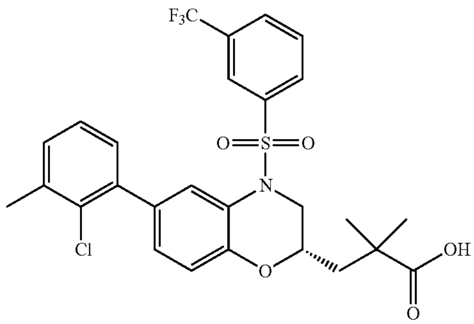 [SMILES: Cc1cccc(-c2ccc3c(c2)N(S(=O)(=O)c2cccc(C(F)(F)F)c2)C[C@H](CC(C)(C)C(=O)O)O3)c1Cl] | (S)-3-(6-(2-chloro-3-methyl-phenyl)-4-((3-(trifluoromethyl)-phenyl)sulfonyl)-3,4-dihydro-2H-benzo[b][1,4]oxazin-2-yl)-2,2-dimethylpropanoic acid | 590 (M + Na)+ |
| 32AY | 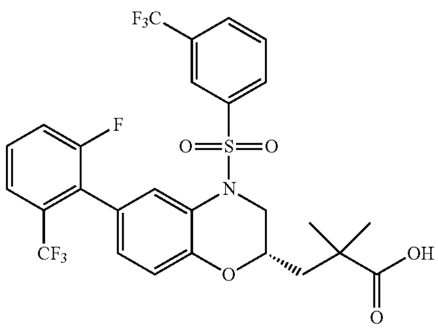 [SMILES: CC(C)(C[C@H]1CN(S(=O)(=O)c2cccc(C(F)(F)F)c2)c2cc(-c3c(F)cccc3C(F)(F)F)ccc2O1)C(=O)O] | (S)-3-(6-(2-fluoro-6-(trifluoro-methyl)phenyl)-4-((3-(trifluoro-methyl)phenyl)sulfonyl)-3,4-dihydro-2H-benzo[b][1,4]oxazin-2-yl)-2,2-dimethylpropanoic acid | 628 (M + Na)+ |
| 32AZ | 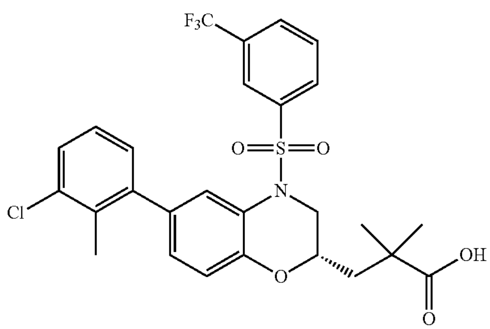 [SMILES: Cc1c(Cl)cccc1-c1ccc2c(c1)N(S(=O)(=O)c1cccc(C(F)(F)F)c1)C[C@H](CC(C)(C)C(=O)O)O2] | (S)-3-(6-(3-chloro-2-methyl-phenyl)-4-((3-(trifluoromethyl)-phenyl)sulfonyl)-3,4-dihydro-2H-benzo[b][1,4]oxazin-2-yl)-2,2-dimethylpropanoic acid | 590 (M + Na)+ |
| 32BA | 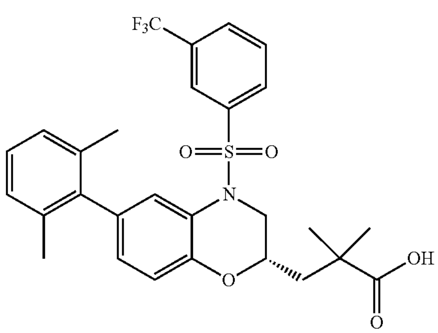 [SMILES: Cc1cccc(C)c1-c1ccc2c(c1)N(S(=O)(=O)c1cccc(C(F)(F)F)c1)C[C@H](CC(C)(C)C(=O)O)O2] | (S)-3-(6-(2,6-dimethylphenyl)-4-((3-(trifluoromethyl)phenyl)-sulfonyl)-3,4-dihydro-2H-benzo[b][1,4]oxazin-2-yl)-2,2-dimethylpropanoic acid | 570 (M + Na)+ |

TABLE 10A-continued

| Compd No. | Structure | Name | Observed m/z |
|---|---|---|---|
| 32BB | 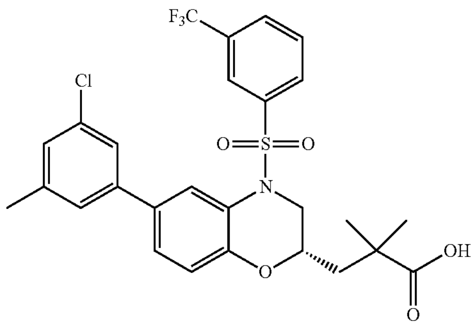 [SMILES: Cc1cc(Cl)cc(-c2ccc3c(c2)N(S(=O)(=O)c2cccc(C(F)(F)F)c2)C[C@H](CC(C)(C)C(=O)O)O3)c1] | (S)-3-(6-(3-chloro-5-methyl-phenyl)-4-((3-(trifluoromethyl)-phenyl)sulfonyl)-3,4-dihydro-2H-benzo[b][1,4]oxazin-2-yl)-2,2-dimethylpropanoic acid | 590 (M + Na)+ |
| 32BC | 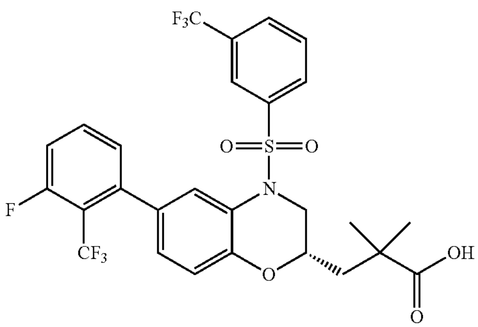 [SMILES: CC(C)(C[C@H]1CN(S(=O)(=O)c2cccc(C(F)(F)F)c2)c2cc(-c3cccc(F)c3C(F)(F)F)ccc2O1)C(=O)O] | (S)-3-(6-(3-fluoro-2-(trifluoromethyl)phenyl)-4-((3-(trifluoromethyl)phenyl)sulfonyl)-3,4-dihydro-2H-benzo[b][1,4]oxazin-2-yl)-2,2-dimethylpropanoic acid | 628 (M + Na)+ |
| 32BD | 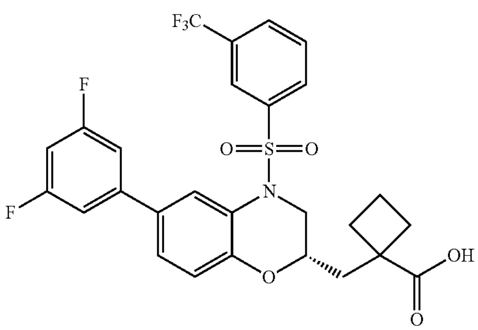 [SMILES: O=C(O)C1(C[C@H]2CN(S(=O)(=O)c3cccc(C(F)(F)F)c3)c3cc(-c4cc(F)cc(F)c4)ccc3O2)CCC1] | (S)-1-((6-(3,5-difluorophenyl)-4-((3-(trifluoromethyl)phenyl)-sulfonyl)-3,4-dihydro-2H-benzo[b][1,4]oxazin-2-yl)methyl)cyclobutane-1-carboxylic acid | 568 (M + H)+ |
| 32BE | 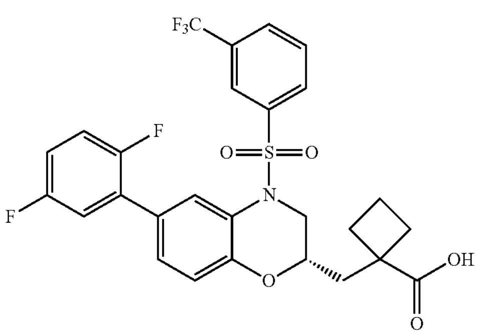 [SMILES: O=C(O)C1(C[C@H]2CN(S(=O)(=O)c3cccc(C(F)(F)F)c3)c3cc(-c4cc(F)ccc4F)ccc3O2)CCC1] | (S)-1-((6-(2,5-difluorophenyl)-4-((3-(trifluoromethyl)phenyl)-sulfonyl)-3,4-dihydro-2H-benzo[b][1,4]oxazin-2-yl)methyl)cyclobutane-1-carboxylic acid | 568 (M + H)+ |

TABLE 10A-continued

| Compd No. | Structure | Name | Observed m/z |
|---|---|---|---|
| 32BF | 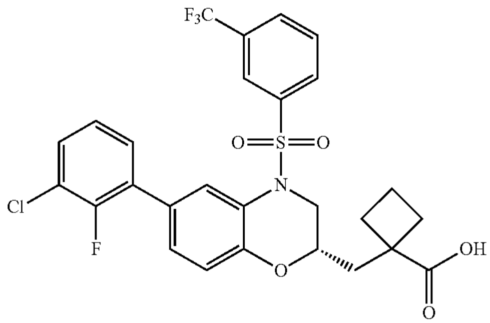 [SMILES: O=C(O)C1(C[C@H]2CN(S(=O)(=O)c3cccc(C(F)(F)F)c3)c3cc(-c4cccc(Cl)c4F)ccc3O2)CCC1] | (S)-1-((6-(3-chloro-2-fluoro-phenyl)-4-((3-(trifluoromethyl)-phenyl)sulfonyl)-3,4-dihydro-2H-benzo[b][1,4]oxazin-2-yl)-methyl)cyclobutane-1-carboxylic acid | 584 (M + H)+ |
| 32BG | 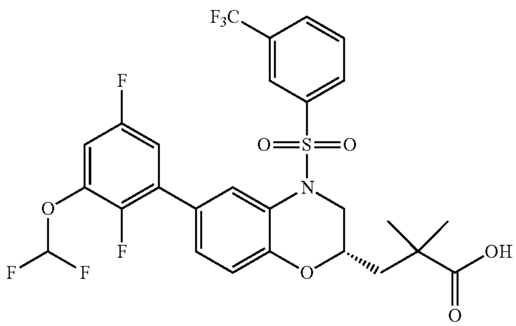 [SMILES: CC(C)(C[C@H]1CN(S(=O)(=O)c2cccc(C(F)(F)F)c2)c2cc(-c3cc(F)cc(OC(F)F)c3F)ccc2O1)C(=O)O] | (S)-3-(6-(3-(difluoromethoxy)-2,5-difluorophenyl)-4-((3-(trifluoromethyl)phenyl)sulfonyl)-3,4-dihydro-2H-benzo[b][1,4]-oxazin-2-yl)-2,2-dimethyl-propanoic acid | 620 (M − H)− |
| 32BH | 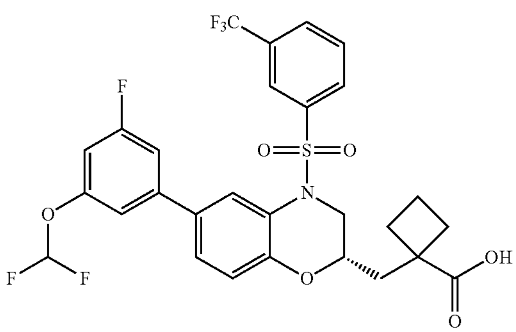 [SMILES: O=C(O)C1(C[C@H]2CN(S(=O)(=O)c3cccc(C(F)(F)F)c3)c3cc(-c4cc(F)cc(OC(F)F)c4)ccc3O2)CCC1] | (S)-1-((6-(3-(difluoromethoxy)-5-fluorophenyl)-4-((3-(trifluoro-methyl)phenyl)sulfonyl)-3,4-dihydro-2H-benzo[b][1,4]oxazin-2-yl)methyl)cyclobutane-1-carboxylic acid | 633 (M + NH4)+ |
| 32BI | 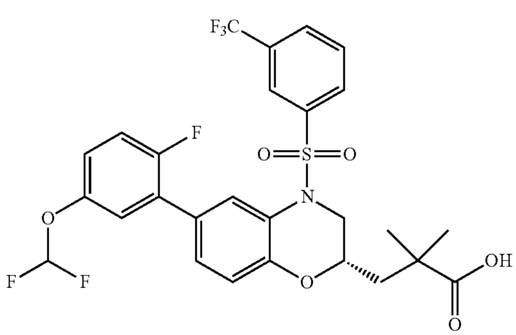 [SMILES: CC(C)(C[C@H]1CN(S(=O)(=O)c2cccc(C(F)(F)F)c2)c2cc(-c3cc(OC(F)F)ccc3F)ccc2O1)C(=O)O] | (S)-3-(6-(5-(difluoromethoxy)-2-fluorophenyl)-4-((3-(trifluoromethyl)phenyl)sulfonyl)-3,4-dihydro-2H-benzo[b][1,4]oxazin-2-yl)-2,2-dimethylpropanoic acid | 602 (M − H)− |

TABLE 10A-continued

| Compd No. | Structure | Name | Observed m/z |
|---|---|---|---|
| 32BJ | 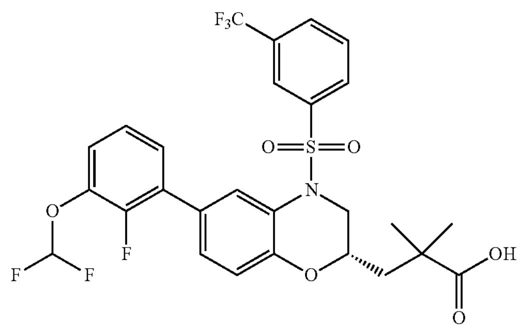 [SMILES: CC(C)(C[C@H]1CN(S(=O)(=O)c2cccc(C(F)(F)F)c2)c2cc(-c3cccc(OC(F)F)c3F)ccc2O1)C(=O)O] | (S)-3-(6-(3-(difluoromethoxy)-2-fluorophenyl)-4-((3-(trifluoromethyl)phenyl)sulfonyl)-3,4-dihydro-2H-benzo[b][1,4]oxazin-2-yl)-2,2-dimethylpropanoic acid | 602 (M − H)− |
| 32BK | 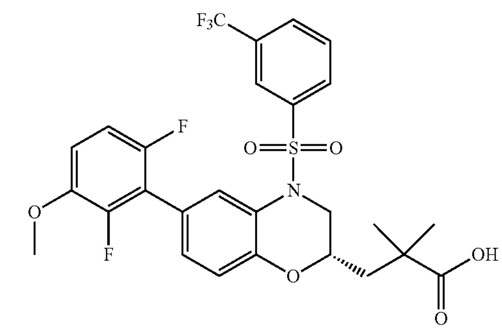 [SMILES: COc1ccc(F)c(-c2ccc3c(c2)N(S(=O)(=O)c2cccc(C(F)(F)F)c2)C[C@H](CC(C)(C)C(=O)O)O3)c1F] | (S)-3-(6-(2,6-difluoro-3-methoxyphenyl)-4-((3-(trifluoromethyl)phenyl)sulfonyl)-3,4-dihydro-2H-benzo[b][1,4]oxazin-2-yl)-2,2-dimethylpropanoic acid | 608 (M + Na)+ |
| 32BL | 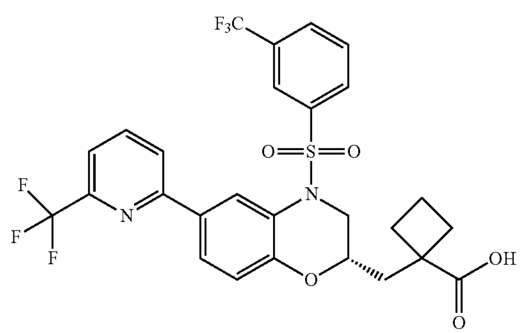 [SMILES: O=C(O)C1(C[C@H]2CN(S(=O)(=O)c3cccc(C(F)(F)F)c3)c3cc(-c4cccc(C(F)(F)F)n4)ccc3O2)CCC1] | (S)-1-((4-((3-(trifluoromethyl)phenyl)sulfonyl)-6-(6-(trifluoromethyl)pyridin-2-yl)-3,4-dihydro-2H-benzo[b][1,4]oxazin-2-yl)methyl)cyclobutane-1-carboxylic acid | 601 (M + H)+ |
| 32BM | 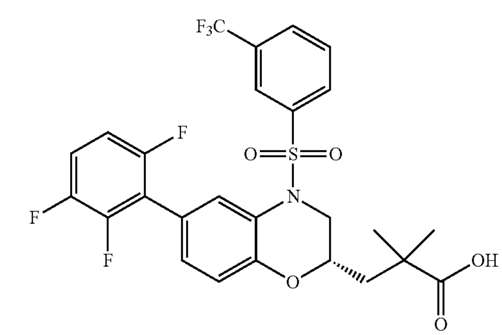 [SMILES: CC(C)(C[C@H]1CN(S(=O)(=O)c2cccc(C(F)(F)F)c2)c2cc(-c3c(F)ccc(F)c3F)ccc2O1)C(=O)O] | (S)-2,2-dimethyl-3-(4-((3-(trifluoromethyl)phenyl)sulfonyl)-6-(2,3,6-trifluorophenyl)-3,4-dihydro-2H-benzo[b][1,4]oxazin-2-yl)propanoic acid | 572 (M − H)− |

TABLE 10A-continued

| Compd No. | Structure | Name | Observed m/z |
|---|---|---|---|
| 32BN | 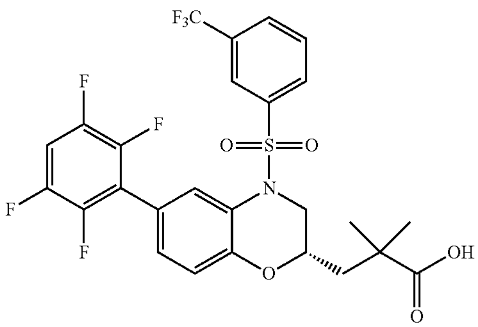 [SMILES: CC(C)(C[C@H]1CN(S(=O)(=O)c2cccc(C(F)(F)F)c2)c2cc(-c3c(F)c(F)cc(F)c3F)ccc2O1)C(=O)O] | (S)-2,2-dimethyl-3-(6-(2,3,5,6-tetrafluorophenyl)-4-((3-(trifluoromethyl)phenyl)sulfonyl)-3,4-dihydro-2H-benzo[b][1,4]oxazin-2-yl)propanoic acid | 592 (M + H)+ |

TABLE 10B

| Compd No. | Physical Characterization Data |
|---|---|
| 32B | $^1$H NMR (300 MHz, CD$_3$OD-d$_4$) δ 8.06 (s, 1H), 8.02-7.94 (m, 2H), 7.90 (s, 1H), 7.78 (t, J = 8.8 Hz, 1H), 7.38 (t, J = 9.6 Hz, 2H), 7.14 (d, J = 7.6 Hz, 1H), 7.12 (s, 1H), 6.96 (d, J = 10.4 Hz, 1H), 6.86 (d, J = 8.8 Hz, 1H), 4.42 (d, J = 16.8 Hz, 1H), 3.88 (s, 3H), 3.50-3.47 (m, 1H), 3.28 (m, 1H), 1.87-1.75 (m, 2H), 1.32 (d, J = 8.4 Hz, 6H). |
| 32C | $^1$H NMR (300 MHz, CD$_3$OD-d$_4$) δ 8.00 (s, 1H), 7.97-7.95 (m, 2H), 7.89 (s, 1H), 7.76 (t, J = 8.0 Hz, 1H), 7.26 (d, J = 8.8 Hz, 1H), 6.94-6.89 (m, 1H), 6.84 (d, J = 8.4 Hz, 1H), 6.75-6.70 (m, 1H), 4.42 (d, J = 17.2 Hz, 1H), 3.92 (s, 3H), 3.52-3.47 (m, 1H), 3.27-3.23 (m, 1H), 1.84-1.75 (m, 2H), 1.12 (d, J = 9.2 Hz, 6H). |
| 32D | $^1$H NMR (300 MHz, CD$_3$OD-d$_4$) δ 8.31 (s 1H), 8.02 (s, J = 8.0 Hz, 2H), 7.98-7.94 (m, 2H), 7.80 (t, J = 7.8 Hz, 1H), 7.61 (d, J = 10.8 Hz, 1H), 7.11-7.08 (m, 2H), 6.98 (d, J = 8.4 Hz, 1H), 4.42 (d, J = 16.8 Hz, 1H), 3.51-3.47 (m, 1H), 3.32 (s, 6H), 3.31-3.27 (m, 1H), 1.87-1.77 (m, 2H), 1.15 (d, J = 10.4 Hz, 6H). |
| 32E | $^1$H NMR (300 MHz, CD$_3$OD-d$_4$) δ 8.61 (s, 1H), 8.08 (d, J = 4.0 Hz 2H), 8.05-7.98 (m, 3H), 7.89 (d, J = 8.4 Hz, 1H), 7.37 (t, J = 8.0 Hz, 1H), 7.70 (t, J = 6.6 Hz, 1H), 6.92 (d, J = 8.4 Hz 1H), 4.44 (d, J = 16.8 Hz, 1H), 3.64-3.58 (m, 1H), 3.40-3.35 (m, 1H), 1.97-4.78 (m, 2H), 1.17 (d, J = 11.2 Hz, 6H). |
| 32F | $^1$H NMR (400 MHz, d$_6$ DMSO) δ 8.1 (m, 1H), 8.04 (m, 1H), 7.95 (s, 1H), 7.9-7.8 (m, 2H), 7.60 (m, 2H), 7.48 (s, 1H), 7.42 (m, 1H), 7.35 (m, 1H), 6.86 (m, 1H), 4.62 (m, 1H), 3.58 (m, 1H), 3.22 (m, 1H), 1.80 (m, 1H), 1.38 (m, 1H), 0.98 (s, 3H), 0.90 (s, 3H). |
| 32G | $^1$H NMR (400 MHz, d$_6$ DMSO) δ 8.1 (m, 1H), 8.04 (m, 1H), 7.95 (s, 1H), 7.9-7.8 (m, 2H), 7.5 (m, 1H), 7.44-7.38 (m, 3H), 7.36 (m, 1H), 7.18 (m, 1H), 6.84 (m, 1H), 4.62 (m, 1H), 3.56 (m, 1H), 3.2 (m, 1H), 1.80 (m, 1H), 1.38 (m, 1H), 0.98 (s, 3H), 0.88 (s, 3H). |
| 32H | $^1$H NMR (400 MHz, d$_6$ DMSO) δ 12.24 (s, 1H), 8.14 (m, 1H), 8.00 (m, 1H), 7.86 (m, 2H), 7.75 (m, 1H), 7.44 (m, 2H), 7.24-7.18 (m, 2H), 6.84 (m, 1H), 4.35 (m, 1H), 3.5-3.3 (m, 2H), 1.75 (m, 2H), 1.02 (m, 6H). |
| 32I | $^1$H NMR (400 MHz, d$_6$ DMSO) δ 8.14 (m, 1H), 8.00 (m, 1H), 7.86 (m, 2H), 7.78 (m, 1H), 7.62 (m, 1H), 7.3-7.2 (m, 2H), 7.18 (m, 1H), 6.84 (m, 1H), 4.35 (m, 1H), 3.5-3.3 (m, 2H), 1.75 (m, 2H), 1.0 (m, 6H). |
| 32J | $^1$H NMR (400 MHz, d$_6$ DMSO) δ 8.19 (d, 1H, J = 7.8 Hz), 8.05 (d, 1H, J = 7.7 Hz), 7.94 (d, 1H, J = 2.2 Hz), 7.86-7.82 (m, 2H), 7.44 (dd, 1H, J = 8.6, 2.2 Hz), 7.39 (t, 1H, J = 73.6 Hz), 7.28 (m, 1H), 7.20 (m, 1H), 7.10 (m, 1H), 6.87 (d, 1H, J = 8.6 Hz), 4.63 (dd, 1H, J = 14.4, 2.1 Hz), 3.53 (m, 1H), 3.19 (m, 1H), 1.79 (dd, 1H, J = 13.9, 6.0 Hz), 1.37 (dd, 1H, J = 14.0, 2.2 Hz), 0.95 (s, 3H), 0.86 (s, 3H). |
| 32K | $^1$H NMR (400 MHz, d$_6$ DMSO) δ 12.24 (s, 1H), 8.14 (m, 1H), 7.98 (m, 1H), 7.94 (m, 1H), 7.90-7.82 (m, 2H), 7.42 (m, 1H), 7.36-7.25 (m, 3H), 6.86 (m, 1H), 4.35 (m, 1H), 3.5 (m, 1H), 3.4 (m, 1H), 1.75 (m, 2H), 1.02 (m, 6H). |
| 32L | $^1$H NMR (400 MHz, d$_6$ DMSO) δ 12.24 (s, 1H), 8.14 (m, 1H), 8.0-7.82 (m, 4H), 7.58 (m, 1H), 7.44 (m, 1H), 7.32 (m, 2H), 6.85 (m, 1H), 4.35 (m, 1H), 3.5 (m, 1H), 3.4 (m, 1H), 1.75 (m, 2H), 1.02 (m, 6H). |
| 32M | $^1$H NMR (300 MHz, CD$_3$OD-d$_4$) δ 8.07 (s, 1H), 7.61-7.59 (m, 1H), 7.55-7.47 (m, 3H), 7.35-7.14 (m, 4H), 7.13-7.10 (m, 1H), 6.86 (d, J = 8.4 Hz, 1H), 4.35 (dd, J = 14.3, 2.4 Hz, 1H), 3.22-3.16 (m, 2H), 2.90-2.87 (m, 1H), 1.79-1.76 (m, 2H), 1.15-1.11 (m, 12H). |
| 32N | $^1$H NMR (400 MHz, d$_6$ DMSO) δ 12.22 (s, 1H), 8.14 (m, 1H), 7.96 (m, 2H), 7.82 (m, 1H), 7.52 (m, 1H), 7.3 (m, 2H), 7.2 (m, 1H), 6.84 (m, 1H), 4.35 (m, 1H), 3.45-3.3 (m, 2H), 1.75 (m, 2H), 1.02 (m, 6H). |
| 32O | $^1$H NMR (400 MHz, d$_6$ DMSO) δ 12.2 (s, 1H), 8.14 (m, 1H), 7.96-7.82 (m, 4H), 7.72 (m, 2H), 7.52 (m, 1H), 6.86 (m, 1H), 4.32 (m, 1H), 3.5-3.3 (m, 2H), 1.75 (m, 2H), 1.02 (m, 6H). |
| 32P | $^1$H NMR (300 MHz, CD$_3$OD-d$_4$) δ 8.59 (s, 1H), 8.10-8.08 (m, 2H), 8.07-7.99 (m, 2H), 7.89-7.86 (m, 1H), 7.80-7.76 (m, 1H), 7.73-7.68 (m, 1H), 6.98 (d, J = 8.4 Hz, 1H), 4.43 (dd, J = 14.4 Hz, J = 2.4 Hz, 1H), 3.50-3.33 (m, 2H), 1.77-1.50 (m, 4H), 1.19 (s, 3H), 1.18 (s, 3H). |

TABLE 10B-continued

| Compd No. | Physical Characterization Data |
|---|---|
| 32Q | $^1$H NMR (400 MHz, d$_6$-DMSO) δ 12.2 (s, 1H), 8.14 (m, 1H), 7.94-7.82 (m, 4H), 7.42 (m, 1H), 6.82 (m, 1H), 6.68 (s, 2H), 6.5 (s, 1H), 4.30 (m, 1H), 3.80 (s, 6H), 3.6 (m, 1H), 3.4 (m, 1H), 1.75 (m, 2H), 1.02 (m, 6H). |
| 32R | $^1$H NMR (400 MHz, d$_6$-DMSO) δ 12.22 (s, 1H), 8.14 (m, 1H), 7.92 (m, 2H), 7.82 (m, 1H), 7.52 (m, 2H), 7.4-7.2 (m, 2H), 6.84 (m, 1H), 4.32 (m, 1H), 3.45-3.3 (m, 2H), 1.75 (m, 2H), 1.0 (m, 6H). |
| 32S | $^1$H NMR (300 MHz, CD$_3$OD-d$_4$) δ 8.05 (s, 1H), 7.38-7.22 (m, 4H), 6.96-6.92 (m, 2H), 6.69-6.74 (m, 1H), 4.39 (d, J = 14.8 Hz, 1H), 3.94 (s, 3H), 3.74 (s, 3H), 3.29-3.15 (m, 2H), 1.73-1.69 (m, 1H), 1.60-1.51 (m, 3H), 1.36-1.27 (m, 1H), 1.20 (s, 6H). |
| 32T | $^1$H NMR (300 MHz, CD$_3$OD-d$_4$) δ 8.02 (s, 1H), 7.63-7.54 (m, 2H), 7.47-7.44 (m, 2H), 7.32-7.19 (m, 3H), 7.14-7.07 (m, 1H), 6.93 (d, J = 11.2 Hz, 1H), 6.85 (t, J = 97.2 Hz, 1H), 4.39 (d, J = 16.4 Hz, 1H), 3.31-3.09 (m, 2H), 1.73-1.45 (m, 4H), 1.18 (s, 6H). |
| 32U | $^1$H NMR (300 MHz, CD$_3$OD-d$_4$) δ 8.02-7.99 (m, 2H), 7.93 (s, 1H), 7.87 (s, 1H), 7.81 (t, J = 7.8 Hz, 1H), 7.23-7.18 (m, 2H), 7.07-7.04 (m, 1H), 6.89 (d, J = 8.4 Hz 1H), 4.45 (d, J = 16.8 Hz, 1H), 3.52-3.46 (m, 1H), 3.31-3.27 (m, 1H), 1.86-1.78 (m, 2H), 1.15 (d, J = 8.4 Hz, 6H) |
| 32V | $^1$H NMR (400 MHz, d$_6$-DMSO) δ 12.22 (s, 1H), 8.12 (m, 1H), 7.96 (m, 1H), 7.82 (m, 3H), 7.24 (m, 1H), 7.16 (m, 1H), 7.05 (m, 1H), 6.86 (m, 1H), 6.78 (m, 1H), 4.34 (m, 1H), 3.83 (s, 3H), 3.56 (s, 3H), 3.44-3.3 (m, 2H), 1.75 (m, 2H), 1.02 (m, 6H). |
| 32W | $^1$H NMR (400 MHz, d$_6$-DMSO) δ 12.2 (s, 1H), 8.14 (m, 1H), 7.96-7.82 (m, 4H), 7.5-7.4 (m, 5H), 6.83 (m, 1H), 4.32 (m, 1H), 3.4-3.3 (m, 2H), 1.75 (m, 2H), 1.0 (m, 6H). |
| 32X | $^1$H NMR (400 MHz, d$_6$-DMSO) δ 12.2 (s, 1H), 8.14 (m, 1H), 7.98-7.82 (m, 4H), 7.55 (m, 1H), 7.36 (m, 1H), 7.23 (m, 1H), 6.88 (m, 1H), 4.34 (m, 1H), 3.5-3.3 (m, 2H), 1.75 (m, 2H), 1.02 (m, 6H). |
| 32Y | $^1$H NMR (400 MHz, d$_6$-DMSO) δ 12.2 (s, 1H), 8.14 (m, 1H), 7.98-7.92 (m, 3H), 7.83 (m, 1H), 7.52 (m, 2H), 7.42 (m, 2H), 6.84 (m, 1H), 4.3 (m, 1H), 3.5-3.3 (m, 2H), 1.75 (m, 2H), 1.0 (m, 6H). |
| 32AG | $^1$H NMR (400 MHz, d$_6$-DMSO) δ 12.2 (s, 1H), 8.14 (m, 1H), 7.95-7.82 (m, 4H), 7.46 (m, 1H), 6.92 (m, 1H), 6.82 (m, 1H), 4.29 (m, 1H), 3.82 (s, 3H), 3.44-3.3 (m, 2H), 1.75 (m, 2H), 1.0 (m, 6H). |
| 32AH | $^1$H NMR (400 MHz, d$_6$-DMSO) δ 12.2 (s, 1H), 8.14 (m, 1H), 7.95-7.82 (m, 4H), 7.48 (m, 1H), 7.18 (m, 1H), 7.04 (m, 2H), 6.82 (m, 1H), 4.3 (m, 1H), 3.83 (s, 3H), 3.44-3.3 (m, 2H), 1.75 (m, 2H), 1.0 (m, 6H). |
| 32AI | $^1$H NMR (400 MHz, d$_6$-DMSO) δ 12.24 (s, 1H), 8.14 (m, 1H), 7.98-7.92 (m, 2H), 7.90-7.82 (m, 2H), 7.62 (m, 1H), 7.41-7.32 (m, 2H), 6.88 (m, 1H), 4.36 (m, 1H), 3.5-3.3 (m, 2H), 1.75 (m, 2H), 1.02 (m, 6H). |
| 32AJ | $^1$H NMR (300 MHz, CD$_3$OD-d$_4$) δ 8.62 (s, 1H), 8.09-8.08 (m, 2H), 7.90-7.87 (m, 1H), 7.72-7.70 (m, 1H), 7.42-7.27 (m, 3H), 6.99 (d, J = 8.4 Hz, 1H), 4.39 (dd, J = 14.4 Hz, J = 2.4 Hz, 1H), 3.74 (s, 3H), 3.33-3.24 (m, 2H), 1.75-1.54 (m, 4H), 1.21 (s, 3H), 1.20 (s, 3H). |
| 32AK | $^1$H NMR (400 MHz, d$_6$-DMSO) δ 12.2 (s, 1H), 8.44 (s, 1H), 8.12 (m, 1H), 8.05 (m, 2H), 7.98 (m, 2H), 7.84 (m, 2H), 7.61 (m, 1H), 7.0 (t, 1H), 6.88 (m, 1H), 4.34 (m, 1H), 3.58 (m, 1H), 3.4 (m, 1H), 1.76 (m, 2H), 1.04 (m, 6H). |
| 32AL | $^1$H NMR (400 MHz, d$_6$-DMSO) δ 12.2 (s, 1H), 8.44 (s, 1H), 8.12 (m, 1H), 7.96 (m, 3H), 7.84 (m, 1H), 7.76 (m, 1H), 7.62 (m, 1H), 7.56 (m, 1H), 7.48 (m, 1H), 7.1 (t, 1H), 6.84 (m, 1H), 4.34 (m, 1H), 3.5-3.3 (m, 2H), 1.76 (m, 2H), 1.0 (m, 6H). |
| 32AN | $^1$H NMR (400 MHz, CD$_3$OD-d$_4$) δ 8.11-7.71 (m, 5H), 7.42 (dd, J = 8.5, 2.3 Hz, 1H), 7.30-6.67 (m, 5H), 4.56 (m, 1H), 3.55-3.31 (m, 2H), 1.94-1.70 (m, 2H), 1.13 (d, J = 8.2 Hz, 6H). |
| 32AO | $^1$H NMR (400 MHz, CD$_3$OD-d$_4$) δ 8.04-7.73 (m, 5H), 7.26-7.12 (m, 2H), 7.05 (dt, J = 8.9, 2.4 Hz, 1H), 6.88 (d, J = 8.5 Hz, 1H), 4.43 (dd, J = 14.6, 2.4 Hz, 1H), 3.47 (s, 2H), 1.85-1.76 (m, 2H), 1.14 (d, J = 5.9 Hz, 6H). |
| 32AP | $^1$H NMR (400 MHz, CD$_3$OD-d$_4$) δ 8.07-8.00 (m, 1H), 7.98-7.96 (m, 2H), 7.89 (s, 1H), 7.79-7.77 (m, 1H), 7.44-7.41 (m, 1H), 7.22-7.19 (m, 2H), 6.96-6.88 (m, 2H) 4.45 (dd, J = 14.4, 2.4 Hz, 1H), 3.44-3.43 (m, 1H), 3.32-3.33 (m, 1H), 2.44-2.41 (m, 2H), 2.18-2.02 (m, 2H), 1.97-1.93 (m, 3H) , 1.89-1.86 (m, 1H). |
| 32AQ | $^1$H NMR (400 MHz, CD$_3$OD-d$_4$) δ 8.06-8.05 (m, 1H), 8.00-7.91 (m, 2H), 7.81 (s, 1H), 7.79-7.77 (m, 1H), 7.32-7.30 (m, 1H) , 7.29-7.20 (m, 2H), 7.14-7.12 (m, 1H), 6.89-6.87 (m, 1H) , 4.45 (dd, J = 14.4, 2.4 Hz, 1H), 3.44-3.43 (m, 1H), 3.32-3.33 (m, 1H), 2.46-2.41 (m, 2H), 2.10-1.92 (m, 6H). |
| 32AR | $^1$H NMR (400 MHz, CDCl$_3$) δ 7.85 (s, 1H), 7.81 (m, 2H), 7.73 (m, 1H), 7.60 (m, 1H), 7.18 (m, 3H), 6.95 (m, 1H), 6.78 (m, 1H), 4.30 (d, 1H), 4.12 (m, 1H), 3.59 (m, 1H), 3.23 (m, 1H), 2.24 (s, 3H), 2.07 (s, 1H), 1.92 (m, 1H), 1.73 (m, 1H), 1.25 (s, 6H), 1.20 (s, 2H). |
| 32AS | $^1$H NMR (400 MHz, CDCl$_3$) δ 7.98 (m, 2H), 7.75 (m, 2H), 7.53 (t, 1H), 7.13 (s, 2H), 6.96 (s, 1H), 6.78 (d, 1H), 4.30 (d, 1H), 3.59 (m, 1H), 3.25 (dd, 1H), 2.40 (s, 6H), 1.90 (m, 2H), 1.73 (m, 2H), 1.23 (s, 3H), 1.20 (s, 3H). |
| 32AV | $^1$H NMR (400 MHz, CDCl$_3$) δ 7.93 (s, 1H), 7.75 (m, 4H), 7.55 (t, 1H), 7.13 (m, 1H), 7.00 (m, 2H), 6.76 (d, 1H), 4.34 (d, 1H), 3.55 (m, 1H), 3.24 (dd, 1H), 1.90 (m, 1H), 1.72 (m, 1H), 1.25 (s, 3H), 1.20 (s, 3H). |
| 32AW | $^1$H NMR (400 MHz, CDCl$_3$) δ 7.80 (m, 4H), 7.60 (m, 1H), 6.91 (m, 3H), 6.76 (d, 1H), 4.30 (d, 1H), 3.60 (m, 1H), 3.25 (m, 1H), 1.88 (m, 1H), 1.75 (m, 1H), 1.23 (s, 3H), 1.20 (s, 3H). |
| 32AX | $^1$H NMR (400 MHz, CDCl$_3$) δ 7.96 (s, 1H), 7.88 (s, 1H), 7.82 (m, 2H), 7.58 (t, 1H), 7.0-7.2 (m, 4H), 6.77 (d, 1H), 4.33 (d, 1H), 3.62 (m, 1H), 3.26 (dd, 1H), 2.44 (s, 3H), 1.93 (m, 1H), 1.72 (m, 1H), 1.24 (s, 3H), 1.20 (s, 3H). |
| 32AZ | $^1$H NMR (400 MHz, CDCl$_3$) δ 7.88 (s, 1H), 7.82 (m, 2H), 7.74 (s, 1H), 7.60 (t, 1H), 7.32 (d, 1H), 7.13 (t, 1H), 7.06 (d, 1H), 6.92 (d, 1H), 6.76 (d, 1H), 4.32 (d, 1H), 3.61 (m, 1H), 3.25 (dd, 1H), 2.35 (s, 3H), 1.92 (m, 1H), 1.78 (m, 1H), 1.25 (s, 3H), 1.20 (s, 3H). |

TABLE 10B-continued

| Compd No. | Physical Characterization Data |
|---|---|
| 32BA | $^1$H NMR (400 MHz, CDCl$_3$) δ 7.82 (s, 1H), 7.79 (m, 2H), 7.60 (s, 1H), 7.57 (m, 1H), 7.10 (m, 3H), 6.79 (m, 2H), 4.31 (d, 1H), 3.58 (m, 1H), 3.23 (dd, 1H), 2.07 (s, 3H), 2.01 (s, 3H), 1.90 (m, 1H), 1.72 (m, 1H), 1.23 (s, 3H), 1.20 (s, 3H). |
| 32BB | $^1$H NMR (400 MHz, CDCl$_3$) δ 7.95 (s, 2H), 7.76 (m, 2H), 7.56 (t, 1H), 7.28 (s, 1H), 7.22 (m, 2H), 7.12 (s, 1H), 6.75 (d, 1H), 4.27 (d, 1H), 3.56 (m, 1H), 3.22 (dd, 1H), 2.40 (s, 3H), 1.88 (m, 1H), 1.73 (m, 1H), 1.23 (s, 3H), 1.20 (s, 3H). |
| 32BC | $^1$H NMR (400 MHz, CDCl$_3$) δ 7.92 (s, 1H), 7.80 (m, 3H), 7.58 (t, 1H), 7.52 (m, 1H), 7.20 (m, 1H), 7.05 (d, 1H), 6.98 (d, 1H), 6.72 (d, 1H), 4.37 (d, 1H), 3.58 (m, 1H), 3.25 (dd, 1H), 1.95 (m, 1H), 1.75 (m, 1H), 1.23 (s, 3H), 1.20 (s, 3H). |
| 32BD | $^1$H NMR (400 MHz, CD$_3$OD-d$_4$) δ 8.07-8.00 (m, 1H), 7.98-7.96 (m, 2H), 7.89 (s, 1H), 7.79-7.77 (m, 1H), 7.44-7.41 (m, 1H), 7.22-7.19 (m, 2H), 6.96-6.88 (m, 2H) 4.45 (dd, J = 14.4, 2.4 Hz, 1H), 3.44-3.43 (m, 1H), 3.32-3.33 (m, 1H), 2.44-2.41 (m, 2H), 2.18-2.02 (m, 2H), 1.97-1.93 (m, 3H) , 1.89-1.86 (m, 1H). |
| 32BE | $^1$H NMR (400 MHz, CD$_3$OD-d$_4$) δ 8.06-8.05 (m, 1H), 8.00-7.91 (m, 2H), 7.81 (s, 1H), 7.79-7.77 (m, 1H), 7.32-7.30 (m, 1H) , 7.29-7.20 (m, 2H), 7.14-7.12 (m, 1H), 6.89-6.87 (m, 1H), 4.45 (dd, J = 14.4, 2.4 Hz, 1H), 3.44-3.43 (m, 1H), 3.32-3.33 (m, 1H), 2.46-2.41 (m, 2H), 2.10-1.92 (m, 6H). |
| 32BF | $^1$H NMR (400 MHz, CD$_3$OD-d$_4$) δ 8.04-7.97 (m, 1H), 8.02-7.96 (m, 2H), 7.91 (s, 1H), 7.81-7.77 (m, 1H), 7.50-7.47 (m, 1H), 7.46-7.40 (m, 1H), 7.30-7.24 (m, 2H) 6.88 (d, J = 8.5 Hz, 1H), 4.45 (dd, J = 14.4, 2.4 Hz, 1H), 3.44-3.43 (m, 1H), 3.32-3.33 (m, 1H), 2.44-2.41 (m, 2H), 2.18-2.02 (m, 2H), 2.00-1.84 (m, 4H). |
| 32BG | $^1$H NMR (400 MHz, CD$_3$OD-d$_4$) δ 8.11-7.85 (m, 4H), 7.78 (t, J = 7.9 Hz, 1H), 7.43-6.67 (m, 5H), 4.44 (d, J = 14.3 Hz, 1H), 3.53 (d, J = 9.1 Hz, 1H), 3.25 (s, 1H), 1.90-1.71 (m, 2H), 1.15 (d, J = 6.3 Hz, 6H). |
| 32BH | $^1$H NMR (400 MHz, CD$_3$OD-d$_4$) δ 8.06 (s, 1H), 7.99-7.05 (m, 2H), 7.89 (s, 1H), 7.81-7.77 (m, 1H), 7.42 (dd, J = 8.6, 2.3 Hz, 1H), 7.24-7.16 (m, 2H), 6.97-6.79 (m, 3H), 4.42 (dd, J = 14.4, 2.3 Hz, 1H), 3.44-3.43 (m, 1H), 3.32-3.33 (m, 1H), 2.46-2.37 (m, 2H), 2.14-2.01 (m, 2H), 2.00-1.83 (m, 4H). |
| 32BI | $^1$H NMR (400 MHz, CD$_3$OD-d$_4$) δ 8.07-7.87 (m, 4H), 7.78 (t, J = 7.9 Hz, 1H), 7.39-7.10 (m, 4H), 7.11-6.55 (m, 2H), 4.43 (dd, J = 14.6, 2.5 Hz, 1H), 3.32-3.15 (m, 2H), 1.81 (dd, J = 5.8, 2.8 Hz, 2H), 1.32 (t, J = 7.3 Hz, 2H), 1.15 (d, J = 6.2 Hz, 6H). |
| 32BJ | $^1$H NMR (400 MHz, CD$_3$OD-d$_4$) δ 8.08-7.85 (m, 4H), 7.78 (t, J = 7.9 Hz, 1H), 7.44-7.21 (m, 4H), 7.18-6.61 (m, 2H), 4.43 (dd, J = 14.5, 2.5 Hz, 1H), 3.60-3.45 (m, 1H), 3.30-3.21 (m, 1H), 1.88-1.73 (m, 2H), 1.42-1.26 (m, 1H), 1.14 (d, J = 6.6 Hz, 6H). |
| 32BL | $^1$H NMR (400 MHz, CD$_3$OD-d$_4$) δ 8.61 (s, 1H), 8.08-8.07 (m, 2H), 8.04-8.02 (m, 1H), 7.98-7.97 (m, 2H), 7.89-7.86 (m, 1H), 7.80-7.69 (m, 2H), 6.91 (d, J = 8.4 Hz, 1H), 4.45 (dd, J = 14.3, 2.4 Hz, 1H), 3.56-3.54 (m, 1H), 3.41-3.36 (m, 1H), 2.50-2.30 (m, 2H), 2.20-1.85 (m, 6H). |
| 32BM | $^1$H NMR (400 MHz, CD$_3$OD-d$_4$) δ 8.00-7.95 (m, 3H), 7.86 (s, 1H), 7.79-7.75 (m, 1H), 7.35-7.27 (m, 1H), 7.21-7.19 (m, 1H), 7.11-7.05 (m, 1H), 6.87 (d, J = 8.8 Hz, 1H), 4.45 (dd, J = 14.4 Hz, J = 2.4 Hz, 1H), 3.55-3.49 (m, 1H), 3.31-3.25 (m, 1H), 1.80 (d, J = 5.6 Hz, 2H), 1.15 (s, 3H), 1.13 (s, 3H). |

Example 33—Synthesis of (S)-3-(6-(2,5-difluorophenyl)-4-((3-(trifluoromethyl)phenyl)sulfonyl)-3,4-dihydro-2H-benzo[b][1,4]oxazin-2-yl)propan-1-ol

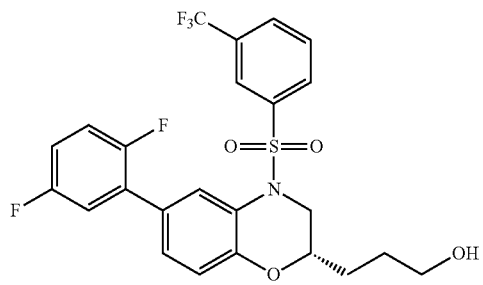 [SMILES: O=S(=O)(c1cccc(C(F)(F)F)c1)N1C[C@H](CCCO)Oc2ccc(-c3cc(F)ccc3F)cc21]

A solution of 1M borane in THF (12.2 mL, 12.2 mmol) was added to a solution of (S)-3-(6-(2,5-difluorophenyl)-4-((3-(trifluoromethyl)phenyl)sulfonyl)-3,4-dihydro-2H-benzo[b][1,4]oxazin-2-yl)propanoic acid (2.2 g, 4.06 mmol) in tetrahydrofuran (18 mL), and the mixture was stirred overnight at room temperature. Then, the mixture was concentrated and purified via MPLC eluting with a gradient of 50-100% ethyl acetate in petroleum ether to afford (S)-3-(6-(2,5-difluorophenyl)-4-((3-(trifluoromethyl)phenyl)sulfonyl)-3,4-dihydro-2H-benzo[b][1,4]oxazin-2-yl)propan-1-ol (1.6 g, 77%) as a white solid.

Example 34—Preparation of Additional Substituted 4-(aryl sulfonyl)-3,4-dihydro-2H-benzo[b][1,4]oxazin-2-yl) Compounds Compounds in Table 11 were prepared based on experimental procedures described in Example 33 and the detailed description. $^1$H NMR data for exemplary compounds from Table 11 is provided in Table 11A.

TABLE 11

| Compd No. | Structure | Name | Observed m/z |
|---|---|---|---|
| 34A | 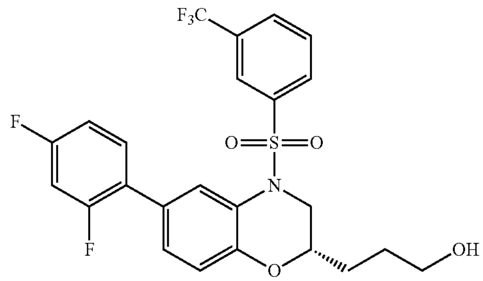 [SMILES: O=S(=O)(c1cccc(C(F)(F)F)c1)N1C[C@H](CCCO)Oc2ccc(-c3ccc(F)cc3F)cc21] | (S)-3-(6-(2,4-difluorophenyl)-4-((3-(trifluoromethyl)phenyl)-sulfonyl)-3,4-dihydro-2H-benzo[b][1,4]oxazin-2-yl)propan-1-ol | 536 (M + Na)+ |
| 34B | 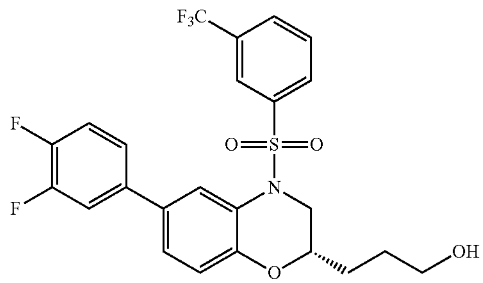 [SMILES: O=S(=O)(c1cccc(C(F)(F)F)c1)N1C[C@H](CCCO)Oc2ccc(-c3ccc(F)c(F)c3)cc21] | (S)-3-(6-(3,4-difluorophenyl)-4-((3-(trifluoromethyl)phenyl)-sulfonyl)-3,4-dihydro-2H-benzo[b][1,4]oxazin-2-yl)propan-1-ol | 536 (M + Na)+ |
| 34C | 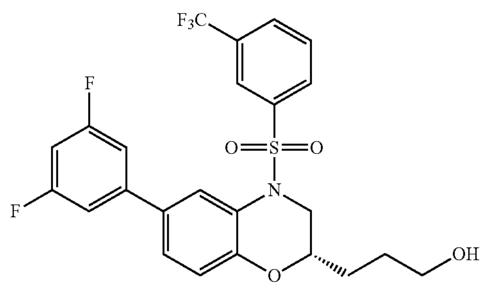 [SMILES: O=S(=O)(c1cccc(C(F)(F)F)c1)N1C[C@H](CCCO)Oc2ccc(-c3cc(F)cc(F)c3)cc21] | (S)-3-(6-(3,5-difluorophenyl)-4-((3-(trifluoromethyl)phenyl)-sulfonyl)-3,4-dihydro-2H-benzo[b][1,4]oxazin-2-yl)propan-1-ol | 536 (M + Na)+ |
| 34D | 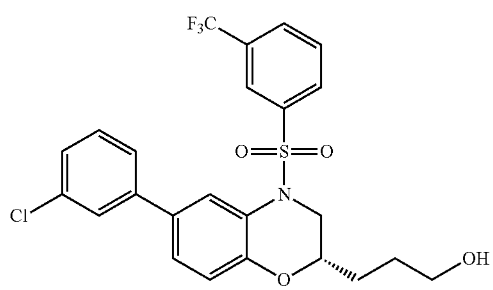 [SMILES: O=S(=O)(c1cccc(C(F)(F)F)c1)N1C[C@H](CCCO)Oc2ccc(-c3cccc(Cl)c3)cc21] | (S)-3-(6-(3-chlorophenyl)-4-((3-(trifluoromethyl)phenyl)sulfonyl)-3,4-dihydro-2H-benzo[b][1,4]-oxazin-2-yl)propan-1-ol | 534 (M + Na)+ |
| 34E | 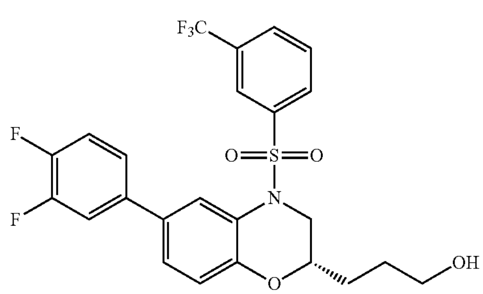 [SMILES: O=S(=O)(c1cccc(C(F)(F)F)c1)N1C[C@H](CCCO)Oc2ccc(-c3ccc(F)c(F)c3)cc21] | (S)-3-(6-(2,3-difluorophenyl)-4-((3-(trifluoromethyl)phenyl)-sulfonyl)-3,4-dihydro-2H-benzo[b][1,4]oxazin-2-yl)propan-1-ol | 536 (M + Na)+ |

TABLE 11-continued

| Compd No. | Structure | Name | Observed m/z |
|---|---|---|---|
| 34F | 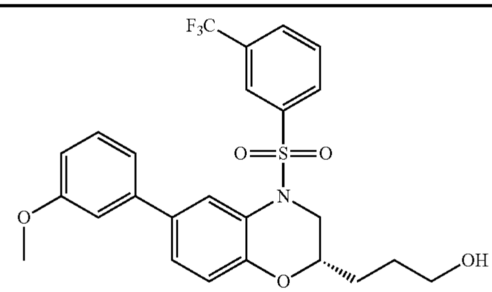 | (S)-3-(6-(3-methoxyphenyl)-4-((3-(trifluoromethyl)phenyl)sulfonyl)-3,4-dihydro-2H-benzo[b][1,4]-oxazin-2-yl)propan-1-ol | 508 (M + H)+ |
| 34G | 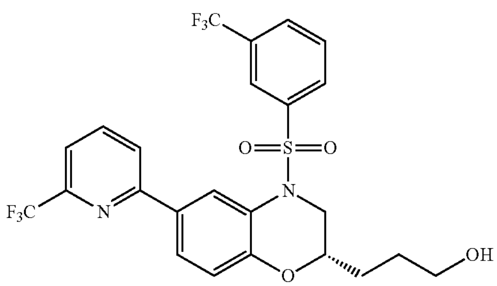 [SMILES: O=S(=O)(c1cccc(C(F)(F)F)c1)N1C[C@H](CCCO)Oc2ccc(-c3cccc(C(F)(F)F)n3)cc21] | (S)-3-(4-((3-(trifluoromethyl)-phenyl)sulfonyl)-6-(6-(trifluoromethyl)pyridin-2-yl)-3,4-dihydro-2H-benzo[b][1,4]oxazin-2-yl)propan-1-ol | 547 (M + H)+ |
| 34H | 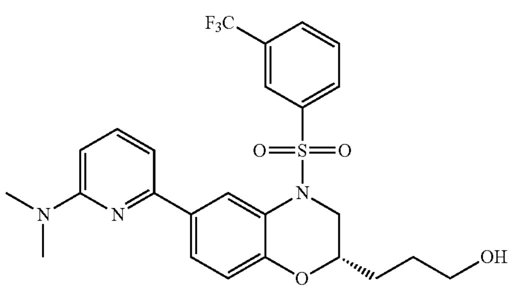 [SMILES: CN(C)c1cccc(-c2ccc3c(c2)N(S(=O)(=O)c2cccc(C(F)(F)F)c2)C[C@H](CCCO)O3)n1] | (S)-3-(6-(6-(dimethylamino)-pyridin-2-yl)-4-((3-(trifluoromethyl)phenyl)sulfonyl)-3,4-dihydro-2H-benzo[b][1,4]oxazin-2-yl)propan-1-ol | 522 (M + H)+ |

TABLE 11A

| Compd No. | Physical Characterization Data |
|---|---|
| 34A | $^1$H NMR (400 MHz, CDCl$_3$) δ 8.01-7.95 (m, 2H), 7.86-7.83 (m, 2H), 7.64-7.60 (m, 1H), 7.41-7.34 (m, 1H), 7.23-7.20 (m, 3H) 6.98-6.86 (m, 3H), 4.38-4.33 (m, 1H), 3.67 (br s, 2H), 3.55-3.49 (m, 1H), 3.27-3.21 (m, 1H), 1.75-1.61 (m, 4H) |
| 34B | $^1$H NMR (400 MHz, CDCl$_3$) δ 8.00-7.98 (m, 2H), 7.86-7.80 (m, 2H), 7.64-7.60 (m, 1H), 7.37-7.20 (m, 4H) 6.88 (d, J = 8.5 Hz, 1H), 4.35-4.30 (m, 1H), 3.66 (br s, 2H), 3.46-3.42 (m, 1H), 3.25-3.19 (m, 1H), 1.71-1.61 (m, 4H) |
| 34C | $^1$H NMR (400 MHz, CDCl$_3$) δ 8.01-7.99 (m, 2H), 7.86-7.80 (m, 2H), 7.65-7.60 (m, 1H), 7.30-7.27 (m, 1H), 7.10-7.04 (m, 2H), 6.89 (d, J = 8.5 Hz, 1H), 4.35-4.31 (m, 1H), 3.66 (br s, 2H), 3.47-3.42 (m, 1H), 3.25-3.19 (m, 1H), 1.71-1.61 (m, 4H), 1.34 (br s, 1H) |
| 34D | $^1$H NMR (400 MHz, CDCl$_3$) δ 8.01-8.00 (m, 2H), 7.85-7.80 (m, 2H), 7.63-7.60 (m, 1H), 7.54-7.52 (m, 1H), 7.45-7.28 (m, 4H), 6.88 (d, J = 8.5 Hz, 1H), 4.36-4.32 (m, 1H), 3.65 (br s, 2H), 3.47-3.43 (m, 1H), 3.25-3.19 (m, 1H), 1.71-1.61 (m, 4H), 1.37 (br s, 1H) |
| 34E | $^1$H NMR (400 MHz, CDCl$_3$) δ 8.02-8.00 (m, 2H), 7.87-7.84 (m, 2H), 7.65-7.60 (m, 1H), 7.28-7.25 (m, 1H), 7.20-7.11 (m, 3H), 6.89 (d, J = 8.5 Hz, 1H), 4.38-4.34 (m, 1H), 3.67 (br s, 2H), 3.56-3.51 (m, 1H), 3.28-3.21 (m, 1H), 1.74-1.61 (m, 4H), 1.38 (br s, 1H) |

Example 35—Synthesis (S)-3-(3-(6-(6-(dimethylamino)pyridin-2-yl)-4-((3-(trifluoromethyl)phenyl)sulfonyl)-3,4-dihydro-2H-benzo[b][1,4]oxazin-2-yl)propoxy)-1,2,4-oxadiazol-5(4H)-one

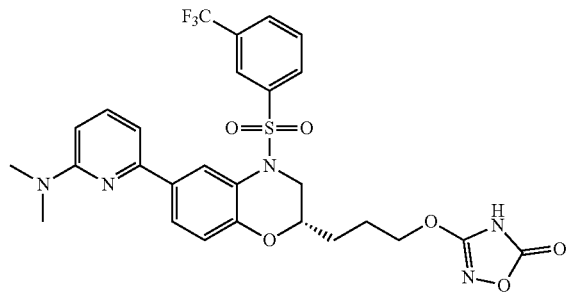 [SMILES: CN(C)c1cccc(-c2ccc3c(c2)N(S(=O)(=O)c2cccc(C(F)(F)F)c2)C[C@H](CCCOc2noc(=O)[nH]2)O3)n1]

Part I—Synthesis of ethyl N-([3-[(2S)-6-[6-(dimethylamino)pyridin-2-yl]-4-([oxo[3-(trifluoromethyl)phenyl]-ˆ[6]-sulfanylidene]oxo)-3,4-dihydro-2H-1,4-benzoxazin-2-yl]propoxy]methanethioyl)carbamate

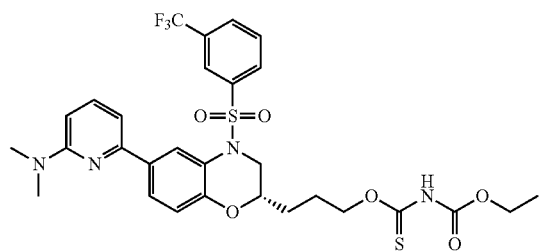 [SMILES: CCOC(=O)NC(=S)OCCC[C@H]1CN(S(=O)(=O)c2cccc(C(F)(F)F)c2)c2cc(-c3cccc(N(C)C)n3)ccc2O1]

A solution of (S)-3-(6-(6-(dimethylamino)pyridin-2-yl)-4-((3-(trifluoromethyl)phenyl)sulfonyl)-3,4-dihydro-2H-benzo[b][1,4]oxazin-2-yl)propan-1-ol (221 mg, 0.42 mmol) in ethyl acetate (3 mL) was added dropwise to a stirred solution of ethyl N-carbothioylcarbamate (56 mg, 0.43 mmol) in ethyl acetate (3 mL). The mixture was stirred overnight at 80° C. Then, the mixture was concentrated and the resulting residue was purified via MPLC eluting with 25% ethyl acetate in petroleum ether to afford ethyl N-([3-[(2S)-6-[6-(dimethylamino)pyridin-2-yl]-4-([oxo[3-(trifluoromethyl)phenyl]-ˆ[6]-sulfanylidene]oxo)-3,4-dihydro-2H-1,4-benzoxazin-2-yl]propoxy]methanethioyl)carbamate (132 mg, 48%) as a yellow oil.

Part II—Synthesis of (S)-3-(3-(6-(6-(dimethylamino)pyridin-2-yl)-4-((3-(trifluoromethyl)phenyl)sulfonyl)-3,4-dihydro-2H-benzo[b][1,4]oxazin-2-yl)propoxy)-1,2,4-oxadiazol-5(4H)-one

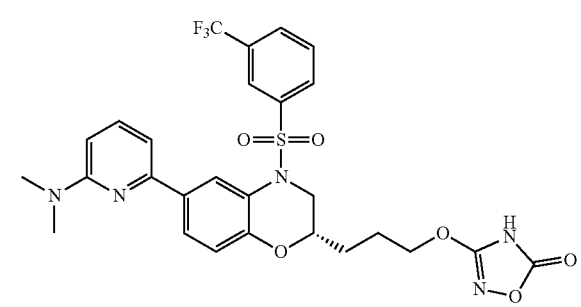 [SMILES: CN(C)c1cccc(-c2ccc3c(c2)N(S(=O)(=O)c2cccc(C(F)(F)F)c2)C[C@H](CCCOc2noc(=O)[nH]2)O3)n1]

A mixture of ethyl N-([3-[(2S)-6-[6-(dimethylamino)pyridin-2-yl]-4-([oxo[3-(trifluoromethyl)phenyl]-ˆ[6]-sulfanylidene]oxo)-3,4-dihydro-2H-1,4-benzoxazin-2-yl]propoxy]methanethioyl)carbamate (132 mg, 0.20 mmol), ethanol (5 mL), and hydroxylamine hydrochloride (21 mg) was stirred for ten minutes. Next, sodium hydride (13 mg) was added, and the mixture was stirred for an hour at room temperature, then stirred at 80° C. overnight. Next, the mixture was concentrated; the resulting residue was dissolved in water, and then extracted three times with dichloromethane. The combined organic layers were washed with water, brine, dried ($Na_2SO_4$) and concentrated. The resulting residue was purified by Prep-HPLC eluting with a gradient of 32-56% acetonitrile in water with 0.05% trifluoroacetic acid to afford (S)-3-(3-(6-(6-(dimethylamino)pyridin-2-yl)-4-((3-(trifluoromethyl)phenyl)sulfonyl)-3,4-dihydro-2H-benzo[b][1,4]oxazin-2-yl)propoxy)-1,2,4-oxadiazol-5(4H)-one (44.2 mg, 36%) as a white solid. $^1$H-NMR (400 MHz, $CD_3OD$) δ 8.31 (s, 1H), 8.09-7.99 (m, 3H), 7.93 (t, J=8.2 Hz, 1H), 7.80 (t, J=8.1 Hz, 1H), 7.62 (dd, J=8.6, 2.2 Hz, 1H), 7.06 (dd, J=20.0, 8.1 Hz, 3H), 4.44 (dd, J=14.3, 2.3 Hz, 1H), 4.29 (t, J=6.4 Hz, 2H), 3.73-3.46 (m, 1H), 3.36 (m, 1H), 3.15 (m, 6H), 2.00-1.90 (m, 2H), 1.78-1.72 (m, 2H). (ES, m/z): $(M+H)^+$ 606.

Example 36—Preparation of Additional Substituted 4-(aryl sulfonyl)-3,4-dihydro-2H-benzo[b][1,4]oxazin-2-yl) Compounds Compounds in Table 12 were prepared based on experimental procedures described in Examples 1, 3, 5, 21, 24, and 31 and the detailed description. $^1$H NMR data for exemplary compounds from Table 12 is provided in Table 12A.

TABLE 12

| Compd No. | Structure | Name | Observed m/z |
|---|---|---|---|
| 36A | 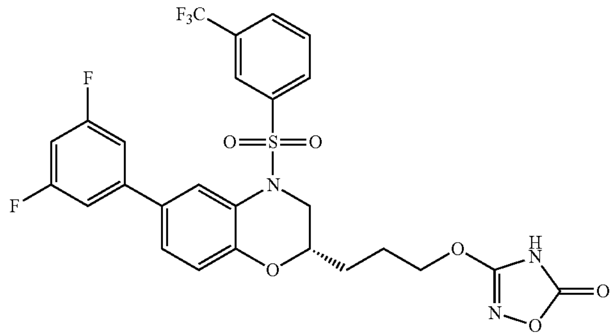 [SMILES: O=c1[nH]c(OCCC[C@H]2CN(S(=O)(=O)c3cccc(C(F)(F)F)c3)c3cc(-c4cc(F)cc(F)c4)ccc3O2)no1] | (S)-3-(3-(6-(3,5-difluorophenyl)-4-((3-(trifluoromethyl)phenyl)sulfonyl)-3,4-dihydro-2H-benzo[b][1,4]-oxazin-2-yl)propoxy)-1,2,4-oxadiazol-5(4H)-one | 620 (M + Na)+ |
| 36B | 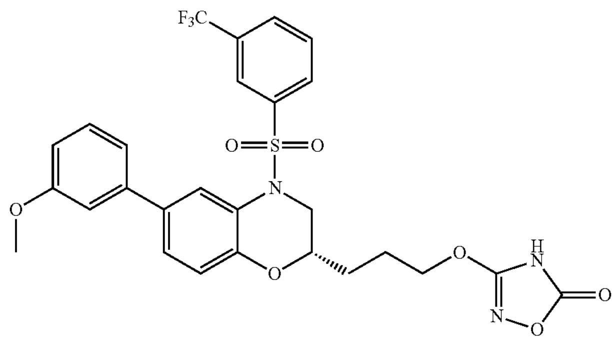 | (S)-3-(3-(6-(3-methoxyphenyl)-4-((3-(trifluoromethyl)phenyl)-sulfonyl)-3,4-dihydro-2H-benzo[b][1,4]oxazin-2-yl)propoxy)-1,2,4-oxadiazol-5(4H)-one | 592 (M + H)+ |
| 36C | 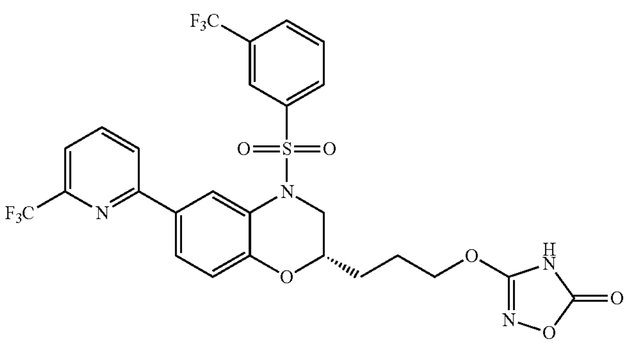 [SMILES: O=c1[nH]c(OCCC[C@H]2CN(S(=O)(=O)c3cccc(C(F)(F)F)c3)c3cc(-c4cccc(C(F)(F)F)n4)ccc3O2)no1] | (S)-3-(3-(4-((3-(trifluoromethyl)phenyl)sulfonyl)-6-(6-(trifluoromethyl)-pyridin-2-yl)-3,4-dihydro-2H-benzo[b][1,4]oxazin-2-yl)propoxy)-1,2,4-oxadiazol-5(4H)-one | 631 (M + H)+ |

TABLE 12A

| Compd No. | Physical Characterization Data |
|---|---|
| 36A | $^1$H NMR (400 MHz, CDCl$_3$) δ 8.01 (s, 1H), 7.90-7.87 (m, 3H), 7.67-7.64 (m, 1H), 7.28-7.26 (m, 1H), 7.06-7.00 (m, 2H), 6.89 (d, J = 8.5 Hz, 1H), 6.80-6.74 (m, 1H), 4.35-4.29 (m, 3H), 3.59-3.53 (m, 1H), 3.27-3.19 (m, 1H), 2.00-1.84 (m, 2H), 1.74-1.66 (m, 4H). |
| 36B | $^1$H NMR (400 MHz, CD$_3$OD-d$_4$) δ 8.04-7.98 (m, 4H), 7.81-7.77 (m, 1H), 7.40-7.35 (m, 2H), 7.17-7.11 (m, 2H), 6.94-6.89 (m, 2H), 4.45 (dd, J = 14.4, 2.4 Hz, 1H), 4.01-3.99 (m, 1H), 3.88 (s, 3H), 3.57-3.54 (m, 1H), 3.38-3.36 (m, 1H), 3.30-3.25 (m, 1H), 1.69-1.59 (m, 4H). |
| 36C | $^1$H NMR (400 MHz, CD$_3$OD-d$_4$) δ 8.60 (s, 1H), 8.10-8.07 (m, 4H), 8.01-7.99 (m, 1H), 7.85-7.71 (m, 3H), 6.98 (d, J = 8.8 Hz, 1H), 4.46 (dd, J = 14.3, 2.4 Hz, 1H), 4.34-4.30 (m, 2H), 3.68-6.42 (m, 2H), 2.03-1.73 (m, 4H). |

Example 37 and 38—Synthesis of (S)-4-((S)-6-(2,5-difluorophenyl)-4-((3-(trifluoromethyl)phenyl)sulfonyl)-3,4-dihydro-2H-benzo[b][1,4]oxazin-2-yl)-2-hydroxybutanoic acid and (R)-4-((S)-6-(2,5-difluorophenyl)-4-((3-(trifluoromethyl)phenyl)sulfonyl)-3,4-dihydro-2H-benzo[b][1,4]oxazin-2-yl)-2-hydroxybutanoic acid

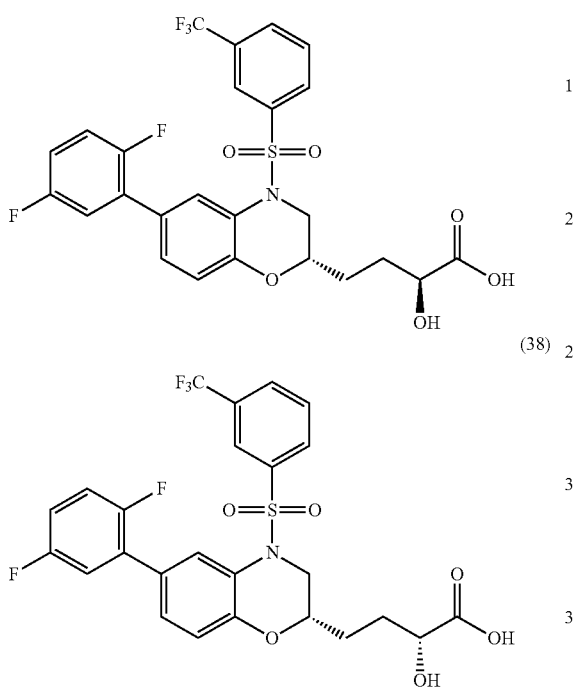

(37)

(38)

Part I—Synthesis of (S)-3-(6-(2,5-difluorophenyl)-4-((3-(trifluoromethyl)phenyl)sulfonyl)-3,4-dihydro-2H-benzo[b][1,4]oxazin-2-yl)propanal

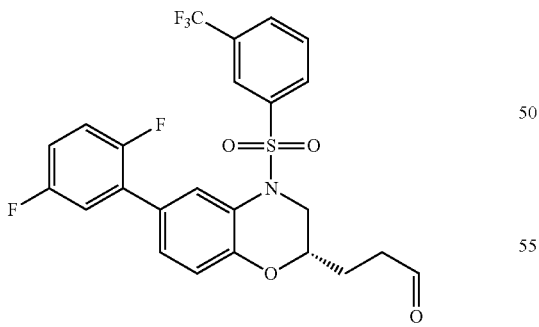

A solution of (S)-3-(6-(2,5-difluorophenyl)-4-((3-(trifluoromethyl)phenyl) sulfonyl)-3,4-dihydro-2H-benzo[b][1,4]oxazin-2-yl)propan-1-ol (1.6 g, 3.12 mmol) and 1,1,1-tris(acetyloxy)-1,1-dihydro-1,2-benziodoxol-3-(1H)-one (3.96 g, 8.98 mmol) in dichloromethane (50 mL) was stirred for four hours at room temperature. Then, aqueous sodium hydroxide was added to the reaction mixture and the resulting mixture was extracted three times with dichloromethane. The combined organic layers were dried (Na$_2$SO$_4$) and concentrated. The resulting residue was purified via MPLC eluting with a gradient of 20-50% ethyl acetate in petroleum ether to afford (S)-3-(6-(2,5-difluorophenyl)-4-((3-(trifluoromethyl)phenyl)sulfonyl)-3,4-dihydro-2H-benzo[b][1,4]oxazin-2-yl)propanal (1.4 g, 88%) as a light yellow oil.

Part II—Synthesis of 4-((S)-6-(2,5-difluorophenyl)-4-((3-(trifluoromethyl)phenyl)sulfonyl)-3,4-dihydro-2H-benzo[b][1,4]oxazin-2-yl)-2-hydroxybutanenitrile

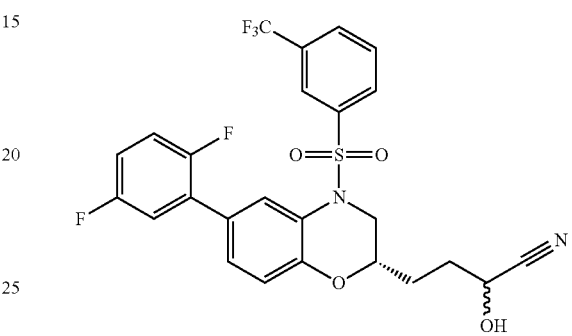

A solution of (S)-3-(6-(2,5-difluorophenyl)-4-((3-(trifluoromethyl)phenyl) sulfonyl)-3,4-dihydro-2H-benzo[b][1,4]oxazin-2-yl)propanal (280 mg, 0.55 mmol), methanol (15 mL), water (2 mL), acetic acid (1 mL), and sodium cyanide (80 mg) was stirred for one hour at room temperature. Then, the mixture was concentrated and partitioned between ethyl acetate and aqueous iron sulfate. Next, the organic layer was dried (Na$_2$SO$_4$) and concentrated. The resulting residue was purified via MPLC eluting with a gradient of 20-50% ethyl acetate in petroleum ether to afford 4-((S)-6-(2,5-difluorophenyl)-4-((3-(trifluoromethyl)phenyl)sulfonyl)-3,4-dihydro-2H-benzo[b][1,4]oxazin-2-yl)-2-hydroxybutanenitrile (240 mg, 81%) as a light yellow oil.

Part III—Synthesis of (S)-4-((S)-6-(2,5-difluorophenyl)-4-((3-(trifluoromethyl)phenyl)sulfonyl)-3,4-dihydro-2H-benzo[b][1,4]oxazin-2-yl)-2-hydroxybutanoic acid and (R)-4-((S)-6-(2,5-difluorophenyl)-4-((3-(trifluoromethyl)phenyl)sulfonyl)-3,4-dihydro-2H-benzo[b][1,4]oxazin-2-yl)-2-hydroxybutanoic acid (37)

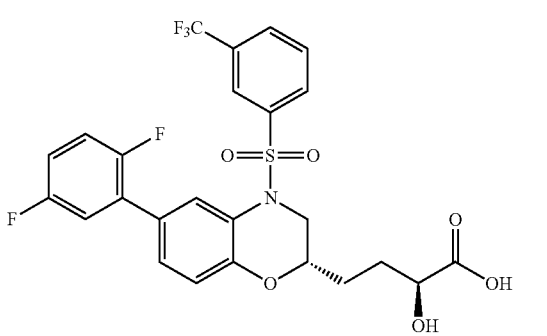

(38)

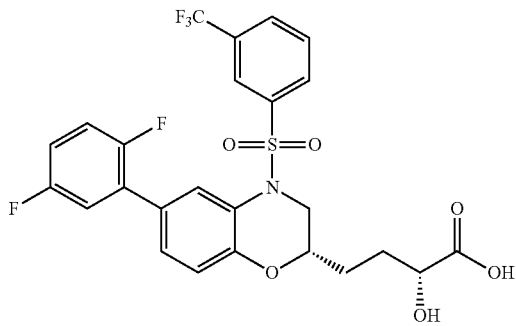

A mixture of 4-((S)-6-(2,5-difluorophenyl)-4-((3-(trifluoromethyl)phenyl) sulfonyl)-3,4-dihydro-2H-benzo[b][1,4]oxazin-2-yl)-2-hydroxybutanenitrile (200 mg, 0.37 mmol), 12M hydrogen chloride (5 mL), 1,4-dioxane (30 mL) was stirred overnight at 50° C. Then, the mixture was concentrated, and the resulting residue was purified by Chiral-Prep-HPLC to afford (R)-4-((S)-6-(2,5-difluorophenyl)-4-((3-(trifluoromethyl)phenyl)sulfonyl)-3,4-dihydro-2H-benzo[b][1,4]oxazin-2-yl)-2-hydroxybutanoic acid (35.3 mg, 17%) and (S)-4-((S)-6-(2,5-difluorophenyl)-4-((3-(trifluoromethyl)phenyl)sulfonyl)-3,4-dihydro-2H-benzo[b][1,4]oxazin-2-yl)-2-hydroxybutanoic acid (64.6 mg, 31%) as white solids. $^1$H-NMR (400 MHz, CD$_3$OD) δ 8.03-7.99 (m, 4H), 7.82-7.78 (m, 1H), 7.32-7.20 (m, 3H), 7.15-7.10 (m, 1H), 6.94 (d, J=8.4 Hz, 1H), 4.47 (dd, J=14.4 Hz, 2.4 Hz, 1H), 4.15-4.11 (m, 1H), 3.71-3.64 (m, 1H), 3.50-3.48 (m, 1H), 3.30-3.28 (m, 1H), 1.88-1.68 (m, 4H). (ES, m/z): (M+Na)$^+$ 580 and $^1$H-NMR (400 MHz, CD$_3$OD) δ 8.02-7.99 (m, 4H), 7.80 (t, J=7.6 Hz, 1H), 7.32-7.20 (m, 3H), 7.15-7.10 (m, 1H), 6.94 (d, J=8.4 Hz, 1H), 4.47 (dd, J=14.4 Hz, 2.4 Hz, 1H), 4.14-4.10 (m, 1H), 3.80-3.62 (m, 1H), 3.50-3.48 (m, 1H), 3.30-3.27 (m, 1H), 1.88-1.68 (m, 4H). (ES, m/z): (M+Na)$^+$ 580.

Example 39 and 40—Synthesis of (S)-4-((S)-6-(2,5-difluorophenyl)-4-((3-(trifluoromethyl)phenyl) sulfonyl)-3,4-dihydro-2H-benzo[b][1,4]oxazin-2-yl)-2-hydroxy-2-methylbutanoic acid and (R)-4-((S)-6-(2,5-difluorophenyl)-4-((3-(trifluoromethyl)phenyl)sulfonyl)-3,4-dihydro-2H-benzo[b][1,4]oxazin-2-yl)-2-hydroxy-2-methylbutanoic acid (39)

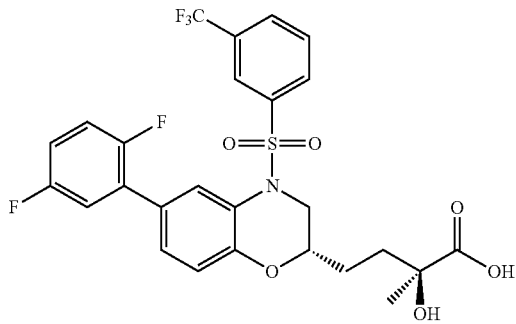

(40)

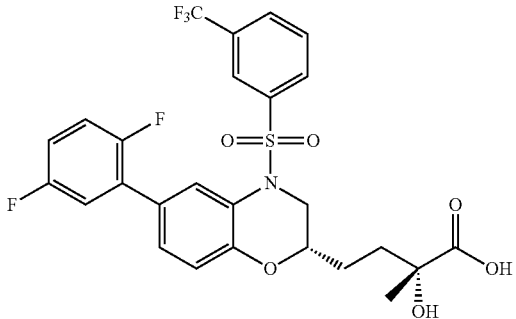

Part I—Synthesis of methyl 4-((S)-6-(2,5-difluorophenyl)-4-((3-(trifluoromethyl)phenyl)sulfonyl)-3,4-dihydro-2H-benzo[b][1,4]oxazin-2-yl)-2-hydroxybutanoate

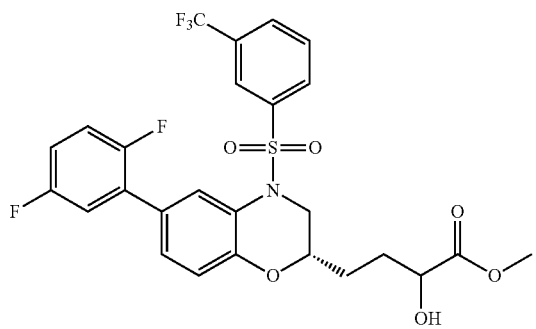 [SMILES: COC(=O)C(O)CC[C@H]1CN(S(=O)(=O)c2cccc(C(F)(F)F)c2)c2cc(-c3cc(F)ccc3F)ccc2O1]

A mixture of 4-((S)-6-(2,5-difluorophenyl)-4-((3-(trifluoromethyl)phenyl) sulfonyl)-3,4-dihydro-2H-benzo[b][1,4]oxazin-2-yl)-2-hydroxybutanenitrile (240 mg, 0.45 mmol), methanol (30 mL), and concentrated hydrogen chloride (5 mL) was stirred overnight at 50° C. Then, the mixture was concentrated, and the resulting residue was purified via MPLC eluting with a gradient of 20-50% ethyl acetate to afford methyl 4-((S)-6-(2,5-difluorophenyl)-4-((3-(trifluoromethyl)phenyl)sulfonyl)-3,4-dihydro-2H-benzo[b][1,4]oxazin-2-yl)-2-hydroxybutanoate (200 mg, 79%) as a light yellow oil.

Part II—Synthesis of methyl (S)-4-(6-(2,5-difluorophenyl)-4-((3-(trifluoromethyl)phenyl)sulfonyl)-3,4-dihydro-2H-benzo[b][1,4]oxazin-2-yl)-2-oxobutanoate

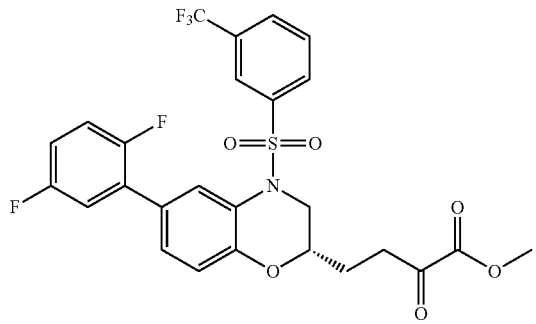 [SMILES: COC(=O)C(=O)CC[C@H]1CN(S(=O)(=O)c2cccc(C(F)(F)F)c2)c2cc(-c3cc(F)ccc3F)ccc2O1]

A solution of methyl 4-((S)-6-(2,5-difluorophenyl)-4-((3-(trifluoromethyl)phenyl)sulfonyl)-3,4-dihydro-2H-benzo[b][1,4]oxazin-2-yl)-2-hydroxybutanoate (180 mg, 0.31 mmol), 1,1,1-tris(acetyloxy)-1,1-dihydro-1,2-benziodoxol-3-(1H)-one (407 mg, 0.93 mmol), and dichloromethane (30 mL) was stirred for four hours at room temperature. Then, the mixture was diluted with 2N sodium hydroxide and extracted three times with dichloromethane. The combined organic layers were dried (Na₂SO₄) and concentrated. The resulting residue was purified via MPLC eluting with a gradient of 20-50% ethyl acetate in petroleum ether to afford methyl (S)-4-(6-(2,5-difluorophenyl)-4-((3-(trifluoromethyl)phenyl)sulfonyl)-3,4-dihydro-2H-benzo[b][1,4]oxazin-2-yl)-2-oxobutanoate (150 mg, 84%) as a light yellow oil.

Part III—Synthesis of methyl 4-((S)-6-(2,5-difluorophenyl)-4-((3-(trifluoromethyl)phenyl)sulfonyl)-3,4-dihydro-2H-benzo[b][1,4]oxazin-2-yl)-2-hydroxy-2-methylbutanoate

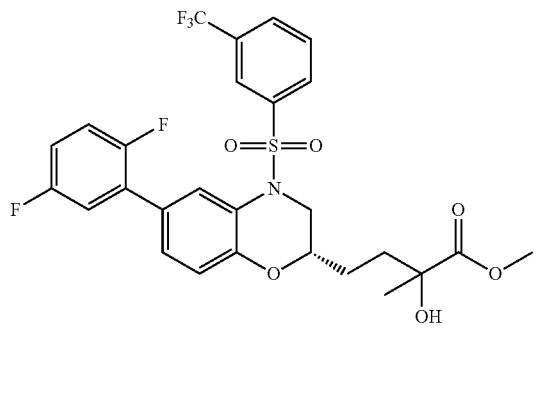 [SMILES: COC(=O)C(C)(O)CC[C@H]1CN(S(=O)(=O)c2cccc(C(F)(F)F)c2)c2cc(-c3cc(F)ccc3F)ccc2O1]

Methyl magnesium bromide (0.46 mmol) in THF as added to a stirred solution of methyl (S)-4-(6-(2,5-difluorophenyl)-4-((3-(trifluoromethyl)phenyl)sulfonyl)-3,4-dihydro-2H-benzo[b][1,4]oxazin-2-yl)-2-oxobutanoate (130 mg, 0.23 mmol) in tetrahydrofuran (10 mL) at 0° C. The mixture was stirred at this temperature for thirty minutes, and for then addition two hours at room temperature. Next water (1 mL) was added to the reaction mixture and the resulting mixture was concentrated. The resulting residue was purified via MPLC eluting with a gradient of 20-50% ethyl acetate in petroleum ether to afford methyl 4-((S)-6-(2,5-difluorophenyl)-4-((3-(trifluoromethyl)phenyl)sulfonyl)-3,4-dihydro-2H-benzo[b][1,4]oxazin-2-yl)-2-hydroxy-2-methylbutanoate (130 mg, 97%) as a light yellow oil.

Part IV— Synthesis of (S)-4-((S)-6-(2,5-difluorophenyl)-4-((3-(trifluoromethyl)phenyl)sulfonyl)-3,4-dihydro-2H-benzo[b][1,4]oxazin-2-yl)-2-hydroxy-2-methylbutanoic acid and (R)-4-((S)-6-(2,5-difluorophenyl)-4-((3-(trifluoromethyl)phenyl)sulfonyl)-3,4-dihydro-2H-benzo[b][1,4]oxazin-2-yl)-2-hydroxy-2-methylbutanoic acid (39)

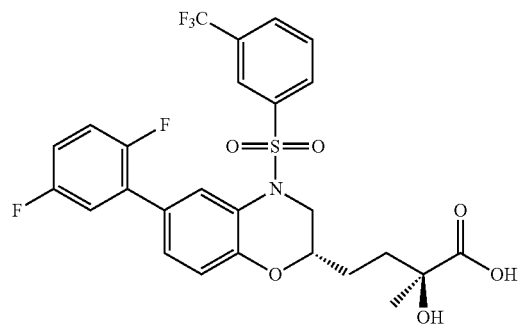

(40)

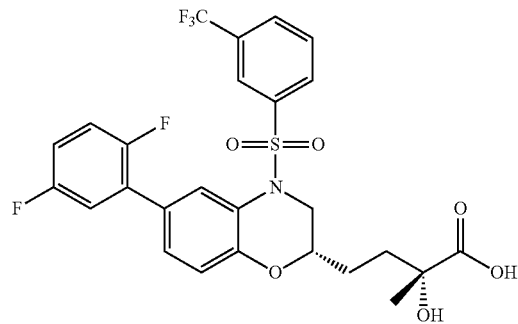

Based on the procedure in Example 1, Part VII; after separation on a chiral HPLC column two compounds were isolated: ¹H-NMR (400 MHz, CD₃OD) δ 8.02-7.99 (m, 4H), 7.82-7.78 (m, 1H), 7.32-7.20 (m, 3H), 7.15-7.10 (m, 1H), 6.94 (d, J=8.4 Hz, 1H), 4.47 (dd, J=14.4 Hz, 2.4 Hz, 1H), 3.47-3.44 (m, 1H), 3.33-3.29 (m, 1H), 1.99-1.95 (m, 1H), 1.82-1.78 (m, 1H), 1.66-1.52 (m, 2H), 1.43 (s, 3H). (ES, m/z): (M+Na)⁺ 594 and ¹H-NMR (400 MHz, CD₃OD) δ 8.02-7.99 (m, 4H), 7.82-7.78 (m, 1H), 7.32-7.20 (m, 3H), 7.15-7.10 (m, 1H), 6.94 (d, J=8.8 Hz, 1H), 4.47 (dd, J=14.4 Hz, 2.4 Hz, 1H), 3.50-3.40 (m, 1H), 3.33-3.25 (m, 1H), 1.83-1.77 (m, 3H), 1.61-1.55 (m, 1H), 1.42 (s, 3H). (ES, m/z): (M+Na)⁺ 594.

Example 41—Synthesis of (R)-1-((R)-6-(2,5-difluorophenyl)-4-((3-(trifluoromethyl)phenyl)sulfonyl)-3,4-dihydro-2H-benzo[b][1,4]oxazin-2-yl)ethane-1,2-diol

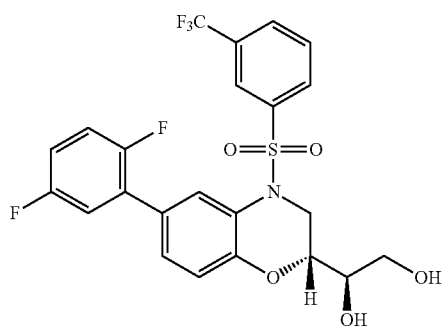 [SMILES: O=S(=O)(c1cccc(C(F)(F)F)c1)N1C[C@H]([C@H](O)CO)Oc2ccc(-c3cc(F)ccc3F)cc21]

Part I—Synthesis of diisopropyl (2S,3S)-2-hydroxy-3-((triisopropylsilyl)oxy)succinate

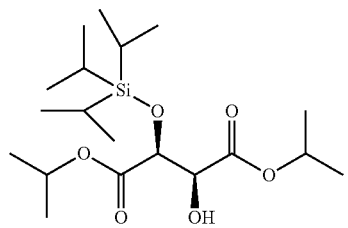 [SMILES: CC(C)OC(=O)[C@@H](O)[C@H](O[Si](C(C)C)(C(C)C)C(C)C)C(=O)OC(C)C]

2,6-Dimethylpyridine (11 g, 102.66 mmol) was added dropwise to a stirred solution of diisopropyl (2S,3S)-2,3-dihydroxysuccinate (20 g, 85.38 mmol) and triisopropylsilyl trifluoromethanesulfonate (31 g, 102 mmol) in dichloromethane (400 mL). The mixture was stirred overnight at room temperature. Then, the mixture was washed with saturated ammonium chloride, dried ($Na_2SO_4$), and concentrated. The resulting residue was purified via MPLC eluting with 10% ethyl acetate in petroleum ether to afford diisopropyl (2S,3S)-2-hydroxy-3-((triisopropylsilyl)oxy)succinate (20 g, 55%) as a colorless oil.

Part II—Synthesis of isopropyl (2S,3R)-3,4-dihydroxy-2-((triisopropylsilyl)oxy)butanoate

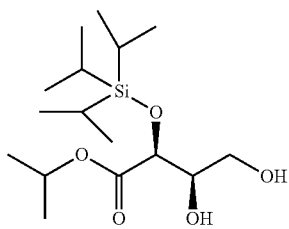 [SMILES: CC(C)OC(=O)[C@@H](O[Si](C(C)C)(C(C)C)C(C)C)[C@H](O)CO]

A 10M solution of borane dimethyl sulfide (5.3 mL, 53 mmol) in THF was added dropwise to a solution of diisopropyl (2S,3S)-2-hydroxy-3-((triisopropylsilyl)oxy)succinate (20 g, 51.2 mmol) in tetrahydrofuran (200 mL) at 0° C. To this was added sodium borohydride (95 mg, 2.51 mmol), and the resulting solution was stirred overnight at room temperature. Next, ethanol (40 mL) was added to the reaction mixture and the resulting solution was stirred for thirty minutes at room temperature. The mixture was then concentrated, and the resulting residue was purified via MPLC eluting with 12% ethyl acetate in petroleum ether to afford isopropyl (2S,3R)-3,4-dihydroxy-2-((triisopropylsilyl)oxy)butanoate as a colorless oil.

Part III—Synthesis of isopropyl (S)-2-((R)-2,2-dimethyl-1,3-dioxolan-4-yl)-2-((triisopropylsilyl)oxy)acetate

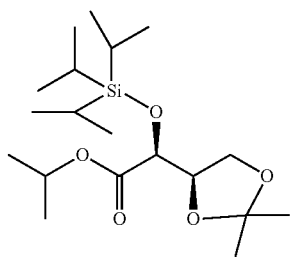 [SMILES: CC(C)OC(=O)[C@@H](O[Si](C(C)C)(C(C)C)C(C)C)[C@H]1COC(C)(C)O1]

A solution of isopropyl (2S,3R)-3,4-dihydroxy-2-((triisopropylsilyl)oxy)butanoate (1.5 g, 4.48 mmol), 2,2-dimethoxypropane (2.6 mL), p-toluene sulfonic acid (700 mg, 4.07 mmol) and acetone (15 mL) was stirred for overnight at room temperature. Then, the reaction solution was diluted with water and extracted twice with ethyl acetate. The combined organic layers were dried ($Na_2SO_4$) and concentrated. The resulting residue was purified via MPLC eluting with 10% ethyl acetate in petroleum ether to afford isopropyl (S)-2-((R)-2,2-dimethyl-1,3-dioxolan-4-yl)-2-((triisopropylsilyl)oxy)acetate (1 g, 60%) as a colorless oil.

Part IV—Synthesis of isopropyl (S)-2-((R)-2,2-dimethyl-1,3-dioxolan-4-yl)-2-hydroxyacetate

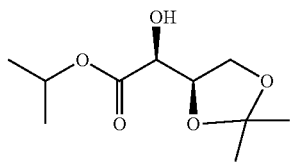

A 1M solution of tetrabutylammonium fluoride (2.7 mL) in THF was added to a solution of isopropyl (S)-2-((R)-2,2-dimethyl-1,3-dioxolan-4-yl)-2-((triisopropylsilyl)oxy)acetate (1 g, 2.67 mmol) in THF (10 mL). The solution was stirred for three hours at room temperature. Then, the reaction mixture was diluted with saturated sodium bicarbonate, and was extracted twice with dichloromethane. The combined organic layers were dried ($Na_2SO_4$) and concentrated. The resulting residue was purified by MPLC eluting with 12% ethyl acetate in petroleum ether to afford isopropyl (S)-2-((R)-2,2-dimethyl-1,3-dioxolan-4-yl)-2-hydroxyacetate (500 mg, 86%) as a colorless oil.

Part V—Synthesis of 2,4',5-trifluoro-3'-nitro-1,1'-biphenyl

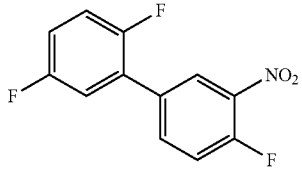 [SMILES: O=[N+]([O-])c1cc(-c2cc(F)ccc2F)ccc1F]

A mixture of 4-bromo-1-fluoro-2-nitrobenzene (2 g, 9.09 mmol), (2,5-difluorophenyl)boronic acid (1.7 g, 10.77 mmol), sodium carbonate (2.9 g), tetrakis(triphenylphosphine)palladium (1 g, 0.87 mmol), toluene (20 mL), methanol (5 mL) and water (5 mL) was stirred overnight at 90° C. Then, the mixture was partitioned between water and ethyl acetate, and the organic layer was concentrated. The resulting residue was purified via MPLC eluting with 10% ethyl acetate in petroleum ether to afford 2,4',5-trifluoro-3'-nitro-1,1'-biphenyl (2 g, 87%) as an off-white solid.

Part VI—Synthesis of isopropyl (S)-2-((2',5'-difluoro-3-nitro-[1,1'-biphenyl]-4-yl)oxy)-2-((R)-2,2-dimethyl-1,3-dioxolan-4-yl)acetate

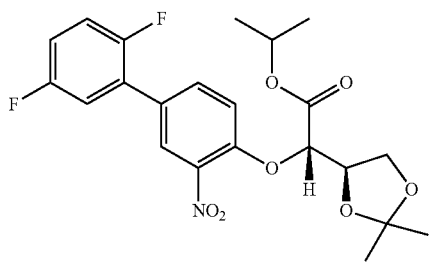 [SMILES: CC(C)OC(=O)[C@@H](Oc1ccc(-c2cc(F)ccc2F)cc1[N+](=O)[O-])[C@H]1COC(C)(C)O1]

Isopropyl (S)-2-((R)-2,2-dimethyl-1,3-dioxolan-4-yl)-2-hydroxyacetate (500 mg, 2.29 mmol) was added to a stirred mixture of a sodium hydride (100 mg, 4.17 mmol) in tetrahydrofuran (15 mL) at 0° C. in 10 min. To this was added 4-(2,5-difluorophenyl)-1-fluoro-2-nitrobenzene (580 mg, 2.29 mmol) and the mixture was stirred overnight at room temperature. Methanol (0.5 mL) was added and the mixture was partitioned between ethyl acetate and water. The organic layer was dried ($Na_2SO_4$) and concentrated. The residue was purified by MPLC eluting with 25% ethyl acetate in petroleum ether to afford isopropyl (S)-2-((2',5'-difluoro-3-nitro-[1,1'-biphenyl]-4-yl)oxy)-2-((R)-2,2-dimethyl-1,3-dioxolan-4-yl)acetate (300 mg, 29%) as a colorless oil.

Part VII—Synthesis of (S)-6-(2,5-difluorophenyl)-2-((R)-2,2-dimethyl-1,3-dioxolan-4-yl)-2H-benzo[b][1,4]oxazin-3(4H)-one

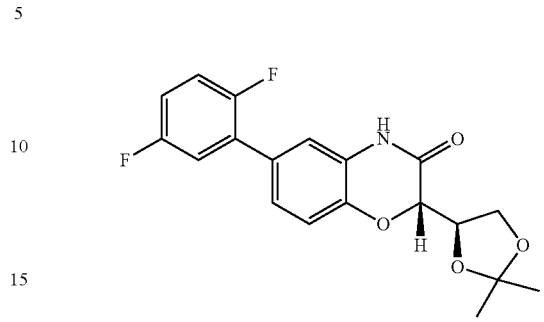

A mixture of isopropyl (S)-2-((2',5'-difluoro-3-nitro-[1,1'-biphenyl]-4-yl)oxy)-2-((R)-2,2-dimethyl-1,3-dioxolan-4-yl)acetate (200 mg, 0.44 mmol), acetic acid (5 mL), and iron powder (199 mg) was stirred for one hour at 80° C. Then, the mixture was cooled, diluted with ethyl acetate and filtered. The filtrate was concentrated. The resulting residue was diluted with ethyl acetate and washed twice with saturated sodium bicarbonate, dried ($Na_2SO_4$) and concentrated. The resulting residue was purified via MPLC eluting with 25% ethyl acetate in petroleum ether to afford (S)-6-(2,5-difluorophenyl)-2-((R)-2,2-dimethyl-1,3-dioxolan-4-yl)-2H-benzo[b][1,4]oxazin-3(4H)-one (130 mg, 81%) as a white solid.

Part VIII—Synthesis of (R)-6-(2,5-difluorophenyl)-2-((R)-2,2-dimethyl-1,3-dioxolan-4-yl)-3,4-dihydro-2H-benzo[b][1,4]oxazine

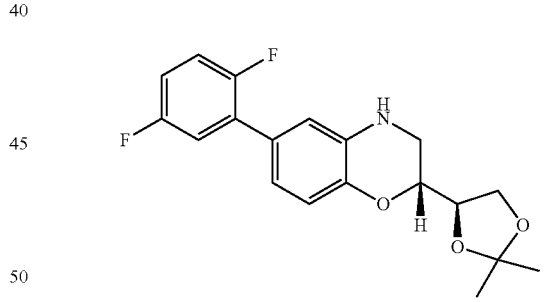

A solution of (S)-6-(2,5-difluorophenyl)-2-((R)-2,2-dimethyl-1,3-dioxolan-4-yl)-2H-benzo[b][1,4]oxazin-3(4H)-one (100 mg, 0.28 mmol), tetrahydrofuran (5 mL), and 10M borane dimethylsulfide in THF (0.8 mL) was added to a reaction vessel. The reaction mixture was stirred for three hours at room temperature. Then, methanol (1 mL) was added to the reaction mixture and the resulting mixture was then diluted with water, and extracted twice with ethyl acetate. The combined organic layers were dried ($Na_2SO_4$) and concentrated. The resulting residue was purified via MPLC eluting with 25% ethyl acetate in petroleum ether to afford (R)-6-(2,5-difluorophenyl)-2-((R)-2,2-dimethyl-1,3-dioxolan-4-yl)-3,4-dihydro-2H-benzo[b][1,4]oxazine (80 mg, 83%) as a white solid.

Part IX—Synthesis of (R)-6-(2,5-difluorophenyl)-2-((R)-2,2-dimethyl-1,3-dioxolan-4-yl)-4-((3-(trifluoromethyl)phenyl)sulfonyl)-3,4-dihydro-2H-benzo[b][1,4]oxazine

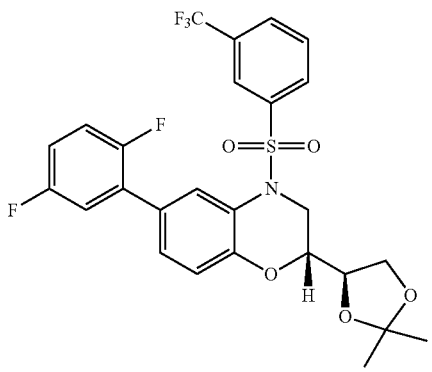 [SMILES: CC1(C)OC[C@H]([C@H]2CN(S(=O)(=O)c3cccc(C(F)(F)F)c3)c3cc(-c4cc(F)ccc4F)ccc3O2)O1]

A solution of (R)-6-(2,5-difluorophenyl)-2-((R)-2,2-dimethyl-1,3-dioxolan-4-yl)-3,4-dihydro-2H-benzo[b][1,4]oxazine (80 mg, 0.23 mmol) in dichloromethane (5 mL), 3-(trifluoromethyl)benzene-1-sulfonyl chloride (84 mg, 0.34 mmol), pyridine (91 mg, 1.15 mmol), and 4-dimethylaminopyridine (19 mg, 0.16 mmol) was stirred overnight at room temperature. Then, the mixture was diluted dichloromethane and washed twice with 1M hydrogen chloride. The organic layer was dried (Na$_2$SO$_4$) and concentrated. The resulting residue was purified by MPLC eluting with 25% ethyl acetate in petroleum ether to afford (R)-6-(2,5-difluorophenyl)-2-((R)-2,2-dimethyl-1,3-dioxolan-4-yl)-4-((3-(trifluoromethyl)phenyl)sulfonyl)-3,4-dihydro-2H-benzo[b][1,4]oxazine (100 mg, 78%) as a light yellow solid.

Part X—Synthesis of (R)-1-((R)-6-(2,5-difluorophenyl)-4-((3-(trifluoromethyl)phenyl)sulfonyl)-3,4-dihydro-2H-benzo[b][1,4]oxazin-2-yl)ethane-1,2-diol

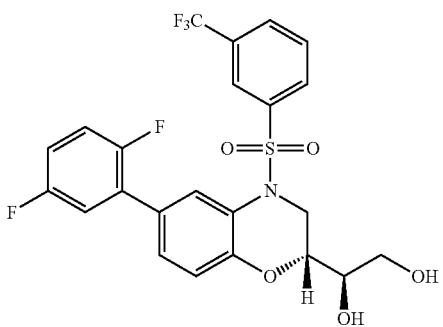 [SMILES: O=S(=O)(c1cccc(C(F)(F)F)c1)N1C[C@H]([C@H](O)CO)Oc2ccc(-c3cc(F)ccc3F)cc21]

A solution of (R)-6-(2,5-difluorophenyl)-2-((R)-2,2-dimethyl-1,3-dioxolan-4-yl)-4-((3-(trifluoromethyl)phenyl)sulfonyl)-3,4-dihydro-2H-benzo[b][1,4]oxazine (100 mg, 0.18 mmol) acetic acid (2 mL), and water (0.5 mL) was stirred overnight at room temperature. Then, the mixture was concentrated. The resulting residue was diluted ethyl acetate and washed twice with saturated sodium bicarbonate. The organic layer was concentrated, and the residue was purified via Prep-HPLC eluting with a gradient of 42-66% acetonitrile in water with 0.05% trifluoroacetic acid to afford (R)-1-((R)-6-(2,5-difluorophenyl)-4-((3-(trifluoromethyl)phenyl)sulfonyl)-3,4-dihydro-2H-benzo[b][1,4]oxazin-2-yl)ethane-1,2-diol (57.3 mg, 62%) as a white solid. $^1$H-NMR (400 MHz, CD$_3$OD) δ 9.07 (d, J=2.1 Hz, 1H), 8.89 (m, 1H), 8.31 (d, J=2.2 Hz, 1H), 8.14-8.06 (m, 2H), 8.05-7.98 (m, 2H), 7.83 (t, J=7.7 Hz, 1H), 7.53 (dd, J=8.5, 2.2 Hz, 1H), 7.07 (d, J=8.5 Hz, 1H), 4.47 (dd, J=14.4, 2.5 Hz, 1H), 3.67-3.56 (m, 1H), 3.46-3.35 (m, 2H), 3.28 (m, 1H), 1.96-1.73 (m, 2H), 1.37 (d, J=5.0 Hz, 6H). (ES, m/z): (M+Na)$^+$ 516.

Example 42—Synthesis of (S)-3-(6-(2,5-difluorophenyl)-4-((3-(trifluoromethyl)phenyl)sulfonyl)-3,4-dihydro-2H-benzo[b][1,4]oxazin-2-yl)-N-(methylsulfonyl)propanamide

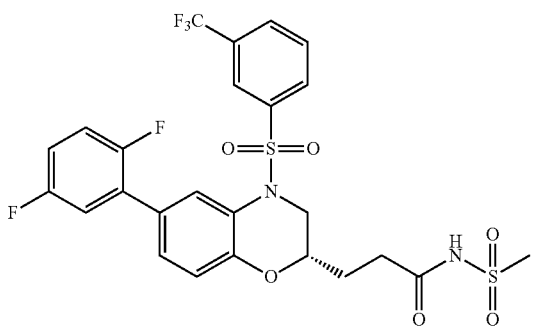 [SMILES: CS(=O)(=O)NC(=O)CC[C@H]1CN(S(=O)(=O)c2cccc(C(F)(F)F)c2)c2cc(-c3cc(F)ccc3F)ccc2O1]

A solution of (S)-3-(6-(2,5-difluorophenyl)-4-((3-(trifluoromethyl)-phenyl)sulfonyl)-3,4-dihydro-2H-benzo[b][1,4]oxazin-2-yl)propanoic acid (150 mg, 0.28 mmol), dichloromethane (5 mL), methanesulfonamide (19 mg, 0.20 mmol), 1-ethyl-3-(3-dimethylaminopropyl)carbodiimide hydrochloride (45 mg, 0.23 mmol), and 4-dimethylaminopyridine (5 mg, 0.04 mmol) was stirred overnight at room temperature and concentrated. The resulting residue was dissolved in water and the resulting mixture was extracted three times with dichloromethane. The combined organic layers were washed water, brine, dried (Na$_2$SO$_4$) and concentrated. The resulting residue was purified by Prep-HPLC eluting with a gradient of 54-72% acetonitrile in water with 0.05% trifluoroacetic acid to afford (S)-3-(6-(2,5-difluorophenyl)-4-((3-(trifluoromethyl)phenyl)sulfonyl)-3,4-dihydro-2H-benzo[b][1,4]oxazin-2-yl)-N-(methylsulfonyl)propanamide (18.5 mg, 11%) as a white solid. $^1$H-NMR (400 MHz, CD$_3$OD) δ 8.06-8.03 (m, 2H), 7.99-7.93 (m, 2H), 7.82 (m, 1H), 7.30-7.24 (m, 3H), 7.14 (m, 1H), 6.96 (d, J=8.5 Hz, 1H), 4.50 (dd, J=14.5, 2.4 Hz, 1H), 3.57 (m, 1H), 3.33 (m, 1H), 3.25 (s, 3H), 2.50 (td, J=7.0, 2.4 Hz, 2H), 2.01 (m, 1H), 1.85 (m, 1H). (ES, m/z): (M+H)$^+$ 605.

Example 43—Preparation of Additional Substituted 4-(aryl sulfonyl)-3,4-dihydro-2H-benzo[b][1,4]oxazin-2-yl) Compounds Compounds in Table 13 were prepared based on experimental procedures described in Example 42 and the detailed description. $^1$H NMR data for exemplary compounds from Table 13 is provided in Table 13A.

TABLE 13

| Compd No. | Structure | Name | Observed m/z |
|---|---|---|---|
| 43A | 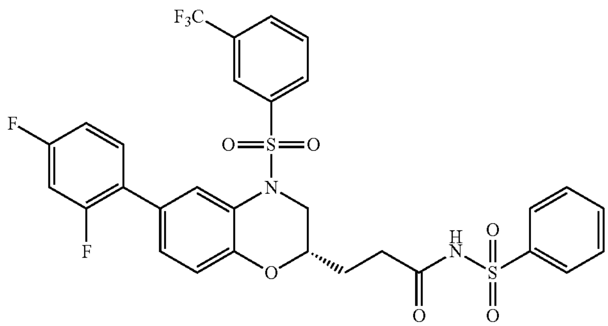 [SMILES: O=C(CC[C@H]1CN(S(=O)(=O)c2cccc(C(F)(F)F)c2)c2cc(-c3ccc(F)cc3F)ccc2O1)NS(=O)(=O)c1ccccc1] | (S)-3-(6-(2,4-difluorophenyl)-4-((3-(trifluoromethyl)phenyl)-sulfonyl)-3,4-dihydro-2H-benzo[b][1,4]oxazin-2-yl)-N-(phenylsulfonyl)propanamide | 667 (M + H)+ |
| 43B | 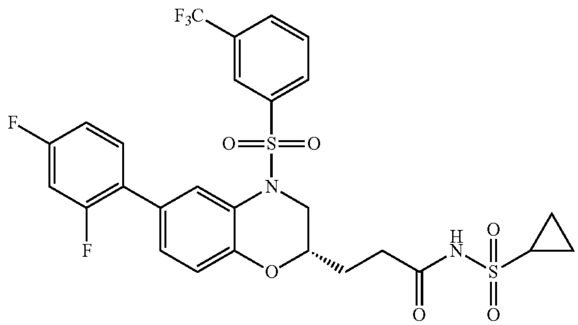 [SMILES: O=C(CC[C@H]1CN(S(=O)(=O)c2cccc(C(F)(F)F)c2)c2cc(-c3ccc(F)cc3F)ccc2O1)NS(=O)(=O)C1CC1] | (S)-N-(cyclopropylsulfonyl)-3-(6-(2,4-difluorophenyl)-4-((3-(trifluoromethyl)phenyl)-sulfonyl)-3,4-dihydro-2H-benzo[b][1,4]oxazin-2-yl)propanamide | 631 (M + H)+ |

TABLE 13A

| Compd No. | Physical Characterization Data |
|---|---|
| 43A | ¹H NMR (400 MHz, CD₃OD-d₄) δ 8.05-7.90 (m, 5H), 7.80-7.59 (m, 5H), 7.29-7.12 (m, 4H), 6.82 (d, J = 8.4 Hz, 1H), 4.43 (dd, J = 14.3, 2.4 Hz, 1H), 3.50-3.40 (m, 1H), 3.34-3.21 (m, 1H), 2.43-2.40 (m, 2H), 1.87-1.76 (m, 2H). |
| 43B | ¹H NMR (400 MHz, CD₃OD-d₄) δ 8.07-7.81 (m, 5H), 7.32-7.12 (m, 4H), 6.96 (d, J = 8.4 Hz, 1H), 4.52 (dd, J = 14.3, 2.4 Hz, 1H), 3.53 (m, 1H), 3.33 (m, 1H), 2.53-2.48 (m, 2H), 2.10-1.80 (m, 2H), 1.26-1.25 (m, 2H), 1.12-1.07 (m, 2H). |

Example 44—Synthesis of ([[(2S)-6-(2,5-difluorophenyl)-4-[[3-(trifluoromethyl)benzene]sulfonyl]-3,4-dihydro-2H-1,4-benzoxazin-2-yl]methyl]sulfamoyl)(methyl)amine

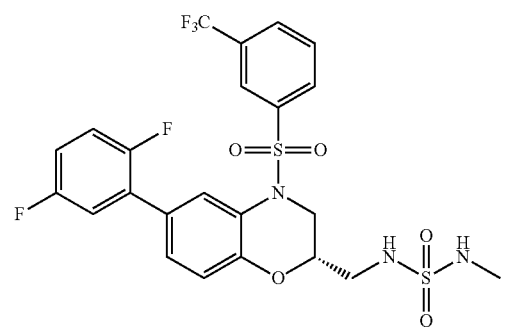 [SMILES: CN(C)S(=O)(=O)NC[C@H]1CN(S(=O)(=O)c2cccc(C(F)(F)F)c2)c2cc(-c3cc(F)ccc3F)ccc2O1]

N-Methylsulfamoyl chloride (64 mg, 0.49 mmol) was added dropwise to a stirred solution of ((S)-(6-(2,5-difluorophenyl)-4-((3-(trifluoromethyl)phenyl)sulfonyl)-3,4-dihydro-2H-benzo[b][1,4]oxazin-2-yl)methanamine (120 mg, 0.25 mmol) in dichloromethane (5 mL) and triethylamine (75 mg, 0.74 mmol). The mixture was stirred for two hours at room temperature and then was diluted dichloromethane, washed with water, dried (Na₂SO₄) and concentrated. The resulting residue was purified by Prep-HPLC eluting with a gradient of 30-60% acetonitrile in water with 0.05% trifluoroacetic acid to afford ([[(2S)-6-(2,5-difluorophenyl)-4-[[3-(trifluoromethyl) benzene]sulfonyl]-3,4-dihydro-2H-1,4-benzoxazin-2-yl]methyl]sulfamoyl)(methyl)amine (35 mg, 24%) as a white solid. ¹H-NMR (400 MHz, CD₃OD) δ 8.08-7.99 (m, 2H), 7.95 (d, J=7.9 Hz, 1H), 7.90 (m, 1H), 7.78 (t, J=7.9 Hz, 1H), 7.29 (m, 1H), 7.26-7.16 (m, 2H), 7.10 (m, 1H), 6.95 (d, J=8.6 Hz, 1H), 4.60 (dd, J=14.6, 2.6 Hz, 11H), 3.65 (m, 11H), 3.33 (m, 11H), 3.23-3.06 (m, 2H), 2.58 (s, 3H). (ES, m/z): (M+H)+ 578.

Example 45—Preparation of Additional Substituted 4-(aryl sulfonyl)-3,4-dihydro-2H-benzo[b][1,4]oxazin-2-yl) Compounds Compounds in Tables 14 and 14A were prepared based on experimental procedures described in Example 44 and the detailed description. ¹H NMR data for exemplary compounds is provided in Table 141B.

TABLE 14

| Compd No. | Structure | Name | Observed m/z |
|---|---|---|---|
| 45A | 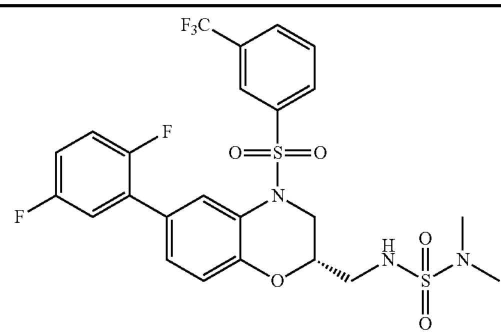 | ([[(2S)-6-(2,5-difluorophenyl)-4-[[3-(trifluoromethyl)-benzene]-sulfonyl]-3,4-dihydro-2H-1,4-benzoxazin-2-yl]methyl]sulfamoyl)-(dimethyl)amine | 592 (M + H)+ |
| 45C | 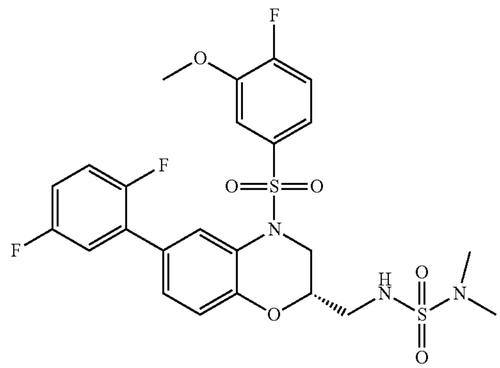 [SMILES: COc1cc(S(=O)(=O)N2C[C@H](CNS(=O)(=O)N(C)C)Oc3ccc(-c4cc(F)ccc4F)cc32)ccc1F] | ([[(2S)-6-(2,5-difluorophenyl)-4-[[4-fluoro-3-methoxy-benzene]-sulfonyl]-3,4-dihydro-2H-1,4-benzoxazin-2-yl]methyl]sulfamoyl)-(dimethyl)amine | 572 (M + H)+ |
| 45D | 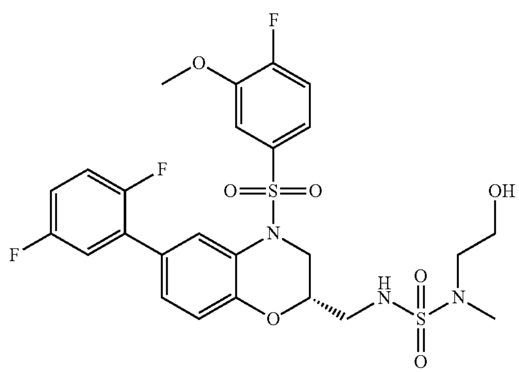 [SMILES: COc1cc(S(=O)(=O)N2C[C@H](CNS(=O)(=O)N(C)CCO)Oc3ccc(-c4cc(F)ccc4F)cc32)ccc1F] | ([[(2S)-6-(2,5-difluorophenyl)-4-[[4-fluoro-3-methoxy-benzene]-sulfonyl]-3,4-dihydro-2H-1,4-benzoxazin-2-yl]methyl]sulfamoyl)-(N-methyl-N-2-hydroxyethyl)-amine | 602 (M + H)+ |

TABLE 14A

| Compd No. | Structure | Name | Observed m/z |
|---|---|---|---|
| 45E | 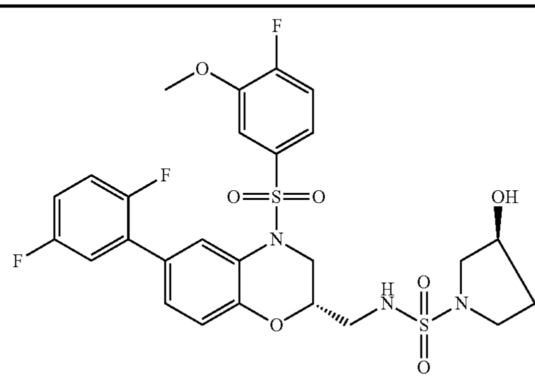 | (S)-N-(((S)-6-(2,5-difluoro-phenyl)-4-((4-fluoro-3-methoxyphenyl)sulfonyl)-3,4-dihydro-2H-benzo[b][1,4]oxazin-2-yl)methyl)-3-hydroxy-pyrrolidine-1-sulfonamide | 614 (M + H)+ |

TABLE 14A-continued

| Compd No. | Structure | Name | Observed m/z |
|---|---|---|---|
| 45F | 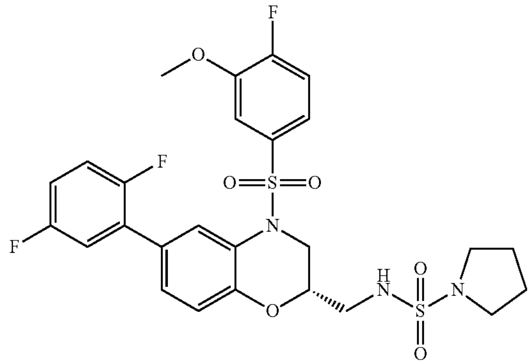 | (S)-N-((6-(2,5-difluorophenyl)-4-((4-fluoro-3-methoxyphenyl)sulfonyl)-3,4-dihydro-2H-benzo[b][1,4]oxazin-2-yl)methyl)pyrrolidine-1-sulfonamide | 618 (M + H)+ |

TABLE 14B

| Compd No. | Physical Characterization Data |
|---|---|
| 45A | $^1$H NMR (400 MHz, CD$_3$OD-d$_4$) δ 8.07-8.00 (m, 2H), 7.97 (d, J = 7.8 Hz, 1H), 7.90 (s, 1H), 7.78 (t, J = 7.9 Hz, 1H), 7.34-7.28 (m, 1H), 7.26-7.17 (m, 2H), 7.14-7.05 (m, 1H), 6.96 (d, J = 8.5 Hz, 1H), 4.57 (dd, J = 14.6, 2.6 Hz, 1H), 3.66-3.55 (m, 1H), 3.33 (d, J = 3.9 Hz, 1H), 3.20 (dd, J = 5.6, 3.2 Hz, 2H), 2.74 (s, 6H). |
| 45C | $^1$H NMR (400 MHz, CD$_3$OD-d$_4$) δ 8.08 (m, 1H), 7.35-7.19 (m, 6H), 7.15-7.05 (m, 1H), 6.98 (d, J = 8.6 Hz, 1H), 4.64-4.44 (m, 1H), 3.53-3.42 (m, 1H), 3.27-3.08 (m, 3H), 2.74 (s, 6H). |
| 45D | $^1$H NMR (400 MHz, CD$_3$OD-d$_4$) δ 8.07 (t, J = 1.8 Hz, 1H), 7.39-7.15 (m, 6H), 7.17-7.02 (m, 1H), 6.97 (d, J = 8.6 Hz, 1H), 4.54 (dd, J = 14.7, 2.5 Hz, 1H), 3.75-3.63 (m, 5H), 3.57-3.43 (m, 1H), 3.30-3.09 (m, 5H), 2.84 (s, 3H). |
| 45F | $^1$H NMR (400 MHz, CD$_3$OD-d$_4$) δ 8.10 (t, J = 1.8 Hz, 1H), 7.39-7.31 (m, 2H), 7.31-7.19 (m, 4H), 7.17-7.08 (m, 1H), 6.99 (d, J = 8.6 Hz, 1H), 4.56 (dd, J = 14.7, 2.5 Hz, 1H), 3.76 (s, 3H), 3.59-3.48 (m, 1H), 3.30-3.23 (m, 5H), 3.23-3.15 (m, 2H), 1.98-1.87 (m, 4H). |

Example 46—Preparation of Additional Substituted 4-(aryl sulfonyl)-3,4-dihydro-2H-benzo[b][1,4]oxazin-2-yl) Compounds Compounds in Tables 15 and 15A were prepared based on experimental procedures described in Examples 19 and 20 and the detailed description. $^1$H NMR for exemplary compounds is provided in Table 15B.

TABLE 15

| Compd No. | Structure | Name | Observed m/z |
|---|---|---|---|
| 46A | 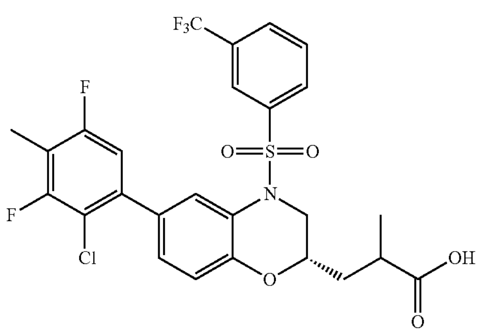 [SMILES: Cc1c(F)cc(-c2ccc3c(c2)N(S(=O)(=O)c2cccc(C(F)(F)F)c2)C[C@H](CC(C)C(=O)O)O3)c(Cl)c1F] | 3-((S)-6-(2-chloro-3,5-difluoro-4-methylphenyl)-4-((3-(trifluoromethyl)phenyl)sulfonyl)-3,4-dihydro-2H-benzo[b][1,4]oxazin-2-yl)-2-methylpropanoic acid | 590 (M + H)+ |

TABLE 15-continued

| Compd No. | Structure | Name | Observed m/z |
|---|---|---|---|
| 46B | 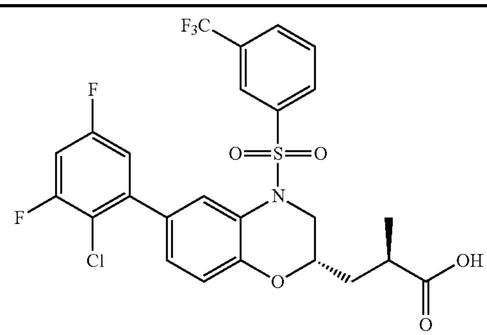 | (R)-3-((S)-6-(2-chloro-3,5-difluorophenyl)-4-((3-(trifluoromethyl)phenyl)sulfonyl)-3,4-dihydro-2H-benzo[b][1,4]oxazin-2-yl)-2-methylpropanoic acid | 576 (M + H)+ |
| 46C | 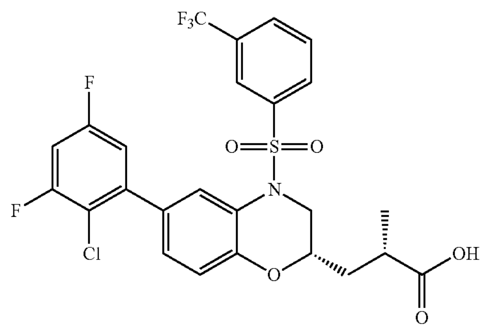 [SMILES: C[C@@H](C[C@H]1CN(S(=O)(=O)c2cccc(C(F)(F)F)c2)c2cc(-c3cc(F)cc(F)c3Cl)ccc2O1)C(=O)O] | (S)-3-((S)-6-(2-chloro-3,5-difluorophenyl)-4-((3-(trifluoromethyl)phenyl)sulfonyl)-3,4-dihydro-2H-benzo[b][1,4]oxazin-2-yl)-2-methylpropanoic acid | 576 (M + H)+ |

TABLE 15A

| Compd No. | Structure | Name | Observed m/z |
|---|---|---|---|
| 46D | 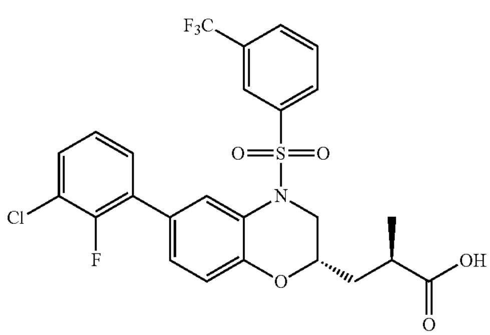 [SMILES: C[C@H](C[C@H]1CN(S(=O)(=O)c2cccc(C(F)(F)F)c2)c2cc(-c3cccc(Cl)c3F)ccc2O1)C(=O)O] | (R)-3-((S)-6-(3-chloro-2-fluorophenyl)-4-((3-(trifluoromethyl)phenyl)sulfonyl)-3,4-dihydro-2H-benzo[b][1,4]oxazin-2-yl)-2-methylpropanoic acid | 558 (M + H)+ |
| 46E | 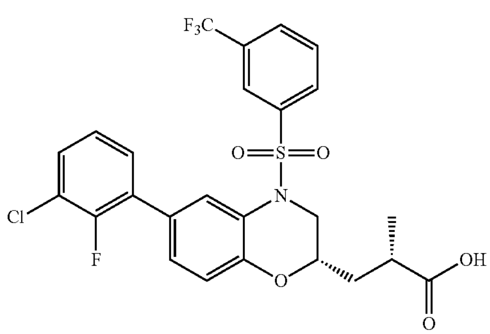 [SMILES: C[C@@H](C[C@H]1CN(S(=O)(=O)c2cccc(C(F)(F)F)c2)c2cc(-c3cccc(Cl)c3F)ccc2O1)C(=O)O] | (S)-3-((S)-6-(3-chloro-2-fluorophenyl)-4-((3-(trifluoromethyl)phenyl)sulfonyl)-3,4-dihydro-2H-benzo[b][1,4]oxazin-2-yl)-2-methylpropanoic acid | 558 (M + H)+ |

TABLE 15A-continued

| Compd No. | Structure | Name | Observed m/z |
|---|---|---|---|
| 46F | 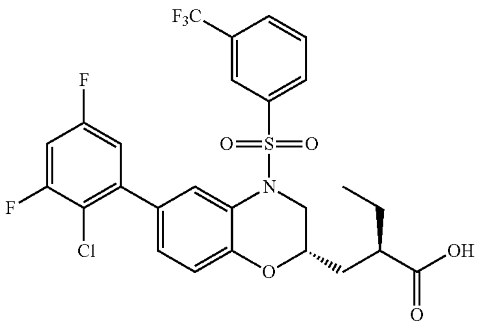 [SMILES: CC[C@H](C[C@H]1CN(S(=O)(=O)c2cccc(C(F)(F)F)c2)c2cc(-c3cc(F)cc(F)c3Cl)ccc2O1)C(=O)O] | (R)-2-(((S)-6-(2-chloro-3,5-difluorophenyl)-4-((3-(trifluoromethyl)phenyl)sulfonyl)-3,4-dihydro-2H-benzo[b][1,4]oxazin-2-yl)methyl)butanoic acid | 607 (M + NH$_4$)$^+$ |
| 46G | 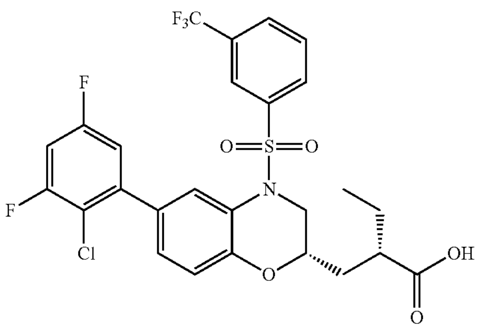 [SMILES: CC[C@@H](C[C@H]1CN(S(=O)(=O)c2cccc(C(F)(F)F)c2)c2cc(-c3cc(F)cc(F)c3Cl)ccc2O1)C(=O)O] | (S)-2-(((S)-6-(2-chloro-3,5-difluorophenyl)-4-((3-(trifluoromethyl)phenyl)sulfonyl)-3,4-dihydro-2H-benzo[b][1,4]oxazin-2-yl)methyl)butanoic acid | 612 (M + Na)$^+$ |
| 46H | 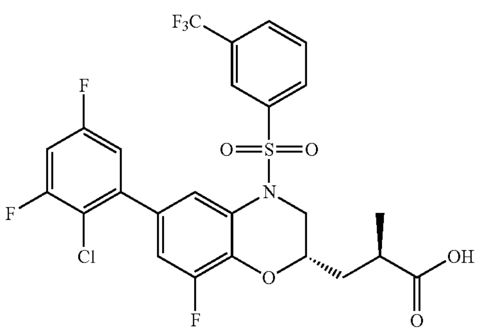 [SMILES: C[C@H](C[C@H]1CN(S(=O)(=O)c2cccc(C(F)(F)F)c2)c2cc(-c3cc(F)cc(F)c3Cl)cc(F)c2O1)C(=O)O] | (R)-3-((S)-6-(2-chloro-3,5-difluorophenyl)-8-fluoro-4-((3-(trifluoromethyl)phenyl)sulfonyl)-3,4-dihydro-2H-benzo[b][1,4]-oxazin-2-yl)-2-methylpropanoic acid | 616 (M + Na)$^+$ |
| 46I | 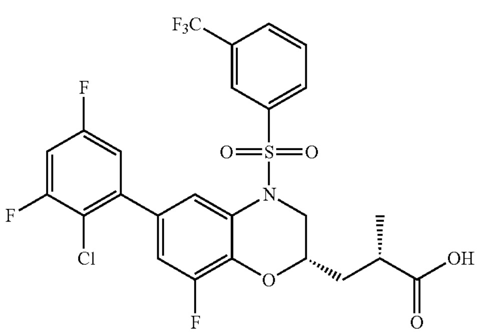 [SMILES: C[C@@H](C[C@H]1CN(S(=O)(=O)c2cccc(C(F)(F)F)c2)c2cc(-c3cc(F)cc(F)c3Cl)cc(F)c2O1)C(=O)O] | (S)-3-((S)-6-(2-chloro-3,5-difluorophenyl)-8-fluoro-4-((3-(trifluoromethyl)phenyl)sulfonyl)-3,4-dihydro-2H-benzo[b][1,4]-oxazin-2-yl)-2-methylpropanoic acid | 616 (M + Na)$^+$ |

TABLE 15A-continued

| Compd No. | Structure | Name | Observed m/z |
|---|---|---|---|
| 46J | 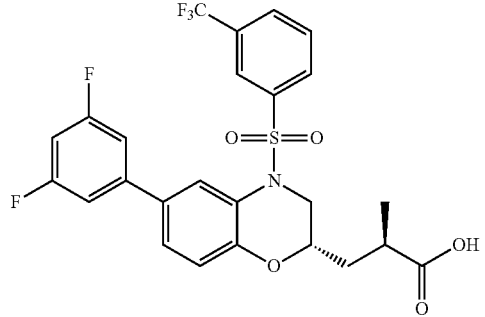 [SMILES: C[C@H](C[C@H]1CN(S(=O)(=O)c2cccc(C(F)(F)F)c2)c2cc(-c3cc(F)cc(F)c3)ccc2O1)C(=O)O] | (R)-3-((S)-6-(3,5-difluorophenyl)-4-((3-(trifluoromethyl)phenyl)-sulfonyl)-3,4-dihydro-2H-benzo[b][1,4]oxazin-2-yl)-2-methylpropanoic acid | 540 (M − H)− |
| 46K | 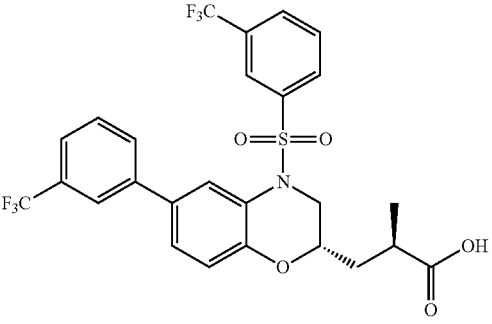 | (R)-2-methyl-3-((S)-6-(3-(trifluoromethyl)phenyl)-4-((3-(trifluoromethyl)phenyl)sulfonyl)-3,4-dihydro-2H-benzo[b][1,4]-oxazin-2-yl)propanoic acid | 572 (M − H)− |
| 46L | 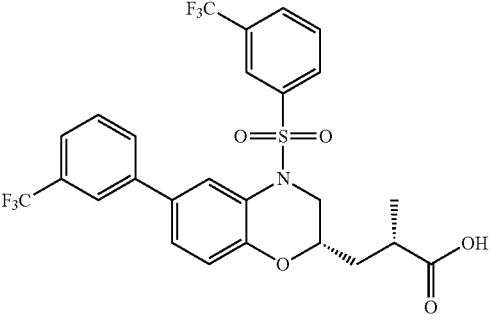 [SMILES: C[C@@H](C[C@H]1CN(S(=O)(=O)c2cccc(C(F)(F)F)c2)c2cc(-c3cccc(C(F)(F)F)c3)ccc2O1)C(=O)O] | (S)-2-methyl-3-((S)-6-(3-(trifluoromethyl)phenyl)-4-((3-(trifluoromethyl)phenyl)sulfonyl)-3,4-dihydro-2H-benzo[b][1,4]-oxazin-2-yl)propanoic acid | 572 (M + H)− |
| 46M | 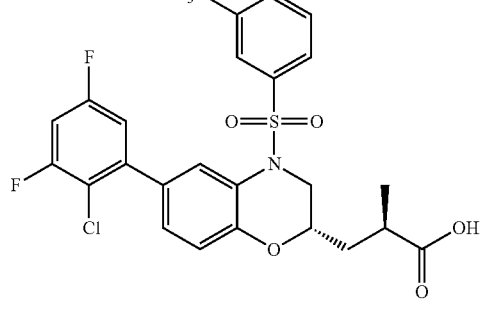 | (R)-3-((S)-6-(2-chloro-3,5-difluorophenyl)-4-((3-(trifluoromethyl)phenyl)sulfonyl)-3,4-dihydro-2H-benzo[b][1,4]oxazin-2-yl)-2-methylpropanoic acid | 576 (M + H)+ |

TABLE 15A-continued

| Compd No. | Structure | Name | Observed m/z |
|---|---|---|---|
| 46N | 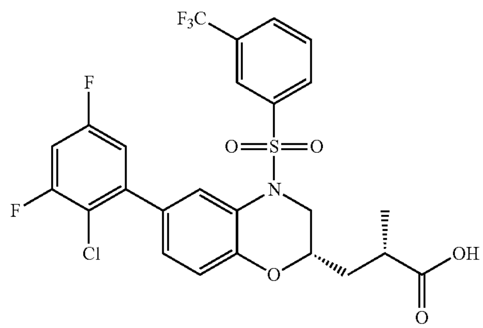 [SMILES: C[C@@H](C[C@H]1CN(S(=O)(=O)c2cccc(C(F)(F)F)c2)c2cc(-c3cc(F)cc(F)c3Cl)ccc2O1)C(=O)O] | (S)-3-((S)-6-(2-chloro-3,5-difluorophenyl)-4-((3-(trifluoromethyl)phenyl)sulfonyl)-3,4-dihydro-2H-benzo[b][1,4]oxazin-2-yl)-2-methylpropanoic acid | 576 (M + H)+ |
| 46O | 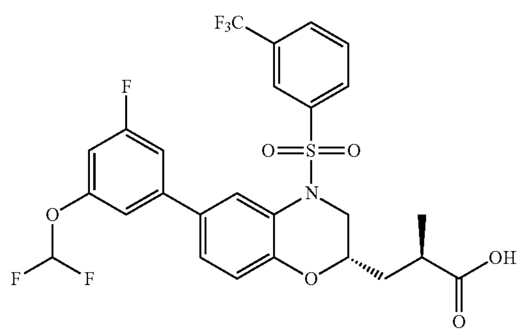 [SMILES: C[C@H](C[C@H]1CN(S(=O)(=O)c2cccc(C(F)(F)F)c2)c2cc(-c3cc(F)cc(OC(F)F)c3)ccc2O1)C(=O)O] | (R)-3-((S)-6-(3-(difluoromethoxy)-5-fluorophenyl)-4-((3-(trifluoromethyl)phenyl)sulfonyl)-3,4-dihydro-2H-benzo[b][1,4]-oxazin-2-yl)-2-methylpropanoic acid | 588 (M − H)− |
| 46P | 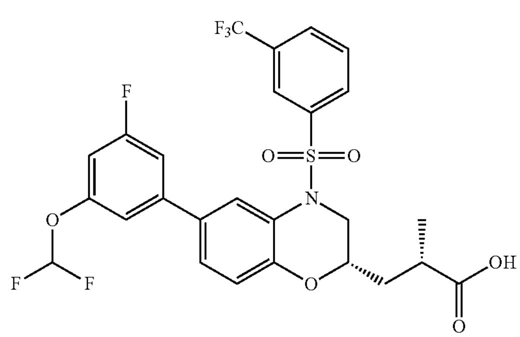 [SMILES: C[C@@H](C[C@H]1CN(S(=O)(=O)c2cccc(C(F)(F)F)c2)c2cc(-c3cc(F)cc(OC(F)F)c3)ccc2O1)C(=O)O] | (S)-3-((S)-6-(3-(difluoromethoxy)-5-fluorophenyl)-4-((3-(trifluoromethyl)phenyl)sulfonyl)-3,4-dihydro-2H-benzo[b][1,4]-oxazin-2-yl)-2-methylpropanoic acid | 588 (M − H)− |
| 46Q | 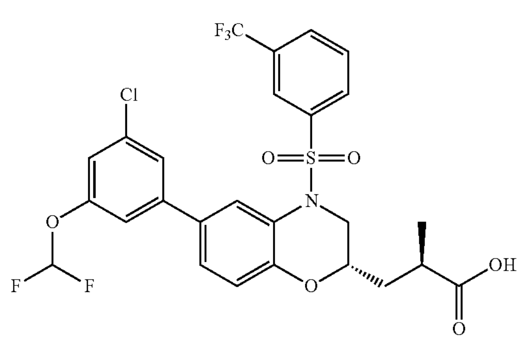 [SMILES: C[C@H](C[C@H]1CN(S(=O)(=O)c2cccc(C(F)(F)F)c2)c2cc(-c3cc(Cl)cc(OC(F)F)c3)ccc2O1)C(=O)O] | (R)-3-((S)-6-(3-chloro-5-(difluoromethoxy)phenyl)-4-((3-(trifluoromethyl)phenyl)sulfonyl)-3,4-dihydro-2H-benzo[b][1,4]-oxazin-2-yl)-2-methylpropanoic acid | 606 (M + H)+ |

TABLE 15A-continued

| Compd No. | Structure | Name | Observed m/z |
|---|---|---|---|
| 46R | 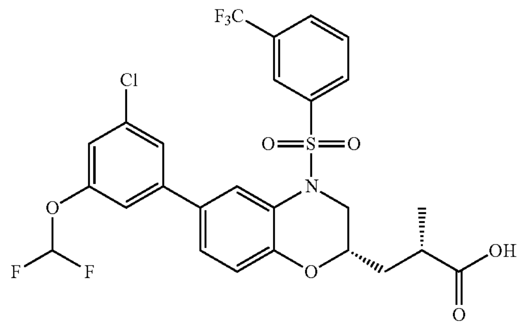 | (S)-3-((S)-6-(3-chloro-5-(difluoromethoxy)phenyl)-4-((3-(trifluoromethyl)phenyl)sulfonyl)-3,4-dihydro-2H-benzo[b][1,4]-oxazin-2-yl)-2-methylpropanoic acid | 604 (M − H)− |
| 46S | 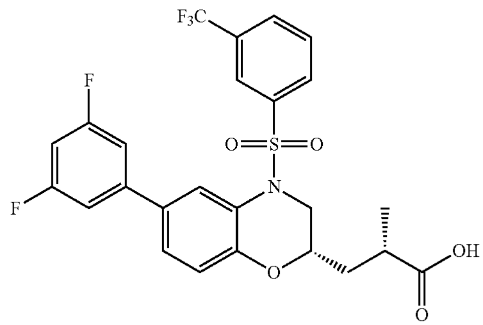 [SMILES: C[C@@H](C[C@H]1CN(S(=O)(=O)c2cccc(C(F)(F)F)c2)c2cc(-c3cc(F)cc(F)c3)ccc2O1)C(=O)O] | (S)-3-((S)-6-(3,5-difluorophenyl)-4-((3-(trifluoromethyl)phenyl)-sulfonyl)-3,4-dihydro-2H-benzo[b][1,4]oxazin-2-yl)-2-methylpropanoic acid | 542 (M + H)+ |
| 46T | 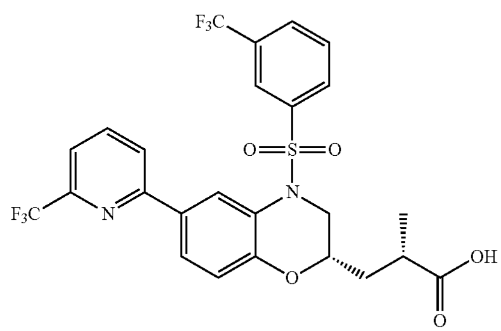 [SMILES: C[C@@H](C[C@H]1CN(S(=O)(=O)c2cccc(C(F)(F)F)c2)c2cc(-c3cccc(C(F)(F)F)n3)ccc2O1)C(=O)O] | (S)-2-methyl-3-((S)-4-((3-(trifluoromethyl)phenyl)sulfonyl)-6-(6-(trifluoromethyl)pyridin-2-yl)-3,4-dihydro-2H-benzo[b][1,4]-oxazin-2-yl)propanoic acid | 575 (M + H)+ |
| 46U | 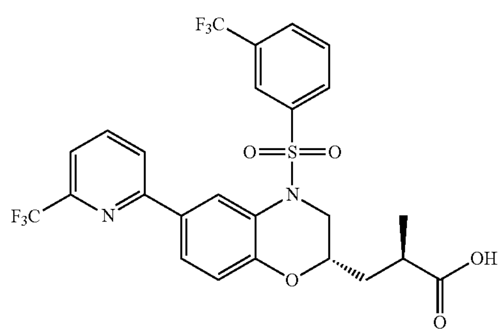 [SMILES: C[C@H](C[C@H]1CN(S(=O)(=O)c2cccc(C(F)(F)F)c2)c2cc(-c3cccc(C(F)(F)F)n3)ccc2O1)C(=O)O] | (R)-2-methyl-3-((S)-4-((3-(trifluoromethyl)phenyl)sulfonyl)-6-(6-(trifluoromethyl)pyridin-2-yl)-3,4-dihydro-2H-benzo[b][1,4]-oxazin-2-yl)propanoic acid | 575 (M + H)+ |

TABLE 15A-continued

| Compd No. | Structure | Name | Observed m/z |
|---|---|---|---|
| 46V | 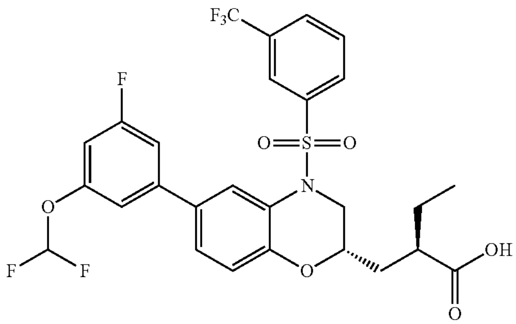 [SMILES: CC[C@H](C[C@H]1CN(S(=O)(=O)c2cccc(C(F)(F)F)c2)c2cc(-c3cc(F)cc(OC(F)F)c3)ccc2O1)C(=O)O] | (R)-2-(((S)-6-(3-(difluoromethoxy)-5-fluorophenyl)-4-((3-(trifluoromethyl)phenyl)sulfonyl)-3,4-dihydro-2H-benzo[b][1,4]oxazin-2-yl)methyl)butanoic acid | 604 (M + H)+ |

TABLE 15B

| Compd No. | Physical Characterization Data |
|---|---|
| 46D | $^1$H NMR (300 MHz, CD$_3$OD-d$_4$) δ 8.02 (s, 1H), 8.02-7.97 (m, 2H), 7.88 (s, 1H), 7.80 (m, 1H), 7.52-7.25 (m, 4H), 6.94 (d, 1H), 4.44 (dd, 1H), 3.50 (m, 1H), 3.31 (m, 1H), 2.69 (m, 1H), 1.94 (m, 1H), 1.62 (m, 1H), 1.59 (d, 3H). |
| 46E | $^1$H NMR (300 MHz, CD$_3$OD-d$_4$) δ 8.03 (s, 1H), 8.02-7.99 (m, 2H), 7.96 (s, 1H), 7.82 (m, 1H), 7.51-7.27 (m, 4H), 6.95 (d, 1H), 4.48 (dd, 1H), 3.49 (m, 1H), 3.31 (m, 1H), 2.63 (m, 1H), 1.98 (m, 1H), 1.66 (m, 1H), 1.10 (d, 3H). |
| 46F | $^1$H NMR (300 MHz, CD$_3$OD-d$_4$) δ 8.07-7.91 (m, 3H), 7.87-7.78 (m, 2H), 7.26-7.16 (m, 2H), 7.06 (ddd, J = 8.9, 2.9, 1.7 Hz, 1H), 6.95 (d, J = 8.5 Hz, 1H), 4.43 (dd, J = 14.3, 2.0 Hz, 1H), 3.39 (d, J = 10.3 Hz, 1H), 3.30-3.25 (m, 1H), 2.54 (d, J = 9.4 Hz, 1H), 1.90 (ddd, J = 14.1, 10.7, 3.3 Hz, 1H), 1.72-1.49 (m, 3H), 0.95 (t, J = 7.4 Hz, 3H). |
| 46G | $^1$H NMR (300 MHz, CD$_3$OD-d$_4$) δ 8.09-7.98 (m, 2H), 7.91 (dd, J = 11.8, 2.1 Hz, 2H), 7.82 (t, J = 7.9 Hz, 1H), 7.20 (tq, J = 6.2, 3.2 Hz, 2H), 7.05 (ddd, J = 8.9, 2.9, 1.7 Hz, 1H), 6.93 (d, J = 8.5 Hz, 1H), 4.48 (dd, J = 14.6, 2.4 Hz, 1H), 3.46 (dddd, J = 10.1, 7.7, 5.3, 2.4 Hz, 1H), 3.31-3.26 (m, 1H), 2.59-2.28 (m, 1H), 1.93 (dt, J = 14.1, 8.1 Hz, 1H), 1.72 (dt, J = 14.2, 5.6 Hz, 1H), 1.63-1.45 (m, 2H), 0.93 (t, J = 7.4 Hz, 3H). |
| 46H | $^1$H NMR (300 MHz, CD$_3$OD-d$_4$) δ 8.08-8.01 (m, 2H), 7.90 (s, 1H), 7.83 (t, J = 8.0 Hz, 1H), 7.74 (s, 1H), 7.24 (t, J = 10.2 Hz, 1H), 7.13-7.06 (m, 2H), 4.50 (d, J = 16.8 Hz, 1H), 3.51 (m, 1H), 3.39 (m, 1H), 2.79 (m, 1H), 1.95 (m, 1H), 1.64 (m, 1H), 1.21 (d, J = 7.2 Hz, 3H). |
| 46I | $^1$H NMR (300 MHz, CD$_3$OD-d$_4$) δ 8.05 (t, J = 9.2 Hz, 2H), 7.96 (s, 1H), 7.85 (t, J = 7.8 Hz, 1H), 7.74 (s, 1H), 7.24 (t, J = 10.2 Hz, 1H), 7.13-7.06 (m, 2H), 4.53 (d, J = 16.8 Hz, 1H), 3.51 (m, 1H), 3.39 (m, 1H), 2.79 (m, 1H), 2.02 (m, 1H), 1.70 (m, 1H), 1.12 (d, J = 7.6 Hz, 3H). |
| 46J | $^1$H NMR (300 MHz, CD$_3$OD-d$_4$) δ 8.07 (s, 1H), 7.99 (m 2H), 7.86 (s, 1H), 7.82 (m, 1H), 7.44 (m, 1H), 7.24-7.18 (m, 2H), 6.97-6.93 (m, 2H), 4.43 (dd, 1H), 3.41 (m, 1H), 3.32 (m, 1H), 2.67 (m, 1H), 1.90 (m, 1H), 1.61 (m, 1H), 1.19 (d, 3H). |
| 46K | $^1$H NMR (300 MHz, CD$_3$OD-d$_4$) δ 8.09 (s, 1H), 8.02-7.96 (m, 2H), 7.87-7.76 (m, 4H), 7.69-7.65 (m, 2H), 7.45 (m, 1H), 6.96 (d, 1H), 4.44 (dd, 1H), 3.45 (m, 1H), 3.29 (m, 1H), 2.68 (m, 1H), 1.92 (m, 1H), 1.62 (m, 1H), 1.18 (d, 3H). |
| 46L | $^1$H NMR (300 MHz, CD$_3$OD-d$_4$) δ 8.09 (s, 1H), 8.03-7.95 (m, 2H), 7.95 (s, 1H), 7.90-7.76 (m, 3H), 7.69-7.65 (m, 2H), 7.45 (m, 1H), 6.96 (d, 1H), 4.46 (dd, 1H), 3.46 (m, 1H), 3.30 (m, 1H), 2.65 (m, 1H), 1.96 (m, 1H), 1.65 (m, 1H), 1.09 (d, 3H). |
| 46M | $^1$H NMR (300 MHz, CD$_3$OD-d$_4$) δ 8.05-8.00 (m, 2H), 7.91-7.79 (m, 3H), 7.29 (m, 1H), 7.04 (s, 1H), 7.02 (m, 1H), 4.45 (dd, 1H), 3.51 (m, 1H), 3.28 (m, 1H), 2.68 (m, 1H), 1.93 (m, 1H), 1.61 (m, 1H), 1.18 (d, 3H). |
| 46N | $^1$H NMR (300 MHz, CD$_3$OD-d$_4$) δ 8.05-7.99 (m, 2H), 7.90-7.74 (m, 3H), 7.30 (m, 1H), 7.02 (s, 1H), 7.00 (m, 1H), 4.47 (dd, 1H), 3.50 (m, 1H), 3.30 (m, 1H), 2.63 (m, 1H), 1.96 (m, 1H), 1.66 (m, 1H), 1.10 (d, 3H). |
| 46O | $^1$H NMR (300 MHz, CD$_3$OD-d$_4$) δ 8.03 (d, J = 2.2 Hz, 1H), 7.99-7.93 (m, 2H), 7.84 (d, J = 1.9 Hz, 1H), 7.77 (t, J = 7.9 Hz, 1H), 7.41 (dd, J = 8.6, 2.2 Hz, 1H), 7.24-7.16 (m, 2H), 7.15-6.75 (m, 3H), 4.39 (dd, J = 14.5, 2.4 Hz, 1H), 3.41 (tt, J = 8.8, 3.1 Hz, 1H), 3.28-3.20 (m, 1H), 2.73-2.59 (m, 1H), 1.88 (ddd, J = 13.9, 10.0, 3.5 Hz, 1H), 1.57 (ddd, J = 14.2, 8.8, 4.1 Hz, 1H), 1.16 (d, J = 7.1 Hz, 3H). |
| 46P | $^1$H NMR (300 MHz, CD$_3$OD-d$_4$) δ 8.03 (s, 1H), 8.00-7.92 (m, 3H), 7.78 (t, 1H), 7.41 (dd, 1H), 7.22 (m, 2H), 6.93 (t, 1H), 6.92 (d, 1H), 4.43 (m, 1H), 3.41 (m, 1H), 3.28 (m, 1H), 2.61 (m, 1H), 1.93 (m, 1H), 1.63 (m, 1H). |
| 46Q | $^1$H NMR (300 MHz, CD$_3$OD-d$_4$) δ 8.01 (d, J = 2.2 Hz, 1H), 7.99-7.93 (m, 2H), 7.84 (d, J = 2.0 Hz, 1H), 7.77 (t, J = 7.9 Hz, 1H), 7.45 (t, J = 1.7 Hz, 1H), 7.40 (dd, J = 8.6, 2.3 Hz, 1H), 7.27 (t, J = 1.8 Hz, 1H), 7.18 (t, J = 2.0 Hz, 1H), 7.15-6.74 (m, 2H), 4.39 (dd, J = 14.6, 2.3 Hz, 1H), 3.47-3.36 (m, 1H), 3.27-3.17 (m, 1H), 2.66 (ddd, J = 10.9, 7.2, 4.1 Hz, 1H), 1.88 (ddd, J = 13.9, 10.0, 3.5 Hz, 1H), 1.57 (ddd, J = 14.1, 8.8, 4.0 Hz, 1H), 1.16 (d, J = 7.1 Hz, 3H). |

TABLE 15B-continued

| Compd No. | Physical Characterization Data |
|---|---|
| 46R | $^1$H NMR (300 MHz, CD$_3$OD-d$_4$) δ 8.04-7.90 (m, 4H), 7.78 (t, J = 7.9 Hz, 1H), 7.45 (t, J = 1.7 Hz, 1H), 7.40 (dd, J = 8.6, 2.3 Hz, 1H), 7.27 (t, J = 1.8 Hz, 1H), 7.20-7.12 (m, 1H), 6.99-6.73 (m, 2H), 4.43 (dd, J = 14.5, 2.4 Hz, 1H), 3.42 (dddd, J = 10.6, 8.7, 4.5, 2.4 Hz, 1H), 3.30-3.19 (m, 1H), 2.60 (h, J = 7.1 Hz, 1H), 1.93 (ddd, J = 14.1, 8.5, 6.8 Hz, 1H), 1.61 (ddd, J = 14.1, 7.5, 4.5 Hz, 1H), 1.06 (d, J = 7.0 Hz, 3H). |
| 46S | $^1$H NMR (300 MHz, CD$_3$OD-d$_4$) δ 8.07 (s, 1H), 8.02-7.94 (m, 3H), 7.80 (m, 1H), 7.43 (dd, 1H), 7.22 (d, 1H), 6.97-6.92 (m, 2H), 4.46 (dd, 1H), 3.42 (m, 1H), 3.30 (m, 1H), 2.64 (m, 1H), 1.95 (m, 1H), 1.65 (m, 1H), 1.07 (d, 3H). |
| 46T | $^1$H NMR (300 MHz, CD$_3$OD-d$_4$) δ 8.58 (d, J = 2.1 Hz, 1H), 8.10-7.93 (m, 5H), 7.86 (dd, J = 8.6, 2.2 Hz, 1H), 7.76 (t, J = 7.9 Hz, 1H), 7.68 (p, J = 4.6 Hz, 1H), 6.95 (d, J = 8.6 Hz, 1H), 4.45 (dd, J = 14.3, 2.4 Hz, 1H), 3.57 (s, 1H), 3.40-3.33 (m, 1H), 2.63 (q, J = 7.1 Hz, 1H), 2.03-1.90 (m, 1H), 1.65 (ddd, J = 14.1, 7.4, 4.5 Hz, 1H), 1.09 (d, J = 6.9 Hz, 3H). |
| 46U | $^1$H NMR (300 MHz, CD$_3$OD-d$_4$) δ 8.58 (d, J = 2.1 Hz, 1H), 8.09-8.01 (m, 3H), 7.94 (d, J = 7.5 Hz, 2H), 7.86 (dd, J = 8.6, 2.2 Hz, 1H), 7.76 (t, J = 7.9 Hz, 1H), 7.68 (dd, J = 4.8, 3.7 Hz, 1H), 6.95 (d, J = 8.6 Hz, 1H), 4.41 (dd, J = 14.4, 2.4 Hz, 1H), 3.56 (ddt, J = 11.3, 6.1, 3.0 Hz, 1H), 3.34 (d, J = 9.7 Hz, 1H), 2.69 (dqd, J = 11.2, 7.1, 4.0 Hz, 1H), 2.01-1.85 (m, 1H), 1.61 (ddd, J = 14.2, 8.9, 4.1 Hz, 1H), 1.18 (d, J = 7.1 Hz, 3H). |
| 46V | $^1$H NMR (300 MHz, CD$_3$OD-d$_4$) δ 8.09-7.90 (m, 4H), 7.81 (t, J = 7.9 Hz, 1H), 7.43 (dd, J = 8.5, 2.3 Hz, 1H), 7.26-7.16 (m, 2H), 7.01-6.91 (m, 2H), 6.80 (s, 0H), 4.46 (dd, J = 14.5, 2.3 Hz, 1H), 3.46 (s, 1H), 3.29 (d, J = 10.1 Hz, 1H), 2.43 (s, 1H), 1.93 (dd, J = 14.3, 7.8 Hz, 1H), 1.77-1.66 (m, 1H), 1.60-1.45 (m, 2H), 0.93 (t, J = 7.4 Hz, 3H). |

Example 47—Synthesis of (S)-(3-((6-(2,5-difluorophenyl)-4-((3-(trifluoromethyl)phenyl)sulfonyl)-3,4-dihydro-2H-benzo[b][1,4]oxazin-2-yl)methyl)oxetan-3-yl)methanol

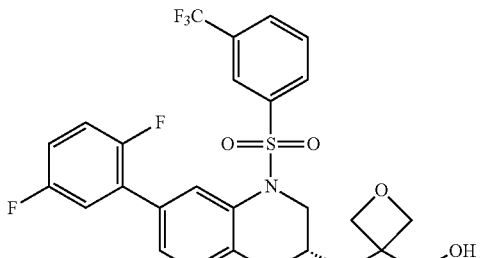

Part I—Synthesis of dimethyl (S)-2-((6-bromo-4-((3-(trifluoromethyl)phenyl)sulfonyl)-3,4-dihydro-2H-benzo[b][1,4]oxazin-2-yl)methyl)malonate

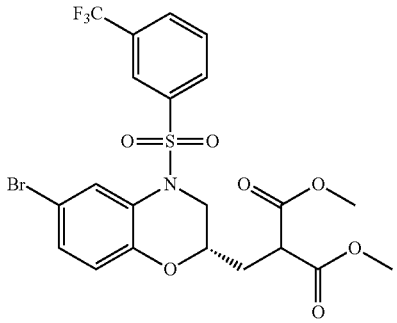

A solution of 1M LiHMDS (88.8 mL, 88.8 mmol) was added dropwise to a stirred solution of (S)-methyl 3-(6-bromo-4-((3-(trifluoromethyl)phenyl)sulfonyl)-3,4-dihydro-2H-benzo[b][1,4]oxazin-2-yl)propanoate (3 g, 5.90 mmol) in tetrahydrofuran (30 mL) at −65° C. The mixture was stirred for an hour, and then dimethylcarbonate (10.65 g, 118 mmol) was added dropwise with stirring at −65° C. The mixture was warmed to room temperature and stirred for two hours. The reaction was quenched by the addition of saturated ammonium chloride (30 mL), and was extracted three times with dichloromethane. The combined organic layers were dried (Na$_2$SO$_4$), filtered and concentrated. The residue was purified via MPLC eluting with 12% ethyl acetate in petroleum ether to afford dimethyl (S)-2-((6-bromo-4-((3-(trifluoromethyl)phenyl)sulfonyl)-3,4-dihydro-2H-benzo[b][1,4]oxazin-2-yl)methyl)malonate (3.0 g, 90%) as a solid.

Part II—Synthesis of dimethyl (S)-2-((6-bromo-4-((3-(trifluoromethyl)phenyl)sulfonyl)-3,4-dihydro-2H-benzo[b][1,4]oxazin-2-yl)methyl)-2-(hydroxymethyl)malonate

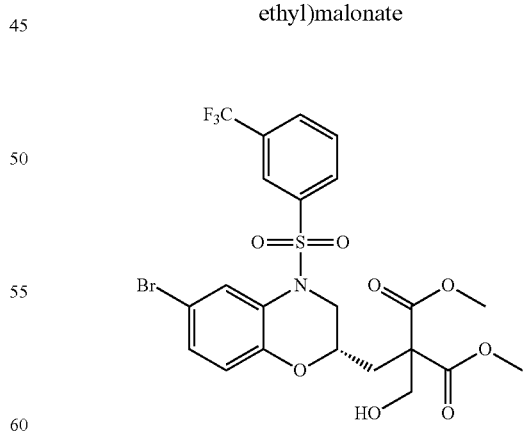

A mixture of dimethyl (S)-2-((6-bromo-4-((3-(trifluoromethyl)phenyl)sulfonyl)-3,4-dihydro-2H-benzo[b][1,4] oxazin-2-yl)methyl)malonate (3.0 g, 5.30 mmol), acetonitrile (30 mL), water (15 mL), sodium bicarbonate (446 mg, 5.31 mmol), 37% aqueous formaldehyde (3 mL) was stirred overnight at room temperature. The mixture was concentrated to remove volatile organic components and the solution was extracted three times with dichloromethane. The combined, dried (Na$_2$SO$_4$), and concentrated. The residue was purified via MPLC eluting with 16% ethyl acetate in petroleum ether to afford dimethyl (S)-2-((6-bromo-4-((3-(trifluoromethyl)phenyl)sulfonyl)-3,4-dihydro-2H-benzo[b][1,4]oxazin-2-yl)methyl)-2-(hydroxymethyl)malonate (2.7 g, 85%) as a yellow solid.

Part III—Synthesis of (S)-2-((6-bromo-4-((3-(trifluoromethyl)phenyl)sulfonyl)-3,4-dihydro-2H-benzo[b][1,4]oxazin-2-yl)methyl)-2-(hydroxymethyl)propane-1,3-diol

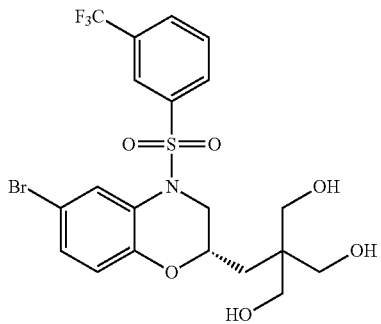 [SMILES: O=S(=O)(c1cccc(C(F)(F)F)c1)N1C[C@H](CC(CO)(CO)CO)Oc2ccc(Br)cc21]

Lithium borohydride (325.4 mg, 14.79 mmol) was added with stirring to a solution of dimethyl (S)-2-((6-bromo-4-((3-(trifluoromethyl)phenyl)sulfonyl)-3,4-dihydro-2H-benzo[b][1,4]oxazin-2-yl)methyl)-2-(hydroxymethyl)malonate (2.2 g, 3.69 mmol) in tetrahydrofuran (40 mL) at 0° C. The mixture was warmed and was stirred for three hours at room temperature. Methanol (1 mL) was added to quench the hydride, and the mixture was concentrated. The residue was diluted with water, and extracted three times with dichloromethane. The combined organic layers were dried (Na$_2$SO$_4$) and concentrated. The residue was purified via MPLC eluting with 10% methanol in dichloromethane to afford (S)-2-((6-bromo-4-((3-(trifluoromethyl)phenyl)sulfonyl)-3,4-dihydro-2H-benzo[b][1,4]oxazin-2-yl)methyl)-2-(hydroxymethyl)propane-1,3-diol (1.1 g, 55%) as a white solid.

Part IV—Synthesis of (S)-3-(6-bromo-4-((3-(trifluoromethyl)phenyl)sulfonyl)-3,4-dihydro-2H-benzo[b][1,4]oxazin-2-yl)-2,2-bis(hydroxymethyl)propyl 4-methylbenzenesulfonate

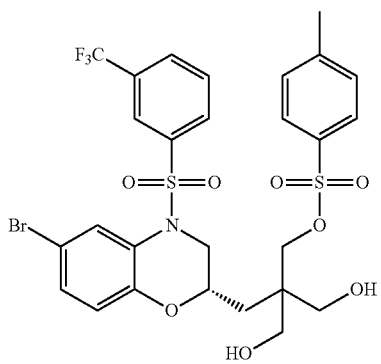 [SMILES: Cc1ccc(S(=O)(=O)OCC(CO)(CO)C[C@H]2CN(S(=O)(=O)c3cccc(C(F)(F)F)c3)c3cc(Br)ccc3O2)cc1]

A solution of para-toluenesulfonyl chloride (1.13 g, 5.93 mmol) in dichloromethane (2 mL) was added dropwise to a stirred solution of (S)-2-((6-bromo-4-((3-(trifluoromethyl)phenyl)sulfonyl)-3,4-dihydro-2H-benzo[b][1,4]oxazin-2-yl)methyl)-2-(hydroxymethyl)propane-1,3-diol (800 mg, 1.48 mmol), dichloromethane (10 mL), and triethylamine (600 mg, 5.93 mmol) at 0° C. The mixture was stirred overnight at room temperature. Methanol (1 mL) was added and the mixture was concentrated. The residue was purified via MPLC eluting with 5% methanol in dichloromethane/methanol to afford (S)-3-(6-bromo-4-((3-(trifluoromethyl)phenyl)sulfonyl)-3,4-dihydro-2H-benzo[b][1,4]oxazin-2-yl)-2,2-bis(hydroxymethyl)propyl 4-methylbenzenesulfonate (400 mg, 39%) as a yellow oil.

Part V—Synthesis of (S)-(3-((6-bromo-4-((3-(trifluoromethyl)phenyl)sulfonyl)-3,4-dihydro-2H-benzo[b][1,4]oxazin-2-yl)methyl)oxetan-3-yl)methanol

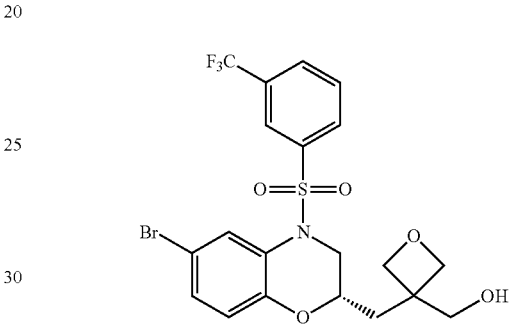

Sodium hydride (231 mg, 9.62 mmol) was added in portions to a solution of (S)-3-(6-bromo-4-((3-(trifluoromethyl)phenyl)sulfonyl)-3,4-dihydro-2H-benzo[b][1,4]oxazin-2-yl)-2,2-bis(hydroxymethyl)propyl 4-methylbenzenesulfonate (1 g, 1.44 mmol) in tetrahydrofuran (10 mL) at 0° C. The mixture was stirred overnight at room temperature, and quenched by the addition of saturated ammonium chloride (10 mL). The mixture was extracted twice with dichloromethane. The combined organic layers were dried (Na$_2$SO$_4$) and concentrated. The residue was purified via MPLC eluting with 5% methanol in dichloromethane to afford (S)-(3-((6-bromo-4-((3-(trifluoromethyl)phenyl)sulfonyl)-3,4-dihydro-2H-benzo[b][1,4]oxazin-2-yl)methyl)oxetan-3-yl)methanol (540 mg, 72%) as a yellow oil.

Part VI—Synthesis of (S)-(3-((6-(2,5-difluorophenyl)-4-((3-(trifluoromethyl)phenyl-sulfonyl)-3,4-dihydro-2H-benzo[b][1,4]oxazin-2-yl)methyl)oxetan-3-yl)methanol

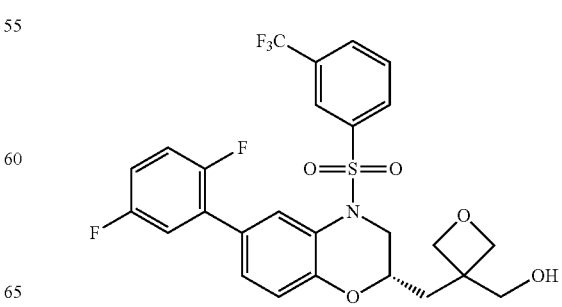

A mixture of (S)-(3-((6-bromo-4-((3-(trifluoromethyl)phenyl)sulfonyl)-3,4-dihydro-2H-benzo[b][1,4]oxazin-2-yl)methyl)oxetan-3-yl)methanol (100 mg, 0.19 mmol), sodium carbonate (61 mg, 0.58 mmol), toluene (1.5 mL), ethanol (0.5 mL), water (0.5 mL), (2,5-difluorophenyl)boronic acid (45.5 mg, 0.29 mmol), and tetrakis(triphenylphosphine)palladium (11.1 mg, 0.01 mmol) was stirred overnight at 90° C. The resulting mixture was concentrated, and the residue was purified by MPLC eluting with 50% ethyl acetate in petroleum ether to afford (S)-(3-((6-(2,5-difluorophenyl)-4-((3-(trifluoromethyl)phenyl)-sulfonyl)-3,4-dihydro-2H-benzo[b][1,4]oxazin-2-yl)methyl)oxetan-3-yl)methanol (80 mg, 75%) as a yellow oil.

Example 48—Synthesis of (S)-3-((6-(2,5-difluorophenyl)-4-((3-(trifluoromethyl)phenyl)-sulfonyl)-3,4-dihydro-2H-benzo[b][1,4]oxazin-2-yl)methyl)oxetane-3-carboxylicacid

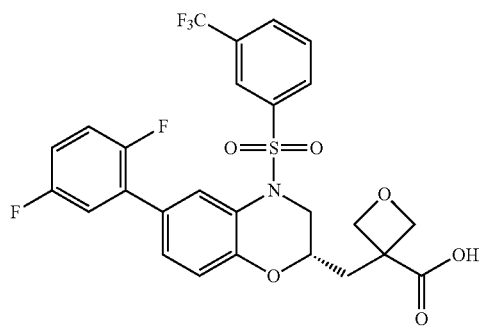 [SMILES: O=C(O)C1(C[C@H]2CN(S(=O)(=O)c3cccc(C(F)(F)F)c3)c3cc(-c4cc(F)ccc4F)ccc3O2)COC1]

A mixture of (S)-(3-((6-(2,5-difluorophenyl)-4-((3-(trifluoromethyl)phenyl)-sulfonyl)-3,4-dihydro-2H-benzo[b][1,4]oxazin-2-yl)methyl)oxetan-3-yl)methanol (100 mg, 0.18 mmol), 2,2,6,6-tetramethyl-1-piperidinyloxy (3.9 mg, 0.02 mmol), acetonitrile (2 mL), water (0.5 mL), NaClO (10.7 mg, 0.14 mmol), NaClO$_2$ (64.9 mg, 0.72 mmol) was stirred for two hours at room temperature. The mixture was concentrated to remove volatile organic solvent and the aqueous mixture was extracted twice with dichloromethane. The combined organic layers were dried (Na$_2$SO$_4$) and concentrated. The residue was purified by Prep-HPLC eluting with a gradient of 48-72% acetonitrile in water with 0.05% trifluoroacetic acid to afford (S)-3-((6-(2,5-difluorophenyl)-4-((3-(trifluoromethyl)phenyl)-sulfonyl)-3,4-dihydro-2H-benzo[b][1,4]oxazin-2-yl)methyl)oxetane-3-carboxylic acid (42.2 mg, 41%) as a white solid. $^1$H-NMR (400 MHz, CD$_3$OD) δ 8.05-7.93 (m, 3H), 7.89 (s, 1H), 7.77 (t, J=7.9 Hz, 1H), 7.32-7.16 (m, 3H), 7.10 (ddt, J=7.7, 5.4, 3.5 Hz, 1H), 6.85 (d, J=8.6 Hz, 1H), 4.91 (d, J=6.2 Hz, 1H), 4.82 (d, J=6.1 Hz, 1H), 4.58 (d, J=6.3 Hz, 1H), 4.49 (d, J=6.1 Hz, 1H), 4.43 (dd, J=14.5, 2.5 Hz, 1H), 3.54 (dddd, J=10.2, 7.5, 4.6, 2.4 Hz, 1H), 3.36 (dd, J=14.5, 9.8 Hz, 1H), 2.35-2.22 (m, 2H). (ES, m/z): (M−H)$^-$ 567.95.

Example 49—Synthesis of (S)-(3-((6-(3-(difluoromethoxy)-5-fluorophenyl)-4-((3-(trifluoromethyl)phenyl)sulfonyl)-3,4-dihydro-2H-benzo[b][1,4]oxazin-2-yl)methyl)oxetan-3-yl)methanol

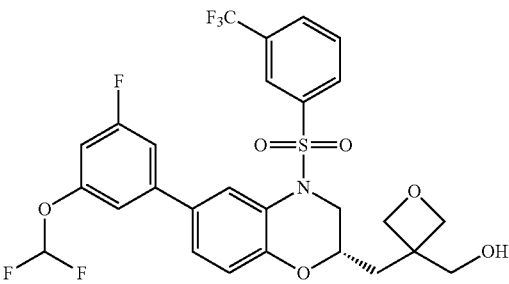 [SMILES: O=S(=O)(c1cccc(C(F)(F)F)c1)N1C[C@H](CC2(CO)COC2)Oc2ccc(-c3cc(F)cc(OC(F)F)c3)cc21]

Part I—Synthesis of (S)-(3-((6-(4,4,5,5-tetramethyl-1,3,2-dioxaborolan-2-yl)-4-((3-(trifluoromethyl)phenyl)sulfonyl)-3,4-dihydro-2H-benzo[b][1,4]oxazin-2-yl)methyl)oxetan-3-yl)methanol

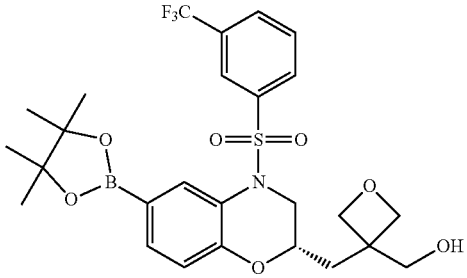 [SMILES: CC1(C)OB(c2ccc3c(c2)N(S(=O)(=O)c2cccc(C(F)(F)F)c2)C[C@H](CC2(CO)COC2)O3)OC1(C)C]

A mixture of placed (S)-(3-((6-bromo-4-((3-(trifluoromethyl)phenyl)sulfonyl)-3,4-dihydro-2H-benzo[b][1,4]oxazin-2-yl)methyl)oxetan-3-yl)methanol (400 mg, 0.77 mmol), potassium acetate (301 mg, 3.07 mmol), ethylene glycol dimethyl ether (4 mL), 4,4,5,5-tetramethyl-2-(tetramethyl-1,3,2-dioxaborolan-2-yl)-1,3,2-dioxaborolane (390 mg, 1.54 mmol), and [1,1'-bis(diphenylphosphino)ferrocene] dichloropalladium (II) complex with dichloromethane (56.2 mg, 0.08 mmol) was stirred for two hours at 80° C. The mixture was concentrated, and the residue was purified via MPLC eluting with 50% ethyl acetate in petroleum ether to afford (S)-(3-((6-(4,4,5,5-tetramethyl-1,3,2-dioxaborolan-2-yl)-4-((3-(trifluoromethyl)phenyl)sulfonyl)-3,4-dihydro-2H-benzo[b][1,4]oxazin-2-yl)methyl)oxetan-3-yl)methanol (400 mg, 92%) as a brown oil.

Part II—Synthesis of (S-(3-((6-(3-(difluoromethoxy)-5-fluorophenyl)-4-((3-(trifluoromethyl)phenyl)sulfonyl)-3,4-dihydro-2H-benzo[b][1,4]oxazin-2-yl)methyl)oxetan-3-yl)methanol

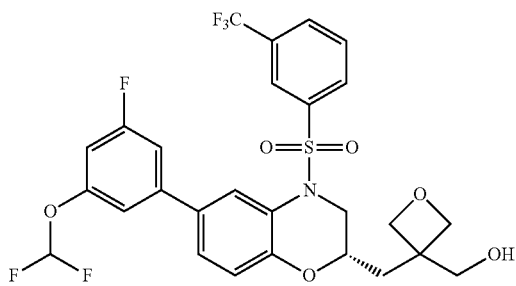 [SMILES: O=S(=O)(c1cccc(C(F)(F)F)c1)N1C[C@H](CC2(CO)COC2)Oc2ccc(-c3cc(F)cc(OC(F)F)c3)cc21]

A mixture of (S)-(3-((6-(4,4,5,5-tetramethyl-1,3,2-dioxaborolan-2-yl)-4-((3-(trifluoromethyl)phenyl)sulfonyl)-3,4-dihydro-2H-benzo[b][1,4]oxazin-2-yl)methyl)oxetan-3-yl)methanol (150 mg, 0.26 mmol), 1-bromo-3-(difluoromethoxy)-5-fluorobenzene (95 mg, 0.39 mmol), sodium carbonate (83.8 mg, 0.79 mmol), toluene (1.5 mL), ethanol (0.5 mL), water (0.5 mL), and tetrakis(triphenylphosphine)palladium (15.2 mg, 0.01 mmol) was stirred for two hours at 90° C. The mixture was concentrated and the residue was purified by Prep-HPLC eluting with a gradient of 50-80% acetonitrile in water with 0.05% trifluoroacetic acid to afford (S)-(3-((6-(3-(difluoromethoxy)-5-fluorophenyl)-4-((3-(trifluoromethyl)phenyl)sulfonyl)-3,4-dihydro-2H-benzo[b][1,4]oxazin-2-yl)methyl)oxetan-3-yl)methanol as a white solid. $^{1}$H-NMR (400 MHz, CD$_{3}$OD) δ 8.10-7.93 (m, 4H), 7.80 (t, J=7.9 Hz, 1H), 7.42 (dd, J=8.6, 2.3 Hz, 1H), 7.26-7.18 (m, 2H), 7.17-6.78 (m, 3H), 4.72-4.31 (m, 5H), 3.82 (d, J=11.2 Hz, 1H), 3.72-3.35 (m, 3H), 2.11-1.90 (m, 2H). (ES, m/z): (M+H)$^{+}$ 602.

Example 50—Synthesis of (S)-3-((6-(3-(difluoromethoxy)-5-fluorophenyl)-4-((3-(trifluoromethyl)phenyl)sulfonyl)-3,4-dihydro-2H-benzo[b][1,4]oxazin-2-yl)methyl)oxetane-3-carboxylic acid

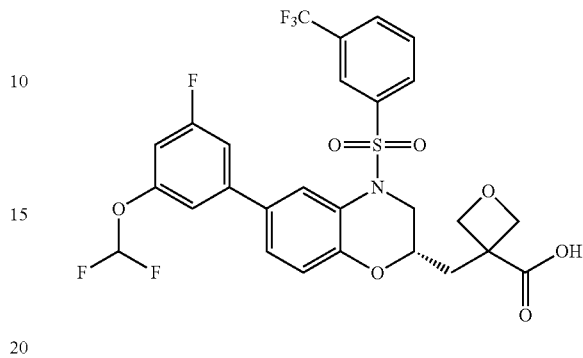

A mixture of (S)-(3-((6-(3-(difluoromethoxy)-5-fluorophenyl)-4-((3-(trifluoromethyl)phenyl)sulfonyl)-3,4-dihydro-2H-benzo[b][1,4]oxazin-2-yl)methyl)oxetan-3-yl)methanol (80 mg, 0.13 mmol), 2,2,6,6-tetramethyl-1-piperidinyloxy (2.9 mg, 0.02 mmol), acetonitrile (4 mL), water (1 mL), NaClO (7.9 mg, 0.11 mmol), NaClO$_{2}$ (48 mg, 0.53 mmol) was stirred overnight at room temperature. The mixture was concentrated to remove volatile organic solvent and the aqueous mixture was extracted twice with dichloromethane. The combined organic layers were dried (Na$_{2}$SO$_{4}$) and concentrated. The residue was purified by Prep-HPLC eluting 64% acetonitrile in water with 0.05% trifluoroacetic acid to afford (S)-3-((6-(3-(difluoromethoxy)-5-fluorophenyl)-4-((3-(trifluoromethyl)phenyl)sulfonyl)-3,4-dihydro-2H-benzo[b][1,4]oxazin-2-yl)methyl)oxetane-3-carboxylic acid (13.6 mg, 17%) as a white solid. $^{1}$H-NMR (400 MHz, CD$_{3}$OD) δ 8.08-7.95 (m, 3H), 7.89 (s, 1H), 7.78 (t, J=7.9 Hz, 1H), 7.41 (dd, J=8.5, 2.2 Hz, 1H), 7.27-6.69 (m, 5H), 4.95-4.90 (m, 1H), 4.82 (d, J=6.1 Hz, 1H), 4.58 (d, J=6.3 Hz, 1H), 4.49 (d, J=6.2 Hz, 1H), 4.41 (dd, J=14.3, 2.3 Hz, 1H), 3.56-3.45 (m, 1H), 3.42-3.35 (m, 1H), 2.28 (dd, J=6.2, 3.7 Hz, 2H). (ES, m/z): (M−H)$^{−}$ 616.

Example 51—Preparation of Additional Substituted 4-(aryl sulfonyl)-3,4-dihydro-2H-benzo[b][1,4]oxazin-2-yl) Compounds Compounds in Table 16 were prepared based on experimental procedures described in Examples 47, 48, 49, and 50 and the detailed description. $^{1}$H NMR data for exemplary compounds from Table 16 is provided in Table 16A.

TABLE 16

| Compd No. | Structure | Name | Observed m/z |
|---|---|---|---|
| 51A | 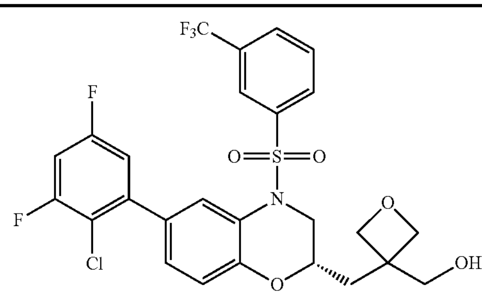 | (S)-(3-((6-(2-chloro-3,5-difluorophenyl)-4-((3-(trifluoromethyl)phenyl)sulfonyl)-3,4-dihydro-2H-benzo[b][1,4]oxazin-2-yl)methyl)oxetan-3-yl)methanol | 588 (M − H)$^{−}$ |

TABLE 16-continued

| Compd No. | Structure | Name | Observed m/z |
|---|---|---|---|
| 51B | 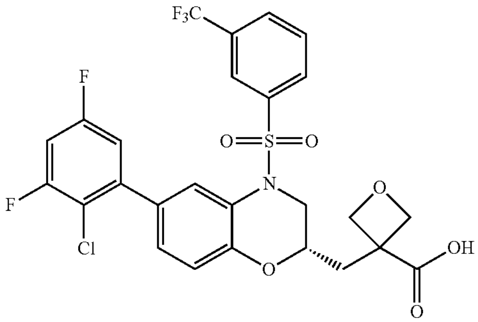 [SMILES: O=C(O)C1(C[C@H]2CN(S(=O)(=O)c3cccc(C(F)(F)F)c3)c3cc(-c4cc(F)cc(F)c4Cl)ccc3O2)COC1] | (S)-3-((6-(2-chloro-3,5-difluorophenyl)-4-((3-(trifluoromethyl)phenyl)sulfonyl)-3,4-dihydro-2H-benzo[b][1,4]oxazin-2-yl)methyl)oxetane-3-carboxylic acid | 602 (M − H)⁻ |
| 51C | 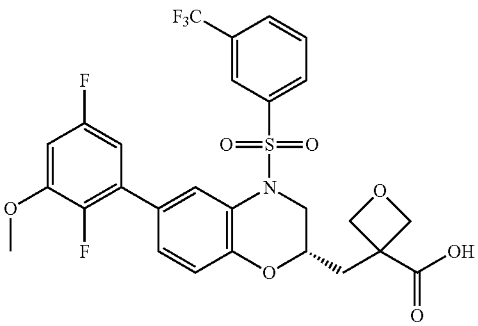 [SMILES: COc1cc(F)cc(-c2ccc3c(c2)N(S(=O)(=O)c2cccc(C(F)(F)F)c2)C[C@H](CC2(C(=O)O)COC2)O3)c1F] | (S)-3-((6-(2,5-difluoro-3-methoxyphenyl)-4-((3-(trifluoromethyl)phenyl)sulfonyl)-3,4-dihydro-2H-benzo[b][1,4]oxazin-2-yl)methyl)oxetane-3-carboxylic acid | 598 (M − H)⁻ |
| 51D | 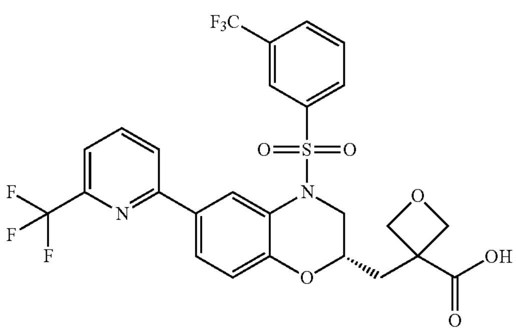 [SMILES: O=C(O)C1(C[C@H]2CN(S(=O)(=O)c3cccc(C(F)(F)F)c3)c3cc(-c4cccc(C(F)(F)F)n4)ccc3O2)COC1] | (S)-3-((4-((3-(trifluoromethyl)phenyl)sulfonyl)-6-(6-(trifluoromethyl)pyridin-2-yl)-3,4-dihydro-2H-benzo[b][1,4]oxazin-2-yl)methyl)oxetane-3-carboxylic acid | 603 (M + H)⁺ |
| 51E | 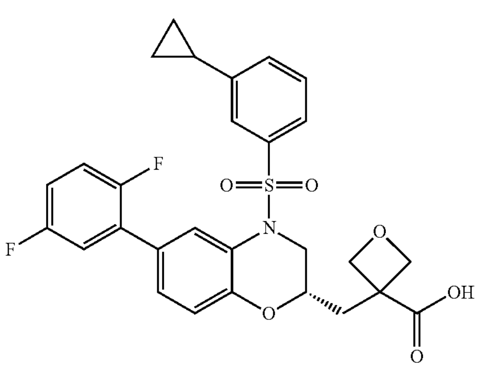 [SMILES: O=C(O)C1(C[C@H]2CN(S(=O)(=O)c3cccc(C4CC4)c3)c3cc(-c4cc(F)ccc4F)ccc3O2)COC1] | (S)-3-((4-((3-cyclopropylphenyl)sulfonyl)-6-(2,5-difluorophenyl)-3,4-dihydro-2H-benzo[b][1,4]oxazin-2-yl)methyl)oxetane-3-carboxylic acid | 542 (M + H)⁺ |

TABLE 16-continued

| Compd No. | Structure | Name | Observed m/z |
|---|---|---|---|
| 51F | 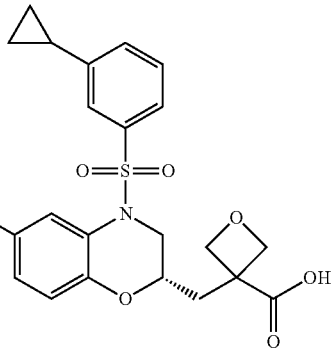 | (S)-3-((4-((3-cyclopropyl-phenyl)sulfonyl)-6-(3-(difluoro-methoxy)-5-fluorophenyl)-3,4-dihydro-2H-benzo[b][1,4]oxazin-2-yl)methyl)oxetane-3-carboxylic acid | 590 (M + H)+ |
| 51G | 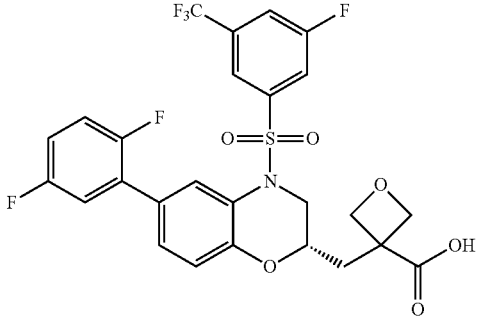 | (S)-3-((6-(2,5-difluorophenyl)-4-((3-fluoro-5-(trifluoromethyl)-phenyl)sulfonyl)-3,4-dihydro-2H-benzo[b][1,4]oxazin-2-yl)methyl)oxetane-3-carboxylic acid | 586 (M − H)− |
| 51H | 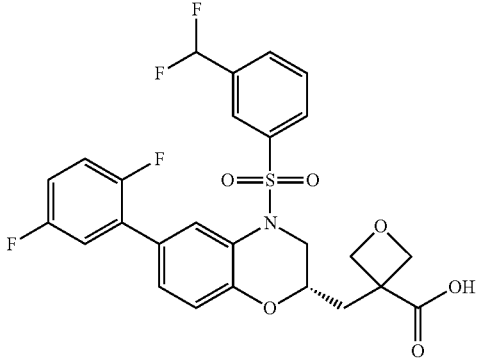 [SMILES: O=C(O)C1(C[C@H]2CN(S(=O)(=O)c3cccc(C(F)F)c3)c3cc(-c4cc(F)ccc4F)ccc3O2)COC1] | (S)-3-((4-((3-(difluoromethyl)-phenyl)sulfonyl)-6-(2,5-difluorophenyl)-3,4-dihydro-2H-benzo[b][1,4]oxazin-2-yl)methyl)oxetane-3-carboxylic acid | 550 (M − H)− |
| 51I | 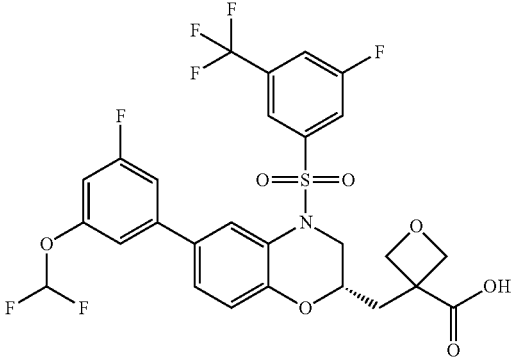 [SMILES: O=C(O)C1(C[C@H]2CN(S(=O)(=O)c3cc(F)cc(C(F)(F)F)c3)c3cc(-c4cc(F)cc(OC(F)F)c4)ccc3O2)COC1] | (S)-3-((6-(3-(difluoromethoxy)-5-fluorophenyl)-4-((3-fluoro-5-(trifluoromethyl)phenyl)sulfonyl)-3,4-dihydro-2H-benzo[b][1,4]-oxazin-2-yl)methyl)oxetane-3-carboxylic acid | 634 (M − H)− |

TABLE 16-continued

| Compd No. | Structure | Name | Observed m/z |
|---|---|---|---|
| 51J | 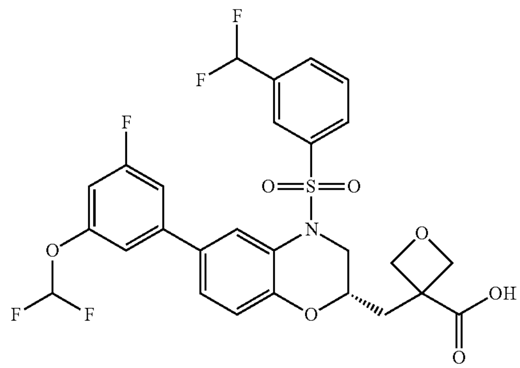 [SMILES: O=C(O)C1(C[C@H]2CN(S(=O)(=O)c3cccc(C(F)F)c3)c3cc(-c4cc(F)cc(OC(F)F)c4)ccc3O2)COC1] | (S)-3-((6-(3-(difluoromethoxy)-5-fluorophenyl)-4-((3-(difluoromethyl)phenyl)sulfonyl)-3,4-dihydro-2H-benzo[b][1,4]oxazin-2-yl)methyl)oxetane-3-carboxylic acid | 598 (M − H)⁻ |
| 51K | 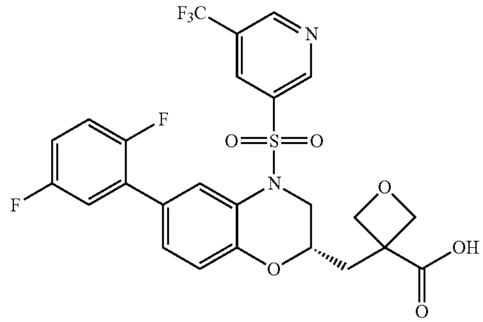 | (S)-3-((6-(2,5-difluorophenyl)-4-((5-(trifluoromethyl)pyridin-3-yl)sulfonyl)-3,4-dihydro-2H-benzo[b][1,4]oxazin-2-yl)methyl)oxetane-3-carboxylic acid | 571 (M + H)⁺ |
| 51L | 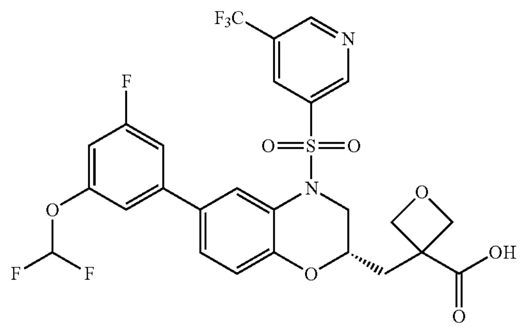 | (S)-3-((6-(3-(difluoromethoxy)-5-fluorophenyl)-4-((5-(trifluoromethyl)pyridin-3-yl)sulfonyl)-3,4-dihydro-2H-benzo[b][1,4]oxazin-2-yl)methyl)oxetane-3-carboxylic acid | 619 (M + H)⁺ |
| 51M | 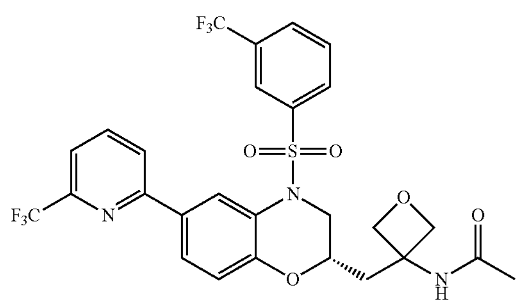 [SMILES: CC(=O)NC1(C[C@H]2CN(S(=O)(=O)c3cccc(C(F)(F)F)c3)c3cc(-c4cccc(C(F)(F)F)n4)ccc3O2)COC1] | (S)-N-(3-((4-((3-(trifluoromethyl)phenyl)sulfonyl)-6-(6-(trifluoromethyl)pyridin-2-yl)-3,4-dihydro-2H-benzo[b][1,4]oxazin-2-yl)methyl)oxetan-3-yl)acetamide | 616 (M + H)⁺ |

TABLE 16A

| Compd No. | Physical Characterization Data |
|---|---|
| 51A | ¹H NMR (400 MHz, CD₃OD-d₄) δ 8.10-7.88 (m, 4H), 7.82 (t, J = 7.9 Hz, 1H), 7.26-7.16 (m, 2H), 7.05 (ddd, J = 8.9, 2.9, 1.7 Hz, 1H), 6.90 (d, J = 8.3 Hz, 1H), 4.69-4.32 (m, 5H), 3.83 (d, J = 11.2 Hz, 1H), 3.68 (tdt, J = 9.3, 6.3, 2.8 Hz, 1H), 3.63-3.35 (m, 2H), 2.13-1.91 (m, 2H). |

TABLE 16A-continued

| Compd No. | Physical Characterization Data |
|---|---|
| 51B | $^1$H NMR (300 MHz, CD$_3$OD-d$_4$) δ 8.08-7.96 (m, 2H), 7.94-7.75 (m, 3H), 7.19 (ddt, J = 8.9, 5.9, 3.3 Hz, 2H), 7.04 (ddd, J = 8.9, 2.9, 1.7 Hz, 1H), 6.87 (d, J = 8.5 Hz, 1H), 5.03-4.91 (m, 1H), 4.87-4.82 (m, 1H), 4.62-4.39 (m, 3H), 3.58-3.35 (m, 2H), 2.33-2.26 (m, 2H). |
| 51C | $^1$H NMR (300 MHz, CD$_3$OD-d$_4$) δ 8.06-7.95 (m, 3H), 7.91 (s, 1H), 7.79 (t, J = 7.9 Hz, 1H), 7.28 (dt, J = 8.6, 1.6 Hz, 1H), 6.94 (ddd, J = 9.7, 6.5, 3.0 Hz, 1H), 6.86 (d, J = 8.5 Hz, 1H), 6.74 (ddd, J = 8.6, 5.2, 3.0 Hz, 1H), 4.93 (d, J = 6.3 Hz, 1H), 4.84 (d, J = 6.1 Hz, 1H), 4.60 (d, J = 6.2 Hz, 1H), 4.51 (d, J = 6.1 Hz, 1H), 4.44 (dd, J = 14.5, 2.4 Hz, 1H), 3.94 (s, 3H), 3.55 (dtd, J = 10.3, 7.5, 6.9, 3.0 Hz, 1H), 3.44-3.36 (m, 1H), 2.30 (dd, J = 6.3, 3.9 Hz, 2H). |
| 51D | $^1$H NMR (300 MHz, CD$_3$OD-d$_4$) δ 8.60 (d, J = 2.1 Hz, 1H), 8.15-8.02 (m, 3H), 7.98 (d, J = 8.1 Hz, 2H), 7.87 (dd, J = 8.7, 2.2 Hz, 1H), 7.78 (t, J = 7.8 Hz, 1H), 7.75-7.68 (m, 1H), 6.91 (d, J = 8.6 Hz, 1H), 4.94 (d, J = 6.3 Hz, 1H), 4.86 (d, J = 6.1 Hz, 1H), 4.61 (d, J = 6.2 Hz, 1H), 4.53 (d, J = 6.1 Hz, 1H), 4.44 (dd, J = 14.4, 2.5 Hz, 1H), 3.72-3.62 (m, 1H), 3.45 (dd, J = 14.3, 9.5 Hz, 1H), 2.41-2.27 (m, 2H). |
| 51E | $^1$H NMR (300 MHz, CD$_3$OD-d$_4$) δ 8.00 (s, 1H), 7.55-7.50 (m, 1H), 7.40-7.30 (m, 2H), 7.25-7.15 (m, 4H), 7.12-7.05 (m, 1H), 6.82 (d, J = 8.4 Hz, 1H), 4.92 (d, J = 6.0 Hz, 1H), 4.82 (d, J = 8.4 Hz, 1H), 4.52-4.45 (m, 3H), 3.55-3.45 (m, 1H), 3.25-3.17 (m, 1H), 2.25-2.15 (m, 2H), 1.90-1.80 (m, 1H), 0.95-0.85 (m, 2H), 0.55-0.50 (m, 1H), 0.40-0.30 (m, 1H). |
| 51F | $^1$H NMR (300 MHz, CD$_3$OD-d$_4$) δ 8.00 (s, 1H), 7.55-7.35 (m, 4H), 7.20-6.70 (m, 6H), 4.90 (d, J = 6.0 Hz, 1H), 4.82 (d, J = 8.4 Hz, 1H), 4.48 (d, J = 8.0 Hz, 1H), 4.40 (d, J = 8.0 Hz, 1H), 4.35 (d, J = 6.0 Hz, 1H), 4.30 (d, J = 6.0 Hz, 1H), 3.50-3.38 (m, 1H), 3.28-3.20 (m, 1H), 2.20-2.10 (m, 2H), 1.92-1.80 (m, 1H), 0.95-0.85 (m, 2H), 0.55-0.50 (m, 1H), 0.40-0.30 (m, 1H). |
| 51G | $^1$H NMR (300 MHz, CD$_3$OD-d$_4$) δ 8.02 (t, J = 1.7 Hz, 1H), 7.91-7.80 (m, 2H), 7.77 (s, 1H), 7.34-7.29 (m, 1H), 7.24 (tt, J = 9.6, 5.2 Hz, 2H), 7.13 (td, J = 8.6, 8.1, 4.0 Hz, 1H), 6.92 (d, J = 8.6 Hz, 1H), 4.97 (d, J = 6.2 Hz, 1H), 4.87 (d, J = 5.9 Hz, 1H), 4.58 (d, J = 6.2 Hz, 1H), 4.55-4.42 (m, 2H), 3.70 (td, J = 8.8, 7.6, 4.2 Hz, 1H), 3.42 (dd, J = 14.5, 9.7 Hz, 1H), 2.40-2.25 (m, 2H). |
| 51H | $^1$H NMR (300 MHz, CD$_3$OD-d$_4$) δ 8.02 (t, J = 1.8 Hz, 1H), 7.88-7.77 (m, 3H), 7.66 (t, J = 7.8 Hz, 1H), 7.32-7.16 (m, 3H), 7.10 (ddd, J = 8.7, 6.6, 3.6 Hz, 1H), 6.99-6.63 (m, 2H), 4.85-4.33 (m, 4H), 3.55-3.32 (m, 3H), 2.28 (t, J = 6.1 Hz, 2H). |
| 51I | $^1$H NMR (300 MHz, CD$_3$OD-d$_4$) δ 8.02 (d, J = 2.2 Hz, 1H), 7.90-7.81 (m, 2H), 7.74 (s, 1H), 7.43 (dd, J = 8.6, 2.2 Hz, 1H), 7.26-6.76 (m, 5H), 4.98 (d, J = 6.1 Hz, 1H), 4.87 (s, 1H), 4.55 (d, J = 6.1 Hz, 1H), 4.52-4.42 (m, 2H), 3.67 (tt, J = 7.4, 3.7 Hz, 1H), 3.40 (dd, J = 14.5, 9.8 Hz, 1H), 2.36-2.23 (m, 2H). |
| 51J | $^1$H NMR (300 MHz, CD$_3$OD-d$_4$) δ 8.03 (d, J = 2.2 Hz, 1H), 7.85-7.75 (m, 3H), 7.67 (t, J = 7.7 Hz, 1H), 7.39 (dd, J = 8.6, 2.3 Hz, 1H), 7.23-7.11 (m, 2H), 7.06-6.62 (m, 4H), 4.84-4.31 (m, 4H), 3.52-3.31 (m, 3H), 2.26 (t, J = 6.1 Hz, 2H). |
| 51K | $^1$H NMR (400 MHz, CD$_3$OD-d$_4$) δ 9.27-9.12 (m, 2H), 8.44 (t, J = 2.0 Hz, 1H), 8.03 (t, J = 1.8 Hz, 1H), 7.34-7.19 (m, 3H), 7.12 (ddd, J = 12.2, 8.0, 3.5 Hz, 1H), 6.96 (d, J = 8.5 Hz, 1H), 5.02 (d, J = 5.9 Hz, 1H), 4.89 (d, J = 8.7 Hz, 1H), 4.57 (dd, J = 14.3, 2.5 Hz, 1H), 4.47 (t, J = 5.8 Hz, 2H), 3.86 (s, 1H), 3.45 (dd, J = 14.2, 9.6 Hz, 1H), 2.46-1.98 (m, 2H). |
| 51L | $^1$H NMR (400 MHz, CD$_3$OD-d$_4$) δ 9.25-9.10 (m, 2H), 8.44 (t, J = 2.0 Hz, 1H), 8.03 (d, J = 2.2 Hz, 1H), 7.42 (dd, J = 8.6, 2.2 Hz, 1H), 7.30-6.75 (m, 5H), 5.01 (d, J = 6.0 Hz, 1H), 4.87 (d, J = 5.9 Hz, 1H), 4.54 (dd, J = 14.2, 2.5 Hz, 1H), 4.47 (t, J = 5.9 Hz, 2H), 3.82 (s, 1H), 3.43 (dd, J = 14.3, 9.7 Hz, 1H), 2.35-2.18 (m, 2H). |
| 51M | $^1$H NMR (400 MHz, CDCl$_3$) δ 8.42 (d, J = 2.1 Hz, 1H), 8.10 (d, J = 8.0 Hz, 1H), 8.05 (s, 1H), 7.97-7.82 (m, 4H), 7.71 (t, J = 7.9 Hz, 1H), 7.62 (dd, J = 7.5, 1.1 Hz, 1H), 6.87 (d, J = 8.6 Hz, 1H), 4.74 (dd, J = 16.5, 6.9 Hz, 2H), 4.62 (d, J = 6.9 Hz, 2H), 4.31 (d, J = 13.9, 2.5 Hz, 1H), 3.93 (dd, J = 10.8, 8.5 Hz, 1H), 3.42 (dd, J = 13.9, 9.1 Hz, 1H), 2.02 (s, 3H), 1.29 (d, J = 5.4 Hz, 2H). |

Example 52—Synthesis of (R)-3-(6-(2,5-difluorophenyl)-4-((3-(trifluoromethyl)phenyl)sulfonyl)-3,4-dihydro-2H-benzo[b][1,4]oxazin-2-yl)-2,2-dimethylpropanoic acid

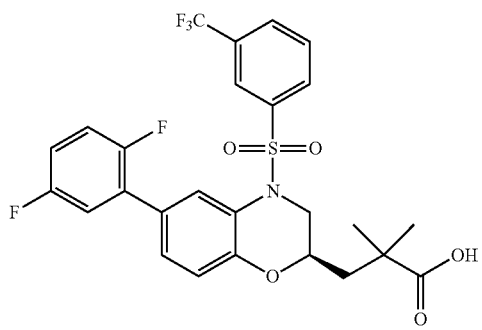 [SMILES: CC(C)(C[C@@H]1CN(S(=O)(=O)c2cccc(C(F)(F)F)c2)c2cc(-c3cc(F)ccc3F)ccc2O1)C(=O)O]

Part I— Synthesis of N-(5-bromo-2-fluorophenyl)-3-(trifluoromethyl)benzenesulfonamide

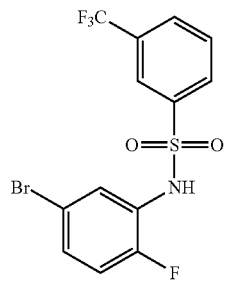 [SMILES: O=S(=O)(Nc1cc(Br)ccc1F)c1cccc(C(F)(F)F)c1]

A mixture of 5-bromo-2-fluoroaniline (10 g, 52.6 mmol), 3-(trifluoromethyl)benzene-1-sulfonyl chloride (12.9 g, 52.6 mmol) and pyridine (30 mL) was stirred overnight at 60° C. The pH value of the solution was adjusted to 3-4 with 1M aqueous hydrogen chloride. The mixture was extracted three times with dichloromethane. The combined organic layers combined were dried (Na₂SO₄) and concentrated. The residue was purified via MPLC eluting with 10% ethyl acetate in petroleum ether to afford N-(5-bromo-2-fluorophenyl)-3-(trifluoromethyl)benzenesulfonamide (19.3 g, 92%) as a light yellow solid.

Part II—Synthesis of (R)-2,2-dimethyl-3-(oxiran-2-yl)propanenitrile

A 2.5M solution of n-butyl lithium (78 mL) was added dropwise to a stirred solution of (R)-2-(chloromethyl)oxirane (15 g, 162 mmol), 2-methylpropanenitrile (33.6 g, 486 mmol), and tetrahydrofuran (150 mL) at −78° C. The mixture was stirred for two hours at −78° C., and allowed to stir an additional 36 hours at room temperature. The mixture was quenched by the addition of saturated ammonium chloride, and extracted five times with ethyl acetate. The combined organic layers were dried (Na₂SO₄) and concentrated. The residue was purified by MPLC eluting with a gradient of 10-20% ethyl acetate in petroleum ether to afford (R)-2,2-dimethyl-3-(oxiran-2-yl)propanenitrile (18 g, 89%) as a light yellow oil.

Part III—Synthesis of (R)-3-(6-bromo-4-((3-(trifluoromethyl)phenyl)sulfonyl)-3,4-dihydro-2H-benzo[b][1,4]oxazin-2-yl)-2,2-dimethylpropanenitrile

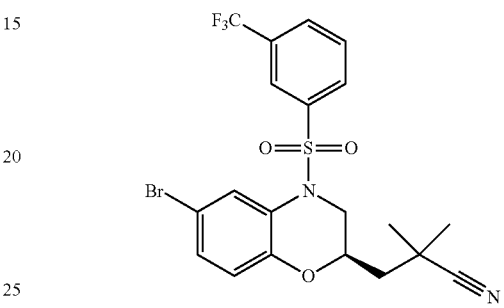

A mixture of (R)-2,2-dimethyl-3-(oxiran-2-yl)propanenitrile (2.5 g, 19.97 mmol), N-(5-bromo-2-fluorophenyl)-3-(trifluoromethyl)benzenesulfonamide (3.2 g, 8.04 mmol), tetra-n-butylammonium bromide (210 mg, 0.65 mmol), potassium carbonate (110 mg, 0.80 mmol) was stirred for twelve hours at 60° C. Tetrahydrofuran (30 mL) and sodium hydroxide (1.28 g, 32.00 mmol) were then added and the mixture was allowed to stir for an additional two hours at 60° C. The reaction was cooled and quenched by the addition of water. The mixture was extracted three times with ethyl acetate. The combined organic layers were dried (Na₂SO₄) and concentrated. The residue was purified via MPLC eluting with a gradient of 5-10% ethyl acetate in petroleum ether to afford (R)-3-(6-bromo-4-((3-(trifluoromethyl)phenyl)sulfonyl)-3,4-dihydro-2H-benzo[b][1,4]oxazin-2-yl)-2,2-dimethylpropanenitrile (2.4 g, 59%) as a light yellow oil.

Part IV—Synthesis of (R)-3-(6-bromo-4-((3-(trifluoromethyl)phenyl)sulfonyl)-3,4-dihydro-2H-benzo[b][1,4]oxazin-2-yl)-2,2-dimethylpropanoic acid

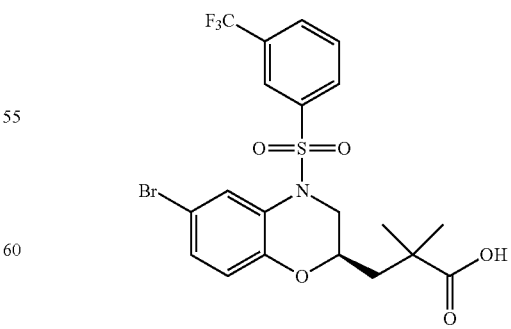

A mixture of (R)-3-(6-bromo-4-((3-(trifluoromethyl)phenyl)sulfonyl)-3,4-dihydro-2H-benzo[b][1,4]oxazin-2-yl)-2,2-dimethylpropanenitrile (2.4 g, 4.77 mmol), 1,4-dioxane (20 mL), hydrogen chloride (6 mL), sulfuric acid (2 mL), and acetic acid (2 mL) was stirred for 3 days at 100° C. The reaction was cooled and diluted with water. The mixture was extracted three times with ethyl acetate, the combined organic layers were dried (Na$_2$SO$_4$) and concentrated. The residue was purified via MPLC eluting with a gradient of 50-100% ethyl acetate in petroleum ether to afford (R)-3-(6-bromo-4-((3-(trifluoromethyl)phenyl)sulfonyl)-3,4-dihydro-2H-benzo[b][1,4]oxazin-2-yl)-2,2-dimethylpropanoic acid (2.2 g, 88%) as a light yellow oil.

Part V—Synthesis of (R)-3-(6-(2,5-difluorophenyl)-4-((3-(trifluoromethyl)phenyl)sulfonyl)-3,4-dihydro-2H-benzo[b][1,4]oxazin-2-yl)-2,2-dimethylpropanoic acid

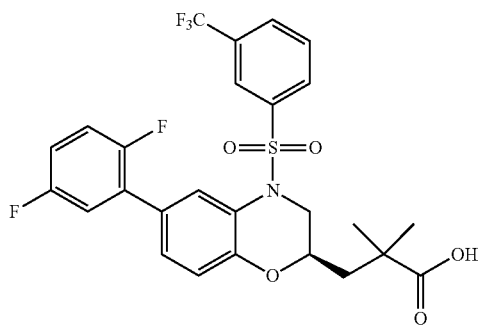 [SMILES: CC(C)(C[C@@H]1CN(S(=O)(=O)c2cccc(C(F)(F)F)c2)c2cc(-c3cc(F)ccc3F)ccc2O1)C(=O)O]

A mixture of (R)-3-(6-bromo-4-((3-(trifluoromethyl)phenyl)sulfonyl)-3,4-dihydro-2H-benzo[b][1,4]oxazin-2-yl)-2,2-dimethylpropanoic acid (522 mg, 1.00 mmol), (2,5-difluorophenyl)boronic acid (190 mg, 1.20 mmol), tetrakis(triphenylphosphine)palladium (115 mg, 0.10 mmol), sodium carbonate (318 mg, 3.0 mmol), toluene (10 mL), methanol (2 mL), and water (2 mL) was stirred for four hours at 80° C. The mixture was concentrated and the residue was purified by MPLC eluting with a gradient of 5-10% methanol in dichloromethane to afford 500 mg of the target compound. A portion of the product was further purified by Prep-HPLC eluting with a gradient of 57-85% acetonitrile in water with 0.05% trifluoroacetic acid to afford (R)-3-(6-(2,5-difluorophenyl)-4-((3-(trifluoromethyl)phenyl)sulfonyl)-3,4-dihydro-2H-benzo[b][1,4]oxazin-2-yl)-2,2-dimethylpropanoic acid (20 mg) as a white solid. $^1$H-NMR (400 MHz, CD$_3$OD) δ 8.04 (s, 1H), 7.98 (m, 2H), 7.90 (s, 1H), 7.78 (m, 1H), 7.31-7.07 (m, 4H), 6.87 (d, J=8.4 Hz, 1H), 4.43 (dd, J=14 Hz, 2.4 Hz, 1H), 3.52 (m, 1H), 3.22 (dd, J=14 Hz, 9.6 Hz, 1H), 1.82-1.76 (m, 2H), 1.16-1.14 (m, 6H). (ES, m/z): (M−H)$^-$ 554.

Example 53 and 54—Synthesis of (1R,2R)-2-((S)-6-(2,5-difluorophenyl)-4-((3-(trifluoromethyl)phenyl)sulfonyl)-3,4-dihydro-2H-benzo[b][1,4]oxazin-2-yl)cyclopropane-1-carboxylic acid and (1S,2S)-2-((S)-6-(2,5-difluorophenyl)-4-((3-(trifluoromethyl)phenyl)sulfonyl)-3,4-dihydro-2H-benzo[b][1,4]oxazin-2-yl)cyclopropane-1-carboxylic acid

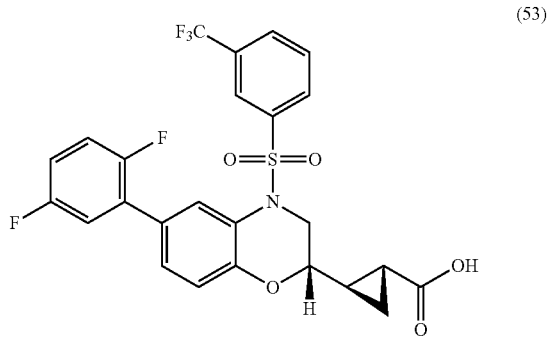

(53)

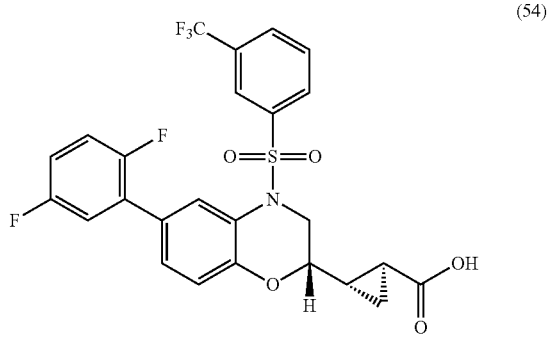

(54)

Part I—Synthesis of tert-butyl (SE)-3-(2,2-dimethyl-1,3-dioxolan-4-yl)acrylate

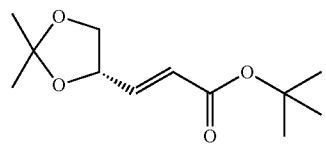 [SMILES: CC(C)(C)OC(=O)/C=C/[C@H]1COC(C)(C)O1]

A solution of tert-butyl 2-(diethoxyphosphoryl) acetate (21.3 g, 84.44 mmol) was added dropwise to a stirred suspension of 60% sodium hydride in mineral oil (3.1 g, 77.5 mmol) in tetrahydrofuran (150 mL) at −15° C. The mixture was stirred for an additional thirty minutes at room temperature; cooled to −15° C., and (R)-2,2-dimethyl-1,3-dioxolane-4-carbaldehyde (22.9 g, 76.72 mmol) was added dropwise. The mixture was allowed to react for an additional hour at −15° C. Saturated ammonium chloride was added, and the mixture was extracted twice with ethyl acetate. The combined organic layers were dried (Na$_2$SO$_4$) and concentrated. The residue was purified by MPLC eluting with 10% ethyl acetate in petroleum ether to afford tert-butyl (S,E)-3-(2,2-dimethyl-1,3-dioxolan-4-yl)acrylate (17 g, 97%) as a clear oil.

Part II—Synthesis of tert-butyl (1R,2R)-2-((S)-2,2-dimethyl-1,3-dioxolan-4-yl)cyclopropane-1-carboxylate and tert-butyl (1S,2S)-2-((S)-2,2-dimethyl-1,3-dioxolan-4-yl)cyclopropane-1-carboxylate

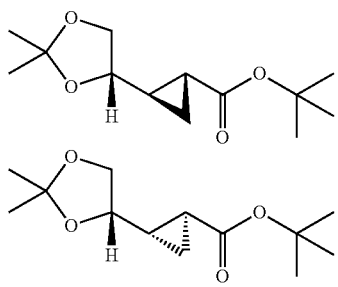

Sodium hydride (4.2 g, 175 mmol) was added portionwise to a stirred solution of trimethylsulfoxonium iodide (16.4 g, 80 mmol), in DMSO (20 mL) at 0° C. The mixture was stirred for ten minutes, and a solution of afford tert-butyl (S,E)-3-(2,2-dimethyl-1,3-dioxolan-4-yl)acrylate (17 g, 74.47 mmol) in tetrahydrofuran (150 ml) was added dropwise with stirring at 0° C. The mixture was allowed to warm to room temperature and was stirred overnight. Saturated ammonium chloride was added, and the mixture was extracted three times with ethyl acetate. The combined organic layers were dried (Na$_2$SO$_4$) and concentrated. The residue was purified via MPLC eluting with 10% ethyl acetate in petroleum ether to afford tert-butyl (1R,2R)-2-((S)-2,2-dimethyl-1,3-dioxolan-4-yl)cyclopropane-1-carboxylate and tert-butyl (1S,2S)-2-((S)-2,2-dimethyl-1,3-dioxolan-4-yl)cyclopropane-1-carboxylate (11.7 g, 65%) as a white solid.

Part III—Synthesis of tert-butyl (1R,2R)-2-((S)-1,2-dihydroxyethyl)cyclopropane-1-carboxylate and tert-butyl (1S,2S)-2-((S)-1,2-dihydroxyethyl)cyclopropane-1-carboxylate

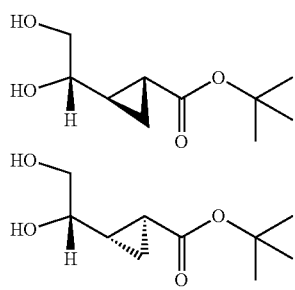

A mixture of tert-butyl (1R,2R)-2-((S)-2,2-dimethyl-1,3-dioxolan-4-yl)cyclopropane-1-carboxylate and tert-butyl (1S,2S)-2-((S)-2,2-dimethyl-1,3-dioxolan-4-yl)cyclopropane-1-carboxylate (300 mg, 1.24 mmol), 2-methylpropan-2-ol (10 mL), pyridinium para-toluenesulfonate (62 mg, 0.25 mmol) was stirred overnight at 60° C. Saturated sodium bicarbonate was added and the mixture was extracted twice with ethyl acetate. The combined organic layers were washed with brine, dried (Na$_2$SO$_4$), and concentrated. The residue was purified by MPLC eluting with 50% ethyl acetate in petroleum ether to afford tert-butyl (1R,2R)-2-((S)-1,2-dihydroxyethyl)cyclopropane-1-carboxylate and tert-butyl (1S,2S)-2-((S)-1,2-dihydroxyethyl)cyclopropane-1-carboxylate (150 mg, 60%) as a white solid.

Part IV— Synthesis of tert-butyl (1R,2R)-2-((S)-1-hydroxy-2-(tosyloxy)ethyl)cyclopropane-1-carboxylate and tert-butyl (1R,2R)-2-((S)-1-hydroxy-2-(tosyloxy)ethyl)cyclopropane-1-carboxylate

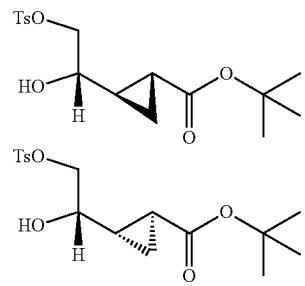

To a stirred mixture of tert-butyl (1R,2R)-2-((S)-1,2-dihydroxyethyl)cyclopropane-1-carboxylate and tert-butyl (1S,2S)-2-((S)-1,2-dihydroxyethyl)cyclopropane-1-carboxylate (3.4 g, 16.81 mmol), dichloromethane (25 mL), and triethylamine (2.6 g, 25.69 mmol) was added para-toluene sulfonyl chloride (3.2 g, 16.78 mmol) in dichloromethane (10 mL) dropwise at 0° C. The mixture was allowed to warm to room temperature and stirred overnight. Saturated ammonium chloride was added and the mixture was extracted three times with dichloromethane. The combined organic layers were dried (Na$_2$SO$_4$) and concentrated to afford tert-butyl (1R,2R)-2-((S)-1-hydroxy-2-(tosyloxy)ethyl)cyclopropane-1-carboxylate and tert-butyl (1R,2R)-2-((S)-1-hydroxy-2-(tosyloxy)ethyl)cyclopropane-1-carboxylate (2 g, 33%) as a white solid.

Part V— Synthesis of tert-butyl (1R,2R)-2-((S)-oxiran-2-yl)cyclopropane-1-carboxylate and tert-butyl (1S,2S)-2-((S)-oxiran-2-yl)cyclopropane-1-carboxylate

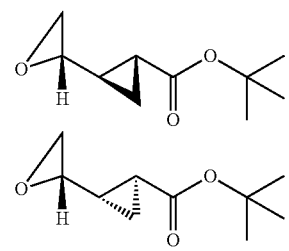

A mixture of tert-butyl (1R,2R)-2-((S)-1-hydroxy-2-(tosyloxy)ethyl)cyclopropane-1-carboxylate and tert-butyl (1R,2R)-2-((S)-1-hydroxy-2-(tosyloxy)ethyl)cyclopropane-1-carboxylate (1.9 g, 5.33 mmol) and potassium carbonate (883 mg, 6.39 mmol), in methanol (15 mL) was stirred for an hour at room temperature. The mixture was concentrated, and the residue was purified via MPLC eluting with 20% ethyl acetate in petroleum ether to afford tert-butyl (1R,2R)-2-((S)-oxiran-2-yl)cyclopropane-1-carboxylate and tert-butyl (1S,2S)-2-((S)-oxiran-2-yl)cyclopropane-1-carboxylate (800 mg, 81%) as a white solid.

Part VI— Synthesis of tert-butyl (1R,2R)-2-((S)-6-bromo-4-((3-(trifluoromethyl)phenyl)sulfonyl)-3,4-dihydro-2H-benzo[b][1,4]oxazin-2-yl)cyclopropane-1-carboxylate and tert-butyl (1S,2S)-2-((S)-6-bromo-4-((3-(trifluoromethyl)phenyl)sulfonyl)-3,4-dihydro-2H-benzo[b][1,4]oxazin-2-yl)cyclopropane-1-carboxylate

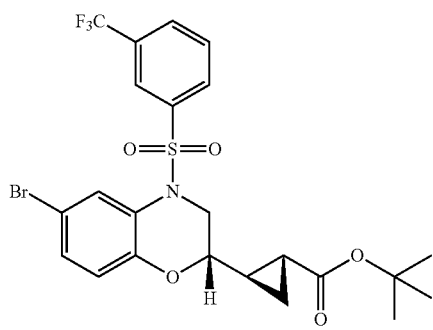

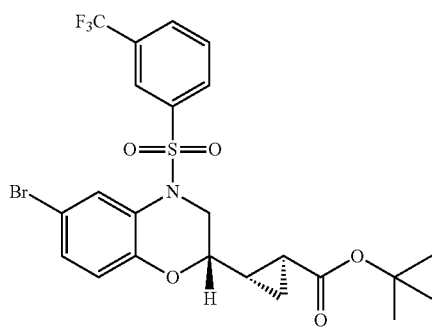

A mixture of tert-butyl (1R,2R)-2-((S)-oxiran-2-yl)cyclopropane-1-carboxylate and tert-butyl (1S,2S)-2-((S)-oxiran-2-yl)cyclopropane-1-carboxylate (750 mg, 4.07 mmol), N-(5-bromo-2-fluorophenyl)-3-(trifluoromethyl)benzene-1-sulfonamide (1.6 g, 4.02 mmol), potassium carbonate (56 mg, 0.41 mmol), tetra-n-butylammonium bromide (131 mg, 0.41 mmol) was stirred overnight at 60° C. Tetrahydrofuran (10 mL) and sodium hydroxide (652 mg, 16.30 mmol) was then added and allowed to react, with stirring, for an additional three hours while the temperature was maintained at 60° C. The mixture was cooled, water was added and the mixture was extracted twice with ethyl acetate. The combined organic layers were dried (Na$_2$SO$_4$) and concentrated. The residue was purified via MPLC eluting with 33% ethyl acetate to afford tert-butyl (1R,2R)-2-((S)-6-bromo-4-((3-(trifluoromethyl)phenyl)sulfonyl)-3,4-dihydro-2H-benzo[b][1,4]oxazin-2-yl)cyclopropane-1-carboxylate and tert-butyl (1S,2S)-2-((S)-6-bromo-4-((3-(trifluoromethyl)phenyl)sulfonyl)-3,4-dihydro-2H-benzo[b][1,4]oxazin-2-yl)cyclopropane-1-carboxylate (400 mg, 17%) as a yellow oil.

Part VII— Synthesis of tert-butyl (1R,2R)-2-((S)-6-(2,5-difluorophenyl)-4-((3-(trifluoromethyl)phenyl)sulfonyl)-3,4-dihydro-2H-benzo[b][1,4]oxazin-2-yl)cyclopropane-1-carboxylate and tert-butyl (1S,2S)-2-((S)-6-(2,5-difluorophenyl)-4-((3-(trifluoromethyl)phenyl)sulfonyl)-3,4-dihydro-2H-benzo[b][1,4]oxazin-2-yl)cyclopropane-1-carboxylate

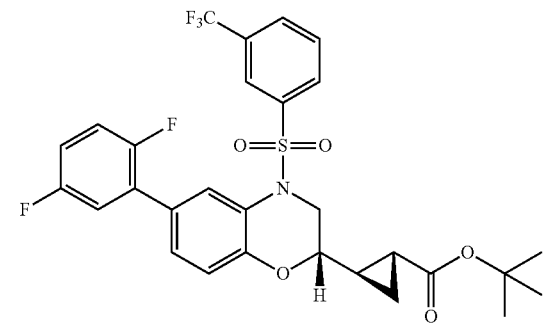

A mixture of tert-butyl (1R,2R)-2-((S)-6-bromo-4-((3-(trifluoromethyl)phenyl)sulfonyl)-3,4-dihydro-2H-benzo[b][1,4]oxazin-2-yl)cyclopropane-1-carboxylate and tert-butyl (1S,2S)-2-((S)-6-bromo-4-((3-(trifluoromethyl)phenyl)sulfonyl)-3,4-dihydro-2H-benzo[b][1,4]oxazin-2-yl)cyclopropane-1-carboxylate (455 mg, 0.81 mmol), (2,5-difluorophenyl)boronic acid (192 mg, 1.22 mmol), tetrakis(triphenylphosphine)palladium (140 mg, 0.12 mmol), sodium carbonate (257 mg, 2.42 mmol), toluene (6 mL), ethanol (2 mL), water (2 mL) was stirred for three hours at 90° C. The mixture was concentrated, and the residue was purified via MPLC eluting with 33% ethyl acetate in petroleum ether to afford tert-butyl (1R,2R)-2-((S)-6-(2,5-difluorophenyl)-4-((3-(trifluoromethyl)phenyl)sulfonyl)-3,4-dihydro-2H-benzo[b][1,4]oxazin-2-yl)cyclopropane-1-carboxylate and tert-butyl (1S,2S)-2-((S)-6-(2,5-difluorophenyl)-4-((3-(trifluoromethyl)phenyl)sulfonyl)-3,4-dihydro-2H-benzo[b][1,4]oxazin-2-yl)cyclopropane-1-carboxylate (240 mg, 50%) as a yellow oil.

Part VIII— Synthesis of (1R,2R)-2-((S)-6-(2,5-difluorophenyl)-4-((3-(trifluoromethyl)phenyl)sulfonyl)-3,4-dihydro-2H-benzo[b][1,4]oxazin-2-yl)cyclopropane-1-carboxylic acid and (1S,2S)-2-((S)-6-(2,5-difluorophenyl)-4-((3-(trifluoromethyl)phenyl)sulfonyl)-3,4-dihydro-2H-benzo[b][1,4]oxazin-2-yl)cyclopropane-1-carboxylic acid Example 55 and 56—Synthesis of (1R,2R)-2-((S)-6-(3-(difluoromethoxy)-5-fluorophenyl)-4-((3-(trifluoromethyl)phenyl)sulfonyl)-3,4-dihydro-2H-benzo[b][1,4]oxazin-2-yl)cyclopropane-1-carboxylic acid and (1S,2S)-2-((S)-6-(3-(difluoromethoxy)-5-fluorophenyl)-4-((3-(trifluoromethyl)phenyl)sulfonyl)-3,4-dihydro-2H-benzo[b][1,4]oxazin-2-yl)cyclopropane-1-carboxylic acid

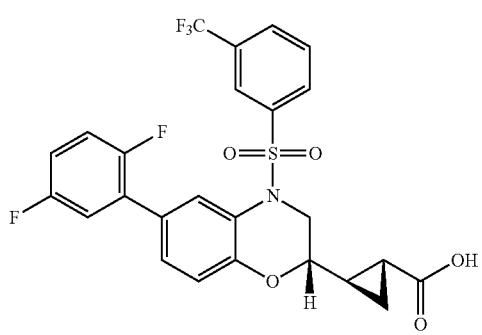

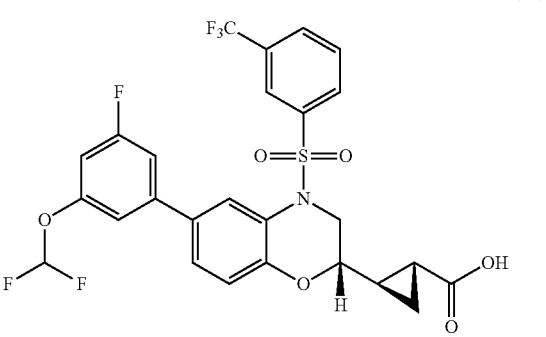
(55)

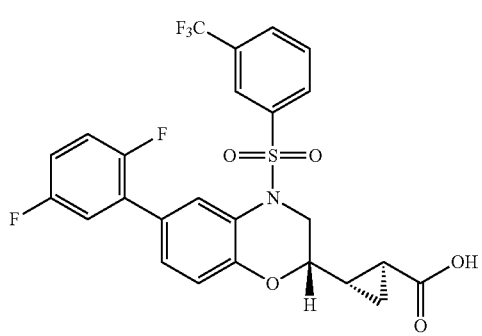

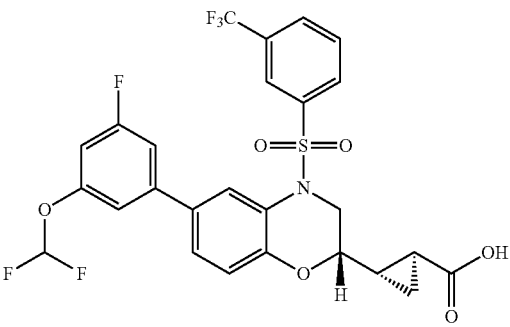
(56)

A mixture of tert-butyl (1R,2R)-2-((S)-6-(2,5-difluorophenyl)-4-((3-(trifluoromethyl)phenyl)sulfonyl)-3,4-dihydro-2H-benzo[b][1,4]oxazin-2-yl)cyclopropane-1-carboxylate and tert-butyl (1S,2S)-2-((S)-6-(2,5-difluorophenyl)-4-((3-(trifluoromethyl)phenyl)sulfonyl)-3,4-dihydro-2H-benzo[b][1,4]oxazin-2-yl)cyclopropane-1-carboxylate (100 mg, 0.17 mmol), trifluoroacetic acid (75 mg, 0.66 mmol), and dichloromethane (5 mL) was stirred for two hours at room temperature. The mixture was concentrated and the residue was purified by Prep-HPLC to afford (1R,2R)-2-((S)-6-(2,5-difluorophenyl)-4-((3-(trifluoromethyl)phenyl)sulfonyl)-3,4-dihydro-2H-benzo[b][1,4]oxazin-2-yl)cyclopropane-1-carboxylic acid (25 mg); $^1$H-NMR (400 MHz, CD$_3$OD) δ 8.04-7.95 (m, 4H), 7.78 (t, J=8.0 Hz, 1H), 7.29 (m, 1H), 7.25-7.16 (m, 2H), 7.13-7.05 (m, 1H), 6.93 (d, J=8.6 Hz, 1H), 4.50 (dd, J=14.5, 2.6 Hz, 1H), 3.44 (m, 1H), 3.13 (m, 1H), 1.68-1.53 (m, 2H), 1.16 (dt, J=9.0, 4.7 Hz, 1H), 0.93 (ddd, J=8.5, 6.2, 4.4 Hz, 1H). (ES, m/z): (M−H)$^−$ 538; and (1S,2S)-2-((S)-6-(2,5-difluorophenyl)-4-((3-(trifluoromethyl)phenyl)sulfonyl)-3,4-dihydro-2H-benzo[b][1,4]oxazin-2-yl)cyclopropane-1-carboxylic acid (12 mg); $^1$H-NMR (400 MHz, CD$_3$OD) δ 8.03-7.93 (m, 4H), 7.77 (t, J=7.9 Hz, 1H), 7.30 (dt, J=8.5, 1.6 Hz, 1H), 7.26-7.16 (m, 2H), 7.14-7.04 (m, 1H), 6.95 (d, J=8.6 Hz, 1H), 4.50 (dd, J=14.5, 2.5 Hz, 1H), 3.46 (dd, J=14.5, 9.9 Hz, 1H), 2.91 (t, J=8.6 Hz, 1H), 1.54 (s, 2H), 1.19 (dt, J=9.2, 4.7 Hz, 1H), 0.92 (t, J=9.1 Hz, 1H). (ES, m/z): (M−H)$^−$ 538.

Based on the procedure in Example 53 and 54, (1R,2R)-2-((S)-6-(3-(difluoromethoxy)-5-fluorophenyl)-4-((3-(trifluoromethyl)phenyl)sulfonyl)-3,4-dihydro-2H-benzo[b][1,4]oxazin-2-yl)cyclopropane-1-carboxylic acid: $^1$H-NMR (400 MHz, CD$_3$OD) δ 8.01 (dd, J=6.6, 3.2 Hz, 4H), 7.81 (t, J=8.2 Hz, 1H), 7.43 (dd, J=8.6, 2.2 Hz, 1H), 7.24-6.77 (m, 5H), 4.50 (dd, J=14.5, 2.6 Hz, 1H), 3.47 (dd, J=14.5, 9.8 Hz, 1H), 3.13 (ddd, J=9.5, 6.6, 2.6 Hz, 1H), 1.63 (tdd, J=10.4, 7.7, 4.3 Hz, 2H), 1.19 (dt, J=9.1, 4.8 Hz, 1H), 1.07-0.89 (m, 1H). (ES, m/z): (M+H)$^+$ 586; and (1S,2S)-2-((S)-6-(3-(difluoromethoxy)-5-fluorophenyl)-4-((3-(trifluoromethyl)phenyl)sulfonyl)-3,4-dihydro-2H-benzo[b][1,4]oxazin-2-yl)cyclopropane-1-carboxylic acid $^1$H-NMR (400 MHz, CD$_3$OD) δ 8.05-7.95 (m, 4H), 7.80 (t, J=8.1 Hz, 1H), 7.43 (dd, J=8.6, 2.3 Hz, 1H), 7.25-6.77 (m, 5H), 4.50 (dd, J=14.6, 2.6 Hz, 1H), 3.57-3.43 (m, 1H), 2.91 (td, J=7.9, 7.2, 4.4 Hz, 1H), 1.57 (q, J=6.8 Hz, 2H), 1.22 (dt, J=9.5, 4.8 Hz, 1H), 0.98-0.91 (m, 1H). (ES, m/z): (M+H)$^+$ 586 were prepared.

Example 57—Synthesis of (S)-4-((6-(2,5-difluorophenyl)-4-((3-(trifluoromethyl)phenyl)sulfonyl)-3,4-dihydro-2H-benzo[b][1,4]oxazin-2-yl)methyl)tetrahydro-2H-pyran-4-carboxylicacid

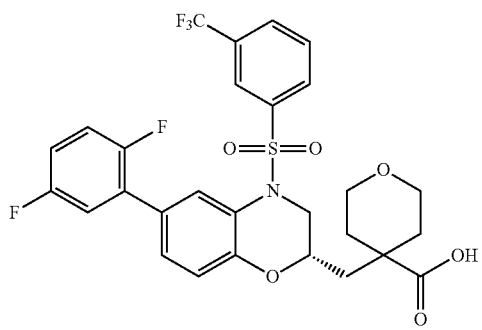 [SMILES: O=C(O)C1(C[C@H]2CN(S(=O)(=O)c3cccc(C(F)(F)F)c3)c3cc(-c4cc(F)ccc4F)ccc3O2)CCOCC1]

Part I—Synthesis of (S)-4-(oxiran-2-ylmethyl)tetrahydro-2H-pyran-4-carbonitrile

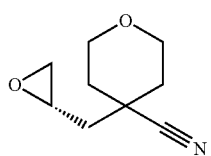 [SMILES: N#CC1(C[C@H]2CO2)CCOCC1]

A solution of 2.46 M n-butyllithium in hexanes (29 mL, 71 mmol) was added dropwise to a stirred solution of (S)-2-(chloromethyl)oxirane (6.0 g, 64.8 mmol) and oxane-4-carbonitrile (8.4 g, 75.6 mmol) in THF (70 mL) at −78° C. The mixture was stirred at −78° C. for two hours and then stirred overnight at room temperature. The mixture was quenched by the addition of saturated ammonium chloride, and extracted twice with dichloromethane. The combined organic layers were dried (Na$_2$SO$_4$) and concentrated. The residue was purified via MPLC eluting with 20% ethyl acetate in petroleum ether to afford (S)-4-(oxiran-2-ylmethyl)tetrahydro-2H-pyran-4-carbonitrile (4.5 g, 42%) as a colorless liquid.

Part II—Synthesis of (S)-4-((6-bromo-4-((3-(trifluoromethyl)phenyl)sulfonyl)-3,4-dihydro-2H-benzo[b][1,4]oxazin-2-yl)methyl)tetrahydro-2H-pyran-4-carbonitrile

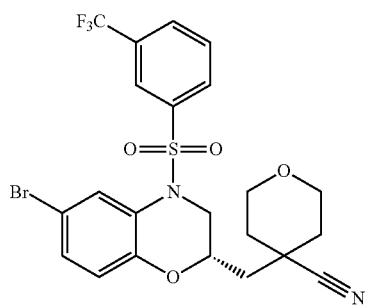 [SMILES: N#CC1(C[C@H]2CN(S(=O)(=O)c3cccc(C(F)(F)F)c3)c3cc(Br)ccc3O2)CCOCC1]

A mixture of (S)-4-(oxiran-2-ylmethyl)tetrahydro-2H-pyran-4-carbonitrile (2.5 g, 14.9 mmol), N-(5-bromo-2-fluorophenyl)-3-(trifluoromethyl)benzenesulfonamide (5.9 g, 14.8 mmol), tetra-n-butylammonium bromide (500 mg, 1.55 mmol), and potassium carbonate (200 mg, 1.45 mmol) was stirred for twelve hours at 60° C. Tetrahydrofuran (30 mL) and sodium hydroxide (2.4 g, 60 mmol) were then added; and the mixture was allowed to stir for an additional three hours at 60° C. The reaction was cooled and water was added. The mixture was extracted twice with ethyl acetate. The combined organic layers were dried (Na$_2$SO$_4$) and concentrated. The residue was purified via MPLC eluting with 33% ethyl acetate in petroleum ether to afford (S)-4-((6-bromo-4-((3-(trifluoromethyl)phenyl)sulfonyl)-3,4-dihydro-2H-benzo[b][1,4]oxazin-2-yl)methyl)tetrahydro-2H-pyran-4-carbonitrile (6.0 g, 74%) as a colorless oil.

Part III—Synthesis of (S)-4-((6-bromo-3,4-dihydro-2H-benzo[b][1,4]oxazin-2-yl)methyl)tetrahydro-2H-pyran-4-carboxylic acid

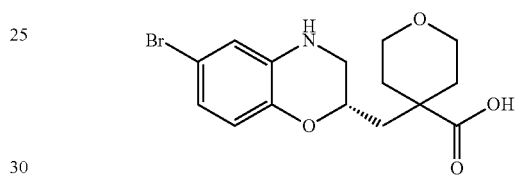

A mixture of (S)-4-((6-bromo-4-((3-(trifluoromethyl)phenyl)sulfonyl)-3,4-dihydro-2H-benzo[b][1,4]oxazin-2-yl)methyl)tetrahydro-2H-pyran-4-carbonitrile (3.0 g, 5.5 mmol), sulfuric acid (20 mL), acetic acid (20 mL), and water (20 mL) was stirred for a day at 100° C. The solution was diluted with water and was extracted three time with ethyl acetate. The combined organic layers were dried (Na$_2$SO$_4$) and concentrated. The residue was purified via MPLC eluting with 10% methanol in dichloromethane to afford (S)-4-((6-bromo-3,4-dihydro-2H-benzo[b][1,4]oxazin-2-yl)methyl)tetrahydro-2H-pyran-4-carboxylic acid (1.6 g, 82%) as a colorless oil.

Part IV—Synthesis of methyl (S)-4-((6-bromo-3,4-dihydro-2H-benzo[b][1,4]oxazin-2-yl)methyl)tetrahydro-2H-pyran-4-carboxylate

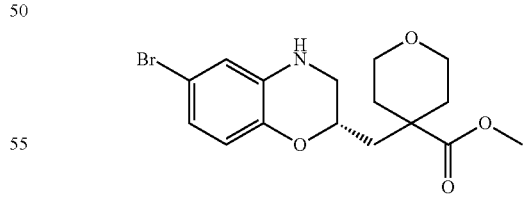

A mixture of (S)-4-((6-bromo-3,4-dihydro-2H-benzo[b][1,4]oxazin-2-yl)methyl)tetrahydro-2H-pyran-4-carboxylic acid (2 g, 5.61 mmol) in methanol (20 mL), and thionyl chloride (1.5 mL) was stirred for two days at 60° C. The pH value of the solution was adjusted to 9 with sodium bicarbonate. The mixture was extracted three times with ethyl acetate. The combined organic layers were dried (Na$_2$SO$_4$) and concentrated. The residue was purified via MPLC eluting with 50% ethyl acetate in petroleum ether to afford methyl (S)-4-((6-bromo-3,4-dihydro-2H-benzo[b][1,4]oxazin-2-yl)methyl)tetrahydro-2H-pyran-4-carboxylate (1.8 g, 87%) as a colorless oil.

Part V—Synthesis of methyl (S)-4-((6-bromo-4-((3-(trifluoromethyl)phenyl)sulfonyl)-3,4-dihydro-2H-benzo[b][1,4]oxazin-2-yl)methyl)tetrahydro-2H-pyran-4-carboxylate

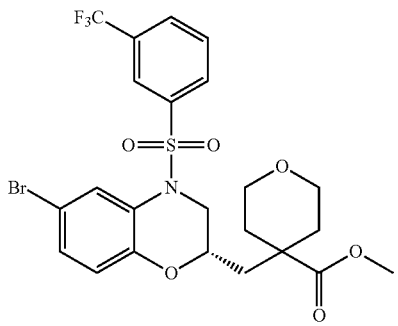 [SMILES: COC(=O)C1(C[C@H]2CN(S(=O)(=O)c3cccc(C(F)(F)F)c3)c3cc(Br)ccc3O2)CCOCC1]

A mixture methyl (S)-4-((6-bromo-3,4-dihydro-2H-benzo[b][1,4]oxazin-2-yl)methyl)tetrahydro-2H-pyran-4-carboxylate (1.8 g, 4.86 mmol), dichloromethane (20 mL), pyridine (10 mL), and 3-(trifluoromethyl)benzene-1-sulfonyl chloride (1.5 g, 6.13 mmol) was stirred overnight at room temperature. The solution was diluted with dichloromethane and washed three times with 1M hydrogen chloride. The organic layer was dried (Na$_2$SO$_4$) and concentrated. The residue was purified via MPLC eluting with 33% ethyl acetate in petroleum ether to afford methyl (S)-4-((6-bromo-4-((3-(trifluoromethyl)phenyl)sulfonyl)-3,4-dihydro-2H-benzo[b][1,4]oxazin-2-yl)methyl)tetrahydro-2H-pyran-4-carboxylate (2.4 g, 85%) as a white solid.

Part VI—Synthesis of methyl (S)-4-((6-(2,5-difluorophenyl)-4-((3-(trifluoromethyl)phenyl)sulfonyl)-3,4-dihydro-2H-benzo[b][1,4]oxazin-2-yl)methyl)tetrahydro-2H-pyran-4-carboxylate

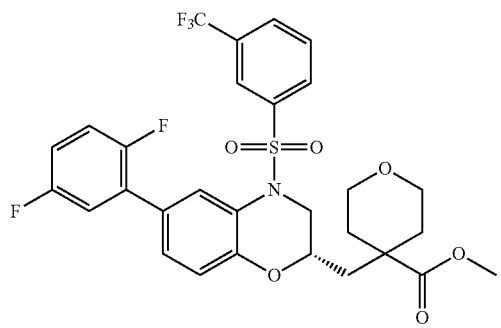 [SMILES: COC(=O)C1(C[C@H]2CN(S(=O)(=O)c3cccc(C(F)(F)F)c3)c3cc(-c4cc(F)ccc4F)ccc3O2)CCOCC1]

A mixture of methyl (S)-4-((6-bromo-4-((3-(trifluoromethyl)phenyl)sulfonyl)-3,4-dihydro-2H-benzo[b][1,4]oxazin-2-yl)methyl)tetrahydro-2H-pyran-4-carboxylate (500 mg, 0.86 mmol), (2,5-difluorophenyl)boronic acid (205 mg, 1.30 mmol), sodium carbonate (277 mg, 3.30 mmol), tetrakis(triphenylphosphine)palladium (100 mg, 0.09 mmol), toluene (10 mL), methanol (3 mL), and water (3 mL) was stirred for two hours at 90° C. The mixture was diluted with water and extracted twice with ethyl acetate. The combined organic layers were dried (Na$_2$SO$_4$) and concentrated. The residue was purified via MPLC eluting with 33% ethyl acetate in petroleum ether to afford methyl (S)-4-((6-(2,5-difluorophenyl)-4-((3-(trifluoromethyl)phenyl)sulfonyl)-3,4-dihydro-2H-benzo[b][1,4]oxazin-2-yl)methyl)tetrahydro-2H-pyran-4-carboxylate (500 mg, 95%) as a colorless oil.

Part VII—Synthesis of (S)-4-((6-(2,5-difluorophenyl)-4-((3-(trifluoromethyl)phenyl)sulfonyl)-3,4-dihydro-2H-benzo[b][1,4]oxazin-2-yl)methyl)tetrahydro-2H-pyran-4-carboxylicacid

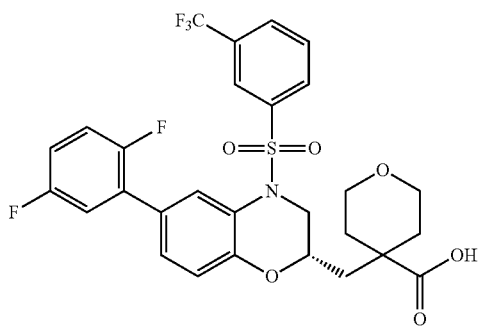 [SMILES: O=C(O)C1(C[C@H]2CN(S(=O)(=O)c3cccc(C(F)(F)F)c3)c3cc(-c4cc(F)ccc4F)ccc3O2)CCOCC1]

A mixture of methyl (S)-4-((6-(2,5-difluorophenyl)-4-((3-(trifluoromethyl)phenyl)sulfonyl)-3,4-dihydro-2H-benzo[b][1,4]oxazin-2-yl)methyl)tetrahydro-2H-pyran-4-carboxylate (70 mg, 0.11 mmol), tetrahydrofuran (3 mL), water (1 mL) and sodium hydroxide (46 mg, 1.15 mmol) was stirred for three days at 60° C. The pH value of the solution was adjusted to 5 with 1M HCl. The mixture was extracted twice with ethyl acetate. The combined organic layers were dried (Na$_2$SO$_4$) and concentrated. The residue was purified by Prep-HPLC eluting with a gradient of 58-67% acetonitrile in water with 0.05% trifluoroacetic acid to afford (S)-4-((6-(2,5-difluorophenyl)-4-((3-(trifluoromethyl)phenyl)sulfonyl)-3,4-dihydro-2H-benzo[b][1,4]oxazin-2-yl)methyl)tetrahydro-2H-pyran-4-carboxylic acid (14.9 mg, 22%) a white solid: $^1$H-NMR (300 MHz, CD$_3$OD) δ 8.09-7.95 (m, 4H), 7.80 (t, J=8.0 Hz, 1H), 7.36-7.19 (m, 3H), 7.13 (td, J=8.7, 8.2, 3.6 Hz, 1H), 6.90 (d, J=8.5 Hz, 1H), 4.41 (dd, J=14.5, 2.5 Hz, 1H), 3.89-3.73 (m, 2H), 3.68-3.44 (m, 3H), 2.09-1.76 (m, 4H), 1.61-1.41 (m, 2H), 1.32 (s, 1H). (ES, m/z): (M+H)$^+$ 598.

Example 58—Synthesis of (S)-4-((6-(3-(difluoromethoxy)-5-fluorophenyl)-4-((3-(trifluoromethyl)phenyl)sulfonyl)-3,4-dihydro-2H-benzo[b][1,4]oxazin-2-yl)methyl)tetrahydro-2H-pyran-4-carboxylicacid

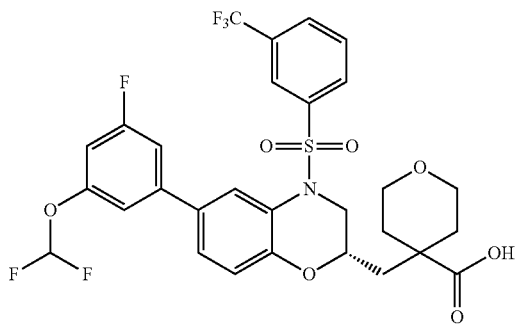 [SMILES: O=C(O)C1(C[C@H]2CN(S(=O)(=O)c3cccc(C(F)(F)F)c3)c3cc(-c4cc(F)cc(OC(F)F)c4)ccc3O2)CCOCC1]

Part I—Synthesis of methyl (S)-4-((6-(4,4,5,5-tetramethyl-1,3,2-dioxaborolan-2-yl)-4-((3-(trifluoromethyl)phenyl)sulfonyl)-3,4-dihydro-2H-benzo[b][1,4]oxazin-2-yl)methyl)tetrahydro-2H-pyran-4-carboxylate

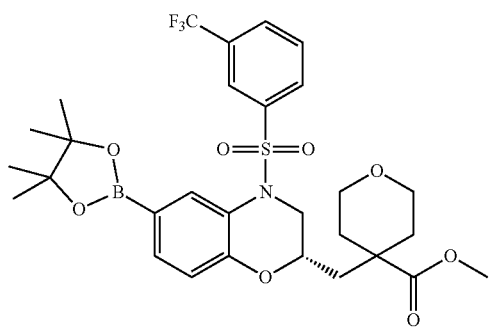

A mixture of methyl (S)-4-((6-bromo-4-((3-(trifluoromethyl)phenyl)sulfonyl)-3,4-dihydro-2H-benzo[b][1,4]oxazin-2-yl)methyl)tetrahydro-2H-pyran-4-carboxylate (1.0 g, 1.73 mmol), 4,4,5,5-tetramethyl-2-(tetramethyl-1,3,2-dioxaborolan-2-yl)-1,3,2-dioxaborolane (900 mg, 3.54 mmol), potassium acetate (800 mg, 8.15 mmol), [1,1'-bis(diphenylphosphino)ferrocene] dichloropalladium (II) complex with dichloromethane (150 mg, 0.21 mmol), and ethylene glycol dimethyl ether (10 mL) was stirred for two hours at 80° C. The mixture was concentrated and the residue was purified via MPLC eluting with 33% ethyl acetate in petroleum ether to afford methyl (S)-4-((6-(4,4,5,5-tetramethyl-1,3,2-dioxaborolan-2-yl)-4-((3-(trifluoromethyl)phenyl)sulfonyl)-3,4-dihydro-2H-benzo[b][1,4]oxazin-2-yl)methyl)tetrahydro-2H-pyran-4-carboxylate (1.0 g, 92%) as a colorless oil.

Part II—Synthesis of methyl (S)-4-((6-(3-(difluoromethoxy)-5-fluorophenyl)-4-((3-(trifluoromethyl)phenyl)sulfonyl)-3,4-dihydro-2H-benzo[b][1,4]oxazin-2-yl)methyl)tetrahydro-2H-pyran-4-carboxylate

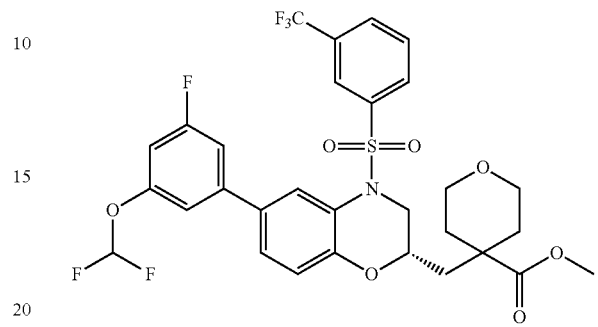

A mixture of methyl (S)-4-((6-(4,4,5,5-tetramethyl-1,3,2-dioxaborolan-2-yl)-4-((3-(trifluoromethyl)phenyl)sulfonyl)-3,4-dihydro-2H-benzo[b][1,4]oxazin-2-yl)methyl)tetrahydro-2H-pyran-4-carboxylate (700 mg, 1.12 mmol), 1-bromo-3-(difluoromethoxy)-5-fluorobenzene (403 mg, 1.67 mmol), sodium carbonate (356 mg, 4.24 mmol), tetrakis(triphenylphosphine)palladium (130 mg, 0.11 mmol), toluene (10 mL), methanol (3 mL) and water (3 mL) was stirred for three hours at 90° C. The mixture was diluted with water and extracted three times with ethyl acetate. The combined organic layers were dried (Na$_2$SO$_4$) and concentrated. The residue was purified via MPLC eluting with 33% ethyl acetate in petroleum ether to afford methyl (S)-4-((6-(3-(difluoromethoxy)-5-fluorophenyl)-4-((3-(trifluoromethyl)phenyl)sulfonyl)-3,4-dihydro-2H-benzo[b][1,4]oxazin-2-yl)methyl)tetrahydro-2H-pyran-4-carboxylate (700 mg, 95%) as a colorless oil.

Part III—Synthesis of (S)-4-((6-(3-(difluoromethoxy)-5-fluorophenyl)-4-((3-(trifluoromethyl)phenyl)sulfonyl)-3,4-dihydro-2H-benzo[b][1,4]oxazin-2-yl)methyl)tetrahydro-2H-pyran-4-carboxylic acid

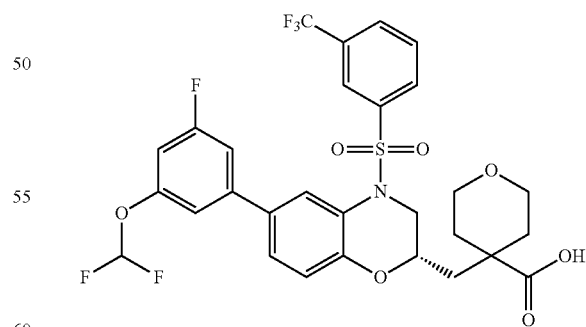

Based on the procedure in Example 57, Part VII, (S)-4-((6-(3-(difluoromethoxy)-5-fluorophenyl)-4-((3-(trifluoromethyl)phenyl)sulfonyl)-3,4-dihydro-2H-benzo[b][1,4]oxazin-2-yl)methyl)tetrahydro-2H-pyran-4-carboxylic acid was prepared: $^1$H-NMR (300 MHz, CD$_3$OD) δ 8.07 (d, J=2.2 Hz, 1H), 8.01 (d, J=7.8 Hz, 1H), 7.95 (d, J=9.8 Hz, 2H), 7.80 (t, J=7.8 Hz, 1H), 7.43 (dd, J=8.6, 2.3 Hz, 1H), 7.27-7.19 (m, 2H), 7.01-6.72 (m, 3H), 4.39 (dd, J=14.5, 2.5 Hz, 1H), 3.80 (dq, J=11.7, 3.9 Hz, 2H), 3.67-3.43 (m, 3H), 3.32-3.26 (m, 1H), 2.08-1.88 (m, 3H), 1.80 (dd, J=14.7, 3.7 Hz, 1H), 1.61-1.29 (m, 2H). (ES, m/z): (M+H)+ 646.

Example 59—Synthesis of (1S,3r)-3-(((S)-6-(3-(difluoromethoxy)-5-fluorophenyl)-4-((3-(trifluoromethyl)phenyl)sulfonyl)-3,4-dihydro-2H-benzo[b][1,4]oxazin-2-yl)methyl)cyclobutane-1-carboxylicacid

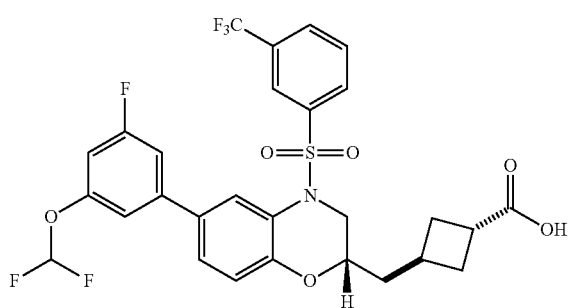

Part I—Synthesis of (S)-2-((6-bromo-4-((3-(trifluoromethyl)phenyl)sulfonyl)-3,4-dihydro-2H-benzo[b][1,4]oxazin-2-yl)methyl)propane-1,3-diol

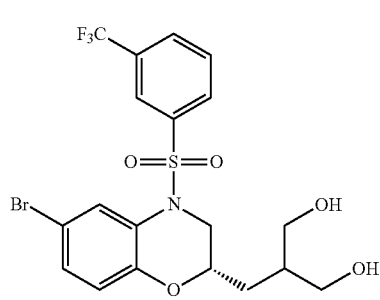 [SMILES: O=S(=O)(c1cccc(C(F)(F)F)c1)N1C[C@H](CC(CO)CO)Oc2ccc(Br)cc21]

A mixture of dimethyl (S)-2-((6-bromo-4-((3-(trifluoromethyl)phenyl)sulfonyl)-3,4-dihydro-2H-benzo[b][1,4]oxazin-2-yl)methyl)malonate (2.2 g, 3.88 mmol), tetrahydrofuran (50 mL) and lithium borohydride (343 mg) was stirred for three hours at room temperature. Methanol was added and the mixture was partitioned between water and ethyl acetate. The organic layers were washed twice with water, dried (Na₂SO₄) and concentrated to afford (S)-2-((6-bromo-4-((3-(trifluoromethyl)phenyl)sulfonyl)-3,4-dihydro-2H-benzo[b][1,4]oxazin-2-yl)methyl)propane-1,3-diol (2 g) as a colorless oil.

Part II—Synthesis of (S)-2-((6-bromo-4-((3-(trifluoromethyl)phenyl)sulfonyl)-3,4-dihydro-2H-benzo[b][1,4]oxazin-2-yl)methyl)propane-1,3-diyl dimethanesulfonate

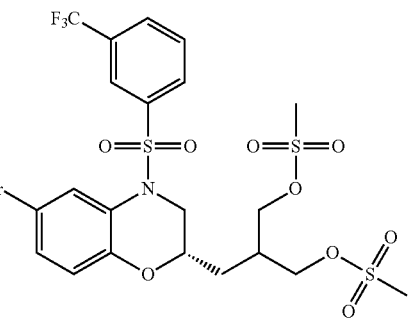

A solution of (S)-2-((6-bromo-4-((3-(trifluoromethyl)phenyl)sulfonyl)-3,4-dihydro-2H-benzo[b][1,4]oxazin-2-yl)methyl)propane-1,3-diol (2.1 g, 4.12 mmol), dichloromethane (20 mL), triethyl amine (2.0 g, 19.8 mmol), and methane sulfonyl chloride (1.28 g) was stirred for an hour at room temperature. The mixture was diluted with water and extracted twice with dichloromethane. The combined organic layers were washed with brine, dried (Na₂SO₄) and concentrated. The residue was purified via MPLC eluting with 50% ethyl acetate in petroleum ether to afford (S)-2-((6-bromo-4-((3-(trifluoromethyl)phenyl)sulfonyl)-3,4-dihydro-2H-benzo[b][1,4]oxazin-2-yl)methyl)propane-1,3-diyl dimethanesulfonate (2.0 g, 73%) as a white solid.

Part III—Synthesis of dimethyl (S)-3-((6-bromo-4-((3-(trifluoromethyl)phenyl)sulfonyl)-3,4-dihydro-2H-benzo[b][1,4]oxazin-2-yl)methyl)cyclobutane-1,1-dicarboxylate

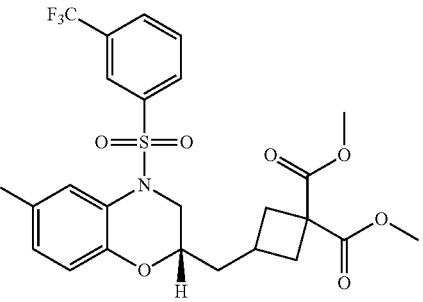

Sodium hydride (180 mg) was added to a solution of (S)-2-((6-bromo-4-((3-(trifluoromethyl)phenyl)sulfonyl)-3,4-dihydro-2H-benzo[b][1,4]oxazin-2-yl)methyl)propane-1,3-diyl dimethanesulfonate (1.5 g, 2.25 mmol) and 1,3-dimethyl propanedioate (540 mg, 4.09 mmol) in dioxane (20 mL). The mixture was stirred overnight at 105° C. Methanol (2 mL) was added and the mixture was diluted ethyl acetate. The mixture was washed twice with water and brine, dried (Na₂SO₄) and concentrated. The residue was purified via MPLC eluting with 25% ethyl acetate in petroleum ether to afford dimethyl (S)-3-((6-bromo-4-((3-(trifluoromethyl)

phenyl)sulfonyl)-3,4-dihydro-2H-benzo[b][1,4]oxazin-2-yl) methyl)cyclobutane-1,1-dicarboxylate (700 mg, 51%) as a white solid.

Part IV—Synthesis of (S)-3-((6-bromo-4-((3-(trifluoromethyl)phenyl)sulfonyl)-3,4-dihydro-2H-benzo[b][1,4]oxazin-2-yl)methyl)cyclobutane-1,1-dicarboxylic acid

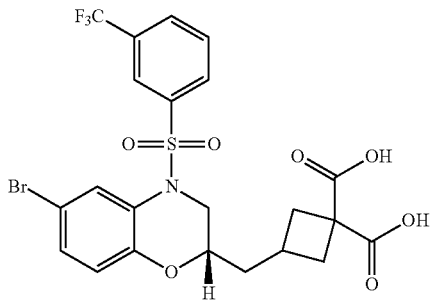 [SMILES: O=C(O)C1(C(=O)O)CC(C[C@H]2CN(S(=O)(=O)c3cccc(C(F)(F)F)c3)c3cc(Br)ccc3O2)C1]

A mixture of dimethyl (S)-3-((6-bromo-4-((3-(trifluoromethyl)phenyl)sulfonyl)-3,4-dihydro-2H-benzo[b][1,4]oxazin-2-yl)methyl)cyclobutane-1,1-dicarboxylate (820 mg, 1.35 mmol), tetrahydrofuran (10 mL), water (3 mL), and lithium hydroxide (325 mg, 13.6 mmol) was stirred for three hours at room temperature. 1 N HCl was added, and the mixture was extracted twice with ethyl acetate. The combined organic layers were washed with brine, dried (Na$_2$SO$_4$) and concentrated to afford (S)-3-((6-bromo-4-((3-(trifluoromethyl)phenyl)sulfonyl)-3,4-dihydro-2H-benzo[b][1,4]oxazin-2-yl)methyl)cyclobutane-1,1-dicarboxylic acid (750 mg, 96%) as a colorless oil.

Part V—Synthesis of (1S,3r)-3-(((S)-6-bromo-4-((3-(trifluoromethyl)phenyl)sulfonyl)-3,4-dihydro-2H-benzo[b][1,4]oxazin-2-yl)methyl)cyclobutane-1-carboxylicacid

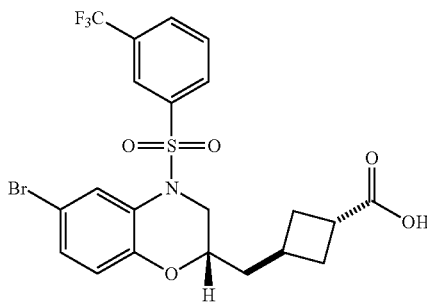

A mixture of (S)-3-((6-bromo-4-((3-(trifluoromethyl)phenyl)sulfonyl)-3,4-dihydro-2H-benzo[b][1,4]oxazin-2-yl) methyl)cyclobutane-1,1-dicarboxylic acid (700 mg, 1.21 mmol) and pyridine (5 mL) was stirred overnight at 120° C. The mixture was diluted with ethyl acetate and washed three times with 1M hydrogen chloride. The organic layer was dried (Na$_2$SO$_4$) and concentrated. The residue was purified via MPLC eluting with 50% ethyl acetate in petroleum ether to afford (1S,3r)-3-(((S)-6-bromo-4-((3-(trifluoromethyl) phenyl)sulfonyl)-3,4-dihydro-2H-benzo[b][1,4]oxazin-2-yl) methyl)cyclobutane-1-carboxylic acid (400 mg, 62%) as a colorless oil.

Part VI—Synthesis of (1,3r)-3-(((S)-6-(4,4,5,5-tetramethyl-1,3,2-dioxaborolan-2-yl)-4-((3-(trifluoromethyl)phenyl)sulfonyl)-3,4-dihydro-2H-benzo[b][1,4]oxazin-2-yl)methyl)cyclobutane-1-carboxylicacid

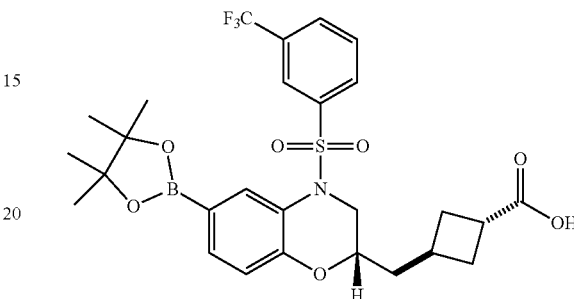

A mixture of (1S,3r)-3-(((S)-6-bromo-4-((3-(trifluoromethyl)phenyl)sulfonyl)-3,4-dihydro-2H-benzo[b][1,4]oxazin-2-yl)methyl)cyclobutane-1-carboxylic acid (300 mg, 0.56 mmol), 4,4,5,5-tetramethyl-2-(tetramethyl-1,3,2-dioxaborolan-2-yl)-1,3,2-dioxaborolane (286 mg), potassium acetate (221 mg, 2.25 mmol), [1,1'-bis(diphenylphosphino) ferrocene]dichloropalladium (II) complex with dichloromethane (65 mg, 0.09 mmol), and ethylene glycol dimethyl ether (10 mL) was stirred for four hours at 80° C. The mixture was diluted with water and extracted three times with ethyl acetate. The combined organic layers were dried (Na$_2$SO$_4$) and concentrated. The residue was purified via MPLC eluting with 33% ethyl acetate in petroleum ether to afford (1S,3r)-3-(((S)-6-(4,4,5,5-tetramethyl-1,3,2-dioxaborolan-2-yl)-4-((3-(trifluoromethyl)phenyl)sulfonyl)-3,4-dihydro-2H-benzo[b][1,4]oxazin-2-yl)methyl)cyclobutane-1-carboxylic acid (300 mg, 92%) as a colorless oil.

Part VII—Synthesis of (1S,3r)-3-(((S)-6-(3-(difluoromethoxy)-5-fluorophenyl)-4-((3-(trifluoromethyl) phenyl)sulfonyl)-3,4-dihydro-2H-benzo[b][1,4]oxazin-2-yl)methyl)cyclobutane-1-carboxylicacid

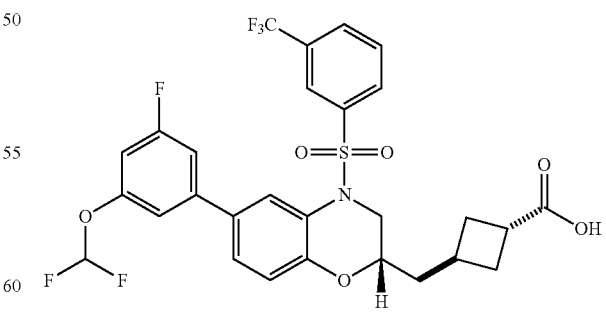

A mixture of (1S,3r)-3-(((S)-6-(4,4,5,5-tetramethyl-1,3,2-dioxaborolan-2-yl)-4-((3-(trifluoromethyl)phenyl)sulfonyl)-3,4-dihydro-2H-benzo[b][1,4]oxazin-2-yl)methyl)cyclobutane-1-carboxylic acid (100 mg, 0.17 mmol), 1-bromo-3-(difluoromethoxy)-5-fluorobenzene (66 mg, 0.27 mmol), sodium carbonate (55 mg, 0.52 mmol), tetrakis(triphenylphosphine)palladium (20 mg, 0.02 mmol), toluene (6 mL), methanol (2 mL) and water (2 mL) was stirred for two hours at 90° C. The mixture was diluted with water and extracted twice with ethyl acetate. The combined organic layers were dried (Na₂SO₄) and concentrated. The residue was purified by Prep-HPLC eluting with a gradient of 60-80% acetonitrile in water with 0.05% trifluoroacetic acid to afford (1S,3r)-3-(((S)-6-(3-(difluoromethoxy)-5-fluorophenyl)-4-((3-(trifluoromethyl)phenyl)sulfonyl)-3,4-dihydro-2H-benzo[b][1,4]oxazin-2-yl)methyl)cyclobutane-1-carboxylic acid (20.3 mg, 19%) as a white solid: ¹H-NMR (300 MHz, CD₃OD) δ 8.12-7.89 (m, 4H), 7.78 (t, J=7.9 Hz, 1H), 7.41 (dd, J=8.6, 2.3 Hz, 1H), 7.27-7.14 (m, 2H), 7.02-6.66 (m, 3H), 4.43-4.26 (m, 1H), 3.29-3.19 (m, 2H), 3.12-2.95 (m, 11H), 2.64-2.17 (m, 3H), 2.01-1.76 (m, 2H), 1.75-1.56 (m, 2H). (ES, m/z): (M+H)⁺ 616.

Example 60—Preparation of Additional Substituted 4-(Aryl sulfonyl)-3,4-dihydro-2H-benzo[b][1,4]oxazin-2-yl) Compounds Compounds in Table 17 were prepared based on experimental procedures described in Examples 12, 13, 59, 69, 70, 71, and 72 and the detailed description. ¹H NMR data for exemplary compounds from Table 17 is provided in Table 17A.

TABLE 17

| Compd No. | Structure | Name | Observed m/z |
|---|---|---|---|
| 60A | 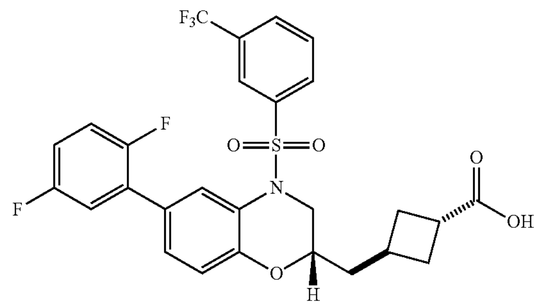 | (1S,3r)-3-(((S)-6-(2,5-difluorophenyl)-4-((3-(trifluoromethyl)-phenyl)sulfonyl)-3,4-dihydro-2H-benzo[b][1,4]oxazin-2-yl)methyl)cyclobutane-1-carboxylic acid | 568 (M + H)⁺ |
| 60B | 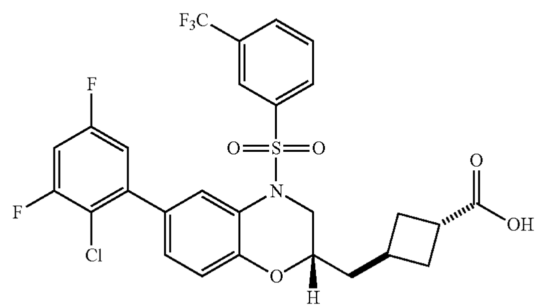 | (1S,3r)-3-(((S)-6-(2-chloro-3,5-difluorophenyl)-4-((3-(trifluoromethyl)phenyl)sulfonyl)-3,4-dihydro-2H-benzo[b][1,4]oxazin-2-yl)methyl)cyclobutane-1-carboxylic acid | 600 (M − H)⁻ |
| 60C | 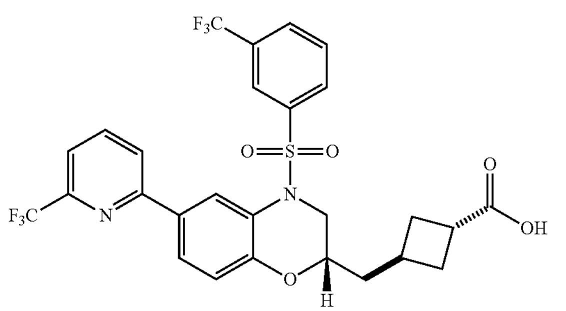 | (1S,3r)-3-(((S)-4-((3-(trifluoromethyl)phenyl)sulfonyl)-6-(6-(trifluoromethyl)pyridin-2-yl)-3,4-dihydro-2H-benzo[b][1,4]-oxazin-2-yl)methyl)cyclobutane-1-carboxylic acid | 601 (M + H)⁺ |
| 60D | 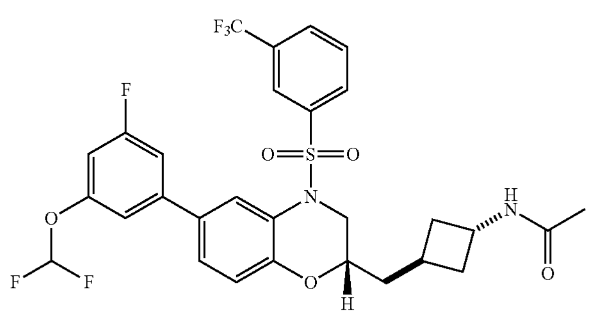 | N-((1S,3r)-3-(((S)-6-(3-(difluoro-methoxy)-5-fluorophenyl)-4-((3-(trifluoromethyl)-phenyl)sulfonyl)-3,4-dihydro-2H-benzo[b][1,4]-oxazin-2-yl)methyl)cyclobutyl)-acetamide | 629 (M + H)⁺ |

TABLE 17-continued

| Compd No. | Structure | Name | Observed m/z |
|---|---|---|---|
| 60E | 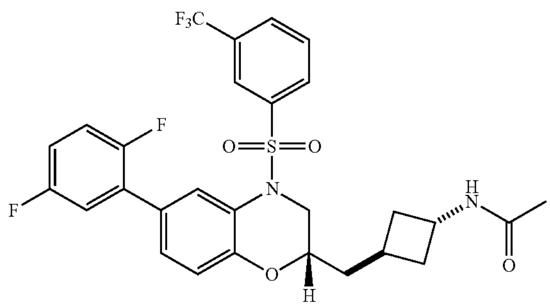 | N-((1S,3r)-3-(((S)-6-(2,5-difluorophenyl)-4-((3-(trifluoromethyl)phenyl)sulfonyl)-3,4-dihydro-2H-benzo[b][1,4]oxazin-2-yl)methyl)cyclobutyl)-acetamide | 581 (M + H)+ |
| 60F | 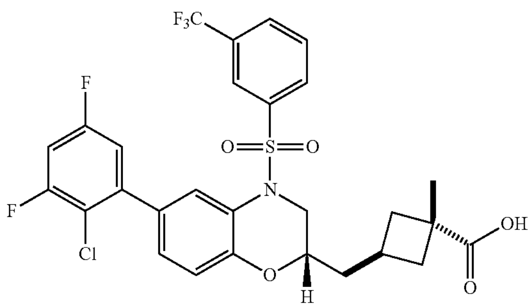 | (1S,3r)-3-(((S)-6-(2-chloro-3,5-difluorophenyl)-4-((3-(trifluoromethyl)phenyl)sulfonyl)-3,4-dihydro-2H-benzo[b][1,4]oxazin-2-yl)methyl)-1-methylcyclobutane-1-carboxylic acid | 614 (M − H)− |
| 60G | 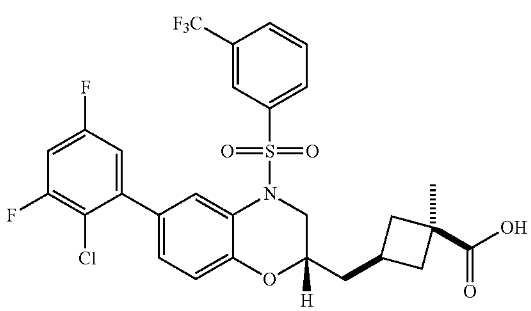 | (1R,3s)-3-(((S)-6-(2-chloro-3,5-difluorophenyl)-4-((3-(trifluoromethyl)phenyl)sulfonyl)-3,4-dihydro-2H-benzo[b][1,4]oxazin-2-yl)methyl)-1-methylcyclobutane-1-carboxylic acid | 614 (M − H)− |
| 60H | 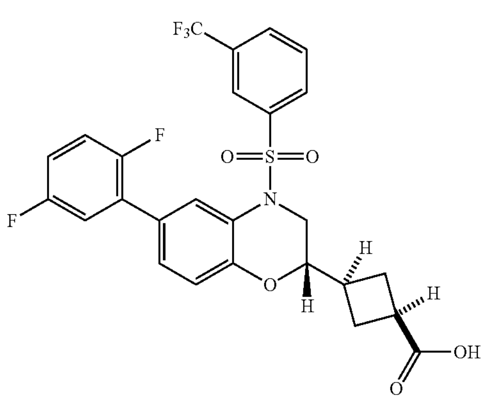 [SMILES: O=C(O)[C@H]1C[C@@H]([C@H]2CN(S(=O)(=O)c3cccc(C(F)(F)F)c3)c3cc(-c4cc(F)ccc4F)ccc3O2)C1] | (1R,3s)-3-((S)-6-(2,5-difluorophenyl)-4-((3-(trifluoromethyl)phenyl)sulfonyl)-3,4-dihydro-2H-benzo[b][1,4]oxazin-2-yl)cyclobutane-1-carboxylic acid | 571 (M + NH4)+ |

TABLE 17-continued

| Compd No. | Structure | Name | Observed m/z |
|---|---|---|---|
| 60I | 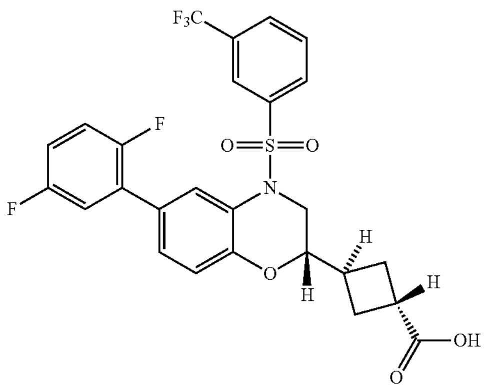 [SMILES: O=C(O)[C@H]1C[C@H]([C@H]2CN(S(=O)(=O)c3cccc(C(F)(F)F)c3)c3cc(-c4cc(F)ccc4F)ccc3O2)C1] | (1S,3r)-3-((S)-6-(2,5-difluoro-phenyl)-4-((3-(trifluoromethyl)-phenyl)sulfonyl)-3,4-dihydro-2H-benzo[b][1,4]oxazin-2-yl)cyclobutane-1-carboxylic acid | 571 (M + NH$_4$)$^+$ |
| 60J | 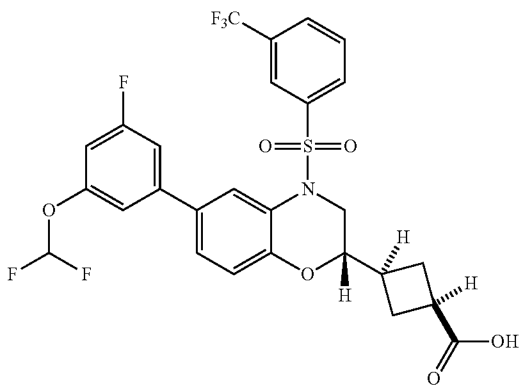 [SMILES: O=C(O)[C@H]1C[C@@H]([C@H]2CN(S(=O)(=O)c3cccc(C(F)(F)F)c3)c3cc(-c4cc(F)cc(OC(F)F)c4)ccc3O2)C1] | (1R,3s)-3-((S)-6-(3-(difluoro-methoxy)-5-fluorophenyl)-4-((3-(trifluoromethyl)phenyl)-sulfonyl)-3,4-dihydro-2H-benzo[b][1,4]-oxazin-2-yl)cyclobutane-1-carboxylic acid | 624 (M + Na)$^+$ |
| 60K | 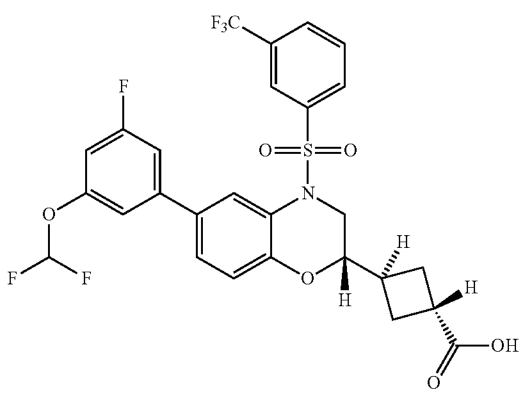 [SMILES: O=C(O)[C@H]1C[C@H]([C@H]2CN(S(=O)(=O)c3cccc(C(F)(F)F)c3)c3cc(-c4cc(F)cc(OC(F)F)c4)ccc3O2)C1] | (1S,3r)-3-((S)-6-(3-(difluoro-methoxy)-5-fluorophenyl)-4-((3-(trifluoromethyl)phenyl)-sulfonyl)-3,4-dihydro-2H-benzo[b][1,4]oxazin-2-yl)cyclobutane-1-carboxylic acid | 600 (M − H)$^-$ |
| 60L | 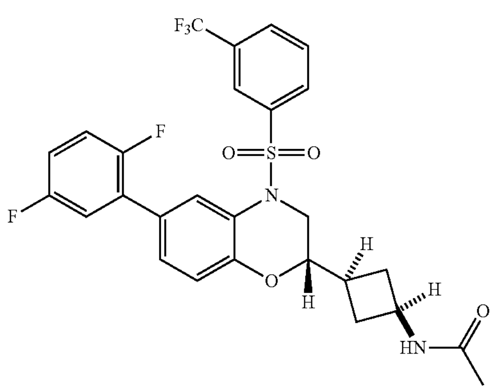 [SMILES: CC(=O)N[C@H]1C[C@@H]([C@H]2CN(S(=O)(=O)c3cccc(C(F)(F)F)c3)c3cc(-c4cc(F)ccc4F)ccc3O2)C1] | N-((1R,3s)-3-((S)-6-(2,5-difluorophenyl)-4-((3-(trifluoro-methyl)phenyl)sulfonyl)-3,4-dihydro-2H-benzo[b][1,4]-oxazin-2-yl)cyclobutyl)-acetamide | 567 (M + H)$^+$ |

TABLE 17-continued

| Compd No. | Structure | Name | Observed m/z |
|---|---|---|---|
| 60M | 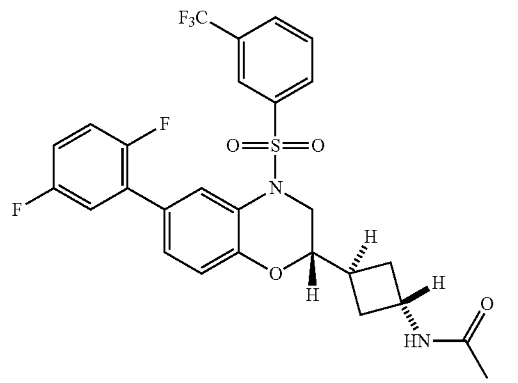 [SMILES: CC(=O)N[C@H]1C[C@H]([C@H]2CN(S(=O)(=O)c3cccc(C(F)(F)F)c3)c3cc(-c4cc(F)ccc4F)ccc3O2)C1] | N-((1S,3r)-3-((S)-6-(2,5-difluorophenyl)-4-((3-(trifluoromethyl)phenyl)sulfonyl)-3,4-dihydro-2H-benzo[b][1,4]-oxazin-2-yl)cyclobutyl)-acetamide | 567 (M + H)+ |
| 60N | 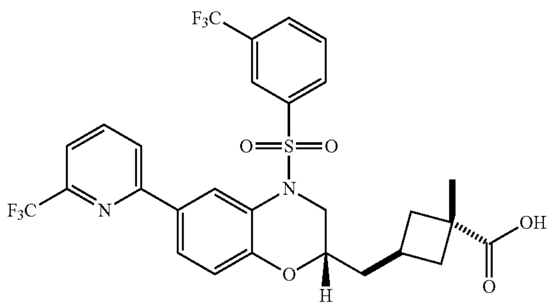 | (1S,3r)-1-methyl-3-(((S)-4-((3-(trifluoromethyl)phenyl)-sulfonyl)-6-(6-(trifluoromethyl)pyridin-2-yl)-3,4-dihydro-2H-benzo[b][1,4]-oxazin-2-yl)methyl)cyclobutane-1-carboxylic acid | 615 (M + H)+ |
| 60O | 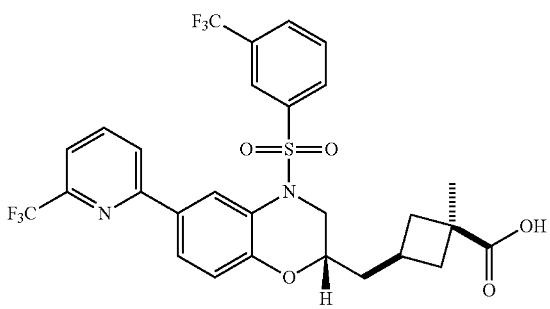 | (1R,3s)-1-methyl-3-(((S)-4-((3-(trifluoromethyl)phenyl)-sulfonyl)-6-(6-(trifluoromethyl)pyridin-2-yl)-3,4-dihydro-2H-benzo[b][1,4]-oxazin-2-yl)methyl)cyclobutane-1-carboxylic acid | 615 (M + H)+ |

TABLE 17A

| Compd No. | Physical Characterization Data |
|---|---|
| 60A | $^1$H NMR (400 MHz, CD$_3$OD-d$_4$) δ 8.07-7.92 (m, 4H), 7.84-7.71 (m, 1H), 7.35-7.02 (m, 4H), 6.89 (dd, J = 8.4, 1.0 Hz, 1H), 4.45-4.26 (m, 1H), 3.30-3.17 (m, 2H), 3.14-2.92 (m, 1H), 2.64-2.19 (m, 3H), 2.00-1.78 (m, 2H), 1.76-1.54 (m, 2H). |
| 60B | $^1$H NMR (400 MHz, CD$_3$OD-d$_4$) δ 7.99 (t, J = 7.1 Hz, 2H), 7.94-7.88 (m, 2H), 7.80 (t, J = 7.9 Hz, 1H), 7.25-7.11 (m, 2H), 7.10-6.98 (m, 1H), 6.91 (dd, J = 8.5, 1.0 Hz, 1H), 4.45-4.29 (m, 1H), 3.29-3.20 (m, 2H), 3.13-2.92 (m, 1H), 2.64-2.15 (m, 3H), 2.00-1.78 (m, 2H), 1.77-1.54 (m, 2H). |
| 60C | $^1$H NMR (300 MHz, CD$_3$OD-d$_4$) δ 8.61-8.53 (m, 1H), 8.11-7.93 (m, 5H), 7.85 (dd, J = 8.6, 2.1 Hz, 1H), 7.76 (t, J = 7.9 Hz, 1H), 7.71-7.64 (m, 1H), 6.93 (d, J = 8.6 Hz, 1H), 4.42-4.29 (m, 1H), 3.47-3.32 (m, 2H), 3.15-2.91 (m, 1H), 2.67-2.16 (m, 3H), 2.08-1.55 (m, 4H). |
| 60D | $^1$H NMR (300 MHz, CD$_3$OD-d$_4$) δ 8.08-7.89 (m, 4H), 7.78 (t, J = 8.1 Hz, 1H), 7.42 (dd, J = 8.6, 2.2 Hz, 1H), 7.30-6.68 (m, 5H), 4.48-4.04 (m, 2H), 3.30-3.20 (m, 2H), 2.57-1.96 (m, 4H), 1.92 (d, J = 7.2 Hz, 3H), 1.80-1.64 (m, 2H), 1.62-1.46 (m, 1H). |
| 60E | $^1$H NMR (300 MHz, CD$_3$OD-d$_4$) δ 8.03-7.88 (m, 4H), 7.74 (t, J = 7.9 Hz, 1H), 7.34-7.14 (m, 3H), 7.13-6.99 (m, 1H), 6.91-6.81 (m, 1H), 4.43-3.98 (m, 2H), 3.27-3.16 (m, 2H), 2.54-1.92 (m, 4H), 1.88 (d, J = 7.3 Hz, 3H), 1.79-1.58 (m, 2H), 1.54-1.37 (m, 1H). |
| 60F | $^1$H NMR (300 MHz, CD$_3$OD-d$_4$) δ 8.03 (d, J = 7.9 Hz, 1H), 8.00-7.91 (m, 3H), 7.81 (t, J = 7.9 Hz, 1H), 7.25-7.17 (m, 2H), 7.07 (ddd, J = 9.1, 3.0, 1.8 Hz, 1H), 6.93 (d, J = 8.5 Hz, |

TABLE 17A-continued

| Compd No. | Physical Characterization Data |
|---|---|
| | 1H), 4.37 (d, J = 12.6 Hz, 1H), 3.31-3.18 (m, 2H), 2.64-2.54 (m, 1H), 2.48 (p, J = 7.4, 6.9 Hz, 2H), 1.76-1.48 (m, 4H), 1.34 (s, 3H). |
| 60G | $^1$H NMR (300 MHz, CD$_3$OD-d$_4$) δ 8.06-7.89 (m, 4H), 7.80 (t, J = 7.7 Hz, 1H), 7.24-7.14 (m, 2H), 7.04 (dt, J = 8.7, 2.3 Hz, 1H), 6.92 (d, J = 8.5 Hz, 1H), 4.42-4.30 (m, 1H), 2.47 (q, J = 8.2 Hz, 1H), 2.14-1.81 (m, 4H), 1.75-1.56 (m, 2H), 1.42 (s, 3H). |
| 60H | $^1$H NMR (300 MHz, CD$_3$OD-d$_4$) δ 8.02-7.97 (m, 4H), 7.82 (t, J = 8.0 Hz, 1H), 7.35 (d, J = 8.1 Hz, 1H), 7.27-7.20 (m, 2H), 7.15-7.05 (m, 1H), 6.96 (d, J = 8.8 Hz, 1H), 4.32 (d, J = 14.4 Hz, 1H), 3.40-3.32 (m, 1H), 3.22-3.11 (m, 1H), 3.10-3.05 (m, 1H), 2.49-2.41 (m, 1H), 2.36-2.28 (m, 2H), 2.17-2.05 (m, 2H). |
| 60I | $^1$H NMR (300 MHz, CD$_3$OD-d$_4$) δ 8.02-7.97 (m, 4H), 7.82 (t, J = 8.0 Hz, 1H), 7.35 (d, J = 8.1 Hz, 1H), 7.27-7.20 (m, 2H), 7.15-7.05 (m, 1H), 6.96 (d, J = 8.8 Hz, 1H), 4.32 (d, J = 14.4 Hz, 1H), 3.40-3.32 (m, 1H), 3.22-3.11 (m, 1H), 3.10-2.95 (m, 1H), 2.59-2.51 (m, 1H), 2.42-2.35 (m, 2H), 2.25-2.15 (m, 2H) |
| 60J | $^1$H NMR (300 MHz, CD$_3$OD-d$_4$) δ 8.08-7.98 (m, 4H), 7.82 (t, J = 7.8 Hz, 1H), 7.45 (d, J = 10.4 Hz, 1H), 7.25-6.80 (m, 5H), 4.32 (d, J = 14.4 Hz, 1H), 3.40-3.36 (m, 1H), 3.22-3.17 (m, 1H), 3.15-2.85 (m, 1H), 2.60-2.50 (m, 1H), 2.45-2.32 (m, 2H), 2.22-2.12 (m, 2H) |
| 60K | $^1$H NMR (300 MHz, CD$_3$OD-d$_4$) δ 8.05-7.95 (m, 4H), 7.83 (t, J = 7.8 Hz, 1H), 7.42 (d, J = 10.4 Hz, 1H), 7.25-6.80 (m, 5H), 4.30 (d, J = 14.4 Hz, 1H), 3.31-3.27 (m, 1H), 3.22-3.18 (m, 1H), 3.10-2.85 (m, 1H), 2.45-2.37 (m, 1H), 2.32-2.28 (m, 2H), 2.15-2.05 (m, 2H) |
| 60L | $^1$H NMR (300 MHz, CD$_3$OD-d$_4$) δ 8.02-7.98 (m, 4H), 7.82 (t, J = 8.0 Hz, 1H), 7.35 (d, J = 8.1 Hz, 1H), 7.28-7.20 (m, 2H), 7.13-7.08 (m, 1H), 6.97 (d, J = 8.8 Hz, 1H), 4.36 (d, J = 14.4 Hz, 1H), 4.25-4.15 (m, 1H), 3.45-3.35 (m, 1H), 3.25-3.18 (m, 1H), 2.45-2.05 (m, 5H), 1.95 (s, 3H) |
| 60M | $^1$H NMR (300 MHz, CD$_3$OD-d$_4$) δ 8.02-7.98 (m, 4H), 7.82 (t, J = 8.0 Hz, 1H), 7.35 (d, J = 8.1 Hz, 1H), 7.28-7.20 (m, 2H), 7.13-7.08 (m, 1H), 6.97 (d, J = 8.8 Hz, 1H), 4.36 (d, J = 14.4 Hz, 1H), 4.25-4.15 (m, 1H), 3.45-3.35 (m, 1H), 3.25-3.18 (m, 1H), 2.42-2.38 (m, 2H), 2.30-2.20 (m, 1H), 1.95 (s, 3H), 1.90-1.80 (m, 2H) |
| 60N | $^1$H NMR (300 MHz, CD$_3$OD-d$_4$) δ 8.58 (d, J = 2.1 Hz, 1H), 8.06 (d, J = 4.2 Hz, 2H), 8.03-7.93 (m, 3H), 7.87 (dd, J = 8.7, 2.2 Hz, 1H), 7.76 (t, J = 7.9 Hz, 1H), 7.71-7.61 (m, 1H), 6.94 (d, J = 8.6 Hz, 1H), 4.35 (dd, J = 13.8, 1.7 Hz, 1H), 3.42-3.35 (m, 1H), 3.28-3.20 (m, 1H), 2.57-2.43 (m, 1H), 2.19-1.94 (m, 3H), 1.93-1.84 (m, 1H), 1.77-1.55 (m, 2H), 1.42 (s, 3H). |
| 60O | $^1$H NMR (300 MHz, CD$_3$OD-d$_4$) δ 8.60 (d, J = 2.1 Hz, 1H), 8.09-8.06 (m, 2H), 8.04 (d, J = 1.7 Hz, 1H), 8.03-7.98 (m, 2H), 7.88 (dd, J = 8.6, 2.1 Hz, 1H), 7.82 (s, 2H), 7.78 (t, J = 7.9 Hz, 1H), 7.72-7.68 (m, 1H), 6.96 (d, J = 8.6 Hz, 1H), 4.36 (dd, J = 13.7, 1.6 Hz, 1H), 3.44-3.36 (m, 1H), 3.32-3.20 (m, 1H), 2.68-2.57 (m, 1H), 2.57-2.44 (m, 2H), 1.81-1.60 (m, 3H), 1.60-1.50 (m, 1H), 1.34 (s, 3H). |

Example 61—Synthesis of (S)-1-(3-((6-(3-(difluoromethoxy)-5-fluorophenyl)-4-((3-(trifluoromethyl)phenyl)sulfonyl)-3,4-dihydro-2H-benzo[b][1,4]oxazin-2-yl)methyl)azetidin-1-yl)ethan-1-one

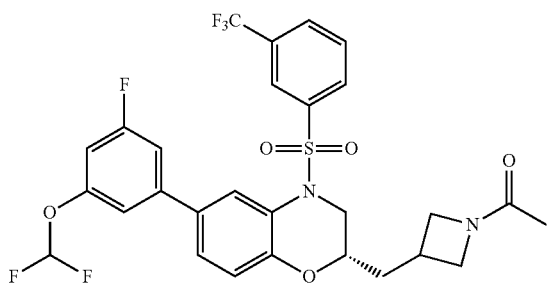 [SMILES: CC(=O)N1CC(C[C@H]2CN(S(=O)(=O)c3cccc(C(F)(F)F)c3)c3cc(-c4cc(F)cc(OC(F)F)c4)ccc3O2)C1]

Part I—Synthesis of (S)-2-((1-benzylazetidin-3-yl)methyl)-6-bromo-4-((3-(trifluoromethyl)phenyl)sulfonyl)-3,4-dihydro-2H-benzo[b][1,4]oxazine

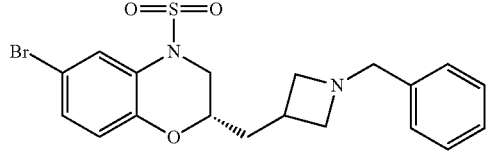

A mixture of (S)-2-((6-bromo-4-((3-(trifluoromethyl)phenyl)sulfonyl)-3,4-dihydro-2H-benzo[b][1,4]oxazin-2-yl)methyl)propane-1,3-diyl dimethanesulfonate (2.1 g, 3.15 mmol), toluene (20 mL), and benzylamine (1.1 g, 10.3 mmol) was stirred overnight at 110° C. The mixture was concentrated, diluted with water, and extracted three times with dichloromethane. The combined organic layers were dried (Na₂SO₄) and concentrated. The residue was purified via MPLC eluting with 50% ethyl acetate in hexanes to afford (S)-2-((1-benzylazetidin-3-yl)methyl)-6-bromo-4-((3-(trifluoromethyl)phenyl)sulfonyl)-3,4-dihydro-2H-benzo[b][1,4]oxazine (1.12 g, 61%) as a yellow oil.

Part II—Synthesis of (S)-2-((1-benzylazetidin-3-yl)methyl)-6-(4,4,5,5-tetramethyl-1,3,2-dioxaborolan-2-yl)-4-((3-(trifluoromethyl)phenyl)sulfonyl)-3,4-dihydro-2H-benzo[b][1,4]oxazine

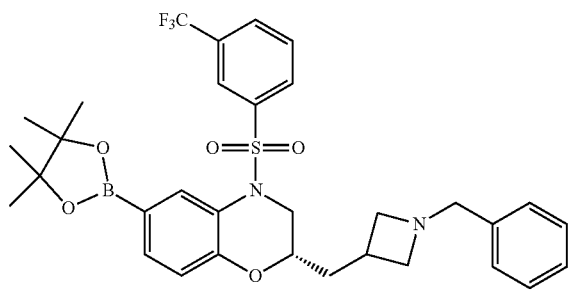 [SMILES: CC1(C)OB(c2ccc3c(c2)N(S(=O)(=O)c2cccc(C(F)(F)F)c2)C[C@H](CC2CN(Cc4ccccc4)C2)O3)OC1(C)C]

A mixture (S)-2-((1-benzylazetidin-3-yl)methyl)-6-bromo-4-((3-(trifluoromethyl)phenyl)sulfonyl)-3,4-dihydro-2H-benzo[b][1,4]oxazine (800 mg, 1.38 mmol), ethylene glycol dimethyl ether (10 mL), 4,4,5,5-tetramethyl-2-(tetramethyl-1,3,2-dioxaborolan-2-yl)-1,3,2-dioxaborolane (700 mg), potassium acetate (540 mg, 5.50 mmol), [1,1'-bis(diphenylphosphino)ferrocene] dichloropalladium (II) complex with dichloromethane (100 mg, 0.14 mmol) was stirred for three hours at 90° C. The mixture was diluted with water and extracted three times with dichloromethane. The combined organic layers were dried (Na₂SO₄) and concentrated. The residue was purified via MPLC eluting with 5% methanol to afford (S)-2-((1-benzylazetidin-3-yl)methyl)-6-(4,4,5,5-tetramethyl-1,3,2-dioxaborolan-2-yl)-4-((3-(trifluoromethyl)phenyl)sulfonyl)-3,4-dihydro-2H-benzo[b][1,4]oxazine (530 mg, 61%) as a yellow oil.

Part III—Synthesis of (S)-2-((1-benzylazetidin-3-yl)methyl)-6-(3-(difluoromethoxy)-5-fluorophenyl)-4-((3-(trifluoromethyl)phenyl)sulfonyl)-3,4-dihydro-2H-benzo[b][1,4]oxazine

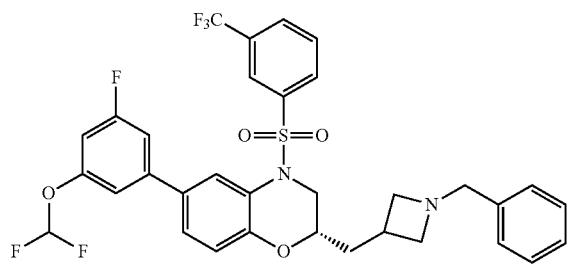 [SMILES: O=S(=O)(c1cccc(C(F)(F)F)c1)N1C[C@H](CC2CN(Cc3ccccc3)C2)Oc2ccc(-c3cc(F)cc(OC(F)F)c3)cc21]

A mixture of (S)-2-((1-benzylazetidin-3-yl)methyl)-6-(4,4,5,5-tetramethyl-1,3,2-dioxaborolan-2-yl)-4-((3-(trifluoromethyl)phenyl)sulfonyl)-3,4-dihydro-2H-benzo[b][1,4]oxazine (300 mg, 0.48 mmol), toluene (3 mL), ethanol (0.4 mL), water (1.6 mL), 1-bromo-3-(difluoromethoxy)-5-fluorobenzene (115.1 mg, 0.48 mmol), sodium carbonate (405 mg, 3.82 mmol), and tetrakis(triphenylphosphine)palladium (55 mg, 0.05 mmol) was stirred for five hours at 95° C. The mixture was diluted with water, and extracted three times with dichloromethane. The combined organic layers were dried (Na₂SO₄) and concentrated. The residue was purified via MPLC eluting with 5% methanol in dichloromethane to afford (S)-2-((1-benzylazetidin-3-yl)methyl)-6-(3-(difluoromethoxy)-5-fluorophenyl)-4-((3-(trifluoromethyl)phenyl)sulfonyl)-3,4-dihydro-2H-benzo[b][1,4]oxazine (210 mg, 66%) as a yellow oil.

Part IV—Synthesis of (S)-2-(azetidin-3-ylmethyl)-6-(3-(difluoromethoxy)-5-fluorophenyl)-4-((3-(trifluoromethyl)phenyl)sulfonyl)-3,4-dihydro-2H-benzo[b][1,4]oxazine

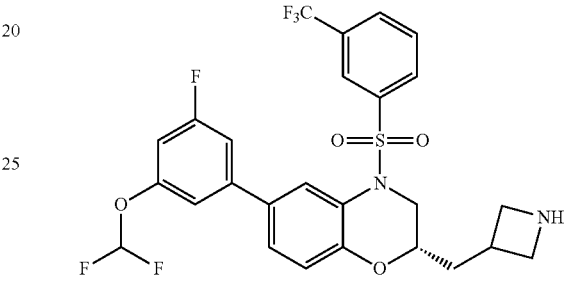

A mixture of (S)-2-((1-benzylazetidin-3-yl)methyl)-6-(3-(difluoromethoxy)-5-fluorophenyl)-4-((3-(trifluoromethyl)phenyl)sulfonyl)-3,4-dihydro-2H-benzo[b][1,4]oxazine (180 mg, 0.27 mmol), acetic acid (5 mL), and 10% palladium hydroxide on carbon (180 mg) was stirred overnight at 60° C. under an atmosphere of hydrogen. The mixture was cooled and filtered through Celite. The filtrate was concentrated to afford (S)-2-(azetidin-3-ylmethyl)-6-(3-(difluoromethoxy)-5-fluorophenyl)-4-((3-(trifluoromethyl)phenyl)sulfonyl)-3,4-dihydro-2H-benzo[b][1,4]oxazine (150 mg, 96%) as a yellow solid.

Part V—Synthesis of (S)-1-(3-((6-(3-(difluoromethoxy)-5-fluorophenyl)-4-((3-(trifluoromethyl)phenyl)sulfonyl)-3,4-dihydro-2H-benzo[b][1,4]oxazin-2-yl)methyl)azetidin-1-yl)ethan-1-one

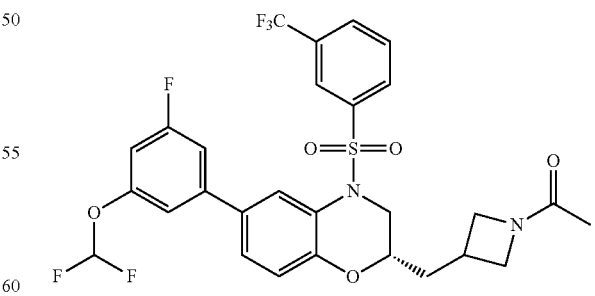

A mixture of (S)-2-(azetidin-3-ylmethyl)-6-(3-(difluoromethoxy)-5-fluorophenyl)-4-((3-(trifluoromethyl)phenyl)sulfonyl)-3,4-dihydro-2H-benzo[b][1,4]oxazine (150 mg, 0.26 mmol), pyridine (6 mL), and acetic anhydride (3 mL) was stirred overnight at room temperature and concentrated. The residue was purified by Prep-HPLC eluting with a gradient of 55-72% acetonitrile in water with 0.05% trifluoroacetic acid to afford (S)-1-(3-((6-(3-(difluoromethoxy)-5-fluorophenyl)-4-((3-(trifluoromethyl)phenyl)sulfonyl)-3,4-dihydro-2H-benzo[b][1,4]oxazin-2-yl)methyl)azetidin-1-yl)ethan-1-one (48.5 mg, 30%) as a white solid: ¹H-NMR (400 MHz, CD₃OD) δ 8.04-7.93 (m, 4H), 7.84-7.74 (m, 1H), 7.41 (dd, J=8.6, 2.2 Hz, 1H), 7.26-6.74 (m, 5H), 4.45-4.18 (m, 2H), 4.05 (dt, J=31.6, 9.3 Hz, 1H), 3.83 (ddd, J=34.6, 8.8, 5.9 Hz, 1H), 3.59 (ddd, J=28.0, 10.0, 5.9 Hz, 1H), 3.42-3.31 (m, 2H), 2.86-2.78 (m, 1H), 1.99-1.81 (m, 5H). (ES, m/z): (M+H)⁺ 615.

Example 62—Synthesis of (S)-1-(3-((6-(2,5-difluorophenyl)-4-((3-(trifluoromethyl)phenyl)sulfonyl)-3,4-dihydro-2H-benzo[b][1,4]oxazin-2-yl)methyl)azetidin-1-yl)ethan-1-one

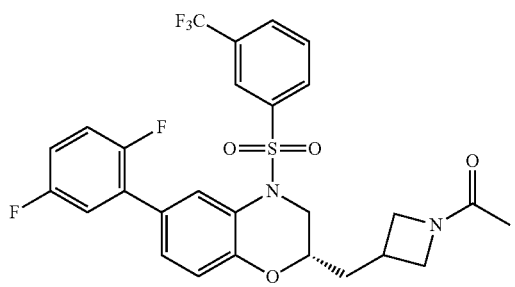 [SMILES: CC(=O)N1CC(C[C@H]2CN(S(=O)(=O)c3cccc(C(F)(F)F)c3)c3cc(-c4cc(F)ccc4F)ccc3O2)C1]

Part I—Synthesis of (S)-2-((1-benzylazetidin-3-yl)methyl)-6-(2,5-difluorophenyl)-4-((3-(trifluoromethyl)phenyl)sulfonyl)-3,4-dihydro-2H-benzo[b][1,4]oxazine

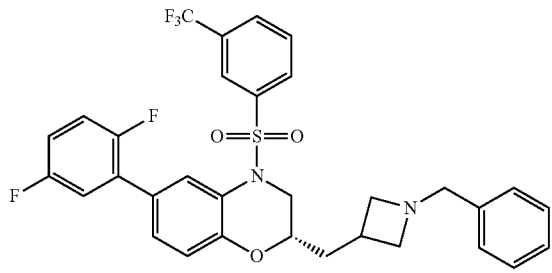 [SMILES: O=S(=O)(c1cccc(C(F)(F)F)c1)N1C[C@H](CC2CN(Cc3ccccc3)C2)Oc2ccc(-c3cc(F)ccc3F)cc21]

A mixture of (S)-2-((1-benzylazetidin-3-yl)methyl)-6-bromo-4-((3-(trifluoromethyl)phenyl)sulfonyl)-3,4-dihydro-2H-benzo[b][1,4]oxazine (300 mg, 0.52 mmol), toluene (4.5 mL), ethanol (0.6 mL), water (2.4 mL), (2,5-difluorophenyl)boronic acid (98 mg, 0.62 mmol), sodium carbonate (438 mg, 4.13 mmol), and tetrakis(triphenylphosphine)palladium (59.7 mg, 0.05 mmol) was stirred for three hours at 95° C. The mixture was diluted with water and extracted three times with dichloromethane. The combined organic layers were dried (Na₂SO₄) and concentrated. The residue was purified via MPLC eluting with 5% methanol in dichloromethane to afford (S)-2-((1-benzylazetidin-3-yl)methyl)-6-(2,5-difluorophenyl)-4-((3-(trifluoromethyl)phenyl)sulfonyl)-3,4-dihydro-2H-benzo[b][1,4]oxazine (180 mg, 57%) as a yellow oil.

Part II—Synthesis of (S)-2-(azetidin-3-ylmethyl)-6-(2,5-difluorophenyl)-4-((3-(trifluoromethyl)phenyl)sulfonyl)-3,4-dihydro-2H-benzo[b][1,4]oxazine

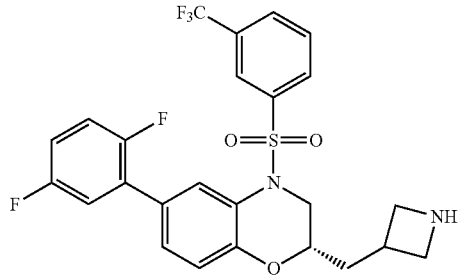 [SMILES: O=S(=O)(c1cccc(C(F)(F)F)c1)N1C[C@H](CC2CNC2)Oc2ccc(-c3cc(F)ccc3F)cc21]

A mixture of (S)-2-((1-benzylazetidin-3-yl)methyl)-6-(2,5-difluorophenyl)-4-((3-(trifluoromethyl)phenyl)sulfonyl)-3,4-dihydro-2H-benzo[b][1,4]oxazine (100 mg, 0.16 mmol), acetic acid (10 mL), and 10% palladium hydroxide on carbon (100 mg) was stirred overnight at 60° C. under an atmosphere of hydrogen. The mixture was cooled and filtered through Celite. The filtrate was concentrated to afford (S)-2-(azetidin-3-ylmethyl)-6-(2,5-difluorophenyl)-4-((3-(trifluoromethyl)phenyl)sulfonyl)-3,4-dihydro-2H-benzo[b][1,4]oxazine (80 mg, 94%) as a yellow oil.

Part III—Synthesis of (S)-1-(3-((6-(2,5-difluorophenyl)-4-((3-(trifluoromethyl)phenyl)sulfonyl)-3,4-dihydro-2H-benzo[b][1,4]oxazin-2-yl)methyl)azetidin-1-yl)ethan-1-one

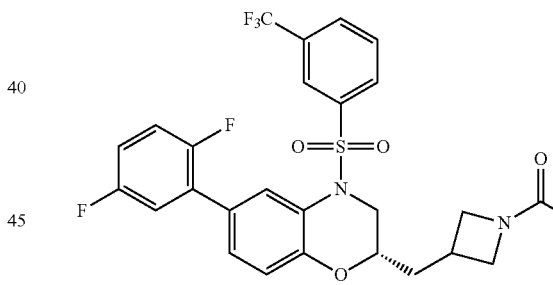

A mixture of (S)-2-(azetidin-3-ylmethyl)-6-(2,5-difluorophenyl)-4-((3-(trifluoromethyl)phenyl)sulfonyl)-3,4-dihydro-2H-benzo[b][1,4]oxazine (100 mg, 0.19 mmol), pyridine (6 mL), and acetic anhydride (3 mL) was stirred overnight at room temperature and concentrated. The residue was purified by Prep-HPLC eluting with a gradient of 50-72% acetonitrile in water with 0.05% trifluoroacetic acid to afford (S)-1-(3-((6-(2,5-difluorophenyl)-4-((3-(trifluoromethyl)phenyl)sulfonyl)-3,4-dihydro-2H-benzo[b][1,4]oxazin-2-yl)methyl)azetidin-1-yl)ethan-1-one (31.9 mg, 30%) as a white solid: ¹H-NMR (400 MHz, CD₃OD) δ 8.02 (d, J=8.3 Hz, 4H), 7.81 (q, J=7.3, 6.3 Hz, 1H), 7.35-7.18 (m, 3H), 7.14 (d, J=8.7 Hz, 1H), 6.93 (d, J=8.5 Hz, 1H), 4.49-4.41 (m, 1H), 4.31 (dt, J=32.8, 8.6 Hz, 1H), 4.09 (dt, J=30.5, 9.3 Hz, 1H), 3.87 (dt, J=29.7, 7.1 Hz, 1H), 3.64 (dt, J=24.0, 8.5 Hz, 1H), 3.48 (s, 1H), 3.39 (d, J=2.3 Hz, 1H), 2.90-2.82 (m, 1H), 2.02-1.84 (m, 5H). (ES, m/z): (M+H)⁺ 567.

Example 63—Synthesis of (S)-1-((6-(3-(difluoromethoxy)-5-fluorophenyl)-4-((3-(trifluoromethyl)phenyl)sulfonyl)-3,4-dihydro-2H-benzo[b][1,4]oxazin-2-yl)methyl)cyclopent-3-ene-1-carboxylic acid

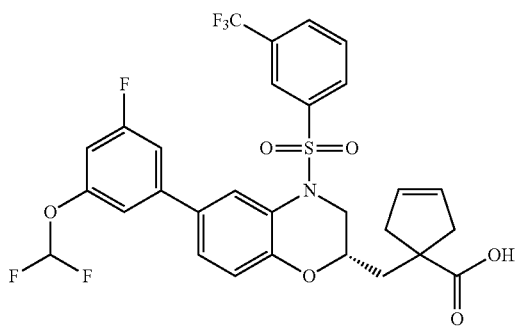 [SMILES: O=C(O)C1(C[C@H]2CN(S(=O)(=O)c3cccc(C(F)(F)F)c3)c3cc(-c4cc(F)cc(OC(F)F)c4)ccc3O2)CC=CC1]

Part I—Synthesis of (S)-1-(oxiran-2-ylmethyl)cyclopent-3-ene-1-carbonitrile

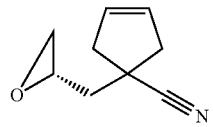 [SMILES: N#CC1(C[C@H]2CO2)CC=CC1]

A 2.5 M solution of n-butyl lithium (2.8 mL) was added dropwise to a stirred solution of cyclopent-3-ene-1-carbonitrile (600 mg, 6.44 mmol), and (S)-2-(chloromethyl)oxirane (594 mg, 6.42 mmol) in tetrahydrofuran (6 mL) at −78° C. The mixture was stirred for an hour at −78° C. and warmed to room temperature overnight. Saturated ammonium chloride was added and the mixture was extracted twice with ethyl acetate. The combined organic layers were dried (Na₂SO₄) and concentrated. The residue was purified via MPLC eluting with 10% ethyl acetate in petroleum ether to afford (S)-1-(oxiran-2-ylmethyl)cyclopent-3-ene-1-carbonitrile (500 mg, 52%).

Part II—Synthesis of (S)-1-((6-bromo-4-((3-(trifluoromethyl)phenyl)sulfonyl)-3,4-dihydro-2H-benzo[b][1,4]oxazin-2-yl)methyl)cyclopent-3-ene-1-carbonitrile

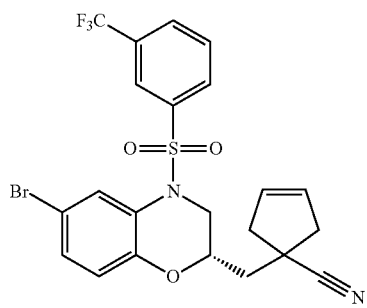 [SMILES: N#CC1(C[C@H]2CN(S(=O)(=O)c3cccc(C(F)(F)F)c3)c3cc(Br)ccc3O2)CC=CC1]

A mixture of (S)-1-(oxiran-2-ylmethyl)cyclopent-3-ene-1-carbonitrile (500 mg, 3.35 mmol), tetra-n-butylammonium bromide (108 mg, 0.34 mmol), potassium carbonate (46.3 mg, 0.33 mmol), and N-(5-bromo-2-fluorophenyl)-3-(trifluoromethyl)benzene-sulfonamide (1.3 g, 3.26 mmol) was stirred overnight at 60° C. Then sodium hydroxide (537 mg, 13.43 mmol) and tetrahydrofuran (5 mL) was added. The mixture was stirred for an additional two hours at 60° C., diluted with water, and extracted twice with ethyl acetate. The combined organic layers were dried (Na₂SO₄) and concentrated. The residue was purified via MPLC, eluting with 12% ethyl acetate in petroleum ether to afford (S)-1-((6-bromo-4-((3-(trifluoromethyl)phenyl)sulfonyl)-3,4-dihydro-2H-benzo[b][1,4]oxazin-2-yl)methyl)cyclopent-3-ene-1-carbonitrile as a yellow solid.

Part III—Synthesis of (S)-1-((6-bromo-4-((3-(trifluoromethyl)phenyl)sulfonyl)-3,4-dihydro-2H-benzo[b][1,4]oxazin-2-yl)methyl)cyclopent-3-ene-1-carboxylicacid

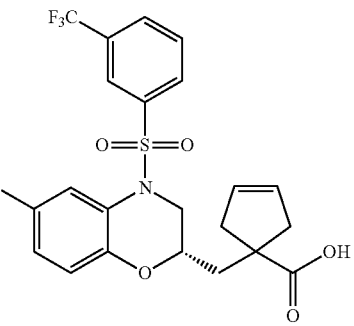

A mixture of (S)-1-((6-bromo-4-((3-(trifluoromethyl)phenyl)sulfonyl)-3,4-dihydro-2H-benzo[b][1,4]oxazin-2-yl)methyl)cyclopent-3-ene-1-carbonitrile (700 mg, 1.33 mmol), dioxane (7 mL), concentrated hydrogen chloride (2 mL), sulfuric acid (1 mL) and acetic acid (1 mL) was stirred for two days at 100° C. The mixture was diluted with water and extracted twice with ethyl acetate. The combined organic layers were dried (Na₂SO₄) and concentrated. The residue was purified via MPLC eluting with 33% ethyl acetate in petroleum ether to afford (S)-1-((6-bromo-4-((3-(trifluoromethyl)phenyl)sulfonyl)-3,4-dihydro-2H-benzo[b][1,4]oxazin-2-yl)methyl)cyclopent-3-ene-1-carboxylic acid (460 mg, 63%) as a yellow oil.

Part IV—Synthesis of (S)-1-((6-(3-(difluoromethoxy)-5-fluorophenyl)-4-((3-(trifluoromethyl)phenyl)sulfonyl)-3,4-dihydro-2H-benzo[b][1,4]oxazin-2-yl)methyl)cyclopent-3-ene-1-carboxylic acid Example 64 and 65—Synthesis of (1s,3R,4S)-1-(((S)-6-(3-(difluoromethoxy)-5-fluorophenyl)-4-((3-(trifluoromethyl)phenyl)sulfonyl)-3,4-dihydro-2H-benzo[b][1,4]oxazin-2-yl)methyl)-3,4-dihydroxycyclopentane-1-carboxylic acid and (1r,3R,4S)-1-(((S)-6-(3-(difluoromethoxy)-5-fluorophenyl)-4-((3-(trifluoromethyl)phenyl)sulfonyl)-3,4-dihydro-2H-benzo[b][1,4]oxazin-2-yl)methyl)-3,4-dihydroxycyclopentane-1-carboxylic acid

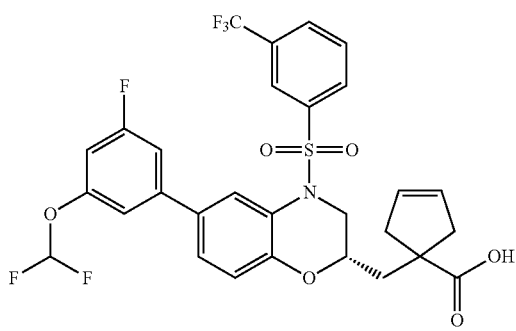 [SMILES: O=C(O)C1(C[C@H]2CN(S(=O)(=O)c3cccc(C(F)(F)F)c3)c3cc(-c4cc(F)cc(OC(F)F)c4)ccc3O2)CC=CC1]

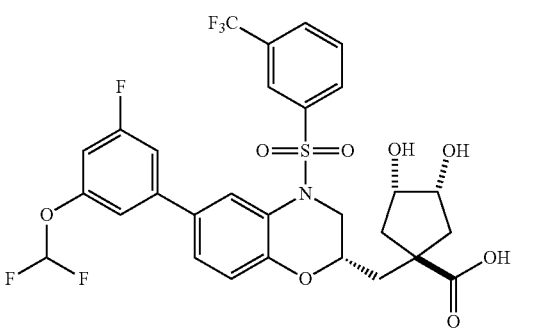
(64)

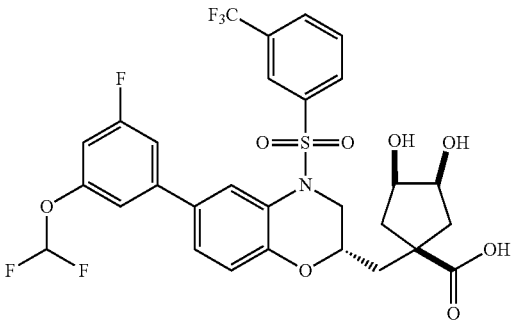
(65)

A mixture of (S)-1-((6-bromo-4-((3-(trifluoromethyl)phenyl)sulfonyl)-3,4-dihydro-2H-benzo[b][1,4]oxazin-2-yl)methyl)cyclopent-3-ene-1-carboxylic acid (50 mg, 0.09 mmol), toluene (2 mL), ethanol (0.5 mL), water (0.5 mL), 2-[3-(difluoromethoxy)-5-fluorophenyl]-4,4,5,5-tetramethyl-1,3,2-dioxaborolane (39.6 mg, 0.14 mmol), sodium carbonate (29.2 mg, 0.28 mmol), and tetrakis(triphenylphosphine)palladium (10.6 mg, 0.01 mmol) was stirred for two hours at 90° C. The resulting mixture was concentrated, and the residue was purified by Prep-HPLC eluting with a gradient of 57-78% acetonitrile in water with 0.05% trifluoroacetic acid to afford (S)-1-((6-(3-(difluoromethoxy)-5-fluorophenyl)-4-((3-(trifluoromethyl)phenyl)sulfonyl)-3,4-dihydro-2H-benzo[b][1,4]oxazin-2-yl)methyl)cyclopent-3-ene-1-carboxylic acid (24.3 mg, 42%) as a white solid: $^1$H-NMR (400 MHz, CD$_3$OD) δ 8.08 (d, J=2.3 Hz, 1H), 7.99 (dd, J=17.8, 7.9 Hz, 2H), 7.89 (s, 1H), 7.80 (t, J=7.9 Hz, 1H), 7.43 (dd, J=8.6, 2.3 Hz, 1H), 7.27-7.19 (m, 2H), 7.17-6.78 (m, 3H), 5.60 (tdd, J=7.9, 5.9, 2.0 Hz, 2H), 4.46 (dd, J=14.5, 2.5 Hz, 1H), 3.52-3.40 (m, 1H), 3.31-3.26 (m, 1H), 2.90-2.79 (m, 2H), 2.26 (dd, J=24.3, 16.8 Hz, 2H), 1.95 (d, J=5.4 Hz, 2H). (ES, m/z): (M+NH$_4$)$^+$ 645.

A solution of osmium oxide (8.1 mg, 0.03 mmol) in tert-butanol (1 mL) was added to a mixture of (S)-1-((6-(3-(difluoromethoxy)-5-fluorophenyl)-4-((3-(trifluoromethyl)phenyl)sulfonyl)-3,4-dihydro-2H-benzo[b][1,4]oxazin-2-yl)methyl)cyclopent-3-ene-1-carboxylic acid (200 mg, 0.32 mmol), acetone (4 mL), water (1 mL), and N-methyl morpholine oxide (112 mg, 0.96 mmol). The mixture was stirred overnight at room temperature. The reaction was then quenched by the addition of a saturated solution of NaHSO$_3$. The mixture was extracted twice with ethyl acetate. The combined organic layers were dried (Na$_2$SO$_4$) and concentrated. The residue was purified by Prep-HPLC eluting with a gradient of 55-68% acetonitrile in water with 0.05% trifluoroacetic acid to afford (1s,3R,4S)-1-(((S)-6-(3-(difluoromethoxy)-5-fluorophenyl)-4-((3-(trifluoromethyl)phenyl)sulfonyl)-3,4-dihydro-2H-benzo[b][1,4]oxazin-2-yl)methyl)-3,4-dihydroxycyclopentane-1-carboxylic acid (50.4 mg, 24%): $^1$H-NMR (400 MHz, CD$_3$OD) δ 8.09-7.98 (m, 3H), 7.89-7.79 (m, 2H), 7.42 (dd, J=8.6, 2.3 Hz, 1H), 7.25-6.78 (m, 5H), 4.43 (dd, J=14.5, 2.5 Hz, 1H), 4.10-3.92 (m, 2H), 3.53-3.41 (m, 1H), 3.31-3.24 (m, 1H), 2.29 (ddd, J=18.0, 13.9, 5.0 Hz, 2H), 1.94-1.87 (m, 1H), 1.83 (dd, J=13.9, 5.8 Hz, 1H), 1.73 (dd, J=13.9, 5.8 Hz, 1H); (ES, m/z): (M+NH$_4$)$^+$ 679; and (1r,3R,4S)-1-(((S)-6-(3-(difluoromethoxy)-5-fluorophenyl)-4-((3-(trifluoromethyl)phenyl)

sulfonyl)-3,4-dihydro-2H-benzo[b][1,4]oxazin-2-yl)methyl)-3,4-dihydroxycyclopentane-1-carboxylic acid (56.2 mg, 27%): ¹H-NMR (400 MHz, CD₃OD) δ 8.08-7.97 (m, 3H), 7.86-7.78 (m, 2H), 7.42 (dd, J=8.6, 2.3 Hz, 1H), 7.25-6.78 (m, 5H), 4.44 (dd, J=14.5, 2.5 Hz, 1H), 4.04 (td, J=6.1, 3.1 Hz, 2H), 3.54-3.43 (m, 1H), 3.28 (dd, J=14.6, 10.0 Hz, 1H), 2.39-2.24 (m, 2H), 2.15-2.00 (m, 2H), 1.80-1.70 (m, 1H), 1.62 (dd, J=13.5, 5.7 Hz, 1H); (ES, m/z): (M+NH₄)⁺ 679; as white solids.

Example 66—Synthesis of (S)-1-((6-(3-(difluoromethoxy)-5-fluorophenyl)-4-((3-(trifluoromethyl)phenyl)sulfonyl)-3,4-dihydro-2H-benzo[b][1,4]oxazin-2-yl)methyl)-3-oxocyclobutane-1-carboxylic acid

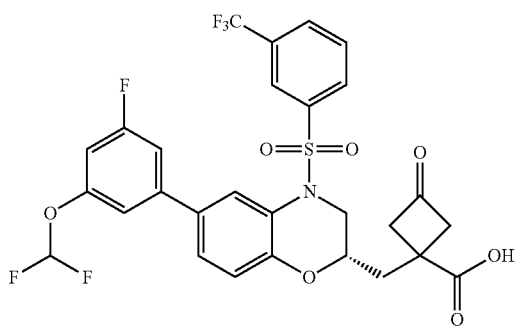 [SMILES: O=C1CC(C[C@H]2CN(S(=O)(=O)c3cccc(C(F)(F)F)c3)c3cc(-c4cc(F)cc(OC(F)F)c4)ccc3O2)(C(=O)O)C1]

Part I—Synthesis of (S)-3-methylene-1-(oxiran-2-ylmethyl)cyclobutane-1-carbonitrile

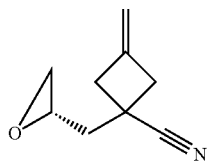

A 2.5 M solution of n-butyl lithium (10 mL) was added dropwise to a stirred solution of 3-methylidenecyclobutane-1-carbonitrile (2.6 g, 27.92 mmol), and (S)-2-(chloromethyl)oxirane (2.1 g, 22.7 mmol) in tetrahydrofuran (30 mL) at −78° C. The mixture was stirred for two hours at −78° C. and warmed to room temperature overnight. Saturated ammonium chloride was added and the mixture was extracted with dichloromethane. The organic layer was dried (Na₂SO₄) and concentrated. The residue was purified via MPLC eluting with 15% ethyl acetate in petroleum ether to afford (S)-3-methylene-1-(oxiran-2-ylmethyl)cyclobutane-1-carbonitrile (1.5 g, 44%) as a colorless liquid.

Part II—Synthesis of (S)-1-((6-bromo-4-((3-(trifluoromethyl)phenyl)sulfonyl)-3,4-dihydro-2H-benzo[b][1,4]oxazin-2-yl)methyl)-3-methylenecyclobutane-1-carbonitrile

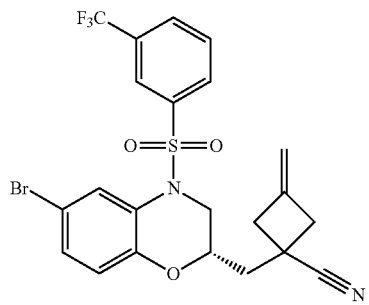 [SMILES: C=C1CC(C#N)(C[C@H]2CN(S(=O)(=O)c3cccc(C(F)(F)F)c3)c3cc(Br)ccc3O2)C1]

A mixture of (S)-3-methylene-1-(oxiran-2-ylmethyl)cyclobutane-1-carbonitrile (1.1 g, 7.37 mmol), tetra-n-butylammonium bromide (238 mg), potassium carbonate (102 mg), and N-(5-bromo-2-fluorophenyl)-3-(trifluoromethyl)benzene-sulfonamide (2.9 g, 7.28 mmol) was stirred for four hours at 60° C. Then sodium hydroxide (1.2 g, 30.00 mmol) and tetrahydrofuran (20 mL) were added. The mixture was stirred for an additional three hours at 60° C., diluted with water, and extracted twice with ethyl acetate. The combined organic layers were dried (Na₂SO₄) and concentrated. The residue was purified via MPLC, eluting with 33% ethyl acetate in petroleum ether to afford (S)-1-((6-bromo-4-((3-(trifluoromethyl)phenyl)sulfonyl)-3,4-dihydro-2H-benzo[b][1,4]oxazin-2-yl)methyl)-3-methylenecyclobutane-1-carbonitrile (1.8 g, 46%) as a white solid.

Part III—Synthesis of (S)-1-((6-bromo-4-((3-(trifluoromethyl)phenyl)sulfonyl)-3,4-dihydro-2H-benzo[b][1,4]oxazin-2-yl)methyl)-3-oxocyclobutane-1-carbonitrile

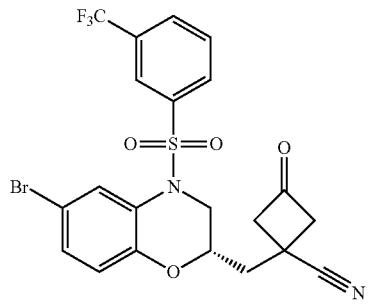 [SMILES: N#CC1(C[C@H]2CN(S(=O)(=O)c3cccc(C(F)(F)F)c3)c3cc(Br)ccc3O2)CC(=O)C1]

A solution of osmium oxide (0.09 g) in tert-butanol (2 mL) was added to a mixture of (S)-1-((6-bromo-4-((3-(trifluoromethyl)phenyl)sulfonyl)-3,4-dihydro-2H-benzo[b][1,4]oxazin-2-yl)methyl)-3-methylenecyclobutane-1-carbonitrile (3.7 g, 7.02 mmol), dioxane (60 mL), and water (20 mL). The mixture was stirred for ten minutes at room temperature. To this was added sodium periodate (3.00 g), in portions. The resulting mixture was stirred overnight at room temperature. The mixture was diluted with dichloromethane and washed twice with saturated sodium bicarbonate. The organic layer was dried (Na₂SO₄) and concentrated. The residue was purified via MPLC eluting with 25% ethyl acetate in petroleum ether to afford (S)-1-((6-bromo-4-((3-(trifluoromethyl)phenyl)sulfonyl)-3,4-dihydro-2H-benzo[b][1,4]oxazin-2-yl)methyl)-3-oxocyclobutane-1-carbonitrile (2.6 g, 70%) as a colorless oil.

Part IV—Synthesis of (S)-1-((6-bromo-4-((3-(trifluoromethyl)phenyl)sulfonyl)-3,4-dihydro-2H-benzo[b][1,4]oxazin-2-yl)methyl)-3-oxocyclobutane-1-carboxylicacid

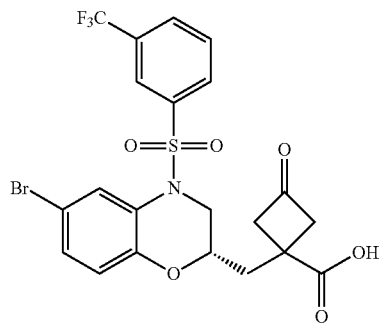 [SMILES: O=C1CC(C[C@H]2CN(S(=O)(=O)c3cccc(C(F)(F)F)c3)c3cc(Br)ccc3O2)(C(=O)O)C1]

A mixture of (S)-1-((6-bromo-4-((3-(trifluoromethyl)phenyl)sulfonyl)-3,4-dihydro-2H-benzo[b][1,4]oxazin-2-yl)methyl)-3-oxocyclobutane-1-carbonitrile (2.0 g, 3.78 mmol), dioxane (20 mL), hydrogen chloride (8 mL), sulfuric acid (4 mL), and acetic acid (4 mL) was stirred overnight at 100° C. The mixture was diluted with ethyl acetate and washed twice with water. The organic layer was dried ($Na_2SO_4$) and concentrated. The residue was purified via MPLC eluting with 10% ethyl acetate in petroleum ether to afford (S)-1-((6-bromo-4-((3-(trifluoromethyl)phenyl)sulfonyl)-3,4-dihydro-2H-benzo[b][1,4]oxazin-2-yl)methyl)-3-oxocyclobutane-1-carboxylic acid (1.6 g, 77%) as a colorless oil.

Part V—Synthesis of (S)-3-oxo-1-((6-(4,4,5,5-tetramethyl-1,3,2-dioxaborolan-2-yl)-4-((3-(trifluoromethyl)phenyl)sulfonyl)-3,4-dihydro-2H-benzo[b][1,4]oxazin-2-yl)methyl)cyclobutane-1-carboxylicacid

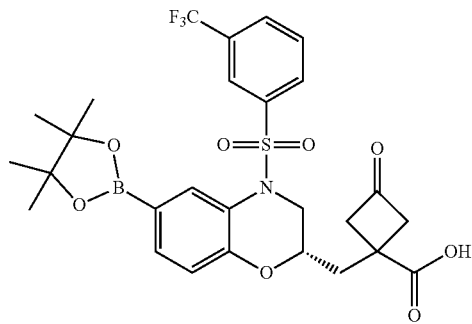 [SMILES: CC1(C)OB(c2ccc3c(c2)N(S(=O)(=O)c2cccc(C(F)(F)F)c2)C[C@H](CC2(C(=O)O)CC(=O)C2)O3)OC1(C)C]

A mixture of (S)-1-((6-bromo-4-((3-(trifluoromethyl)phenyl)sulfonyl)-3,4-dihydro-2H-benzo[b][1,4]oxazin-2-yl)methyl)-3-oxocyclobutane-1-carboxylic acid (500 mg, 0.91 mmol), 4,4,5,5-tetramethyl-2-(tetramethyl-1,3,2-dioxaborolan-2-yl)-1,3,2-dioxaborolane (464 mg), potassium acetate (358 mg, 3.65 mmol), [1,1'-bis(diphenylphosphino)ferrocene]dichloropalladium (II) complex with dichloromethane (67 mg, 0.09 mmol), and ethylene glycol dimethyl ether (10 mL) was stirred overnight at 80° C. The mixture was concentrated and the residue was purified via MPLC eluting with 10% methanol in dichloromethane to afford (S)-3-oxo-1-((6-(4,4,5,5-tetramethyl-1,3,2-dioxaborolan-2-yl)-4-((3-(trifluoromethyl)phenyl)sulfonyl)-3,4-dihydro-2H-benzo[b][1,4]oxazin-2-yl)methyl)cyclobutane-1-carboxylic acid (400 mg, 74%) as a colorless oil.

Part VI—Synthesis of (S)-1-((6-(3-(difluoromethoxy)-5-fluorophenyl)-4-((3-(trifluoromethyl)phenyl)sulfonyl)-3,4-dihydro-2H-benzo[b][1,4]oxazin-2-yl)methyl)-3-oxocyclobutane-1-carboxylic acid

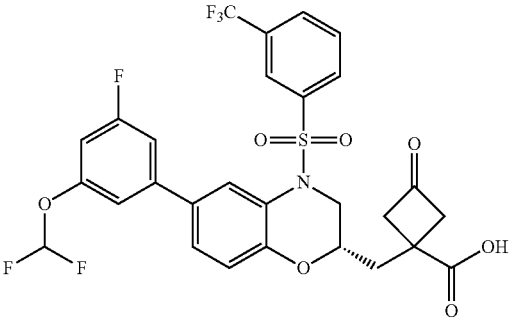

A mixture of (S)-3-oxo-1-((6-(4,4,5,5-tetramethyl-1,3,2-dioxaborolan-2-yl)-4-((3-(trifluoromethyl)phenyl)sulfonyl)-3,4-dihydro-2H-benzo[b][1,4]oxazin-2-yl)methyl)cyclobutane-1-carboxylic acid (400 mg, 0.67 mmol), 1-bromo-3-(difluoromethoxy)-5-fluorobenzene (222 mg, 0.92 mmol), sodium carbonate (214 mg, 2.02 mmol), tetrakis(triphenylphosphine)palladium (77 mg, 0.07 mmol), toluene (10 mL), ethanol (3 mL), and water (3 mL) was stirred overnight at 90° C. The mixture was concentrated and the residue was purified via MPLC eluting with 10% methanol in dichloromethane to afford (S)-1-((6-(3-(difluoromethoxy)-5-fluorophenyl)-4-((3-(trifluoromethyl)phenyl)sulfonyl)-3,4-dihydro-2H-benzo[b][1,4]oxazin-2-yl)methyl)-3-oxocyclobutane-1-carboxylic acid (350 mg, 83%) as a colorless oil.

Example 67 and 68—Synthesis of (1s,3S)-1-(((S)-6-(3-(difluoromethoxy)-5-fluorophenyl)-4-((3-(trifluoromethyl)phenyl)sulfonyl)-3,4-dihydro-2H-benzo[b][1,4]oxazin-2-yl)methyl)-3-hydroxycyclobutane-1-carboxylic acid and (1r,3R)-1-(((S)-6-(3-(difluoromethoxy)-5-fluorophenyl)-4-((3-(trifluoromethyl)phenyl)sulfonyl)-3,4-dihydro-2H-benzo[b][1,4]oxazin-2-yl)methyl)-3-hydroxycyclobutane-1-carboxylic acid (67)

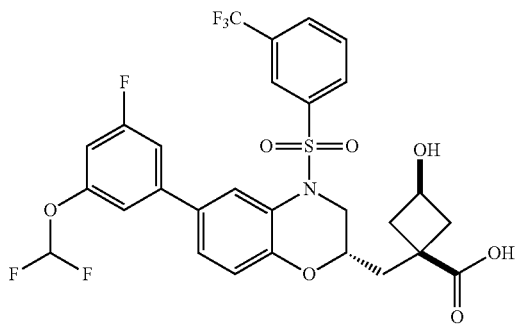

(68)

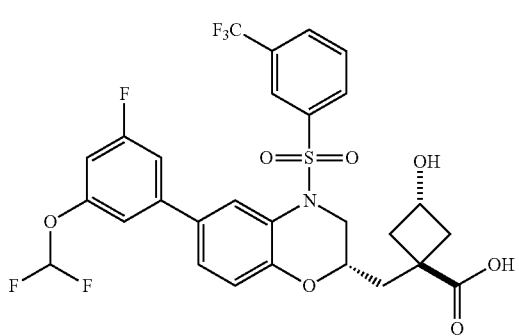

A mixture of (S)-1-((6-(3-(difluoromethoxy)-5-fluorophenyl)-4-((3-(trifluoromethyl)phenyl)sulfonyl)-3,4-dihydro-2H-benzo[b][1,4]oxazin-2-yl)methyl)-3-oxocyclobutane-1-carboxylic acid (150 mg, 0.24 mmol), tetrahydrofuran (3 mL), methanol (3 mL), and sodium borohydride (18 mg, 0.48 mmol) was stirred for an hour at room temperature. The mixture was concentrated and the residue was purified via Prep HPLC eluting with a gradient of 52-75% acetonitrile in water with 0.05% trifluoroacetic acid to afford (1s,3S)-1-(((S)-6-(3-(difluoromethoxy)-5-fluorophenyl)-4-((3-(trifluoromethyl)phenyl)sulfonyl)-3,4-dihydro-2H-benzo[b][1,4]oxazin-2-yl)methyl)-3-hydroxycyclobutane-1-carboxylic acid (27.5 mg, 18%): $^1$H-NMR (400 MHz, CD$_3$OD) δ 8.09-7.97 (m, 3H), 7.88-7.77 (m, 2H), 7.42 (dd, J=8.6, 2.2 Hz, 1H), 7.25-6.78 (m, 5H), 4.40 (dd, J=14.5, 2.4 Hz, 1H), 4.30 (p, J=7.4 Hz, 1H), 3.53-3.42 (m, 1H), 3.29 (d, J=10.1 Hz, 1H), 2.77-2.67 (m, 2H), 2.05 (d, J=6.0 Hz, 2H), 1.96 (dd, J=12.2, 7.7 Hz, 1H), 1.84 (dd, J=12.0, 7.7 Hz, 1H); (ES, m/z): (M+H)$^+$ 632; and (1r,3R)-1-(((S)-6-(3-(difluoromethoxy)-5-fluorophenyl)-4-((3-(trifluoromethyl)phenyl)sulfonyl)-3,4-dihydro-2H-benzo[b][1,4]oxazin-2-yl)methyl)-3-hydroxycyclobutane-1-carboxylic acid (52.9 mg, 39%): $^1$H-NMR (400 MHz, CD$_3$OD) δ 8.07 (d, J=2.2 Hz, 1H), 7.98 (dd, J=12.3, 8.0 Hz, 2H), 7.90 (s, 1H), 7.79 (t, J=7.9 Hz, 1H), 7.42 (dd, J=8.6, 2.3 Hz, 1H), 7.26-6.79 (m, 5H), 4.44 (dd, J=14.3, 2.2 Hz, 1H), 4.21 (p, J=7.4 Hz, 1H), 3.41 (ddd, J=8.6, 5.5, 2.6 Hz, 1H), 3.32 (m, 1H), 2.39-2.25 (m, 3H), 2.19 (ddd, J=11.6, 7.2, 3.9 Hz, 1H), 2.06-1.98 (m, 2H); (ES, m/z): (M+H)$^+$ 632; as white solids.

Example 69 and 70—Synthesis of (1S,3r)-3-(((S)-6-(3-(difluoromethoxy)-5-fluorophenyl)-4-((3-(trifluoromethyl)phenyl)sulfonyl)-3,4-dihydro-2H-benzo[b][1,4]oxazin-2-yl)methyl)-1-methylcyclobutane-1-carboxylic acid and (1R,3s)-3-(((S)-6-(3-(difluoromethoxy)-5-fluorophenyl)-4-((3-(trifluoromethyl)phenyl)sulfonyl)-3,4-dihydro-2H-benzo[b][1,4]oxazin-2-yl)methyl)-1-methylcyclobutane-1-carboxylicacid (69)

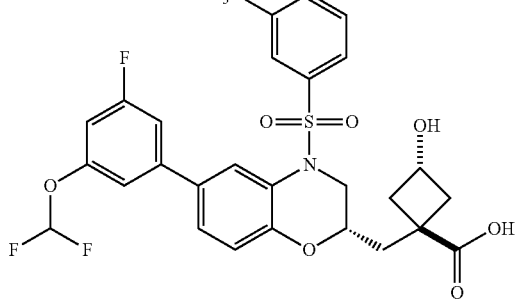

(70)

Part I—Synthesis of methyl (S)-3-((6-bromo-4-((3-(trifluoromethyl)phenyl)sulfonyl)-3,4-dihydro-2H-benzo[b][1,4]oxazin-2-yl)methyl)-1-cyanocyclobutane-1-carboxylate

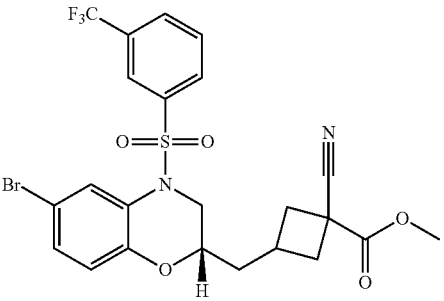 [SMILES: COC(=O)C1(C#N)CC(C[C@H]2CN(S(=O)(=O)c3cccc(C(F)(F)F)c3)c3cc(Br)ccc3O2)C1]

Sodium hydride (450 mg, 18.7 mmol) was added to a stirred mixture of (S)-2-((6-bromo-4-((3-(trifluoromethyl)phenyl)sulfonyl)-3,4-dihydro-2H-benzo[b][1,4]oxazin-2-yl)

methyl)propane-1,3-diyl dimethanesulfonate (3.0 g, 4.5 mmol), methyl 2-cyanoacetate (900 mg, 9.1 mmol), and dioxane (50 mL). The mixture was warmed to 105° C., and stirred overnight. Methanol was added to the cooled mixture and the mixture was concentrated. The residue was dissolved in ethyl acetate and washed twice with water, brine, dried (Na₂SO₄) and concentrated. The residue was purified via MPLC eluting with 33% ethyl acetate in petroleum ether to afford methyl (S)-3-((6-bromo-4-((3-(trifluoromethyl)phenyl)sulfonyl)-3,4-dihydro-2H-benzo[b][1,4]oxazin-2-yl)methyl)-1-cyanocyclobutane-1-carboxylate (1.0 g, 39%) as a colorless oil.

Part II—Synthesis of (S)-3-((6-bromo-4-((3-(trifluoromethyl)phenyl)sulfonyl)-3,4-dihydro-2H-benzo[b][1,4]oxazin-2-yl)methyl)-1-(hydroxymethyl)cyclobutane-1-carbonitrile

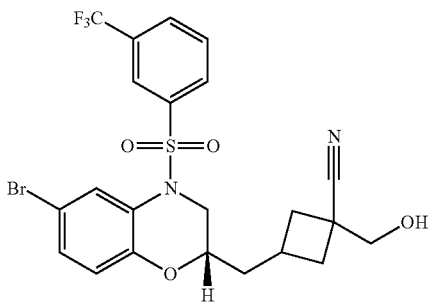 [SMILES: N#CC1(CO)CC(C[C@H]2CN(S(=O)(=O)c3cccc(C(F)(F)F)c3)c3cc(Br)ccc3O2)C1]

A mixture of methyl (S)-3-((6-bromo-4-((3-(trifluoromethyl)phenyl)sulfonyl)-3,4-dihydro-2H-benzo[b][1,4]oxazin-2-yl)methyl)-1-cyanocyclobutane-1-carboxylate (1.0 g, 1.74 mmol), tetrahydrofuran (20 mL), water (2 mL), and sodium borohydride (200 mg, 5.29 mmol) was stirred for two hours at room temperature. Methanol (2 mL) was added, and the mixture was concentrated. The residue was purified via MPLC eluting with 50% ethyl acetate in petroleum ether to afford (S)-3-((6-bromo-4-((3-(trifluoromethyl)phenyl)sulfonyl)-3,4-dihydro-2H-benzo[b][1,4]oxazin-2-yl)methyl)-1-(hydroxymethyl)cyclobutane-1-carbonitrile (0.7 g, 74%) as a colorless oil.

Part III—Synthesis of (S)-3-((6-bromo-4-((3-(trifluoromethyl)phenyl)sulfonyl)-3,4-dihydro-2H-benzo[b][1,4]oxazin-2-yl)methyl)-1-(iodomethyl)cyclobutane-1-carbonitrile

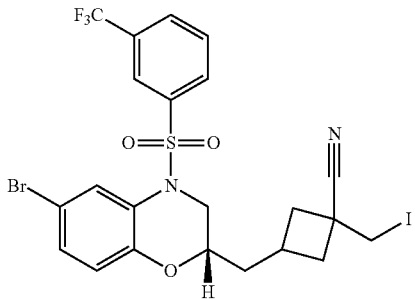 [SMILES: N#CC1(CI)CC(C[C@H]2CN(S(=O)(=O)c3cccc(C(F)(F)F)c3)c3cc(Br)ccc3O2)C1]

A mixture of (S)-3-((6-bromo-4-((3-(trifluoromethyl)phenyl)sulfonyl)-3,4-dihydro-2H-benzo[b][1,4]oxazin-2-yl)methyl)-1-(hydroxymethyl)cyclobutane-1-carbonitrile (700 mg, 1.28 mmol), triphenylphosphine (405 mg, 1.54 mmol), imidazole (263 mg), iodine (490 mg), and toluene (10 mL) was stirred for two hours at room temperature. The mixture was concentrated and purified via MPLC eluting with 20% ethyl acetate in petroleum ether to afford (S)-3-((6-bromo-4-((3-(trifluoromethyl)phenyl)sulfonyl)-3,4-dihydro-2H-benzo[b][1,4]oxazin-2-yl)methyl)-1-(iodomethyl)cyclobutane-1-carbonitrile (600 mg, 71%) as an oil.

Part IV—Synthesis of (S)-3-((6-bromo-4-((3-(trifluoromethyl)phenyl)sulfonyl)-3,4-dihydro-2H-benzo[b][1,4]oxazin-2-yl)methyl)-1-methylcyclobutane-1-carbonitrile

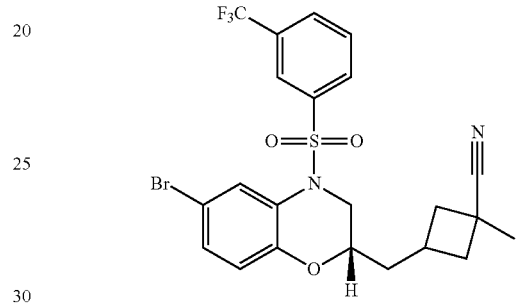

A mixture of (S)-3-((6-bromo-4-((3-(trifluoromethyl)phenyl)sulfonyl)-3,4-dihydro-2H-benzo[b][1,4]oxazin-2-yl)methyl)-1-(iodomethyl)cyclobutane-1-carbonitrile (300 mg, 0.46 mmol), tetrahydrofuran (10 mL), and Raney-Ni (0.3 g) was stirred for three hours at room temperature. The mixture was filtered, and the filtrate was concentrated to afford (S)-3-((6-bromo-4-((3-(trifluoromethyl)phenyl)sulfonyl)-3,4-dihydro-2H-benzo[b][1,4]oxazin-2-yl)methyl)-1-methylcyclobutane-1-carbonitrile (150 mg, 62%) as a colorless oil.

Part V—Synthesis of (S)-3-((6-bromo-4-((3-(trifluoromethyl)phenyl)sulfonyl)-3,4-dihydro-2H-benzo[b][1,4]oxazin-2-yl)methyl)-1-methylcyclobutane-1-carboxylicacid

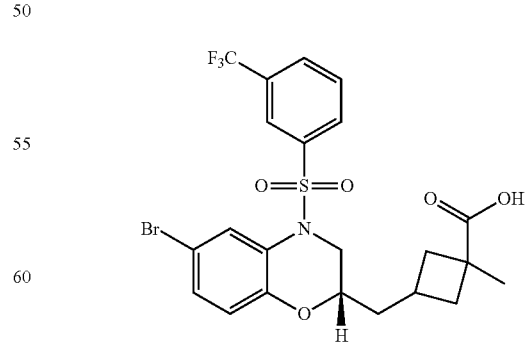

A mixture of (S)-3-((6-bromo-4-((3-(trifluoromethyl)phenyl)sulfonyl)-3,4-dihydro-2H-benzo[b][1,4]oxazin-2-yl)methyl)-1-methylcyclobutane-1-carbonitrile (250 mg, 0.47 mmol), dioxane (5 mL), hydrogen chloride (1 mL), sulfuric acid (0.5 mL), and acetic acid (0.5 mL) was stirred overnight at 100° C. The mixture was diluted in ethyl acetate and was washed twice with water. The organic layer was dried ($Na_2SO_4$) and concentrated. The residue was purified via MPLC eluting with 10% ethyl acetate in petroleum ether to afford (S)-3-((6-bromo-4-((3-(trifluoromethyl)phenyl)sulfonyl)-3,4-dihydro-2H-benzo[b][1,4]oxazin-2-yl)methyl)-1-methylcyclobutane-1-carboxylic acid (220 mg, 85%) as a colorless oil.

Part VI—Synthesis of (S)-1-methyl-3-((6-(4,4,5,5-tetramethyl-1,3,2-dioxaborolan-2-yl)-4-((3-(trifluoromethyl)phenyl)sulfonyl)-3,4-dihydro-2H-benzo[b][1,4]oxazin-2-yl)methyl)cyclobutane-1-carboxylicacid

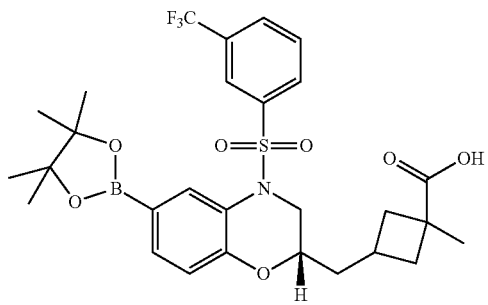 [SMILES: CC1(C(=O)O)CC(C[C@H]2CN(S(=O)(=O)c3cccc(C(F)(F)F)c3)c3cc(B4OC(C)(C)C(C)(C)O4)ccc3O2)C1]

A mixture of (S)-3-((6-bromo-4-((3-(trifluoromethyl)phenyl)sulfonyl)-3,4-dihydro-2H-benzo[b][1,4]oxazin-2-yl)methyl)-1-methylcyclobutane-1-carboxylicacid (400 mg, 0.73 mmol), ethylene glycol dimethyl ether (10 mL), 4,4,5,5-tetramethyl-2-(tetramethyl-1,3,2-dioxaborolan-2-yl)-1,3,2-dioxaborolane (371 mg), potassium acetate (287 mg, 2.92 mmol), and [1,1'-bis(diphenylphosphino)ferrocene] dichloropalladium (II) complex with dichloromethane (53 mg, 0.07 mmol) was stirred overnight at 80° C. The mixture was concentrated and the residue was purified via MPLC eluting with 10% methanol in dichloromethane to afford (S)-1-methyl-3-((6-(4,4,5,5-tetramethyl-1,3,2-dioxaborolan-2-yl)-4-((3-(trifluoromethyl)phenyl)sulfonyl)-3,4-dihydro-2H-benzo[b][1,4]oxazin-2-yl)methyl)cyclobutane-1-carboxylic acid (350 mg, 81%) as a colorless solid.

Part VII—Synthesis of (1S,3r)-3-(((S)-6-(3-(difluoromethoxy)-5-fluorophenyl)-4-((3-(trifluoromethyl)phenyl)sulfonyl)-3,4-dihydro-2H-benzo[b][1,4]oxazin-2-yl)methyl)-1-methylcyclobutane-1-carboxylic acid and (1R,3s)-3-(((S)-6-(3-(difluoromethoxy)-5-fluorophenyl)-4-((3-(trifluoromethyl)phenyl)sulfonyl)-3,4-dihydro-2H-benzo[b][1,4]oxazin-2-yl)methyl)-1-methylcyclobutane-1-carboxylic acid (69)

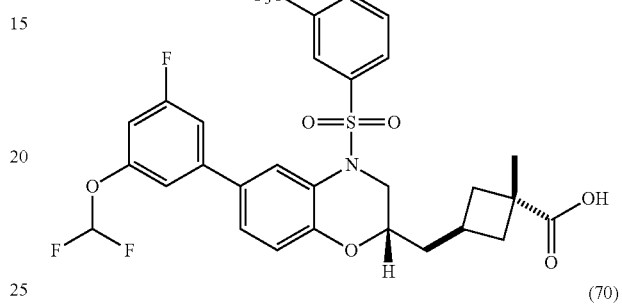

(70)

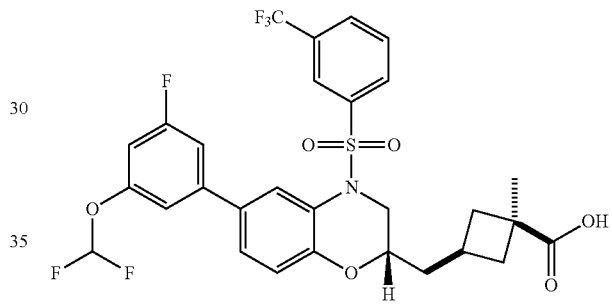

A mixture of (S)-1-methyl-3-((6-(4,4,5,5-tetramethyl-1,3,2-dioxaborolan-2-yl)-4-((3-(trifluoromethyl)phenyl)sulfonyl)-3,4-dihydro-2H-benzo[b][1,4]oxazin-2-yl)methyl)cyclobutane-1-carboxylic acid (100 mg, 0.17 mmol), 1-bromo-3-(difluoromethoxy)-5-fluorobenzene (61 mg, 0.25 mmol), toluene (3 mL), ethanol (2 mL), water (1 mL), sodium carbonate (54 mg, 0.51 mmol), and tetrakis(triphenylphosphine)palladium (19 mg, 0.02 mmol) was stirred overnight at 90° C. The mixture was diluted in water and was extracted twice with ethyl acetate, The combined organic layers were dried ($Na_2SO_4$) and concentrated. The residue was purified by Prep-HPLC eluting with a gradient of 62-82% acetonitrile in water with 0.05% trifluoroacetic acid to afford (1S,3r)-3-(((S)-6-(3-(difluoromethoxy)-5-fluorophenyl)-4-((3-(trifluoromethyl)phenyl)sulfonyl)-3,4-dihydro-2H-benzo[b][1,4]oxazin-2-yl)methyl)-1-methylcyclobutane-1-carboxylic acid (27.9 mg, 26%): $^1$H-NMR (400 MHz, $CD_3OD$) δ 8.10-7.87 (m, 4H), 7.78 (t, J=7.8 Hz, 1H), 7.42 (dd, J=8.6, 2.3 Hz, 1H), 7.27-6.69 (m, 5H), 4.33 (d, J=12.6 Hz, 1H), 3.29-3.16 (m, 2H), 2.64-2.38 (m, 3H), 1.77-1.43 (m, 4H), 1.32 (s, 3H); (ES, m/z): $(M+H)^+$ 630; and (1R,3s)-3-(((S)-6-(3-(difluoromethoxy)-5-fluorophenyl)-4-((3-(trifluoromethyl)phenyl)sulfonyl)-3,4-dihydro-2H-benzo[b][1,4]oxazin-2-yl)methyl)-1-methylcyclobutane-1-carboxylic acid (52.9 mg, 39%): $^1$H-NMR (400 MHz, $CD_3OD$) δ 8.08-7.89 (m, 4H), 7.78 (t, J=7.9 Hz, 1H), 7.42 (dd, J=8.6, 2.3 Hz, 1H), 7.26-6.70 (m, 5H), 4.34 (d, J=12.1 Hz, 1H), 3.24 (d, J=12.0 Hz, 2H), 2.54-2.41 (m, 1H), 2.13-1.80 (m, 4H), 1.71-1.55 (m, 2H), 1.41 (s, 3H); (ES, m/z): $(M+H)^+$ 630; as white solids.

Example 71 and 72—Synthesis of (1R,3s)-3-((S)-4-((3-(trifluoromethyl)phenyl)sulfonyl)-6-(6-(trifluoromethyl)pyridin-2-yl)-3,4-dihydro-2H-benzo[b][1,4]oxazin-2-yl)cyclobutane-1-carboxylic acid and (1S,3r)-3-((S)-4-((3-(trifluoromethyl)phenyl)sulfonyl)-6-(6-(trifluoromethyl)pyridin-2-yl)-3,4-dihydro-2H-benzo[b][1,4]oxazin-2-yl)cyclobutane-1-carboxylic acid (71)

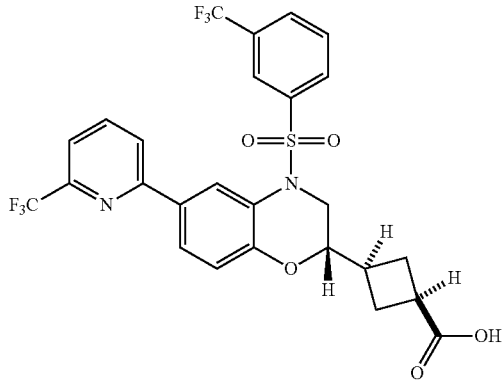

(72)

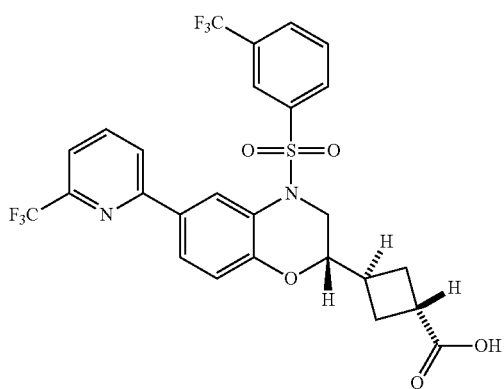

Part I—Synthesis of (3R,4R)-4-((benzyloxy)methyl)-3-hydroxydihydrofuran-2(3H)-one

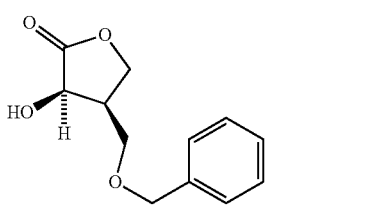 [SMILES: O=C1OC[C@@H](COCc2ccccc2)[C@H]1O]

A mixture of (S)-3-(benzyloxy)-2-((R)-2,2-dimethyl-5-oxo-1,3-dioxolan-4-yl)propanoic acid (1.1 g, 3.74 mmol), tetrahydrofuran (20 mL), and 1M borane in THF (4.12 mL) was stirred overnight at room temperature. The pH value of the solution was adjusted to 1.0 with hydrogen chloride (1.0M) and stirred overnight at room temperature. The mixture was diluted with water and extracted three times with ethyl acetate. The combined organic layers were washed with brine, dried (Na$_2$SO$_4$) and concentrated. The residue was purified by MPLC eluting with a gradient of 0-50% ethyl acetate in petroleum ether to afford (3R,4R)-4-((benzyloxy)methyl)-3-hydroxydihydrofuran-2(3H)-one (400 mg, 48%) as an oil.

Part II—Synthesis of (3S,4R)-4-((benzyloxy)methyl)-3-(4-bromo-2-nitrophenoxy)dihydrofuran-2(3H)-one

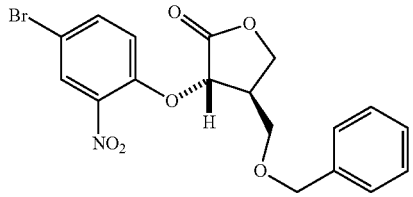 [SMILES: O=C1OC[C@@H](COCc2ccccc2)[C@@H]1Oc1ccc(Br)cc1[N+](=O)[O-]]

Diisopropyl azodicarboxylate (660 mg, 5.0 mmol) was added dropwise to a stirred solution of (3R,4R)-4-((benzyloxy)methyl)-3-hydroxydihydrofuran-2(3H)-one (600 mg, 2.70 mmol), THF (20 mL), 4-bromo-2-nitrophenol (710 mg, 3.26 mmol), and triphenylphosphane (850 mg, 3.24 mmol) at 0° C. The mixture was stirred overnight at 30° C. and was concentrated. The residue was purified by MPLC eluting with a gradient of 0-20% ethyl acetate in petroleum ether to afford (3S,4R)-4-((benzyloxy)methyl)-3-(4-bromo-2-nitrophenoxy)dihydrofuran-2(3H)-one (800 mg, 70%) as a light yellow oil.

Part III—Synthesis of (S)-2-((S)-1-(benzyloxy)-3-hydroxypropan-2-yl)-6-bromo-2H-benzo[b][1,4]oxazin-3(4H)-one

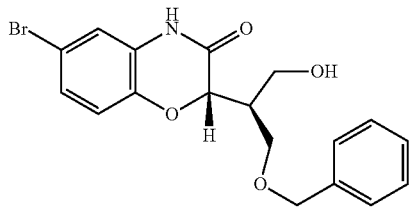 [SMILES: O=C1Nc2cc(Br)ccc2O[C@H]1[C@@H](CO)COCc1ccccc1]

A mixture of (3S,4R)-4-((benzyloxy)methyl)-3-(4-bromo-2-nitrophenoxy)dihydrofuran-2(3H)-one (2.5 g, 5.92 mmol), acetic acid (50 mL), and iron (5.0 g, 90 mmol) was stirred for two and a half hours at 90° C. The mixture was filtered, and the filtrate was concentrated. The residue was purified by MPLC eluting a gradient of 0-50% ethyl acetate in petroleum ether to afford (S)-2-((S)-1-(benzyloxy)-3-hydroxypropan-2-yl)-6-bromo-2H-benzo[b][1,4]oxazin-3(4H)-one (1.5 g, 65%) as a light yellow oil.

Part IV—Synthesis of (S)-3-(benzyloxy)-2-((S)-6-bromo-3,4-dihydro-2H-benzo[b][1,4]oxazin-2-yl)propan-1-ol

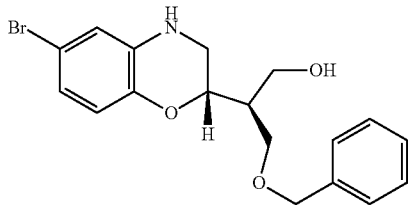 [SMILES: OC[C@@H](COCc1ccccc1)[C@H]1CNc2cc(Br)ccc2O1]

A 10 M solution of (methylsulfanyl)methane borane in THF (1.15 mL) was added dropwise to a stirred solution of (S)-2-((S)-1-(benzyloxy)-3-hydroxypropan-2-yl)-6-bromo-2H-benzo[b][1,4]oxazin-3(4H)-one (1.5 g, 3.82 mmol) in tetrahydrofuran (10 mL) at 0° C. The mixture was stirred for an additional four hours at room temperature. Methanol was added and the mixture was concentrated. The residue was purified by MPLC eluting with a gradient of 0-50% ethyl acetate in petroleum ether to afford (S)-3-(benzyloxy)-2-((S)-6-bromo-3,4-dihydro-2H-benzo[b][1,4]oxazin-2-yl)propan-1-ol (1.0 g, 69%) as a light yellow oil.

Part V—Synthesis of (R)-3-(benzyloxy)-2-((S)-6-bromo-4-((3-(trifluoromethyl)phenyl)sulfonyl)-3,4-dihydro-2H-benzo[b][1,4]oxazin-2-yl)propyl 3-(trifluoromethyl)benzenesulfonate

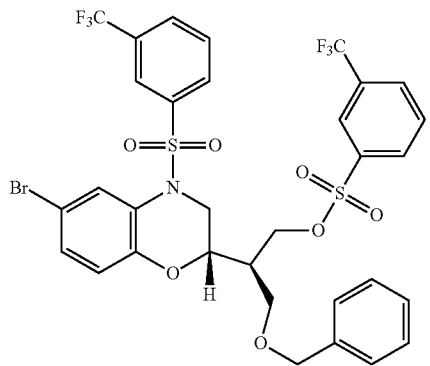 [SMILES: O=S(=O)(OC[C@@H](COCc1ccccc1)[C@H]1CN(S(=O)(=O)c2cccc(C(F)(F)F)c2)c2cc(Br)ccc2O1)c1cccc(C(F)(F)F)c1]

Pyridine (7.8 g, 98.61 mmol) was added dropwise to a stirred solution of (S)-3-(benzyloxy)-2-((S)-6-bromo-3,4-dihydro-2H-benzo[b][1,4]oxazin-2-yl)propan-1-ol (2.3 g, 6.08 mmol), dichloromethane (40 mL), 3-(trifluoromethyl)benzene-1-sulfonyl chloride (8.9 g, 36.38 mmol) at 0° C. The mixture was stirred overnight at room temperature and was concentrated. The residue was diluted in ethyl acetate, washed with 1N hydrogen chloride, dried (Na$_2$SO$_4$) and concentrated. The residue was purified by MPLC eluting with a gradient of 0-33% ethyl acetate in petroleum ether to afford (R)-3-(benzyloxy)-2-((S)-6-bromo-4-((3-(trifluoromethyl)phenyl)sulfonyl)-3,4-dihydro-2H-benzo[b][1,4]oxazin-2-yl)propyl 3-(trifluoromethyl)benzenesulfonate (2.8 g, 58%) as a light yellow oil.

Part VI—Synthesis of (R)-2-((S)-6-bromo-4-((3-(trifluoromethyl)phenyl)sulfonyl)-3,4-dihydro-2H-benzo[b][1,4]oxazin-2-yl)-3-hydroxypropyl 3-(trifluoromethyl)benzenesulfonate

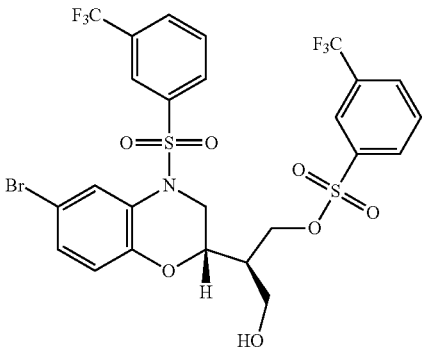 [SMILES: O=S(=O)(OC[C@@H](CO)[C@H]1CN(S(=O)(=O)c2cccc(C(F)(F)F)c2)c2cc(Br)ccc2O1)c1cccc(C(F)(F)F)c1]

A 1M solution of trichloroborane in dichloromethane (3.7 mL) was added to a stirred solution of (R)-3-(benzyloxy)-2-((S)-6-bromo-4-((3-(trifluoromethyl)phenyl)sulfonyl)-3,4-dihydro-2H-benzo[b][1,4]oxazin-2-yl)propyl 3-(trifluoromethyl)benzenesulfonate (1.0 g, 1.26 mmol), dichloromethane (20 mL) at 0° C. The mixture was stirred for an additional two and a half hours at room temperature and concentrated. The residue was purified by MPLC eluting with a gradient of 0-50% ethyl acetate in petroleum ether to afford (R)-2-((S)-6-bromo-4-((3-(trifluoromethyl)phenyl)sulfonyl)-3,4-dihydro-2H-benzo[b][1,4]oxazin-2-yl)-3-hydroxypropyl 3-(trifluoromethyl)benzenesulfonate (0.8 g, 90%) as a light yellow oil.

Part VII— Synthesis of (R)-2-((S)-6-bromo-4-((3-(trifluoromethyl)phenyl)sulfonyl)-3,4-dihydro-2H-benzo[b][1,4]oxazin-2-yl)-3-(tosyloxy)propyl 3-(trifluoromethyl)benzenesulfonate

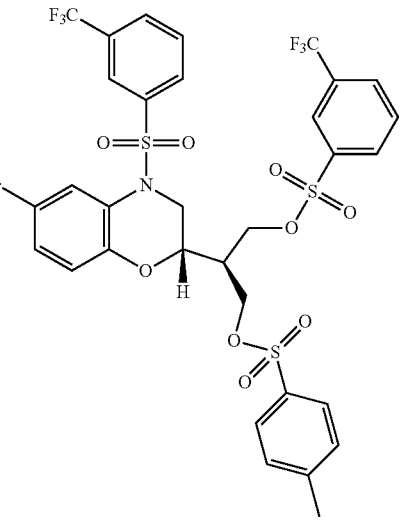

Triethyl amine (910 mg, 8.99 mmol) was added dropwise to a stirred solution of (R)-2-((S)-6-bromo-4-((3-(trifluoromethyl)phenyl)sulfonyl)-3,4-dihydro-2H-benzo[b][1,4]

oxazin-2-yl)-3-hydroxypropyl 3-(trifluoromethyl)benzenesulfonate (1.0 g, 1.42 mmol), dichloromethane (20 mL), and 4-methylbenzene-1-sulfonyl chloride (1.35 g, 7.08 mmol) at 0° C. The solution was stirred overnight at room temperature and concentrated. The residue was purified by MPLC eluting with a gradient of 0-33% ethyl acetate in petroleum ether to afford of (R)-2-((S)-6-bromo-4-((3-(trifluoromethyl)phenyl)sulfonyl)-3,4-dihydro-2H-benzo[b][1,4]oxazin-2-yl)-3-(tosyloxy)propyl 3-(trifluoromethyl)benzenesulfonate (800 mg, 66%) as a light yellow oil.

Part VIII— Synthesis of dimethyl (S)-3-(6-bromo-4-((3-(trifluoromethyl)phenyl)sulfonyl)-3,4-dihydro-2H-benzo[b][1,4]oxazin-2-yl)cyclobutane-1,1-dicarboxylate

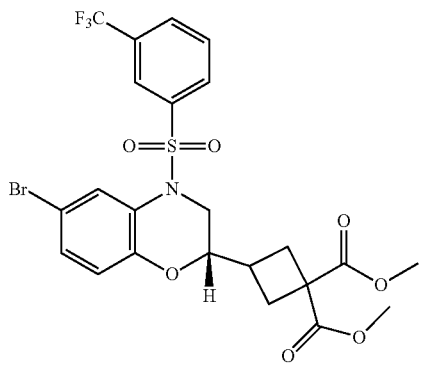 [SMILES: COC(=O)C1(C(=O)OC)CC([C@H]2CN(S(=O)(=O)c3cccc(C(F)(F)F)c3)c3cc(Br)ccc3O2)C1]

Sodium hydride (84 mg) was added to a mixture of (R)-2-((S)-6-bromo-4-((3-(trifluoromethyl)phenyl)sulfonyl)-3,4-dihydro-2H-benzo[b][1,4]oxazin-2-yl)-3-(tosyloxy)propyl 3-(trifluoromethyl)benzenesulfonate (900 mg, 1.05 mmol), 1,3-dimethyl propanedioate (310 mg, 2.35 mmol), and 1,4-dioxane (10 mL). The mixture was warmed to 105° C. and stirred overnight. Water was added, and the mixture was extracted three times with ethyl acetate. The combined organic layers were dried ($Na_2SO_4$) and concentrated. The residue was purified by MPLC eluting with a gradient of 0-33% ethyl acetate in petroleum ether to afford dimethyl (S)-3-(6-bromo-4-((3-(trifluoromethyl)phenyl)sulfonyl)-3,4-dihydro-2H-benzo[b][1,4]oxazin-2-yl)cyclobutane-1,1-dicarboxylate (0.45 g, 73%) as a light yellow oil.

Part IX— Synthesis of (S)-3-(6-bromo-4-((3-(trifluoromethyl)phenyl)sulfonyl)-3,4-dihydro-2H-benzo[b][1,4]oxazin-2-yl)cyclobutane-1,1-dicarboxylic acid

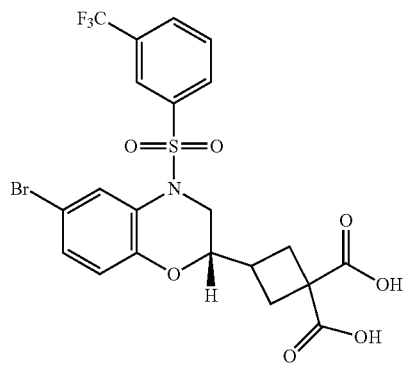 [SMILES: O=C(O)C1(C(=O)O)CC([C@H]2CN(S(=O)(=O)c3cccc(C(F)(F)F)c3)c3cc(Br)ccc3O2)C1]

A mixture of dimethyl (S)-3-(6-bromo-4-((3-(trifluoromethyl)phenyl)sulfonyl)-3,4-dihydro-2H-benzo[b][1,4]oxazin-2-yl)cyclobutane-1,1-dicarboxylate (650 mg, 1.10 mmol), lithium hydroxide monohydrate (0.25 g), tetrahydrofuran (10 mL), and water (3 mL) was stirred overnight at room temperature. The pH value of the solution was adjusted to 1.0 with hydrogen chloride aqueous solution (1.0 M), and was extracted three times with ethyl acetate. The combined organic layers were dried ($Na_2SO_4$) and concentrated to afford (S)-3-(6-bromo-4-((3-(trifluoromethyl)phenyl)sulfonyl)-3,4-dihydro-2H-benzo[b][1,4]oxazin-2-yl)cyclobutane-1,1-dicarboxylic acid (0.5 g, 81%) as a light yellow oil.

Part X— Synthesis of (S)-3-(6-bromo-4-((3-(trifluoromethyl)phenyl)sulfonyl)-3,4-dihydro-2H-benzo[b][1,4]oxazin-2-yl)cyclobutane-1-carboxylic acid

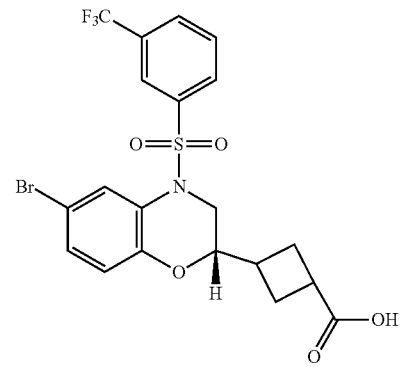 [SMILES: O=C(O)C1CC([C@H]2CN(S(=O)(=O)c3cccc(C(F)(F)F)c3)c3cc(Br)ccc3O2)C1]

A mixture of (S)-3-(6-bromo-4-((3-(trifluoromethyl)phenyl)sulfonyl)-3,4-dihydro-2H-benzo[b][1,4]oxazin-2-yl)cyclobutane-1,1-dicarboxylic acid (500 mg, 0.89 mmol) and pyridine (10 mL) was stirred overnight at 120° C. and concentrated. The residue was diluted in ethyl acetate and was washed twice with 1N hydrogen chloride. The organic layer was dried ($Na_2SO_4$) and concentrated. The residue was purified by MPLC eluting with a gradient of 0-66% ethyl acetate in petroleum ether to afford (S)-3-(6-bromo-4-((3-

(trifluoromethyl)phenyl)sulfonyl)-3,4-dihydro-2H-benzo[b][1,4]oxazin-2-yl)cyclobutane-1-carboxylic acid (0.35 g, 76%) as a light yellow oil.

Part XI— Synthesis of (S)-3-(6-(4,4,5,5-tetramethyl-1,3,2-dioxaborolan-2-yl)-4-((3-(trifluoromethyl)phenyl)sulfonyl)-3,4-dihydro-2H-benzo[b][1,4]oxazin-2-yl)cyclobutane-1-carboxylic acid

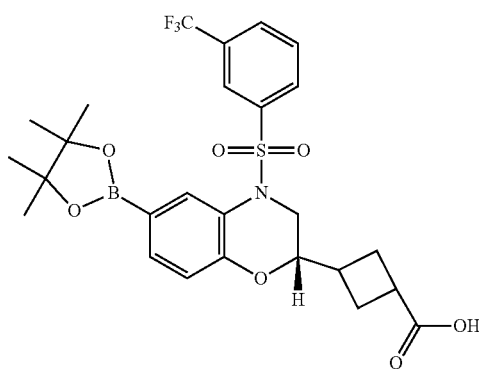 [SMILES: CC1(C)OB(c2ccc3c(c2)N(S(=O)(=O)c2cccc(C(F)(F)F)c2)C[C@H](C2CC(C(=O)O)C2)O3)OC1(C)C]

A mixture of (S)-3-(6-bromo-4-((3-(trifluoromethyl)phenyl)sulfonyl)-3,4-dihydro-2H-benzo[b][1,4]oxazin-2-yl)cyclobutane-1-carboxylic acid (400 mg, 0.77 mmol), 4,4,5,5-tetramethyl-2-(tetramethyl-1,3,2-dioxaborolan-2-yl)-1,3,2-dioxaborolane (390 mg, 1.54 mmol), [1,1'-bis(diphenylphosphino)ferrocene] dichloropalladium (II) complex with dichloromethane (57 mg), potassium acetate (300 mg, 3.06 mmol), and ethylene glycol dimethyl ether (10 mL) was stirred for four hours at 90° C. The mixture was concentrated, and the residue was purified by MPLC eluting via gradient of 0-66% ethyl acetate in petroleum ether to afford (S)-3-(6-(4,4,5,5-tetramethyl-1,3,2-dioxaborolan-2-yl)-4-((3-(trifluoromethyl)phenyl)sulfonyl)-3,4-dihydro-2H-benzo[b][1,4]oxazin-2-yl)cyclobutane-1-carboxylic acid (400 mg, 92%) as a yellow oil.

Part XII—Synthesis of (1R,3s)-3-((S)-4-((3-(trifluoromethyl)phenyl)sulfonyl)-6-(6-(trifluoromethyl)pyridin-2-yl)-3,4-dihydro-2H-benzo[b][1,4]oxazin-2-yl)cyclobutane-1-carboxylic acid and (1,3r)-3-((S)-4-((3-(trifluoromethyl)phenyl)sulfonyl)-6-(6-(trifluoromethyl)pyridin-2-yl)-3,4-dihydro-2H-benzo[b][1,4]oxazin-2-yl)cyclobutane-1-carboxylic acid (71)

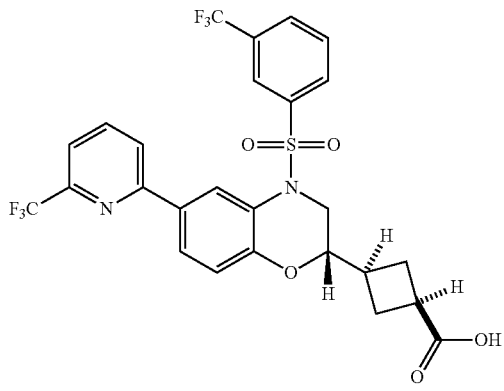

(72)

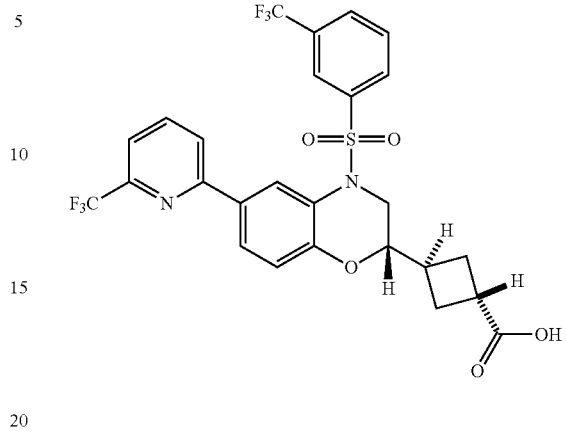

A mixture of (S)-3-(6-(4,4,5,5-tetramethyl-1,3,2-dioxaborolan-2-yl)-4-((3-(trifluoromethyl)phenyl)sulfonyl)-3,4-dihydro-2H-benzo[b][1,4]oxazin-2-yl)cyclobutane-1-carboxylic acid (250 mg, 0.44 mmol), 2-chloro-6-(trifluoromethyl)pyridine (163 mg, 0.90 mmol), sodium carbonate (150 mg, 1.42 mmol), tetrakis(triphenylphosphane) palladium (63 mg, 0.05 mmol), toluene (10 mL), ethanol (2.0 mL), water (2.0 mL) was stirred overnight at 90° C. The pH value of the solution was adjusted to 1.0 with hydrogen chloride aqueous solution (1.0 M). The mixture was extracted three times with ethyl acetate. The combined organic layers were dried ($Na_2SO_4$) and concentrated. The residue was purified by Prep-HPLC eluting with a gradient of 61-64% acetonitrile in water with 0.05% trifluoroacetic acid to afford (1R,3s)-3-((S)-4-((3-(trifluoromethyl)phenyl)sulfonyl)-6-(6-(trifluoromethyl)pyridin-2-yl)-3,4-dihydro-2H-benzo[b][1,4]oxazin-2-yl)cyclobutane-1-carboxylic acid (21.8 mg, 8%) as a white solid: $^1$H-NMR (400 MHz, $CD_3OD$) δ 8.58 (s, 1H), 8.12-7.98 (m, 5H), 7.88 (d, J=7.8 Hz, 1H), 7.80 (t, J=8.2 Hz, 1H), 7.70 (t, J=6.8 Hz, 1H), 7.00 (d, J=8.8 Hz, 1H), 4.32 (d, J=14.0 Hz, 1H), 3.43-3.40 (m, 1H), 3.27-3.20 (m, 1H), 3.12-3.07 (m, 1H), 2.52-2.46 (m, 1H), 2.36-2.28 (m, 2H), 2.19-2.05 (m, 2H); (ES, m/z): (M+H)$^+$ 587; and (1S,3r)-3-((S)-4-((3-(trifluoromethyl)phenyl)sulfonyl)-6-(6-(trifluoromethyl)pyridin-2-yl)-3,4-dihydro-2H-benzo[b][1,4]oxazin-2-yl)cyclobutane-1-carboxylic acid ($^1$H-NMR (400 MHz, $CD_3OD$) δ 8.59 (s, 1H), 8.15-8.02 (m, 5H), 7.98 (d, J=7.8 Hz, 1H), 7.80 (t, J=8.2 Hz, 1H), 7.70 (t, J=6.8 Hz, 1H), 7.02 (d, J=8.4 Hz, 1H), 4.36 (d, J=14.0 Hz, 1H), 3.55-3.50 (m, 1H), 3.31-3.25 (m, 1H), 3.10-3.02 (m, 1H), 2.60-2.25 (m, 1H), 2.45-2.35 (m, 2H), 2.28-2.15 (m, 2H); (ES, m/z): (M+H)$^+$ 587.

Example 73 and 74—Synthesis of (S)-3-(((S)-6-(3-(difluoromethoxy)-5-fluorophenyl)-4-((3-(trifluoromethyl)phenyl)sulfonyl)-3,4-dihydro-2H-benzo[b][1,4]oxazin-2-yl)methyl)-2-oxopyrrolidine-3-carboxylic acid and (R)-3-(((S)-6-(3-(difluoromethoxy)-5-fluorophenyl)-4-((3-(trifluoromethyl)phenyl)sulfonyl)-3,4-dihydro-2H-benzo[b][1,4]oxazin-2-yl)methyl)-2-oxopyrrolidine-3-carboxylicacid

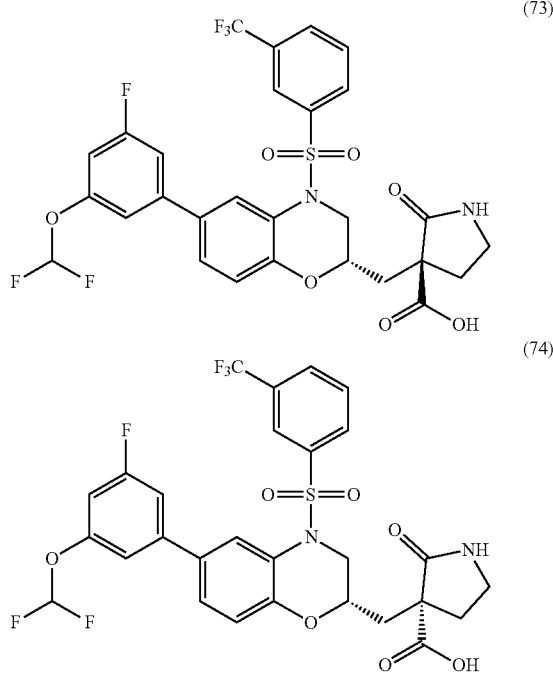

Part I—Synthesis of dimethyl (S)-2-(2-azidoethyl)-2-((6-bromo-4-((3-(trifluoromethyl)phenyl)sulfonyl)-3,4-dihydro-2H-benzo[b][1,4]oxazin-2-yl)methyl)malonate

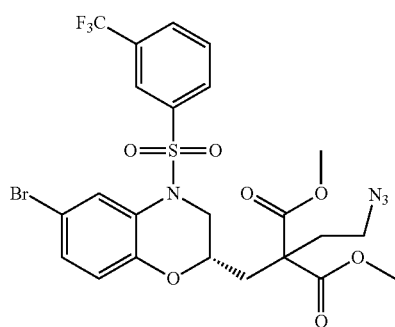 [SMILES: COC(=O)C(CCN=[N+]=[N-])(C[C@H]1CN(S(=O)(=O)c2cccc(C(F)(F)F)c2)c2cc(Br)ccc2O1)C(=O)OC]

A mixture of dimethyl (S)-2-((6-bromo-4-((3-(trifluoromethyl)phenyl)sulfonyl)-3,4-dihydro-2H-benzo[b][1,4]oxazin-2-yl)methyl)malonate (2.0 g, 3.53 mmol), tetrahydrofuran (10 mL), 1-azido-2-iodoethane (1.39 g), and sodium hydride (130 mg, 5.42 mmol) was stirred for fifteen minutes at minutes at room temperature, and then stirred overnight at 70° C. The mixture was diluted with water and extracted three times with dichloromethane. The combined organic layers were dried (Na₂SO₄) and concentrated. The residue was purified via MPLC eluting with 25% ethyl acetate in petroleum ether to afford dimethyl (S)-2-(2-azidoethyl)-2-((6-bromo-4-((3-(trifluoromethyl)phenyl)sulfonyl)-3,4-dihydro-2H-benzo[b][1,4]oxazin-2-yl)methyl)malonate (1.0 g, 45%) as a yellow oil.

Part II—Synthesis of methyl 3-(((S)-6-bromo-4-((3-(trifluoromethyl)phenyl)sulfonyl)-3,4-dihydro-2H-benzo[b][1,4]oxazin-2-yl)methyl)-2-oxopyrrolidine-3-carboxylate

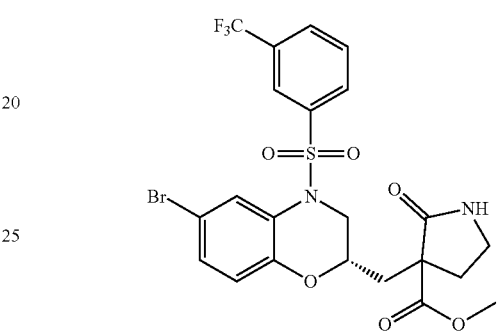

A mixture of dimethyl (S)-2-(2-azidoethyl)-2-((6-bromo-4-((3-(trifluoromethyl)phenyl)sulfonyl)-3,4-dihydro-2H-benzo[b][1,4]oxazin-2-yl)methyl)malonate (450 mg, 0.71 mmol), acetic acid (10 mL), and iron powder (595 mg) was stirred overnight at 90° C. The mixture was filtered and the filtrate was concentrated. The residue was purified via MPLC eluting with 66% ethyl acetate in petroleum to afford methyl 3-(((S)-6-bromo-4-((3-(trifluoromethyl)phenyl)sulfonyl)-3,4-dihydro-2H-benzo[b][1,4]oxazin-2-yl)methyl)-2-oxopyrrolidine-3-carboxylate (157 mg, 38%) as a yellow solid.

Part III—Synthesis of methyl 3-(((S)-6-(3-(difluoromethoxy)-5-fluorophenyl)-4-((3-(trifluoromethyl)phenyl)sulfonyl)-3,4-dihydro-2H-benzo[b][1,4]oxazin-2-yl)methy)-2-oxopyrrolidine-3-carboxylate

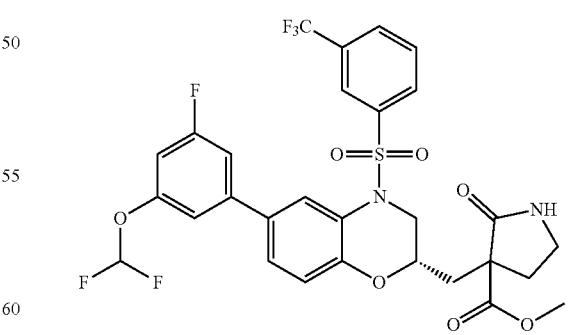

A mixture of methyl 3-(((S)-6-bromo-4-((3-(trifluoromethyl)phenyl)sulfonyl)-3,4-dihydro-2H-benzo[b][1,4]oxazin-2-yl)methyl)-2-oxopyrrolidine-3-carboxylate (100 mg, 0.17 mmol), toluene (1.5 mL), ethanol (0.2 mL), water (0.8 mL), 2-[3-(difluoromethoxy)-5-fluorophenyl]-4,4,5,5- tetramethyl-1,3,2-dioxaborolane (75 mg, 0.26 mmol), sodium carbonate (150 mg, 1.42 mmol), and tetrakis(triphenylphosphine)palladium (20 mg, 0.02 mmol) was stirred for three hours at 95° C. The mixture was diluted with water and extracted three times with dichloromethane. The combined organic layers were dried (Na$_2$SO$_4$) and concentrated. The residue was purified via MPLC eluting with 75% ethyl acetate in petroleum ether to afford methyl 3-(((S)-6-(3-(difluoromethoxy)-5-fluorophenyl)-4-((3-(trifluoromethyl)phenyl)sulfonyl)-3,4-dihydro-2H-benzo[b][1,4]oxazin-2-yl)methyl)-2-oxopyrrolidine-3-carboxylate (91 mg, 80%) as a yellow oil.

Part IV—Synthesis of (S)-3-(((S)-6-(3-(difluoromethoxy)-5-fluorophenyl)-4-((3-(trifluoromethyl)phenyl)sulfonyl)-3,4-dihydro-2H-benzo[b][1,4]oxazin-2-yl)methy)-2-oxopyrrolidine-3-carboxylic acid and (R)-3-(((S)-6-(3-(difluoromethoxy)-5-fluorophenyl)-4-((3-(trifluoromethyl)phenyl)sulfonyl)-3,4-dihydro-2H-benzo[b][1,4]oxazin-2-yl)methyl)-2-oxopyrrolidine-3-carboxylicacid

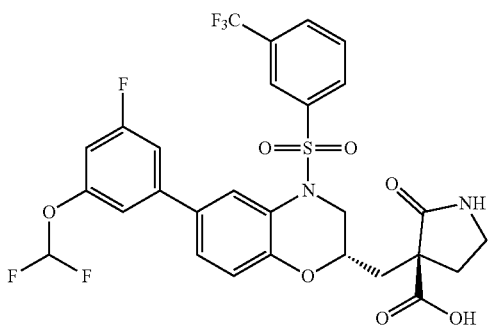

(73)

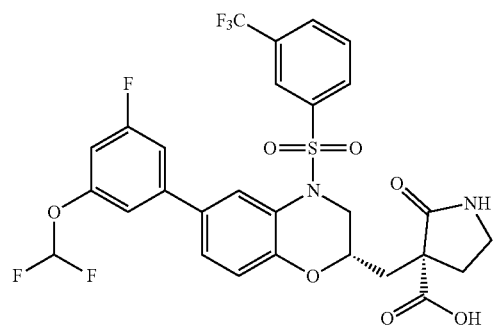

(74)

A mixture of methyl 3-(((S)-6-(3-(difluoromethoxy)-5-fluorophenyl)-4-((3-(trifluoromethyl)phenyl)sulfonyl)-3,4-dihydro-2H-benzo[b][1,4]oxazin-2-yl)methyl)-2-oxopyrrolidine-3-carboxylate (91 mg, 0.14 mmol), water (0.5 mL), tetrahydrofuran (2 mL), and lithium hydroxide (17 mg, 0.71 mmol) was stirred for two hours at room temperature. The pH value of the solution was adjusted to <3 with 1N hydrogen chloride. The mixture was diluted with water and extracted three times with dichloromethane. The combined organic layers were dried (Na$_2$SO$_4$) and concentrated. The residue was purified by Prep-HPLC eluting with a gradient of 48-70% acetonitrile in water with 0.05% trifluoroacetic acid to afford (S)-3-(((S)-6-(3-(difluoromethoxy)-5-fluorophenyl)-4-((3-(trifluoromethyl)phenyl)sulfonyl)-3,4-dihydro-2H-benzo[b][1,4]oxazin-2-yl)methyl)-2-oxopyrrolidine-3-carboxylic acid (13.8 mg, 15%): $^1$H-NMR (400 MHz, CD$_3$OD) δ 8.05-7.90 (m, 3H), 7.79 (d, J=7.8 Hz, 2H), 7.38 (dd, J=8.6, 2.2 Hz, 1H), 7.24-6.66 (m, 5H), 4.43 (dd, J=14.4, 2.4 Hz, 1H), 3.52-3.31 (m, 3H), 3.22 (dd, J=9.6, 2.8 Hz, 1H), 2.49 (dq, J=10.2, 4.0, 2.8 Hz, 1H), 2.25-1.95 (m, 3H); (ES, m/z): (M+H)$^+$ 645; and (R)-3-(((S)-6-(3-(difluoromethoxy)-5-fluorophenyl)-4-((3-(trifluoromethyl)phenyl)sulfonyl)-3,4-dihydro-2H-benzo[b][1,4]oxazin-2-yl)methyl)-2-oxopyrrolidine-3-carboxylic acid (8.9 mg, 10%): $^1$H-NMR (400 MHz, CD$_3$OD) δ 8.09-7.92 (m, 3H), 7.89-7.72 (m, 2H), 7.41 (dd, J=8.5, 2.2 Hz, 1H), 7.28-6.69 (m, 5H), 4.56 (d, J=14.0 Hz, 1H), 3.68 (s, 1H), 3.55 (s, 3H), 2.54 (s, 1H), 2.32 (s, 1H), 2.18 (s, 1H), 1.79 (s, 1H), 1.30 (s, 1H); (ES, m/z): (M+H)$^+$ 645; as white solids.

Example 75 and 76—Synthesis of (R)-2-(((S)-6-(2,5-difluorophenyl)-4-((3-(trifluoromethyl)phenyl)sulfonyl)-3,4-dihydro-2H-benzo[b][1,4]oxazin-2-yl)methyl)-5-oxopyrrolidine-2-carboxylic acid and (S)-2-(((S)-6-(2,5-difluorophenyl)-4-((3-(trifluoromethyl)phenyl)sulfonyl)-3,4-dihydro-2H-benzo[b][1,4]oxazin-2-yl)methyl)-5-oxopyrrolidine-2-carboxylicacid

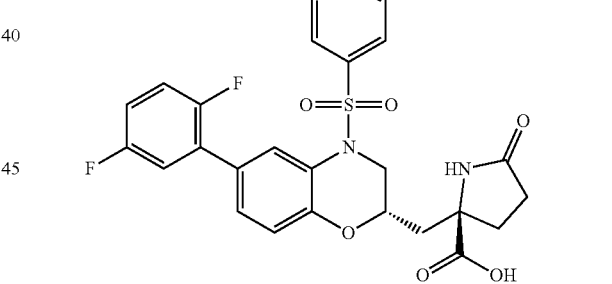

(75)

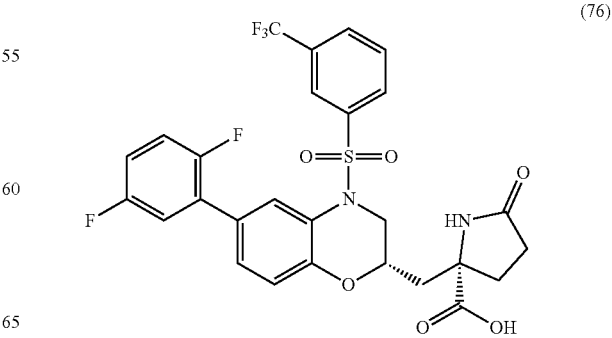

(76)

453

Part I—Synthesis of ethyl 2-(((S)-oxiran-2-yl)methyl)-5-oxopyrrolidine-2-carboxylate

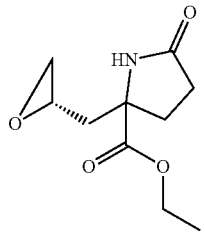

A 1M solution of lithium hexamethyldisilazide in THF (39.7 mL, 39.7 mmol) was added dropwise to a stirred solution of ethyl (2S)-5-oxopyrrolidine-2-carboxylate (2.97 g, 18.90 mmol) and (S)-2-(chloromethyl)oxirane (6 mL) in THF (24 mL) at −40° C. The mixture was stirred for an additional two hours at room temperature. Saturated ammonium chloride was added, and the mixture was extracted three times with dichloromethane and concentrated. The residue was purified by MPLC eluting with 10% methanol in dichloromethane to afford ethyl 2-(((S)-oxiran-2-yl)methyl)-5-oxopyrrolidine-2-carboxylate (1.5 g, 37%) as a clear oil.

Part II—Synthesis of 2-(((S)-6-bromo-4-((3-(trifluoromethyl)phenyl)sulfonyl)-3,4-dihydro-2H-benzo[b][1,4]oxazin-2-yl)methyl)-5-oxopyrrolidine-2-carboxylicacid

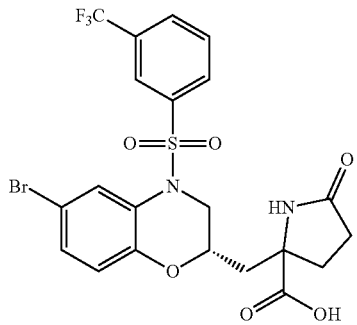 [SMILES: O=C1CCC(C[C@H]2CN(S(=O)(=O)c3cccc(C(F)(F)F)c3)c3cc(Br)ccc3O2)(C(=O)O)N1]

A mixture of ethyl 2-(((S)-oxiran-2-yl)methyl)-5-oxopyrrolidine-2-carboxylate (100 mg, 0.47 mmol), N-(5-bromo-2-fluorophenyl)-3-(trifluoromethyl)benzene-sulfonamide (186 mg, 0.47 mmol), tetra-n-butylammonium bromide (15 mg, 0.05 mmol), and potassium carbonate (6.5 mg) was stirred overnight at 60° C. Sodium hydroxide (75 mg, 1.88 mmol) and tetrahydrofuran (5 mL) was added and the mixture was stirred for an additional five hours at 60° C. The mixture was diluted in water, the pH value of the mixture was adjusted to <3 with 1N hydrochloric acid, and was extracted twice with ethyl acetate. The combined organic layers were dried ($Na_2SO_4$) and concentrated. The residue was purified via MPLC eluting with 20% methanol in dichloromethane to afford 2-(((S)-6-bromo-4-((3-(trifluoromethyl)phenyl)sulfonyl)-3,4-dihydro-2H-benzo[b][1,4]oxazin-2-yl)methyl)-5-oxopyrrolidine-2-carboxylic acid (120 mg, 45%) as a yellow oil.

454

Part III—Synthesis of (R)-2-(((S)-6-(2,5-difluorophenyl)-4-((3-(trifluoromethyl)phenyl)sulfonyl)-3,4-dihydro-2H-benzo[b][1,4]oxazin-2-yl)methy)-5-oxopyrrolidine-2-carboxylic acid and (S)-2-(((S)-6-(2,5-difluorophenyl)-4-((3-(trifluoromethyl)phenyl)sulfonyl)-3,4-dihydro-2H-benzo[b][1,4]oxazin-2-yl)methy)-5-oxopyrrolidine-2-carboxylic acid

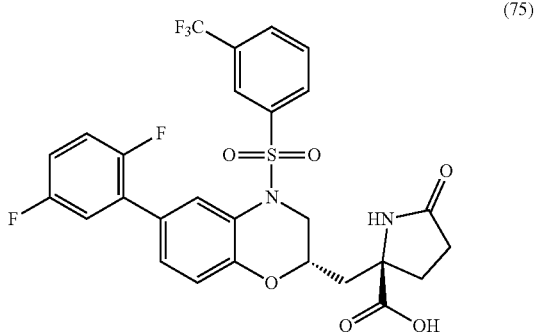

(75)

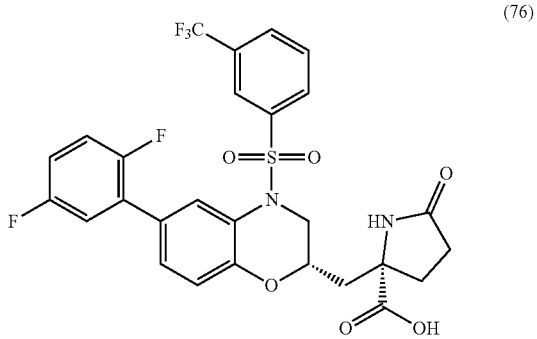

(76)

A mixture of 2-(((S)-6-bromo-4-((3-(trifluoromethyl)phenyl)sulfonyl)-3,4-dihydro-2H-benzo[b][1,4]oxazin-2-yl)methyl)-5-oxopyrrolidine-2-carboxylic acid (200 mg, 0.36 mmol), toluene (5 mL), sodium carbonate (110 mg, 1.04 mmol), methanol (1 mL), water (1 mL), (2,5-difluorophenyl)boronic acid (110 mg, 0.70 mmol), and tetrakis(triphenylphosphine)palladium (40 mg, 0.03 mmol) was stirred overnight at 90° C. The mixture was concentrated. The crude residue was purified by Prep-HPLC eluting with a gradient of 46-65% acetonitrile in water with 0.05% trifluoroacetic acid to afford (R)-2-(((S)-6-(2,5-difluorophenyl)-4-((3-(trifluoromethyl)phenyl)sulfonyl)-3,4-dihydro-2H-benzo[b][1,4]oxazin-2-yl)methyl)-5-oxopyrrolidine-2-carboxylic acid (5.5 mg, 3%): $^1$H-NMR (400 MHz, $CD_3OD$) δ 8.08-8.00 (m, 4H), 7.79-7.83 (m, 1H), 7.30-7.20 (m, 3H), 7.19-7.10 (m, 1H), 6.92 (d, J=8.4 Hz, 1H), 4.44 (dd, J=14.3, 2.4 Hz, 1H), 3.83-3.80 (m, 1H), 3.48-3.43 (m, 1H), 2.39-2.33 (m, 3H), 2.23-2.20 (m, 3H); (ES, m/z): (M+H)$^+$ 597; and (S)-2-(((S)-6-(2,5-difluorophenyl)-4-((3-(trifluoromethyl)phenyl)sulfonyl)-3,4-dihydro-2H-benzo[b][1,4]oxazin-2-yl)methyl)-5-oxopyrrolidine-2-carboxylic acid (7.2 mg, 3%): $^1$H-NMR (400 MHz, $CD_3OD$) δ 8.08-8.05 (m, 2H), 8.05-7.97 (m, 1H), 7.85-7.81 (m, 2H), 7.34-7.32 (m, 1H), 7.28-7.20 (m, 2H), 7.20-7.10 (m, 1H), 7.03-7.01 (d, J=8.8 Hz, 1H), 4.44 (dd, J=14.3, 2.4 Hz, 1H), 3.69-3.65 (m, 1H), 3.42-3.39 (m, 1H), 2.44-2.23 (m, 3H), 2.23-2.17 (m, 2H), 2.10-2.04 (m, 1H); (ES, m/z): (M+H)$^+$ 597; as white solids.

Example 77—Preparation of Additional Substituted 4-(Aryl sulfonyl)-3,4-dihydro-2H-benzo[b][1,4]oxazin-2-yl) Compounds Compounds in Table 18 were prepared based on experimental procedures described in Examples 73, 74, 75, and 76 and the detailed description. ¹H NMR data for compounds from Table 18 is provided in Table 18A.

TABLE 18

| Compd No. | Structure | Name | Observed m/z |
|---|---|---|---|
| 77A | 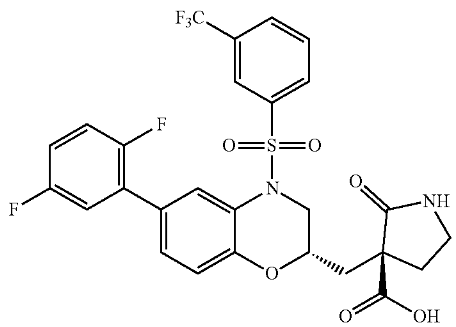 [SMILES: O=C(O)[C@]1(C[C@H]2CN(S(=O)(=O)c3cccc(C(F)(F)F)c3)c3cc(-c4cc(F)ccc4F)ccc3O2)CCNC1=O] | (S)-3-(((S)-6-(2,5-difluorophenyl)-4-((3-(trifluoromethyl)phenyl)-sulfonyl)-3,4-dihydro-2H-benzo[b][1,4]oxazin-2-yl)methyl)-2-oxopyrrolidine-3-carboxylic acid | 597 (M + H)⁺ |
| 77B | 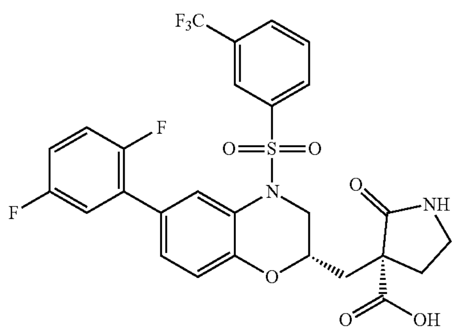 [SMILES: O=C(O)[C@@]1(C[C@H]2CN(S(=O)(=O)c3cccc(C(F)(F)F)c3)c3cc(-c4cc(F)ccc4F)ccc3O2)CCNC1=O] | (R)-3-(((S)-6-(2,5-difluorophenyl)-4-((3-(trifluoromethyl)phenyl)-sulfonyl)-3,4-dihydro-2H-benzo[b][1,4]oxazin-2-yl)methyl)-2-oxopyrrolidine-3-carboxylic acid | 597 (M + H)⁺ |
| 77C | 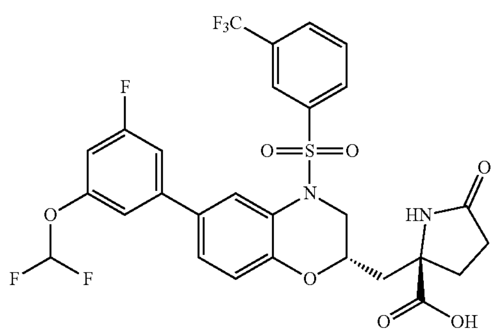 [SMILES: O=C1CC[C@@](C[C@H]2CN(S(=O)(=O)c3cccc(C(F)(F)F)c3)c3cc(-c4cc(F)cc(OC(F)F)c4)ccc3O2)(C(=O)O)N1] | (R)-2-(((S)-6-(3-(difluoromethoxy)-5-fluorophenyl)-4-((3-(trifluoromethyl)phenyl)sulfonyl)-3,4-dihydro-2H-benzo[b][1,4]-oxazin-2-yl)methyl)-5-oxopyrrolidine-2-carboxylic acid | 645 (M + H)⁺ |
| 77D | 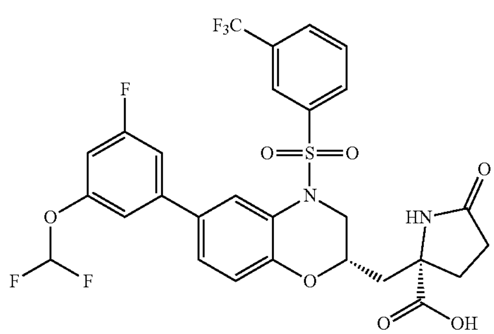 [SMILES: O=C1CC[C@](C[C@H]2CN(S(=O)(=O)c3cccc(C(F)(F)F)c3)c3cc(-c4cc(F)cc(OC(F)F)c4)ccc3O2)(C(=O)O)N1] | (S)-2-(((S)-6-(3-(difluoromethoxy)-5-fluorophenyl)-4-((3-(trifluoromethyl)phenyl)sulfonyl)-3,4-dihydro-2H-benzo[b][1,4]-oxazin-2-yl)methyl)-5-oxopyrrolidine-2-carboxylic acid | 645 (M + H)⁺ |

TABLE 18A

| Compd No. | Physical Characterization Data |
|---|---|
| 77A | $^1$H NMR (300 MHz, CD$_3$OD-d$_4$) δ 8.09-7.92 (m, 3H), 7.87-7.75 (m, 2H), 7.34-7.05 (m, 4H), 6.88 (d, J = 8.6 Hz, 1H), 4.50 (dd, J = 14.4, 2.4 Hz, 1H), 3.32 (d, J = 1.6 Hz, 4H), 2.62-2.47 (m, 1H), 2.29-2.01 (m, 3H). |
| 77B | $^1$H NMR (300 MHz, CD$_3$OD-d$_4$) δ 8.06 (d, J = 6.4 Hz, 2H), 7.96 (d, J = 7.8 Hz, 1H), 7.88 (s, 1H), 7.78 (t, J = 7.9 Hz, 1H), 7.35-7.08 (m, 4H), 6.91 (d, J = 8.6 Hz, 1H), 4.58 (dd, J = 14.4, 2.5 Hz, 1H), 3.33 (s, 4H), 2.63-2.48 (m, 1H), 2.34 (dd, J = 14.7, 3.2 Hz, 1H), 2.28-2.14 (m, 1H), 1.78 (dd, J = 14.7, 7.6 Hz, 1H). |
| 77C | $^1$H NMR (300 MHz, CD$_3$OD-d$_4$) δ 8.14-7.94 (m, 4H), 7.79 (t, J = 8.1 Hz, 1H), 7.38 (dd, J = 8.6, 2.3 Hz, 1H), 7.25-6.70 (m, 5H), 4.49-4.29 (m, 1H), 3.76 (s, 1H), 3.52-3.37 (m, 1H), 2.41-2.24 (m, 3H), 2.22-2.01 (m, 3H). |
| 77D | $^1$H NMR (300 MHz, CD$_3$OD-d$_4$) δ 8.07-8.01 (m, 2H), 7.97 (d, J = 7.9 Hz, 1H), 7.85-7.78 (m, 2H), 7.42 (dd, J = 8.6, 2.3 Hz, 1H), 7.23-6.76 (m, 5H), 4.39 (dd, J = 14.5, 2.5 Hz, 1H), 3.60 (t, J = 9.2 Hz, 1H), 3.42-3.34 (m, 1H), 2.45-2.22 (m, 3H), 2.22-2.12 (m, 2H), 2.08-2.04 (m, 1H). |

Example 78—Preparation of Additional Substituted 4-(aryl sulfonyl)-3,4-dihydro-2H-benzo[b][1,4]oxazin-2-yl) Compounds Compounds in Table 19 were prepared based on experimental procedures described in Examples 12, 13, 57, and 58 and the detailed description. $^1$H NMR data for exemplary compounds from Table 19 is provided in Table 19A.

TABLE 19

| Compd No. | Structure | Name | Observed m/z |
|---|---|---|---|
| 78A | 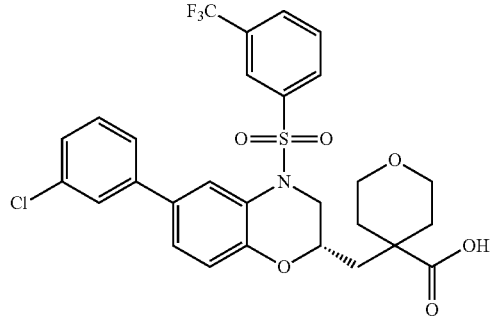 [SMILES: O=C(O)C1(C[C@H]2CN(S(=O)(=O)c3cccc(C(F)(F)F)c3)c3cc(-c4cccc(Cl)c4)ccc3O2)CCOCC1] | (S)-4-((6-(3-chlorophenyl)-4-((3-(trifluoromethyl)phenyl)sulfonyl)-3,4-dihydro-2H-benzo[b][1,4]-oxazin-2-yl)methyl)tetrahydro-2H-pyran-4-carboxylic acid | 594 (M − H)$^-$ |
| 78B | 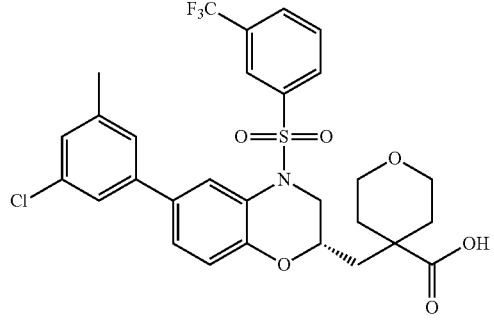 [SMILES: Cc1cc(Cl)cc(-c2ccc3c(c2)N(S(=O)(=O)c2cccc(C(F)(F)F)c2)C[C@H](CC2(C(=O)O)CCOCC2)O3)c1] | (S)-4-((6-(3-chloro-5-methyl-phenyl)-4-((3-(trifluoromethyl)-phenyl)sulfonyl)-3,4-dihydro-2H-benzo[b][1,4]oxazin-2-yl)methyl)tetrahydro-2H-pyran-4-carboxylic acid | 627 (M + NH$_4$)$^+$ |

TABLE 19-continued

| Compd No. | Structure | Name | Observed m/z |
|---|---|---|---|
| 78C | 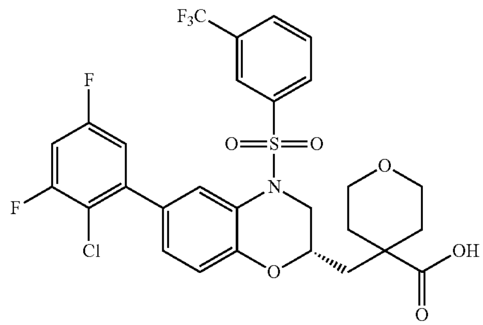 | (S)-4-((6-(2-chloro-3,5-difluoro-phenyl)-4-((3-(trifluoromethyl)-phenyl)sulfonyl)-3,4-dihydro-2H-benzo[b][1,4]oxazin-2-yl)methyl)tetrahydro-2H-pyran-4-carboxylic acid | 630 (M − H)− |
| 78D | 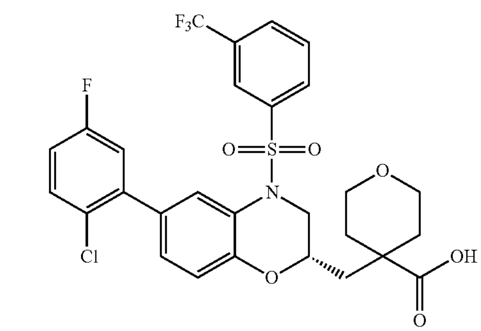 [SMILES: O=C(O)C1(C[C@H]2CN(S(=O)(=O)c3cccc(C(F)(F)F)c3)c3cc(-c4cc(F)ccc4Cl)ccc3O2)CCOCC1] | (S)-4-((6-(2-chloro-5-fluoro-phenyl)-4-((3-(trifluoromethyl)-phenyl)sulfonyl)-3,4-dihydro-2H-benzo[b][1,4]oxazin-2-yl)methyl)tetrahydro-2H-pyran-4-carboxylic acid | 612 (M − H)− |
| 78E | 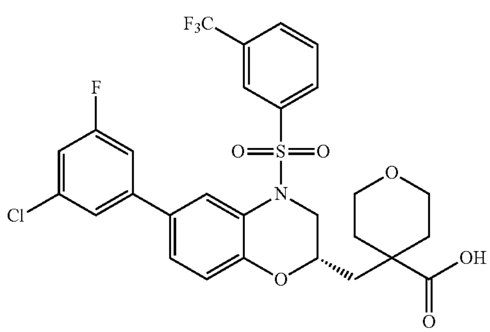 [SMILES: O=C(O)C1(C[C@H]2CN(S(=O)(=O)c3cccc(C(F)(F)F)c3)c3cc(-c4cc(F)cc(Cl)c4)ccc3O2)CCOCC1] | (S)-4-((6-(3-chloro-5-fluoro-phenyl)-4-((3-(trifluoromethyl)-phenyl)sulfonyl)-3,4-dihydro-2H-benzo[b][1,4]oxazin-2-yl)methyl)tetrahydro-2H-pyran-4-carboxylic acid | 612 (M − H)− |
| 78F | 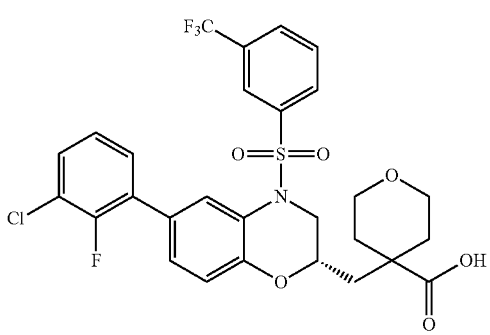 [SMILES: O=C(O)C1(C[C@H]2CN(S(=O)(=O)c3cccc(C(F)(F)F)c3)c3cc(-c4cccc(Cl)c4F)ccc3O2)CCOCC1] | (S)-4-((6-(3-chloro-2-fluoro-phenyl)-4-((3-(trifluoromethyl)-phenyl)sulfonyl)-3,4-dihydro-2H-benzo[b][1,4]oxazin-2-yl)methyl)tetrahydro-2H-pyran-4-carboxylic acid | 612 (M − H)− |

TABLE 19-continued

| Compd No. | Structure | Name | Observed m/z |
|---|---|---|---|
| 78G | 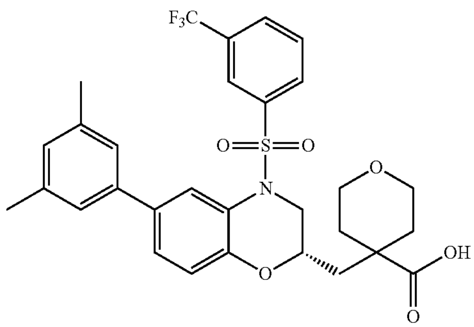 | (S)-4-((6-(3,5-dimethylphenyl)-4-((3-(trifluoromethyl)phenyl)-sulfonyl)-3,4-dihydro-2H-benzo[b][1,4]oxazin-2-yl)methyl)tetrahydro-2H-pyran-4-carboxylic acid | 590 (M + H)+ |
| 78H | 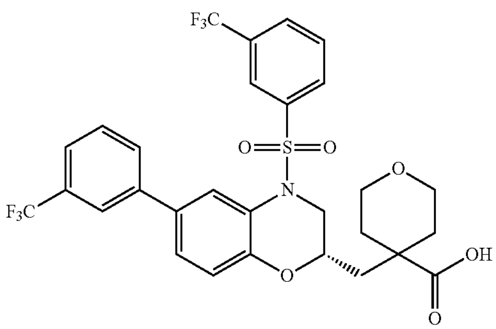 [SMILES: O=C(O)C1(C[C@H]2CN(S(=O)(=O)c3cccc(C(F)(F)F)c3)c3cc(-c4cccc(C(F)(F)F)c4)ccc3O2)CCOCC1] | (S)-4-((6-(3-(trifluoromethyl)-phenyl)-4-((3-(trifluoromethyl)-phenyl)sulfonyl)-3,4-dihydro-2H-benzo[b][1,4]oxazin-2-yl)methyl)tetrahydro-2H-pyran-4-carboxylic acid | 647 (M + NH$_4$)+ |
| 78I | 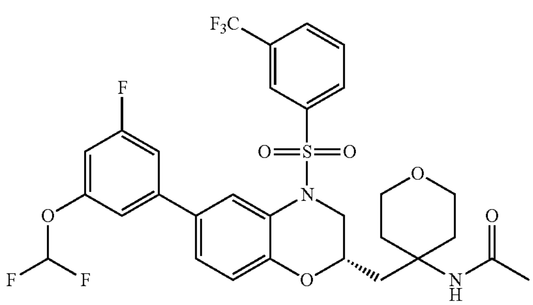 [SMILES: CC(=O)NC1(C[C@H]2CN(S(=O)(=O)c3cccc(C(F)(F)F)c3)c3cc(-c4cc(F)cc(OC(F)F)c4)ccc3O2)CCOCC1] | (S)-N-(4-((6-(3-(difluoro-methoxy)-5-fluorophenyl)-4-((3-(trifluoromethyl)phenyl)sulfonyl)-3,4-dihydro-2H-benzo[b][1,4]-oxazin-2-yl)methyl)tetrahydro-2H-pyran-4-yl)acetamide | 659 (M + H)+ |
| 78J | 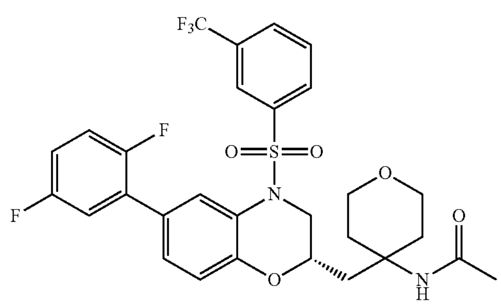 [SMILES: CC(=O)NC1(C[C@H]2CN(S(=O)(=O)c3cccc(C(F)(F)F)c3)c3cc(-c4cc(F)ccc4F)ccc3O2)CCOCC1] | (S)-N-(4-((6-(2,5-difluorophenyl)-4-((3-(trifluoromethyl)phenyl)-sulfonyl)-3,4-dihydro-2H-benzo[b][1,4]oxazin-2-yl)methyl)tetrahydro-2H-pyran-4 yl)acetamide | 611 (M + H)+ |
| 78K | 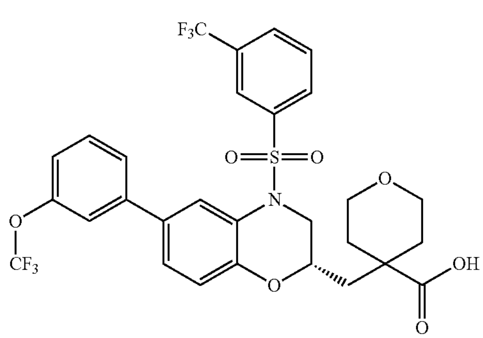 [SMILES: O=C(O)C1(C[C@H]2CN(S(=O)(=O)c3cccc(C(F)(F)F)c3)c3cc(-c4cccc(OC(F)(F)F)c4)ccc3O2)CCOCC1] | (S)-4-((6-(3-(trifluoromethoxy)-phenyl)-4-((3-(trifluoromethyl)-phenyl)sulfonyl)-3,4-dihydro-2H-benzo[b][1,4]oxazin-2-yl)methyl)tetrahydro-2H-pyran-4-carboxylic acid | 644 (M − H)− |

TABLE 19-continued

| Compd No. | Structure | Name | Observed m/z |
|---|---|---|---|
| 78L | 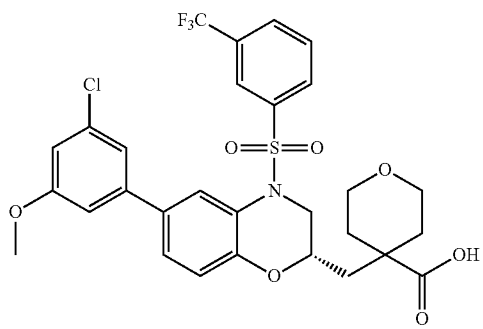 | (S)-4-((6-(3-chloro-5-methoxy-phenyl)-4-((3-(trifluoromethyl)-phenyl)sulfonyl)-3,4-dihydro-2H-benzo[b][1,4]oxazin-2-yl)methyl)tetrahydro-2H-pyran-4-carboxylic acid | 624 (M − H)⁻ |
| 78M | 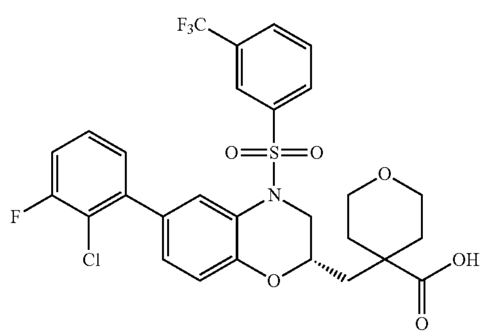 [SMILES: O=C(O)C1(C[C@H]2CN(S(=O)(=O)c3cccc(C(F)(F)F)c3)c3cc(-c4cccc(F)c4Cl)ccc3O2)CCOCC1] | (S)-4-((6-(2-chloro-3-fluoro-phenyl)-4-((3-(trifluoromethyl)-phenyl)sulfonyl)-3,4-dihydro-2H-benzo[b][1,4]oxazin-2-yl)methyl)tetrahydro-2H-pyran-4-carboxylic acid | 612 (M − H)⁻ |
| 78N | 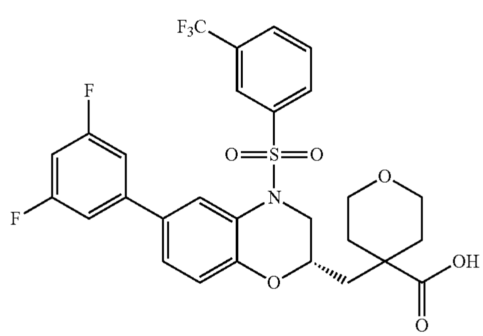 [SMILES: O=C(O)C1(C[C@H]2CN(S(=O)(=O)c3cccc(C(F)(F)F)c3)c3cc(-c4cc(F)cc(F)c4)ccc3O2)CCOCC1] | (S)-4-((6-(3,5-difluorophenyl)-4-((3-(trifluoromethyl)phenyl)-sulfonyl)-3,4-dihydro-2H-benzo[b][1,4]oxazin-2-yl)methyl)tetrahydro-2H-pyran-4-carboxylic acid | 596 (M − H)⁻ |
| 78O | 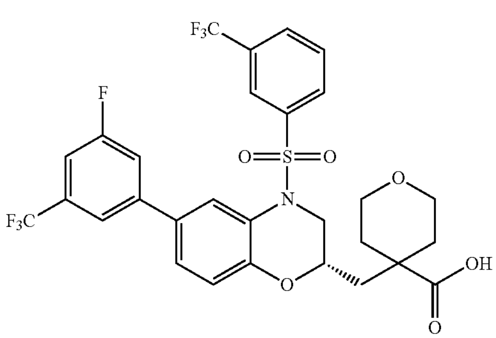 [SMILES: O=C(O)C1(C[C@H]2CN(S(=O)(=O)c3cccc(C(F)(F)F)c3)c3cc(-c4cc(F)cc(C(F)(F)F)c4)ccc3O2)CCOCC1] | (S)-4-((6-(3-fluoro-5-(trifluoro-methyl)phenyl)-4-((3-(trifluoro-methyl)phenyl)sulfonyl)-3,4-dihydro-2H-benzo[b][1,4]oxazin-2-yl)methyl)tetrahydro-2H-pyran-4-carboxylic acid | 646 (M − H)⁻ |

TABLE 19-continued

| Compd No. | Structure | Name | Observed m/z |
|---|---|---|---|
| 78P | 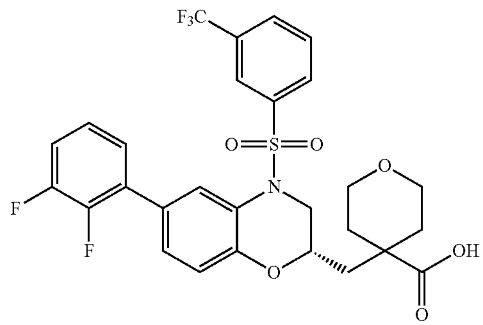 [SMILES: O=C(O)C1(C[C@H]2CN(S(=O)(=O)c3cccc(C(F)(F)F)c3)c3cc(-c4cccc(F)c4F)ccc3O2)CCOCC1] | (S)-4-((6-(2,3-difluorophenyl)-4-((3-(trifluoromethyl)phenyl)-sulfonyl)-3,4-dihydro-2H-benzo[b][1,4]oxazin-2-yl)methyl)tetrahydro-2H-pyran-4-carboxylic acid | 596 (M − H)⁻ |
| 78Q | 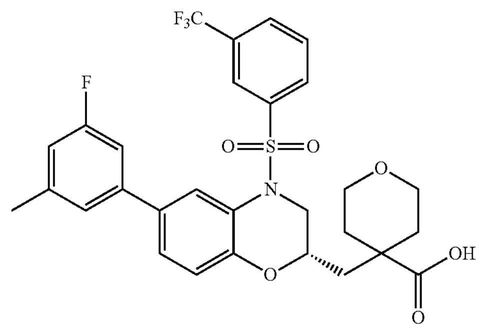 [SMILES: Cc1cc(F)cc(-c2ccc3c(c2)N(S(=O)(=O)c2cccc(C(F)(F)F)c2)C[C@H](CC2(C(=O)O)CCOCC2)O3)c1] | (S)-4-((6-(3-fluoro-5-methyl-phenyl)-4-((3-(trifluoromethyl)-phenyl)sulfonyl)-3,4-dihydro-2H-benzo[b][1,4]oxazin-2-yl)methyl)tetrahydro-2H-pyran-4-carboxylic acid | 592 (M − H)⁻ |
| 78R | 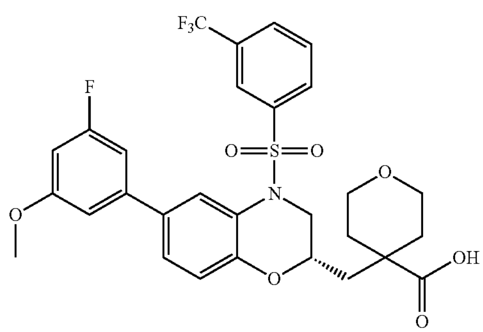 | (S)-4-((6-(3-fluoro-5-methoxy-phenyl)-4-((3-(trifluoromethyl)-phenyl)sulfonyl)-3,4-dihydro-2H-benzo[b][1,4]oxazin-2-yl)methyl)tetrahydro-2H-pyran-4-carboxylic acid | 608 (M − H)⁻ |
| 78S | 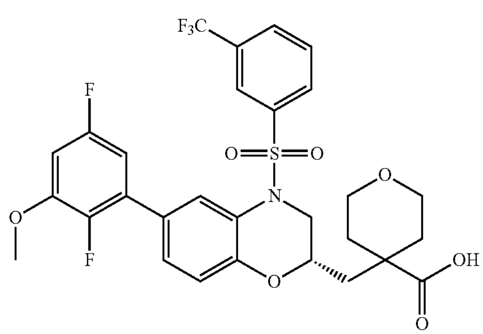 [SMILES: O=C(O)C1(C[C@H]2CN(S(=O)(=O)c3cccc(C(F)(F)F)c3)c3cc(-c4cc(F)cc(F)c4F)ccc3O2)CCOCC1] | (S)-4-((6-(2,5-difluoro-3-methoxyphenyl)-4-((3-(trifluoromethyl)phenyl)sulfonyl)-3,4-dihydro-2H-benzo[b][1,4]oxazin-2-yl)methyl)tetrahydro-2H-pyran-4-carboxylic acid | 626 (M − H)⁻ |

TABLE 19-continued

| Compd No. | Structure | Name | Observed m/z |
|---|---|---|---|
| 78T | 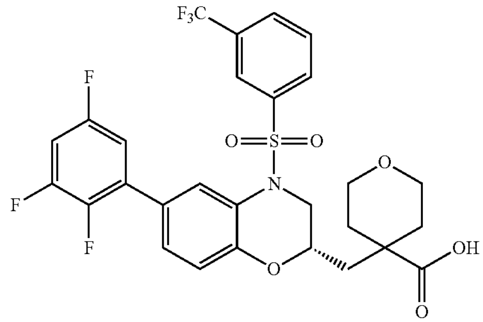 | (S)-4-((4-((3-(trifluoromethyl)-phenyl)sulfonyl)-6-(2,3,5-trifluorophenyl)-3,4-dihydro-2H-benzo[b][1,4]oxazin-2-yl)methyl)tetrahydro-2H-pyran-4-carboxylic acid | 614 (M − H)⁻ |
| 78U | 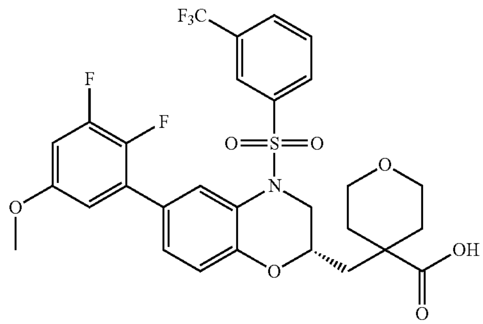 [SMILES: COc1cc(F)c(F)c(-c2ccc3c(c2)N(S(=O)(=O)c2cccc(C(F)(F)F)c2)C[C@H](CC2(C(=O)O)CCOCC2)O3)c1] | (S)-4-((6-(2,3-difluoro-5-methoxyphenyl)-4-((3-(trifluoromethyl)phenyl)sulfonyl)-3,4-dihydro-2H-benzo[b][1,4]oxazin-2-yl)methyl)tetrahydro-2H-pyran-4-carboxylic acid | 626 (M − H)⁻ |
| 78V | 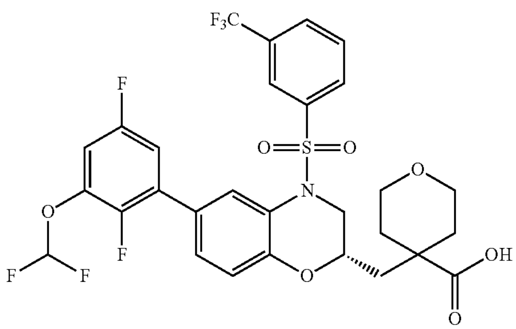 [SMILES: O=C(O)C1(C[C@H]2CN(S(=O)(=O)c3cccc(C(F)(F)F)c3)c3cc(-c4cc(F)cc(OC(F)F)c4F)ccc3O2)CCOCC1] | (S)-4-((6-(3-(difluoromethoxy)-2,5-difluorophenyl)-4-((3-(trifluoromethyl)phenyl)sulfonyl)-3,4-dihydro-2H-benzo[b][1,4]oxazin-2-yl)methyl)tetrahydro-2H-pyran-4-carboxylic acid | 662 (M − H)⁻ |
| 78W | 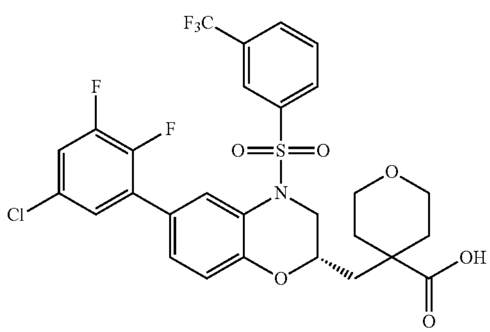 [SMILES: O=C(O)C1(C[C@H]2CN(S(=O)(=O)c3cccc(C(F)(F)F)c3)c3cc(-c4cc(Cl)cc(F)c4F)ccc3O2)CCOCC1] | (S)-4-((6-(5-chloro-2,3-difluorophenyl)-4-((3-(trifluoromethyl)phenyl)sulfonyl)-3,4-dihydro-2H-benzo[b][1,4]oxazin-2-yl)methyl)tetrahydro-2H-pyran-4-carboxylic acid | 630 (M − H)⁻ |

TABLE 19A

| Compd No. | Physical Characterization Data |
|---|---|
| 78A | $^1$H NMR (300 MHz, CD$_3$OD-d$_4$) δ 8.04 (d, J = 2.2 Hz, 1H), 8.02-7.88 (m, 3H), 7.78 (t, J = 7.8 Hz, 1H), 7.58 (t, J = 1.8 Hz, 1H), 7.56-7.50 (m, 1H), 7.48-7.32 (m, 3H), 6.88 (d, J = 8.6 Hz, 1H), 4.37 (dd, J = 14.6, 2.5 Hz, 1H), 3.85-3.70 (m, 2H), 3.62-3.40 (m, 3H), 2.08-1.84 (m, 3H), 1.78 (dd, J = 14.7, 3.7 Hz, 1H), 1.58-1.35 (m, 2H). |

TABLE 19A-continued

| Compd No. | Physical Characterization Data |
|---|---|
| 78B | $^1$H NMR (400 MHz, CD$_3$OD-d$_4$) δ 8.04-7.91 (m, 4H), 7.79 (t, J = 7.9 Hz, 1H), 7.40-7.32 (m, 3H), 7.20 (s, 1H), 6.88 (dd, J = 8.5, 1.2 Hz, 1H), 4.38 (dd, J = 14.6, 2.5 Hz, 1H), 3.79 (dq, J = 12.2, 4.3 Hz, 2H), 3.61-3.44 (m, 3H), 3.31-3.24 (m, 1H), 2.43 (s, 3H), 2.04-1.97 (m, 1H), 1.96-1.87 (m, 2H), 1.82-1.75 (m, 1H), 1.48 (dddd, J = 24.5, 14.3, 10.8, 4.3 Hz, 2H). |
| 78C | $^1$H NMR (300 MHz, CD$_3$OD-d$_4$) δ 7.96 (t, J = 7.2 Hz, 2H), 7.89 (d, J = 2.1 Hz, 2H), 7.77 (t, J = 7.8 Hz, 1H), 7.23-7.09 (m, 2H), 7.07-6.96 (m, 1H), 6.86 (d, J = 8.5 Hz, 1H), 4.36 (dd, J = 14.6, 2.5 Hz, 1H), 3.81-3.69 (m, 2H), 3.59-3.37 (m, 3H), 3.27-3.11 (m, 1H), 2.03-1.70 (m, 4H), 1.55-1.33 (m, 2H). |
| 78D | $^1$H NMR (300 MHz, CD$_3$OD-d$_4$) δ 7.95 (dd, J = 8.0, 4.7 Hz, 2H), 7.92-7.85 (m, 2H), 7.76 (t, J = 7.9 Hz, 1H), 7.56-7.45 (m, 1H), 7.19-7.04 (m, 3H), 6.84 (d, J = 8.5 Hz, 1H), 4.36 (dd, J = 14.6, 2.5 Hz, 1H), 3.82-3.68 (m, 2H), 3.59-3.38 (m, 3H), 3.26-3.15 (m, 1H), 2.05-1.70 (m, 4H), 1.55-1.34 (m, 2H). |
| 78E | $^1$H NMR (300 MHz, CD$_3$OD-d$_4$) δ 8.04-7.84 (m, 4H), 7.75 (t, J = 7.8 Hz, 1H), 7.47-7.32 (m, 2H), 7.34-7.21 (m, 1H), 7.21-7.08 (m, 1H), 6.86 (d, J = 8.6 Hz, 1H), 4.33 (dd, J = 14.6, 2.5 Hz, 1H), 3.81-3.67 (m, 2H), 3.58-3.36 (m, 3H), 3.26-3.17 (m, 1H), 2.12-1.80 (m, 3H), 1.74 (dd, J = 14.7, 3.7 Hz, 1H), 1.54-1.31 (m, 2H). |
| 78F | $^1$H NMR (300 MHz, CD$_3$OD-d$_4$) δ 8.03-7.89 (m, 4H), 7.76 (t, J = 8.2 Hz, 1H), 7.51-7.32 (m, 2H), 7.31-7.16 (m, 2H), 6.86 (d, J = 8.5 Hz, 1H), 4.37 (dd, J = 14.5, 2.5 Hz, 1H), 3.81-3.68 (m, 2H), 3.62-3.38 (m, 3H), 3.27-3.21 (m, 1H), 2.05-1.70 (m, 4H), 1.56-1.34 (m, 2H). |
| 78G | $^1$H NMR (300 MHz, CD$_3$OD-d$_4$) δ 8.03-7.91 (m, 4H), 7.78 (dd, J = 8.6, 7.2 Hz, 1H), 7.38-7.33 (m, 1H), 7.18 (s, 2H), 7.01 (d, J = 2.0 Hz, 1H), 6.85 (dd, J = 8.5, 1.2 Hz, 1H), 4.37 (dt, J = 14.4, 2.1 Hz, 1H), 3.79 (dq, J = 12.6, 4.3 Hz, 2H), 3.61-3.45 (m, 3H), 3.30-3.24 (m, 1H), 2.39 (s, 6H), 2.01 (d, J = 13.8 Hz, 1H), 1.96-1.87 (m, 2H), 1.83-1.75 (m, 1H), 1.56-1.41 (m, 2H). |
| 78H | $^1$H NMR (400 MHz, CD$_3$OD-d$_4$) δ 8.09 (dd, J = 2.2, 1.0 Hz, 1H), 8.03-7.93 (m, 3H), 7.88-7.78 (m, 3H), 7.70-7.65 (m, 2H), 7.45 (dd, J = 8.6, 2.2 Hz, 1H), 6.93 (d, J = 8.6 Hz, 1H), 4.39 (dd, J = 14.6, 2.5 Hz, 1H), 3.85-3.74 (m, 2H), 3.63-3.46 (m, 3H), 3.29 (d, J = 10.2 Hz, 1H), 2.01 (d, J = 14.3 Hz, 1H), 1.93 (dd, J = 14.6, 7.6 Hz, 2H), 1.80 (dd, J = 14.7, 3.6 Hz, 1H), 1.49 (dddd, J = 24.6, 14.0, 10.7, 4.3 Hz, 2H). |
| 78I | $^1$H NMR (400 MHz, CD$_3$OD-d$_4$) δ 8.10-7.96 (m, 4H), 7.83 (t, J = 7.9 Hz, 1H), 7.42 (dd, J = 8.4, 2.2 Hz, 1H), 7.25-7.15 (m, 2H), 7.02-6.77 (m, 3H), 4.31 (dd, J = 14.4, 2.4 Hz, 1H), 3.83-3.68 (m, 3H), 3.61 (dt, J = 11.9, 9.6 Hz, 2H), 3.37 (d, J = 9.9 Hz, 1H), 2.34-2.22 (m, 1H), 2.11-2.03 (m, 2H), 2.00 (s, 1H), 1.98 (s, 3H), 1.61 (dq, J = 14.5, 8.5, 6.5 Hz, 2H). |
| 78J | $^1$H NMR (400 MHz, CD$_3$OD-d$_4$) δ 8.12-7.96 (m, 4H), 7.83 (t, J = 7.8 Hz, 1H), 7.35-7.17 (m, 3H), 7.12 (td, J = 8.7, 8.1, 3.8 Hz, 1H), 6.93 (d, J = 8.5 Hz, 1H), 4.33 (dd, J = 14.3, 2.4 Hz, 1H), 3.76 (dt, J = 26.3, 6.8 Hz, 3H), 3.67-3.57 (m, 2H), 3.38 (d, J = 9.5 Hz, 1H), 2.27 (d, J = 14.1 Hz, 1H), 2.16-2.02 (m, 3H), 1.99 (s, 3H), 1.62 (tt, J = 11.9, 5.6 Hz, 2H). |
| 78K | $^1$H NMR (400 MHz, CD$_3$OD-d$_4$) δ 8.06 (d, J = 2.2 Hz, 1H), 8.02-7.92 (m, 3H), 7.79 (t, J = 7.8 Hz, 1H), 7.63-7.53 (m, 2H), 7.47-7.39 (m, 2H), 7.27 (ddt, J = 7.9, 2.4, 1.1 Hz, 1H), 6.91 (d, J = 8.6 Hz, 1H), 4.38 (dd, J = 14.6, 2.5 Hz, 1H), 3.79 (dq, J = 12.2, 4.2 Hz, 2H), 3.62-3.44 (m, 3H), 3.31-3.26 (m, 1H), 2.06-1.97 (m, 1H), 1.96-1.88 (m, 2H), 1.79 (dd, J = 14.7, 3.6 Hz, 1H), 1.48 (dddd, J = 24.4, 13.5, 10.9, 4.3 Hz, 2H). |
| 78L | $^1$H NMR (400 MHz, CD$_3$OD-d$_4$) δ 8.05-7.97 (m, 2H), 7.79 (t, J = 7.9 Hz, 1H), 7.37 (dd, J = 8.5, 2.2 Hz, 1H), 7.17-7.13 (m, 1H), 7.06-7.02 (m, 1H), 6.95 (t, J = 2.0 Hz, 1H), 6.88 (d, J = 8.6 Hz, 1H), 4.37 (dd, J = 14.6, 2.5 Hz, 1H), 3.88 (s, 3H), 3.83-3.74 (m, 2H), 3.52 (dddd, J = 27.2, 14.1, 9.0, 2.6 Hz, 3H), 3.27 (dd, J = 14.6, 10.0 Hz, 1H), 2.07-1.97 (m, 1H), 1.95-1.86 (m, 2H), 1.78 (dd, J = 14.7, 3.6 Hz, 1H), 1.55-1.39 (m, 2H). |
| 78M | $^1$H NMR (400 MHz, CD$_3$OD-d$_4$) δ 8.04-7.94 (m, 2H), 7.89 (dd, J = 6.1, 2.1 Hz, 2H), 7.78 (t, J = 7.9 Hz, 1H), 7.43-7.33 (m, 1H), 7.30-7.12 (m, 3H), 6.86 (d, J = 8.5 Hz, 1H), 4.38 (dd, J = 14.6, 2.5 Hz, 1H), 3.82-3.71 (m, 2H), 3.59-3.41 (m, 3H), 3.28-3.21 (m, 1H), 2.09-1.96 (m, 1H), 1.95-1.85 (m, 2H), 1.78 (dd, J = 14.7, 3.6 Hz, 1H), 1.55-1.37 (m, 2H). |
| 78N | $^1$H NMR (300 MHz, CD$_3$OD-d$_4$) δ 8.03 (d, J = 2.2 Hz, 1H), 8.02-7.82 (m, 3H), 7.76 (t, J = 7.8 Hz, 1H), 7.39 (dd, J = 8.6, 2.3 Hz, 1H), 7.24-7.09 (m, 2H), 6.98-6.82 (m, 2H), 4.34 (dd, J = 14.6, 2.5 Hz, 1H), 3.82-3.68 (m, 2H), 3.59-3.39 (m, 3H), 3.23 (d, J = 9.9 Hz, 1H), 2.06-1.82 (m, 3H), 1.75 (dd, J = 14.7, 3.6 Hz, 1H), 1.55-1.32 (m, 2H). |
| 78O | $^1$H NMR (400 MHz, CD$_3$OD-d$_4$) δ 8.08 (d, J = 2.2 Hz, 1H), 8.04-7.92 (m, 3H), 7.80 (t, J = 7.9 Hz, 1H), 7.69 (s, 1H), 7.62 (dt, J = 9.9, 1.9 Hz, 1H), 7.45 (td, J = 9.0, 2.1 Hz, 2H), 6.94 (d, J = 8.6 Hz, 1H), 4.38 (dd, J = 14.7, 2.5 Hz, 1H), 3.79 (dq, J = 12.4, 4.2 Hz, 2H), 3.62-3.44 (m, 3H), 3.31-3.26 (m, 1H), 2.07-1.97 (m, 1H), 1.92 (dd, J = 14.7, 7.9 Hz, 2H), 1.79 (dd, J = 14.7, 3.6 Hz, 1H), 1.48 (dddd, J = 24.9, 13.5, 10.8, 4.3 Hz, 2H). |
| 78P | $^1$H NMR (400 MHz, CD$_3$OD-d$_4$) δ 8.10-7.93 (m, 4H), 7.80 (t, J = 8.1 Hz, 1H), 7.35-7.22 (m, 4H), 6.96-6.87 (m, 1H), 4.45-4.37 (m, 1H), 3.80 (dq, J = 11.6, 3.8 Hz, 2H), 3.63-3.45 (m, 3H), 3.32-3.27 (m, 1H), 2.06-1.98 (m, 1H), 1.97-1.87 (m, 2H), 1.81 (dd, J = 14.7, 3.7 Hz, 1H), 1.49 (dddd, J = 22.0, 13.5, 10.8, 4.3 Hz, 2H). |
| 78Q | $^1$H NMR (400 MHz, CD$_3$OD-d$_4$) δ 8.04-7.87 (m, 4H), 7.77 (t, J = 7.9 Hz, 1H), 7.36 (dd, J = 8.6, 2.2 Hz, 1H), 7.21 (s, 1H), 7.12-7.03 (m, 2H), 6.88 (d, J = 18.9, 9.1 Hz, 2H), 4.35 (dd, J = 14.6, 2.5 Hz, 1H), 3.82-3.71 (m, 2H), 3.59-3.41 (m, 3H), 3.29-3.23 (m, 1H), 2.42 (s, 3H), 1.98 (d, J = 14.5 Hz, 1H), 1.94-1.86 (m, 2H), 1.81-1.72 (m, 1H), 1.55-1.36 (m, 2H). |
| 78R | $^1$H NMR (300 MHz, CD$_3$OD-d$_4$) δ 8.04-7.84 (m, 4H), 7.81-7.69 (m, 1H), 7.35 (dd, J = 8.6, 2.2 Hz, 1H), 6.95-6.79 (m, 3H), 6.66 (dt, J = 10.8, 2.3 Hz, 1H), 4.33 (dd, J = 14.6, |

TABLE 19A-continued

| Compd No. | Physical Characterization Data |
|---|---|
| | 2.5 Hz, 1H), 3.84 (s, 3H), 3.81-3.66 (m, 2H), 3.59-3.37 (m, 3H), 3.26-3.18 (m, 1H), 2.03-1.82 (m, 3H), 1.74 (dd, J = 14.7, 3.7 Hz, 1H), 1.55-1.32 (m, 2H). |
| 78S | $^1$H NMR (300 MHz, CD$_3$OD-d$_4$) δ 8.02-7.86 (m, 4H), 7.74 (t, J = 8.1 Hz, 1H), 7.23 (dt, J = 8.5, 1.7 Hz, 1H), 6.95-6.79 (m, 2H), 6.70 (ddd, J = 8.6, 5.2, 3.0 Hz, 1H), 4.35 (dd, J = 14.5, 2.5 Hz, 1H), 3.90 (s, 3H), 3.79-3.68 (m, 2H), 3.64-3.38 (m, 3H), 3.23 (d, J = 10.0 Hz, 1H), 2.05-1.70 (m, 4H), 1.44 (tdd, J = 15.6, 10.9, 4.3 Hz, 2H). |
| 78T | $^1$H NMR (300 MHz, CD$_3$OD-d$_4$) δ 8.10-7.91 (m, 4H), 7.78 (t, J = 8.1 Hz, 1H), 7.30 (dt, J = 8.6, 1.7 Hz, 1H), 7.23-7.03 (m, 2H), 6.90 (d, J = 8.5 Hz, 1H), 4.38 (dd, J = 14.6, 2.5 Hz, 1H), 3.77 (dq, J = 11.6, 3.8 Hz, 2H), 3.62-3.41 (m, 3H), 3.28 (d, J = 9.9 Hz, 1H), 2.01-1.85 (m, 3H), 1.79 (dd, J = 14.7, 3.6 Hz, 1H), 1.59-1.37 (m, 2H). |
| 78U | $^1$H NMR (300 MHz, CD$_3$OD-d$_4$) δ 8.03-7.91 (m, 3H), 7.77 (t, J = 8.1 Hz, 1H), 7.32-7.24 (m, 1H), 6.91-6.81 (m, 2H), 6.79-6.71 (m, 1H), 4.38 (dd, J = 14.6, 2.5 Hz, 1H), 3.82 (s, 3H), 3.78-3.70 (m, 1H), 3.62-3.41 (m, 3H), 3.28-3.20 (m, 1H), 2.05-1.84 (m, 3H), 1.78 (dd, J = 14.7, 3.6 Hz, 1H), 1.56-1.84 (m, 2H). |
| 78V | $^1$H NMR (300 MHz, CD$_3$OD-d$_4$) δ 8.03 (t, J = 1.7 Hz, 1H), 8.01-7.92 (m, 3H), 7.78 (t, J = 8.1 Hz, 1H), 7.30 (dt, J = 8.5, 1.7 Hz, 1H), 7.16-7.10 (m, 2H), 6.96 (s, 1H), 6.89 (d, J = 8.6 Hz, 1H), 4.38 (dd, J = 14.6, 2.5 Hz, 1H), 3.77 (dq, J = 11.7, 3.9 Hz, 2H), 3.61-3.42 (m, 3H), 3.28-3.22 (m, 1H), 2.04-1.96 (m, 1H), 1.94-1.86 (m, 2H), 1.79 (dd, J = 14.7, 3.6 Hz, 1H), 1.47 (dddd, J = 22.4, 13.5, 10.9, 4.4 Hz, 2H). |
| 78W | $^1$H NMR (300 MHz, CD$_3$OD-d$_4$) δ 8.04-7.91 (m, 4H), 7.78 (t, J = 8.1 Hz, 1H), 7.43-7.34 (m, 1H), 7.33-7.25 (m, 2H), 6.90 (d, J = 8.6 Hz, 1H), 4.38 (dd, J = 14.5, 2.5 Hz, 1H), 3.82-3.72 (m, 2H), 3.59-3.41 (m, 3H), 3.28-3.20 (m, 1H), 2.07-1.95 (m, 1H), 1.96-1.86 (m, 2H), 1.79 (dd, J = 14.7, 3.6 Hz, 1H), 1.56-1.38 (m, 2H). |

Example 79—Synthesis of (R)-3-((S)-6-(3-(difluoromethoxy)-5-fluorophenyl-4-((3-(trifluoromethyl)phenyl)sulfonyl)-3,4-dihydro-2H-benzo[b][1,4]oxazin-2-yl)butanoic acid

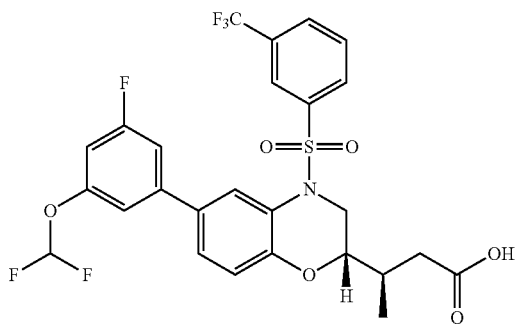 [SMILES: C[C@H](CC(=O)O)[C@H]1CN(S(=O)(=O)c2cccc(C(F)(F)F)c2)c2cc(-c3cc(F)cc(OC(F)F)c3)ccc2O1]

Part I—Synthesis of (R)-3-((S)-6-bromo-4-((3-(trifluoromethyl)phenyl)sulfonyl)-3,4-dihydro-2H-benzo[b][1,4]oxazin-2-yl)butanoic acid

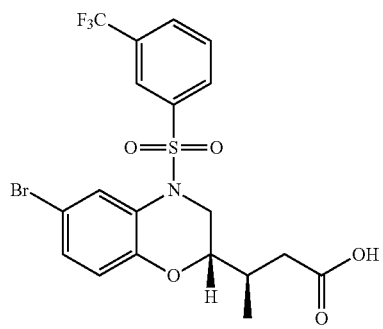 [SMILES: C[C@H](CC(=O)O)[C@H]1CN(S(=O)(=O)c2cccc(C(F)(F)F)c2)c2cc(Br)ccc2O1]

A mixture methyl (R)-3-((S)-oxiran-2-yl)butanoate (362 mg, 2.51 mmol) [prepared by hydrolytic kinetic resolution as described in Org. Biomolecular Chemistry (2013) vol. 11 (8), pages 1280-1285], N-(5-bromo-2-fluorophenyl)-3-(trifluoromethyl)benzene-sulfonamide (1.0 g, 2.51 mmol), tetra-n-butylammonium bromide (80.8 mg, 0.25 mmol), and potassium carbonate (36.2 mg, 0.26 mmol) was stirred overnight at 60° C. Sodium hydroxide (402 mg, 10.05 mmol) and tetrahydrofuran (5.0 mL) was added and the mixture was stirred for an additional four hours at 60° C. Water was added, and the pH value of the mixture was adjusted to 1.0 with 1N hydrogen chloride. The mixture was extracted three times with ethyl acetate. The combined organic layers were dried (Na$_2$SO$_4$) and concentrated. The residue was purified by MPLC eluting with a gradient of 0-66% ethyl acetate in petroleum ether to afford (R)-3-((S)-6-bromo-4-((3-(trifluoromethyl)phenyl)sulfonyl)-3,4-dihydro-2H-benzo[b][1,4]oxazin-2-yl)butanoic acid (700 mg, 55%) as a light yellow oil.

Part II—Synthesis of (R)-3-((S)-6-(4,4,5,5-tetramethyl-1,3,2-dioxaborolan-2-yl)-4-((3-(trifluoromethyl)phenyl)sulfonyl)-3,4-dihydro-2H-benzo[b][1,4]oxazin-2-yl)butanoic acid

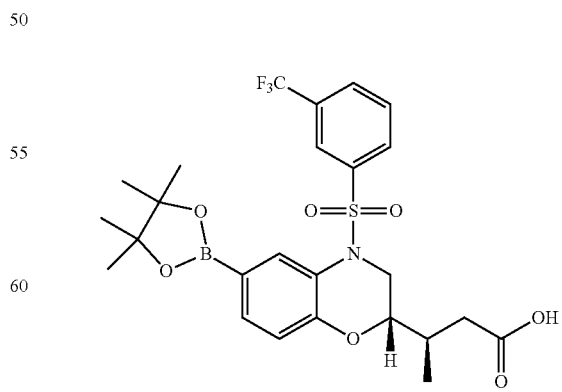

A mixture of (R)-3-((S)-6-bromo-4-((3-(trifluoromethyl)phenyl)sulfonyl)-3,4-dihydro-2H-benzo[b][1,4]oxazin-2-yl)

butanoic acid (740 mg, 1.46 mmol), 4,4,5,5-tetramethyl-2-(tetramethyl-1,3,2-dioxaborolan-2-yl)-1,3,2-dioxaborolane (740 mg, 2.91 mmol), potassium acetate (570 mg, 5.81 mmol), [1,1'-bis(diphenylphosphino)ferrocene] dichloropalladium (II) complex with dichloromethane (105 mg), and ethylene glycol dimethyl ether (10 mL) was stirred overnight at 90° C. Water was added, and the pH value of the mixture was adjusted to 1.0 with 1N HCl. The mixture was extracted three times with ethyl acetate. The combined organic layers were dried ($Na_2SO_4$) and concentrated. The residue was purified by MPLC eluting with a gradient of 0-50% ethyl acetate in petroleum ether to afford (R)-3-((S)-6-(4,4,5,5-tetramethyl-1,3,2-dioxaborolan-2-yl)-4-((3-(trifluoromethyl)phenyl)sulfonyl)-3,4-dihydro-2H-benzo[b][1,4]oxazin-2-yl)butanoic acid (750 mg, 93%) as a solid.

Part III—Synthesis of (R)-3-((S)-6-(3-(difluoromethoxy)-5-fluorophenyl)-4-((3-(trifluoromethyl)phenyl)sulfonyl)-3,4-dihydro-2H-benzo[b][1,4]oxazin-2-yl)butanoic acid A mixture of (R)-3-((S)-6-(4,4,5,5-tetramethyl-1,3,2-dioxaborolan-2-yl)-4-((3-(trifluoromethyl)phenyl)sulfonyl)-3,4-dihydro-2H-benzo[b][1,4]oxazin-2-yl)butanoic acid (110 mg, 0.20 mmol), 1-bromo-3-(difluoromethoxy)-5-fluorobenzene (127 mg, 0.53 mmol), sodium carbonate (76.2 mg, 0.72 mmol), tetrakis(triphenylphosphane) palladium (25.4 mg, 0.02 mmol), toluene (5.0 mL), ethanol (1.0 mL), and water (1.0 mL) was stirred overnight at 90° C. Water was added, and the pH value of the solution was adjusted to 1.0 with 1M hydrogen chloride. The mixture was extracted three times with ethyl acetate. The combined organic layers were dried ($Na_2SO_4$) and concentrated. The residue was purified by Prep-HPLC eluting with 61% acetonitrile in water with 0.05% trifluoroacetic acid to afford (R)-3-((S)-6-(3-(difluoromethoxy)-5-fluorophenyl)-4-((3-(trifluoromethyl)phenyl)sulfonyl)-3,4-dihydro-2H-benzo[b][1,4]oxazin-2-yl)butanoic acid (6.7 mg, 6%) as a white solid: $^1$H-NMR (400 MHz, $CD_3OD$) δ 8.01-7.88 (m, 4H), 7.75 (t, J=11.55 Hz, 1H), 7.38 (d, J=10.2 Hz, 1H), 7.20-6.69 (m, 5H), 4.46-4.37 (m, 1H), 3.36-3.32 (m, 2H), 2.40-2.34 (m, 1H), 2.21-2.14 (m, 1H), 0.95 (d, J=15.6 Hz, 3H). (ES, m/z): (M+H)=590.

Example 80—Preparation of Additional Substituted 4-(aryl sulfonyl)-3,4-dihydro-2H-benzo[b][1,4]oxazin-2-yl) Compounds Compounds in Table 20 were prepared based on experimental procedures described in Example 79 and the detailed description using the appropriate Co salen complex. $^1$H NMR data for compounds from Table 20 is provided in Table 20A.

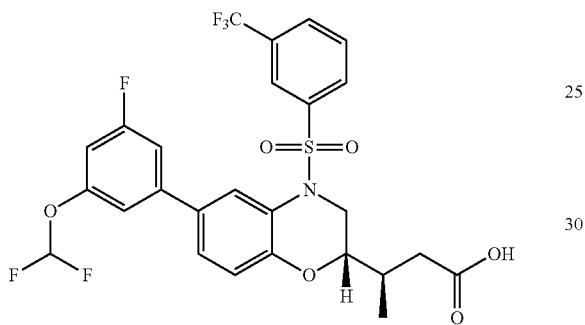

TABLE 20

| Compd No. | Structure | Name | Observed m/z |
|---|---|---|---|
| 80A | ![structure] | (S)-3-((S)-6-(3-(difluoromethoxy)-5-fluorophenyl)-4-((3-(trifluoromethyl)phenyl)sulfonyl)-3,4-dihydro-2H-benzo[b][1,4]-oxazin-2-yl)butanoic acid | 588 (M − H)$^−$ |
| 80B | ![structure] | (R)-3-((S)-6-(2-chloro-3,5-difluorophenyl)-4-((3-(trifluoromethyl)phenyl)sulfonyl)-3,4-dihydro-2H-benzo[b][1,4]-oxazin-2-yl)butanoic acid | 593 (M + NH$_4$)$^+$ |

TABLE 20-continued

| Compd No. | Structure | Name | Observed m/z |
|---|---|---|---|
| 80C | 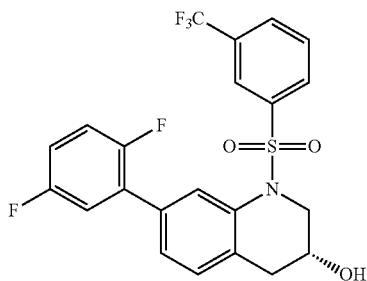 [SMILES: O=S(=O)(c1cccc(C(F)(F)F)c1)N1C[C@H](O)Cc2ccc(-c3cc(F)ccc3F)cc21] | (S)-3-((S)-6-(2-chloro-3,5-difluorophenyl)-4-((3-(trifluoromethyl)phenyl)sulfonyl)-3,4-dihydro-2H-benzo[b][1,4]-oxazin-2-yl)butanoic acid | 593 (M + NH$_4$)$^+$ |

TABLE 20A

| Compd No. | Physical Characterization Data |
|---|---|
| 80A | $^1$H NMR (300 MHz, CD$_3$OD-d$_4$) δ 8.07-7.94 (m, 4H), 7.82-7.78 (m, 1H), 7.45-7.42 (m, 1H), 7.24-6.80 (m, 5H), 4.46 (dd, J = 14.3, 2.4 Hz, 1H), 3.39-3.36 (m, 1H), 3.23-3.15 (m, 1H), 2.57-2.48 (m, 1H), 2.20-2.18 (m, 2H), 1.03 (d, J = 6.8 Hz, 3H). |
| 80B | $^1$H NMR (300 MHz, CD$_3$OD-d$_4$) δ 7.96 (t, J = 7.95 Hz, 2H), 7.86 (d, J = 10.5 Hz, 2H), 7.76 (t, J = 7.8 Hz, 1H), 7.17-7.13 (m, 2H), 7.00 (d, J = 6.3 Hz, 1H), 6.92 (d, J = 8.7 Hz, 1H), 4.44 (d, J = 12.3 Hz, 1H), 3.37-3.30 (m, 2H), 2.41 (t, J = 9.0 Hz, 1H), 2.23 (t, J = 8.85 Hz, 1H), 0.96 (d, J = 6.6 Hz, 3H). |
| 80C | $^1$H NMR (300 MHz, CD$_3$OD-d$_4$) δ 8.02-7.93 (m, 2H), 7.87-7.79 (m, 2H), 7.78-7.77 (m, 1H), 7.19-7.12 (m, 2H), 7.04-7.01 (m, 1H), 7.00-6.90 (m, 1H), 4.44 (dd, J = 14.3, 2.4 Hz, 1H)), 3.35-3.31 (m, 1H), 3.20-3.15 (m, 1H), 2.51-2.45 (m, 1H), 2.17-2.13 (m, 2H), 1.00 (d, J = 6.6 Hz, 3H). |

Example 81—Synthesis of (R)-7-(2,5-difluorophenyl)-1-((3-(trifluoromethyl)phenyl)sulfonyl)-1,2,3,4-tetrahydroquinolin-3-ol

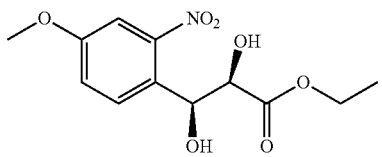

Part I— Synthesis of (E)-ethyl 3-(4-methoxy-2-nitrophenyl)acrylate

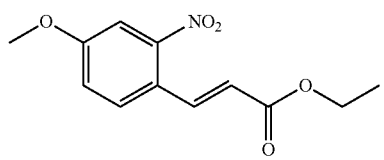 [SMILES: CCOC(=O)/C=C/c1ccc(OC)cc1[N+](=O)[O-]]

A mixture of 1-iodo-4-methoxy-2-nitrobenzene (279 mg, 1.00 mmol), palladium acetate (11.2 mg, 0.05 mmol), triethylamine (202 mg, 2.00 mmol), and ethyl acrylate (110 mg, 1.10 mmol) was heated to reflux for five hours. Then, the mixture was cooled, concentrated and diluted with ethyl acetate. The resulting organic mixture was washed with water, then brine, dried (Na$_2$SO$_4$) and concentrated. The resulting residue was purified via MPLC eluting with 3:1 hexane:ethyl acetate to afford (E)-ethyl 3-(4-methoxy-2-nitrophenyl)acrylate (201 mg, 80%) as a yellow solid.

Part II—Synthesis of (2R,3S)-ethyl 2,3-dihydroxy-3-(4-methoxy-2-nitrophenyl)propanoate To a solution of (E)-ethyl 3-(4-methoxy-2-nitrophenyl)acrylate (5 g, 19.90 mmol) in tert-butanol/water (1:1) (150 mL) was added methanesulfonamide (2 g, 21.03 mmol) followed by the addition of AD-mix-α (16.4 g, 21.05 mmol) in several portions at 0° C. The reaction mixture was stirred overnight at room temperature and then quenched by the addition of saturated aqueous NaHSO$_3$ (200 mL). The resulting mixture was extracted three times with ethyl acetate, and the combined organic layers were concentrated. The resulting residue was purified via MPLC eluting with ethyl acetate/petroleum ether (4:1). Concentration of the major UV active component afforded (2R,3S)-ethyl 2,3-dihydroxy-3-(4-methoxy-2-nitrophenyl)propanoate (4.95 g, 87%) as a yellow solid.

Part III—Synthesis of (4R,5S)-ethyl 5-(4-methoxy-2-nitrophenyl)-1,3,2-dioxathiolane-4-carboxylate 2-oxide

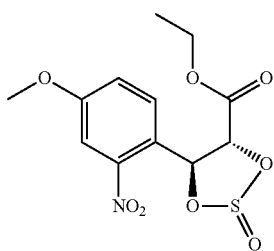

To a stirred solution of ethyl (2R,3S)-2,3-dihydroxy-3-(4-methoxy-2-nitrophenyl)propanoate (5 g, 17.53 mmol) and triethylamine (5.3 g, 52.38 mmol) in dichloromethane (150 mL) at 0° C. was added thionyl chloride (2.7 g, 22.69 mmol) dropwise. The mixture was stirred for 1 hour, and then quenched by the addition of water. The resulting mixture was extracted three times with dichloromethane. The combined organic layers were dried ($Na_2SO_4$) and concentrated. The resulting residue was purified via MPLC eluting with a gradient of ethyl acetate/petroleum ether (1:10-1:2). Concentration of the major UV active component afforded (4R,5S)-ethyl 5-(4-methoxy-2-nitrophenyl)-1,3,2-dioxathiolane-4-carboxylate 2-oxide (5.2 g, 90%) as a yellow oil.

Part IV—Synthesis of (R)-7-methoxy-1,2,3,4-tetrahydroquinolin-3-ol

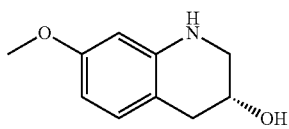

To a solution of (4R,5S)-ethyl 5-(4-methoxy-2-nitrophenyl)-1,3,2-dioxathiolane-4-carboxylate 2-oxide (1.5 g, 4.53 mmol) in 190 proof ethanol (60 mL) at 0° C. was added cobalt (II) chloride hexahydrate (213 mg, 0.90 mmol) followed by the addition of sodium borohydride (1.33 g, 36.1 mmol). The mixture was stirred overnight at room temperature. Then, the mixture was poured into ice water (100 mL), and extracted four times with ethyl acetate. The combined organic layers were concentrated and the resulting residue was purified via MPLC eluting with ethyl acetate/petroleum ether (1:1) to afford (R)-7-methoxy-1,2,3,4-tetrahydroquinolin-3-ol (550 mg, 68%) as a yellow solid.

Part V—Synthesis of (R)-7-methoxy-1-((3-(trifluoromethyl)phenyl)sulfonyl)-1,2,3,4-tetrahydroquinolin-3-ol

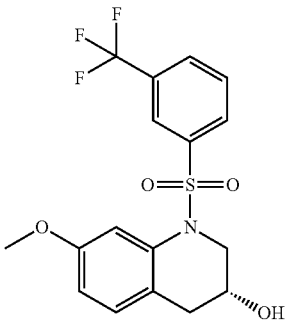 [SMILES: COc1ccc2c(c1)N(S(=O)(=O)c1cccc(C(F)(F)F)c1)C[C@H](O)C2]

To a room temperature solution of (R)-7-methoxy-1,2,3,4-tetrahydroquinolin-3-ol (400 mg, 2.23 mmol) in dichloromethane (12 mL) and pyridine (12 mL) was added 3-(trifluoromethyl)benzene-1-sulfonyl chloride (600 mg, 2.45 mmol). This mixture was stirred for two hours, diluted with dichloromethane and washed twice with 1M hydrogen chloride. The organic layer was dried ($Na_2SO_4$) and concentrated to afford (R)-7-methoxy-1-((3-(trifluoromethyl)phenyl)sulfonyl)-1,2,3,4-tetrahydroquinolin-3-ol (650 mg, 75%) as a colorless oil.

Part VI—Synthesis of (R)-1-((3-(trifluoromethyl)phenyl)sulfonyl)-1,2,3,4-tetrahydroquinoline-3,7-diol

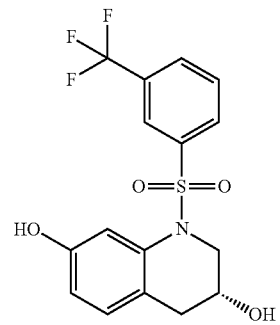 [SMILES: O=S(=O)(c1cccc(C(F)(F)F)c1)N1C[C@H](O)Cc2ccc(O)cc21]

To a solution of (R)-7-methoxy-1-((3-(trifluoromethyl)phenyl)sulfonyl)-1,2,3,4-tetrahydroquinolin-3-ol (1.1 g, 2.84 mmol) in dichloromethane (20 mL) at −78° C. was added boron tribromide (11.2 g, 44.7 mmol) dropwise. The reaction mixture was allowed to warm to room temperature and was stirred for two hours. Then, the reaction was quenched by adding water to the reaction mixture, and the resulting mixture was extracted twice with dichloromethane. The combined organic layers were dried ($Na_2SO_4$) and concentrated. The resulting residue was purified via MPLC eluting with petroleum ether:ethyl acetate (1:1). Concentration of the major UV active component afforded (R)-1-((3-(trifluoromethyl)phenyl)sulfonyl)-1,2,3,4-tetrahydroquinoline-3,7-diol (900 mg, 85%) as a colorless oil.

Part VII—Synthesis of (R)-3-hydroxy-1-((3-(trifluoromethyl)phenyl)sulfonyl)-1,2,3,4-tetrahydroquinolin-7-yl trifluoromethanesulfonate

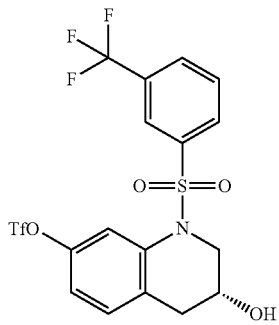 [SMILES: O=S(=O)(c1cccc(C(F)(F)F)c1)N1C[C@H](O)Cc2ccc(OS(=O)(=O)C(F)(F)F)cc21]

To a stirred solution of (R)-1-((3-(trifluoromethyl)phenyl)sulfonyl)-1,2,3,4-tetrahydroquinoline-3,7-diol (800 mg, 2.14 mmol) and pyridine (676 mg, 8.55 mmol) in dichloromethane (70 mL) was added a solution of trifluoromethanesulfonic anhydride (847 mg, 3.00 mmol) in dichloromethane (5 mL) dropwise. The reaction mixture was stirred for two hours at room temperature. Then, the reaction mixture was diluted with water. The resulting mixture was extracted with dichloromethane. The organic layer was washed with water, then brine, and concentrated. The resulting residue was purified via MPLC eluting with ethyl acetate/petroleum ether (1:10-1:3) to afford (R)-3-hydroxy-1-((3-(trifluoromethyl)phenyl)sulfonyl)-1,2,3,4-tetrahydroquinolin-7-yl trifluoromethanesulfonate (950 mg, 88%) as a yellow oil.

Part VIII—Synthesis of (R)-7-(2,5-difluorophenyl)-1-((3-(trifluoromethyl)phenyl)sulfonyl)-1,2,3,4-tetrahydroquinolin-3-ol

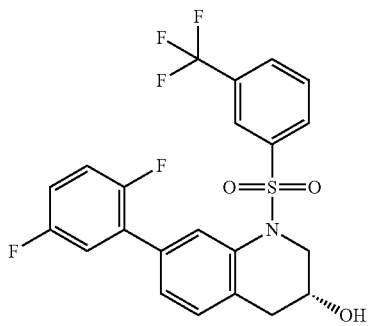 [SMILES: O=S(=O)(c1cccc(C(F)(F)F)c1)N1C[C@H](O)Cc2ccc(-c3cc(F)ccc3F)cc21]

A mixture of (R)-3-hydroxy-1-((3-(trifluoromethyl)phenyl)sulfonyl)-1,2,3,4-tetrahydroquinolin-7-yl trifluoromethanesulfonate (500 mg, 0.99 mmol), (2,5-difluorophenyl) boronic acid (312.9 mg, 1.98 mmol), tetrakis(triphenylphosphane) palladium (57.2 mg, 0.05 mmol), sodium carbonate (314.9 mg, 2.97 mmol), toluene (10 mL), ethanol (3 mL) and water (3 mL) was stirred for two hours at 90° C. The mixture was concentrated, and the residue was purified via MPLC eluting with 33% ethyl acetate in petroleum ether to afford (R)-7-(2,5-difluorophenyl)-1-((3-(trifluoromethyl)phenyl)sulfonyl)-1,2,3,4-tetrahydroquinolin-3-ol (360 mg, 77%).

Example 82—Synthesis of (R)-2-((7-(2,5-difluorophenyl)-1-((3-(trifluoromethyl)phenyl)sulfonyl)-1,2,3,4-tetrahydroquinolin-3-yl)oxy)acetic acid

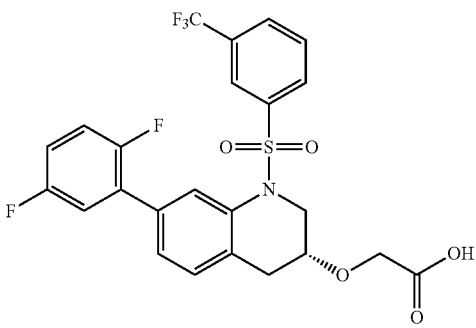 [SMILES: O=C(O)CO[C@@H]1Cc2ccc(-c3cc(F)ccc3F)cc2N(S(=O)(=O)c2cccc(C(F)(F)F)c2)C1]

Part I—Synthesis of methyl (R)-2-((7-(2,5-difluorophenyl)-1-((3-(trifluoromethyl)phenyl)sulfonyl)-1,2,3,4-tetrahydroquinolin-3-yl)oxy)acetate

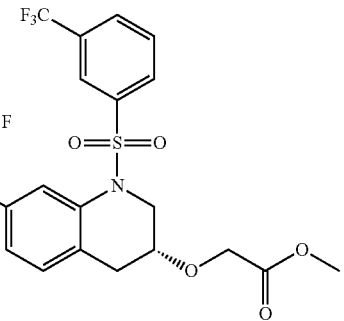

A 60% suspension of sodium hydride in mineral oil (17.1 mg, 0.43 mmol) was added portionwise to a stirred solution of (R)-7-(2,5-difluorophenyl)-1-((3-(trifluoromethyl)phenyl)sulfonyl)-1,2,3,4-tetrahydroquinolin-3-ol (100 mg, 0.21 mmol) in N,N-dimethylformamide (1 mL) at 0° C. Methyl 2-bromoacetate (64.8 mg, 0.42 mmol) was added and the mixture was stirred for two hours at room temperature. Water was added, and the mixture was extracted twice with ethyl acetate. The organic layer was washed with brine, dried, (Na$_2$SO$_4$) and concentrated. The residue was purified via MPLC eluting with 33% ethyl acetate in petroleum ether to afford methyl (R)-2-((7-(2,5-difluorophenyl)-1-((3-(trifluoromethyl)phenyl)sulfonyl)-1,2,3,4-tetrahydroquinolin-3-yl)oxy)acetate (20 mg, 17%) as a yellow oil.

Part II—Synthesis of (R)-2-((7-(2,5-difluorophenyl)-1-((3-(trifluoromethyl)phenyl)sulfonyl)-1,2,3,4-tetrahydroquinolin-3-yl)oxy)acetic acid

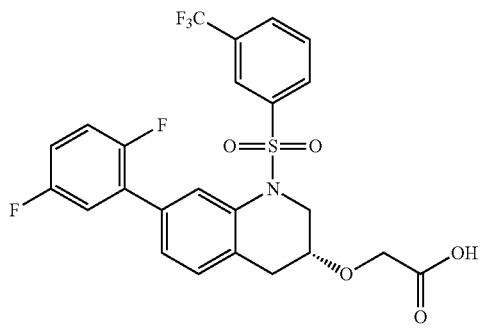 [SMILES: O=C(O)CO[C@@H]1Cc2ccc(-c3cc(F)ccc3F)cc2N(S(=O)(=O)c2cccc(C(F)(F)F)c2)C1]

A mixture of methyl (R)-2-((7-(2,5-difluorophenyl)-1-((3-(trifluoromethyl)phenyl)sulfonyl)-1,2,3,4-tetrahydroquinolin-3-yl)oxy)acetate (80 mg, 0.15 mmol), tetrahydrofuran (2 mL), water (0.5 mL), and lithium hydroxide (12.4 mg, 0.30 mmol) was stirred for two hours at room temperature. The mixture was diluted with 1N HCl, and extracted twice with ethyl acetate. The organic layer was dried ($Na_2SO_4$) and concentrated. The residue was purified by Prep-HPLC eluting with a gradient of 56-75% acetonitrile in water with 0.05% trifluoroacetic acid to afford (R)-2-((7-(2,5-difluorophenyl)-1-((3-(trifluoromethyl)phenyl)sulfonyl)-1,2,3,4-tetrahydroquinolin-3-yl)oxy)acetic acid (10.5 mg, 13%) as a white solid: $^1$H-NMR (400 MHz, $CD_3OD$) δ 8.05 (d, J=8.0 Hz, 1H), 8.00-7.89 (m, 3H), 7.70 (t, J=7.9 Hz, 1H), 7.34-7.09 (m, 5H), 4.22-4.00 (m, 4H), 3.92-3.81 (m, 1H), 2.87 (dd, J=17.0, 5.4 Hz, 1H), 2.65 (dd, J=17.0, 5.8 Hz, 1H). (ES, m/z): $(M+H)^+$ 528.

Example 83—Preparation of Additional Substituted 4-(aryl sulfonyl)-3,4-dihydro-2H-benzo[b][1,4]oxazin-2-yl) Compounds Compounds in Table 21 were prepared based on experimental procedures described in Examples 81 and 82 and the detailed description. $^1$H NMR data for exemplary compounds from Table 21 is provided in Table 21A.

TABLE 21

| Compd No. | Structure | Name | Observed m/z |
|---|---|---|---|
| 83A | 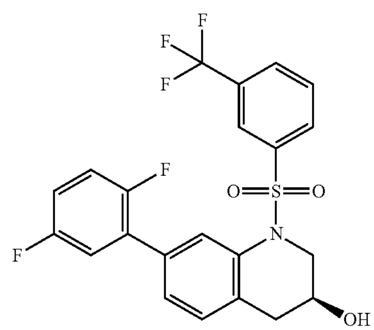 [SMILES: O=S(=O)(c1cccc(C(F)(F)F)c1)N1C[C@@H](O)Cc2ccc(-c3cc(F)ccc3F)cc21] | (S)-7-(2,5-difluorophenyl)-1-((3-(trifluoromethyl)phenyl)sulfonyl)-1,2,3,4-tetrahydroquinolin-3-ol | 470 (M + H)$^+$ |
| 83B | 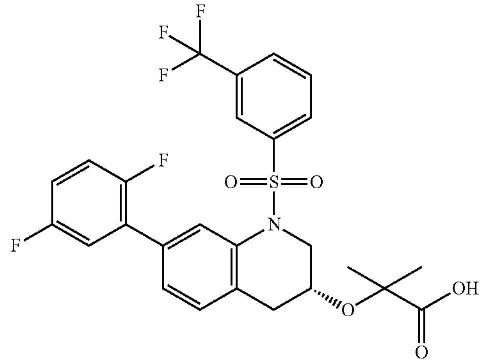 [SMILES: CC(C)(O[C@@H]1Cc2ccc(-c3cc(F)ccc3F)cc2N(S(=O)(=O)c2cccc(C(F)(F)F)c2)C1)C(=O)O] | (R)-2-((7-(2,5-difluorophenyl)-1-((3-(trifluoromethyl)phenyl)sulfonyl)-1,2,3,4-tetrahydroquinolin-3-yl)oxy)-2-methylpropanoic acid | 556 (M + H)$^+$ |

TABLE 21-continued

| Compd No. | Structure | Name | Observed m/z |
|---|---|---|---|
| 83C | 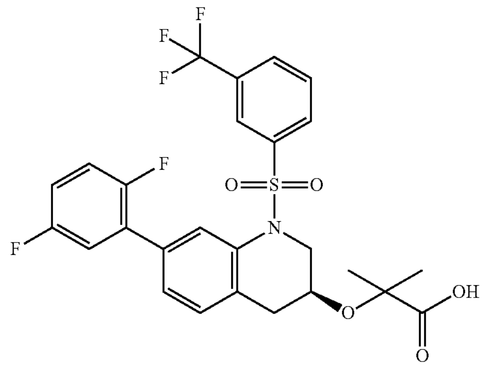 [SMILES: CC(C)(O[C@H]1Cc2ccc(-c3cc(F)ccc3F)cc2N(S(=O)(=O)c2cccc(C(F)(F)F)c2)C1)C(=O)O] | (S)-2-((7-(2,5-difluorophenyl)-1-((3-(trifluoromethyl)phenyl)sulfonyl)-1,2,3,4-tetrahydroquinolin-3-yl)oxy)-2-methylpropanoic acid | 556 (M + H)+ |
| 83D | 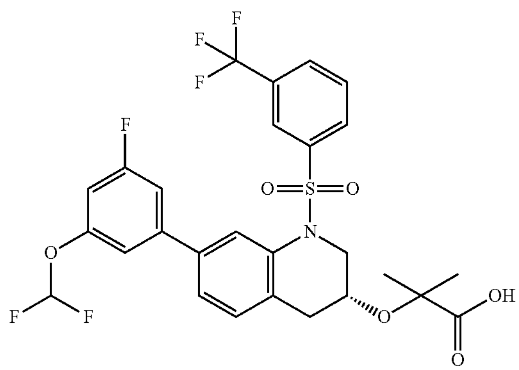 [SMILES: CC(C)(O[C@@H]1Cc2ccc(-c3cc(F)cc(OC(F)F)c3)cc2N(S(=O)(=O)c2cccc(C(F)(F)F)c2)C1)C(=O)O] | (R)-2-((7-(3-(difluoromethoxy)-5-fluorophenyl)-1-((3-(trifluoromethyl)phenyl)sulfonyl)-1,2,3,4-tetrahydroquinolin-3-yl)oxy)-2-methylpropanoic acid | 604 (M + H)+ |
| 83E | 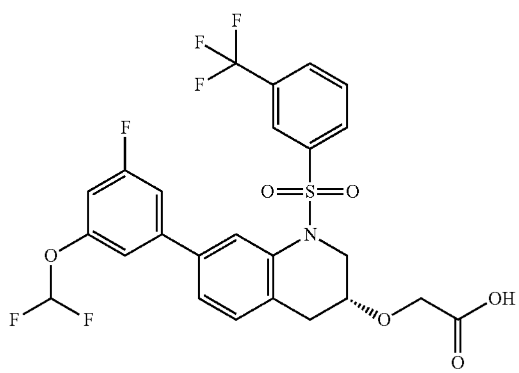 [SMILES: O=C(O)CO[C@@H]1Cc2ccc(-c3cc(F)cc(OC(F)F)c3)cc2N(S(=O)(=O)c2cccc(C(F)(F)F)c2)C1] | (R)-2-((7-(3-(difluoromethoxy)-5-fluorophenyl)-1-((3-(trifluoromethyl)phenyl)sulfonyl)-1,2,3,4-tetrahydroquinolin-3-yl)oxy)acetic acid | 576 (M + H)+ |
| 83F | 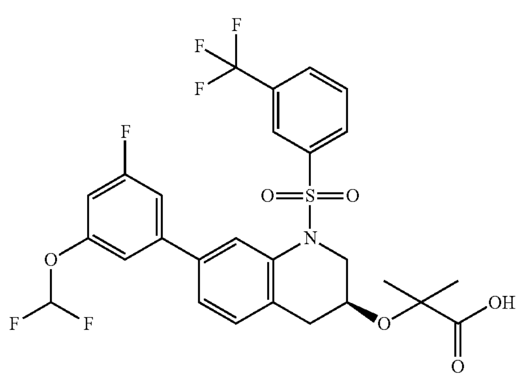 [SMILES: CC(C)(O[C@H]1Cc2ccc(-c3cc(F)cc(OC(F)F)c3)cc2N(S(=O)(=O)c2cccc(C(F)(F)F)c2)C1)C(=O)O] | (S)-2-((7-(3-(difluoromethoxy)-5-fluorophenyl)-1-((3-(trifluoromethyl)phenyl)sulfonyl)-1,2,3,4-tetrahydroquinolin-3-yl)oxy)-2-methylpropanoic acid | 604 (M + H)+ |

TABLE 21A

| Compd No. | Physical Characterization Data |
|---|---|
| 83B | $^1$H NMR (300 MHz, CD$_3$OD-d$_4$) δ 8.00 (d, J = 8.0 Hz, 1H), 7.98-7.91 (m, 2H), 7.87 (s, 1H), 7.73 (t, J = 7.9 Hz, 1H), 7.35 (d, J = 8.0 Hz, 1H), 7.30-7.11 (m, 4H), 4.43 (dd, J = 13.6, 4.4 Hz, 1H), 3.67 (p, J = 7.2, 6.7 Hz, 1H), 3.55 (dd, J = 13.6, 8.7 Hz, 1H), 2.87 (dd, J = 17.0, 6.2 Hz, 1H), 2.53 (dd, J = 16.9, 8.0 Hz, 1H), 1.45 (s, 3H), 1.37 (s, 3H). |
| 83C | $^1$H NMR (300 MHz, CD$_3$OD-d$_4$) δ 8.03-7.91 (m, 3H), 7.87 (s, 1H), 7.73 (t, J = 7.9 Hz, 1H), 7.36 (d, J = 7.9 Hz, 1H), 7.30-7.11 (m, 4H), 4.47-4.39 (m, 1H), 3.67 (p, J = 7.1, 6.7 Hz, 1H), 3.55 (dd, J = 13.7, 8.6 Hz, 1H), 2.87 (dd, J = 17.0, 6.2 Hz, 1H), 2.53 (dd, J = 17.0, 8.0 Hz, 1H), 1.45 (s, 3H), 1.37 (s, 3H). |
| 83D | $^1$H NMR (300 MHz, CD$_3$OD-d$_4$) δ 8.00-7.92 (m, 3H), 7.85 (t, J = 1.8 Hz, 1H), 7.73 (t, J = 7.9 Hz, 1H), 7.46 (dd, J = 8.0, 1.9 Hz, 1H), 7.27-7.19 (m, 3H), 7.18-6.77 (m, 2H), 4.46-4.34 (m, 1H), 3.65 (tdd, J = 8.1, 6.1, 4.4 Hz, 1H), 3.54 (dd, J = 13.5, 8.5 Hz, 1H), 2.85 (dd, J = 17.0, 6.2 Hz, 1H), 2.50 (dd, J = 16.9, 7.9 Hz, 1H), 1.43 (s, 3H), 1.35 (s, 3H). |
| 83E | $^1$H NMR (300 MHz, CD$_3$OD-d$_4$) δ 8.06-8.00 (m, 1H), 7.99-7.91 (m, 3H), 7.71 (t, J = 7.9 Hz, 1H), 7.41 (dd, J = 7.9, 1.9 Hz, 1H), 7.27-6.77 (m, 5H), 4.19-4.01 (m, 4H), 3.84 (dt, J = 10.3, 5.2 Hz, 1H), 2.85 (dd, J = 17.0, 5.4 Hz, 1H), 2.64 (dd, J = 17.0, 5.8 Hz, 1H). |
| 83F | $^1$H NMR (300 MHz, CD$_3$OD-d$_4$) δ 8.03-7.93 (m, 3H), 7.85 (s, 1H), 7.74 (t, J = 7.9 Hz, 1H), 7.47 (d, J = 7.9 Hz, 1H), 7.29-6.79 (m, 5H), 4.46-4.36 (m, 1H), 3.66 (p, J = 7.2, 6.6 Hz, 1H), 3.60-3.49 (m, 1H), 2.85 (dd, J = 17.1, 6.2 Hz, 1H), 2.51 (dd, J = 16.9, 7.9 Hz, 1H), 1.43 (s, 3H), 1.36 (s, 3H). |

Example 84 and 85—Synthesis of (1s,3R)-3-acetamido-1-(((S)-6-(3-(difluoromethoxy)-5-fluorophenyl)-4-((3-(trifluoromethyl)phenyl)sulfonyl)-3,4-dihydro-2H-benzo[b][1,4]oxazin-2-yl)methyl)cyclobutane-1-carboxylic acid and (1r,3S)-3-acetamido-1-(((S)-6-(3-(difluoromethoxy)-5-fluorophenyl)-4-((3-(trifluoromethyl)phenyl)sulfonyl)-3,4-dihydro-2H-benzo[b][1,4]oxazin-2-yl)methyl)cyclobutane-1-carboxylicacid (84)

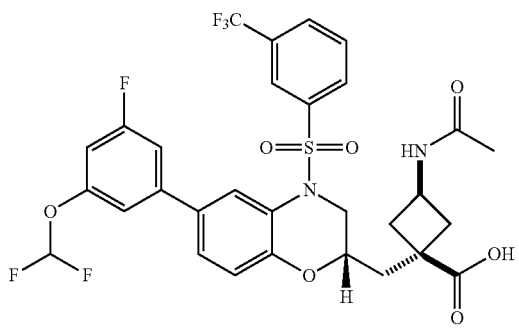

(85)

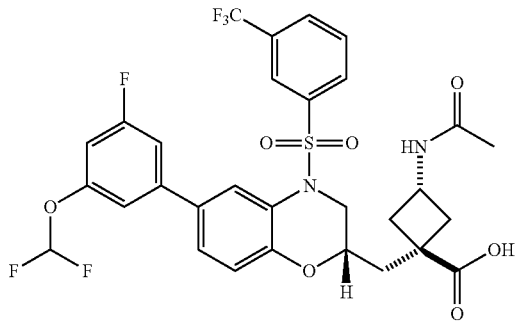

Part I—Synthesis of (S)-1-((6-bromo-4-((3-(trifluoromethyl)phenyl)sulfonyl)-3,4-dihydro-2H-benzo[b][1,4]oxazin-2-yl)methyl)-3-((4-methoxybenzyl)amino)cyclobutane-1-carboxylic acid

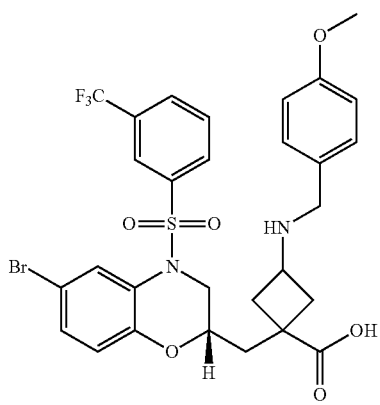 [SMILES: COc1ccc(CNC2CC(C[C@H]3CN(S(=O)(=O)c4cccc(C(F)(F)F)c4)c4cc(Br)ccc4O3)(C(=O)O)C2)cc1]

A mixture of (S)-1-((6-bromo-4-((3-(trifluoromethyl)phenyl)sulfonyl)-3,4-dihydro-2H-benzo[b][1,4]oxazin-2-yl)methyl)-3-oxocyclobutane-1-carboxylic acid (1.0 g, 1.82 mmol), dichloroethane (15 mL), (4-methoxyphenyl)methanamine (0.30 g), and sodium triacetoxyborohydride (1.6 g) was stirred for four hours at room temperature. The mixture was diluted with saturated sodium bicarbonate and was extracted three times with ethyl acetate. The combined organic layers were dried (Na$_2$SO$_4$) and concentrated to afford (S)-1-((6-bromo-4-((3-(trifluoromethyl)phenyl)sulfonyl)-3,4-dihydro-2H-benzo[b][1,4]oxazin-2-yl)methyl)-3-((4-methoxybenzyl)amino)cyclobutane-1-carboxylic acid (1 g, 82%) as a colorless oil.

Part II—Synthesis of (S)-1-((6-bromo-4-((3-(trifluoromethyl)phenyl)sulfonyl)-3,4-dihydro-2H-benzo[b][1,4]oxazin-2-yl)methyl)-3-(N-(4-methoxybenzyl)acetamido)cyclobutane-1-carboxylic acid

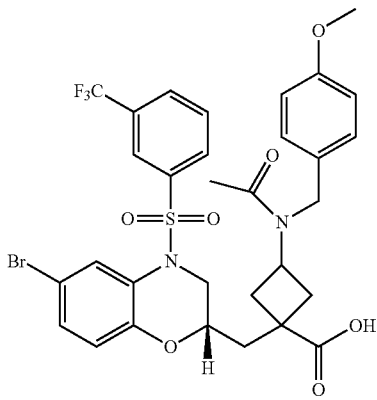 [SMILES: COc1ccc(CN(C(C)=O)C2CC(C[C@H]3CN(S(=O)(=O)c4cccc(C(F)(F)F)c4)c4cc(Br)ccc4O3)(C(=O)O)C2)cc1]

A mixture of (S)-1-((6-bromo-4-((3-(trifluoromethyl)phenyl)sulfonyl)-3,4-dihydro-2H-benzo[b][1,4]oxazin-2-yl)methyl)-3-((4-methoxybenzyl)amino)cyclobutane-1-carboxylic acid (1 g, 1.49 mmol), dichloromethane (15 mL), triethylamine (450 mg, 4.45 mmol), and acetyl chloride (230 mg, 2.93 mmol) was stirred for two hours at room temperature. The mixture was diluted with dichloromethane and was washed twice with water, dried (Na$_2$SO$_4$) and concentrated. Tetrahydrofuran (10 mL), water (3 mL), and lithium hydroxide (200 mg, 8.35 mmol) was added to the residue, and the mixture was stirred for four hours at room temperature. The mixture was diluted with 1N HCl, and extracted twice with ethyl acetate. The combined organic layers were dried (Na$_2$SO$_4$) and concentrated. The residue was purified via MPLC eluting with 10% methanol in dichloromethane to afford (S)-1-((6-bromo-4-((3-(trifluoromethyl)phenyl)sulfonyl)-3,4-dihydro-2H-benzo[b][1,4]oxazin-2-yl)methyl)-3-(N-(4-methoxybenzyl)acetamido)cyclobutane-1-carboxylic acid (800 mg, 85%) as a colorless oil.

Part III—Synthesis of (S)-1-((6-(3-(difluoromethoxy)-5-fluorophenyl)-4-((3-(trifluoromethyl)phenyl)sulfonyl)-3,4-dihydro-2H-benzo[b][1,4]oxazin-2-yl)methyl)-3-(N-(4-methoxybenzyl)acetamido)cyclobutane-1-carboxylic acid

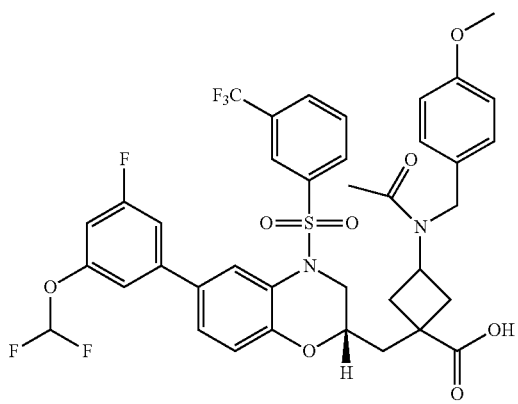 [SMILES: COc1ccc(CN(C(C)=O)C2CC(C[C@H]3CN(S(=O)(=O)c4cccc(C(F)(F)F)c4)c4cc(-c5cc(F)cc(OC(F)F)c5)ccc4O3)(C(=O)O)C2)cc1]

A mixture of (S)-1-((6-bromo-4-((3-(trifluoromethyl)phenyl)sulfonyl)-3,4-dihydro-2H-benzo[b][1,4]oxazin-2-yl)methyl)-3-(N-(4-methoxybenzyl)acetamido)cyclobutane-1-carboxylic acid (400 mg, 0.56 mmol), 2-[3-(difluoromethoxy)-5-fluorophenyl]-4,4,5,5-tetramethyl-1,3,2-dioxaborolane (252 mg, 0.87 mmol), sodium carbonate (179 mg, 1.69 mmol), tetrakis(triphenylphosphane) palladium (65 mg, 0.06 mmol), toluene (10 mL), methanol (3 mL), and water (3 mL) was stirred for three hours at 90° C. The mixture was with water and was extracted three times with ethyl acetate. The combined organic layers were dried (Na$_2$SO$_4$) and concentrated. The residue was purified via MPLC eluting with 10% methanol in dichloromethane to afford (S)-1-((6-(3-(difluoromethoxy)-5-fluorophenyl)-4-((3-(trifluoromethyl)phenyl)sulfonyl)-3,4-dihydro-2H-benzo[b][1,4]oxazin-2-yl)methyl)-3-(N-(4-methoxybenzyl)acetamido)cyclobutane-1-carboxylic acid (300 mg, 67%) as a colorless oil.

Part IV—Synthesis of (1s,3R)-3-acetamido-1-(((S)-6-(3-(difluoromethoxy)-5-fluorophenyl)-4-((3-(trifluoromethyl)phenyl)sulfonyl)-3,4-dihydro-2H-benzo[b][1,4]oxazin-2-yl)methyl)cyclobutane-1-carboxylic acid and (1r,3S)-3-acetamido-1-(((S)-6-(3-(difluoromethoxy)-5-fluorophenyl)-4-((3-(trifluoromethyl)phenyl)sulfonyl)-3,4-dihydro-2H-benzo[b][1,4]oxazin-2-yl)methyl)cyclobutane-1-carboxylic acid (84)

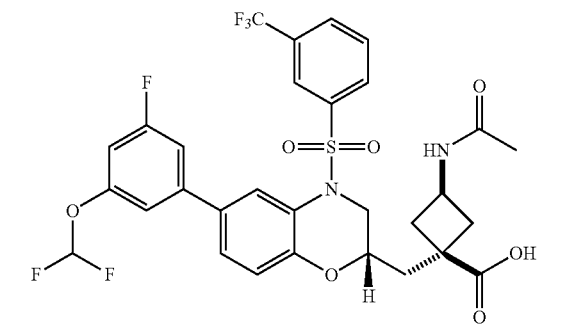

(85)

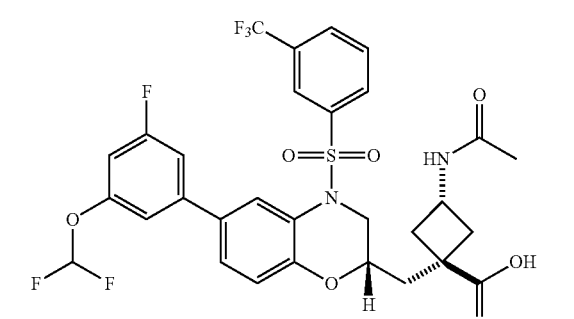

A mixture of (S)-1-((6-(3-(difluoromethoxy)-5-fluorophenyl)-4-((3-(trifluoromethyl)phenyl)sulfonyl)-3,4-dihydro-2H-benzo[b][1,4]oxazin-2-yl)methyl)-3-(N-(4-methoxybenzyl)acetamido)cyclobutane-1-carboxylic acid (150 mg, 0.19 mmol), dichloromethane (3 mL), and trifluoroacetic acid (3 mL) was stirred overnight at 50° C. The mixture was concentrated and the residue was diluted with saturated sodium bicarbonate and extracted twice with ethyl acetate. The combined organic layers combined were dried (Na$_2$SO$_4$) and concentrated. The residue was purified by Prep-HPLC eluting with a gradient of 52-70% acetonitrile in water with 0.05% trifluoroacetic acid to afford (1s,3R)-3-acetamido-1-(((S)-6-(3-(difluoromethoxy)-5-fluorophenyl)-4-((3-(trifluoromethyl)phenyl)sulfonyl)-3,4-dihydro-2H-benzo[b][1,4]oxazin-2-yl)methyl)cyclobutane-1-carboxylic acid (48.1 mg, 38%): $^1$H-NMR (400 MHz, CD$_3$OD) δ 8.04-7.93 (m, 3H), 7.85-7.74 (m, 2H), 7.40 (dd, J=8.6, 2.2 Hz, 1H), 7.27-6.75 (m, 5H), 4.43-4.30 (m, 2H), 3.52-3.41 (m, 1H), 3.36-3.31 (m, 7H), 2.79-2.67 (m, 2H), 2.10-1.94 (m, 3H), 1.90 (s, 4H); (ES, m/z): (M+H)$^+$ 672; and (1r,3S)-3-acetamido-1-(((S)-6-(3-(difluoromethoxy)-5-fluorophenyl)-4-((3-(trifluoromethyl)phenyl)sulfonyl)-3,4-dihydro-2H-benzo[b][1,4]oxazin-2-yl)methyl)cyclobutane-1-carboxylic acid (13.6 mg, 11%): $^1$H-NMR (400 MHz, CD$_3$OD) δ 8.04 (d, J=2.2 Hz, 1H), 7.97 (dd, J=7.7, 1.7 Hz, 2H), 7.88 (s, 1H), 7.77 (t, J=7.9 Hz, 1H), 7.44-7.36 (m, 1H), 7.25-7.12 (m, 2H), 7.01-6.68 (m, 3H), 4.44 (dd, J=14.5, 2.3 Hz, 1H), 4.34-4.21 (m, 1H), 3.48-3.39 (m, 1H), 3.36 (s, 1H), 2.46-2.26 (m, 3H), 2.24-2.16 (m, 1H), 2.12-2.01 (m, 2H), 1.91 (s, 3H). (ES, m/z): (M+H)$^+$ 672; as white solids.

Example 86—Synthesis of (S)-1-((6-(3-(difluoromethoxy)-5-fluorophenyl)-4-((3-(trifluoromethyl)phenyl)sulfonyl)-3,4-dihydro-2H-benzo[b][1,4]oxazin-2-yl)methy)-3-methylenecyclobutane-1-carboxylic acid

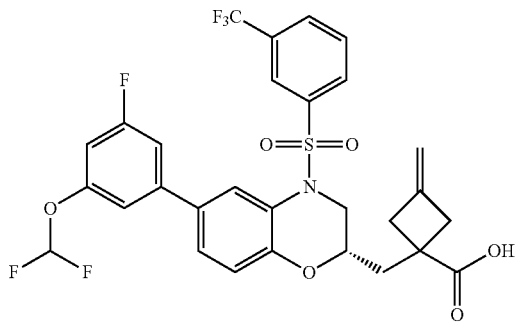 [SMILES: C=C1CC(C[C@H]2CN(S(=O)(=O)c3cccc(C(F)(F)F)c3)c3cc(-c4cc(F)cc(OC(F)F)c4)ccc3O2)(C(=O)O)C1]

Part I—Synthesis of (S)-1-((6-bromo-4-((3-(trifluoromethyl)phenyl)sulfonyl)-3,4-dihydro-2H-benzo[b][1,4]oxazin-2-yl)methyl)-3-methylenecyclobutane-1-carboxylicacid

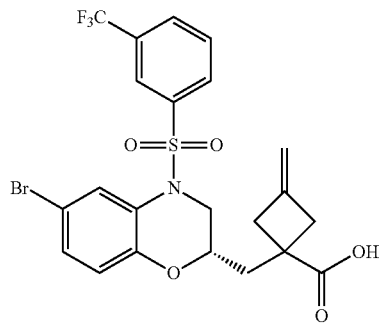

A mixture of (S)-1-((6-bromo-4-((3-(trifluoromethyl)phenyl)sulfonyl)-3,4-dihydro-2H-benzo[b][1,4]oxazin-2-yl)methyl)-3-methylenecyclobutane-1-carbonitrile (1.0 g, 1.90 mmol), ethanol (15 mL), water (15 mL), and potassium hydroxide (1 g) was stirred for two days at 90° C. The mixture was diluted with 1N HCl, and extracted twice with ethyl acetate. The combined organic layers were dried (Na$_2$SO$_4$) and concentrated. The residue was purified via MPLC eluting with 33% ethyl acetate in petroleum ether to afford (S)-1-((6-bromo-4-((3-(trifluoromethyl)phenyl)sulfonyl)-3,4-dihydro-2H-benzo[b][1,4]oxazin-2-yl)methyl)-3-methylenecyclobutane-1-carboxylic acid (700 mg, 68%) as a colorless oil.

Part II—Synthesis of (S)-1-((6-(3-(difluoromethoxy)-5-fluorophenyl)-4-((3-(trifluoromethyl)phenyl)sulfonyl)-3,4-dihydro-2H-benzo[b][1,4]oxazin-2-yl)methyl)-3-methylenecyclobutane-1-carboxylicacid

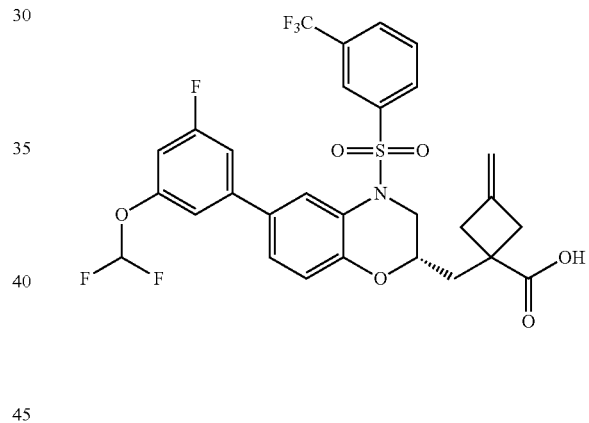

A mixture of (S)-1-((6-bromo-4-((3-(trifluoromethyl)phenyl)sulfonyl)-3,4-dihydro-2H-benzo[b][1,4]oxazin-2-yl)methyl)-3-methylenecyclobutane-1-carboxylicacid (400 mg, 0.73 mmol), 2-[3-(difluoromethoxy)-5-fluorophenyl]-4,4,5,5-tetramethyl-1,3,2-dioxaborolane (326 mg, 1.13 mmol), sodium carbonate (233 mg, 2.20 mmol), tetrakis(triphenylphosphane) palladium (85 mg, 0.07 mmol), toluene (10 mL), methanol (3 mL), and water (3 mL) was stirred for three hours at 90° C. The mixture was diluted with water, and extracted twice with ethyl acetate. The combined organic layers were dried (Na$_2$SO$_4$) and concentrated. The residue was purified via MPLC eluting with 10% methanol in dichloromethane to afford (S)-1-((6-(3-(difluoromethoxy)-5-fluorophenyl)-4-((3-(trifluoromethyl)phenyl)sulfonyl)-3,4-dihydro-2H-benzo[b][1,4]oxazin-2-yl)methyl)-3-methylenecyclobutane-1-carboxylic acid (300 mg, 65%).

Example 87 and 88—Synthesis of (1r,3R)-1-(((S)-6-(3-(difluoromethoxy)-5-fluorophenyl)-4-((3-(trifluoromethyl)phenyl)sulfonyl)-3,4-dihydro-2H-benzo[b][1,4]oxazin-2-yl)methyl)-3-hydroxy-3-(hydroxymethyl)cyclobutane-1-carboxylic acid and (1s,3S)-1-(((S)-6-(3-(difluoromethoxy)-5-fluorophenyl)-4-((3-(trifluoromethyl)phenyl)sulfonyl)-3,4-dihydro-2H-benzo[b][1,4]oxazin-2-yl)methyl)-3-hydroxy-3-(hydroxymethyl)cyclobutane-1-carboxylic acid

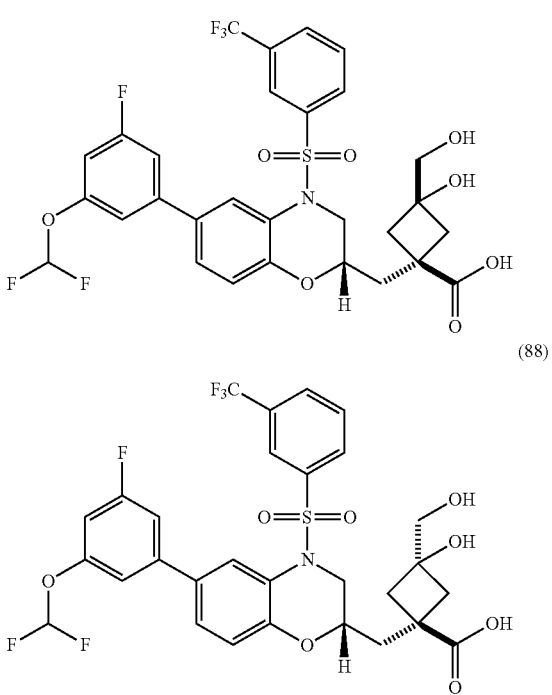

A mixture of (S)-1-((6-(3-(difluoromethoxy)-5-fluorophenyl)-4-((3-(trifluoromethyl)phenyl)sulfonyl)-3,4-dihydro-2H-benzo[b][1,4]oxazin-2-yl)methyl)-3-methylenecyclobutane-1-carboxylic acid (120 mg, 0.19 mmol), acetone (5 mL), water (1 mL), N-methyl morpholine oxide (67 mg, 0.57 mmol), tetraoxoosmium (5 mg, 0.02 mmol), and tert-butyl alcohol (1 mL) was stirred overnight. A solution of sodium bisulfite was added and the mixture was extracted twice with ethyl acetate. The combined organic layers were dried ($Na_2SO_4$) and concentrated. The residue was purified by Prep-HPLC eluting with a gradient of 53-75% acetonitrile in water with 0.05% trifluoroacetic acid to afford (1r,3R)-1-(((S)-6-(3-(difluoromethoxy)-5-fluorophenyl)-4-((3-(trifluoromethyl)phenyl)sulfonyl)-3,4-dihydro-2H-benzo[b][1,4]oxazin-2-yl)methyl)-3-hydroxy-3-(hydroxymethyl)cyclobutane-1-carboxylic acid (10.9 mg, 9%): $^1$H-NMR (400 MHz, $CD_3OD$) δ 8.10-7.91 (m, 3H), 7.80 (dd, J=15.2, 7.4 Hz, 2H), 7.39 (dd, J=8.6, 2.2 Hz, 1H), 7.24-6.74 (m, 5H), 4.40 (dd, J=14.5, 2.5 Hz, 1H), 3.54-3.40 (m, 3H), 3.39-3.33 (m, 1H), 2.68-2.58 (m, 2H), 2.26-2.07 (m, 2H), 1.97 (d, J=12.9 Hz, 1H), 1.86 (d, J=12.8 Hz, 1H); (ES, m/z): (M−H)$^-$; 660 and (1s,3S)-1-(((S)-6-(3-(difluoromethoxy)-5-fluorophenyl)-4-((3-(trifluoromethyl)phenyl)sulfonyl)-3,4-dihydro-2H-benzo[b][1,4]oxazin-2-yl)methyl)-3-hydroxy-3-(hydroxymethyl)cyclobutane-1-carboxylic acid (13.3, 11%): $^1$H-NMR (400 MHz, $CD_3OD$) δ 8.06-7.93 (m, 3H), 7.87-7.74 (m, 2H), 7.43-7.35 (m, 1H), 7.26-6.74 (m, 5H), 4.40 (dd, J=14.3, 2.4 Hz, 1H), 3.44-3.37 (m, 3H), 3.28-3.23 (m, 1H), 2.42 (t, J=14.7 Hz, 2H), 2.23 (d, J=13.2 Hz, 1H), 2.15-1.97 (m, 3H); (ES, m/z): (M−H)$^-$; 660 as white solids.

Example 89—Preparation of Additional Substituted 4-(aryl)sulfonyl)-3,4-dihydro-2H-benzo[b][1,4]oxazin-2-yl) Compounds Compounds in Table 22 were prepared based on experimental procedures described in Examples 84, 85, 86, 87, and 88 and the detailed description. $^1$H NMR data for exemplary compounds from Table 22 is provided in Table 22A.

TABLE 22

| Compd No. | Structure | Name | Observed m/z |
|---|---|---|---|
| 89A | 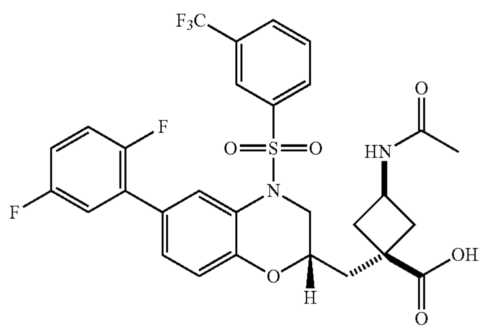 | (1s,3R)-3-acetamido-1-(((S)-6-(2,5-difluorophenyl)-4-((3-(trifluoromethyl)phenyl)sulfonyl)-3,4-dihydro-2H-benzo[b][1,4]oxazin-2-yl)methyl)cyclobutane-1-carboxylic acid | 625 (M + H)$^+$ |

TABLE 22-continued

| Compd No. | Structure | Name | Observed m/z |
|---|---|---|---|
| 89B | 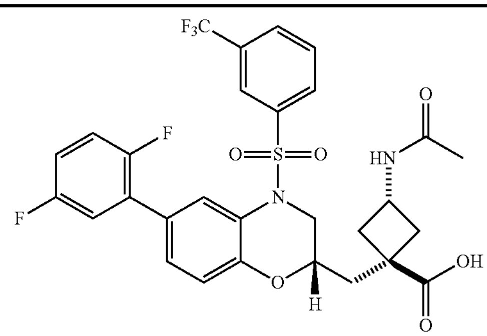 | (1r,3S)-3-acetamido-1-(((S)-6-(2,5-difluorophenyl)-4-((3-(trifluoromethyl)phenyl)sulfonyl)-3,4-dihydro-2H-benzo[b][1,4]oxazin-2-yl)methyl)cyclobutane-1-carboxylic acid | 625 (M + H)+ |
| 89C | 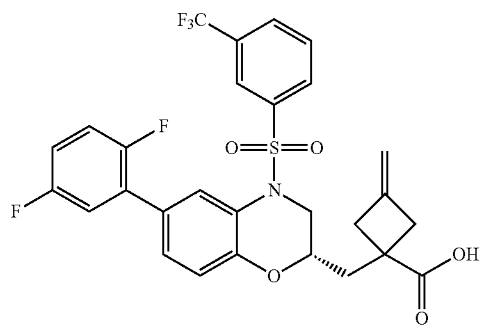 [SMILES: C=C1CC(C[C@H]2CN(S(=O)(=O)c3cccc(C(F)(F)F)c3)c3cc(-c4cc(F)ccc4F)ccc3O2)(C(=O)O)C1] | (S)-1-((6-(2,5-difluorophenyl)-4-((3-(trifluoromethyl)phenyl)sulfonyl)-3,4-dihydro-2H-benzo[b][1,4]-oxazin-2-yl)methyl)-3-methylene-cyclobutane-1-carboxylic acid | 578 (M − H)− |
| 89D | 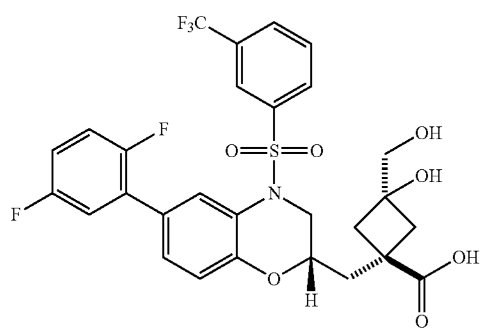 | (1r,3R)-1-(((S)-6-(2,5-difluoro-phenyl)-4-((3-(trifluoromethyl)-phenyl)sulfonyl)-3,4-dihydro-2H-benzo[b][1,4]oxazin-2-yl)methyl)-3-hydroxy-3-(hydroxymethyl)-cyclobutane-1-carboxylic acid | 612 (M − H)− |
| 89E | 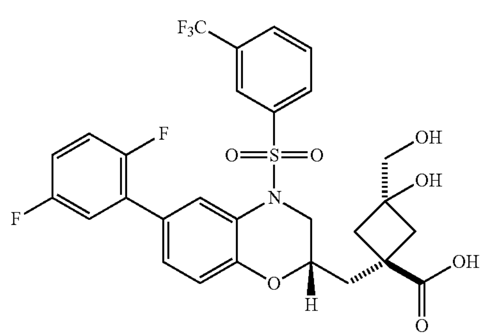 | (1s,3S)-1-(((S)-6-(2,5-difluoro-phenyl)-4-((3-(trifluoromethyl)-phenyl)sulfonyl)-3,4-dihydro-2H-benzo[b][1,4]oxazin-2-yl)methyl)-3-hydroxy-3-(hydroxymethyl)-cyclobutane-1-carboxylic acid | 612 (M − H)− |

TABLE 22A

| Compd No. | Physical Characterization Data |
|---|---|
| 89A | $^1$H NMR (300 MHz, CD$_3$OD-d$_4$) δ 8.03-7.92 (m, 3H), 7.90-7.82 (m, 1H), 7.78 (t, J = 7.9 Hz, 1H), 7.34-7.15 (m, 3H), 7.15-7.03 (m, 1H), 6.86 (d, J = 8.5 Hz, 1H), 4.44-4.31 (m, 2H), 3.56-3.46 (m, 1H), 3.39-3.32 (m, 1H), 2.79-2.69 (m, 2H), 2.11-1.94 (m, 3H), 1.90 (s, 3H). |

TABLE 22A-continued

| Compd No. | Physical Characterization Data |
|---|---|
| 89B | $^1$H NMR (300 MHz, CD$_3$OD-d$_4$) δ 8.10-7.92 (m, 3H), 7.90 (s, 1H), 7.77 (t, J = 7.9 Hz, 1H), 7.32-7.16 (m, 3H), 7.15-7.05 (m, 1H), 6.87 (d, J = 8.5 Hz, 1H), 4.47 (dd, J = 14.5, 2.4 Hz, 1H), 4.35-4.22 (m, 1H), 3.55-3.44 (m, 1H), 3.38-3.33 (m, 1H), 2.45-2.27 (m, 3H), 2.26-2.17 (m, 1H), 2.08 (d, J = 5.7 Hz, 2H), 1.91 (s, 3H). |
| 89D | $^1$H NMR (300 MHz, CD$_3$OD-d$_4$) δ 8.16-7.93 (m, 3H), 7.85 (s, 1H), 7.79 (t, J = 7.9 Hz, 1H), 7.35-7.15 (m, 3H), 7.16-7.06 (m, 1H), 6.86 (d, J = 8.5 Hz, 1H), 4.43 (dd, J = 14.5, 2.5 Hz, 1H), 3.60-3.43 (m, 3H), 3.42-3.33 (m, 1H), 2.72-2.59 (m, 2H), 2.28-2.17 (m, 1H), 2.17-1.82 (m, 3H). |
| 89E | $^1$H NMR (300 MHz, CD$_3$OD-d$_4$) δ 8.14-7.92 (m, 3H), 7.91-7.70 (m, 2H), 7.38-7.16 (m, 3H), 7.16-7.07 (m, 1H), 6.87 (d, J = 8.5 Hz, 1H), 4.43 (dd, J = 14.4, 2.4 Hz, 1H), 3.54-3.37 (m, 3H), 3.28-3.21 (m, 1H), 2.54-2.37 (m, 2H), 2.29-2.10 (m, 2H), 2.10-1.98 (m, 2H). |

Example 90 and 91—Synthesis of (R)-3-((S)-6-(3-(difluoromethoxy)-5-fluorophenyl)-4-((3-(trifluoromethyl)phenyl)sulfonyl)-3,4-dihydro-2H-benzo[b][1,4]oxazin-2-yl)-2-(methoxymethyl)-2-methylpropanoic acid and (S)-3-((S)-6-(3-(difluoromethoxy)-5-fluorophenyl)-4-((3-(trifluoromethyl)phenyl)sulfonyl)-3,4-dihydro-2H-benzo[b][1,4]oxazin-2-yl)-2-(methoxymethyl)-2-methylpropanoic acid

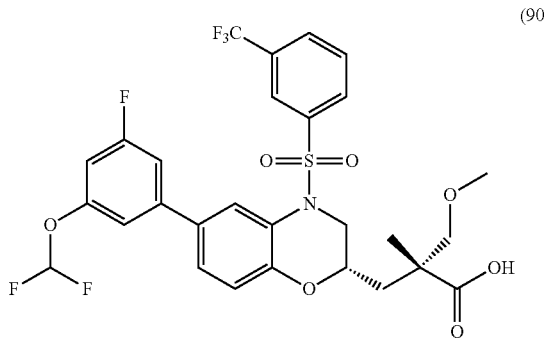

(90)

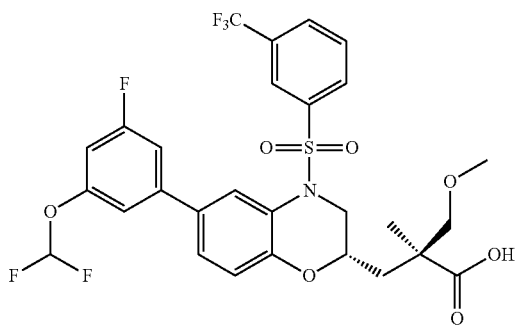

(91)

Part I—Synthesis of dimethyl (S)-2-((6-bromo-4-((3-(trifluoromethyl)phenyl)sulfonyl)-3,4-dihydro-2H-benzo[b][1,4]oxazin-2-yl)methyl)-2-methylmalonate

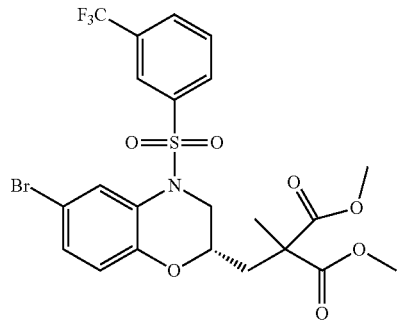 [SMILES: COC(=O)C(C)(C[C@H]1CN(S(=O)(=O)c2cccc(C(F)(F)F)c2)c2cc(Br)ccc2O1)C(=O)OC]

Methyl iodide (2.01 g, 14.15 mmol) was added to a stirred mixture of dimethyl (S)-2-((6-bromo-4-((3-(trifluoromethyl)phenyl)sulfonyl)-3,4-dihydro-2H-benzo[b][1,4]oxazin-2-yl)methyl)malonate (4.0 g, 7.06 mmol), acetone (40 mL), potassium carbonate (3.9 mg, 28.3 mmol), 18-crown-6 ether (373.8 mg, 1.42 mmol) at room temperature and was stirred overnight. The mixture was partitioned between ethyl acetate and water. The aqueous layer was reextracted with ethyl acetate. The combined organic layers were concentrated. The residue was purified via MPLC eluting with 20% ethyl acetate in petroleum ether to afford onto a silica gel column with ethyl acetate/petroleum ether (1:4) to afford dimethyl (S)-2-((6-bromo-4-((3-(trifluoromethyl)phenyl)sulfonyl)-3,4-dihydro-2H-benzo[b][1,4]oxazin-2-yl)methyl)-2-methylmalonate (3.15 g, 77%) as a yellow oil.

Part II—Synthesis of 2-(((S)-6-bromo-4-((3-(trifluoromethyl)phenyl)sulfonyl)-3,4-dihydro-2H-benzo[b][1,4]oxazin-2-yl)methyl)-3-methoxy-2-methyl-3-oxopropanoic acid

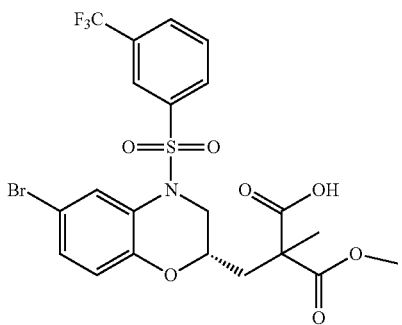 [SMILES: COC(=O)C(C)(C[C@H]1CN(S(=O)(=O)c2cccc(C(F)(F)F)c2)c2cc(Br)ccc2O1)C(=O)O]

A mixture of dimethyl (S)-2-((6-bromo-4-((3-(trifluoromethyl)phenyl)sulfonyl)-3,4-dihydro-2H-benzo[b][1,4]oxazin-2-yl)methyl)-2-methylmalonate (3.15 g, 5.43 mmol), methanol (300 mL), water (150 mL), and potassium hydroxide (3.05 g, 54 mmol) was stirred overnight at room temperature. The mixture was concentrated and extracted twice with ethyl acetate. The combined organic layers were dried (Na$_2$SO$_4$) and concentrated. The residue was purified via MPLC eluting with 10% methanol in dichloromethane to afford 2-(((S)-6-bromo-4-((3-(trifluoromethyl)phenyl)sulfonyl)-3,4-dihydro-2H-benzo[b][1,4]oxazin-2-yl)methyl)-3-methoxy-2-methyl-3-oxopropanoic acid (2.9 g, 94%) as a yellow oil.

Part III—Synthesis of methyl 3-((S)-6-bromo-4-((3-(trifluoromethyl)phenyl)sulfonyl)-3,4-dihydro-2H-benzo[b][1,4]oxazin-2-yl)-2-(hydroxymethyl)-2-methylpropanoate

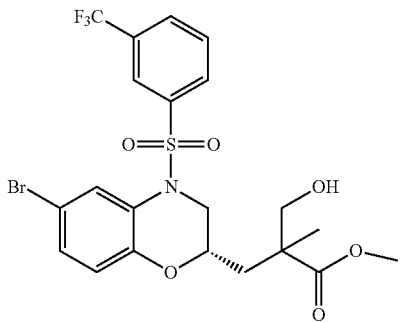 [SMILES: COC(=O)C(C)(CO)C[C@H]1CN(S(=O)(=O)c2cccc(C(F)(F)F)c2)c2cc(Br)ccc2O1]

A mixture of 2-(((S)-6-bromo-4-((3-(trifluoromethyl)phenyl)sulfonyl)-3,4-dihydro-2H-benzo[b][1,4]oxazin-2-yl)methyl)-3-methoxy-2-methyl-3-oxopropanoic acid (3.3 g, 5.83 mmol), tetrahydrofuran (33 mL), triethylamine (649 mg, 6.41 mmol) and 2-methylpropyl chloroformate (874 mg, 6.40 mmol) were stirred at 0° C. for ten minutes, warmed to room temperature and stirred for an additional fortyfive minutes. The mixture as filtered, and the filtrate was concentrated. To a stirred solution of the residue in methanol (33 mL) at 0° C. was added sodium borohydride (444 mg, 11.74 mmol) portionwise and was stirred for an additional hour at room temperature. The reaction was quenched with saturated ammonium chloride, and was extracted twice with ethyl acetate. The combined organic layers were dried (Na$_2$SO$_4$) and concentrated. The residue was purified via MPLC eluting with a gradient of 1-10% methanol in dichloromethane to afford methyl 3-((S)-6-bromo-4-((3-(trifluoromethyl)phenyl)sulfonyl)-3,4-dihydro-2H-benzo[b][1,4]oxazin-2-yl)-2-(hydroxymethyl)-2-methylpropanoate (2.9 g, 90%) as a yellow oil.

Part IV—Synthesis of (methyl 3-((S)-6-bromo-4-((3-(trifluoromethyl)phenyl)sulfonyl)-3,4-dihydro-2H-benzo[b][1,4]oxazin-2-yl)-2-(methoxymethyl)-2-methylpropanoate

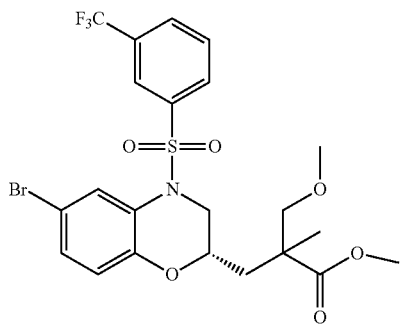 [SMILES: COCC(C)(C[C@H]1CN(S(=O)(=O)c2cccc(C(F)(F)F)c2)c2cc(Br)ccc2O1)C(=O)OC]

Sodium hydride (632 mg, 26.33 mmol) was added in portions to a stirred solution of methyl 3-((S)-6-bromo-4-((3-(trifluoromethyl)phenyl)sulfonyl)-3,4-dihydro-2H-benzo[b][1,4]oxazin-2-yl)-2-(hydroxymethyl)-2-methylpropanoate (2.9 g, 5.25 mmol) in tetrahydrofuran (29 mL) at 0° C. The mixture was stirred for an additional hour at room temperature. Methyl iodide (3.74 g, 26.34 mmol) was added and the mixture was stirred overnight at room temperature. The mixture was diluted with water, and extracted twice with ethyl acetate. The combined organic layers were dried (Na$_2$SO$_4$) and concentrated. The residue was purified via MPLC eluting with 33% ethyl acetate in petroleum ether to afford (methyl 3-((S)-6-bromo-4-((3-(trifluoromethyl)phenyl)sulfonyl)-3,4-dihydro-2H-benzo[b][1,4]oxazin-2-yl)-2-(methoxymethyl)-2-methylpropanoate (2.1 g, 71%) as a yellow oil.

Part V—Synthesis of methyl 3-((S)-6-(3-(difluoromethoxy)-5-fluorophenyl)-4-((3-(trifluoromethyl)phenyl)sulfonyl)-3,4-dihydro-2H-benzo[b][1,4]oxazin-2-yl)-2-(methoxymethyl)-2-methylpropanoate

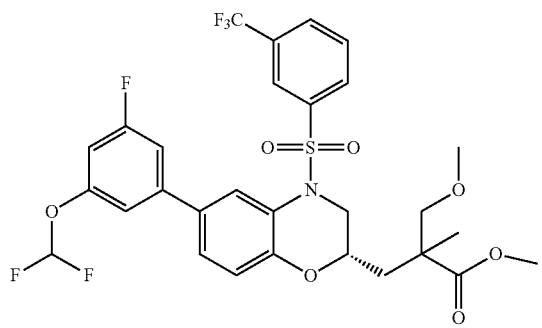 [SMILES: COCC(C)(C[C@H]1CN(S(=O)(=O)c2cccc(C(F)(F)F)c2)c2cc(-c3cc(F)cc(OC(F)F)c3)ccc2O1)C(=O)OC]

A mixture of (methyl 3-((S)-6-bromo-4-((3-(trifluoromethyl)phenyl)sulfonyl)-3,4-dihydro-2H-benzo[b][1,4]oxazin-2-yl)-2-(methoxymethyl)-2-methylpropanoate (700 mg, 1.24 mmol), toluene (6 mL), methanol (2 mL), water (2 mL), 2-[3-(difluoromethoxy)-5-fluorophenyl]-4,4,5,5-tetramethyl-1,3,2-dioxaborolane (535.2 mg, 1.86 mmol), sodium carbonate (394 mg, 3.72 mmol), and tetrakis(triphenylphosphine)palladium (143.2 mg, 0.12 mmol) was stirred for two hours at 90° C. The mixture was partitioned between ethyl acetate and water. The organic layer was concentrated. The residue was purified via MPLC eluting with 20% ethyl acetate in petroleum ether to afford methyl 3-((S)-6-(3-(difluoromethoxy)-5-fluorophenyl)-4-((3-(trifluoromethyl)phenyl)sulfonyl)-3,4-dihydro-2H-benzo[b][1,4]oxazin-2-yl)-2-(methoxymethyl)-2-methylpropanoate (600 mg, 75%) as a yellow oil.

Part VI—Synthesis of (R)-3-((S)-6-(3-(difluoromethoxy)-5-fluorophenyl)-4-((3-(trifluoromethyl)phenyl)sulfonyl)-3,4-dihydro-2H-benzo[b][1,4]oxazin-2-yl)-2-(methoxymethyl)-2-methylpropanoic acid and (S)-3-((S)-6-(3-(difluoromethoxy)-5-fluorophenyl)-4-((3-(trifluoromethyl)phenyl)sulfonyl)-3,4-dihydro-2H-benzo[b][1,4]oxazin-2-yl)-2-(methoxymethyl)-2-methylpropanoic acid

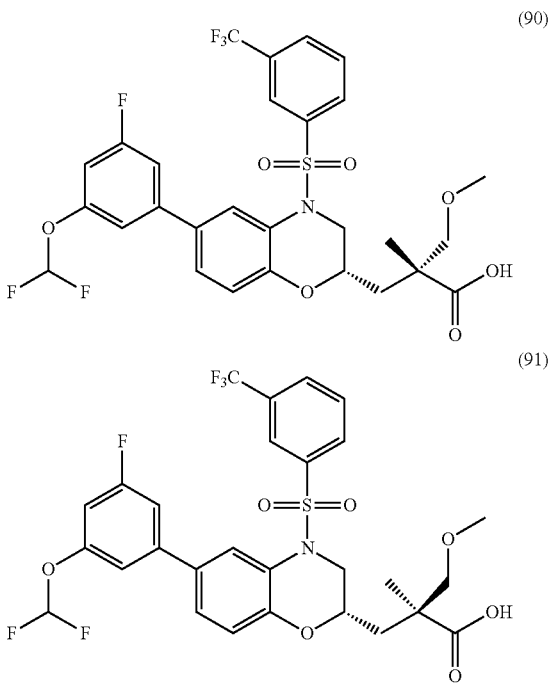 [SMILES: COC[C@@](C)(C[C@H]1CN(S(=O)(=O)c2cccc(C(F)(F)F)c2)c2cc(-c3cc(F)cc(OC(F)F)c3)ccc2O1)C(=O)O ; COC[C@](C)(C[C@H]1CN(S(=O)(=O)c2cccc(C(F)(F)F)c2)c2cc(-c3cc(F)cc(OC(F)F)c3)ccc2O1)C(=O)O]

A mixture of methyl 3-((S)-6-(3-(difluoromethoxy)-5-fluorophenyl)-4-((3-(trifluoromethyl)phenyl)sulfonyl)-3,4-dihydro-2H-benzo[b][1,4]oxazin-2-yl)-2-(methoxymethyl)-2-methylpropanoate (350 mg, 0.54 mmol), tetrahydrofuran (4 mL), water (1 mL), and lithium hydroxide (204 mg, 4.87 mmol) was stirred overnight at 70° C. The mixture was partitioned between ethyl acetate and 1N HCl. The organic layer was dried (Na$_2$SO$_4$) and concentrated. The residue was purified by Prep-HPLC eluting with a gradient of 65-85% acetonitrile in water with 0.05% trifluoroacetic acid to afford (R)-3-((S)-6-(3-(difluoromethoxy)-5-fluorophenyl)-4-((3-(trifluoromethyl)phenyl)sulfonyl)-3,4-dihydro-2H-benzo[b][1,4]oxazin-2-yl)-2-(methoxymethyl)-2-methylpropanoic acid (266 mg, 78%): $^1$H-NMR (400 MHz, CD$_3$OD) δ 8.05 (d, J=2.2 Hz, 1H), 8.03-7.94 (m, 2H), 7.92 (t, J=1.7 Hz, 1H), 7.79 (t, J=7.9 Hz, 1H), 7.42 (dd, J=8.6, 2.3 Hz, 1H), 7.26-7.17 (m, 2H), 7.17-6.78 (m, 3H), 4.39 (dd, J=14.6, 2.6 Hz, 1H), 3.59 (ddt, J=11.2, 8.5, 3.1 Hz, 1H), 3.42 (d, J=8.8 Hz, 1H), 3.34-3.30 (m, 5H), 1.90 (dd, J=14.5, 8.4 Hz, 1H), 1.73 (dd, J=14.6, 3.4 Hz, 1H), 1.10 (s, 3H); (ES, m/z): (M+Na)$^+$ 656; and (S)-3-((S)-6-(3-(difluoromethoxy)-5-fluorophenyl)-4-((3-(trifluoromethyl)phenyl)sulfonyl)-3,4-dihydro-2H-benzo[b][1,4]oxazin-2-yl)-2-(methoxymethyl)-2-methylpropanoic acid (58 mg, 17%): $^1$H-NMR (400 MHz, CD$_3$OD) δ 8.07 (d, J=2.2 Hz, 1H), 8.01-7.97 (m, 2H), 7.86 (s, 1H), 7.79 (t, J=7.9 Hz, 1H), 7.43 (dd, J=8.6, 2.3 Hz, 1H), 7.26-7.19 (m, 2H), 7.17-6.79 (m, 3H), 4.47 (dd, J=14.6, 2.6 Hz, 1H), 3.56 (ddt, J=10.0, 6.7, 3.3 Hz, 1H), 3.46 (d, J=9.0 Hz, 1H), 3.37 (d, J=9.0 Hz, 1H), 3.33 (s, 3H), 3.29-3.24 (m, 1H), 1.95 (dd, J=14.7, 4.0 Hz, 1H), 1.76 (dd, J=14.7, 6.9 Hz, 1H), 1.13 (s, 3H); (ES, m/z): (M–H)$^-$ 632; as white solids.

Example 92 and 93—Synthesis of (R)-3-((S)-6-(3-chloro-2,5-difluorophenyl)-4-((3-(trifluoromethyl)phenyl)sulfonyl)-3,4-dihydro-2H-benzo[b][1,4]oxazin-2-yl)-2-(methoxymethyl)-2-methylpropanoic acid and (S)-3-((S)-6-(3-chloro-2,5-difluorophenyl)-4-((3-(trifluoromethyl)phenyl)sulfonyl)-3,4-dihydro-2H-benzo[b][1,4]oxazin-2-yl)-2-(methoxymethyl)-2-methylpropanoic acid

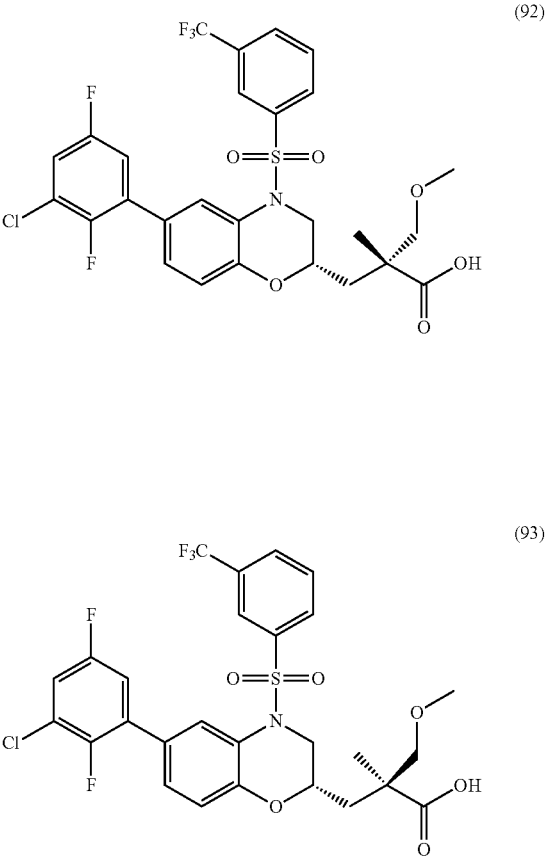

Part I—Synthesis of 3-methoxy-2-methyl-2-(((S)-6-(4,4,5,5-tetramethyl-1,3,2-dioxaborolan-2-yl)-4-((3-(trifluoromethyl)phenyl)sulfonyl)-3,4-dihydro-2H-benzo[b][1,4]oxazin-2-yl)methyl)propanoic acid

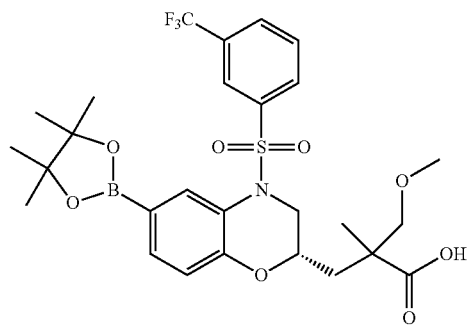 [SMILES: COCC(C)(C[C@H]1CN(S(=O)(=O)c2cccc(C(F)(F)F)c2)c2cc(B3OC(C)(C)C(C)(C)O3)ccc2O1)C(=O)O]

A mixture of (methyl 3-((S)-6-bromo-4-((3-(trifluoromethyl)phenyl)sulfonyl)-3,4-dihydro-2H-benzo[b][1,4]oxazin-2-yl)-2-(methoxymethyl)-2-methylpropanoate (800 mg, 1.41 mmol), ethylene glycol dimethyl ether (8 mL), 4,4,5,5-tetramethyl-2-(tetramethyl-1,3,2-dioxaborolan-2-yl)-1,3,2-dioxaborolane (540 mg, 2.13 mmol), potassium acetate (555 mg, 5.66 mmol), and [1,1'-bis(diphenylphosphino)ferrocene] dichloropalladium (II) (103.6 mg, 0.14 mmol) was stirred for two hours at 80° C. The mixture was concentrated, and the residue was purified via MPLC eluting with 20% ethyl acetate in petroleum ether to afford 3-methoxy-2-methyl-2-(((S)-6-(4,4,5,5-tetramethyl-1,3,2-dioxaborolan-2-yl)-4-((3-(trifluoromethyl)phenyl)sulfonyl)-3,4-dihydro-2H-benzo[b][1,4]oxazin-2-yl)methyl)propanoic acid (800 mg, 92%) as a yellow oil.

Part II—Synthesis of methyl 3-((S)-6-(3-chloro-2,5-difluorophenyl)-4-((3-(trifluoromethyl)phenyl)sulfonyl)-3,4-dihydro-2H-benzo[b][1,4]oxazin-2-yl)-2-(methoxymethyl)-2-methylpropanoate

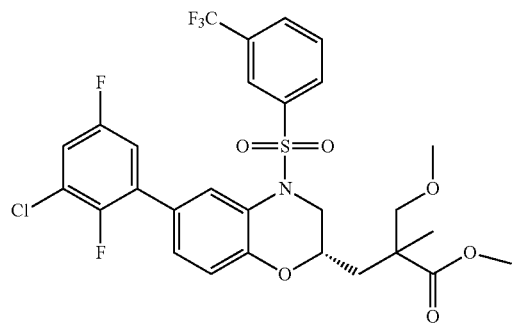 [SMILES: COCC(C)(C[C@H]1CN(S(=O)(=O)c2cccc(C(F)(F)F)c2)c2cc(-c3cc(F)cc(Cl)c3F)ccc2O1)C(=O)OC]

A mixture of 3-methoxy-2-methyl-2-(((S)-6-(4,4,5,5-tetramethyl-1,3,2-dioxaborolan-2-yl)-4-((3-(trifluoromethyl)phenyl)sulfonyl)-3,4-dihydro-2H-benzo[b][1,4]oxazin-2-yl)methyl)propanoic acid (500 mg, 0.82 mmol), toluene (6 mL), methanol (2 mL), water (2 mL), 1-bromo-3-chloro-2,5-difluorobenzene (368.7 mg, 1.62 mmol), sodium carbonate (259 mg, 2.45 mmol), and tetrakis(triphenylphosphine)palladium (94.3 mg, 0.08 mmol) was stirred for two hours at 90° C. The mixture was partitioned between water and ethyl acetate. The organic layer was dried (Na$_2$SO$_4$) and concentrated. The residue was purified via MPLC eluting with ethyl 25% acetate in petroleum ether to afford methyl 3-((S)-6-(3-chloro-2,5-difluorophenyl)-4-((3-(trifluoromethyl)phenyl)sulfonyl)-3,4-dihydro-2H-benzo[b][1,4]oxazin-2-yl)-2-(methoxymethyl)-2-methylpropanoate (400 mg, 77%) as a yellow oil.

Part III—Synthesis of (R)-3-((S)-6-(3-chloro-2,5-difluorophenyl)-4-((3-(trifluoromethyl)phenyl)sulfonyl)-3,4-dihydro-2H-benzo[b][1,4]oxazin-2-yl)-2-(methoxymethyl)-2-methylpropanoic acid and (S)-3-((S)-6-(3-chloro-2,5-difluorophenyl)-4-((3-(trifluoromethyl)phenyl)sulfonyl)-3,4-dihydro-2H-benzo[b][1,4]oxazin-2-yl)-2-(methoxymethyl)-2-methylpropanoic acid

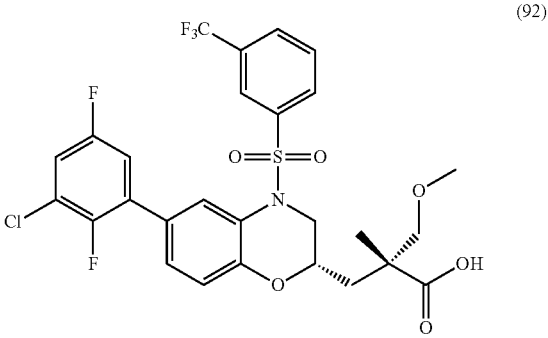
(92)

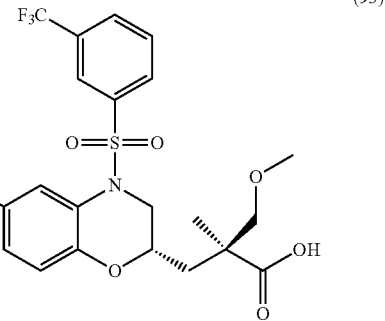
(93)

By the procedure of example 90 and 91, Part VI, using methyl 3-((S)-6-(3-chloro-2,5-difluorophenyl)-4-((3-(trifluoromethyl)phenyl)sulfonyl)-3,4-dihydro-2H-benzo[b][1,4]oxazin-2-yl)-2-(methoxymethyl)-2-methylpropanoate (350 mg, 0.55 mmol) was prepared (R)-3-((S)-6-(3-chloro-2,5-difluorophenyl)-4-((3-(trifluoromethyl)phenyl)sulfonyl)-3,4-dihydro-2H-benzo[b][1,4]oxazin-2-yl)-2-(methoxymethyl)-2-methylpropanoic acid (148 mg, 43%): $^1$H-NMR (400 MHz, CD$_3$OD) δ 8.06-7.92 (m, 4H), 7.80 (t, J=7.9 Hz, 1H), 7.37-7.28 (m, 2H), 7.22 (ddd, J=8.8, 5.6, 3.1 Hz, 1H), 6.90 (d, J=8.5 Hz, 1H), 4.42 (dd, J=14.6, 2.6 Hz, 1H), 3.65 (ddt, J=11.1, 8.4, 3.0 Hz, 1H), 3.43 (d, J=8.8 Hz, 1H), 3.36-3.30 (m, 5H), 1.90 (dd, J=14.5, 8.3 Hz, 1H), 1.75 (dd, J=14.6, 3.4 Hz, 1H), 1.12 (s, 3H); (ES, m/z): (M–H)$^-$ 618; and (S)-3-((S)-6-(3-chloro-2,5-difluorophenyl)-4-((3-(trifluoromethyl)phenyl)sulfonyl)-3,4-dihydro-2H-benzo[b][1,4]oxazin-2-yl)-2-(methoxymethyl)-2-methylpropanoic acid (45 mg, 13%): $^1$H-NMR (400 MHz, CD$_3$OD) δ 8.09-7.96 (m, 3H), 7.89 (s, 1H), 7.80 (t, J=7.9 Hz, 1H), 7.39-7.28 (m, 2H), 7.22 (ddd, J=8.8, 5.6, 3.1 Hz, 1H), 6.91 (d, J=8.5 Hz, 1H), 4.51 (dd, J=14.6, 2.6 Hz, 1H), 3.65-3.57 (m, 1H), 3.47 (d, J=9.0 Hz, 1H), 3.38 (d, J=9.0 Hz, 1H), 3.34 (s, 3H), 3.31-3.24 (m, 1H), 1.96 (dd, J=14.7, 4.0 Hz, 1H), 1.76 (dd, J=14.7, 6.9 Hz, 1H), 1.15 (s, 3H); (ES, m/z): (M–H)⁻ 618; as white solids.

Example 94—Synthesis of sodium (S)-3-(6-(3-(difluoromethoxy)-5-fluorophenyl)-4-((3-(trifluoromethyl)phenyl)sulfonyl)-3,4-dihydro-2H-benzo[b][1,4]oxazin-2-yl)-2,2-dimethylpropanoate

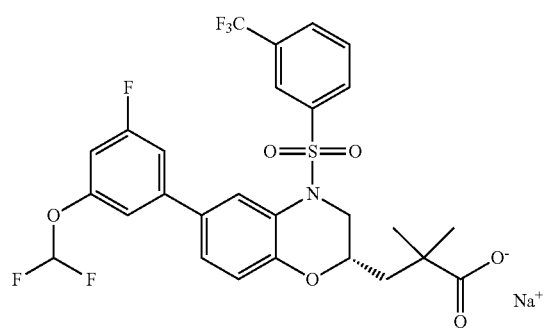 [SMILES: CC(C)(C[C@H]1CN(S(=O)(=O)c2cccc(C(F)(F)F)c2)c2cc(-c3cc(F)cc(OC(F)F)c3)ccc2O1)C(=O)[O-] ; [Na+]]

Part I—Synthesis of (S)-2,2-dimethyl-3-(oxiran-2-yl)propanenitrile

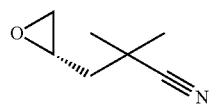

A 2.5M solution of n-butyl lithium (40 mL, 100 mmol) was added dropwise to a stirred solution of diisopropylamine (14.1 mL, 100 mmol) in THF (200 mL) at 0° C. The solution was stirred at 0° C. for thirty minutes. The cold solution was added dropwise to a solution of (S)-2-(chloromethyl)oxirane (9.3 g, 100 mmol), 2-methylpropanenitrile (6.9 g, 100 mmol), and tetrahydrofuran (200 mL) at −45° C. The mixture was stirred at −45° C., and then allowed to warm up to room temperature overnight. The mixture was quenched by the addition of saturated ammonium chloride (100 mL), and extracted with ethyl acetate (100 mL). The organic layers were washed with water (100 mL), dried (Na₂SO₄), filtered and concentrated to afford (S)-2,2-dimethyl-3-(oxiran-2-yl)propanenitrile (10.1 g, 81%) as a light yellow oil.

Part II—Synthesis of (S)-5-(chloromethyl)-3,3-dimethyl-tetrahydrofuran-2-one

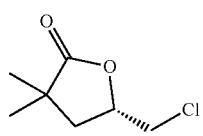

(S)-2,2-dimethyl-3-(oxiran-2-yl)propanenitrile (10.1 g, 80.7 mmol) was dissolved in concentrated hydrogen chloride (20 mL) and stirred at room temperature for ten minutes. The solution was diluted with acetic acid (40 mL) and then heated to 50° C. overnight. The reaction mixture was partitioned between water (50 mL) and ethyl acetate (50 mL). The organic layer was washed with water (50 mL), saturated aqueous sodium bicarbonate (50 mL), saturated aqueous sodium chloride (50 mL), dried (Na₂SO₄), filtered and concentrated to afford (S)-5-(chloromethyl)-3,3-dimethyl-tetrahydrofuran-2-one (9.8 g, 75%) as a pale yellow oil.

Part III—Synthesis of methyl (S)-2,2-dimethyl-3-(oxiran-2-yl)propanoate

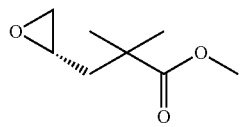

Sodium methoxide solution (25% w/w) (37 mL, 135 mmol) was added to a solution of (S)-5-(chloromethyl)-3,3-dimethyl-tetrahydrofuran-2-one (22.3 g, 137 mmol) in methanol (37 mL). The solution was stirred at room temperature for 2 hours. The reaction mixture was filtered and the filtrate was concentrated. The residue was partitioned between ethyl acetate (100 mL) and water (100 mL). The organic layer was washed with saturated aqueous sodium chloride solution (100 mL), dried (Na₂SO₄), filtered and concentrated. The residue was distilled to afford methyl (S)-2,2-dimethyl-3-(oxiran-2-yl)propanoate (12.3 g, 57%) as a clear, colorless oil (BP=50-53° C. at 1.5 Torr).

Part IV—Synthesis of N-(3'-(difluoromethoxy)-4,5'-difluoro-[1,1'-biphenyl]-3-yl)-3-(trifluoromethyl)benzenesulfonamide

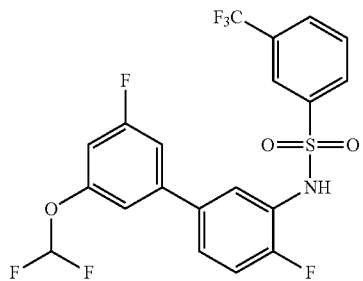 [SMILES: O=S(=O)(Nc1cc(-c2cc(F)cc(OC(F)F)c2)ccc1F)c1cccc(C(F)(F)F)c1]

To a solution of (3-(difluoromethoxy)-5-fluorophenyl) boronic acid (20.0 g, 97.1 mmol), N-(5-bromo-2-fluorophenyl)-3-(trifluoromethyl)benzenesulfonamide (38.7 g, 97.1 mmol), and potassium carbonate (20.1 g, 146 mmol, 1.5 equiv) in 1,4-dioxane (243 ml)/water (60 mL) was added 1,1'-bis (diphenylphosphino)ferrocenepalladium (II) dichloride, toluene (1.6 g, 1.94 mmol, 0.02 equiv). The mixture was heated to 80° C. overnight. Then, the reaction mixture was quenched with water (250 mL) and diluted with tert-butylmethylether (250 mL). The biphasic mixture was filtered through Celite, the phases were separated and the aqueous phase was extracted with tert-butylmethylether (250 mL). The combined organic extracts were washed with saturated aqueous sodium chloride (250 mL). The organic extracts were treated with charcoal, filtered through Celite, and rinsed with tert-butylmethylether. The filtrates were concentrated and then the residue was dissolved in tert-butylmethylether (100 mL) and then diluted with hexane (500 mL). The resulting mixture was stirred at room temperature for 2 hours and the resulting suspension was diluted with hexane (200 mL), filtered, rinsed with hexane (100 mL) and dried to afford N-(3'-(difluoromethoxy)-4,5'-difluoro-[1,1'-biphenyl]-3-yl)-3-(trifluoromethyl)benzenesulfonamide (31.5 g, 68%).

Part V—Synthesis of (S)—N-(3'-(difluoromethoxy)-4,5'-difluoro-[1,1'-biphenyl]-3-yl)-N-((4,4-dimethyl-5-oxotetrahydrofuran-2-yl)methyl)-3-(trifluoromethyl)benzenesulfonamide

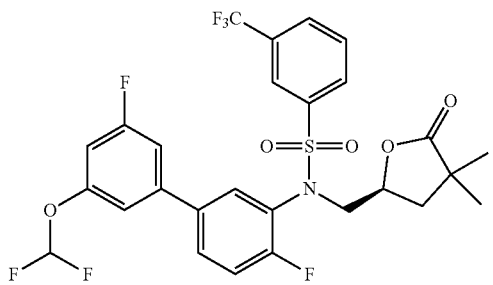 [SMILES: CC1(C)C[C@@H](CN(c2cc(-c3cc(F)cc(OC(F)F)c3)ccc2F)S(=O)(=O)c2cccc(C(F)(F)F)c2)OC1=O]

A mixture of methyl (S)-2,2-dimethyl-3-(oxiran-2-yl)propanoate (11.1 g, 70.5 mmol), of N-(3'-(difluoromethoxy)-4,5'-difluoro-[1,1'-biphenyl]-3-yl)-3-(trifluoromethyl)benzenesulfonamide (26.0 g, 54.2 mmol), tetra-n-butylammonium bromide (1.75 g, 5.42 mmol), and potassium carbonate (750 mg, 5.42 mmol) was stirred at 90° C. overnight. Then, the reaction mixture was quenched with saturated aqueous sodium chloride (250 mL), and extracted with ethyl acetate (250 mL). The organic extracts were washed with saturated aqueous sodium chloride (250 mL), dried (Na$_2$SO$_4$), filtered and concentrated. The resulting residue was dissolved in methanol (150 mL) and warmed to 40° C. for fifteen minutes. The mixture was allowed to cool to room temperature and then further cooled to 0° C. and stirred for thirty minutes. The suspension was filtered, rinsed with methanol (30 mL), and dried to afford (S)—N-(3'-(difluoromethoxy)-4,5'-difluoro-[1,1'-biphenyl]-3-yl)-N-((4,4-dimethyl-5-oxotetrahydrofuran-2-yl)methyl)-3-(trifluoromethyl)benzenesulfonamide (16.0 g, 49%).

Part VI—Synthesis of sodium (S)-3-(6-(3-(difluoromethoxy)-5-fluorophenyl)-4-((3-(trifluoromethyl)phenyl)sulfonyl)-3,4-dihydro-2H-benzo[b][1,4]oxazin-2-yl)-2,2-dimethylpropanoate

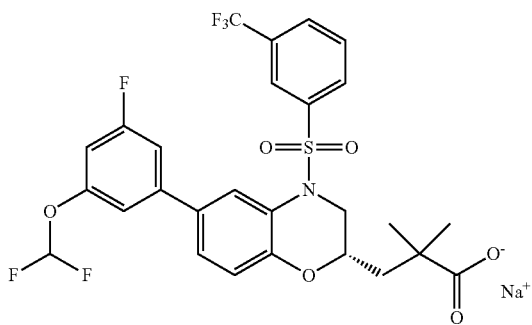 [SMILES: CC(C)(C[C@H]1CN(S(=O)(=O)c2cccc(C(F)(F)F)c2)c2cc(-c3cc(F)cc(OC(F)F)c3)ccc2O1)C(=O)[O-] ; [Na+]]

A solution of (S)—N-(3'-(difluoromethoxy)-4,5'-difluoro-[1,1'-biphenyl]-3-yl)-N-((4,4-dimethyl-5-oxotetrahydrofuran-2-yl)methyl)-3-(trifluoromethyl)benzenesulfonamide (23.6 g, 39.0 mmol), tetra-n-butylammonium bromide (2.26 g, 3.90 mmol), and sodium hydroxide (6.24 g, 156 mmol) in THF (39 mL) was heated to 65° C. for 23 hours. Then, the reaction mixture was quenched with water, extracted with ethyl acetate, dried (Na$_2$SO$_4$), filtered and concentrated. The resulting residue was dissolved in isopropyl alcohol (23 mL), and stirred until solids developed. The thick suspension was diluted with isopropyl alcohol (46 mL) and stirred at room temperature overnight. Next, the suspension was filtered, rinsed with isopropyl alcohol (46 mL), and dried to afford sodium (S)-3-(6-(3-(difluoromethoxy)-5-fluorophenyl)-4-((3-(trifluoromethyl)phenyl)sulfonyl)-3,4-dihydro-2H-benzo[b][1,4]oxazin-2-yl)-2,2-dimethylpropanoate (18.3 g, 78%). $^1$H-NMR (400 MHz, CD$_3$OD) δ 8.18 (d, J=8.0 Hz, 1H), 8.07 (d, J=8.0 Hz, 1H), 7.95 (d, J=2 Hz, 1H), 7.89-7.85 (m, 2H), 7.47 (dd, J=8.4 Hz, 2.4 Hz, 1H), 7.41 (t, J=74 Hz, 1H), 7.31 (m, 1H), 7.22 (m, 1H), 7.12 (m, 1H), 6.89 (d, J=8.8 Hz, 1H), 4.61 (dd, 1H), 3.58 (m, 1H), 3.23 (m, 1H), 1.82 (dd, 1H), 1.43 (dd, 1H), 0.99 (s, 3H), 0.90 (s, 3H). $^{13}$C-NMR (400 MHz, CD$_3$OD) δ 180.7, 163.9 (d, J=245 Hz), 152.4 (dt, J=12.4, 3.4 Hz), 147.6, 143.0 (d, J=9.6 Hz), 138.8, 131.8, 131.6, 130.4 (q, J=3.3 Hz), 129.9 (q, J=32.9 Hz), 130.2 (d, 2.3 Hz), 123.0 (q, J=273 Hz), 125.1, 123.5 (q, J=3.7 Hz), 123.1, 121.7, 116.2 (t, J=258 Hz), 118.2, 112.2 (d, J=2.5 Hz), 109.6 (d, J=22.4 Hz), 104.8 (d, J=25.7 Hz), 71.4, 48.8, 43.7, 40.7, 28.5, 25.4. $^{19}$F-NMR (400 MHz, CD$_3$OD) δ −61.2, −82.6 (d, J=73.6 Hz), −109.5 (t, dd, J=9.7 Hz, 9.7 Hz). (ES, m/z): (M−H)$^-$ 602.

Example 95—Biological Assays for Agonist Activity Towards RORγ

Exemplary compounds from the above Examples were tested for ability to increase RORγ activity using (i) a RORγ-Ligand Binding Domain (LBD) TR-FRET Assay, and (ii) a Gal4-RORγ Luciferase Reporter Assay in HEK-293T Cells. Assay procedures and results are described below.

Part I—Procedures for RORγ-Ligand Binding Domain TR-FRET Assay

HIS-tagged RORγ-LBD protein was expressed in SF9 cells using a baculovirus expression system. The lysate was diluted in assay buffer (50 mM Tris pH 7.0, 50 mM KCl, 1 mM EDTA, 0.1 mM DTT, 0.01% BSA) to obtain RORγ-LBD final concentration of ~3 nM in a 384-well assay plate (need to titrate for each batch of protein).

A stock of biotinylated-LXXLL peptide from coactivator SRC1 (Biotin-CPSSHSSLTERHKILHRLLQEGSPS) was prepared in assay buffer and added to each well (200 nM final concentration). A solution of Europium tagged anti-HIS antibody (0.6 nM final concentration) and APC-conjugated streptavidin (30 nM final concentration) were also added to each well. RORγ antagonist ursolic acid was also included at a final concentration of 2 μM. Compounds were diluted in DMSO and further diluted in assay buffer with a final DMSO concentration at 1%. The highest concentration of test compound analyzed was 10 μM.

The final assay mixture was incubated overnight at 4° C. or 2 hours at room temperature, and the fluorescence signal was measured on an Envision plate reader: (Excitation filter=340 nm; APC emission=665 nm; Europium emission=615 nm; dichroic mirror=D400/D630; delay time=100 μs, integration time=200 μs). 50% Effective concentration (EC$_{50}$) values for test compounds were calculated from the quotient of the fluorescence signal at 665 nm divided by the fluorescence signal at 615 nm. The quotient of the fluorescence signals in the absence of ursolic acid or test compound is set as 100. Max Response is defined as the upper plateau in the signal as determined by line-fit using a 4-parameter logistic model in PRISM (GraphPad).

Part II—Procedures for Gal4-ROR Luciferase Reporter Assay in HEK-293T Cells Transfection of HEK-293 Cells In the following protocol, HEK-293 cells were transfected with a construct comprising the Gal4 DNA binding domain fused to the ligand binding domain of RORγ (Gal4-RORγ-LBD) in a pcDNA3.1neo plasmid, and also with a reporter construct comprising pGL4.31 Gal4-luciferase (Promega). Control cells were prepared similarly using empty pcDNA3.1neo and pGL4.31 vectors.

Trans-IT reagent (Mirus, 60 µL) at room temperature was added drop wise to OptiMEM (Invitrogen, 1.5 ml). This reagent mixture was mixed by inversion then incubated for 5 to 30 minutes at room temperature. It then was added to a solution of both expression vectors (5 µg each), mixed, and incubated at room temperature for about 20 minutes. HEK-293 cells were harvested from incubation flasks by removing the media, treating with TrypLE Express (Invitrogen), and incubating until the cells detached from the bottom of the flask (approximately 2-5 minutes). 10 Million cells were collected by centrifugation and re-suspended in 10 mL of Dulbecco's Modified Eagle Medium, High Glucose (DMEM, Invitrogen) containing 10% Fetal Bovine Serum and 100 IU each of penicillin and streptomycin. The re-suspended cells and the transfection mixture were added to a T75 flask, mixed and incubated overnight at 37° C. and 5% $CO_2$.

Assay for RORγ Activity

The cells were harvested as described above, counted, and centrifuged to obtain the desired number of cells, then re-suspended in complete growth media at $0.75 \times 10^6$ cells/mL. The RORγ antagonist, ursolic acid, was added to the cells at a final concentration of 2 µM. Cells were plated at 20 µL of cell suspension/well (10,000-15,000 cells/well) in white tissue culture treated 384 well plates. Test compounds were dissolved at 10 mM in DMSO then diluted into complete growth medium to 5× the final intended test concentration. These drug stock solutions, 5 µL/well were added to the tissue culture plate. The final DMSO concentration was 0.2%. The plates were briefly centrifuged then incubated overnight at 37° C. and 5% $CO_2$. To conduct the assay, the tissue culture plates were allowed to equilibrate to room temperature and One-Glo luciferase reagent (Promega, 25 µL/well) was added. The plates were briefly centrifuged then incubated at room temperature for 10 minutes. The luciferase intensity was read on an Envision plate reader (PerkinElmer). RORγ activity was determined relative to controls and plotted as a function of test compound concentration using PRISM (GraphPad) to determine a 50/effective concentration (EC$_{50}$). The luciferase signal in the absence of ursolic acid or test compound is defined at 100. The Max Response is the upper plateau in the signal as determined by line-fit using a 4-parameter logistic model in PRISM (GraphPad).

Part III—Results

Experimental results are provided in Tables 23 and 23A below. The symbol "++++" indicates an EC$_{50}$ less than 0.5 µM. The symbol "+++" indicates an EC$_{50}$ in the range of 0.5 µM to 5 µM. The symbol "++" indicates an EC$_{50}$ in the range of greater than 5 µM to 10 µM. The symbol "+" indicates an EC$_{50}$ greater than 10 µM. The symbol "N/A" indicates that no data was available. The symbol "**" indicates a value greater than 200. The symbol "*" indicates a value in the range of greater than 150 to 200. The symbol "**" indicates a value in the range of greater than 90 to 150. The symbol "*" indicates a value in the range of 25 to 90.

TABLE 23

| Title Compound from Example No. | TR-FRET Assay | | Gal4-RORγ Assay | |
|---|---|---|---|---|
| | EC$_{50}$ | Max Response | EC$_{50}$ | Max Response |
| 1 | ++++ | *** | ++++ | *** |
| 2A | ++++ | *** | ++++ | ** |
| 2AA | ++++ | **** | + | N/A |
| 2AB | ++++ | **** | + | ** |
| 2AC | ++++ | **** | ++++ | *** |
| 2AD | ++++ | **** | ++++ | *** |
| 2AE | ++++ | **** | ++++ | *** |
| 2AF | ++++ | **** | + | N/A |
| 2AG | ++++ | **** | ++++ | *** |
| 2AH | ++++ | **** | ++++ | *** |
| 2AI | ++++ | **** | N/A | ** |
| 2AJ | ++++ | **** | ++++ | ** |
| 2AK | ++++ | **** | ++++ | ** |
| 2AL | ++++ | **** | ++++ | *** |
| 2AM | ++++ | **** | ++++ | *** |
| 2AN | ++++ | **** | ++++ | ** |
| 2AO | ++++ | **** | ++++ | *** |
| 2AP | ++++ | **** | ++++ | ** |
| 2AQ | +++ | **** | +++ | * |
| 2AR | +++ | * | + | N/A |
| 2AS | ++++ | **** | +++ | ** |
| 2AT | ++++ | **** | +++ | ** |
| 2AU | ++++ | *** | +++ | * |
| 2AV | ++++ | **** | +++ | * |
| 2AW | ++++ | **** | +++ | ** |
| 2AX | ++++ | **** | ++++ | ** |
| 2AY | ++++ | **** | +++ | **** |
| 2AZ | + | N/A | + | ** |
| 2B | ++++ | ** | N/A | N/A |
| 2BA | ++++ | **** | ++++ | ** |
| 2BC | ++++ | **** | ++++ | *** |
| 2BD | ++++ | **** | ++++ | ** |
| 2BE | ++++ | **** | +++ | ** |
| 2BF | ++++ | **** | ++++ | ** |
| 2BG | ++++ | *** | +++ | ** |
| 2BH | +++ | ** | + | N/A |
| 2BI | +++ | *** | +++ | ** |
| 2BJ | + | N/A | + | ** |
| 2BK | ++++ | *** | ++++ | ** |
| 2BL | ++++ | *** | ++++ | ** |
| 2BM | ++++ | *** | +++ | ** |
| 2BN | ++++ | *** | ++++ | ** |
| 2BO | + | N/A | + | N/A |
| 2C | ++++ | *** | ++++ | ** |
| 2D | ++++ | ** | N/A | N/A |
| 2E | ++++ | *** | ++++ | ** |
| 2F | ++++ | ** | N/A | N/A |
| 2G | ++++ | *** | ++++ | *** |
| 2H | ++++ | *** | ++++ | ** |
| 2I | ++++ | *** | ++++ | *** |
| 2J | ++++ | ** | +++ | * |
| 2K | ++++ | *** | ++++ | ** |
| 2L | ++++ | *** | ++++ | *** |
| 2M | ++++ | *** | ++++ | *** |
| 2N | ++++ | *** | ++++ | *** |
| 2O | ++++ | *** | ++++ | *** |
| 2P | ++++ | *** | ++++ | *** |
| 2Q | ++++ | *** | ++++ | *** |
| 2R | ++++ | **** | ++++ | *** |
| 2S | ++++ | **** | ++++ | ** |
| 2T | ++++ | **** | ++++ | *** |
| 2U | ++++ | *** | +++ | * |

TABLE 23-continued

| Title Compound from Example No. | TR-FRET Assay EC$_{50}$ | TR-FRET Assay Max Response | Gal4-RORγ Assay EC$_{50}$ | Gal4-RORγ Assay Max Response |
|---|---|---|---|---|
| 2V | ++++ | *** | ++++ | ** |
| 2W | ++++ | *** | +++ | ** |
| 2X | ++++ | **** | ++++ | ** |
| 2Y | ++++ | *** | ++++ | ** |
| 2Z | ++++ | ** | + | N/A |
| 3 | ++++ | *** | +++ | *** |
| 4A | ++++ | *** | ++++ | *** |
| 4B | ++++ | *** | ++++ | ** |
| 4C | N/A | N/A | +++ | ** |
| 4D | ++++ | *** | +++ | * |
| 4E | ++++ | **** | +++ | ** |
| 4F | ++++ | **** | +++ | ** |
| 4G | ++++ | **** | +++ | ** |
| 4H | ++++ | *** | +++ | * |
| 4I | ++++ | *** | ++++ | ** |
| 4J | ++++ | **** | +++ | ** |
| 4K | +++ | **** | + | N/A |
| 4L | + | **** | + | N/A |
| 4M | ++++ | **** | + | * |
| 4N | ++++ | **** | +++ | ** |
| 4O | ++++ | *** | +++ | ** |
| 4P | ++++ | ** | ++ | ** |
| 4Q | +++ | ** | + | N/A |
| 4R | ++++ | **** | ++++ | **** |
| 4S | ++++ | **** | +++ | **** |
| 4T | ++++ | **** | ++++ | **** |
| 4U | +++ | * | +++ | * |
| 4V | ++++ | **** | +++ | ** |
| 4W | +++ | **** | +++ | ** |
| 4X | ++++ | **** | ++++ | ** |
| 4Y | ++++ | **** | +++ | * |
| 4Z | +++ | * | + | N/A |
| 4AA | ++++ | **** | ++++ | ** |
| 4AB | + | N/A | + | N/A |
| 4AC | ++++ | **** | ++++ | * |
| 4AD | + | N/A | + | N/A |
| 4AE | ++++ | **** | +++ | ** |
| 4AF | ++++ | **** | ++++ | ** |
| 4AG | ++++ | **** | ++++ | ** |
| 4AH | ++++ | **** | ++++ | ** |
| 4AI | ++++ | ** | N/A | N/A |
| 4AJ | ++++ | **** | ++++ | ** |
| 4AK | ++++ | **** | ++++ | ** |
| 4AL | ++++ | **** | ++++ | ** |
| 4AM | ++++ | **** | +++ | ** |
| 4AN | ++++ | **** | ++++ | ** |
| 4AO | +++ | * | + | * |
| 4AP | ++++ | **** | ++++ | ** |
| 4AQ | ++++ | **** | ++++ | ** |
| 4AR | ++++ | **** | ++++ | ** |
| 4AS | ++++ | **** | ++++ | ** |
| 4AT | +++ | *** | N/A | N/A |
| 4AU | ++++ | **** | +++ | ** |
| 4AV | +++ | *** | N/A | N/A |
| 4AX | +++ | ** | N/A | N/A |
| 4AY | ++++ | *** | ++++ | ** |
| 4AZ | ++++ | **** | ++++ | ** |
| 5 | ++++ | *** | +++ | ** |
| 6A | ++++ | *** | +++ | * |
| 6B | ++++ | **** | +++ | ** |
| 6C | ++++ | **** | +++ | ** |
| 6D | ++++ | **** | +++ | ** |
| 6G | ++++ | **** | +++ | ** |
| 6H | ++++ | **** | ++++ | ** |
| 6I | ++++ | *** | +++ | ** |
| 6J | ++++ | *** | ++++ | ** |
| 6K | ++++ | *** | ++++ | ** |
| 6L | ++++ | *** | ++++ | ** |
| 7 | ++++ | **** | ++++ | ** |
| 8 | ++++ | **** | ++++ | ** |
| 9 | ++++ | **** | ++++ | ** |
| 10 | ++++ | **** | ++++ | ** |
| 11 | ++++ | **** | ++++ | ** |
| 12 | ++++ | **** | ++++ | * |
| 19 | ++++ | **** | ++++ | ** |
| 20 | ++++ | **** | ++++ | ** |
| 21A | ++++ | **** | ++++ | ** |
| 21B | ++++ | **** | ++++ | ** |
| 21C | ++++ | **** | ++++ | *** |
| 21D | ++++ | *** | ++++ | *** |
| 22A | ++++ | **** | ++++ | ** |
| 22B | ++++ | **** | ++++ | ** |
| 22C | ++++ | **** | ++++ | ** |
| 22D | ++++ | **** | ++++ | ** |
| 22E | ++++ | **** | ++++ | ** |
| 22F | + | N/A | N/A | N/A |
| 22G | ++++ | *** | ++++ | ** |
| 23A | ++++ | **** | ++++ | ** |
| 23B | ++++ | **** | ++++ | ** |
| 23C | ++++ | *** | ++++ | ** |
| 23D | ++++ | *** | ++++ | ** |
| 23E | ++++ | **** | ++++ | ** |
| 23F | ++++ | **** | ++++ | ** |
| 23G | ++++ | **** | ++++ | ** |
| 23H | ++++ | **** | ++++ | ** |
| 23I | ++++ | **** | ++++ | ** |
| 23J | ++++ | **** | ++ | *** |
| 23K | ++++ | **** | +++ | ** |
| 23L | ++++ | **** | ++++ | ** |
| 23M | ++++ | **** | ++++ | *** |
| 23N | ++++ | **** | ++++ | *** |
| 23O | ++++ | **** | N/A | N/A |
| 23P | ++++ | **** | ++++ | *** |
| 23Q | ++++ | **** | +++ | *** |
| 23R | ++++ | **** | +++ | ** |
| 23S | ++++ | **** | +++ | ** |
| 23T | ++++ | **** | ++++ | ** |
| 23U | ++++ | **** | ++++ | ** |
| 23V | ++++ | **** | +++ | ** |
| 23W | ++++ | **** | ++++ | ** |
| 23X | ++++ | **** | +++ | ** |
| 23Y | ++++ | *** | ++++ | ** |
| 23Z | ++++ | **** | N/A | N/A |
| 24 | ++++ | **** | ++++ | ** |
| 25 | +++ | ** | N/A | N/A |
| 26 | +++ | *** | +++ | * |
| 27 | ++++ | **** | +++ | * |
| 28A | ++++ | **** | ++++ | ** |
| 28B | ++++ | **** | ++++ | ** |
| 28C | ++++ | **** | ++++ | * |
| 28D | ++++ | **** | ++++ | ** |
| 28E | ++++ | **** | ++++ | ** |
| 28F | ++++ | **** | ++++ | ** |
| 28G | ++++ | **** | ++++ | ** |
| 28H | ++++ | **** | ++++ | * |
| 28I | ++++ | **** | ++++ | ** |
| 28J | ++++ | **** | ++++ | ** |
| 28K | ++++ | **** | ++++ | ** |
| 29 | ++++ | **** | ++++ | ** |
| 30A | ++++ | **** | ++++ | * |
| 30AA | ++++ | **** | ++++ | * |
| 30AB | ++++ | **** | ++++ | * |
| 30AC | ++++ | **** | +++ | * |
| 30AD | ++++ | **** | ++++ | * |
| 30AE | ++++ | *** | ++++ | ** |
| 30AF | ++++ | *** | ++++ | ** |
| 30AG | ++++ | *** | ++++ | ** |
| 30AH | ++++ | *** | ++++ | ** |
| 30AI | ++++ | *** | ++++ | ** |
| 30AJ | ++++ | **** | ++++ | ** |
| 30AK | ++++ | **** | +++ | ** |
| 30AL | ++++ | **** | ++++ | * |
| 30AM | ++++ | **** | ++++ | ** |
| 30AN | ++++ | **** | ++++ | ** |
| 30AO | ++++ | **** | ++++ | * |
| 30AP | ++++ | *** | ++++ | * |
| 30AQ | ++++ | *** | ++++ | * |
| 30AR | ++++ | **** | ++++ | * |

TABLE 23-continued

| Title Compound from Example No. | TR-FRET Assay | | Gal4-RORγ Assay | |
|---|---|---|---|---|
| | EC$_{50}$ | Max Response | EC$_{50}$ | Max Response |
| 30AS | ++++ | *** | +++ | * |
| 30AT | ++++ | *** | +++ | ** |
| 30AU | ++++ | **** | ++++ | ** |
| 30AV | ++++ | *** | ++++ | * |
| 30AW | ++++ | *** | ++++ | ** |
| 30AX | ++++ | *** | ++++ | ** |
| 30AY | ++++ | *** | ++++ | ** |
| 30AZ | ++++ | **** | ++++ | ** |
| 30B | ++++ | **** | ++++ | ** |
| 30BA | ++++ | *** | ++++ | ** |
| 30BB | ++++ | *** | ++++ | * |
| 30BC | ++++ | *** | ++++ | ** |
| 30BD | ++++ | **** | ++++ | ** |
| 30BE | ++++ | *** | ++++ | * |
| 30BF | ++++ | **** | ++++ | * |
| 30BG | ++++ | *** | +++ | ** |
| 30BH | ++++ | *** | +++ | ** |
| 30BI | ++++ | *** | +++ | * |
| 30C | ++++ | **** | ++++ | * |
| 30D | ++++ | **** | ++++ | * |
| 30E | ++++ | **** | ++++ | ** |
| 30F | ++++ | **** | ++++ | * |
| 30G | ++++ | **** | ++++ | * |
| 30H | ++++ | **** | ++++ | * |
| 30I | ++++ | **** | ++++ | * |
| 30J | ++++ | **** | ++++ | * |
| 30K | ++++ | **** | ++++ | * |
| 30L | ++++ | **** | ++++ | * |
| 30M | ++++ | *** | ++++ | * |
| 30N | ++++ | *** | ++++ | * |
| 30O | ++++ | **** | ++++ | ** |
| 30P | ++++ | **** | ++++ | ** |
| 30Q | ++++ | **** | ++++ | * |
| 30R | ++++ | **** | ++++ | ** |
| 30S | ++++ | **** | ++++ | * |
| 30T | N/A | N/A | ++++ | * |
| 30U | ++++ | *** | ++++ | ** |
| 30V | ++++ | **** | ++++ | * |
| 30W | ++++ | **** | ++++ | ** |
| 30X | ++++ | *** | ++++ | * |
| 30Y | ++++ | **** | ++++ | ** |
| 30Z | ++++ | **** | ++++ | * |
| 31 | ++++ | **** | ++++ | ** |
| 32A | ++++ | **** | ++++ | ** |
| 32B | ++++ | *** | ++++ | ** |
| 32C | ++++ | **** | ++++ | ** |
| 32D | ++++ | **** | ++++ | ** |
| 32E | ++++ | **** | ++++ | ** |
| 32F | ++++ | **** | ++++ | ** |
| 32G | ++++ | *** | ++++ | ** |
| 32H | ++++ | **** | +++ | ** |
| 32I | ++++ | **** | +++ | *** |
| 32J | ++++ | **** | ++++ | ** |
| 32K | ++++ | **** | ++++ | ** |
| 32L | ++++ | **** | ++++ | ** |
| 32M | N/A | N/A | +++ | ** |
| 32N | ++++ | *** | ++++ | ** |
| 32O | ++++ | **** | ++++ | * |
| 32P | ++++ | *** | ++++ | ** |
| 32Q | ++++ | **** | ++++ | ** |
| 32R | ++++ | *** | ++++ | ** |
| 34A | ++++ | **** | ++++ | * |
| 34B | ++++ | **** | ++++ | * |
| 34C | ++++ | **** | ++++ | ** |
| 34D | ++++ | **** | ++++ | ** |
| 34E | ++++ | **** | ++++ | **** |
| 35 | ++++ | **** | ++++ | ** |
| 36A | ++++ | **** | ++++ | **** |
| 36B | ++++ | **** | ++++ | ** |
| 36C | ++++ | **** | ++++ | ** |
| 37 | ++++ | *** | +++ | *** |
| 38 | ++++ | *** | ++++ | ** |
| 39 | ++++ | **** | ++++ | ** |
| 40 | ++++ | **** | +++ | ** |
| 41 | ++++ | **** | ++++ | * |
| 42 | ++++ | **** | ++++ | ** |
| 43A | ++++ | **** | +++ | *** |
| 43B | ++++ | **** | +++ | ** |
| 44 | ++++ | **** | ++++ | ** |
| 45A | ++++ | **** | ++++ | ** |
| 45C | ++++ | *** | ++++ | * |
| 46A | ++++ | *** | +++ | ** |
| 46B | ++++ | *** | ++++ | ** |
| 46C | ++++ | *** | ++++ | ** |

TABLE 23A

| Title Compound from Example No. | TR-FRET Assay | | Gal4-RORγ Assay | |
|---|---|---|---|---|
| | EC$_{50}$ | Max Response | EC$_{50}$ | Max Response |
| 2BP | ++++ | *** | N/A | N/A |
| 2BQ | ++++ | *** | N/A | N/A |
| 2BR | ++++ | *** | ++++ | ** |
| 4BB | ++++ | N/A | N/A | N/A |
| 13 | ++++ | **** | ++++ | ** |
| 16 | ++++ | **** | ++++ | ** |
| 17 | ++++ | **** | ++++ | ** |
| 18 | ++++ | **** | +++ | ** |
| 22H | ++++ | *** | ++++ | ** |
| 22I | ++++ | *** | ++++ | ** |
| 22J | ++++ | *** | ++++ | ** |
| 22K | ++++ | *** | ++++ | ** |
| 22L | N/A | N/A | ++++ | ** |
| 22M | ++++ | *** | N/A | N/A |
| 22N | ++++ | *** | N/A | N/A |
| 30BJ | +++ | *** | N/A | N/A |
| 30BK | ++++ | *** | N/A | N/A |
| 30BL | ++++ | *** | N/A | N/A |
| 30BM | ++++ | *** | N/A | N/A |
| 30BN | +++ | *** | + | * |
| 30BY | +++ | *** | +++ | * |
| 30BZ | ++++ | **** | ++++ | * |
| 30CA | ++++ | *** | ++++ | * |
| 30CB | ++++ | *** | ++++ | * |
| 30CC | ++++ | *** | ++++ | ** |
| 30CD | ++++ | *** | ++++ | ** |
| 30CE | ++++ | *** | ++++ | * |
| 30CF | ++++ | **** | ++++ | ** |
| 30CG | ++++ | *** | +++ | * |
| 30CH | ++++ | *** | +++ | * |
| 30CI | ++++ | *** | +++ | * |
| 30CJ | ++++ | ** | +++ | * |
| 30CK | ++++ | ** | +++ | * |
| 30CL | +++ | ** | +++ | * |
| 30CV | ++++ | *** | ++++ | * |
| 30CX | ++++ | ** | ++++ | * |
| 30CY | ++++ | ** | N/A | N/A |
| 30CZ | ++++ | *** | N/A | N/A |
| 30DA | ++++ | *** | +++ | * |
| 30DB | ++++ | *** | N/A | N/A |
| 30DC | ++++ | *** | +++ | * |
| 30DD | ++++ | *** | N/A | N/A |
| 30DE | ++++ | *** | ++++ | * |
| 30DF | ++++ | *** | N/A | N/A |
| 30DG | ++++ | *** | +++ | * |
| 30DH | ++++ | *** | ++++ | * |
| 30DI | ++++ | *** | ++++ | * |
| 30DJ | ++++ | *** | +++ | * |
| 32S | ++++ | *** | ++++ | ** |
| 32T | ++++ | *** | ++++ | ** |
| 32U | ++++ | *** | N/A | N/A |
| 32V | ++++ | *** | ++++ | ** |

TABLE 23A-continued

| Title Compound from Example No. | TR-FRET Assay | | Gal4-RORγ Assay | |
|---|---|---|---|---|
| | EC$_{50}$ | Max Response | EC$_{50}$ | Max Response |
| 32W | ++++ | *** | ++++ | ** |
| 32X | ++++ | *** | ++++ | ** |
| 32Y | ++++ | *** | ++++ | ** |
| 32Z | ++++ | *** | ++++ | ** |
| 32AA | ++++ | **** | ++++ | ** |
| 32AB | ++++ | *** | ++++ | ** |
| 32AC | ++++ | *** | ++++ | ** |
| 32AD | ++++ | *** | ++++ | * |
| 32AE | ++++ | *** | ++++ | * |
| 32AF | ++++ | *** | +++ | ** |
| 32AG | ++++ | **** | ++++ | ** |
| 32AH | ++++ | *** | ++++ | ** |
| 32AI | ++++ | *** | ++++ | ** |
| 32AJ | ++++ | ** | ++++ | ** |
| 32AK | ++++ | ** | ++++ | * |
| 32AL | ++++ | ** | ++++ | ** |
| 32AM | ++++ | * | N/A | N/A |
| 32AN | ++++ | ** | N/A | N/A |
| 32AO | ++++ | ** | +++ | * |
| 32AP | ++++ | ** | N/A | N/A |
| 32AQ | +++ | ** | N/A | N/A |
| 32AR | ++++ | ** | ++++ | ** |
| 32AS | ++++ | ** | ++++ | ** |
| 32AT | ++++ | ** | ++++ | ** |
| 32AU | ++++ | ** | ++++ | ** |
| 32AV | ++++ | ** | ++++ | ** |
| 32AW | ++++ | ** | ++++ | ** |
| 32AX | ++++ | ** | ++++ | ** |
| 32AY | ++++ | ** | N/A | N/A |
| 32AZ | ++++ | ** | ++++ | ** |
| 32BA | ++++ | *** | +++ | ** |
| 32BB | ++++ | * | ++++ | ** |
| 32BC | ++++ | ** | ++++ | ** |
| 32BD | ++++ | ** | ++++ | ** |
| 32BE | ++++ | ** | ++++ | ** |
| 32BF | ++++ | *** | ++++ | ** |
| 32BG | ++++ | ** | ++++ | ** |
| 32BH | ++++ | *** | +++ | ** |
| 32BI | ++++ | *** | ++++ | ** |
| 32BJ | ++++ | *** | ++++ | ** |
| 32BK | ++++ | *** | ++++ | ** |
| 32BL | ++++ | ** | ++++ | * |
| 32BM | ++++ | *** | ++++ | ** |
| 45D | ++++ | *** | ++++ | * |
| 45E | ++++ | *** | ++++ | ** |
| 45F | N/A | N/A | ++++ | * |
| 46D | ++++ | *** | ++++ | ** |
| 46E | ++++ | ** | +++ | * |
| 46F | ++++ | *** | +++ | * |
| 46G | ++++ | ** | ++++ | ** |
| 46H | ++++ | *** | N/A | N/A |
| 46I | ++++ | *** | N/A | N/A |
| 46J | ++++ | *** | N/A | N/A |
| 46K | ++++ | *** | N/A | N/A |
| 46L | ++++ | *** | N/A | N/A |
| 46M | ++++ | *** | N/A | N/A |
| 46N | ++++ | *** | N/A | N/A |
| 46O | ++++ | *** | N/A | N/A |
| 46P | ++++ | *** | N/A | N/A |
| 46Q | ++++ | *** | N/A | N/A |
| 46R | ++++ | *** | N/A | N/A |
| 46S | ++++ | *** | N/A | N/A |
| 46T | ++++ | *** | N/A | N/A |
| 46U | ++++ | *** | N/A | N/A |
| 49 | ++++ | ** | ++++ | ** |
| 50 | ++++ | *** | ++++ | ** |
| 51A | ++++ | ** | ++++ | ** |
| 51B | ++++ | *** | ++++ | ** |
| 51C | ++++ | ** | ++++ | ** |
| 51D | ++++ | *** | N/A | N/A |
| 51E | ++++ | *** | + | *** |
| 51F | ++++ | *** | ++++ | ** |
| 51G | N/A | N/A | ++++ | ** |
| 51H | N/A | N/A | +++ | ** |
| 51I | N/A | N/A | ++++ | * |
| 51J | N/A | N/A | ++++ | ** |
| 51K | N/A | N/A | +++ | *** |
| 51L | N/A | N/A | ++++ | ** |
| 51M | ++++ | *** | ++++ | ** |
| 52 | ++++ | ** | +++ | * |
| 53 | ++++ | ** | ++++ | ** |
| 54 | ++++ | ** | +++ | ** |
| 55 | ++++ | ** | ++++ | * |
| 56 | ++++ | ** | +++ | ** |
| 57 | ++++ | *** | N/A | N/A |
| 58 | ++++ | *** | ++++ | ** |
| 59 | ++++ | *** | ++++ | ** |
| 60A | ++++ | *** | ++++ | ** |
| 60B | ++++ | *** | ++++ | ** |
| 60C | ++++ | ** | ++++ | ** |
| 60D | ++++ | *** | ++++ | * |
| 60E | ++++ | *** | ++++ | ** |
| 60F | N/A | N/A | ++++ | ** |
| 60G | N/A | N/A | ++++ | *** |
| 60H | ++++ | ** | N/A | N/A |
| 60I | ++++ | ** | N/A | N/A |
| 60J | ++++ | *** | N/A | N/A |
| 60K | ++++ | ** | N/A | N/A |
| 60L | N/A | N/A | ++++ | ** |
| 60M | N/A | N/A | ++++ | ** |
| 60N | ++++ | ** | ++++ | ** |
| 60O | ++++ | *** | ++++ | ** |
| 61 | ++++ | *** | ++++ | ** |
| 62 | ++++ | ** | ++++ | ** |
| 63 | N/A | N/A | N/A | N/A |
| 64 | N/A | N/A | +++ | ** |
| 65 | N/A | N/A | +++ | ** |
| 67 | N/A | N/A | ++++ | ** |
| 68 | N/A | N/A | ++++ | ** |
| 69 | N/A | N/A | +++ | ** |
| 70 | N/A | N/A | +++ | *** |
| 71 | ++++ | *** | N/A | N/A |
| 72 | ++++ | ** | N/A | N/A |
| 73 | ++++ | *** | ++++ | ** |
| 74 | ++++ | ** | ++++ | ** |
| 75 | ++++ | ** | ++ | *** |
| 77A | ++++ | ** | N/A | **** |
| 77B | ++++ | *** | ++++ | ** |
| 77C | ++++ | ** | N/A | N/A |
| 77D | ++++ | ** | N/A | N/A |
| 78A | ++++ | ** | ++++ | ** |
| 78B | ++++ | ** | ++++ | ** |
| 78C | ++++ | ** | ++++ | *** |
| 78D | ++++ | ** | ++++ | *** |
| 78E | ++++ | ** | ++++ | ** |
| 78F | ++++ | ** | ++++ | ** |
| 78G | ++++ | ** | ++++ | ** |
| 78H | ++++ | ** | ++++ | * |
| 78I | ++++ | *** | N/A | N/A |
| 78J | ++++ | *** | N/A | N/A |
| 78K | N/A | N/A | ++++ | ** |
| 78L | N/A | N/A | ++++ | ** |
| 78M | N/A | N/A | ++++ | *** |
| 78N | N/A | N/A | ++++ | ** |
| 78O | N/A | N/A | ++++ | ** |
| 78P | N/A | N/A | ++++ | ** |
| 78Q | N/A | N/A | ++++ | ** |
| 78R | N/A | N/A | ++++ | ** |
| 78S | N/A | N/A | ++++ | ** |
| 78T | N/A | N/A | ++++ | ** |
| 78U | N/A | N/A | ++++ | ** |
| 78V | N/A | N/A | ++++ | ** |
| 78W | N/A | N/A | ++++ | ** |
| 80A | +++ | *** | N/A | N/A |
| 80B | ++++ | ** | +++ | ** |
| 80C | ++++ | *** | ++++ | ** |
| 82 | N/A | N/A | +++ | ** |
| 83B | N/A | N/A | +++ | ** |

TABLE 23A-continued

| Title Compound from Example No. | TR-FRET Assay | | Gal4-RORγ Assay | |
|---|---|---|---|---|
| | $EC_{50}$ | Max Response | $EC_{50}$ | Max Response |
| 83C | N/A | N/A | +++ | ** |
| 83D | N/A | N/A | +++ | ** |
| 83E | N/A | N/A | +++ | * |
| 83F | N/A | N/A | +++ | * |
| 84 | ++++ | ** | +++ | * |
| 85 | ++++ | ** | ++++ | ** |
| 87 | N/A | N/A | +++ | ** |
| 89A | +++ | *** | +++ | ** |
| 89B | ++++ | ** | +++ | ** |
| 89D | N/A | N/A | +++ | ** |
| 89E | N/A | N/A | +++ | ** |

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

What is claimed is:

1. A compound represented by Formula I-B:

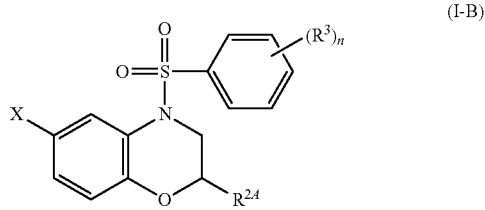

(I-B)

or a pharmaceutically acceptable salt thereof; wherein:
X is phenyl substituted by 1, 2, or 3 substituents independently selected from the group consisting of chloro, fluoro, $C_{1-2}$ fluoroalkyl, $C_{1-2}$ alkoxy, and $C_{1-2}$fluoroalkoxy;
$R^{24}$ is —($C_{1-6}$ alkylene)—$CO_2H$ or —($C_{1-6}$ alkylene)—$N(R^4)C(O)R^7$;
$R^3$ represents independently for each occurrence $C_{1-2}$ fluoroalkyl, chloro, fluoro, cyclopropyl, $C_{1-3}$ alkyl, $C_{1-2}$ alkoxy, or $C_{1-2}$fluoroalkoxy;
$R^4$ is hydrogen or $C_{1-6}$ alkyl;
$R^7$ is $C_{1-6}$ alkyl, $C_{1-6}$ hydroxyalkyl, $C_{1-6}$haloalkyl, $C_{1-6}$hydroxyhaloalkyl, $C_{3-6}$ cycloalkyl, or $C_{3-6}$ hydroxycycloalkyl; and
n is 1.

2. The compound of claim 1, wherein X is phenyl substituted by 1, 2, or 3 substituents independently selected from the group consisting of chloro, fluoro, $C_{1-2}$ fluoroalkyl, $C_{1-2}$ alkoxy, and $C_{1-2}$fluoroalkoxy, where at least 1 substituent is located at a meta-position on the phenyl group.

3. The compound of claim 1, wherein $R^{24}$ is —$(CH_2)_2$—$CO_2H$ or —$CH_2C(CH_3)_2$—$CO_2H$.

4. The compound of claim 1, wherein $R^3$ is —CF3, which is attached at a meta-position on the phenyl group.

5. The compound of claim 2, wherein $R^{24}$ is —$(CH_2)_2$—$CO_2H$ or —$CH_2C(CH_3)_2$—$CO_2H$.

6. The compound of claim 2, wherein $R^3$ is —$CF_3$, which is attached at a meta-position on the phenyl group.

7. The compound of claim 3, wherein $R^3$ is —$CF_3$, which is attached at a meta-position on the phenyl group.

8. A pharmaceutical composition comprising a compound of claim 1 and a pharmaceutically acceptable carrier.

9. A pharmaceutical composition comprising a compound of claim 2 and a pharmaceutically acceptable carrier.

10. A pharmaceutical composition comprising a compound of claim 3 and a pharmaceutically acceptable carrier.

11. A pharmaceutical composition comprising a compound of claim 4 and a pharmaceutically acceptable carrier.

12. A pharmaceutical composition comprising a compound of claim 5 and a pharmaceutically acceptable carrier.

13. A pharmaceutical composition comprising a compound of claim 6 and a pharmaceutically acceptable carrier.

14. A pharmaceutical composition comprising a compound of claim 7 and a pharmaceutically acceptable carrier.

15. A method of treating a disorder selected from the group consisting of cancer, bacterial infection, fungal infection, and immune deficiency disorder, comprising administering a therapeutically effective amount of a compound of claim 1 to a subject in need thereof to ameliorate a symptom of the disorder.

16. The method of claim 15, wherein the disorder is cancer.

17. The method of claim 15, wherein the disorder is colon cancer, pancreatic cancer, breast cancer, ovarian cancer, prostate cancer, squamous cell carcinoma, basal cell carcinoma, adenocarcinoma, sweat gland carcinoma, sebaceous gland carcinoma, lung cancer, leukemia, bladder cancer, stomach cancer, cervical cancer, testicular cancer, skin cancer, rectal cancer, thyroid cancer, kidney cancer, uterus cancer, esophagus cancer, liver cancer, an acoustic neuroma, oligodendroglioma, meningioma, neuroblastoma, or retinoblastoma.

18. A method of increasing the amount of IL-17 in a subject, comprising administering to a subject an effective amount of a compound of claim 1 to increase the amount of IL-17 in the subject.

19. The method of claim 17, wherein the subject is a human.

20. A method of promoting the activity of RORγ, comprising exposing a RORγ to an effective amount of a compound of claim 1 to promote the activity of said RORγ.

* * * * *